(12) United States Patent
Sutton et al.

(10) Patent No.: US 8,637,532 B2
(45) Date of Patent: Jan. 28, 2014

(54) AMINO AZAHETEROCYCLIC CARBOXAMIDES

(75) Inventors: Amanda E. Sutton, Hingham, MA (US); Ruoxi Lan, Waltham, MA (US); Thomas E. Richardson, Durham, NC (US); David Perrey, Durham, NC (US); Harold George Vandeveer, Temple Terrace, FL (US); Bayard R. Huck, Sudbury, MA (US); Srinivasa R. Karra, Pembroke, MA (US); Xiaoling Chen, Chestnut Hill, MA (US); Yufang Xiao, Lexington, MA (US); Lesley Liu-Bujalski, Bedford, MA (US); Andreas Goutopoulos, Boston, MA (US); Frank Stieber, Einhausen (DE); Brian L. Hodous, Cambridge, MA (US); Hui Qiu, Waltham, MA (US); Reinaldo Jones, Lowell, MA (US); Brian H. Heasley, Wake Forest, NC (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/148,903

(22) PCT Filed: Feb. 4, 2010

(86) PCT No.: PCT/US2010/000313
§ 371 (c)(1),
(2), (4) Date: Oct. 31, 2011

(87) PCT Pub. No.: WO2010/093419
PCT Pub. Date: Aug. 19, 2010

(65) Prior Publication Data
US 2012/0046269 A1 Feb. 23, 2012

Related U.S. Application Data

(60) Provisional application No. 61/207,354, filed on Feb. 11, 2009.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC .................. 514/266.1; 544/283; 544/284

(58) Field of Classification Search
USPC ................. 544/283, 284; 514/266.1
See application file for complete search history.

(56) References Cited

U.S. PATENT DOCUMENTS

2002/0151544 A1   10/2002   Hayakawa et al.

FOREIGN PATENT DOCUMENTS

| WO | 9909024 A1 | 2/1999 |
|----|------------|--------|
| WO | 0121596 A1 | 3/2001 |
| WO | 0200649 A1 | 1/2002 |
| WO | 03055491 A1 | 7/2003 |
| WO | 03064397 A1 | 8/2003 |
| WO | 2004092154 A1 | 10/2004 |
| WO | 2005033086 A1 | 4/2005 |
| WO | 2005039506 A2 | 5/2005 |
| WO | 2005054237 A1 | 6/2005 |
| WO | 2005056014 A1 | 6/2005 |
| WO | 2005117909 A2 | 12/2005 |
| WO | 2006071819 A1 | 7/2006 |
| WO | 2006120573 A2 | 11/2006 |
| WO | 2006131835 A2 | 12/2006 |
| WO | 2006136821 A1 | 12/2006 |
| WO | 2008049047 A2 | 4/2008 |
| WO | 2008140947 A1 | 11/2008 |

OTHER PUBLICATIONS

Pinedo et al (2001).*
McMahon et al (2001).*
Vippagunta (2000).*
Hanks & Hunter, FASEB J., (1995) 9: 576-596.
Knighton, et al., Science, (1991) 253: 407-414.
Hiles, et al., Cell, (1992) 70: 419-429.
Kunz, et al., Cell, (1993) 73: 585-596.
Garcia-Bustos, et al., EMBO J., (1994) 13: 2352-2361.
Barlund, O., et al., Cancer Res., (2000) 60: 5340-5344.
Guo-Jun Wu, et al., Cancer Res., (2000) 60: 5371-5375.
Sausville, EA, Nat. Med., (2004), 10: 234-235.
Marumoto T., Nature, (2005) 5: 42-50.
Bishop & Shumacher, J. Biol. Chem., (2002), 277: 27577-27580.
Minoshima Y, et al., Dev. Cell, (2003) 4: 549-560.
Harrington, EA, Nat. Med., (2004) 10: 262-267.
Emanuel, S, Cancer Res., (2005) 65: 9038-9046.

* cited by examiner

*Primary Examiner* — Paul V. Ward
(74) *Attorney, Agent, or Firm* — EMD Serono Research Institute

(57) ABSTRACT

The invention provides novel substituted amino azaheterocyclic carboxamide compounds according to Formula (I), their manufacture and use for the treatment of hyperproliferative diseases, such as cancer.

10 Claims, No Drawings

AMINO AZAHETEROCYCLIC CARBOXAMIDES

FIELD OF THE INVENTION

The invention relates to a series of substituted amino azaheterocyclic carboxamide compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

SUMMARY OF THE RELATED ART

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)). Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

The signal transduction pathway containing the enzymes phosphatidylinositol 3-kinase (PI3K), PDK1 and PKB amongst others, has long been known to mediate increased resistance to apoptosis or survival responses in many cells. There is a substantial amount of data to indicate that this pathway is an important survival pathway used by many growth factors to suppress apoptosis. The enzyme PI3K is activated by a range of growth and survival factors e.g. EGF, PDGF and through the generation of polyphosphatidylinositols, initiates the activation of the downstream signalling events including the activity of the kinases PDK1 and protein kinase B (PKB) also known as Akt. This is also true in host tissues, e.g. vascular endothelial cells as well as neoplasias.

Protein kinase 70S6K, the 70 kDa ribosomal protein kinase p70S6K (also known as SK6, p70/p85 S6 kinase, p70/p85 ribosomal S6 kinase and pp 70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKCζ. Akt directly phosphorylates and inactivates TSC2, thereby activating mTOR. In addition, studies with mutant alleles of p70S6K that inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5'transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on it participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed.

Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported.

In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations.

p70S6K has been implicated in metabolic diseases and disorders. It was reported that the absence of p70S6K protects against age-and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings. Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835 and WO 08/140,947.

Further molecular targets of the compounds of the invention are Aurora kinases (A, B and C). The Aurora family of conserved serine/threonine kinases perform essential functions during cell division. The three mammalian paralogues are very similar in sequence, but differ significantly in their localization, function, substrates and regulatory partners. Aurora A is mainly associated with the spindle poles during mitosis, where it is required for centrosome separation and maturation (Sausville E A. Aurora kinases dawn as cancer drug targets, Nat. Med., (2004) 10: 234-235 (2004). Spindle assembly requires that targeting protein for XKLP 2 (TPX2) targets Aurora A to spindle pole microtubules through a mechanism that requires Ran-GTP (Marumoto T, Zhang D, Saya H. Aurora A—A guardian of poles, Nature, (2005) 5 42-50 (2005). Aurora A also functions in meiosis promoting oocyte maturation, polar-body extrusion, spindle positioning and exit from metaphase I. Regulation of Aurora A occurs through phosphorylation/dephosphorylation and degradation. Protein phosphatase 1 negatively regulates Aurora and this interaction is modulated by TPX2. Aurora B is a chromosomal-passenger protein with multiple functions in mitosis. Inner centromere protein (INCENP) and survivin, two other components of the passenger complex, function as targeting and regulatory factors for the kinase (Bishop J D and Shumacher J M. Phosphorylation of the Carboxyl Terminus of Inner Centromere Protein (INCENP) by the aurora B Kinase Stimulates aurora B Kinase Activity, J. Biol. Chem. (2002) 277:27577-27580. Aurora B is required for phosphorylation of histone H3, targeting of condensin and normal chromosome compaction. It has also been recently shown to be essential for chromosome biorientation, kinetochore-microtubule interactions and the spindle-assembly checkpoint. Aurora B is essential for completion of cytokinesis. Myosin II regulatory chain, vimentin, desmin and glial fibrillary acidic protein are among its cleavage furrow substrates. Aurora B phosphorylates MgcRacGAP, transforming it into an activator of RhoA in the contractile ring (Minoshima Y, Kawashima T, Hirose K, Tonozuka Y, Kawajiri A, Bao Y, Deng X, Tatsuka M, Narumiya S, May W Phosphorylation by aurora B converts MgcRacGAP to a RhoGAP during cytokinesis. Dev. Cell, (2003) 4:549-560. Much less is known about Aurora C kinase, other than that it seems to be preferentially expressed in meiotic cells. During the cell cycle, Aurora kinases travel to their subcellular targets aided by their binding partner-substrates, INCENP, survivin and TPX2. This provides an additional level of regulation that might be essential for the choreography of mitotic events.

Aurora A and B kinases are frequently elevated in human cancers making them attractive targets for therapeutic intervention. Small molecule inhibitors of Aurora kinases have recently been reported, but their effect on cytokinesis has yet to be investigated in detail. For example a high selective and potent small-molecule inhibitor of Aurora kinases, VX-680, blocks cell-cycle progression and induces apoptosis in a diverse range of human tumor types. This compound causes profound inhibition of tumor growth in a variety of in vivo xenograft models, leading to regression of leukemia, colon and pancreatic tumors at well-tolerated doses (Harrington E A, Bebbington D, Moore J, Rasmussen R K, Ajose-Adeogun A O, Nakayama T. Graham J A, Demur C, Hercend T, Diu-Hercend A, Su M, Golec J M, Miller K M VX-680, a potent and selective small-molecule inhibitor of the aurora kinases, suppresses tumor growth in vivo, Nat. Med., (2004) 10: 262-267. Another novel cell cycle inhibitor, JNJ-7706621, showed potent inhibition of several cyclin-dependent kinases (CDK) and Aurora kinases and selectively blocked proliferation of tumor cells of various origins, but was about 10-fold less effective at inhibiting normal human cell growth in vitro. In human cancer cells, treatment with JNJ-7706621 inhibited cell growth independent of p53, retinoblastoma, or P-glycoprotein status; activated apoptosis; and reduced colony formation. At low concentrations, JNJ-7706621 slowed the growth of cells and at higher concentrations induced cytotoxicity. Inhibition of CDK1 kinase activity, altered CDK1 phosphorylation status, and interference with downstream substrates such as retinoblastoma were also shown in human tumor cells following drug treatment. JNJ-7706621 delayed progression through G1 and arrested the cell cycle at the G2-M phase (Emanuel S, Rugg C A, Gruninger R H, Lin R, Fuentes-Pesquera A, Connolly P J, Wetter S K, Hollister B, Kruger W W, Napier C, Jolliffe L, Middleton S A, The in vitro and in vivo effects of JNJ-7706621: A dual inhibitor of cyclin-dependent kinases and aurora kinases, Cancer Res., (2005) 65:9038-9046).

Additional cellular effects due to inhibition of Aurora kinases included endoreduplication and inhibition of histone H3 phosphorylation. In a human tumor xenograft model, several intermittent dosing schedules were identified that produced significant antitumor activity.

Yet another target of the compounds of the invention is phosphoinositide-dependent kinase 1 (PDK1). PDK1 phosphorylates and activates a sub-group of the AGC protein kinase family, comprising PKB, SGK, S6K and PKC isoforms. These kinases are involved in the PI3K signal transduction pathway and control basic cellular functions, such as survival, growth and differentiation. PDK1 is thus an important regulator of diverse metabolic, proliferative and life-sustaining effects.

Diseases caused by protein kinases, such as PDK1, are characterised by anomalous activity or hyperactivity of such protein kinases. Anomalous activity relates either to: (1) the expression in cells which do not usually express these protein kinases; (2) increased kinase expression which results in undesired cell proliferation, such as cancer; (3) increased kinase activity which results in undesired cell proliferation, such as cancer, and/or in hyperactivity of the corresponding protein kinases. Hyperactivity relates either to amplification of the gene which encodes a certain protein kinase or the generation of an activity level which can be correlated with a cell proliferation disease (i.e. the severity of one or more symptoms of the cell proliferation disease increases with increasing kinase level) the bioavailability of a protein kinase can also be influenced by the presence or absence of a set of binding proteins of this kinase.

In the case of PDK1, anomalous activity of the substrates PKB and S6K of this kinase has been observed in a large number of types of cancer which exhibit point mutation of the PTEN gene, which results in uncontrolled proliferation and an increased survival rate. Inhibitors of PDK1 should therefore prove advantageous in the treatment of cancer cells with constitutively activated AGC kinases.

DESCRIPTION OF THE INVENTION

It is the object of the present invention to provide novel p70S6K, Aurora kinase and/or PDK1 inhibitors useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

As a result, this invention provides novel, substituted azaheterocyclic carboxamide compounds and pharmaceutically acceptable salts, solvates or prodrugs thereof, that are kinase inhibitors and useful in the treatment of the above mentioned diseases.

The compounds are defined by Formula (I):

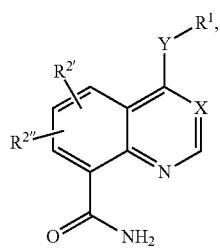

(I)

and pharmaceutically acceptable salts, solvates or prodrugs thereof,
wherein:
X is N or C—$R^3$,
Y is NH, O or absent,
$R^1$ is $L^1$-$R^4$-$L^2$-$R^5$-$L^3$-$R^6$, $L^1$-$R^4$-$L^2$-$R^5$ or $L^1$-$R^4$,
$R^{2'}$, $R^{2''}$ each, independently of one another, are H, A, Hal, OH, OA, SH, CN, $NH_2$, $NO_2$, NHA, NH-$L^1$-Ar, NHCOA, NHCO-$L^1$-Ar, $NHSO_2$-$L^1$-Ar, NHCONHA or NHCONH-$L^1$-Ar, $L^1$-Ar, O-$L^1$-Ar, $L^1$-$R^4$,
$L^1$, $L^3$ each, independently of one another, are a single bond, unbranched or branched alkylene having 1, 2, 3, 4 or 5 C atoms, which may be unsubstituted or mono- or disubstituted with Hal, OH, CN, $NH_2$, NH(LA), $N(LA)_2$, $NO_2$, COOH, $N_3$, ethenyl or ethynyl, and/or monosubstituted with $R^4$, and in which one or two $CH_2$ groups may be replaced by an O or S atom or by an —NH—, —N(LA)-, —CONH—, —N(LA)COO—, —$SO_2$— or —NHCO— group,
$R^3$ is H, A, Hal, OH, COOH, SH, $NH_2$, $NO_2$ or CN,
$R^4$, $R^5$, $R^6$ each, independently of one another, are Ar, or monocyclic alkyl having 3, 4, 5, 6 or 7 ring atoms, in which one or two $CH_2$ groups may be replaced by an O or S atom and/or by an —NH—, —NA—, —CHA—, —CO—, —CH=N— or —CH=CH— group, and/or in which the connecting CH group may be replaced by an N atom, and which may be mono- or disubstituted by Hal or LA,
$L^2$ is —NHCO—, —NHCOO—, —NHCONH—, —NHCONA—, —NHCOA—, —O—, —S—, —NH—, —$NHSO_2$—, —$SO_2NH$—, —CONH—, —CONHCONH—, —NHCONHCO—, or -A-,
Ar is a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono-, di- or trisubstituted by Hal, A, OH, SH, OA, $NH_2$, NHA, $NA_2$, $NO_2$, CN, OCN, SCN, COOH, COOA, $CONH_2$, CONHA, $CONA_2$, NHCOA, NHCONHA, $NHCONH_2$, $NHSO_2A$, CHO, COA, $SO_2NH_2$, $SO_2A$ and/or $SO_2Hal$,
and in which a ring N-atom may be substituted by an O-atom to form an N-oxide group,
and in which in the case of a bicyclic aromatic cycle on of the two rings may be partly saturated,
A is unbranched or branched linear or cyclic alkyl having 1, 2, 3, 4, 5, 6, 7 or 8 C atoms, in which one or two $CH_2$ groups may be replaced by an O or S atom and/or by an —NH—, —CO—, —NHCOO—, —NHCONH—. —N(LA)-, —CONH—, —NHCO— or —CH=CH— group, and in which 1-3 H atoms may be replaced by Hal, and in which one or two $CH_3$ groups may be replaced by OH, SH, $NH_2$, NH(LA), $N(LA)_2$, NHCOOH, $NHCONH_2$ or CN,
LA is unbranched or branched, linear alkyl having 1, 2, 3 or 4 C atoms,
Hal is F, Cl, Br or I.

In general, all residues which occur more than once may be identical or different, i.e. are independent of one another. Above and below, the residues and parameters have the meanings indicated for the Formula (I), unless expressly indicated otherwise. Accordingly, the invention relates, in particular, to the compounds of the Formula (I) in which at least one of the said residues has one of the preferred meanings indicated below.

Hal denotes fluorine, chlorine, bromine or iodine, in particular fluorine or chlorine.

"A" denotes, for example, methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

"A" further denotes alkyl as defined above, in which one or two $CH_2$ groups may be replaced by O or S atoms and/or by NH, N(LA), CONN, NHCO or —CH=CH-groups and/or in addition 1-3 H atoms may be replaced by F and/or Cl, such as, for example, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy.

In other examples of "A", one or two $CH_3$ groups is replaced by OH, SH, $NH_2$, N(LA)H, $N(LA)_2$ or CN, such as, for example, N,N'-dimethylaminoalkyl, 2-aminoethyl, 3-amino-propyl, 4-aminobutyl, 5-aminopentyl, 3-aminomethylcyclobutyl or cyanoalkyl.

Cyclic A preferably denotes cyclopropyl, cyclobutyl, cyclopentyl, cyclohexyl or cycloheptyl.

"LA" denotes unbranched or branched, linear alkyl having 1, 2, 3 or 4 C atoms, i.e. methyl, ethyl, propyl, isopropyl, butyl, isobutyl, sec-butyl or tert-butyl.

"Ar" denotes, for example, unsubstituted phenyl, naphthyl or biphenyl, furthermore preferably, for example, phenyl, naphthyl or biphenyl, each of which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoro-methyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

"Ar" furthermore denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methyl-amino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methyl-sulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxy-phenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4, 6- or 3,4,5-tri-chlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl, (4-methoxyphenyl)methyl, (3-methoxyphenyl)methyl, (4-methoxyphenyl)ethyl, (3-methoxyphenyl)ethyl.

"Ar" furthermore preferably denotes 2-, 3- or 4-phenyl, 2-, 3- or 4-phenylmethyl, 2-, 3- or 4-phenylethyl, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 3- or 4-pyridylmethyl, 2-, 3- or 4-pyridylethyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-oxadiazol-2-yl, 1,3, 4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4- or 5-isoindolyl, 2-, 6-, or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, quinoxalin-2-, 3-, 4- or 5-yl, 4-, 5-, or 6-phthalazinyl, 2-, 3-, 5-, 6-, 7- or 8-2H-benzo-1,4-oxazinyl, further preferably 1,3-benzodioxol-2-, 4- or 5-yl, thiophen-2- or 3-yl, 1,4-benzodioxan-6-yl, 2,1,3-benzothiadiazol-4- or -5-yl or 2,1,3-benzoxadiazol-5-yl, furan-2- or 3-yl, 2,3-dihydro-benzofuran-2-, 3-, 4- or 5-yl, each of which is unsubstituted or may be mono-, di- or trisubstituted, for example, by carbonyl oxygen, F, Cl, Br, methyl, ethyl, propyl, phenyl, benzyl, —$CH_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methyl-sulfonyl.

The heterocyclic "Ar" residues may also be partially or fully hydrogenated and also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3-, 1-, 5- or 6-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxy-phenyl, 3,4-ethylenedioxyphenyl, 3,4-(difluoromethylenedioxy)phenyl, 2,3-dihydro-benzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, indan-1-, 2-, 4- or 5-yl, 1,2,3,4-tetrahydro-naphthalenyl, tetrahydrofuran-2- or 3-yl or 2,3-dihydro-2-oxofuranyl, each of which is unsubstituted or may be mono-, di- or trisubstituted, for example, by carbonyl oxygen, F, Cl, Br, methyl, ethyl, propyl, phenyl, benzyl, —$CH_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methyl-sulfonyl.

In those cases where $R^1$ is $L^1$-$R^4$-$L^2$-$R^5$ $L^1$-$R^4$-$L^2$-$R^5$-$L^3$-$R^6$, residue $R^4$ obviously has a bridging function, and is substituted by linkers $L^1$ and $L^2$, independently of any further substitutions it may have.

The same applies to residue $R^5$ in those cases where $R^1$ is $L^1$-$R^4$-$L^2$-$R^5$-$L^3$-$R^6$. Here $R^5$ is substituted by linkers $L^2$ and $L^3$, independently of any further substitutions it may have. Therefore, in these meanings of $R^4$ and $R^5$, Ar (=aryl) becomes arylene, and monocyclic alkyl becomes monocyclic alkylene. For example, phenyl would become phenylene, pyridyl would become pyridylene, and cyclohexyl cyclolhexylene.

The term "substituted" preferably relates to the substitution by the above-mentioned substituents, where a plurality of different degrees of substitution are possible, unless indicated otherwise.

All physiologically acceptable salts, derivatives, solvates and stereoisomers of these compounds, including mixtures thereof in all ratios, are also in accordance with the invention.

The compounds of the Formula (I) may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantio-mer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

A preferred group of compounds of Formula (I) conform to Formulae (II) or (III)

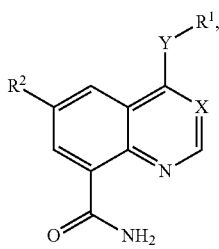

(II)

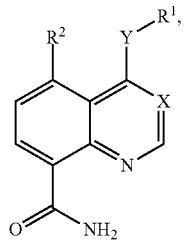

(III)

in which $R^2$ has the meaning indicated for $R^{2'}$, $R^{2''}$ of Formula (I), and $R^1$, X and Y have the meaning indicated for Formula (I).

Particularly preferred are the compounds according to Formula (II).

Further preferred are compounds of Subformulae 1 to 39 of Formulae (I), (II) and (III), and pharmaceutically acceptable salts, solvates or prodrugs thereof, wherein
in Subformula 1
X is C—$R^3$,
Y is NH,
$R^3$ is H,
in Subformula 2
X is C—$R^3$,
Y is O,
$R^3$ is H,
in Subformula 3
X is C—$R^3$,
Y is NH,
$R^3$ is H,
$R^1$ is $L^1$-$R^4$,
$R^{2'}$, $R^{2''}$ are H,
$L^1$ is methylene,
in Subformula 4
X is N,
Y is NH,
in Subformula 5
X is N,
Y is O,
in Subformula 6
X is N,
Y is NH,
$R^1$ is $L^1$-$R^4$-$L^2$-$R^5$ or $L^1$-$R^4$,
$L^1$ is a bond,
in Subformula 7
X is N,
Y is NH,
$L^1$ is methylene,
in Subformula 8
X is N,
Y is NH,
$L^1$ is methylene,
$R^2$ is H, methoxy, ethoxy or amino,
in Subformula 9
X is N,
Y is NH,
$L^1$ is methylene which is unsubstituted or substituted with methyl, aminomethyl, methoxymethyl, azidomethyl or triazolylmethyl
$R^2$ is H, methoxy, ethoxy or amino,
in Subformula 10
X is N,
Y is NH,
$L^1$ is methylene which is substituted with aminomethyl,
in Subformula 11
X is N,
Y is NH,
$L^1$ is methylene which is substituted with aminomethyl,
$R^2$ is H, methoxy, ethoxy or amino,
in Subformula 12
X is N,
Y is NH,
$R^1$ is $L^1$-$R^4$,
$L^1$ is methylene which is substituted with aminomethyl,
$R^2$ is H, methoxy, ethoxy or amino,
in Subformula 13
X is N,
Y is NH,
$R^1$ is $L^1$-$R^4$-$L^2$-$R^5$ or $L^1$-$R^4$,
$L^1$ is methylene which is unsubstituted or substituted with aminomethyl,
$R^2$ is H, methoxy, ethoxy or amino,
in Subformula 14
X is N,
Y is NH,
$R^1$ is $L^1$-$R^4$-$L^2$-$R^5$ or $L^1$-$R^4$,
$L^1$ is methylene,
$R^2$ is H, methoxy, ethoxy or amino,
in Subformula 15
X is N,
Y is NH,
$R^1$ is $L^1$-$R^4$-$L^2$-$R^5$ or $L^1$-$R^4$,
$L^1$ is methylene,
$R^2$ is H, methoxy or amino,
in Subformula 16
X is N, Y is NH,
R$^1$ is L$^1$-R$^4$,
L$^1$ is methylene,
R$^2$ is H, methoxy or amino,
in Subformula 17
X is N,
Y is NH,
R$^1$ is L$^1$-R$^4$,
L$^1$ is methylene,
R$^4$ is phenyl which is unsubstituted or monosubstituted with Hal or CF$_3$, or disubstituted with Hal,
R$^2$ is H, methoxy or amino,
in Subformula 18
X is N,
Y is NH,
R$^1$ is L$^1$-R$^4$,
L$^1$ is methylene,
R$^4$ is phenyl which is unsubstituted or monosubstituted with Hal or CF$_3$, or disubstituted with Hal,
R$^2$ is H,
in Subformula 19
X is N,
Y is NH,
R$^1$ is L$^1$-R$^4$-L$^2$-R$^5$,
L$^1$ is methylene,
R$^4$ is phenyl,
L$^2$ is NHCO or NHCONH,
R$^2$ is H or methoxy,
in Subformula 20
X is N,
Y is NH,
R$^1$ is L$^1$-R$^4$-L$^2$-R$^5$,
L$^1$ is methylene,
R$^4$ is phenyl,
L$^2$ is NHCO or NHCONH,
R$^5$ is phenyl which is unsubstituted or mono- or disubstituted with Hal,
R$^2$ is H or methoxy,
in Subformula 21
X is N,
Y is NH,
R$^1$ is L$^1$-R$^4$-L$^2$-R$^5$,
L$^1$ is methylene,
R$^4$ is phenyl,
L$^2$ is NHCO,
R$^5$ is phenyl which is unsubstituted or mono- or disubstituted with Hal,
R$^2$ is H or methoxy,
in Subformula 22
X is N,
Y is NH,
R$^1$ is L$^1$-R$^4$-L$^2$-R$^5$,
L$^1$ is methylene,
R$^4$ is phenyl,
L$^2$ is NHCO or NHCONH,
R$^5$ is phenyl which is unsubstituted, or mono- or disubstituted with Hal,
R$^2$ is H,
in Subformula 23
X is N,
R$^1$ is L$^1$-R$^4$-L$^2$-R$^5$,
R$^4$ is phenyl,
R$^5$ benzo-1,3-dioxolyl,
in Subformula 24
X is N,
Y is NH,
L$^1$ is methylene which is unsubstituted or substituted with aminomethyl, (methyl-amino)methyl, (dimethyl-amino)methyl, methyl, ethyl, 2-hydroxyethyl, methoxymethyl, 2-(dimethyl-amino)ethyl, (ethyl-amino)methyl, 2-(methoxy)ethyl, 2-(allyl-methyl-amino)ethyl, ((tert. butyl-oxycarbonyl)-methyl-amino)methyl, 2-(pyrrolidin-1-yl)ethyl, 2-(azetidin-1-yl)ethyl, 2-(piperidin-1-yl)ethyl or 2-(piperazin-1-yl)ethyl,
in Subformula 25
X is N,
Y is NH,
L$^1$ is methylene which is unsubstituted or substituted with (methyl-amino)methyl, (dimethyl-amino)methyl, methyl or 2-(dimethyl-amino)ethyl,
in Subformula 26
X is N,
Y is NH,
R$^1$ is L$^1$-R$^4$-L$^2$-R$^5$,
R$^4$ is phenyl,
L$^2$ is —NHCO—, —NH—, —NHCH$_2$—, NHCOOCH$_2$— or —NHCONH—,
in Subformula 27
X is N,
Y is NH,
R$^1$ is L$^1$-R$^4$-L$^2$-R$^5$,
R$^4$ is phenyl,
L$^2$ is —NHCO—, —NH—, —NHCH$_2$—, NHCOOCH$_2$— or —NHCONH—,
R$^5$ is Ar which is unsubstituted or substituted as defined for Ar in claim 1,
in Subformula 28
X is N,
Y is NH,
R$^1$ is L$^1$-R$^4$-L$^2$-R$^5$,
R$^4$ is phenyl,
L$^2$ is —NHCO—, —NH—, —NHCH$_2$—, NHCOOCH$_2$— or —NHCONH—,
R$^5$ is phenyl, pyridyl, benzo-1,3-dioxolyl, pyrazolyl or thiazolyl, all of which are unsubstituted or substituted as defined for Ar in claim 1,
in Subformula 29
X is N,
Y is NH,
L$^1$ is methylene which is unsubstituted or substituted with aminomethyl, (methyl-amino)methyl, (dimethyl-amino)methyl, methyl, ethyl, 2-hydroxyethyl, methoxymethyl, 2-(dimethyl-amino)ethyl, (ethyl-amino)methyl, 2-(methoxy)ethyl, 2-(allyl-methyl-amino)ethyl, ((tert. butyl-oxycarbonyl)-methyl-amino)methyl, 2-(pyrrolidin-1-yl)ethyl, 2-(azetidin-1-yl)ethyl, 2-(piperidin-1-yl)ethyl or 2-(piperazin-1-yl)ethyl,
R$^2$ is H or methoxy,
in Subformula 30
X is N,
Y is NH,
L$^1$ is methylene which is unsubstituted or substituted with (methyl-amino)methyl, (dimethyl-amino)methyl, methyl or 2-(dimethyl-amino)ethyl,
R$^2$ is H or methoxy,
in Subformula 31
X is N,
Y is NH,
R$^1$ is L$^1$-R$^4$-L$^2$-R$^5$,
R$^4$ is phenyl,
L$^2$ is —NHCO—, —NH—, —NHCH$_2$—, NHCOOCH$_2$— or —NHCONH—,
R$^2$ is H or methoxy, in Subformula 32
X is N,
Y is NH,
$R^1$ is $L^1$-$R^4$-$L^2$-$R^5$,
$R^4$ is phenyl,
$L^2$ is —NHCO—, —NH—, —NHCH$_2$—, NHCOOCH$_2$— or —NHCONH—,
$R^5$ is Ar which is unsubstituted or substituted as defined for Ar in claim 1,
$R^2$ is H or methoxy,
in Subformula 33
X is N,
Y is NH,
$R^1$ is $L^1$-$R^4$-$L^2$-$R^5$,
$R^4$ is phenyl,
$L^2$ is —NHCO—, —NH—, —NHCH$_2$—, NHCOOCH$_2$— or —NHCONH—,
$R^5$ is phenyl, pyridyl, benzo-1,3-dioxolyl, pyrazolyl or thiazolyl, all of which are unsubstituted or substituted as defined for Ar in claim 1,
$R^2$ is H or methoxy,
in Subformula 34
X is N,
Y is NH,
$R^1$ is $L^1$-$R^4$-$L^2$-$R^5$,
$L^1$ is methylene which is unsubstituted or substituted with (methyl-amino)methyl, (dimethyl-amino)methyl, methyl or 2-(dimethyl-amino)ethyl,
$R^4$ is phenyl,
$L^2$ is —NHCO—, —NH—, —NHCH$_2$—, NHCOOCH$_2$— or —NHCONH—,
$R^5$ is Ar which is unsubstituted or substituted as defined for Ar in claim 1,
$R^2$ is H or methoxy,
in Subformula 35
X is N,
Y is NH,
$R^1$ is $L^1$-$R^4$,
$R^2$ is $L^1$-Ar,
in Subformula 36
X is N,
Y is NH,
$R^1$ is $L^1$-$R^4$,
$L^1$ is a bond,
in Subformula 37
X is N,
Y is NH,
$R^1$ is $L^1$-$R^4$,
$R^4$ is piperidinyl,
in Subformula 38
X is N,
Y is NH,
$R^1$ is $L^1$-$R^4$,
$R^4$ is piperidinyl,
$R^2$ is $L^1$-Ar,
$L^1$ is a bond,
in Subformula 39
X is CH,
Y is NH,
$R^1$ is $L^1$-$R^4$,
$L^1$ is methylene which is substituted with aminomethyl, (methyl-amino)methyl, (dimethyl-amino)methyl or 2-amino-prop-2-yl,
$R^4$ is phenyl which is unsubstituted or substituted as defined for Ar in claim 1,
$R^2$ is H, methoxy, methyl, ethyl, hydroxymethyl, methoxymethyl or cyano,
and the remaining residues have the meaning as indicated for Formula (I) above.

In more preferred compounds of Subformulae 19, 20, 21, 22, 23, 26, 27, 28, 31, 32, 22 or 34 of Formula (I), (II) or (III), $R^4$ is meta-phenylene.

Especially preferred compounds according to Formula (I), (II) and/or Formula (III) include those listed in Tables 1, 2 and 3 below, or their pharmaceutically acceptable salts, solvates or prodrugs.

TABLE 1

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 1 | 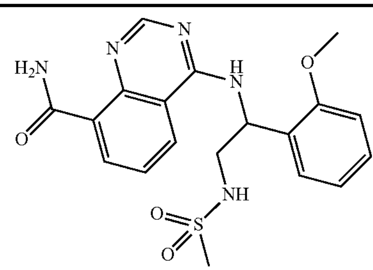 | 4-[2-Methanesulfonylamino-1-(2-methoxyphenyl)ethylamino]-quinazoline-8-carboxylic acid amide | 416 | >10 | 0.91 | | |
| 2 | 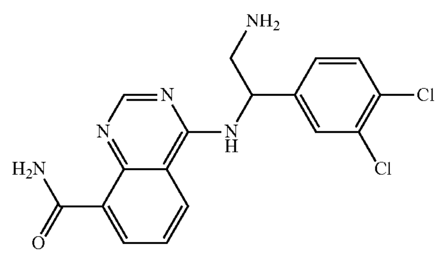 [SMILES: NCC(Nc1ncnc2c(C(N)=O)cccc12)c1ccc(Cl)c(Cl)c1] | 4-[2-Amino-1-(3,4-dichloro-phenyl)-ethylamino]quinazoline-8-carboxylic acid amide | 376 | 0.0005 | 0.43 | | |
| 3 | 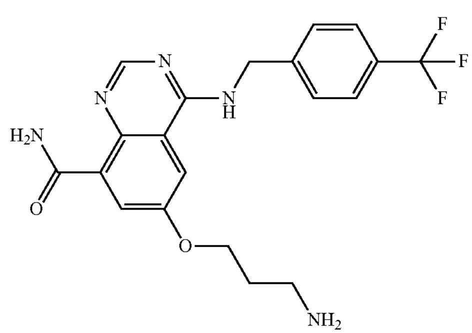 [SMILES: NCCCOc1cc(C(N)=O)c2ncnc(NCc3ccc(C(F)(F)F)cc3)c2c1] | 6-(3-Amino-propoxy)-4-(4-trifluoromethylbenzylamino)-quinazoline-8-carboxylic acid amide | 420 | 0.197 | 7.6 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 4 | 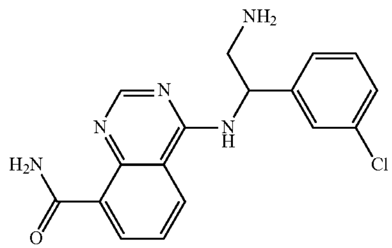 [SMILES: NCC(Nc1ncnc2c(C(N)=O)cccc12)c1cccc(Cl)c1] | 4-[2-Amino-1-(3-chloro-phenyl)-ethylamino] quinazoline-8-carboxylic acid amide | 342 | | 4.9 | | |
| 5 | 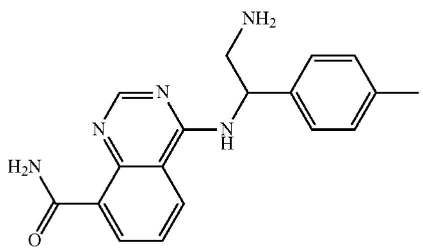 [SMILES: Cc1ccc(C(CN)Nc2ncnc3c(C(N)=O)cccc23)cc1] | 4-(2-Amino-1-p-tolyl-ethylamino)- quinazoline-8-carboxylic acid amide | 322 | 0.0006 | 0.66 | | |
| 6 | 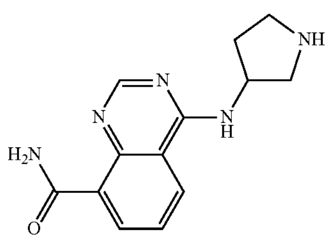 [SMILES: NC(=O)c1cccc2c(NC3CCNC3)ncnc12] | 4-(Pyrrolidin-3-ylamino) quinazoline- 8-carboxylic acid amide | 258 | 0.376 | | | |
| 7 | 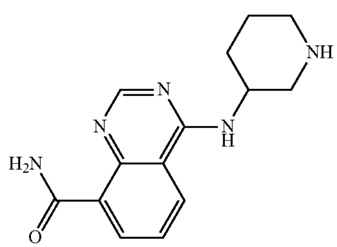 [SMILES: NC(=O)c1cccc2c(NC3CCCNC3)ncnc12] | 4-(Piperidin-3-ylamino)- quinazoline-8-carboxylic acid amide | 272 | 0.0615 | 6.5 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 8 | 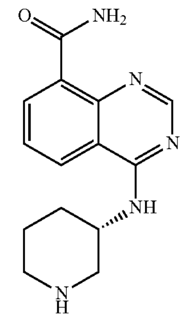 [SMILES: NC(=O)c1cccc2c(N[C@H]3CCCNC3)ncnc12] | 4-((S)-Piperidin-3-ylamino)-quinazoline-8-carboxylic acid amide | 272 | 0.0491 | 4.300 | | |
| 9 | 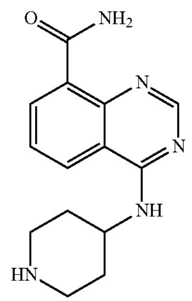 [SMILES: NC(=O)c1cccc2c(NC3CCNCC3)ncnc12] | 4-(Piperidin-4-ylamino)-quinazoline-8-carboxylic acid amide | 272 | 3.92 | 10 | | |
| 10 | 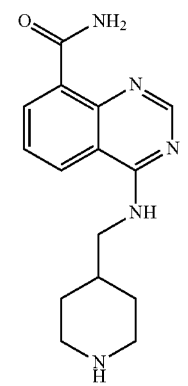 [SMILES: NC(=O)c1cccc2c(NCC3CCNCC3)ncnc12] | 4-[(Piperidin-4-ylmethyl)-amino]-quinazoline-8-carboxylic acid amide | 286 | 2.58 | 1 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 11 | 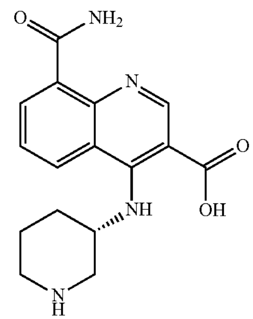 [SMILES: NC(=O)c1cccc2c(N[C@H]3CCCNC3)c(C(=O)O)cnc12] | 8-Carbamoyl-4-((S)-piperidin-3-ylamino)-quinoline-3-carboxylic acid | 315 | 0.218 | 1.3 | | |
| 12 | 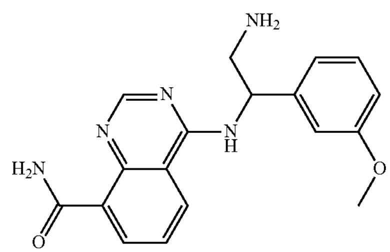 [SMILES: COc1cccc(C(CN)Nc2ncnc3c(C(N)=O)cccc23)c1] | 4-[2-Amino-1-(3-methoxy-phenyl)-ethylamino]-quinazoline-8-carboxylic acid amide | 338 | 0.0034 | 0.77 | | |
| 13 | 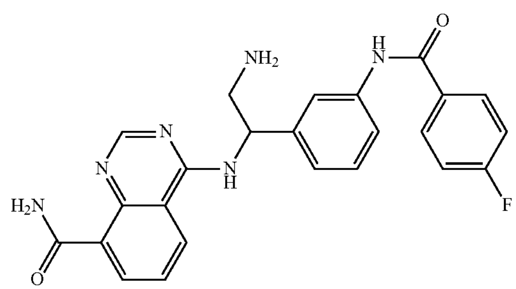 [SMILES: NCC(Nc1ncnc2c(C(N)=O)cccc12)c1cccc(NC(=O)c2ccc(F)cc2)c1] | 4-{2-Amino-1-[3-(4-fluoro-benzoylamino)-phenyl]-ethylamino}-quinazoline-8-carboxylic acid amide | 445 | 0.0012 | 0.0012 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 14 | 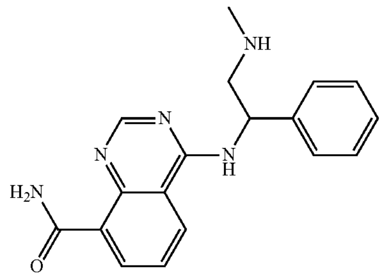 [SMILES: CNCC(Nc1ncnc2c(C(N)=O)cccc12)c1ccccc1] | 4-(2-Methylamino-1-phenyl-ethylamino)-quinazoline-8-carboxylic acid amide | 322 | 0.0038 | 0.45 | | |
| 15 | 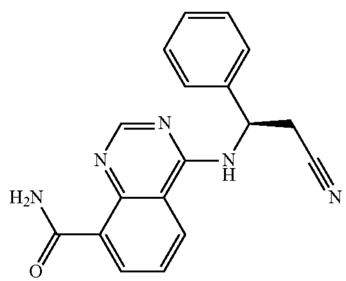 [SMILES: N#CC[C@@H](Nc1ncnc2c(C(N)=O)cccc12)c1ccccc1] | 4-((R)-2-Cyano-1-phenyl-ethylamino)-quinazoline-8-carboxylic acid amide | 318 | 0.0031 | 0.28 | | |
| 16 | 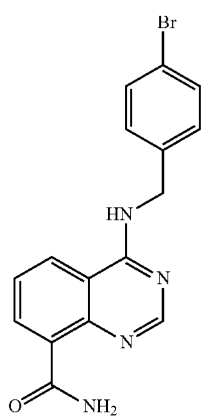 [SMILES: NC(=O)c1cccc2c(NCc3ccc(Br)cc3)ncnc12] | 4-(4-Bromobenzylamino)-quinazoline-8-carboxylic acid amide | 357 | 0.0066 | 0.23 | | |

TABLE 1-continued

| No. | Structure | Chemical Name | MS (M + 1) | p70S6K binding IC50 [µM] | Aurora A binding IC50 [µM] | Aurora B binding IC50 [µM] | PDK1 binding IC50 [µM] |
|---|---|---|---|---|---|---|---|
| 17 | 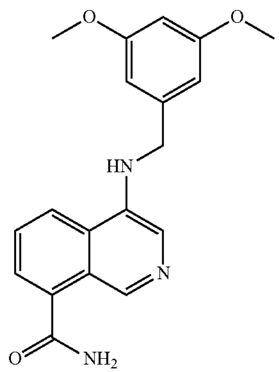 [SMILES: COc1cc(CNc2cncc3c(C(N)=O)cccc23)cc(OC)c1] | 4-(3,5-Dimethoxy-benzylamino)-quinazoline-8-carboxylic acid amide | 339 | 0.111 | 0.0072 | 0.0082 | |
| 18 | 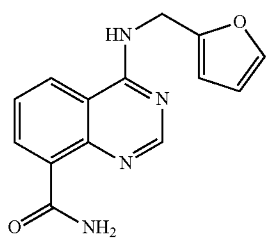 [SMILES: NC(=O)c1cccc2c(NCc3ccco3)ncnc12] | 4-[(Furan-2-ylmethyl)-amino]-quinazoline-8-carboxylic acid amide | 269 | 0.262 | 0.0066 | 0.005 | |
| 19 | 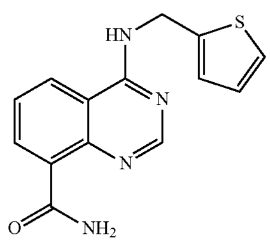 [SMILES: NC(=O)c1cccc2c(NCc3cccs3)ncnc12] | 4-[(Thiophen-2-ylmethyl)-amino]-quinazoline-8-carboxylic acid amide | 285 | 0.145 | 2.6 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 20 | 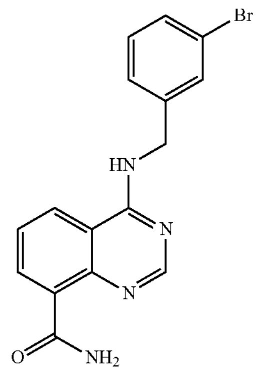 [SMILES: NC(=O)c1cccc2c(NCc3cccc(Br)c3)ncnc12] | 4-(3-Bromobenzylamino)-quinazoline-8-carboxylic acid amide | 357 | 0.0112 | 0.19 | | |
| 21 | 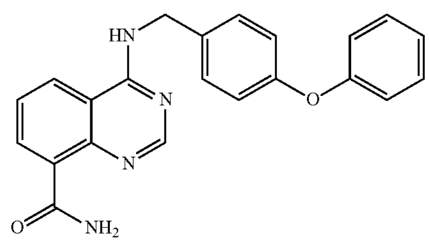 [SMILES: NC(=O)c1cccc2c(NCc3ccc(Oc4ccccc4)cc3)ncnc12] | 4-(4-Phenoxybenzylamino)-quinazoline-8-carboxylic acid amide | 371 | 0.230 | 4.4 | | |
| 22 | 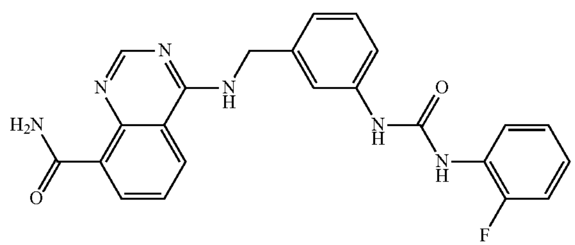 [SMILES: NC(=O)c1cccc2c(NCc3cccc(NC(=O)Nc4ccccc4F)c3)ncnc12] | 4-{3-[3-(2-Fluorophenyl)-ureido]-benzylamino}-quinazoline-8-carboxylic acid amide | 431 | 0.0783 | 0.31 | 0.2 | |

TABLE 1-continued

| No. | Structure | Chemical Name | MS (M + 1) | p70S6K binding IC50 [μM] | Aurora A binding IC50 [μM] | Aurora B binding IC50 [μM] | PDK1 binding IC50 [μM] |
|---|---|---|---|---|---|---|---|
| 23 | 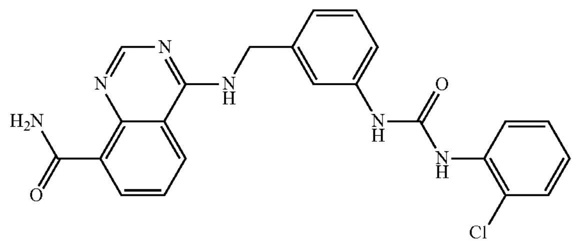 [SMILES: NC(=O)c1cccc2c(NCc3cccc(NC(=O)Nc4ccccc4Cl)c3)ncnc12] | 4-{3-[3-(2-Chlorophenyl)-ureido]-benzylamino}-quinazoline-8-carboxylic acid amide | 447 | 0.0910 | 0.13 | 0.091 | 4.8 |
| 24 | 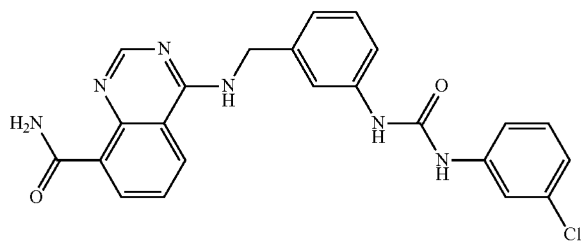 [SMILES: NC(=O)c1cccc2c(NCc3cccc(NC(=O)Nc4cccc(Cl)c4)c3)ncnc12] | 4-{3-[3-(3-Chlorophenyl)-ureido]-benzylamino}-quinazoline-8-carboxylic acid amide | 447 | 0.135 | 1 | | |
| 25 | 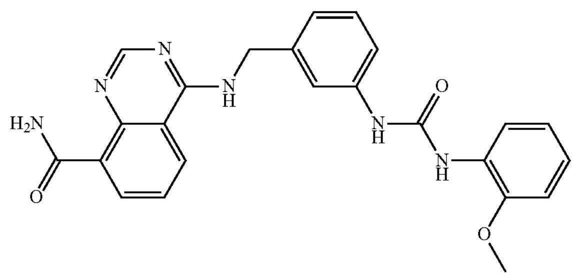 [SMILES: COc1ccccc1NC(=O)Nc1cccc(CNc2ncnc3c(C(N)=O)cccc23)c1] | 4-{3-[3-(2-Methoxyphenyl)-ureido]-benzylamino}-quinazoline-8-carboxylic acid amide | 443 | 0.156 | 0.0026 | 0.0025 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 26 | 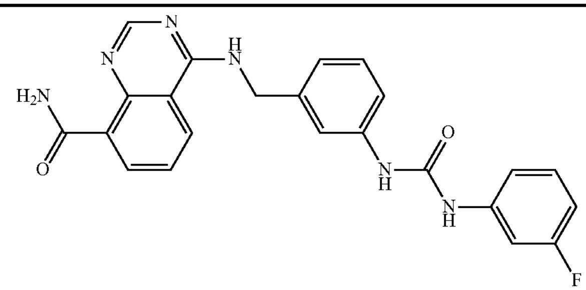 | 4-{3-[3-(3-Fluorophenyl)-ureido]-benzylamino}-quinazoline-8-carboxylic acid amide | 431 | 0.0559 | 0.0011 | 0.0056 | |
| 27 | 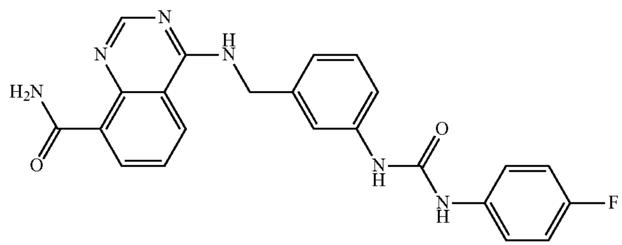 [SMILES: NC(=O)c1cccc2c(NCc3cccc(NC(=O)Nc4ccc(F)cc4)c3)ncnc12] | 4-{3-[3-(4-Fluorophenyl)-ureido]-benzylamino}-quinazoline-8-carboxylic acid amide | 431 | 0.199 | 4.9 | | |
| 28 | 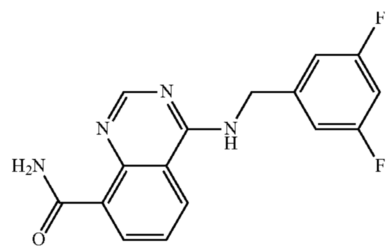 [SMILES: NC(=O)c1cccc2c(NCc3cc(F)cc(F)c3)ncnc12] | 4-(3,5-Difluorobenzylamino)-quinazoline-8-carboxylic acid amide | 315 | 0.0922 | 0.00086 | 0.0039 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 29 | 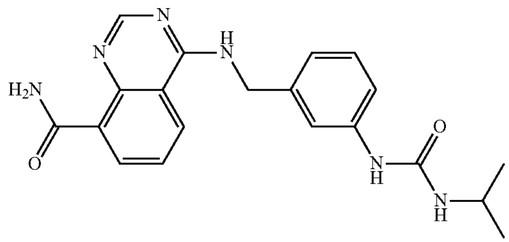 [SMILES: CC(C)NC(=O)Nc1cccc(CNc2ncnc3c(C(N)=O)cccc23)c1] | 4-[3-(3-Isopropyl-ureido)-benzylamino]-quinazoline-8-carboxylic acid amide | 379 | 0.142 | 0.16 | | |
| 30 | 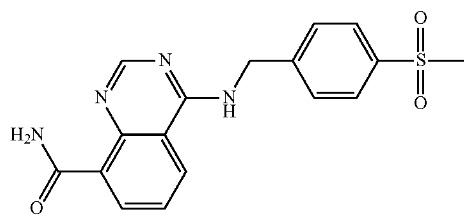 [SMILES: CS(=O)(=O)c1ccc(CNc2ncnc3c(C(N)=O)cccc23)cc1] | 4-(4-Methanesulfonyl-benzylamino)-quinazoline-8-carboxylic acid amide | 357 | 0.0137 | 0.58 | | |
| 31 | 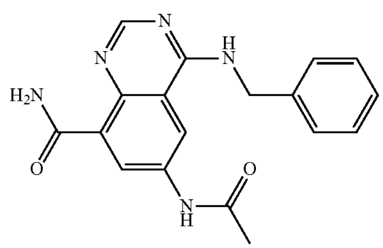 [SMILES: CC(=O)Nc1cc(C(N)=O)c2ncnc(NCc3ccccc3)c2c1] | 6-Acetylamino-4-benzylamino-quinazoline-8-carboxylic acid amide | 336 | 29.2 | 1.4 | | |
| 32 | 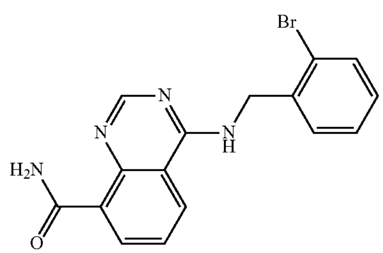 [SMILES: NC(=O)c1cccc2c(NCc3ccccc3Br)ncnc12] | 4-(2-Bromobenzylamino)-quinazoline-8-carboxylic acid amide | 357 | 0.245 | 1.5 | | |

TABLE 1-continued

| No. | Structure | Chemical Name | MS (M + 1) | p70S6K binding IC50 [μM] | Aurora A binding IC50 [μM] | Aurora B binding IC50 [μM] | PDK1 binding IC50 [μM] |
|---|---|---|---|---|---|---|---|
| 33 | 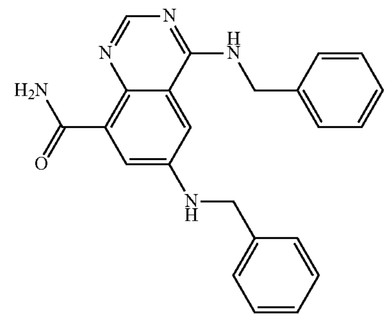 [SMILES: NC(=O)c1cc(NCc2ccccc2)cc2c(NCc3ccccc3)ncnc12] | 4,6-Bis-benzylamino-quinazoline-8-carboxylic acid amide | 384 | 3.00 | 0.34 | | |
| 34 | 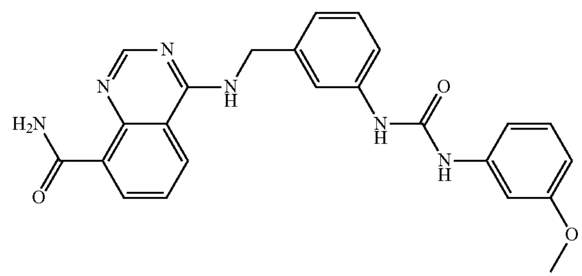 [SMILES: COc1cccc(NC(=O)Nc2cccc(CNc3ncnc4c(C(N)=O)cccc34)c2)c1] | 4-{3-[3-(3-Methoxyphenyl)-ureido]-benzylamino}-quinazoline-8-carboxylic acid amide | 443 | 0.0976 | 0.72 | | 6.3 |
| 35 | 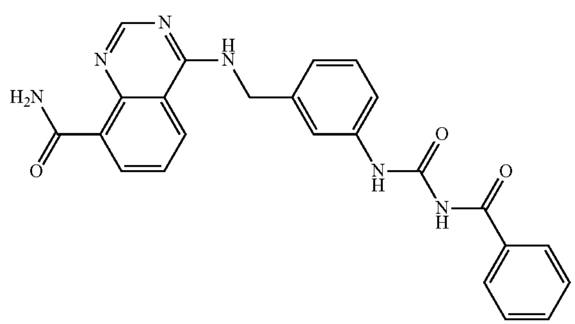 [SMILES: NC(=O)c1cccc2c(NCc3cccc(NC(=O)NC(=O)c4ccccc4)c3)ncnc12] | 4-[3-(3-Benzoyl-ureido)-benzylamino]-quinazoline-8-carboxylic acid amide | 441 | 0.110 | 0.83 | 0.42 | |

TABLE 1-continued

| No. | Structure | Chemical Name | MS (M + 1) | p70S6K binding IC50 [μM] | Aurora A binding IC50 [μM] | Aurora B binding IC50 [μM] | PDK1 binding IC50 [μM] |
|---|---|---|---|---|---|---|---|
| 36 | 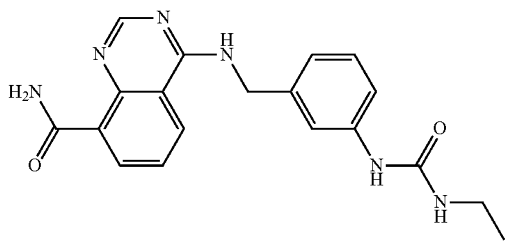 [SMILES: CCNC(=O)Nc1cccc(CNc2ncnc3c(C(N)=O)cccc23)c1] | 4-[3-(3-Ethyl-ureido)-benzylamino]-quinazoline-8-carboxylic acid amide | 365 | 0.0676 | 1.8 | | |
| 37 | 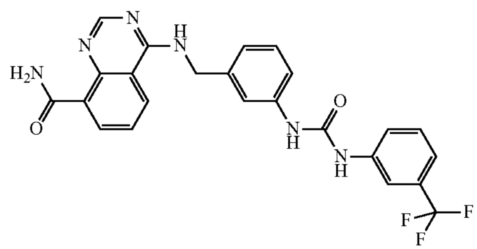 [SMILES: NC(=O)c1cccc2c(NCc3cccc(NC(=O)Nc4cccc(C(F)(F)F)c4)c3)ncnc12] | 4-{3-[3-(3-Trifluoromethyl-phenyl)-ureido]-benzylamino}-quinazoline-8-carboxylic acid amide | 481 | 0.190 | 7.8 | | |
| 38 | 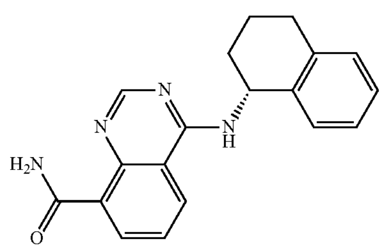 [SMILES: NC(=O)c1cccc2c(N[C@@H]3CCCc4ccccc43)ncnc12] | 4-[(R)-(1,2,3,4-Tetrahydro-naphthalen-1-yl)amino]-quinazoline-8-carboxylic acid amide | 319 | 1.03 | 7.9 | | |
| 39 | 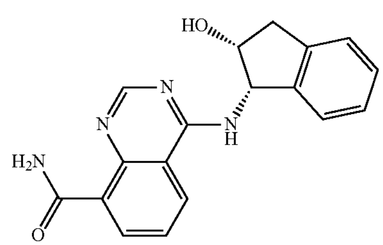 [SMILES: NC(=O)c1cccc2c(N[C@H]3c4ccccc4C[C@H]3O)ncnc12] | 4-((1S,2R)-2-Hydroxy-indan-1-ylamino)-quinazoline-8-carboxylic acid amide | 321 | 3.09 | 4.6 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 40 | 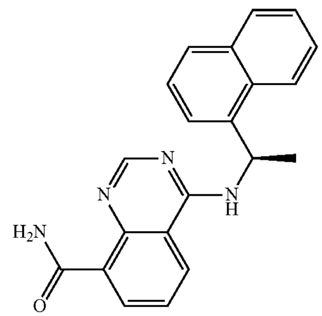 [SMILES: C[C@@H](Nc1ncnc2c(C(N)=O)cccc12)c1cccc2ccccc12] | 4-((R)-1-Naphthalen-1-yl-ethylamino)-quinazoline-8-carboxylic acid amide | 343 | 0.0421 | 0.00066 | 0.011 | |
| 41 | 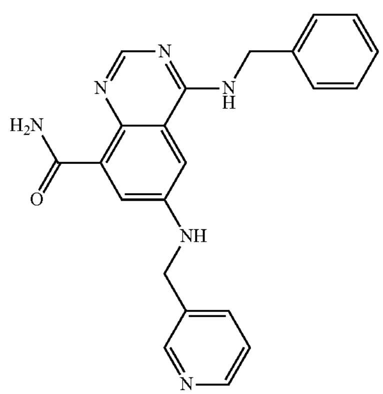 [SMILES: NC(=O)c1cc(NCc2cccnc2)cc2c(NCc3ccccc3)ncnc12] | 4-Benzylamino-6-[(pyridin-3-ylmethyl)-amino]-quinazoline 8-carboxylic acid amide | 385 | 2.69 | 6.9 | | |
| 42 | 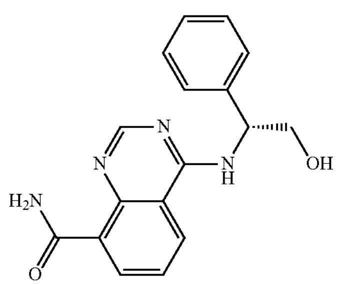 [SMILES: NC(=O)c1cccc2c(N[C@@H](CO)c3ccccc3)ncnc12] | 4-((R)-2-Hydroxy-1-phenyl-ethylamino)-quinazoline-8-carboxylic acid amide | 309 | 20.3 | 1.9 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 43 | 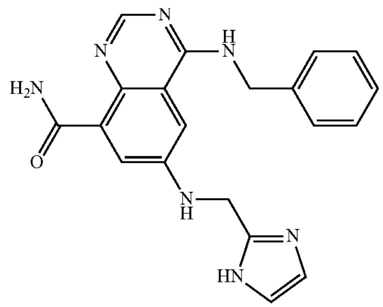 [SMILES: NC(=O)c1cc(NCc2ncc[nH]2)cc2c(NCc3ccccc3)ncnc12] | 4-Benzylamino-6-[(1H-imidazol-2-ylmethyl)-amino]-quinazoline-8-carboxylic acid amide | 374 | 8.40 | 0.7 | | |
| 44 | 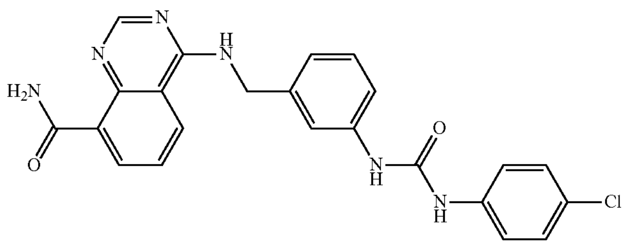 [SMILES: NC(=O)c1cccc2c(NCc3cccc(NC(=O)Nc4ccc(Cl)cc4)c3)ncnc12] | 4-{3-[3-(4-Chlorophenyl)-ureido]-benzyl-amino}-quinazoline-8-carboxylic acid amide | 447 | 0.149 | 0.72 | | |
| 45 | 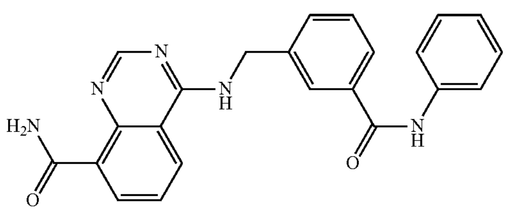 [SMILES: NC(=O)c1cccc2c(NCc3cccc(C(=O)Nc4ccccc4)c3)ncnc12] | 4-(3-Phenylcarbamoyl-benzylamino)-quinazoline-8-carboxylic acid amide | 398 | 0.131 | 9.1 | | |
| 46 | 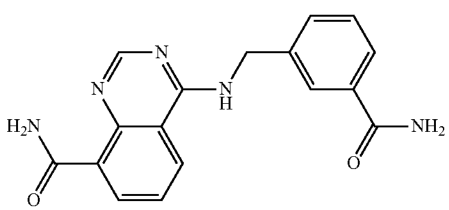 [SMILES: NC(=O)c1cccc(CNc2ncnc3c(C(N)=O)cccc23)c1] | 4-(3-Carbamoyl-benzylamino)-quinazoline-8-carboxylic acid amide | 0 | 0.0482 | 0.013 | 0.0041 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 47 | 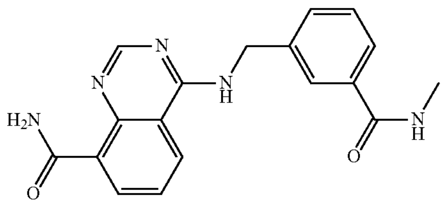 [SMILES: CNC(=O)c1cccc(CNc2ncnc3c(C(N)=O)cccc23)c1] | 4-(3-Methylcarbamoyl-benzylamino)-quinazoline-8-carboxylic acid amide | 336 | 0.176 | 1.2 | 1.8 | |
| 48 | 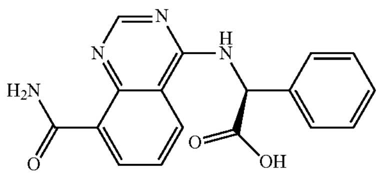 | (S)-(8-Carbamoyl-quinazolin-4-ylamino)-phenyl-acetic acid | 323 | 9.18 | 5.2 | | |
| 49 | 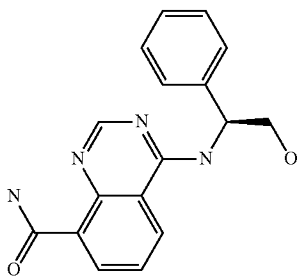 [SMILES: NC(=O)c1cccc2c(N[C@H](CO)c3ccccc3)ncnc12] | 4-((S)-2-Hydroxy-1-phenyl-ethylamino)-quinazoline-8-carboxylic acid amide | 309 | 0.541 | 0.54 | | |
| 50 | 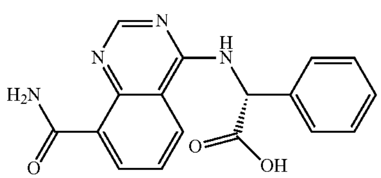 [SMILES: NC(=O)c1cccc2c(N[C@@H](C(=O)O)c3ccccc3)ncnc12] | (R)-(8-Carbamoyl-quinazolin-4-ylamino)-phenyl-acetic acid | 323 | 7.91 | | | |

TABLE 1-continued

| No. | Structure | Chemical Name | MS (M + 1) | p70S6 K binding IC50 [µM] | Aurora A binding IC50 [µM] | Aurora B binding IC50 [µM] | PDK1 binding IC50 [µM] |
|---|---|---|---|---|---|---|---|
| 51 | 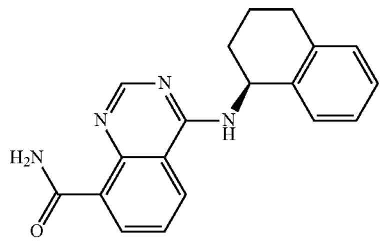 [SMILES: NC(=O)c1cccc2c(N[C@H]3CCCc4ccccc43)ncnc12] | 4-[(S)-(1,2,3,4-Tetrahydronaphthalen-1-yl)amino]-quinazoline-8-carboxylic acid amide | 319 | 1.57 | 1.6 | 0.5 | |
| 52 | 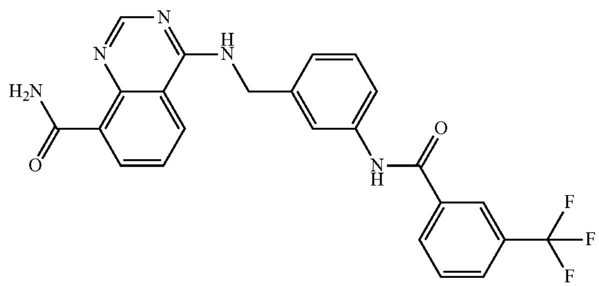 [SMILES: NC(=O)c1cccc2c(NCc3cccc(NC(=O)c4cccc(C(F)(F)F)c4)c3)ncnc12] | 4-[3-(3-Trifluoromethyl-benzoylamino)-benzylamino]-quinazoline-8-carboxylic acid amide | 466 | 0.0307 | 1.2 | | |
| 53 | 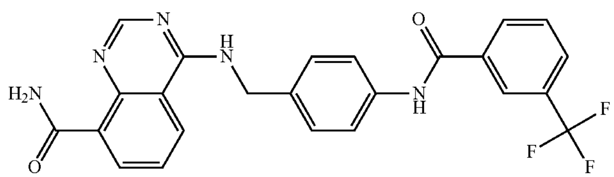 | 4-[4-(3-Trifluoromethyl-benzoylamino)-benzylamino]-quinazoline-8-carboxylic acid amide | 466 | 1.31 | 0.21 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 54 | 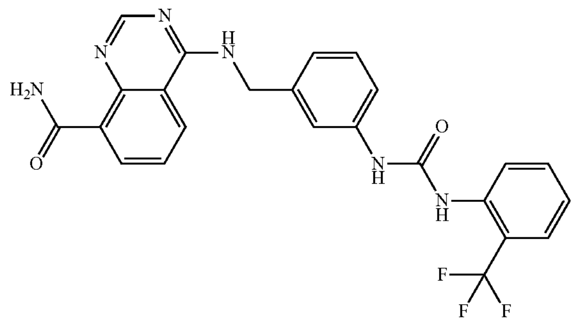 [SMILES: NC(=O)c1cccc2c(NCc3cccc(NC(=O)Nc4ccccc4C(F)(F)F)c3)ncnc12] | 4-{3-[3-(2-Trifluoromethyl-phenyl)-ureido]-benzylamino}-quinazoline-8-carboxylic acid amide | 481 | 0.0469 | 0.0047 | 0.022 | |
| 55 | 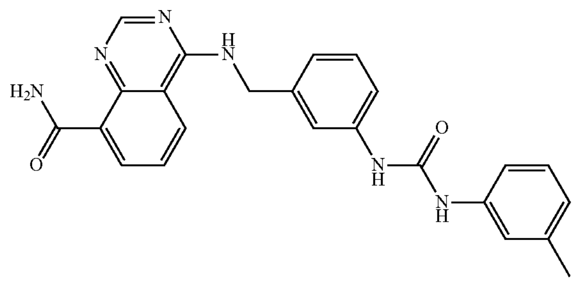 [SMILES: Cc1cccc(NC(=O)Nc2cccc(CNc3ncnc4c(C(N)=O)cccc34)c2)c1] | 4-[3-(3-m-Tolyl-ureido)-benzylamino]-quinazoline-8-carboxylic acid amide | 427 | 0.0830 | 0.0021 | 0.0043 | |
| 56 | 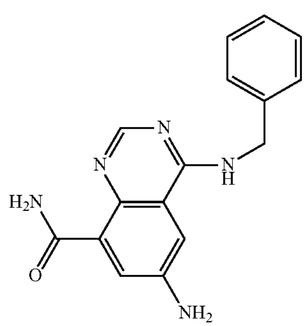 [SMILES: NC(=O)c1cc(N)cc2c(NCc3ccccc3)ncnc12] | 6-Amino-4-benzylamino-quinazoline-8-carboxylic acid amide | 294 | 3.20 | 0.14 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 57 | 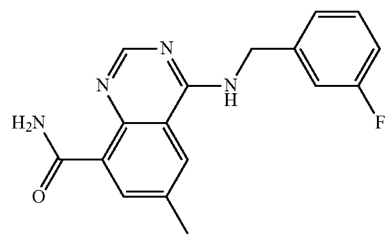 [SMILES: Cc1cc(C(N)=O)c2ncnc(NCc3cccc(F)c3)c2c1] | 4-(3-Fluoro-benzylamino)-6-methyl-quinazoline-8-carboxylic acid amide | 311 | 6.44 | 1.3 | | |
| 58 | 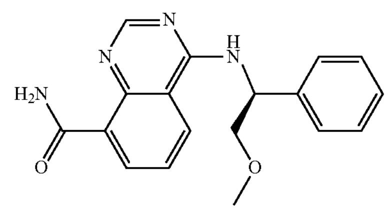 [SMILES: COC[C@@H](Nc1ncnc2c(C(N)=O)cccc12)c1ccccc1] | 4-((S)-2-Methoxy-1-phenyl-ethylamino)-quinazoline-8-carboxylic acid amide | 323 | 0.253 | 2.5 | | |
| 59 | 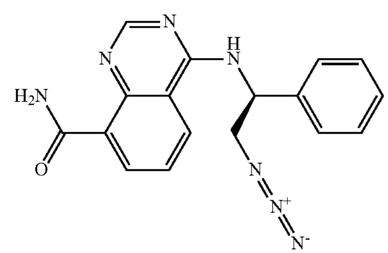 [SMILES: [N-]=[N+]=NC[C@@H](Nc1ncnc2c(C(N)=O)cccc12)c1ccccc1] | 4-((S)-2-Azido-1-phenyl-ethylamino)-quinazoline-8-carboxylic acid amide | 334 | 0.0458 | 0.45 | | |
| 60 | 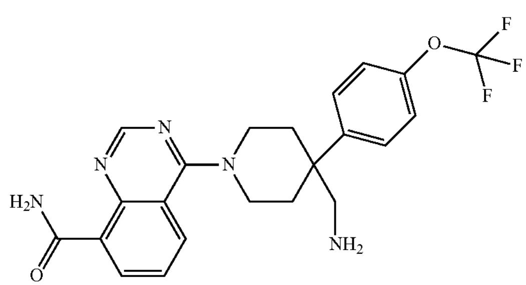 [SMILES: NCC1(c2ccc(OC(F)(F)F)cc2)CCN(c2ncnc3c(C(N)=O)cccc23)CC1] | 4-[4-Aminomethyl-4-(4-trifluoromethoxy-phenyl)piperidin-1-yl]-quinazoline-8-carboxylic acid amide | 0 | 21.2 | 5.5 | | |

TABLE 1-continued

| No. | Structure | Chemical Name | MS (M + 1) | p70S6 K binding IC50 [µM] | Aurora A binding IC50 [µM] | Aurora B binding IC50 [µM] | PDK1 binding IC50 [µM] |
|---|---|---|---|---|---|---|---|
| 61 | 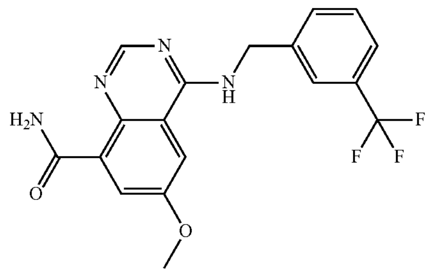 [SMILES: COc1cc(C(N)=O)c2ncnc(NCc3cccc(C(F)(F)F)c3)c2c1] | 6-Methoxy-4-(3-trifluoromethyl-benzylamino)-quinazoline-8-carboxylic acid amide | 377 | 0.0031 | 0.2 | | |
| 62 | 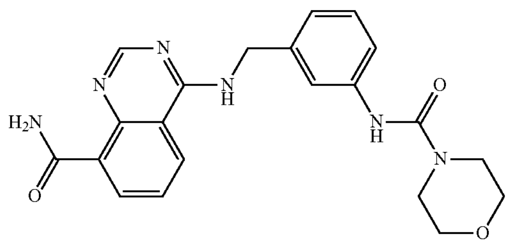 [SMILES: NC(=O)c1cccc2c(NCc3cccc(NC(=O)N4CCOCC4)c3)ncnc12] | 4-{3-[(Morpholine-4-carbonyl)-amino]-benzylamino}quinazoline-8-carboxylic acid amide | 407 | 1.20 | 3.5 | | |
| 63 | 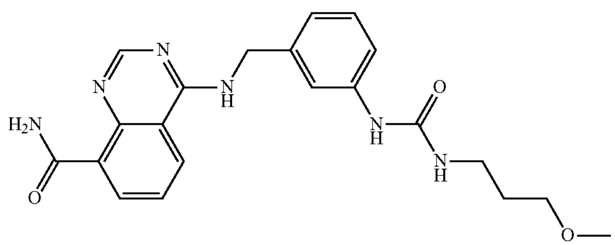 [SMILES: COCCCNC(=O)Nc1cccc(CNc2ncnc3c(C(N)=O)cccc23)c1] | 4-{3-[3-(3-Methoxypropyl)-ureido]-benzylamino}-quinazoline-8-carboxylic acid amide | 409 | 0.456 | 9.7 | | |
| 64 | 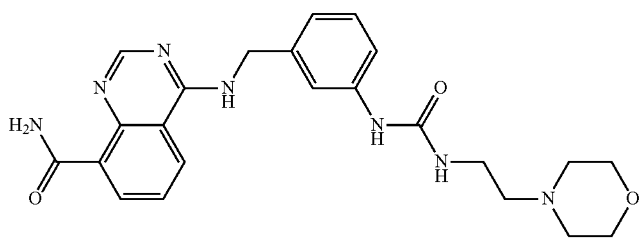 [SMILES: NC(=O)c1cccc2c(NCc3cccc(NC(=O)NCCN4CCOCC4)c3)ncnc12] | 4-{3-[3-(2-Morpholin-4-yl-ethyl)-ureido]-benzylamino}-quinazoline-8-carboxylic acid amide | 450 | 0.836 | 1.7 | | |

TABLE 1-continued

| No. | Structure | Chemical Name | MS (M + 1) | p70S6K binding IC50 [μM] | Aurora A binding IC50 [μM] | Aurora B binding IC50 [μM] | PDK1 binding IC50 [μM] |
|---|---|---|---|---|---|---|---|
| 65 | 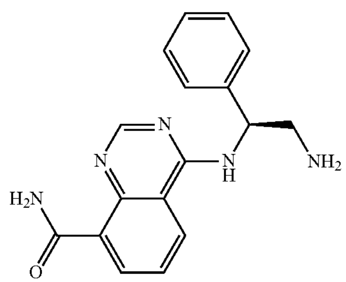 [SMILES: NC[C@@H](Nc1ncnc2c(C(N)=O)cccc12)c1ccccc1] | 4-((S)-2-Amino-1-phenyl-ethylamino)-quinazoline-8-carboxylic acid amide | 308 | 0.0006 | 0.31 | 0.0014 | |
| 66 | 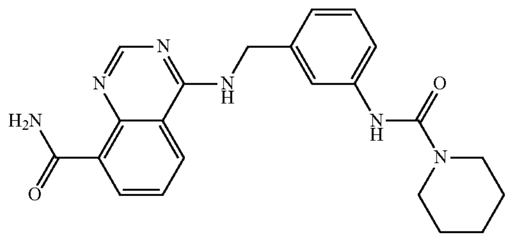 [SMILES: NC(=O)c1cccc2c(NCc3cccc(NC(=O)N4CCCCC4)c3)ncnc12] | 4-{3-[(Piperidine-1-carbonyl)-amino]-benzylamino}-quinazoline-8-carboxylic acid amide | 405 | 0.174 | 0.0084 | 0.0022 | |
| 67 | 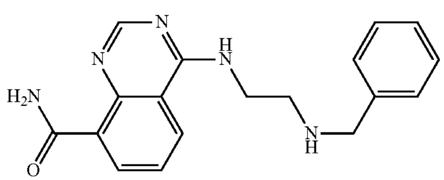 [SMILES: NC(=O)c1cccc2c(NCCNCc3ccccc3)ncnc12] | 4-(2-Benzylamino-ethylamino)-quinazoline-8-carboxylic acid amide | 322 | 0.896 | 0.029 | 0.023 | |
| 68 | 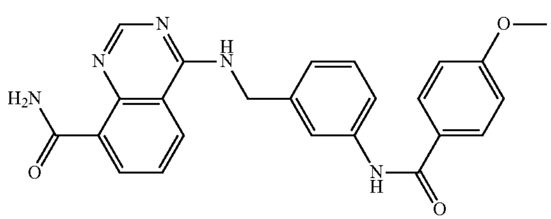 [SMILES: COc1ccc(C(=O)Nc2cccc(CNc3ncnc4c(C(N)=O)cccc34)c2)cc1] | 4-[3-(4-Methoxybenzoylamino)-benzylamino]-quinazoline-8-carboxylic acid amide | 428 | 0.0202 | 0.00029 | 0.00035 | |

TABLE 1-continued

| No. | Structure | Chemical Name | MS (M + 1) | p70S6 K binding IC50 [µM] | Aurora A binding IC50 [µM] | Aurora B binding IC50 [µM] | PDK1 binding IC50 [µM] |
|---|---|---|---|---|---|---|---|
| 69 | 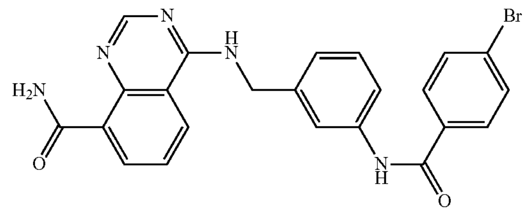 [SMILES: NC(=O)c1cccc2c(NCc3cccc(NC(=O)c4ccc(Br)cc4)c3)ncnc12] | 4-[3-(4-Bromo-benzoylamino)-benzylamino]-quinazoline-8-carboxylic acid amide | 477 | 0.0090 | 0.00065 | 0.00071 | |
| 70 | 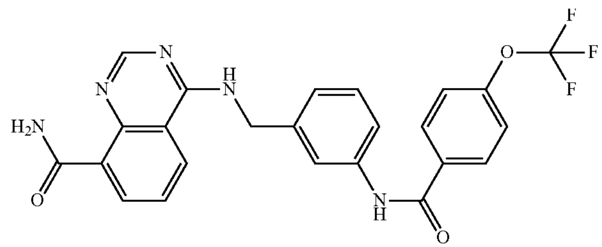 | 4-[3-(4-Trifluoromethoxy-benzoylamino)-benzylamino]-quinazoline-8-carboxylic acid amide | 482 | 0.111 | 1.9 | | |
| 71 | 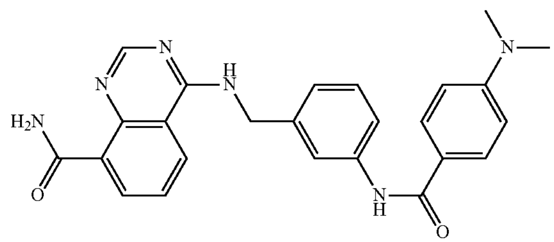 [SMILES: CN(C)c1ccc(C(=O)Nc2cccc(CNc3ncnc4c(C(N)=O)cccc34)c2)cc1] | 4-[3-(4-Dimethylamino-benzoylamino)-benzylamino]-quinazoline-8-carboxylic acid amide | 441 | 0.0117 | 0.00011 | 0.00052 | |
| 72 | 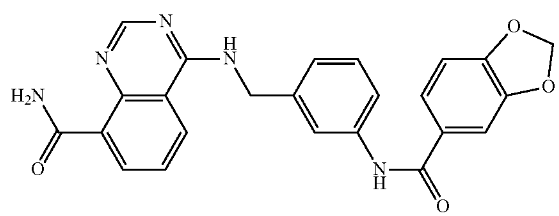 [SMILES: NC(=O)c1cccc2c(NCc3cccc(NC(=O)c4ccc5c(c4)OCO5)c3)ncnc12] | 4-[3-[(Benzo[1,3]dioxole-5-carbonyl)-amino]benzylamino]-quinazoline-8-carboxylic acid amide | 442 | 0.0097 | 0.00051 | 0.0012 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 73 | 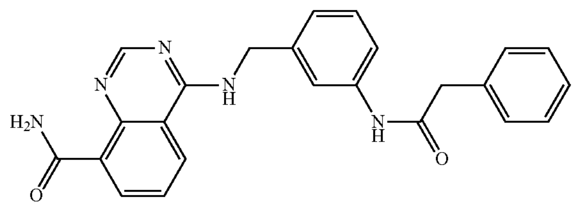 [SMILES: NC(=O)c1cccc2c(NCc3cccc(NC(=O)Cc4ccccc4)c3)ncnc12] | 4-(3-Phenylacetylamino-benzylamino)-quinazoline-8-carboxylic acid amide | 412 | 0.0817 | 0.0026 | 0.0021 | |
| 74 | 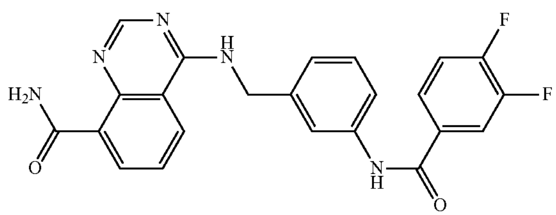 [SMILES: NC(=O)c1cccc2c(NCc3cccc(NC(=O)c4ccc(F)c(F)c4)c3)ncnc12] | 4-[3-(3,4-Difluorobenzoylamino)-benzylamino]-quinazoline-8-carboxylic acid amide | 434 | 0.0146 | 0.0011 | 0.003 | |
| 75 | 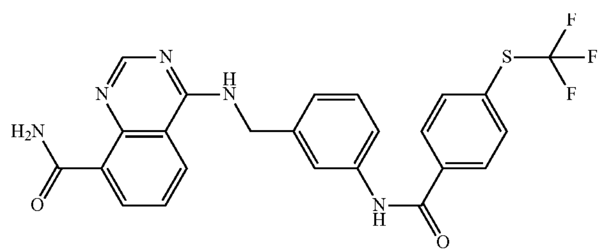 [SMILES: NC(=O)c1cccc2c(NCc3cccc(NC(=O)c4ccc(SC(F)(F)F)cc4)c3)ncnc12] | 4-[3-(4-Trifluoromethylsulfanyl-benzoylamino)-benzylamino]-quinazoline-8-carboxylic acid amide | 498 | 0.123 | 0.00039 | 0.0012 | |
| 76 | 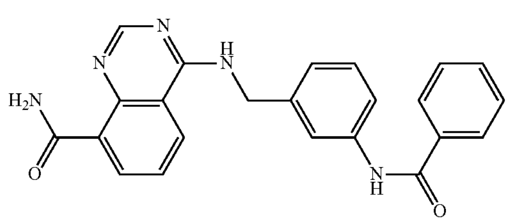 [SMILES: NC(=O)c1cccc2c(NCc3cccc(NC(=O)c4ccccc4)c3)ncnc12] | 4-(3-Benzoylamino-benzylamino)-quinazoline-8-carboxylic acid amide | 398 | 0.0546 | | | 1.9 |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 77 | 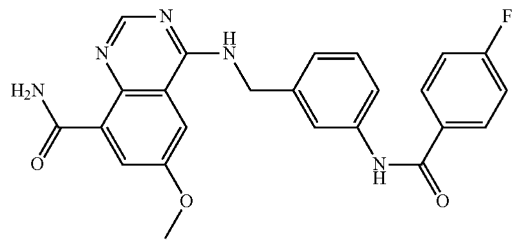 [SMILES: COc1cc(C(N)=O)c2ncnc(NCc3cccc(NC(=O)c4ccc(F)cc4)c3)c2c1] | 4-[3-(4-Fluoro-benzoylamino)-benzylamino]-6-methoxy-quinazoline-8-carboxylic acid amide | 446 | 0.0017 | 0.0004 | 0.0017 | |
| 78 | 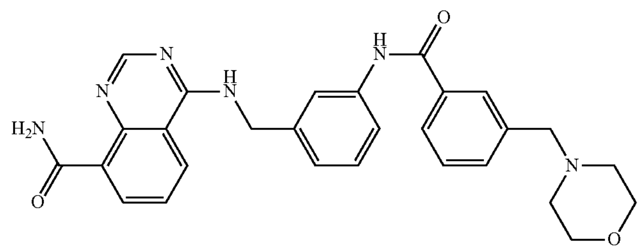 [SMILES: NC(=O)c1cccc2c(NCc3cccc(NC(=O)c4cccc(CN5CCOCC5)c4)c3)ncnc12] | 4-[3-(3-Morpholin-4-ylmethyl-benzoylamino)-benzylamino]-quinazoline-8-carboxylic acid amide | 497 | 0.0462 | 0.2 | | |
| 79 | 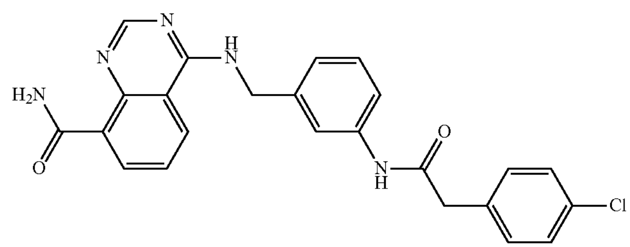 [SMILES: NC(=O)c1cccc2c(NCc3cccc(NC(=O)Cc4ccc(Cl)cc4)c3)ncnc12] | 4-{3-[2-(4-Chloro-phenyl)-acetylamino]-benzylamino}-quinazoline-8-carboxylic acid amide | 446 | 0.0917 | 0.0084 | 0.0016 | |

TABLE 1-continued

| No. | Structure | Chemical Name | MS (M + 1) | p70S6K binding IC50 [μM] | Aurora A binding IC50 [μM] | Aurora B binding IC50 [μM] | PDK1 binding IC50 [μM] |
|---|---|---|---|---|---|---|---|
| 80 | 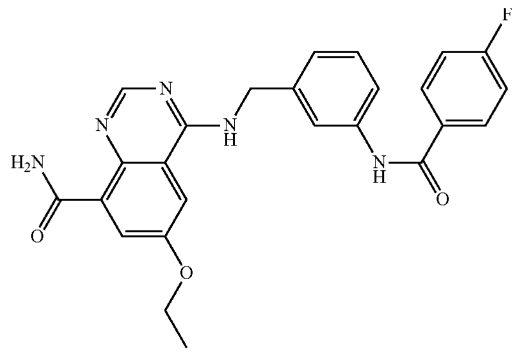 [SMILES: CCOc1cc(C(N)=O)c2ncnc(NCc3cccc(NC(=O)c4ccc(F)cc4)c3)c2c1] | 6-Ethoxy-4-[3-(4-fluoro-benzoylamino)-benzylamino]-quinazoline-8-carboxylic acid amide | 460 | 0.0118 | 0.00063 | 0.0078 | |
| 81 | 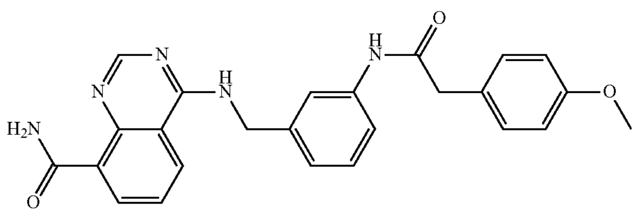 [SMILES: COc1ccc(CC(=O)Nc2cccc(CNc3ncnc4c(C(N)=O)cccc34)c2)cc1] | 4-{3-[2-(4-Methoxyphenyl)-acetylamino]-benzylamino}-quinazoline-8-carboxylic acid amide | 442 | 0.0337 | 2.1 | | |
| 82 | 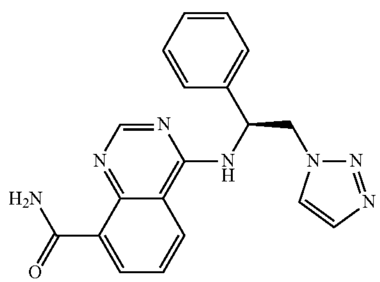 [SMILES: NC(=O)c1cccc2c(N[C@H](Cn3ccnn3)c3ccccc3)ncnc12] | 4-((S)-1-Phenyl-2[1,2,3]triazol-1-yl-ethylamino)-quinazoline-8-carboxylic acid amide | 360 | 0.0292 | 4.2 | | |

TABLE 1-continued

| No. | Structure | Chemical Name | MS (M + 1) | p70S6 K binding IC50 [µM] | Aurora A binding IC50 [µM] | Aurora B binding IC50 [µM] | PDK1 binding IC50 [µM] |
|---|---|---|---|---|---|---|---|
| 83 | 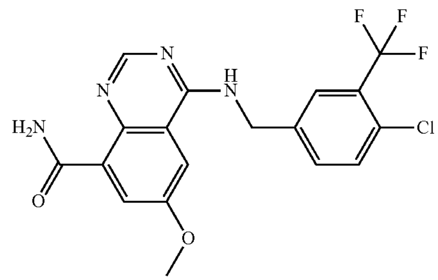 [SMILES: COc1cc(C(N)=O)c2ncnc(NCc3ccc(Cl)c(C(F)(F)F)c3)c2c1] | 4-(4-Chloro-3-trifluoromethyl-benzylamino)-6-methoxy-quinazoline-8-carboxylic acid amide | 411 | 0.0018 | 0.378 | | |
| 84 | 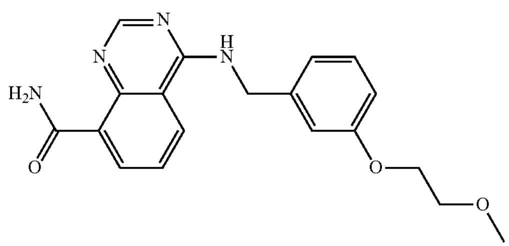 [SMILES: COCCOc1cccc(CNc2ncnc3c(C(N)=O)cccc23)c1] | 4-[3-(2-Methoxy-ethoxy)-benzylamino]-quinazoline-8-carboxylic acid amide | 353 | 0.653 | 6.2 | | |
| 85 | 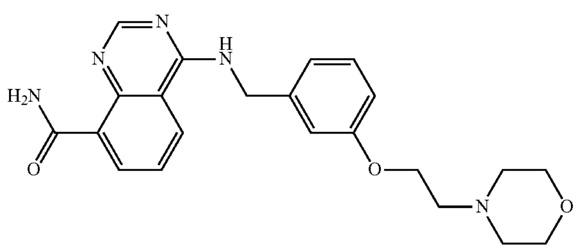 [SMILES: NC(=O)c1cccc2c(NCc3cccc(OCCN4CCOCC4)c3)ncnc12] | 4-[3-(2-Morpholin-4-yl-ethoxy)-benzylamino]-quinazoline-8-carboxylic acid amide | 408 | 5.88 | 1.3 | | |
| 86 | 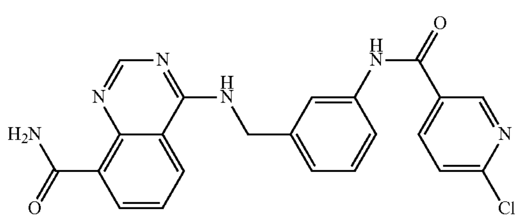 [SMILES: NC(=O)c1cccc2c(NCc3cccc(NC(=O)c4ccc(Cl)nc4)c3)ncnc12] | 4-{3-[(6-Chloro-pyridine-3-carbonyl)-amino]benzylamino}-quinazoline-8-carboxylic acid amide | 433 | 0.0115 | 0.00065 | 0.00046 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 87 | 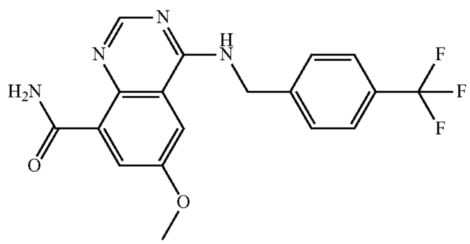 [SMILES: COc1cc(C(N)=O)c2ncnc(NCc3ccc(C(F)(F)F)cc3)c2c1] | 6-Methoxy-4-(4-trifluoromethyl-benzyl-amino)-quinazoline-8-carboxylic acid amide | 377 | 0.0046 | 0.59 | | |
| 88 | 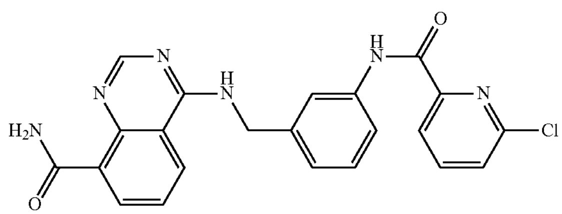 [SMILES: NC(=O)c1cccc2c(NCc3cccc(NC(=O)c4cccc(Cl)n4)c3)ncnc12] | 4-{3-[(6-Chloro-pyridine-2-carbonyl)-amino]-benzylamino}-quinazoline-8-carboxylic acid amide | 433 | 0.199 | 0.005 | 0.0029 | |
| 89 | 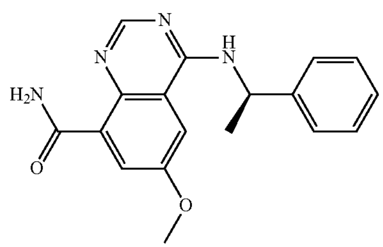 [SMILES: COc1cc(C(N)=O)c2ncnc(N[C@H](C)c3ccccc3)c2c1] | 6-Methoxy-4-((R)-1-phenyl-ethylamino)-quinazoline-8-carboxylic acid amide | 323 | 0.0489 | 0.033 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 90 | 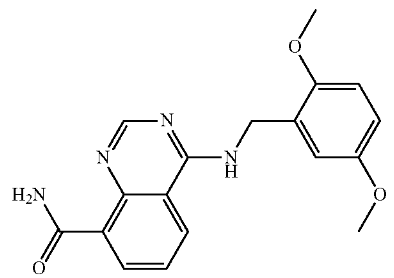 [SMILES: COc1ccc(OC)c(CNc2ncnc3c(C(N)=O)cccc23)c1] | 4-(2,5-Dimethoxybenzylamino)-quinazoline-8-carboxylic acid amide | 339 | 0.0336 | 0.341 | | |
| 91 | 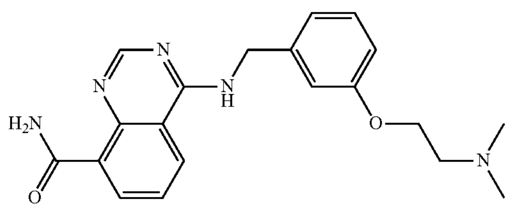 [SMILES: CN(C)CCOc1cccc(CNc2ncnc3c(C(N)=O)cccc23)c1] | 4-[3-(2-Dimethylaminoethoxy)-benzylamino]-quinazoline-8 carboxylic acid amide | 366 | 1.65 | 1.6 | | |
| 92 | 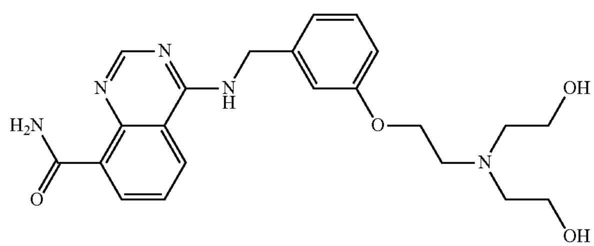 [SMILES: NC(=O)c1cccc2c(NCc3cccc(OCCN(CCO)CCO)c3)ncnc12] | 4-(3-{2-[Bis-(2-hydroxy-ethyl)-amino]-ethoxy}-benzylamino)-quinazoline-8-carboxylic acid amide | 426 | 1.20 | 0.058 | 0.088 | |
| 93 | 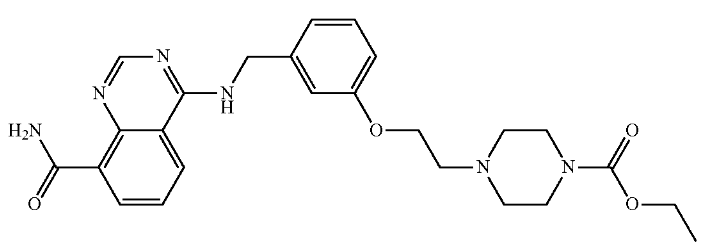 [SMILES: CCOC(=O)N1CCN(CCOc2cccc(CNc3ncnc4c(C(N)=O)cccc34)c2)CC1] | 4-(2-{3-[(8-Carbamoyl-quinazolin-4-ylamino)-methyl]-phenoxy}-ethyl)-piperazine-1-carboxylic acid ethyl ester | 479 | 3.93 | 0.92 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 94 | 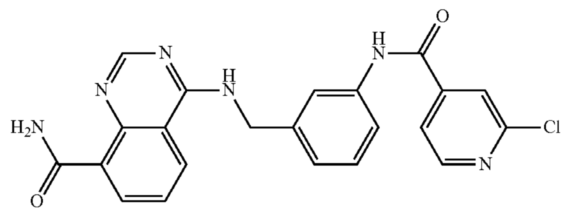 [SMILES: NC(=O)c1cccc2c(NCc3cccc(NC(=O)c4ccnc(Cl)c4)c3)ncnc12] | 4-{3-[(2-Chloropyridine-4-carbonyl)-amino]benzylamino}-quinazoline-8-carboxylic acid amide | 433 | 0.0250 | 0.029 | 0.025 | |
| 95 | 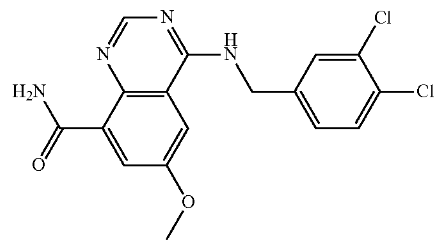 [SMILES: COc1cc(C(N)=O)c2ncnc(NCc3ccc(Cl)c(Cl)c3)c2c1] | 4-(3,4-Dichloro-benzylamino)-6-methoxy-quinazoline-8 carboxylic acid amide | 378 | 0.0027 | 0.22 | | |
| 96 | 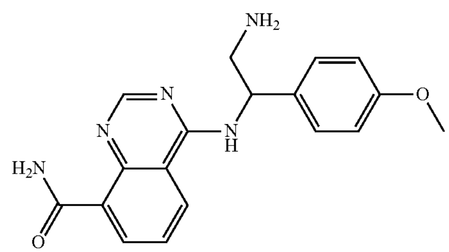 [SMILES: COc1ccc(C(CN)Nc2ncnc3c(C(N)=O)cccc23)cc1] | 4-[2-Amino-1-(4-methoxy-phenyl)-ethylamino]quinazoline-8-carboxylic acid amide | 338 | 0.0007 | 2 | | |

TABLE 1-continued

| No. | Structure | Chemical Name | MS (M + 1) | p70S6 K binding IC50 [µM] | Aurora A binding IC50 [µM] | Aurora B binding IC50 [µM] | PDK1 binding IC50 [µM] |
|---|---|---|---|---|---|---|---|
| 97 | 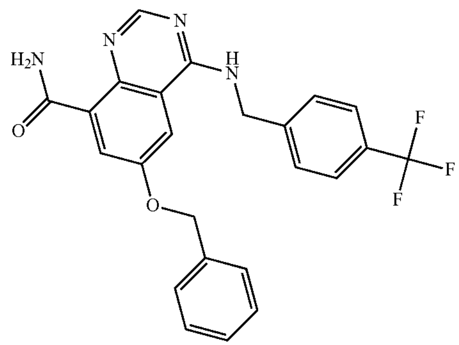 [SMILES: NC(=O)c1cc(OCc2ccccc2)cc2c(NCc3ccc(C(F)(F)F)cc3)ncnc12] | 6-Benzyloxy-4-(4-trifluoromethyl-benzylamino)-quinazoline-8-carboxylic acid amide | 453 | 0.432 | 2.6 | 2.5 | |
| 98 | 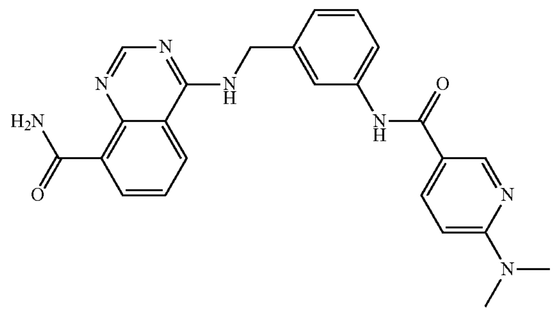 [SMILES: CN(C)c1ccc(C(=O)Nc2cccc(CNc3ncnc4c(C(N)=O)cccc34)c2)cn1] | 4-{3-[(6-Dimethylamino-pyridine-3-carbonyl)-amino]-benzylamino}-quinazoline-8-carboxylic acid amide | 442 | 0.0148 | 0.00097 | 0.00094 | |
| 199 | 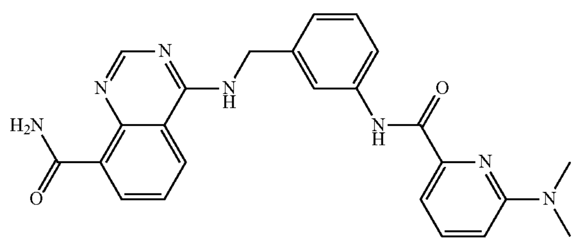 [SMILES: CN(C)c1cccc(C(=O)Nc2cccc(CNc3ncnc4c(C(N)=O)cccc34)c2)n1] | 4-{3-[(6-Dimethylamino-pyridine-2-carbonyl)-amino]-benzylamino}-quinazoline-8-carboxylic acid amide | 442 | 0.136 | 0.0063 | 0.00073 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 100 | 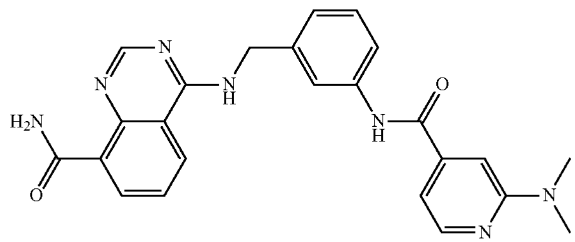 [SMILES: CN(C)c1cc(C(=O)Nc2cccc(CNc3ncnc4c(C(N)=O)cccc34)c2)ccn1] | 4-{3-[(2-Dimethylamino-pyridine-4-carbonyl)-amino]-benzylamino}-quinazoline-8-carboxylic acid amide | 442 | 0.0121 | 0.0015 | 0.0026 | |
| 101 | 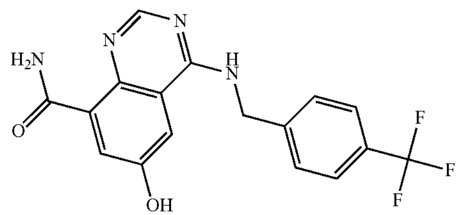 [SMILES: NC(=O)c1cc(O)cc2c(NCc3ccc(C(F)(F)F)cc3)ncnc12] | 6-Hydroxy-4-(4-trifluoromethyl-benzyl-amino)-quinazoline-8-carboxylic acid amide | 363 | 0.0231 | 0.00032 | 0.00024 | |
| 102 | 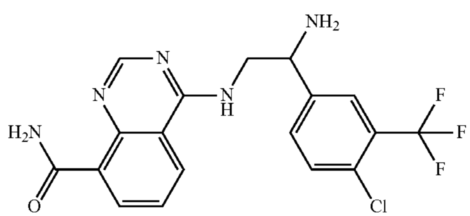 [SMILES: NC(=O)c1cccc2c(NCC(N)c3ccc(Cl)c(C(F)(F)F)c3)ncnc12] | 4-[2-Amino-2-(4-chloro-3-trifluoromethyl-phenyl)-ethylamino]-quinazoline-8-carboxylic acid amide | 410 | 0.0291 | 1 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 103 | 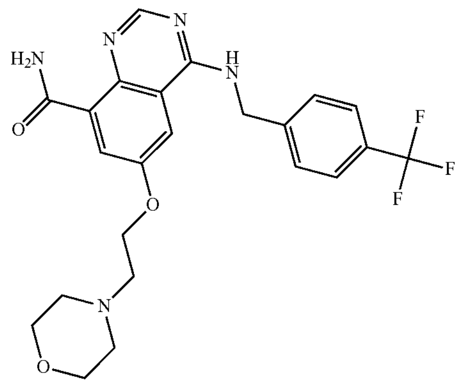 [SMILES: NC(=O)c1cc(OCCN2CCOCC2)cc2c(NCc3ccc(C(F)(F)F)cc3)ncnc12] | 6-(2-Morpholin-4-yl-ethoxy)-4-(4-trifluoro-methyl-benzylamino)-quinazoline-8-carboxylic acid amide | 476 | 0.541 | 0.36 | | 3.5 |
| 104 | 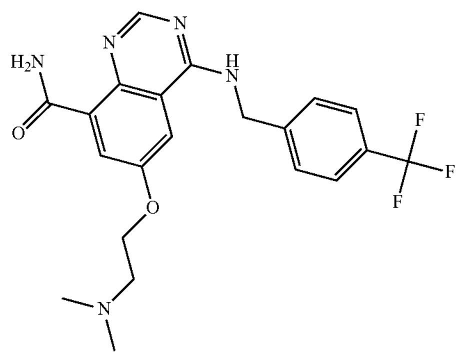 [SMILES: CN(C)CCOc1cc(C(N)=O)c2ncnc(NCc3ccc(C(F)(F)F)cc3)c2c1] | 6-(2-Dimethylamino-ethoxy)-4-(4-trifluoromethyl-benzylamino)-quinazoline-8-carboxylic acid amide | 434 | 0.233 | 10 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 105 | 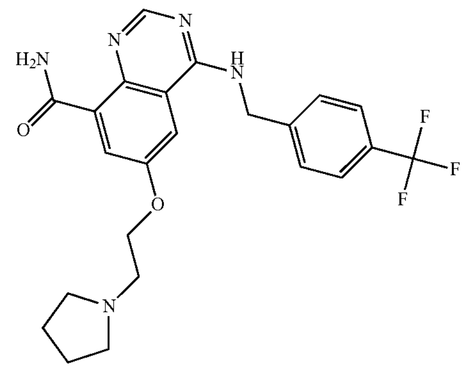 [SMILES: NC(=O)c1cc(OCCN2CCCC2)cc2c(NCc3ccc(C(F)(F)F)cc3)ncnc12] | 6-(2-Pyrrolidin-1-yl-ethoxy)-4-(4-trifluoro-methyl-benzylamino)-quinazoline-8-carboxylic acid amide | 460 | 0.219 | | | |
| 106 | 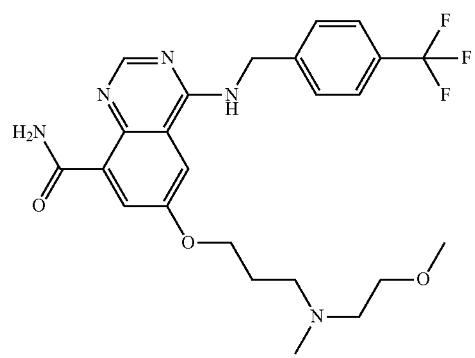 [SMILES: COCCN(C)CCCOc1cc(C(N)=O)c2ncnc(NCc3ccc(C(F)(F)F)cc3)c2c1] | 6-{3-[(2-Methoxy-ethyl)-methyl-amino]-propoxy}-4-(4-trifluoromethyl-benzylamino)-quinazoline-8-carboxylic acid amide | 492 | 0.195 | 0.0035 | 0.001 | |

TABLE 1-continued
| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 107 | 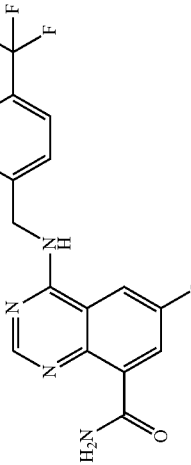 | 6-{3-[4-(2-Hydroxy-ethyl)-piperazin-1-yl]-propoxy}-4-(4-trifluoromethyl-benzylamino)-quinazoline-8-carboxylic acid amide | 533 | 0.144 | 0.0034 | 0.004 | |
| 108 | 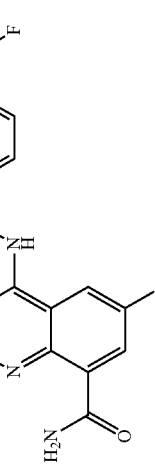 | 6-(3-Morpholin-4-yl-propoxy)-4-(4-trifluoro-methyl-benzylamino)-quinazoline-8-carboxylic acid amide | 490 | 0.250 | 0.088 | 0.6 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 109 | 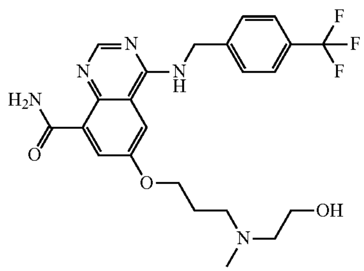 [SMILES: CN(CCO)CCCOc1cc(C(N)=O)c2ncnc(NCc3ccc(C(F)(F)F)cc3)c2c1] | 6-{3-[(2-Hydroxy-ethyl)-methyl-amino]-propoxy}-4-(4-trifluoromethyl-benzylamino)-quinazoline-8-carboxylic acid amide | 478 | 0.288 | 1.1 | | |
| 110 | 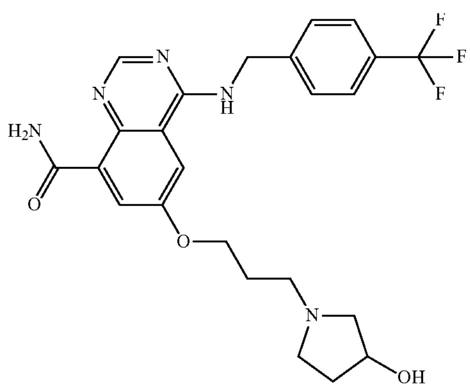 [SMILES: NC(=O)c1cc(OCCCN2CCC(O)C2)cc2c(NCc3ccc(C(F)(F)F)cc3)ncnc12] | 6-[3-(3-Hydroxy-pyrrolidin-1-yl)-propoxy]-4-(4-trifluoromethyl-benzylamino)-quinazoline-8-carboxylic acid amide | 490 | 0.187 | 1.3 | 1.06 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 111 | 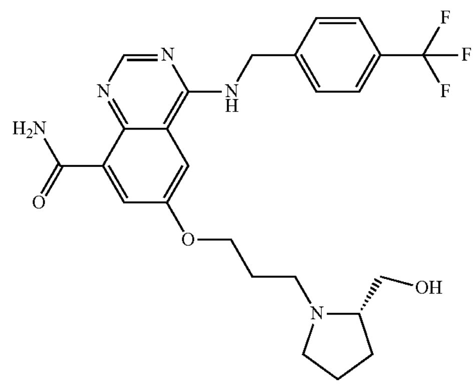 [SMILES: NC(=O)c1cc(OCCCN2CCC[C@H]2CO)cc2c(NCc3ccc(C(F)(F)F)cc3)ncnc12] | 6-[3-((S)-2-Hydroxymethyl-pyrrolidin-1-yl)-propoxy]-4-(4-trifluoromethyl-benzylamino)-quinazoline-8-carboxylic acid amide | 504 | 0.204 | 0.0067 | 0.027 | |
| 112 | 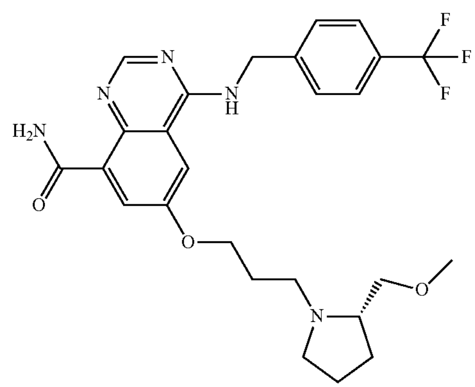 [SMILES: COC[C@@H]1CCCN1CCCOc1cc(C(N)=O)c2ncnc(NCc3ccc(C(F)(F)F)cc3)c2c1] | 6-[3-((S)-2-Methoxymethyl-pyrrolidin-1-yl)-propoxy]-4-(4-trifluoromethyl-benzylamino)-quinazoline-8-carboxylic acid amide | 518 | 0.128 | 7.5 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 113 | 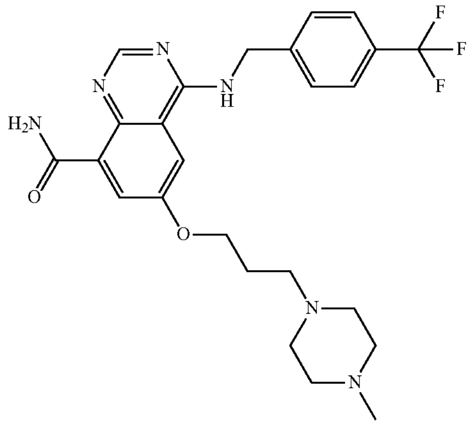 [SMILES: CN1CCN(CCCOc2cc(C(N)=O)c3ncnc(NCc4ccc(C(F)(F)F)cc4)c3c2)CC1] | 6-[3-(4-Methylpiperazin-1-yl)-propoxy]-4-(4-trifluoromethyl-benzylamino)-quinazoline-8-carboxylic acid amide | 503 | 0.138 | 0.0068 | 0.0062 | |
| 114 | 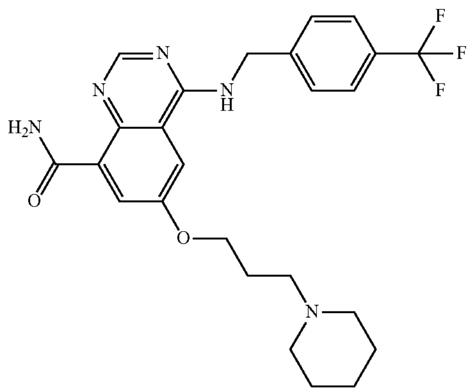 [SMILES: NC(=O)c1cc(OCCCN2CCCCC2)cc2c(NCc3ccc(C(F)(F)F)cc3)ncnc12] | 6-(3-Piperidin-1-yl-propoxy)-4-(4-trifluoromethylbenzylamino)-quinazoline-8-carboxylic acid amide | 488 | 0.127 | 0.00018 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 115 | 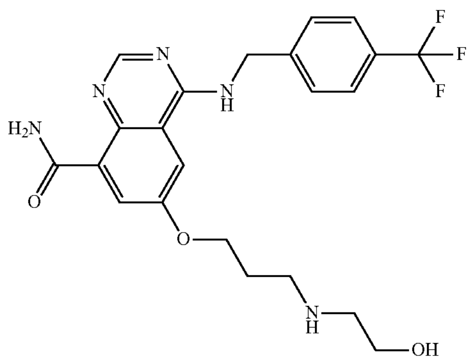 [SMILES: NC(=O)c1cc(OCCCNCCO)cc2c(NCc3ccc(C(F)(F)F)cc3)ncnc12] | 6-[3-(2-Hydroxy-ethylamino)-propoxy]-4-(4-trifluoromethyl-benzylamino)-quinazoline-8-carboxylic acid amide | 464 | 0.0601 | 0.0058 | 0.0016 | |
| 116 | 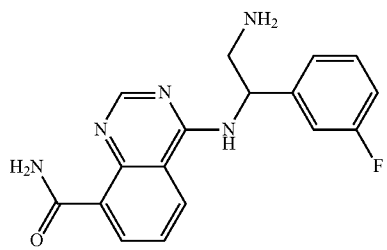 [SMILES: NCC(Nc1ncnc2c(C(N)=O)cccc12)c1cccc(F)c1] | 4-[2-Amino-1-(3-fluoro-phenyl)-ethyl-amino]-quinazoline-8-carboxylic acid amide | 326 | 0.0005 | 0.28 | | |
| 117 | 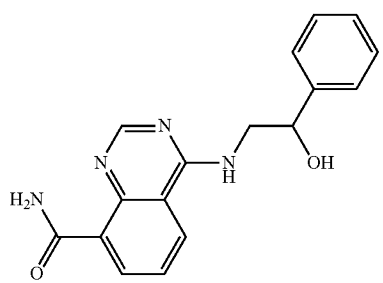 [SMILES: NC(=O)c1cccc2c(NCC(O)c3ccccc3)ncnc12] | 4-(2-Hydroxy-2-phenyl-ethylamino)-quinazoline-8-carboxylic acid amide | 309 | 0.0628 | 0.49 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 118 | 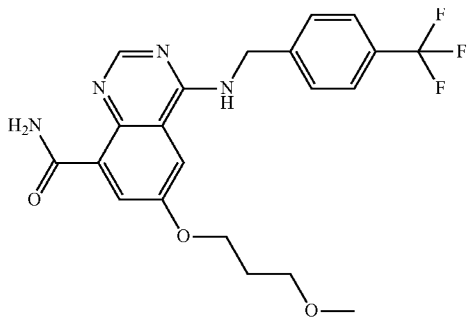 [SMILES: COCCCOc1cc(C(N)=O)c2ncnc(NCc3ccc(C(F)(F)F)cc3)c2c1] | 6-(3-Methoxy-propoxy)-4-(4-trifluoromethyl-benzylamino)-quinazoline-8-carboxylic acid amide | 435 | 0.0238 | 0.078 | 0.17 | |
| 119 | 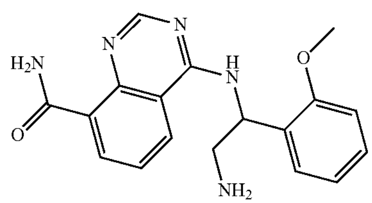 [SMILES: COc1ccccc1C(CN)Nc1ncnc2c(C(N)=O)cccc12] | 4-[2-Amino-1-(2-methoxy-phenyl)-ethylamino]-quinazoline-8-carboxylic acid amide | 338 | 0.0057 | 1.5 | 0.048 | |
| 120 | 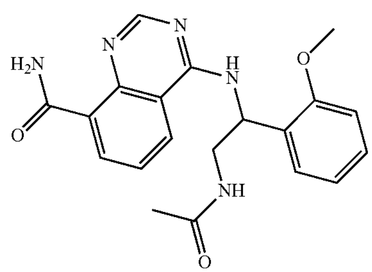 [SMILES: COc1ccccc1C(CNC(C)=O)Nc1ncnc2c(C(N)=O)cccc12] | 4-[2-Acetylamino-1-(2-methoxy-phenyl)-ethyl-amino]-quinazoline-8-carboxylic acid amide | 380 | 0.175 | 0.0019 | 0.0071 | |
| 121 | 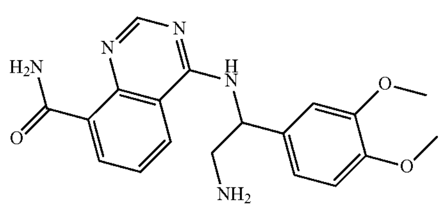 [SMILES: COc1ccc(C(CN)Nc2ncnc3c(C(N)=O)cccc23)cc1OC] | 4-[2-Amino-1-(3,4-dimethoxy-phenyl)-ethylamino]-quinazoline-8-carboxylic acid amide | 368 | 0.0005 | 4.9 | | |

TABLE 1-continued
| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 122 | 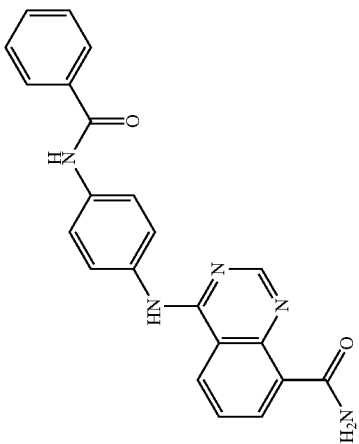 | 4-(4-Benzoylamino-phenylamino)-quinazoline-8-carboxylic acid amide | 384 | 0.658 | 0.59 | | |
| 123 | 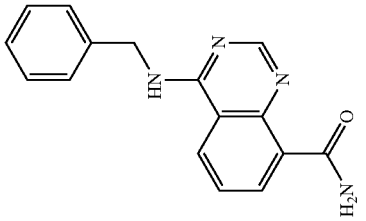 | 4-Benzylamino-quinazoline-8-carboxylic acid amide | 279 | 0.0615 | 4.3 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 124 | 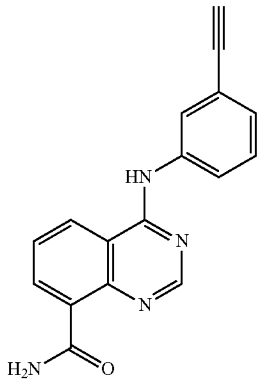 [SMILES: C#Cc1cccc(Nc2ncnc3c(C(N)=O)cccc23)c1] | 4-(3-Ethynyl-phenylamino)-quinazoline-8-carboxylic acid amide | 289 | 1.12 | 1 | | |
| 125 | 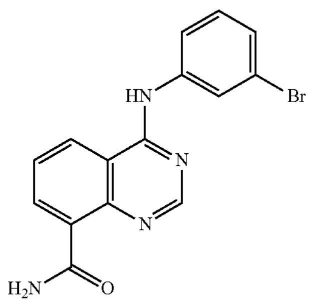 [SMILES: NC(=O)c1cccc2c(Nc3cccc(Br)c3)ncnc12] | 4-(3-Bromo-phenylamino)-quinazoline-8-carboxylic acid amide | 343 | 0.671 | 1.48 | | |
| 126 | 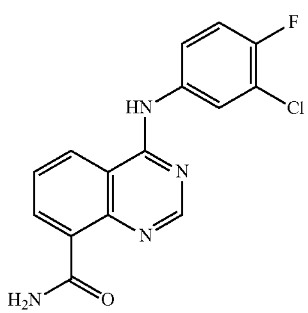 [SMILES: NC(=O)c1cccc2c(Nc3ccc(F)c(Cl)c3)ncnc12] | 4-(3-Chloro-4-fluorophenylamino)-quinazoline-8-carboxylic acid amide | 318 | 3.48 | 6 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 127 | 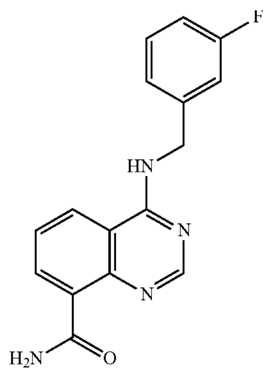 [SMILES: NC(=O)c1cccc2c(NCc3cccc(F)c3)ncnc12] | 4-(3-Fluoro-benzylamino)-quinazoline-8-carboxylic acid amide | 297 | 0.0316 | 0.76 | 0.0015 | |
| 128 | 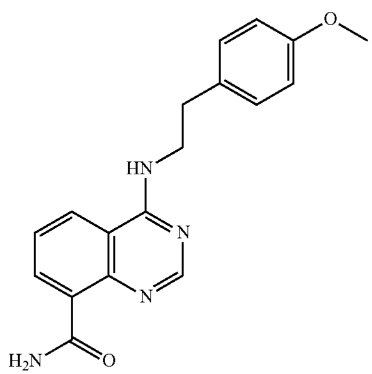 [SMILES: COc1ccc(CCNc2ncnc3c(C(N)=O)cccc23)cc1] | 4-[2-(4-Methoxy-phenyl)-ethylamino]-quinazoline-8-carboxylic acid amide | 323 | 0.242 | 10 | | |

TABLE 1-continued

| No. | Chemical Name | Structure | MS (M + 1) | p70S6 K binding IC50 [µM] | Aurora A binding IC50 [µM] | Aurora B binding IC50 [µM] | PDK1 binding IC50 [µM] |
|---|---|---|---|---|---|---|---|
| 129 | 4-(3,4-Dichloro-benzylamino)-quinazoline-8-carboxylic acid amide | 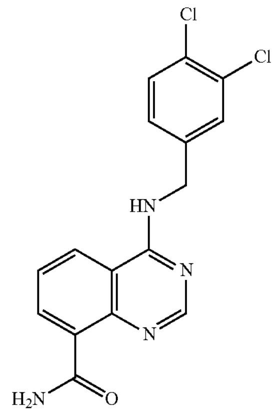 [SMILES: NC(=O)c1cccc2c(NCc3ccc(Cl)c(Cl)c3)ncnc12] | 348 | 0.0016 | 0.13 | | |
| 130 | 4-(4-Methoxy-benzylamino)-quinazoline-8-carboxylic acid amide | 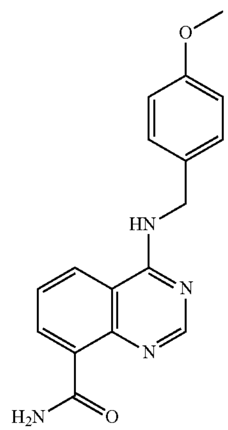 [SMILES: COc1ccc(CNc2ncnc3c(C(N)=O)cccc23)cc1] | 309 | 0.0300 | 0.23 | | |

TABLE 1-continued

| No. | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|
| 131 | 4-[(Naphthalen-1-ylmethyl)-amino]-quinazoline-8-carboxylic acid amide | 329 | 0.0615 | 0.34 | 0.388 | |
| 132 | 4-((S)-1-Phenyl-ethylamino)-quinazoline-8-carboxylic acid amide | 293 | 2.84 | 0.41 | | |

Structure (131): naphthalen-1-ylmethyl-NH linked to quinazoline-8-carboxamide

Structure (132): (S)-1-phenylethyl-NH linked to quinazoline-8-carboxamide

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 133 | 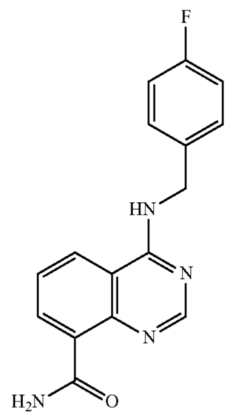 [SMILES: NC(=O)c1cccc2c(NCc3ccc(F)cc3)ncnc12] | 4-(4-Fluoro-benzylamino)-quinazoline-8-carboxylic acid amide | 297 | 0.0431 | 0.092 | | |
| 134 | 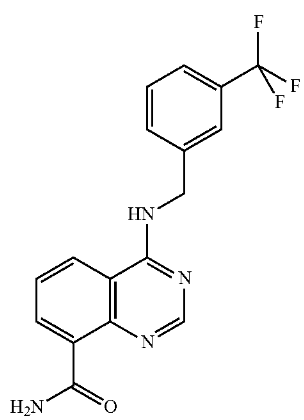 [SMILES: NC(=O)c1cccc2c(NCc3cccc(C(F)(F)F)c3)ncnc12] | 4-(3-Trifluoromethyl-benzylamino)-quinazoline-8-carboxylic acid amide | 347 | 0.0133 0.0207 | 0.58 | | |

TABLE 1-continued
| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 135 | 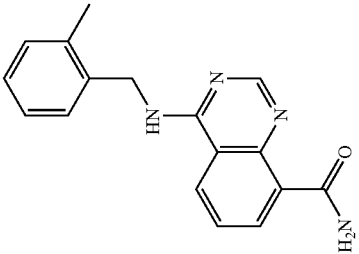 | 4-(2-Methyl-benzylamino)-quinazoline-8-carboxylic acid amide | 293 | 0.321 | 8.8 | | |
| 136 | 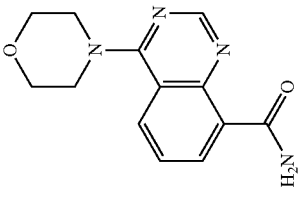 | 4-Morpholin-4-yl-quinazoline-8-carboxylic acid amide | 259 | 7.28 | 7.4 | | |

TABLE 1-continued

| No. | Structure | Chemical Name | MS (M + 1) | p70S6K binding IC50 [μM] | Aurora A binding IC50 [μM] | Aurora B binding IC50 [μM] | PDK1 binding IC50 [μM] |
|---|---|---|---|---|---|---|---|
| 137 | 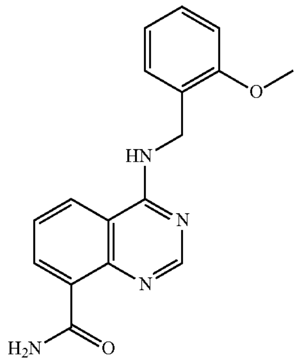 [SMILES: COc1ccccc1CNc1ncnc2c(C(N)=O)cccc12] | 4-(2-Methoxy-benzylamino)-quinazoline-8-carboxylic acid amide | 309 | 0.183 | 0.032 | | |
| 138 | 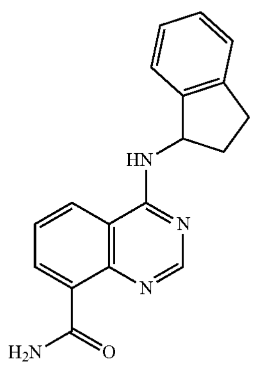 [SMILES: NC(=O)c1cccc2c(NC3CCc4ccccc43)ncnc12] | 4-(Indan-1-ylamino)quinazoline-8-carboxylic acid amide | 305 | 1.98 | 4.3 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 139 | 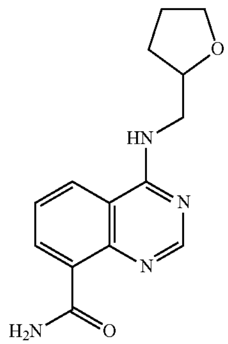 [SMILES: NC(=O)c1cccc2c(NCC3CCCO3)ncnc12] | 4-[(Tetrahydro-furan-2-ylmethyl)-amino]-quinazoline-8-carboxylic acid amide | 273 | 4.31 | 5.8 | | |
| 140 | 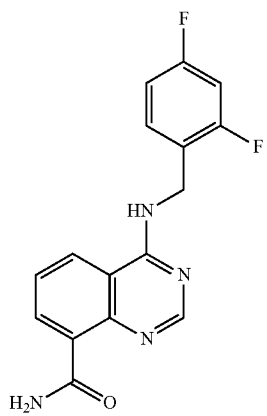 [SMILES: NC(=O)c1cccc2c(NCc3ccc(F)cc3F)ncnc12] | 4-(2,4-Difluoro-benzylamino)-quinazoline-8-carboxylic acid amide | 315 | 0.101 | 0.0022 | 0.00059 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 141 | 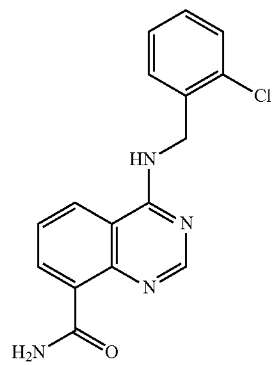 [SMILES: NC(=O)c1cccc2c(NCc3ccccc3Cl)ncnc12] | 4-(2-Chloro-benzylamino)-quinazoline-8-carboxylic acid amide | 314 | 0.243 | 0.74 | | |
| 142 | 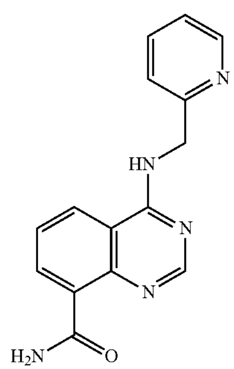 [SMILES: NC(=O)c1cccc2c(NCc3ccccn3)ncnc12] | 4-[(Pyridin-2-ylmethyl)-amino]-quinazoline-8-carboxylic acid amide | 280 | 2.45 | 10 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 143 | 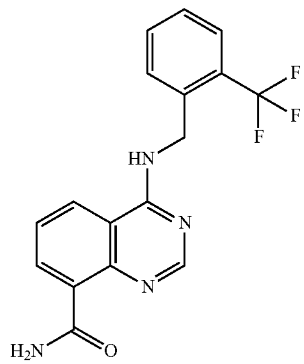 [SMILES: NC(=O)c1cccc2c(NCc3ccccc3C(F)(F)F)ncnc12] | 4-(2-Trifluoromethylenzylamino)-quinazoline-8-carboxylic acid amide | 347 | 0.469 | 0.0081 | 0.0076 | |
| 144 | 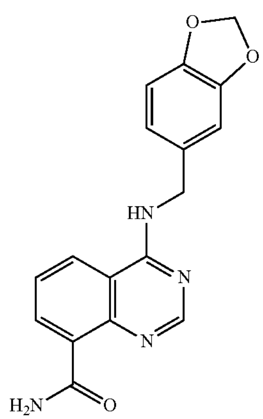 [SMILES: NC(=O)c1cccc2c(NCc3ccc4c(c3)OCO4)ncnc12] | 4-[(Benzo[1,3]dioxol-5]methyl)-amino]-quinazoline-8-carboxylic acid amide | 323 | 0.0272 | 0.00037 | 0.0039 | |

TABLE 1-continued

| No. | Structure | Chemical Name | MS (M + 1) | p70S6 K binding IC50 [µM] | Aurora A binding IC50 [µM] | Aurora B binding IC50 [µM] | PDK1 binding IC50 [µM] |
|---|---|---|---|---|---|---|---|
| 145 | 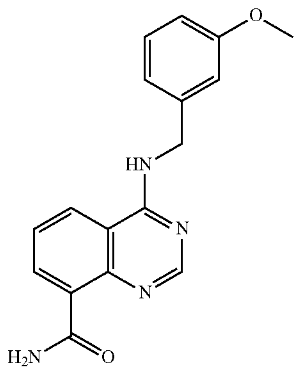 [SMILES: COc1cccc(CNc2ncnc3c(C(N)=O)cccc23)c1] | 4-(3-Methoxy-benzylamino)-quinazoline-8-carboxylic acid amide | 309 | 0.0237 | 0.35 | | |
| 146 | 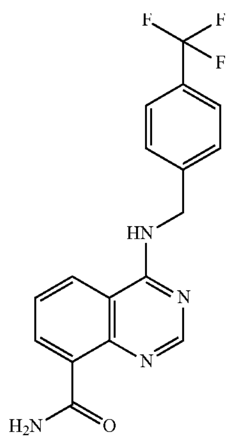 [SMILES: NC(=O)c1cccc2c(NCc3ccc(C(F)(F)F)cc3)ncnc12] | 4-(4-Trifluoromethyl-benzylamino)-quinazoline-8-carboxylic acid amide | 347 | 0.0025 | 0.55 | 0.7 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 147 | 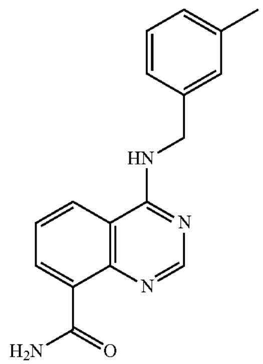 [SMILES: Cc1cccc(CNc2ncnc3c(C(N)=O)cccc23)c1] | 4-(3-Methyl-benzylamino)-quinazoline-8-carboxylic acid amide | 293 | 0.534 | 0.1 | | |
| 148 | 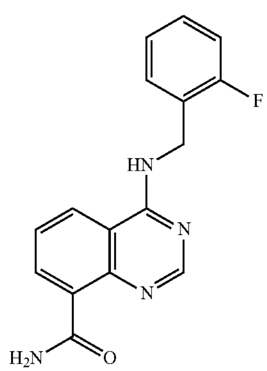 [SMILES: NC(=O)c1cccc2c(NCc3ccccc3F)ncnc12] | 4-(2-Fluoro-benzylamino)-quinazoline-8-carboxylic acid amide | 297 | 0.101 | 1 | | |

TABLE 1-continued

| No. | Structure | Chemical Name | MS (M + 1) | p70S6K binding IC50 [μM] | Aurora A binding IC50 [μM] | Aurora B binding IC50 [μM] | PDK1 binding IC50 [μM] |
|---|---|---|---|---|---|---|---|
| 149 | 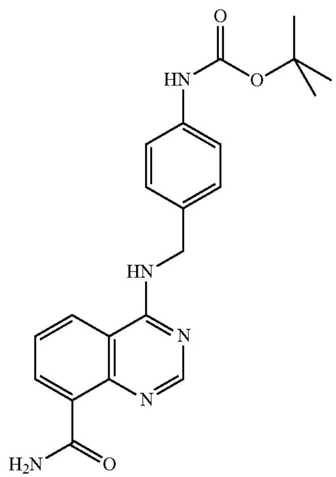 [SMILES: CC(C)(C)OC(=O)Nc1ccc(CNc2ncnc3c(C(N)=O)cccc23)cc1] | {4-[(8-Carbamoyl-quinazolin-4-ylamino)-methyl]-phenyl}-carbamic acid tert-butyl ester | 394 | 5.01 | 7.5 | | |
| 150 | 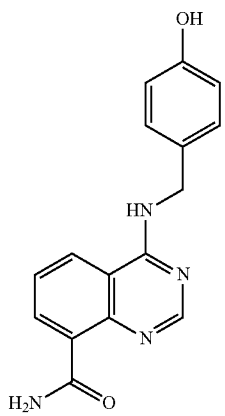 [SMILES: NC(=O)c1cccc2c(NCc3ccc(O)cc3)ncnc12] | 4-(4-Hydroxy-benzylamino)-quinazoline-8-carboxylic acid amide | 295 | 0.0769 | 0.58 | | |

TABLE 1-continued

| No. | Structure | Chemical Name | MS (M + 1) | p70S6 K binding IC50 [µM] | Aurora A binding IC50 [µM] | Aurora B binding IC50 [µM] | PDK1 binding IC50 [µM] |
|---|---|---|---|---|---|---|---|
| 151 | 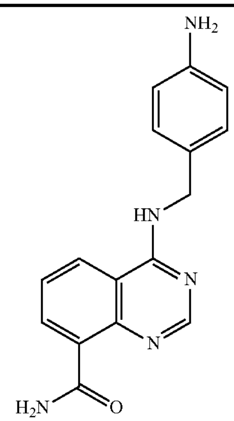 | 4-(4-Amino-benzylamino)-quinazoline-8-carboxylic acid amide | 294 | 0.210 | 9.3 | | |
| 152 | 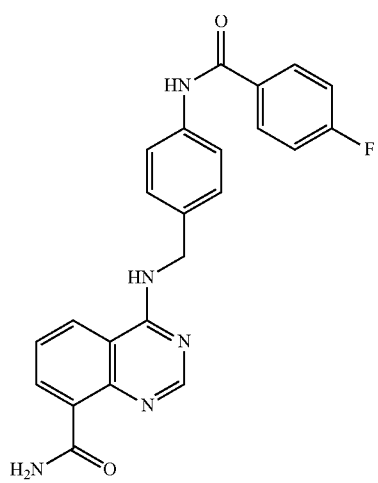 [SMILES: NC(=O)c1cccc2c(NCc3ccc(NC(=O)c4ccc(F)cc4)cc3)ncnc12] | 4-[4-(4-Fluoro-benzoylamino)-benzylamino]-quinazoline-8-carboxylic acid amide | 416 | 1.67 | 1.7 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 153 | 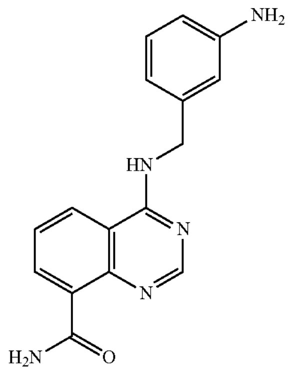 [SMILES: NC(=O)c1cccc2c(NCc3cccc(N)c3)ncnc12] | 4-(3-Amino-benzylamino)-quinazoline-8-carboxylic acid amide | 294 | 0.247 | 1.8 | | |
| 154 | 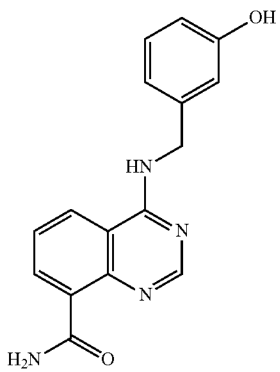 [SMILES: NC(=O)c1cccc2c(NCc3cccc(O)c3)ncnc12] | 4-(3-Hydroxy-benzylamino)-quinazoline-8-carboxylic acid amide | 295 | 0.0243 | 1.9 | 2.5 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 155 | 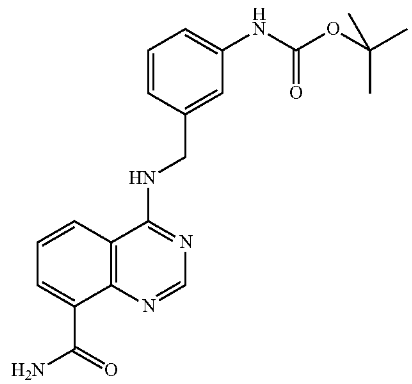 [SMILES: CC(C)(C)OC(=O)Nc1cccc(CNc2ncnc3c(C(N)=O)cccc23)c1] | {3-[(8-Carbamoyl-quinazolin-4-ylamino)-methyl]-phenyl}-carbamic acid tert-butyl ester | 394 | 0.256 | 0.57 | | |
| 156 | 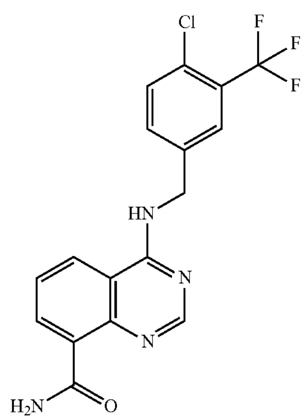 [SMILES: NC(=O)c1cccc2c(NCc3ccc(Cl)c(C(F)(F)F)c3)ncnc12] | 4-(4-Chloro-3-trifluoromethyl-benzylamino)-quinazoline-8-carboxylic acid amide | 382 | 0.0012 | 0.74 | 0.5 | |

TABLE 1-continued

| No. | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|
| 157 | 4-(3,5-Bis-trifluoromethyl-benzylamino)-quinazoline-8-carboxylic acid amide | 415 | 0.268 | 1.5 | | |
| 158 | 4-[(Benzo[1,3]dioxol-5-ylmethyl)-amino]-quinoline-8-carboxylic acid amide | 322 | 0.706 | 5.2 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 159 | 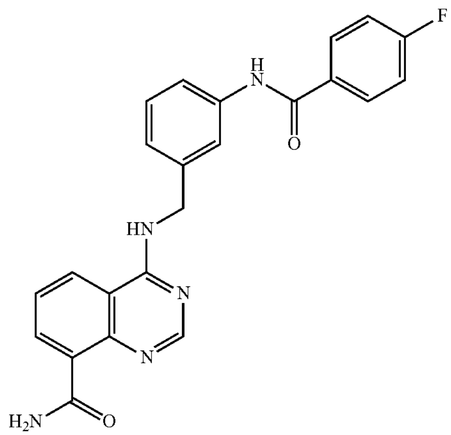 [SMILES: NC(=O)c1cccc2c(NCc3cccc(NC(=O)c4ccc(F)cc4)c3)ncnc12] | 4-[3-(4-Fluoro-benzoylamino)-benzylamino]-quinazoline-8-carboxylic acid amide | 416 | 0.0143 | 0.58 | 0.33 | |
| 160 | 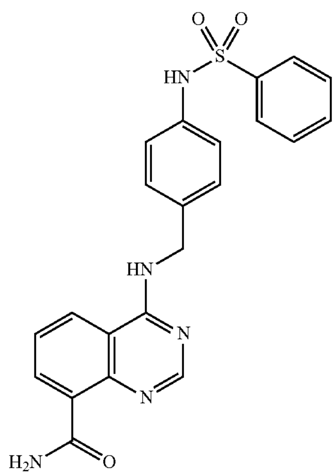 [SMILES: NC(=O)c1cccc2c(NCc3ccc(NS(=O)(=O)c4ccccc4)cc3)ncnc12] | 4-(4-Benzenesulfonylamino-benzylamino)-quinazoline-8-carboxylic acid amide | 434 | 0.285 | 4.2 | | |

TABLE 1-continued

| No. | Structure | Chemical Name | MS (M + 1) | p70S6K binding IC50 [μM] | Aurora A binding IC50 [μM] | Aurora B binding IC50 [μM] | PDK1 binding IC50 [μM] |
|---|---|---|---|---|---|---|---|
| 161 | 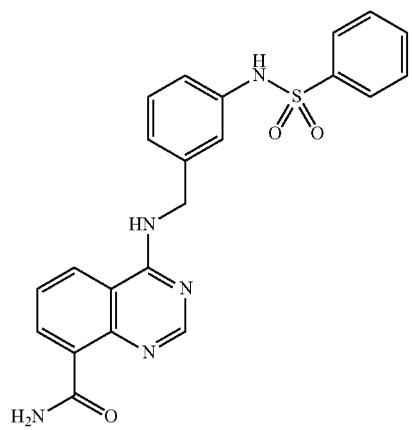 [SMILES: NC(=O)c1cccc2c(NCc3cccc(NS(=O)(=O)c4ccccc4)c3)ncnc12] | 4-(3-Benzenesulfonylamino-benzylamino)-quinazoline-8-carboxylic acid amide | 434 | 0.524 | 4.9 | | |
| 162 | 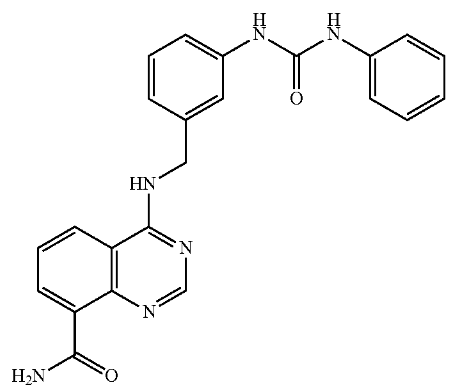 [SMILES: NC(=O)c1cccc2c(NCc3cccc(NC(=O)Nc4ccccc4)c3)ncnc12] | 4-[3-(3-Phenyl-ureido)-benzylamino]-quinazoline-8-carboxylic acid amide | 413 | 0.152 | 0.0016 | 0.0015 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 163 | 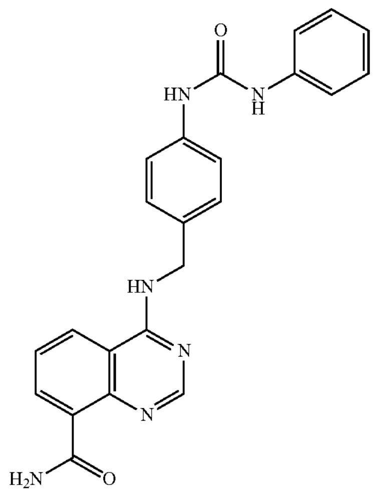 [SMILES: NC(=O)c1cccc2c(NCc3ccc(NC(=O)Nc4ccccc4)cc3)ncnc12] | 4-[4-(3-Phenyl-ureido)-benzylamino]-quinazoline-8-carboxylic acid amide | 413 | >18.5 | 0.41 | | |
| 164 | 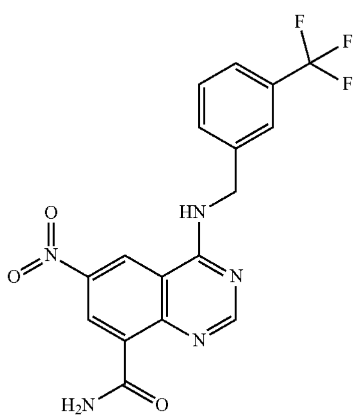 [SMILES: NC(=O)c1cc([N+](=O)[O-])cc2c(NCc3cccc(C(F)(F)F)c3)ncnc12] | 6-Nitro-4-(3-trifluoromethyl-benzylamino)-quinazoline-8-carboxylic acid amide | 392 | 16.8 | 5.9 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 165 | 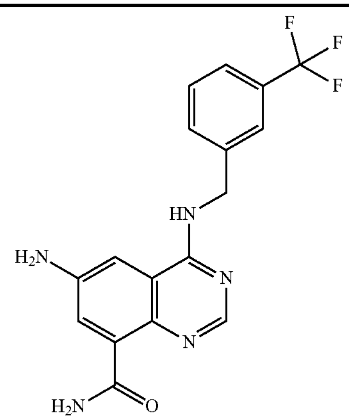 | 6-Amino-4-(3-trifluoromethyl-benzylamino)-quinazoline-8-carboxylic acid amide | 362 | 0.371 | 1.2 | | |
| 166 | 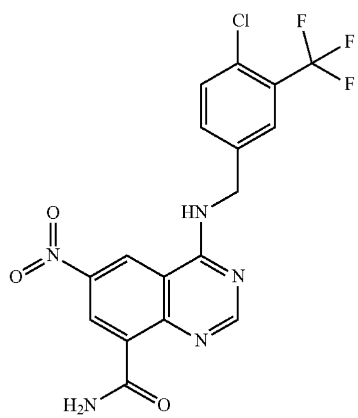 [SMILES: NC(=O)c1cc([N+](=O)[O-])cc2c(NCc3ccc(Cl)c(C(F)(F)F)c3)ncnc12] | 4-(4-Chloro-3-trifluoromethyl-benzylamino)-6-nitroquinazoline-8-carboxylic acid amide | 427 | >24.6 | 10 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 167 | 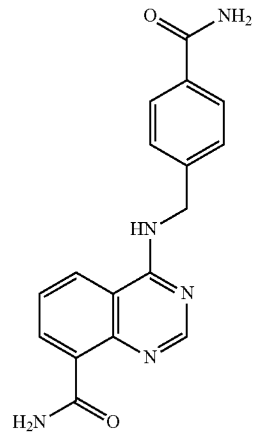 [SMILES: NC(=O)c1ccc(CNc2ncnc3c(C(N)=O)cccc23)cc1] | 4-(4-Carbamoyl-benzylamino)-quinazoline-8-carboxylic acid amide | 322 | 0.394 | 10 | | |
| 168 | 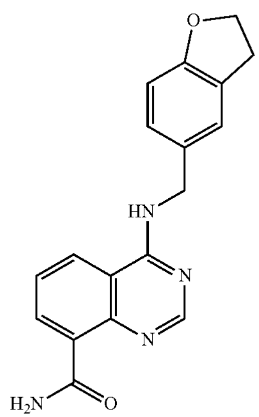 [SMILES: NC(=O)c1cccc2c(NCc3ccc4occc4c3)ncnc12] | 4-[(2,3-Dihydro-benzofuran-5-ylmethyl)-amino]-quinazoline-8-carboxylic acid amide | 321 | 0.0132 | 0.66 | | |

TABLE 1-continued

| No. | Structure | Chemical Name | MS (M + 1) | p70S6K binding IC50 [µM] | Aurora A binding IC50 [µM] | Aurora B binding IC50 [µM] | PDK1 binding IC50 [µM] |
|---|---|---|---|---|---|---|---|
| 169 | 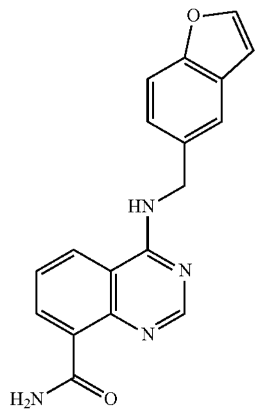 | 4-[(Benzofuran-5-ylmethyl)-amino]-quinazoline-8-carboxylic acid amide | 319 | 0.0142 | 1 | | |
| 170 | 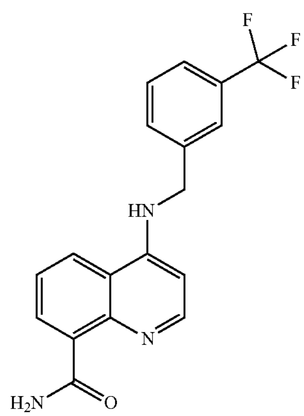 [SMILES: NC(=O)c1cccc2c(NCc3cccc(C(F)(F)F)c3)ccnc12] | 4-(3-Trifluoromethyl-benzylamino)-quinoline-8-carboxylic acid amide | 346 | 0.132 | 0.0039 | 0.012 | |

TABLE 1-continued

| No. | Chemical Name | Structure | MS (M + 1) | p70S6 K binding IC50 [µM] | Aurora A binding IC50 [µM] | Aurora B binding IC50 [µM] | PDK1 binding IC50 [µM] |
|---|---|---|---|---|---|---|---|
| 171 | 4-((R)-1-Phenyl-ethylamino)-quinazoline-8-carboxylic acid amide | 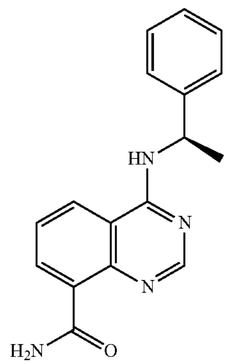 [SMILES: C[C@@H](Nc1ncnc2c(C(N)=O)cccc12)c1ccccc1] | 293 | 0.0850 | 0.002 | 0.00082 | |
| 172 | 6-Amino-4-(4-chloro-3-trifluoromethyl-benzylamino)-quinazoline-8-carboxylic acid amide | 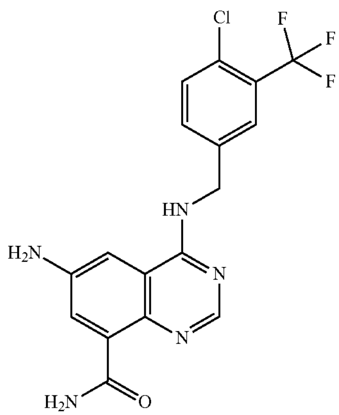 [SMILES: NC(=O)c1cc(N)cc2c(NCc3ccc(Cl)c(C(F)(F)F)c3)ncnc12] | 397 | 0.0723 | 0.0049 | 0.013 | |

TABLE 1-continued
| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 173 | 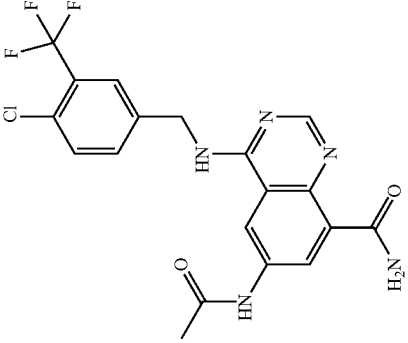 | 6-Acetylamino-4-(4-chloro-3-trifluoromethyl-benzylamino)-quinazoline-8-carboxylic acid amide | 439 | 0.141 | 3.6 | | |
| 174 | 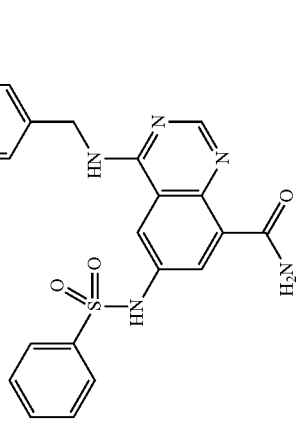 | 6-Benzenesulfonylamino-4-(4-chloro-3-trifluoromethyl-benzylamino)-quinazoline-8-carboxylic acid amide | 537 | 3.13 | 3.4 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 175 | 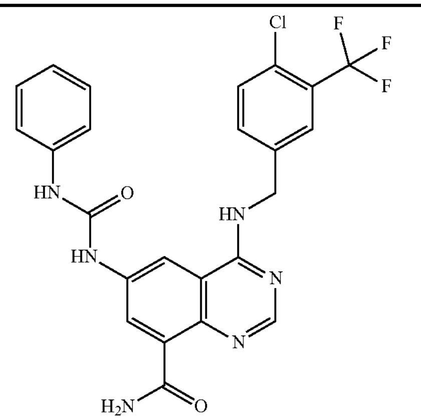 | 4-(4-Chloro-3-trifluoromethyl-benzylamino)-6-(3-phenyl-ureido)-quinazoline-8-carboxylic acid amide | 516 | >36.4 | 6.8 | | |
| 176 | 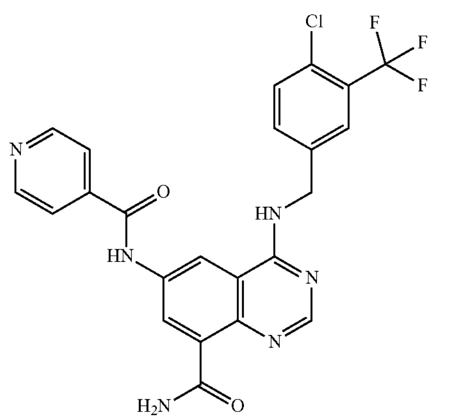 [SMILES: NC(=O)c1cc(NC(=O)c2ccncc2)cc2c(NCc3ccc(Cl)c(C(F)(F)F)c3)ncnc12] | 4-(4-Chloro-3-trifluoromethyl-benzylamino)-6-[(pyridine-4-carbonyl)-amino]-quinazoline-8-carboxylic acid amide | 502 | 0.356 | 0.95 | 0.68 | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 177 | 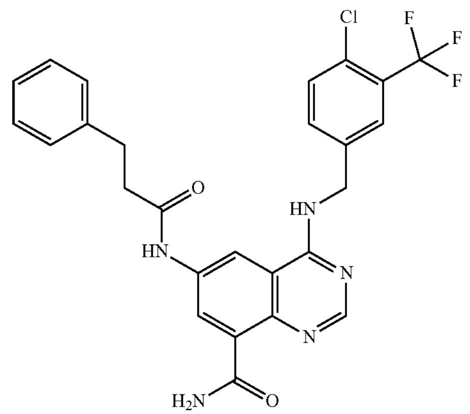 [SMILES: NC(=O)c1cc(NC(=O)CCc2ccccc2)cc2c(NCc3ccc(Cl)c(C(F)(F)F)c3)ncnc12] | 4-(4-Chloro-3-trifluoromethyl-benzylamino)-6-(3-phenyl-propionylamino)-quinazoline-8-carboxylic acid amide | 529 | 16.2 | 3.4 | | |
| 178 | 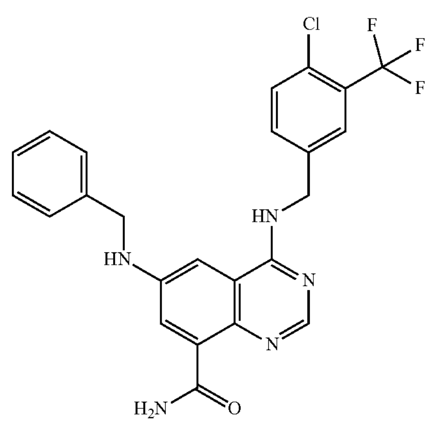 [SMILES: NC(=O)c1cc(NCc2ccccc2)cc2c(NCc3ccc(Cl)c(C(F)(F)F)c3)ncnc12] | 6-Benzylamino-4-(4-chloro-3-trifluoromethyl-benzylamino)-quinazoline-8-carboxylic acid amide | 487 | 1.65 | 1.2 | | |

TABLE 1-continued

| No. | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|
| 179 | 4-(4-Chloro-3-trifluoromethyl-benzylamino)-6-[(isoxazole-5-carbonyl)-amino]-quinazoline-8-carboxylic acid amide | 492 | 5.55 | 0.34 | | |
| 180 | 4-[8-Carbamoyl-4-(4-chloro-3-trifluoromethyl-benzylamino)-quinazolin-6-ylcarbamoyl]-benzenesulfonyl fluoride | 583 | 4.46 | 0.11 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 181 | 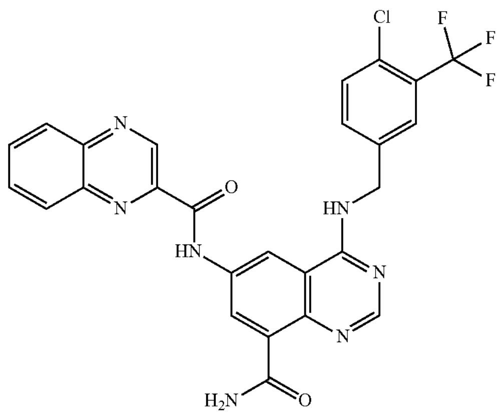 [SMILES: NC(=O)c1cc(NC(=O)c2cnc3ccccc3n2)cc2c(NCc3ccc(Cl)c(C(F)(F)F)c3)ncnc12] | 4-(4-Chloro-3-trifluoromethyl-benzylamino)-6-[(quinoxaline-2-carbonyl)-amino] quinazoline-8-carboxylic acid amide | 553 | 22.1 | 10 | | |
| 182 | 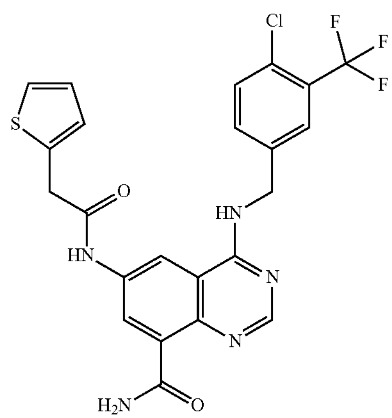 [SMILES: NC(=O)c1cc(NC(=O)Cc2cccs2)cc2c(NCc3ccc(Cl)c(C(F)(F)F)c3)ncnc12] | 4-(4-Chloro-3-trifluoromethyl-benzyl-amino)-6-(2-thiophen-2-yl-acetylamino)-quinazoline-8-carboxylic acid amide | 520 | 2.51 | 7.3 | | |

TABLE 1-continued

| No. | Structure | Chemical Name | MS (M + 1) | p70S6 K binding IC50 [μM] | Aurora A binding IC50 [μM] | Aurora B binding IC50 [μM] | PDK1 binding IC50 [μM] |
|---|---|---|---|---|---|---|---|
| 183 | 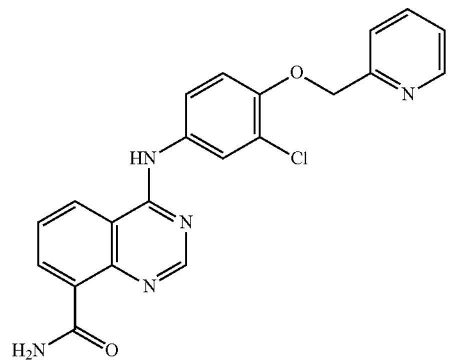 [SMILES: NC(=O)c1cccc2c(Nc3ccc(OCc4ccccn4)c(Cl)c3)ncnc12] | 4-[3-Chloro-4-(pyridin-2-ylmethoxy)-phenylamino]-quinazoline-8-carboxylic acid amide | 407 | 0.828 | 1 | | |

TABLE 2

| No. | MS (M+1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 184 | 352 | 0.2300 | | | 0.00012 | 6-Methoxy-4-(2-methyl-amino-1-phenyl-ethylamino)-quinazoline-8-carboxylic acid amide | 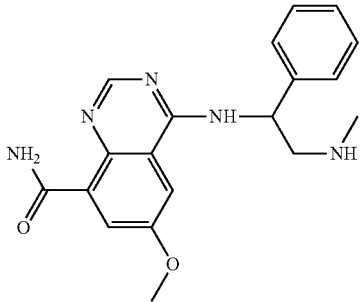 [SMILES: CNCC(Nc1ncnc2c(C(N)=O)cc(OC)cc12)c1ccccc1] |
| 185 | 404 | 1 | | | 0.00014 | 4-[2-Dimethyl-amino-1-(4-trifluoro-methyl-phenyl)-ethylamino]-quinazoline-8-carboxylic acid amide | 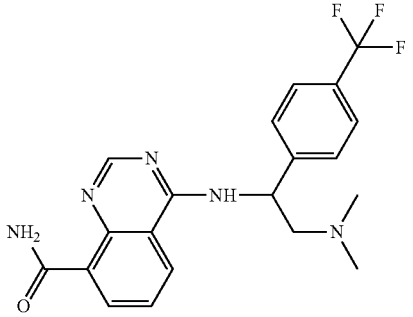 [SMILES: CN(C)CC(Nc1ncnc2c(C(N)=O)cccc12)c1ccc(C(F)(F)F)cc1] |
| 186 | 322 | 0.2200 | | | 0.00028 | 4-((R)-2-Methyl-amino-1-phenyl-ethylamino)-quinazoline-8-carboxylic acid amide | 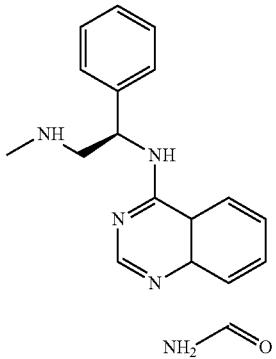 |
| 187 | 391 | 0.5400 | | | 0.00036 | 4-[1-(3,4-Dichloro-phenyl)-2-methyl-amino-ethylamino]-quinazoline-8-carboxylic acid amide | 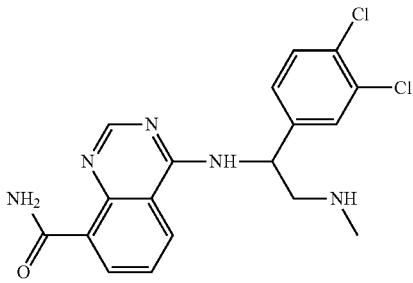 [SMILES: CNCC(Nc1ncnc2c(C(N)=O)cccc12)c1ccc(Cl)c(Cl)c1] |

TABLE 2-continued

| No. | MS (M+1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 188 | 338 | 0.0480 | | | 0.00039 | 4-((S)-2-Amino-1-phenyl-ethylamino)-6-methoxy-quinazoline-8-carboxylic acid amide | 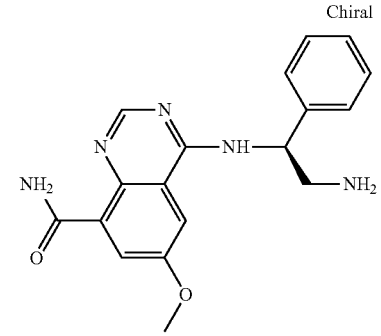 [SMILES: COc1cc(C(N)=O)c2ncnc(N[C@H](CN)c3ccccc3)c2c1] |
| 189 | 477 | 0.00044 | | | 0.00042 | 4-{1-[3-(3,4-Difluoro-benzoyl-amino)-phenyl]-2-methyl-amino-ethylamino}-quinazoline-8-carboxylic acid amide | 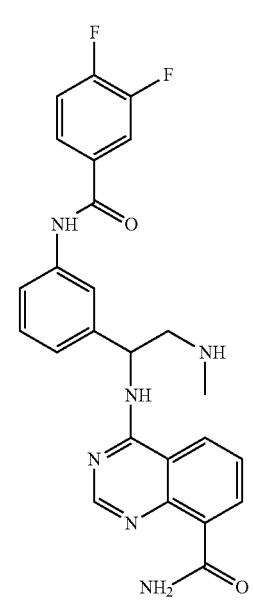 [SMILES: CNCC(Nc1ncnc2c(C(N)=O)cccc12)c1cccc(NC(=O)c2ccc(F)c(F)c2)c1] |
| 190 | 370 | 0.4800 | | | 0.00042 | 4-[1-(3-Fluoro-phenyl)-2-methyl-amino-ethylamino]-6-methoxy-quinazoline-8-carboxylic acid amide | 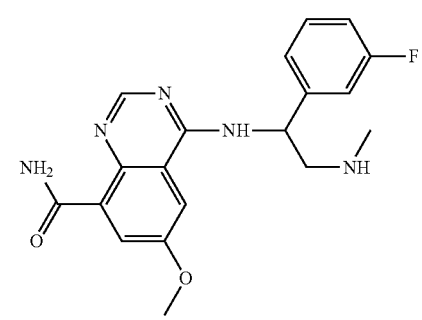 [SMILES: CNCC(Nc1ncnc2c(C(N)=O)cc(OC)cc12)c1cccc(F)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 193 | 307 | | | | 0.00053 | 4-(3,4-Dimethyl-benzyl-amino)-quinazoline-8-carboxylic acid amide | 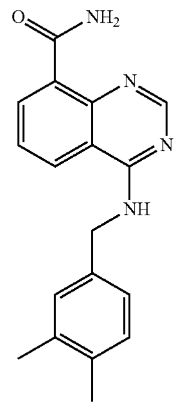 [SMILES: Cc1ccc(CNc2ncnc3c(C(N)=O)cccc23)cc1C] |
| 194 | 523 | 0.00026 | | | 0.00055 | 4-{2-Dimethyl-amino-1-[3-(4-trifluoro-methyl-benzoyl-amino)-phenyl]-ethylamino}-quinazoline-8-carboxylic acid amide | 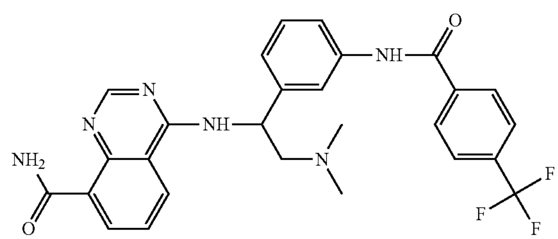 [SMILES: CN(C)CC(Nc1ncnc2c(C(N)=O)cccc12)c1cccc(NC(=O)c2ccc(C(F)(F)F)cc2)c1] |
| 195 | 473 | 0.00076 | | | 0.00058 | 4-{2-Dimethyl-amino-1-[3-(2-fluoro-benzoyl-amino)-phenyl]-ethylamino}-quinazoline-8-carboxylic acid amide | 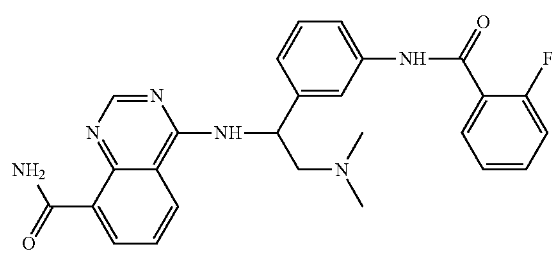 [SMILES: CN(C)CC(Nc1ncnc2c(C(N)=O)cccc12)c1cccc(NC(=O)c2ccccc2F)c1] |
| 196 | 519/520 | 0.00017 | | | 0.00061 | 4-{1-[3-(4-Bromo-benzoyl-amino)-phenyl]-2-methyl-amino-ethylamino}-quinazoline-8-carboxylic acid amide | 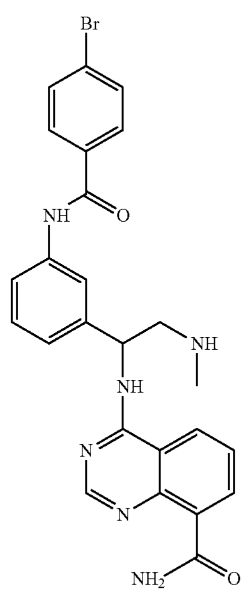 [SMILES: CNCC(Nc1ncnc2c(C(N)=O)cccc12)c1cccc(NC(=O)c2ccc(Br)cc2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 197 | 533-535 | 0.00058 | | | 0.00065 | 4-{1-[3-(4-Bromo-benzoyl-amino)-phenyl]-2-dimethyl-amino-ethylamino}-quinazoline-8-carboxylic acid amide |
| 199 | 356 | 0.0940 | | | 0.00066 | 4-[1-(3-Chloro-phenyl)-2-methyl-amino-ethylamino]-quinazoline-8-carboxylic acid amide |
| 201 | 525 | 0.00027 | 0.0014 | | 0.00068 | 4-(2-Dimethyl-amino-1-{3-[(2-pyrrolidin-1-yl-pyridine-4-carbonyl)-amino]-phenyl}-ethylamino)-quinazoline-8-carboxylic acid amide |
| 202 | 370 | 0.1000 | | | 0.00068 | 4-[(S)-1-(3-Fluoro-phenyl)-2-methyl-amino-ethylamino]-6-methoxy-quinazoline-8-carboxylic acid amide |
| 204 | 386 | 0.2100 | | | 0.00072 | 4-[1-(3-Chloro-phenyl)-2-methyl-amino-ethylamino]-6-methoxy-quinazoline-8-carboxylic acid amide |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 205 | 404 | 0.1400 | | 0.00079 | | 4-[1-(3,4-Dichloro-phenyl)-2-dimethyl-amino-ethylamino]-quinazoline-8-carboxylic acid amide | 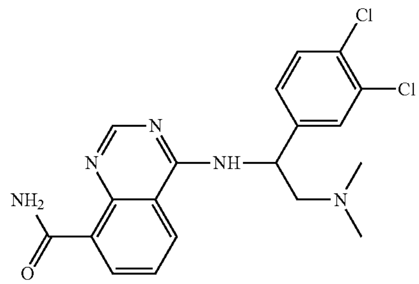 [SMILES: CN(C)CC(Nc1ncnc2c(C(N)=O)cccc12)c1ccc(Cl)c(Cl)c1] |
| 206 | 539 | 0.00061 | | 0.0008 | | 4-(2-Dimethyl-amino-1-{3-[(3,4,5,6-tetrahydro-2H-[1,2']bi-pyridinyl-4'-carbonyl)-amino]-phenyl}-ethylamino)-quinazoline-8-carboxylic acid amide | 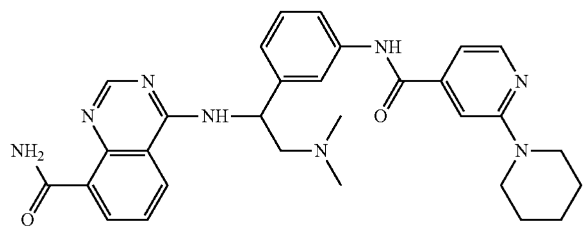 [SMILES: CN(C)CC(Nc1ncnc2c(C(N)=O)cccc12)c1cccc(NC(=O)c2ccnc(N3CCCCC3)c2)c1] |
| 207 | 491 | 0.0013 | | 0.00081 | | 4-(1-{3-[(2-Chloro-pyridine-4-carbonyl)-amino]-phenyl}-2-dimethyl-amino-ethylamino)-quinazoline-8-carboxylic acid amide | 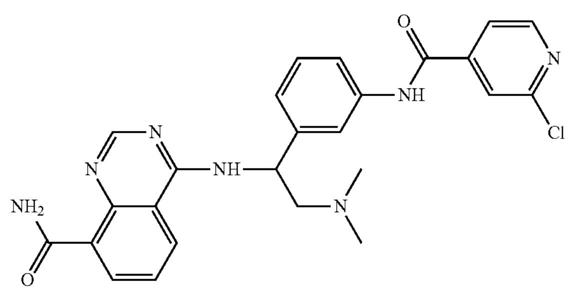 [SMILES: CN(C)CC(Nc1ncnc2c(C(N)=O)cccc12)c1cccc(NC(=O)c2ccnc(Cl)c2)c1] |
| 208 | 441 | 0.00074 | | 0.00082 | | 4-[1-(3-Benzoyl-amino-phenyl)-2-methyl-amino-ethylamino]-quinazoline-8-carboxylic acid amide | 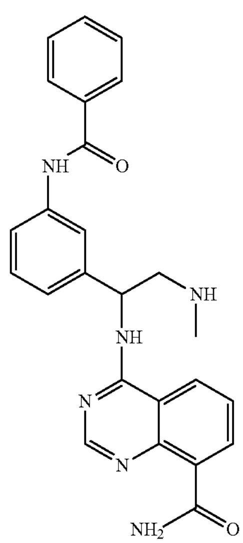 [SMILES: CNCC(Nc1ncnc2c(C(N)=O)cccc12)c1cccc(NC(=O)c2ccccc2)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 209 | 477 | 0.0010 | | 0.00084 | | 4-{1-[3-(2,6-Difluoro-benzoyl-amino)-phenyl]-2-methyl-amino-ethylamino}-quinazoline-8-carboxylic acid amide | 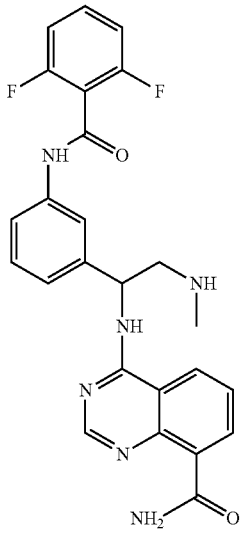 [SMILES: CNCC(Nc1ncnc2c(C(N)=O)cccc12)c1cccc(NC(=O)c2c(F)cccc2F)c1] |
| 210 | 416 | 0.4800 | | 0.00089 | | 4-[1-(3-Bromo-phenyl)-2-dimethyl-amino-ethylamino]-quinazoline-8-carboxylic acid amide | 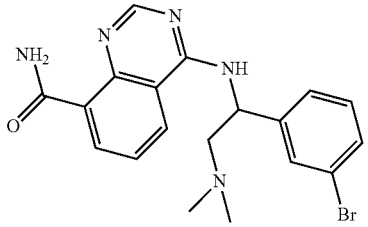 [SMILES: CN(C)CC(Nc1ncnc2c(C(N)=O)cccc12)c1cccc(Br)c1] |
| 211 | 340 | 0.2300 | | 0.00095 | | 4-[1-(3-Fluoro-phenyl)-2-methyl-amino-ethylamino]-quinazoline-8-carboxylic acid amide | 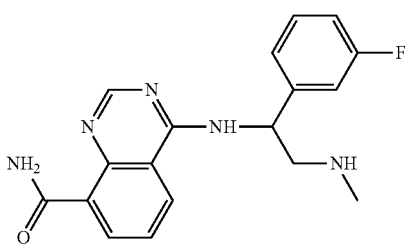 [SMILES: CNCC(Nc1ncnc2c(C(N)=O)cccc12)c1cccc(F)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 212 | 489 | 0.0011 | | 0.00099 | | 4-{1-[3-(3-Fluoro-4-methoxy-benzoyl-amino)-phenyl]-2-methyl-amino-ethylamino}-quinazoline-8-carboxylic acid amide | 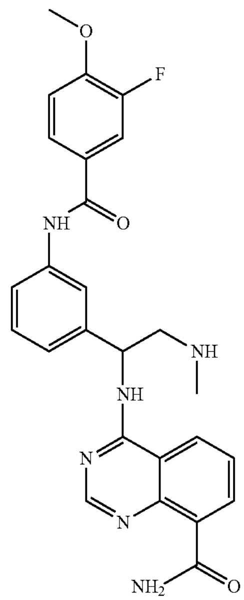 [SMILES: CNCC(Nc1ncnc2c(C(N)=O)cccc12)c1cccc(NC(=O)c2ccc(OC)c(F)c2)c1] |
| 213 | 541 | 0.00025 | | 0.0010 | | 4-{2-Dimethyl-amino-1-[3-(2-fluoro-4-trifluoro-methyl-benzoyl-amino)-phenyl]-ethylamino}-quinazoline-8-carboxylic acid amide | 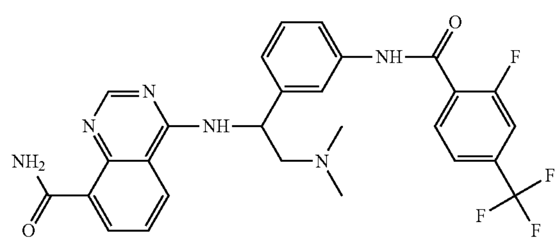 [SMILES: CN(C)CC(Nc1ncnc2c(C(N)=O)cccc12)c1cccc(NC(=O)c2ccc(C(F)(F)F)cc2F)c1] |
| 214 | 499 | 0.0049 | | 0.0010 | | 4-(2-Dimethyl-amino-1-{3-[(2-dimethyl-amino-pyridine-4-carbonyl)-amino]-phenyl}-ethylamino)-quinazoline-8-carboxylic acid amide | 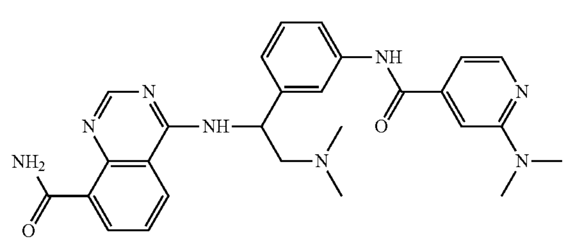 [SMILES: CN(C)CC(Nc1ncnc2c(C(N)=O)cccc12)c1cccc(NC(=O)c2ccnc(N(C)C)c2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 215 | 471 | 0.00024 | | | 0.0011 | 4-{1-[3-(4-Methoxy-benzoyl-amino)-phenyl]-2-methyl-amino-ethylamino}-quinazoline-8-carboxylic acid amide |
| 216 | 525 | 0.00084 | | | 0.0011 | 4-(2-Dimethyl-amino-1-{3-[(5-pyrrolidin-1-yl-pyridine-3-carbonyl)-amino]-phenyl}-ethylamino)-quinazoline-8-carboxylic acid amide |
| 217 | 370 | 0.3800 | | | 0.0011 | 4-[1-(3-Chloro-phenyl)-2-dimethyl-amino-ethylamino]-quinazoline-8-carboxylic acid amide |

TABLE 2-continued

| No. | MS (M+ 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 219 | 485 | 0.00067 | | 0.0013 | | 4-{2-Dimethyl-amino-1-[3-(4-methoxy-benzoyl-amino)-phenyl]-ethylamino}-quinazoline-8-carboxylic acid amide | 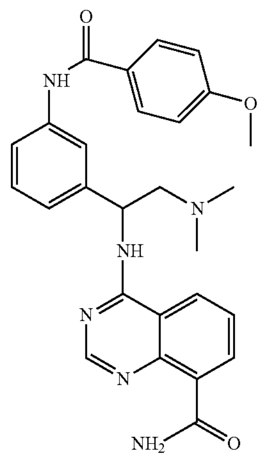 [SMILES: COc1ccc(C(=O)Nc2cccc(C(CN(C)C)Nc3ncnc4c(C(N)=O)cccc34)c2)cc1] |
| 221 | 353 | 0.6700 | | 0.0013 | | 5-Methoxy-4-(2-methyl-amino-1-phenyl-ethylamino)-quinazoline-8-carboxylic acid amide | 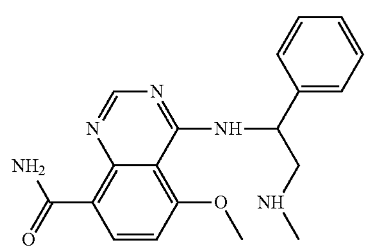 [SMILES: CNCC(Nc1ncnc2c(C(N)=O)ccc(OC)c12)c1ccccc1] |
| 222 | 352 | 2.400 | | 0.0013 | | 4-[1-(4-Methoxy-phenyl)-2-methyl-amino-ethyl-amino]-quinazoline-8-carboxylic acid amide | 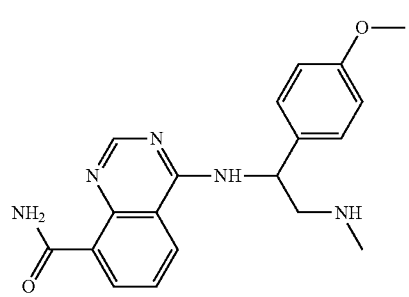 [SMILES: CNCC(Nc1ncnc2c(C(N)=O)cccc12)c1ccc(OC)cc1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 223 | 525 | 0.00017800 | | 0.0014 | | 4-{2-Methyl-amino-1-(3-{4-trifluoro-methoxy-benzoyl-amino)-phenyl]-ethylamino}-quinazoline-8-carboxylic acid amide | 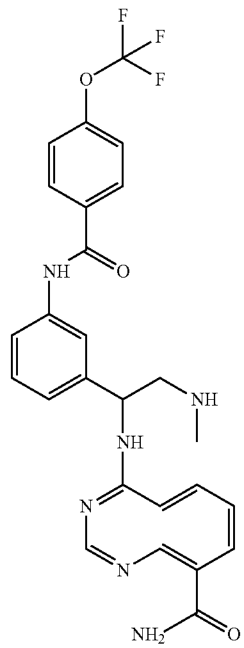 [SMILES: CNCC(Nc1ccccc(C(N)=O)cncn1)c1cccc(NC(=O)c2ccc(OC(F)(F)F)cc2)c1] |
| 224 | 400 | 0.38000 | | 0.0014 | | 4-[1-(4-Chloro-phenyl)-2-dimethyl-amino-ethylamino]-6-methoxy-quinazoline-8-carboxylic acid amide | 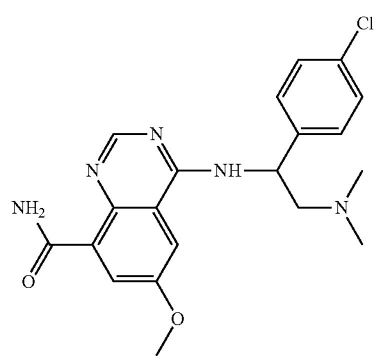 [SMILES: COc1cc(C(N)=O)c2ncnc(NC(CN(C)C)c3ccc(Cl)cc3)c2c1] |
| 225 | 445 | 0.00120 | | 0.0015 | | 4-{2-Amino-1-[3-(4-fluoro-benzoyl-amino)-phenyl]-ethylamino}-quinazoline-8-carboxylic acid amide | 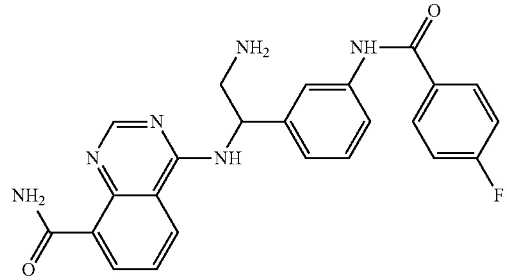 [SMILES: NCC(Nc1ncnc2c(C(N)=O)cccc12)c1cccc(NC(=O)c2ccc(F)cc2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 228 | 489 | 0.00034 | | 0.0021 | | 4-{1-[3-{2-Fluoro-4-methoxy-benzoyl-amino)-phenyl]-2-methyl-amino-ethylamino}-quinazoline-8-carboxylic acid amide |
| 229 | 539 | 0.00110 | | 0.0021 | | 4-[2-Dimethyl-amino-1-(3-{[2-(2-methyl-pyrrolidin-1-yl)-pyridine-4-carbonyl]-amino}-phenyl)-ethylamino]-quinazoline-8-carboxylic acid amide |
| 230 | 352 | | | 0.0022 | | 6-Methoxy-4-((S)-2-methyl-amino-1-phenyl-ethylamino)-quinazoline-8-carboxylic acid amide |

TABLE 2-continued

| No. | MS (M+1) | Aurora A binding, IC50 [µM] | Aurora B binding, IC50 [µM] | p70S6K binding, IC50 [µM] | PDK1 binding, IC50 [µM] | Chemical Name |
|---|---|---|---|---|---|---|
| 231 | 596 | 0.01900 | | | 0.0024 | 4-[1-(3-{[2-(3-Diethyl-amino-pyrrolidin-1-yl)-pyridine-4-carbonyl]-amino}-phenyl)-2-dimethyl-amino-ethylamino]-quinazoline-8-carboxylic acid amide |
| 233 | 503 | 0.00130 | 0.0019 | | 0.0026 | 4-{2-Dimethyl-amino-1-[3-(3-fluoro-4-methoxy-benzoyl-amino)-phenyl]-ethylamino}-quinazoline-8-carboxylic acid amide |
| 234 | 498 | 0.00025 | | | 0.0027 | 4-{(R)-1-[3-(2-Fluoro-4-trifluoro-methyl-benzoyl-amino)-phenyl]-ethylamino}-quinazoline-8-carboxylic acid amide |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 235 | 384 | 0.18000 | | 0.0028 | | 4-((S)-2-Ethylamino-1-phenyl-ethylamino)-6-methoxy-quinazoline-8-carboxylic acid amide | 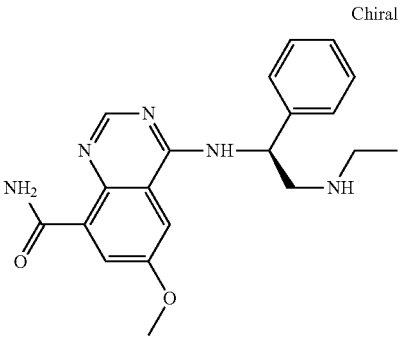 [SMILES: CCNC[C@@H](Nc1ncnc2c(C(N)=O)cc(OC)cc12)c1ccccc1] |
| 236 | 384 | 0.11000 | | 0.0028 | | 4-[(S)-2-Dimethyl-amino-1-(3-fluoro-phenyl)-ethylamino]-6-methoxy-quinazoline-8-carboxylic acid amide | 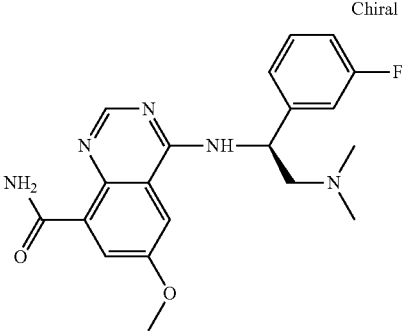 [SMILES: COc1cc(C(N)=O)c2ncnc(N[C@H](CN(C)C)c3cccc(F)c3)c2c1] |
| 237 | 354 | 0.31000 | | 0.0029 | | 4-[(S)-2-Ethylamino-1-(3-fluoro-phenyl)-ethylamino]-quinazoline-8-carboxylic acid amide | 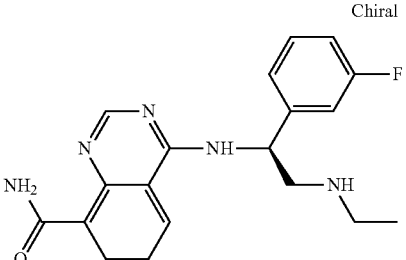 |
| 238 | 574 | 0.00040 | | 0.0032 | | 4-{3-(Allyl-methyl-amino)-1-[3-{4-bromo-benzoyl-amino)-phenyl]-propyl-amino}-quinazoline-8-carboxylic acid amide | 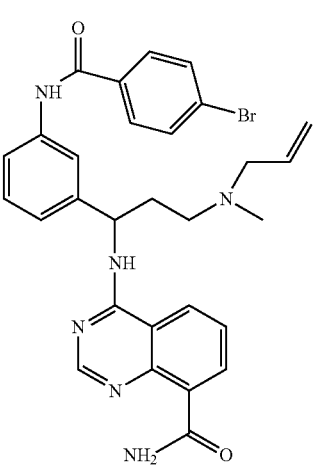 |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 239 | 443 | | 7.0000e−05 | | 0.0033 | 4-((R)-1-{3-[(6-Methoxy-pyridine-3-carbonyl)-amino]-phenyl}-ethylamino)-quinazoline-8-carboxylic acid amide | Chiral |
| 240 | 456 | 0.01500 | 0.00043000 | | 0.0033 | 4-(1-{3-[(Benzo[1,3]dioxole-5-carbonyl)-amino]-phenyl}-ethylamino)-quinazoline-8-carboxylic acid amide | 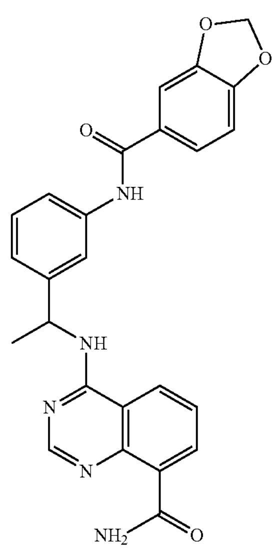 [SMILES: CC(Nc1ncnc2c(C(N)=O)cccc12)c1cccc(NC(=O)c2ccc3c(c2)OCO3)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 241 | 445 | 3.0000e−05 | | 0.0034 | | 4-((R)-1-{3-[(5-Isopropyl-1H-pyrazole-3-carbonyl)-amino]-phenyl}-ethylamino)-quinazoline-8-carboxylic acid amide | 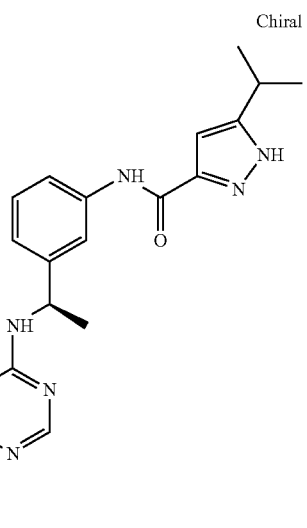 Chiral |
| 242 | 338 | 0.77000 | | 0.0034 | | 4-[2-Amino-1-(3-methoxy-phenyl)-ethylamino]-quinazoline-8-carboxylic acid amide | 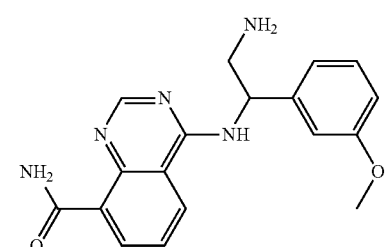 |
| 243 | 467 | 1 | | 0.0034 | | tert-butyl [2-{[8-(amino-carbonyl)quinazolin-4-yl]amino}-2-(3-nitro-phenyl)ethyl]methyl carbamate | 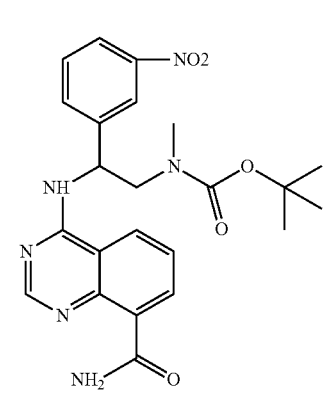 [SMILES: CN(CC(Nc1ncnc2c(C(N)=O)cccc12)c1cccc([N+](=O)[O-])c1)C(=O)OC(C)(C)C] |
| 244 | 434 | 0.00016 | 0.00025 | 0.0035 | | 4-[3-(2,4-Difluoro-benzoyl-amino)-benzyl-amino]-quinazoline-8-carboxylic acid amide | 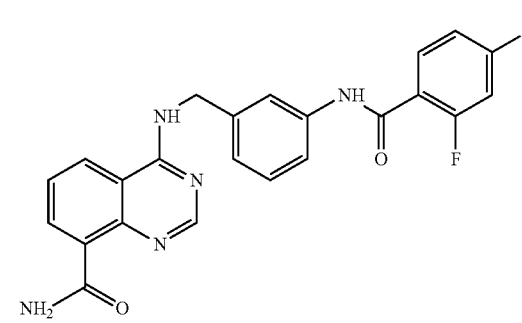 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 245 | 336 | 0.13000 | 0.0024 | | 0.0035 | 4-((S)-2-Dimethyl-amino-1-phenyl-ethylamino)-quinazoline-8-carboxylic acid amide | 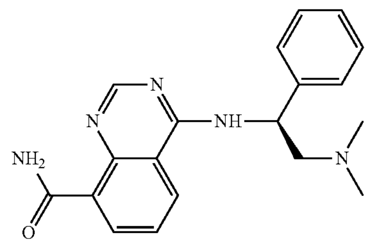 |
| 246 | 444 | 9.0000e−05 | | | 0.0037 | 4-{1-[3-(3-Fluoro-4-methyl-benzoyl-amino)-phenyl]-ethylamino}-quinazoline-8-carboxylic acid amide | 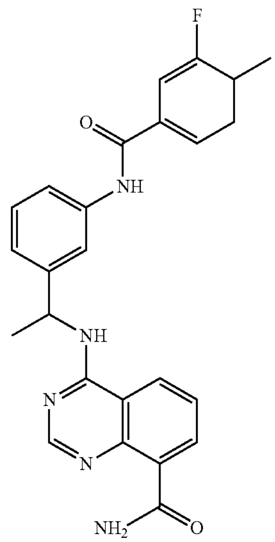 [SMILES: CC1CC=C(C(=O)Nc2cccc(C(C)Nc3ncnc4c(C(N)=O)cccc34)c2)C=C1F] |
| 247 | 446 | 0.00097 | 0.0004 | | 0.0037 | 4-{1-[3-(4-Fluoro-3-hydroxy-benzoyl-amino)-phenyl]-ethylamino}-quinazoline-8-carboxylic acid amide | 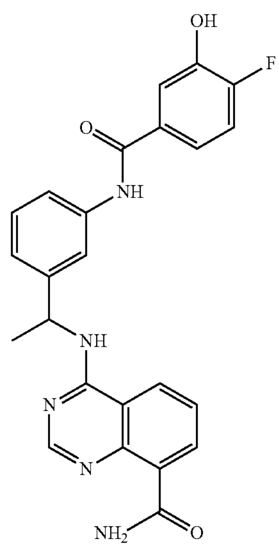 [SMILES: CC(Nc1ncnc2c(C(N)=O)cccc12)c1cccc(NC(=O)c2ccc(F)c(O)c2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 248 | 321.4 | 0.45000 | | | 0.0038 | 4-(2-Methyl-amino-1-phenyl-ethylamino)-quinazoline-8-carboxylic acid amide | 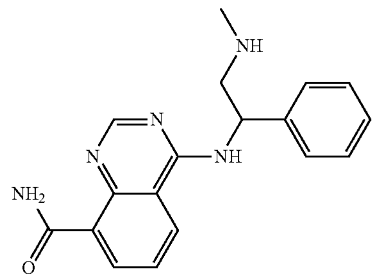 [SMILES: CNCC(Nc1ncnc2c(C(N)=O)cccc12)c1ccccc1] |
| 249 | 505 | 0.00230 | 0.0043 | | 0.0039 | 4-{1-[3-(2,4-Difluoro-benzoyl-amino)-phenyl]-3-dimethyl-amino-propyl-amino}-quinazoline-8-carboxylic acid amide | 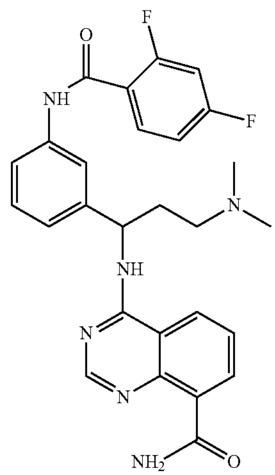 [SMILES: CN(C)CCC(Nc1ncnc2c(C(N)=O)cccc12)c1cccc(NC(=O)c2ccc(F)cc2F)c1] |
| 250 | 467 | 0.00012 | 0.00035 | | 0.0040 | 4-[3-(2,4-Dichloro-benzoyl-amino)-benzyl-amino]-quinazoline-8-carboxylic acid amide | 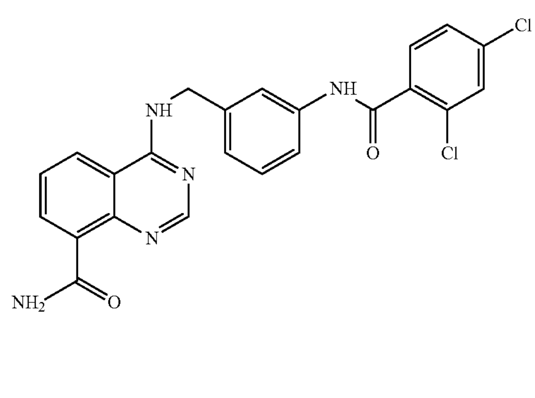 [SMILES: NC(=O)c1cccc2c(NCc3cccc(NC(=O)c4ccc(Cl)cc4Cl)c3)ncnc12] |

TABLE 2-continued
| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 251 | 457 | 0.00033 | | | 0.0040 | 4-(1-{3-[(6-Methoxy-pyridine-3-carbonyl)-amino]-phenyl]-propyl-amino)-quinazoline-8-carboxylic acid amide | 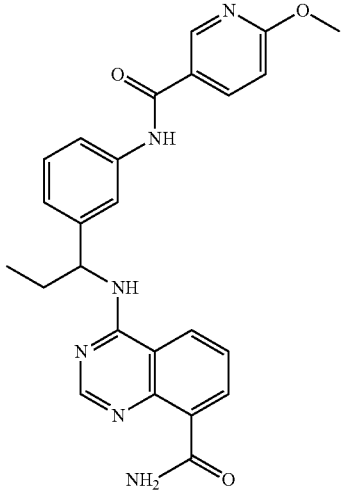 [SMILES: CCC(Nc1ncnc2c(C(N)=O)cccc12)c1cccc(NC(=O)c2ccc(OC)nc2)c1] |
| 252 | 509 | 0.00062400 | | | 0.0040 | 4-{2-Methyl-amino-1-[3-(4-trifluoro-methyl-benzoyl-amino)-phenyl]-ethylamino}-quinazoline-8-carboxylic acid amide | 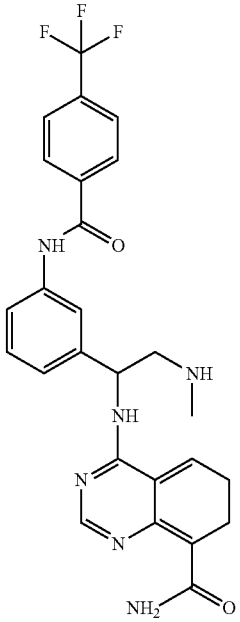 [SMILES: CNCC(Nc1ncnc2c1=CCCC=2C(N)=O)c1cccc(NC(=O)c2ccc(C(F)(F)F)cc2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 253 | 427 | 0.00030 | | | 0.0041 | 4-((R)-1-{3-[(6-Methyl-pyridine-3-carbonyl)-amino]-phenyl}-ethylamino)-quinazoline-8-carboxylic acid amide | 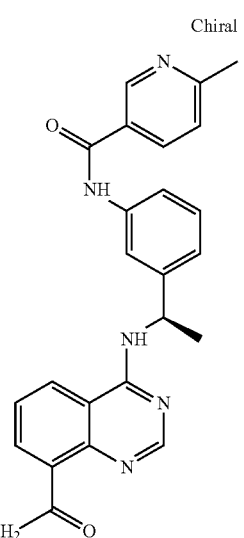 |
| 254 | 537 | 0.00099 | 0.0016 | | 0.0041 | 4-{3-Dimethyl-amino-1-[3-{4-trifluoro-methyl-benzoyl-amino)-phenyl]-propyl-amino}-quinazoline-8-carboxylic acid amide | 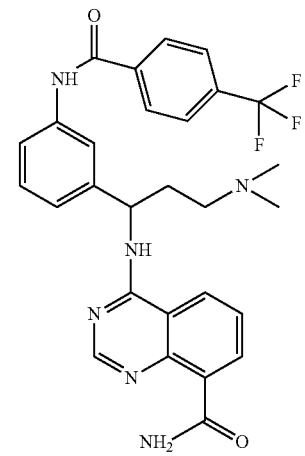 [SMILES: CN(C)CCC(Nc1ncnc2c(C(N)=O)cccc12)c1cccc(NC(=O)c2ccc(C(F)(F)F)cc2)c1] |
| 255 | 492 | 0.00052 | | | 0.0044 | 4-{1-[3-(2,4-Difluoro-benzoyl-amino)-phenyl]-3-methoxy-propyl-amino}-quinazoline-8-carboxylic acid amide | 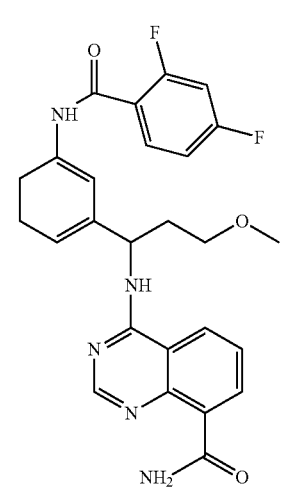 [SMILES: COCCC(Nc1ncnc2c(C(N)=O)cccc12)C1=CCCC(NC(=O)c2ccc(F)cc2F)=C1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 256 | 381 | 1 | | | 0.0044 | 4-{[2-(dimethyl-amino)-1-(3-nitrophenyl)ethyl]amino}quinazoline-8-carbox-amide | 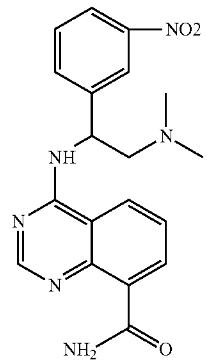 [SMILES: CN(C)CC(Nc1ncnc2c(C(N)=O)cccc12)c1cccc([N+](=O)[O-])c1] |
| 257 | 332 | | | 0.0044 | 79 | 4-[2-(1H-Indol-3-yl)-ethylamino]-quinazoline-8-carboxylic acid amide | 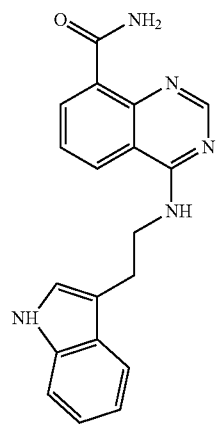 [SMILES: NC(=O)c1cccc2c(NCCc3c[nH]c4ccccc34)ncnc12] |
| 258 | 468 | 0.00034 | 0.0011 | | 0.0045 | 4-{3-[(5-Pyrrolidin-1-yl-pyridine-3-carbonyl)-amino]-benzyl-amino}-quinazoline-8-carboxylic acid amide | 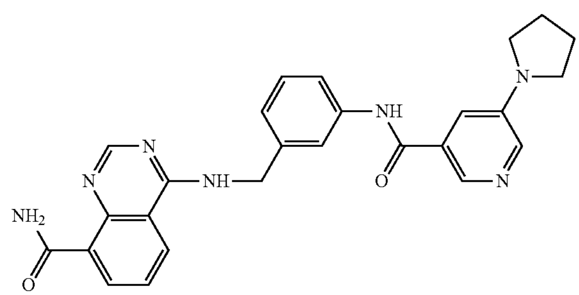 [SMILES: NC(=O)c1cccc2c(NCc3cccc(NC(=O)c4cncc(N5CCCC5)c4)c3)ncnc12] |
| 259 | 424 | 0.05700 | | | 0.0046 | 6-Cyclopropyl methoxy-4-[2-dimethyl-amino-1-(3-fluoro-phenyl)-ethylamino]-quinazoline-8-carboxylic acid amide | 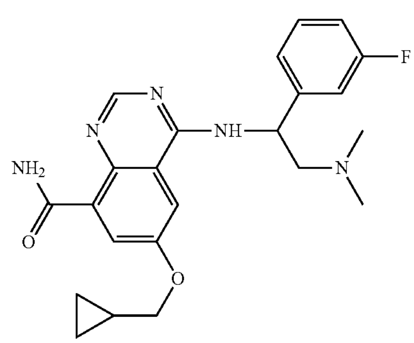 [SMILES: CN(C)CC(Nc1ncnc2c(C(N)=O)cc(OCC3CC3)cc12)c1cccc(F)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 261 | 440 | 0.00027 | | | 0.0048 | 4-{(R)-1-[3-(3,4-Dimethyl-benzoyl-amino)-phenyl]-ethylamino}-quinazoline-8-carboxylic acid amide | 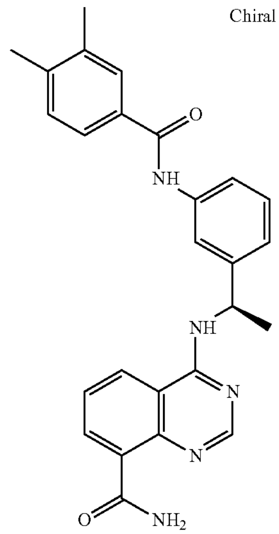 [SMILES: Cc1ccc(C(=O)Nc2cccc([C@@H](C)Nc3ncnc4c(C(N)=O)cccc34)c2)cc1C] |
| 262 | 462 | 0.30000 | | | 0.0049 | 6-Benzyloxy-4-[1-(3-chloro-phenyl)-2-methyl-amino-ethylamino]-quinazoline-8-carboxylic acid amide | 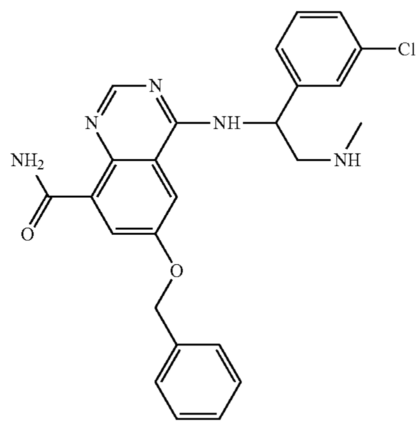 [SMILES: CNCC(Nc1ncnc2c(C(N)=O)cc(OCc3ccccc3)cc12)c1cccc(Cl)c1] |
| 263 | 498 | 0.00011 | | | 0.0050 | 4-[(R)-1-[3-(2-Fluoro-5-trifluoro-methyl-benzoyl-amino)-phenyl]-ethylamino}-quinazoline-8-carboxylic acid amide | 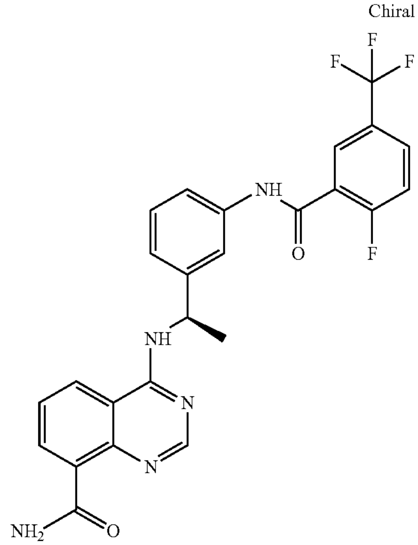 [SMILES: C[C@@H](Nc1ncnc2c(C(N)=O)cccc12)c1cccc(NC(=O)c2cc(C(F)(F)F)ccc2F)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 264 | 472 | 0.00170 | | | 0.0050 | 4-[3-({2-[(2-Hydroxy-ethyl)-methyl-amino]-pyridine-4-carbonyl}-amino)-benzyl-amino)-quinazoline-8-carboxylic acid amide | 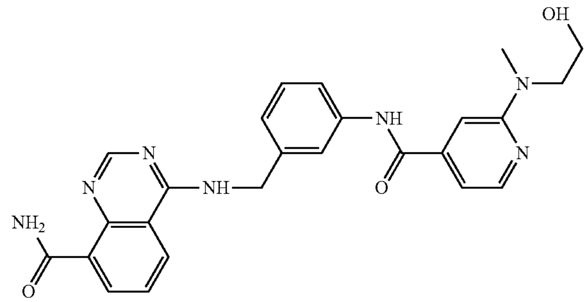 [SMILES: CN(CCO)c1cc(C(=O)Nc2cccc(CNc3ncnc4c(C(N)=O)cccc34)c2)ccn1] |
| 265 | 548 | 0.00012 | 0.00035 | | 0.0051 | 4-{1-[3-(4-Bromo-benzoyl-amino)-phenyl]-3-dimethyl-amino-propyl}-amino}-quinazoline-8-carboxylic acid amide | 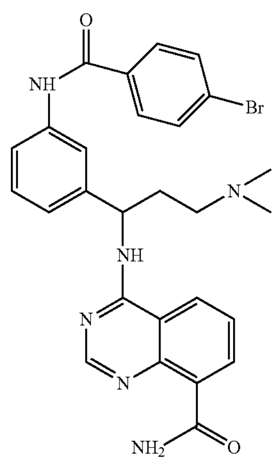 [SMILES: CN(C)CCC(Nc1ncnc2c(C(N)=O)cccc12)c1cccc(NC(=O)c2ccc(Br)cc2)c1] |
| 266 | 438 | | | | 0.0052 | 4-((R)-1-{3-[(6-Cyano-pyridine-3-carbonyl)-amino]-phenyl}-ethylamino)-quinazoline-8-carboxylic acid amide | 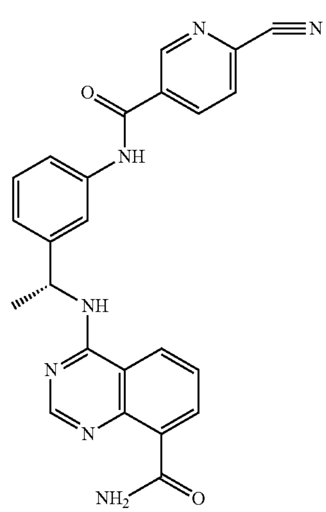 |

TABLE 2-continued
| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 267 | 477/ 479 | | | | 0.0059 | 4-((R)-1-{3-[(5-Chloro-6-methoxy-pyridine-3-carbonyl)-amino]-phenyl}-ethylamino)-quinazoline-8-carboxylic acid amide | 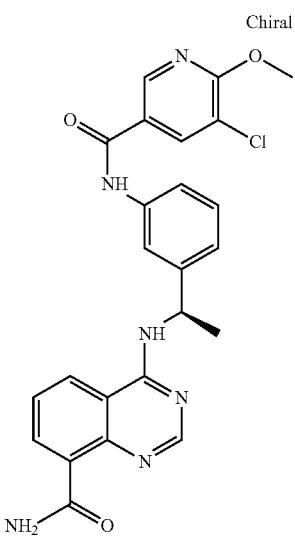 [SMILES: COc1ncc(C(=O)Nc2cccc([C@@H](C)Nc3ncnc4c(C(N)=O)cccc34)c2)cc1Cl] |
| 268 | 458 | 3.0000e−05 | | | 0.0063 | 4-((R)-1-{3-[(5-tert-Butyl-2H-pyrazole-3-carbonyl)-amino]-phenyl}-ethylamino)-quinazoline-8-carboxylic acid amide | 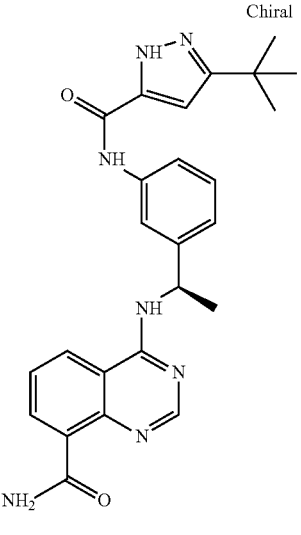 [SMILES: C[C@@H](Nc1ncnc2c(C(N)=O)cccc12)c1cccc(NC(=O)c2cc(C(C)(C)C)n[nH]2)c1] |

TABLE 2-continued
| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 269 | 443 | 0.00022 | | 0.0063 | | 4-((R)-1-{3-[(2-Methoxy-pyridine-4-carbonyl)-amino]-phenyl}-ethylamino)-quinazoline-8-carboxylic acid amide | 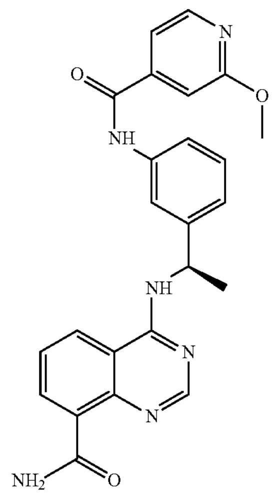 |
| 270 | 456 | | | 0.0065 | | 4-((R)-1-{3-[(Benzo[1,3]dioxole-5-carbonyl)-amino]-phenyl}-ethylamino)-quinazoline-8-carboxylic acid amide | 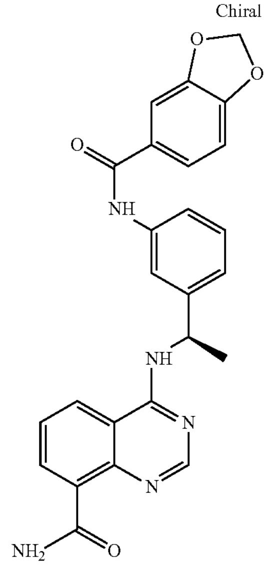 [SMILES: C[C@@H](Nc1ncnc2c(C(N)=O)cccc12)c1cccc(NC(=O)c2ccc3c(c2)OCO3)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 271 | 458 | 8.0000e−05 | 0.0013 | 0.0066 | | 4-(1-{3-[(5-tert-Butyl-2H-pyrazole-3-carbonyl)-amino]-phenyl}-ethylamino)-quinazoline-8-carboxylic acid amide | 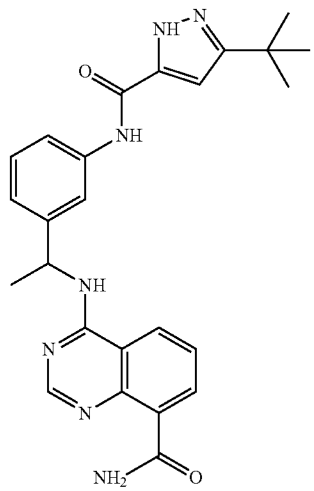 [SMILES: CC(Nc1ncnc2c(C(N)=O)cccc12)c1cccc(NC(=O)c2cc(C(C)(C)C)n[nH]2)c1] |
| 272 | 491 | 0.00026 | 0.00066 | 0.0066 | | 4-{1-[3-(4-Bromo-benzoyl-amino)-phenyl]-ethylamino}-quinazoline-8-carboxylic acid amide | 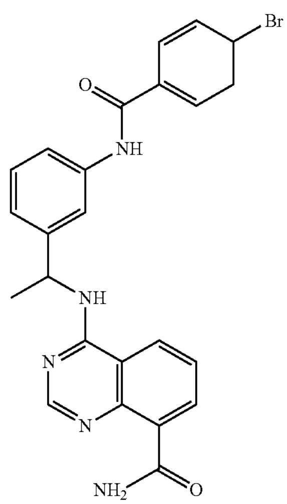 [SMILES: CC(Nc1ncnc2c(C(N)=O)cccc12)c1cccc(NC(=O)C2=CCC(Br)C=C2)c1] |
| 273 | 541 | 0.01300 | | 0.0066 | | [2-(3-Benzoyl-amino-phenyl)-2-(8-carbamoyl-quinazolin-4-ylamino)-ethyl]-methyl-carbamic acid tert-butyl ester | 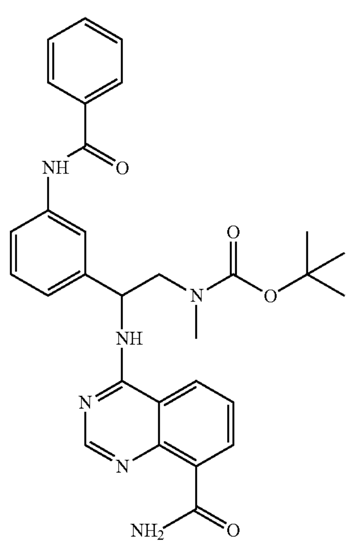 [SMILES: CN(CC(Nc1ncnc2c(C(N)=O)cccc12)c1cccc(NC(=O)c2ccccc2)c1)C(=O)OC(C)(C)C] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 274 | 366 | 0.57000 | | | 0.0068 | 4-[2-Dimethyl-amino-1-(3-methoxy-phenyl)-ethylamino]-quinazoline-8-carboxylic acid amide |
| 275 | 492 | 0.00040 | | | 0.0070 | 4-{1-[3-(2,6-Difluoro-benzoyl-amino)-phenyl]-3-methoxy-propyl-amino}-quinazoline-8-carboxylic acid amide |
| 276 | 460 | 0.00038 | | | 0.0071 | 4-{(R)-1-[3-(4-Chloro-3-methyl-benzoyl-amino)-phenyl]-ethylamino}-quinazoline-8-carboxylic acid amide |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 277 | 398 | 0.09800 | | | 0.0072 | 4-[2-Dimethyl-amino-1-(3-fluoro-phenyl)-ethylamino]-6-ethoxy-quinazoline-8-carboxylic acid amide |
| 278 | 473 | | | | 0.0073 | 4-((R)-1-{3-[(5,6-Dimethoxy-pyridine-3-carbonyl)-amino]-phenyl}-ethylamino)-quinazoline-8-carboxylic acid amide |
| 279 | 336 | 0.67000 | | | 0.0074 | 4-((S)-2-Ethylamino-1-phenyl-ethylamino)-quinazoline-8-carboxylic acid amide |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 280 | 509 | 0.00021 | | 0.0081 | | 4-{1-[3-(4-Bromo-3-fluoro-benzoyl-amino)-phenyl]-ethylamino}-quinazoline-8-carboxylic acid amide | 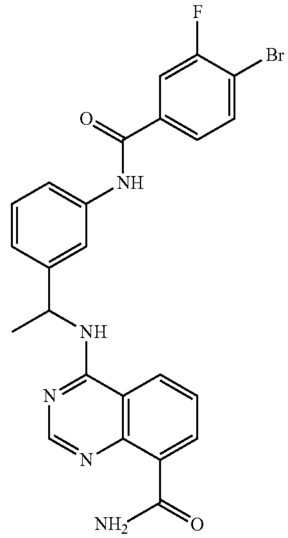 [SMILES: CC(Nc1ncnc2c(C(N)=O)cccc12)c1cccc(NC(=O)c2ccc(Br)c(F)c2)c1] |
| 281 | 442 | 0.00039 | | 0.0081 | | 4-[1-(3-Benzoyl-amino-phenyl)-2-methoxy-ethylamino]-quinazoline-8-carboxylic acid amide | 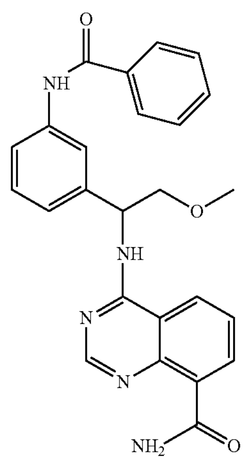 [SMILES: COCC(Nc1ncnc2c(C(N)=O)cccc12)c1cccc(NC(=O)c2ccccc2)c1] |
| 282 | 448 | | | 0.0082 | | 4-{(R)-1-[3-(2,6-Difluoro-benzoyl-amino)-phenyl]-ethylamino}-quinazoline-8-carboxylic acid amide | Chiral |

TABLE 2-continued

| No. | MS (M+1) | Aurora A binding, IC50 [µM] | Aurora B binding, IC50 [µM] | p70S6K binding, IC50 [µM] | PDK1 binding, IC50 [µM] | Chemical Name |
|---|---|---|---|---|---|---|
| 283 | 478 | | | | 0.0086 | 4-{(R)-1-[3-(2,6-Difluoro-4-methoxy-benzoyl-amino)-phenyl]-ethylamino}-quinazoline-8-carboxylic acid amide |
| 284 | 322 | 0.11000 | 0.0096 | | 0.0087 | 4-((R)-3-Amino-1-phenyl-propyl-amino)-quinazoline-8-carboxylic acid amide |
| 285 | 354 | 0.92000 | | | 0.0089 | 4-[2-Dimethyl-amino-1-(4-fluoro-phenyl)-ethylamino]-quinazoline-8-carboxylic acid amide |

TABLE 2-continued

| No. | MS (M+ 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 286 | 524 | 0.00018 | 0.0013 | 0.0090 | | 4-{3-Methoxy-1-[3-(4-trifluoro-methyl-benzoyl-amino)-phenyl]-propyl-amino}-quinazoline-8-carboxylic acid amide | 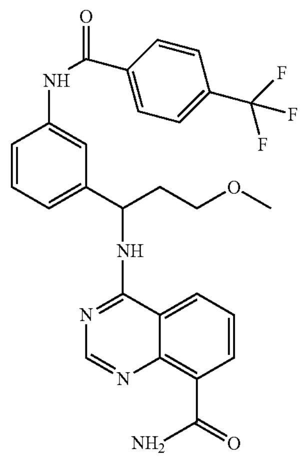 [SMILES: COCCC(Nc1ncnc2c(C(N)=O)cccc12)c1cccc(NC(=O)c2ccc(C(F)(F)F)cc2)c1] |
| 287 | 589 | 0.00220 | | 0.0090 | | {2-(8-Carbamoyl-quinazolin-4-ylamino)-2-[3-(2-fluoro-4-methoxy-benzoyl-amino)-phenyl]-ethyl}-methyl-carbamic acid tert-butyl ester | 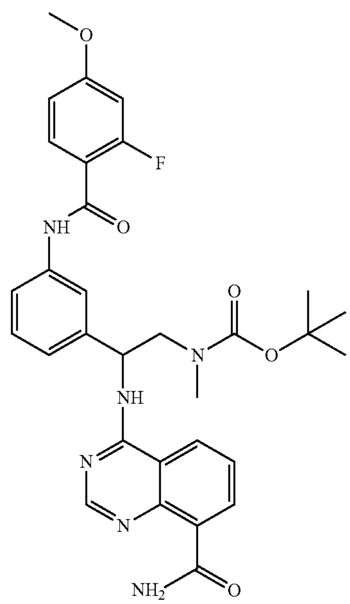 [SMILES: COc1ccc(C(=O)Nc2cccc(C(CN(C)C(=O)OC(C)(C)C)Nc3ncnc4c(C(N)=O)cccc34)c2)c(F)c1] |
| 288 | 322 | 0.13000 | | 0.0090 | | 4-(2-Amino-1-benzyl-ethylamino)-quinazoline-8-carboxylic acid amide | 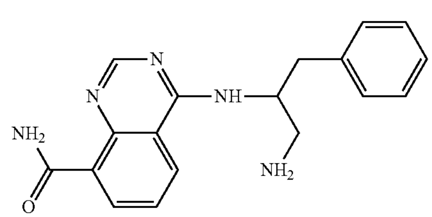 [SMILES: NCC(Cc1ccccc1)Nc1ncnc2c(C(N)=O)cccc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 291 | 481 | 0.00021 | | | 0.0091 | 4-(1-{3-[(6-Trifluoro-methyl-pyridine-3-carbonyl)-amino]-phenyl}-ethylamino)-quinazoline-8-carboxylic acid amide | 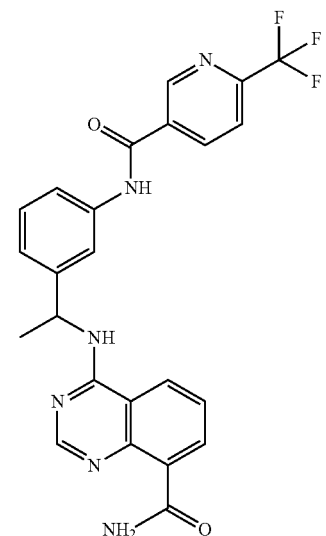 [SMILES: CC(Nc1ncnc2c(C(N)=O)cccc12)c1cccc(NC(=O)c2ccc(C(F)(F)F)nc2)c1] |
| 292 | 443 | 0.00010 | | | 0.0092 | 4-(1-{3-[(6-Methoxy-pyridine-3-carbonyl)-amino]-phenyl}-ethylamino)-quinazoline-8-carboxylic acid amide | 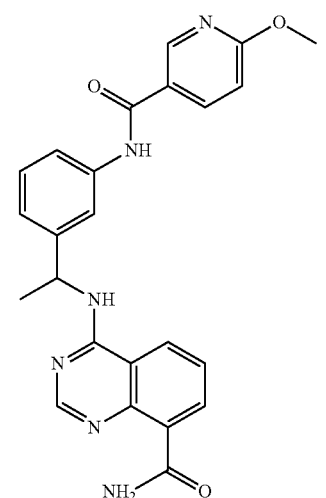 [SMILES: COc1ccc(C(=O)Nc2cccc(C(C)Nc3ncnc4c(C(N)=O)cccc34)c2)cn1] |
| 293 | 381 | 1 | | | 0.0093 | 4-{[3-(methyl-amino)-1-(3-nitrophenyl) propyl] amino} quinazoline-8-carbox-amide | 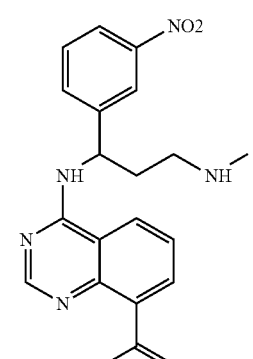 |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 294 | 454 | 0.00046 | | 0.0094 | | 4-{1-[3-(4-Cyano-3-fluoro-benzoyl-amino)-phenyl]-ethylamino}-quinazoline-8-carboxylic acid amide | 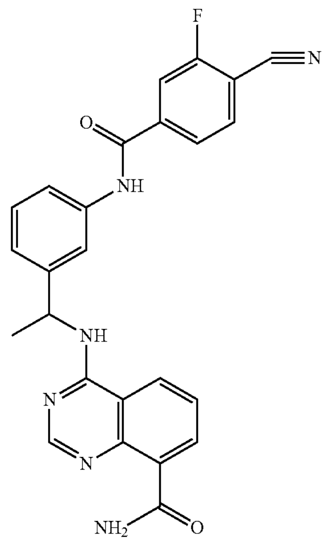 [SMILES: CC(Nc1ncnc2c(C(N)=O)cccc12)c1cccc(NC(=O)c2ccc(C#N)c(F)c2)c1] |
| 295 | 495 | 0.00110 | 0.0014 | 0.0094 | | 4-(1-{3-[(6-Trifluoro-methyl-pyridine-3-carbonyl)-amino]-phenyl}-propyl-amino)-quinazoline-8-carboxylic acid amide | 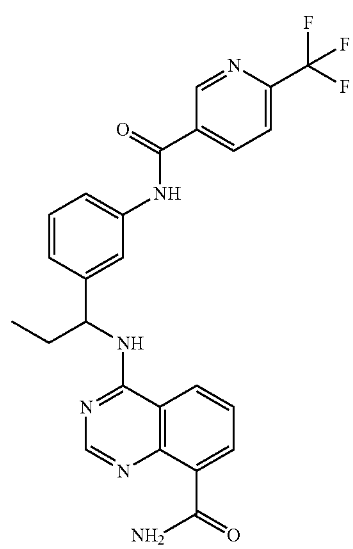 [SMILES: CCC(Nc1ncnc2c(C(N)=O)cccc12)c1cccc(NC(=O)c2ccc(C(F)(F)F)nc2)c1] |

US 8,637,532 B2

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 296 | 589 | 0.00740 | | | 0.0094 | {2-(8-Carbamoyl-quinazolin-4-ylamino)-2-[3-(3,4-difluoro-benzoyl-amino)-phenyl]-ethyl}-methyl-carbamic acid tert-butyl ester | 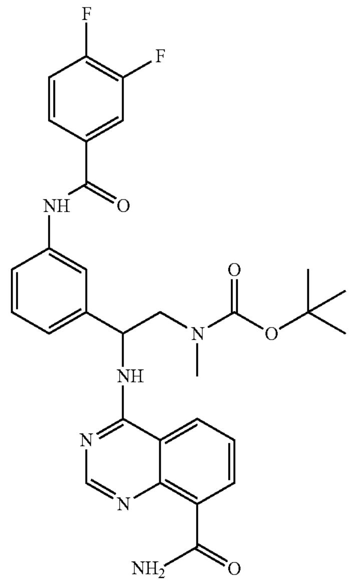 [SMILES: CN(CC(Nc1ncnc2c(C(N)=O)cccc12)c1cccc(NC(=O)c2ccc(F)c(F)c2)c1)C(=O)OC(C)(C)C] |
| 297 | 384 | 0.57000 | | | 0.0095 | 4-[(S)-2-Ethylamino-1-(3-fluoro-phenyl)-ethylamino]-6-methoxy-quinazoline-8-carboxylic acid amide | 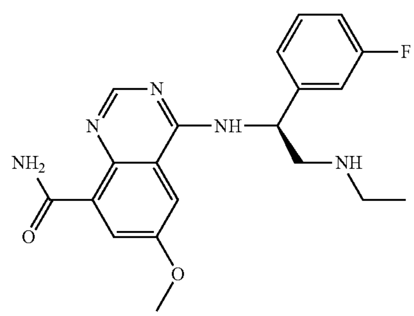 |
| 298 | 447 | 0.00073 | | | 0.0096 | 4-((R)-1-{3-[(2,4-Dimethyl-thiazole-5-carbonyl)-amino]-phenyl}-ethylamino)-quinazoline-8-carboxylic acid amide | 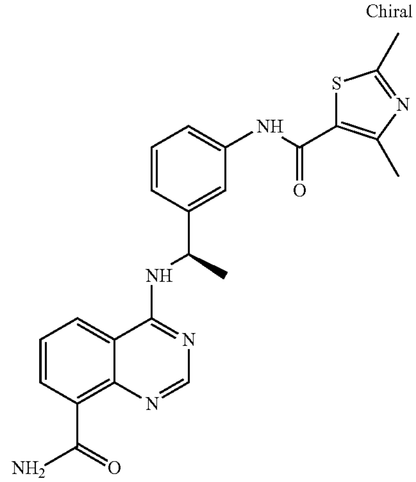 [SMILES: Cc1nc(C)c(C(=O)Nc2cccc([C@@H](C)Nc3ncnc4c(C(N)=O)cccc34)c2)s1] |

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 299 | 464 | 0.00020 | 0.0012 | | 0.0100 | 4-{1-[3-(4-Chloro-3-fluoro-benzoyl-amino)-phenyl]-ethylamino}-quinazoline-8-carboxylic acid amide | 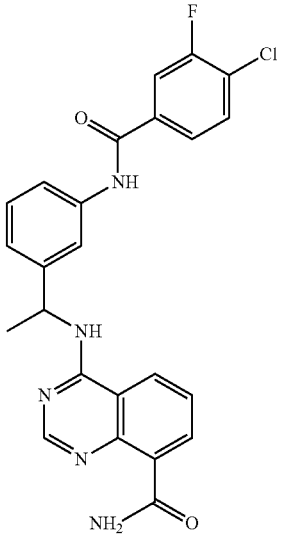 [SMILES: CC(Nc1ncnc2c(C(N)=O)cccc12)c1cccc(NC(=O)c2ccc(Cl)c(F)c2)c1] |
| 300 | 492 | 0.00120 | | | 0.0100 | 4-{1-[3-(2,3-Difluoro-benzoyl-amino)-phenyl]-3-methoxy-propyl-amino}-quinazoline-8-carboxylic acid amide | 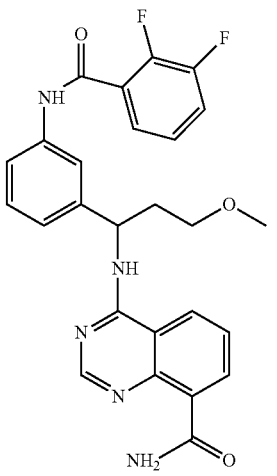 [SMILES: COCCC(Nc1ncnc2c(C(N)=O)cccc12)c1cccc(NC(=O)c2cccc(F)c2F)c1] |
| 301 | 447 | 0.00130 | 0.0004 | | 0.0100 | 4-(1-{3-[(6-Chloro-pyridine-3-carbonyl)-amino]-phenyl}-ethylamino)-quinazoline-8-carboxylic acid amide | 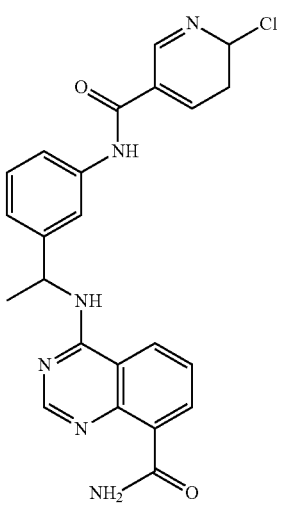 [SMILES: CC(Nc1ncnc2c(C(N)=O)cccc12)c1cccc(NC(=O)C2=CCC(Cl)N=C2)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 302 | 325 | | | | 0.0100 | 4-[1-(3-Fluoro-phenyl)-propyl-amino]-quinazoline-8-carboxylic acid amide | 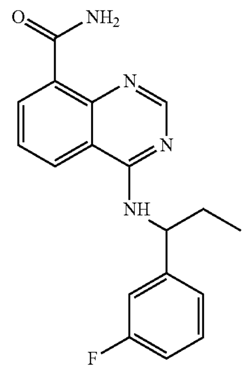 [SMILES: CCC(Nc1ncnc2c(C(N)=O)cccc12)c1cccc(F)c1] |
| 303 | 448 | | | | 0.0100 | 4-{(R)-1-[3-(2,3-Difluoro-benzoyl-amino)-phenyl]-ethylamino}-quinazoline-8-carboxylic acid amide | 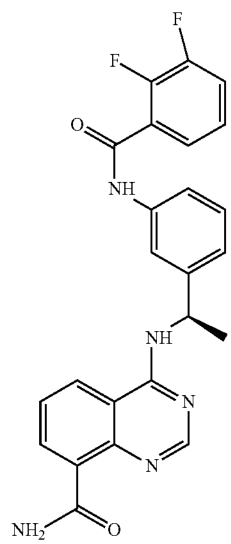 |
| 304 | 322 | 0.05000 | | | 0.0100 | 4-((S)-2-Amino-1-benzyl-ethylamino)-quinazoline-8-carboxylic acid amide | 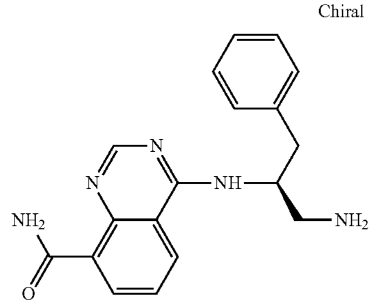 [SMILES: NC[C@H](Cc1ccccc1)Nc1ncnc2c(C(N)=O)cccc12] |
| 305 | 338 | 0.56000 | | | 0.0110 | 6-Hydroxy-4-(2-methyl-amino-1-phenyl-ethylamino)-quinazoline-8-carboxylic acid amide | 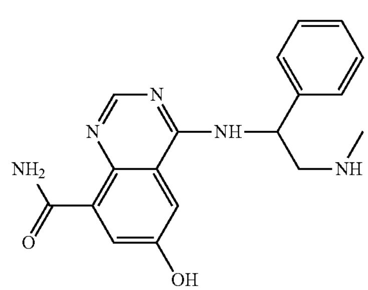 [SMILES: CNCC(Nc1ncnc2c(C(N)=O)cc(O)cc12)c1ccccc1] |

TABLE 2-continued
| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 306 | 448 | | | | 0.0110 | 4-{(R)-1-[3-(2,5-Difluoro-benzoyl-amino)-phenyl]-ethylamino}-quinazoline-8-carboxylic acid amide | 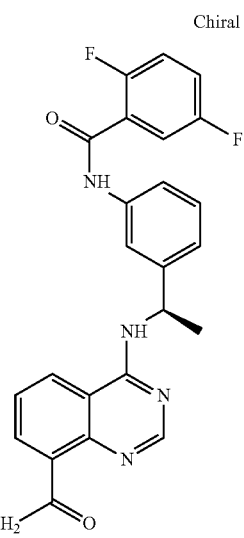 |
| 307 | 433 | 0.00035 | | | 0.0110 | 4-((R)-1-{3-[(2-Methyl-thiazole-5-carbonyl)-amino]-phenyl}-ethylamino)-quinazoline-8-carboxylic acid amide | 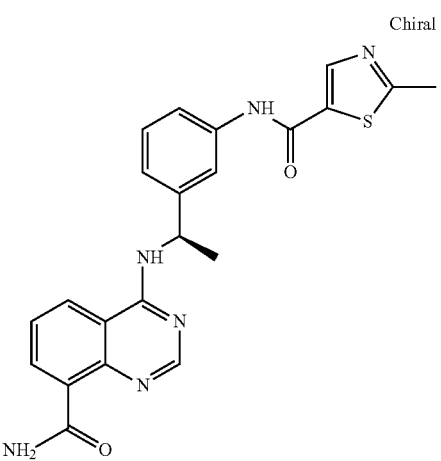 [SMILES: Cc1ncc(C(=O)Nc2cccc([C@@H](C)Nc3ncnc4c(C(N)=O)cccc34)c2)s1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 308 | 470 | 0.00020 | | | 0.0120 | 4-(1-{3-[(5-Trifluoro-methyl-2H-pyrazole-3-carbonyl)-amino]-phenyl}-ethylamino)-quinazoline-8-carboxylic acid amide | 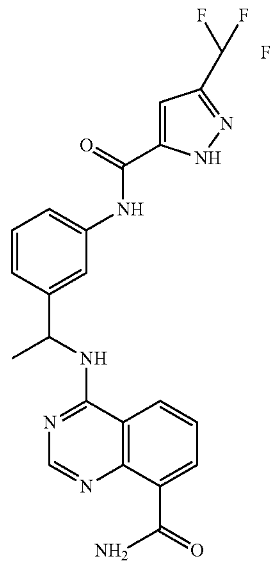 |
| 309 | 427 | 0.00085 | 0.00032 | | 0.0120 | 4-(1-{3-[(6-Methyl-pyridine-3-carbonyl)-amino]-phenyl}-ethylamino)-quinazoline-8-carboxylic acid amide | 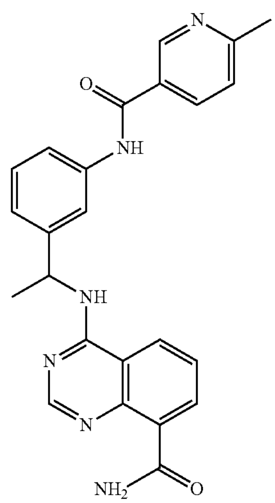 [SMILES: Cc1ccc(C(=O)Nc2cccc(C(C)Nc3ncnc4c(C(N)=O)cccc34)c2)cn1] |
| 310 | 490 | 0.02700 | | | 0.0120 | 4-[2-Dimethyl-amino-1-(3-fluoro-phenyl)-ethylamino]-6-(4-methoxy-benzyloxy)-quinazoline-8-carboxylic acid amide | 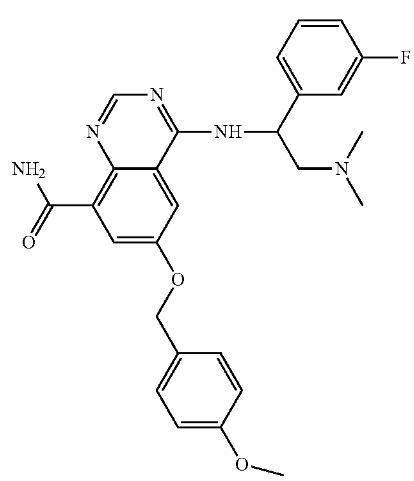 [SMILES: COc1ccc(COc2cc(C(N)=O)c3ncnc(NC(CN(C)C)c4cccc(F)c4)c3c2)cc1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 312 | 497.2 | 0.00230 | | | 0.0130 | 4-(3-{[6-(4-Methyl-piperazin-1-yl)-pyridine-3-carbonyl]-amino}-benzyl-amino)-quinazoline-8-carboxylic acid amide | 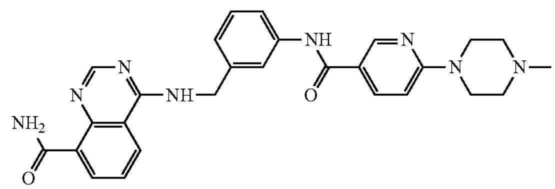 [SMILES: CN1CCN(c2ccc(C(=O)Nc3cccc(CNc4ncnc5c(C(N)=O)cccc45)c3)cn2)CC1] |
| 313 | 505 | 0.00390 | 0.0025 | | 0.0130 | 4-{1-[3-(2,3-Difluoro-benzoyl-amino)-phenyl]-3-dimethyl-amino-propyl-amino}-quinazoline-8-carboxylic acid amide | 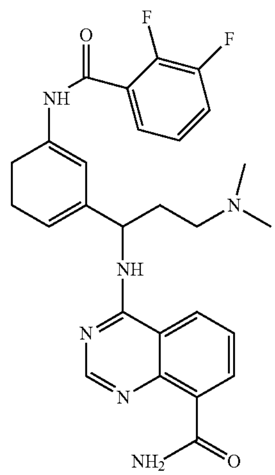 [SMILES: CN(C)CCC(Nc1ncnc2c(C(N)=O)cccc12)C1=CCCC(NC(=O)c2cccc(F)c2F)=C1] |
| 314 | 531 | 0.00390 | | | 0.0130 | 4-{1-[3-(2,4-Difluoro-benzoyl-amino)-phenyl]-3-pyrrolidin-1-yl-propyl-amino}-quinazoline-8-carboxylic acid amide | 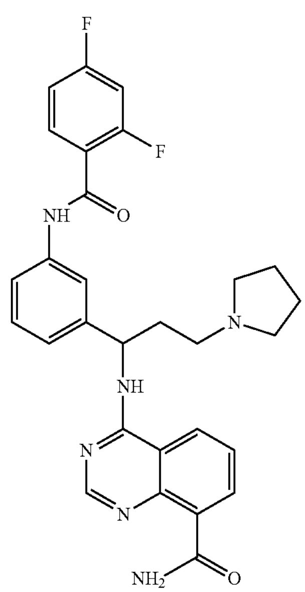 [SMILES: NC(=O)c1cccc2c(NC(CCN3CCCC3)c3cccc(NC(=O)c4ccc(F)cc4F)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 316 | 495 | 0.00073 | 0.00069 | | 0.0140 | 4-[3-(4-Bromo-benzoyl-amino)-4-fluoro-benzyl-amino]-quinazoline-8-carboxylic acid amide | 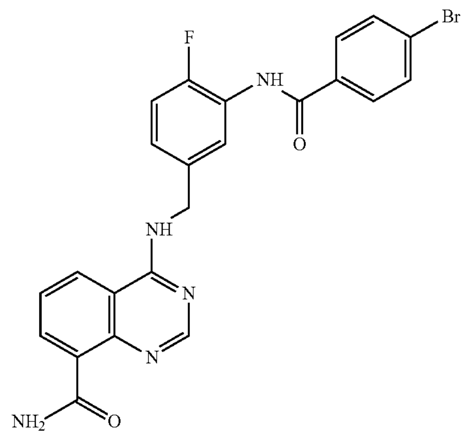 [SMILES: NC(=O)c1cccc2c(NCc3ccc(F)c(NC(=O)c4ccc(Br)cc4)c3)ncnc12] |
| 317 | 351 | 1 | | | 0.0140 | 4-[1-(3-Amino-phenyl)-2-dimethyl-amino-ethylamino]-quinazoline-8-carboxylic acid amide | 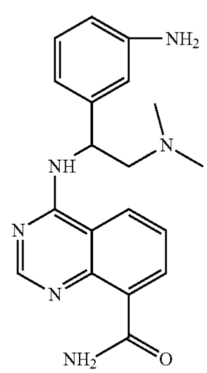 [SMILES: CN(C)CC(Nc1ncnc2c(C(N)=O)cccc12)c1cccc(N)c1] |
| 319 | 535 | 5.0000e−05 | | | 0.0150 | 4-{1-[3-(4-Bromo-benzoyl-amino)-phenyl]-3-methoxy-propyl-amino}-quinazoline-8-carboxylic acid amide | 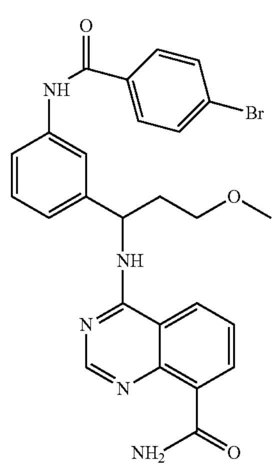 [SMILES: COCCC(Nc1ncnc2c(C(N)=O)cccc12)c1cccc(NC(=O)c2ccc(Br)cc2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 320 | 481 | 7.0000e−05 | | | 0.0150 | 4-((R)-1-{3-[(6-Trifluoro-methyl-pyridine-3-carbonyl)-amino]-phenyl}-ethylamino)-quinazoline-8-carboxylic acid amide | 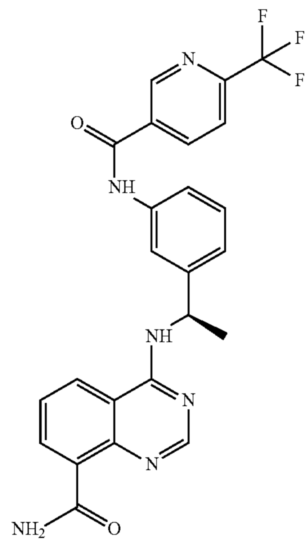 |
| 321 | 450 | 0.00035 | 0.00047 | | 0.0150 | 4-[3-(4-Chloro-3-fluoro-benzoyl-amino)-benzyl-amino]-quinazoline-8-carboxylic acid amide | 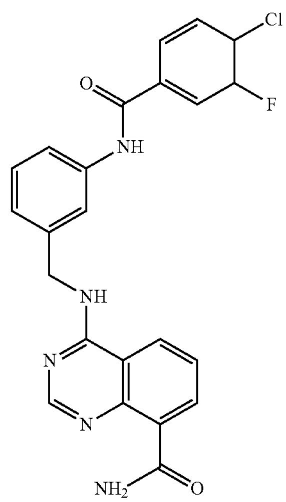 [SMILES: NC(=O)c1cccc2c(NCc3cccc(NC(=O)C4=CC(F)C(Cl)C=C4)c3)ncnc12] |
| 322 | 492 | 0.00063 | | | 0.0150 | 4-{1-[3-(2,5-Difluoro-benzoyl-amino]-phenyl]-3-methoxy-propyl-amino}-quinazoline-8-carboxylic acid amide | 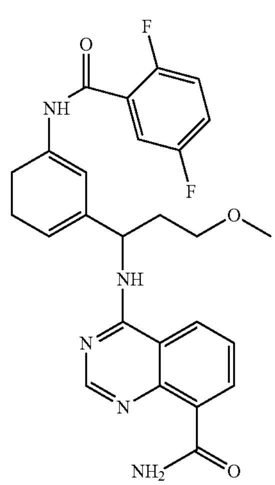 [SMILES: COCCC(Nc1ncnc2c(C(N)=O)cccc12)C1=CCCC(NC(=O)c2cc(F)ccc2F)=C1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 323 | 430 | 0.00094 | | | 0.0150 | 4-{1-[3-(3-Fluoro-benzoyl-amino)-phenyl]-ethylamino}-quinazoline-8-carboxylic acid amide | 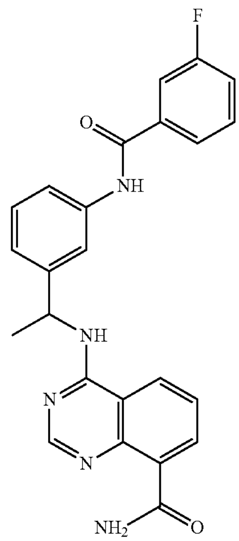 [SMILES: CC(Nc1ncnc2c(C(N)=O)cccc12)c1cccc(NC(=O)c2cccc(F)c2)c1] |
| 324 | 424 | 0.07300 | | | 0.0150 | 6-Cyclo-butoxy-4-[2-dimethyl-amino-1-(3-fluoro-phenyl)-ethylamino]-quinazoline-8-carboxylic acid amide | 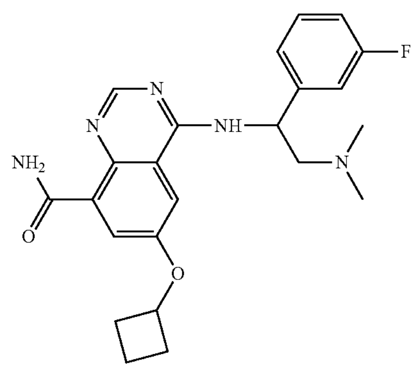 [SMILES: CN(C)CC(Nc1ncnc2c(C(N)=O)cc(OC3CCC3)cc12)c1cccc(F)c1] |
| 325 | 386 | 0.33000 | | | 0.0150 | 4-[1-(3-Chloro-phenyl)-2-dimethyl-amino-ethylamino]-6-hydroxy-quinazoline-8-carboxylic acid amide | 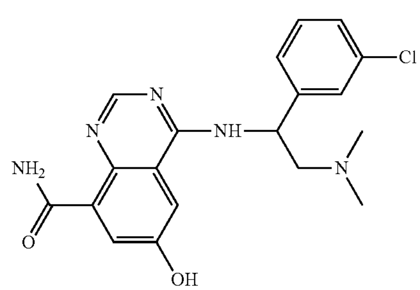 [SMILES: CN(C)CC(Nc1ncnc2c(C(N)=O)cc(O)cc12)c1cccc(Cl)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 326 | 322 | 2.5000 | | | 0.0150 | 4-((S)-2-Methyl-amino-1-phenyl-ethylamino)-quinazoline-8-carboxylic acid amide | 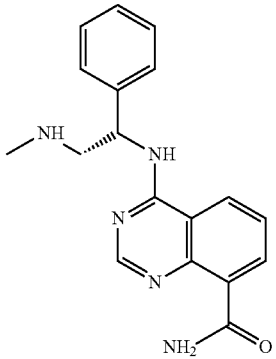 Chiral |
| 329 | 470 | | | | 0.0150 | 4-((R)-1-{3-[(2,3-Dihydro-benzo[1,4]dioxine-6-carbonyl)-amino]-phenyl}-ethylamino)-quinazoline-8-carboxylic acid amide | 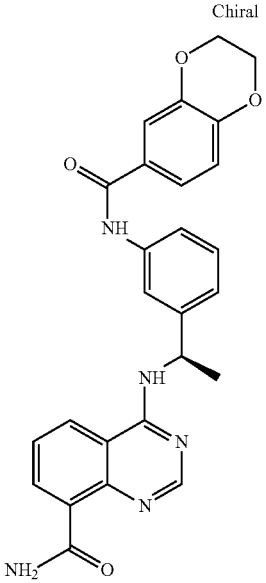 [SMILES: C[C@@H](Nc1ncnc2c(C(N)=O)cccc12)c1cccc(NC(=O)c2ccc3c(c2)OCCO3)c1] Chiral |
| 330 | 525 | 0.00016 | 0.0018 | | 0.0160 | 4-{3-(Allyl-methyl-amino)-1-[3-(4-methoxy-benzoyl-amino)-phenyl]-propyl-amino}-quinazoline-8-carboxylic acid amide | 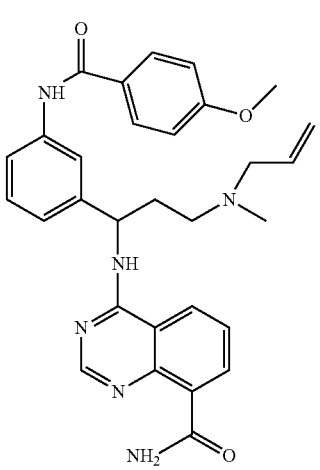 [SMILES: C=CCN(C)CCC(Nc1ncnc2c(C(N)=O)cccc12)c1cccc(NC(=O)c2ccc(OC)cc2)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 331 | 460 | 0.00056 | | | 0.0160 | 4-{(R)-1-[3-(3-Chloro-4-methyl-benzoyl-amino)-phenyl]-ethylamino}-quinazoline-8-carboxylic acid amide | Chiral |
| 332 | 559 | 0.00058 | 0.0045 | | 0.0160 | 4-{3-Azetidin-1-yl-1-[3-(4-bromo-benzoyl-amino)-phenyl]-propyl-amino}-quinazoline-8-carboxylic acid amid | 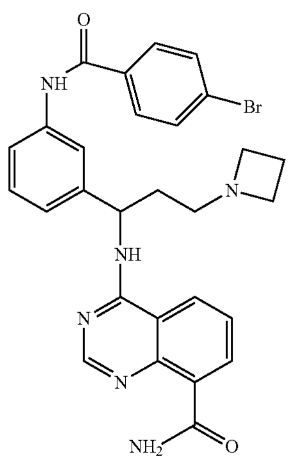 [SMILES: NC(=O)c1cccc2c(NC(CCN3CCC3)c3cccc(NC(=O)c4ccc(Br)cc4)c3)ncnc12] |
| 333 | 450 | 0.00097 | | | 0.0160 | 4-{2-Methoxy-1-[3-(4-methoxy-benzoyl-amino)-phenyl]-ethylamino}-quinazoline-8-carboxylic acid amide | 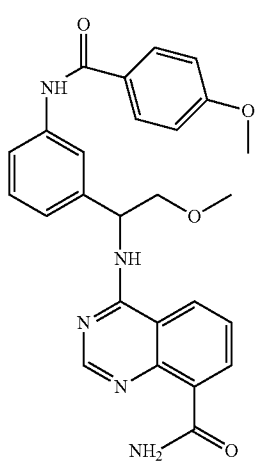 [SMILES: COCC(Nc1ncnc2c(C(N)=O)cccc12)c1cccc(NC(=O)c2ccc(OC)cc2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 334 | 470 | 0.00110 | 0.00089 | | 0.0160 | 4-(1-{3-[(2,3-Dihydro-benzo[1,4]dioxine-6-carbonyl)-amino]-phenyl}-ethylamino)-quinazoline-8-carboxylic acid amide | 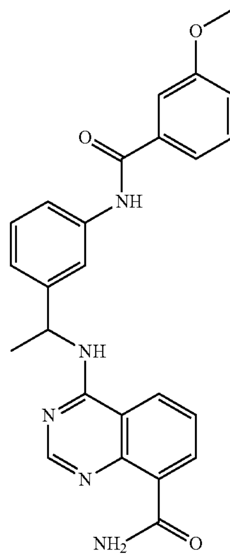 |
| 335 | 577 | 0.00373 | | | 0.0160 | {2-(8-Carbamoyl-quinazolin-4-ylamino)-2-[3-(2,6-difluoro-benzoyl-amino)-phenyl]-ethyl}-methyl-carbamic acid tert-butyl ester | 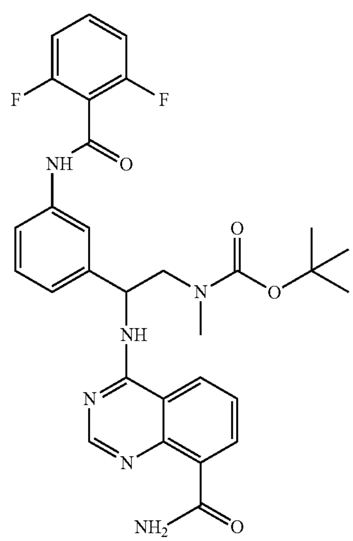 [SMILES: CN(CC(Nc1ncnc2c(C(N)=O)cccc12)c1cccc(NC(=O)c2c(F)cccc2F)c1)C(=O)OC(C)(C)C] |
| 336 | 370 | 0.16000 | | | 0.0160 | 4-[2-Dimethyl-amino-1-(3-fluoro-phenyl)-ethylamino)-6-hydroxy-quinazoline-8-carboxylic acid amide | 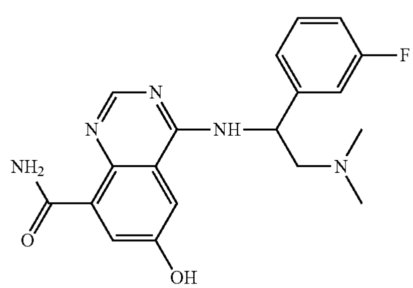 [SMILES: CN(C)CC(Nc1ncnc2c(C(N)=O)cc(O)cc12)c1cccc(F)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 337 | 382 | 0.33000 | | | 0.0160 | 4-[(S)-2-(2-Methyl-sulfanyl-ethylamino)-1-phenyl-ethylamino)-quinazoline-8-carboxylic acid amide | Chiral 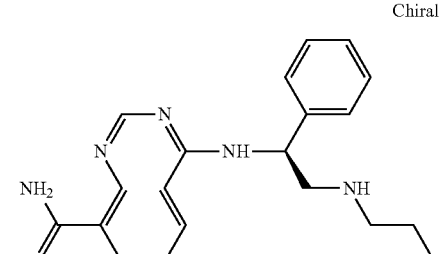 |
| 338 | 472 | 9.0000e−05 | | | 0.0170 | 4-{3-Hydroxy-1-[3-(4-methoxy-benzoyl-amino)-phenyl]-propyl-amino}-quinazoline-8-carboxylic acid amide | 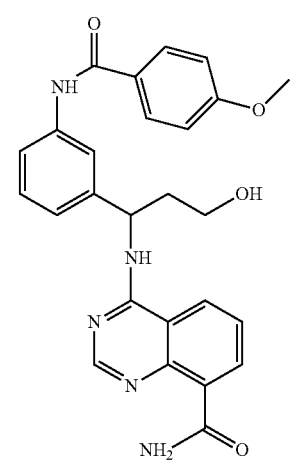 [SMILES: COc1ccc(C(=O)Nc2cccc(C(CCO)Nc3ncnc4c(C(N)=O)cccc34)c2)cc1] |
| 339 | 484 | 0.00017 | 0.00017 | | 0.0170 | 4-[3-(2-Fluoro-5-trifluoro-methyl-benzoyl-amino)-benzyl-amino]-quinazoline-8-carboxylic acid amide | 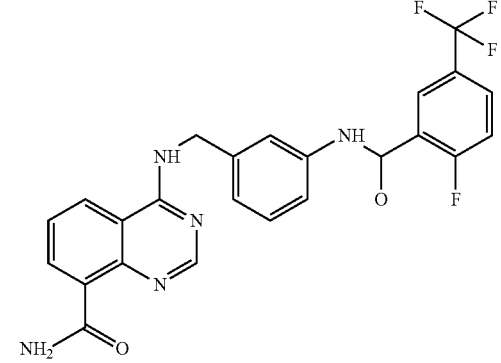 [SMILES: NC(=O)c1cccc2c(NCc3cccc(NC(O)c4cc(C(F)(F)F)ccc4F)c3)ncnc12] |
| 340 | 364 | 0.14000 | | | 0.0180 | 4-[(S)-2-(Isopropyl-methyl-amino)-1-phenyl-ethylamino]-quinazoline-8-carboxylic acid amide | Chiral 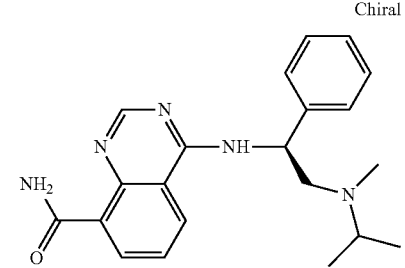 [SMILES: CC(C)N(C)C[C@@H](Nc1ncnc2c(C(N)=O)cccc12)c1ccccc1] |

TABLE 2-continued

| No. | MS (M+1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 341 | 428 | 0.21000 | | 0.0180 | | 4-[2-Dimethyl-amino-1-(3-fluoro-phenyl)-ethylamino]-6-(2-methoxy-ethoxy)-quinazoline-8-carboxylic acid amide | 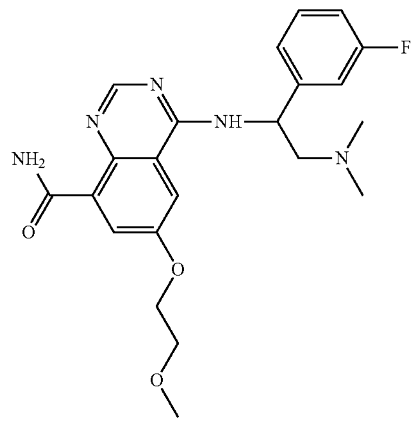 [SMILES: COCCOc1cc(C(N)=O)c2ncnc(NC(CN(C)C)c3cccc(F)c3)c2c1] |
| 342 | 384 | 0.53000 | | 0.0180 | | 4-[2-Dimethyl-amino-1-(4-fluoro-phenyl)-ethylamino]-6-methoxy-quinazoline-8-carboxylic acid amide | 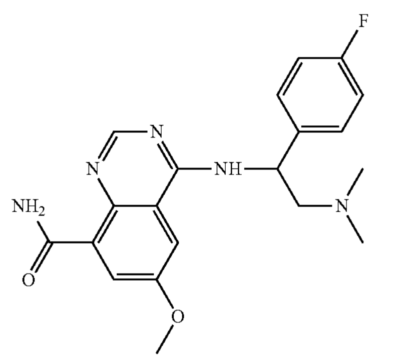 [SMILES: COc1cc(C(N)=O)c2ncnc(NC(CN(C)C)c3ccc(F)cc3)c2c1] |
| 343 | 343 | | | 0.0180 | | 4-[1-(3,5-Difluoro-phenyl)-propyl-amino]-quinazoline-8-carboxylic acid amide | 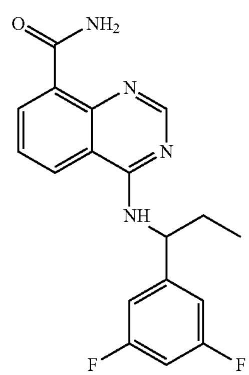 [SMILES: CCC(Nc1ncnc2c(C(N)=O)cccc12)c1cc(F)cc(F)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 344 | 470 | | | | 0.0180 | 4-((R)-1-{3-[(5-Trifluoro-methyl-2H-pyrazole-3-carbonyl)-amino]-phenyl}-ethylamino)-quinazoline-8-carboxylic acid amide | Chiral 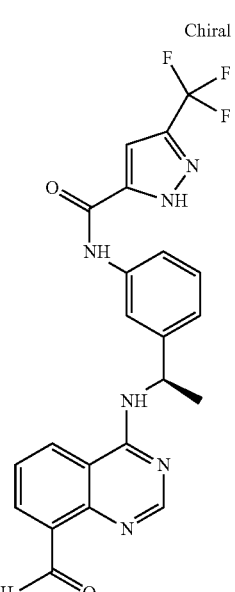 |
| 345 | 460 | | | | 0.0180 | 4-{(R)-1-[3-(2-Fluoro-4-methoxy-benzoyl-amino)-phenyl]-ethylamino}-quinazoline-8-carboxylic acid amide | Chiral 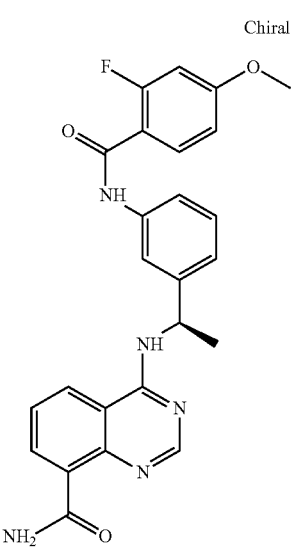 [SMILES: COc1ccc(C(=O)Nc2cccc([C@@H](C)Nc3ncnc4c(C(N)=O)cccc34)c2)c(F)c1] |
| 347 | 428 | 0.00015 | | | 0.0190 | 4-{3-[(2-Methyl-amino-pyridine-4-carbonyl)-amino]-benzyl-amino}-quinazoline-8-carboxylic acid amide | 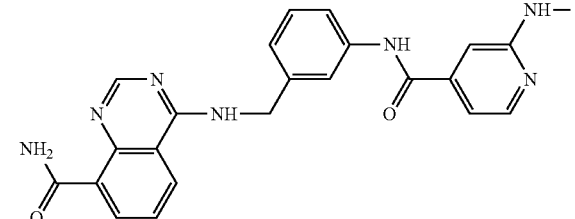 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 348 | 484 | 0.00440 | 0.0210 | | 0.0190 | 4-{3-[(5-Morpholin-4-yl-pyridine-3-carbonyl)-amino]-benzyl-amino}-quinazoline-8-carboxylic acid amide | 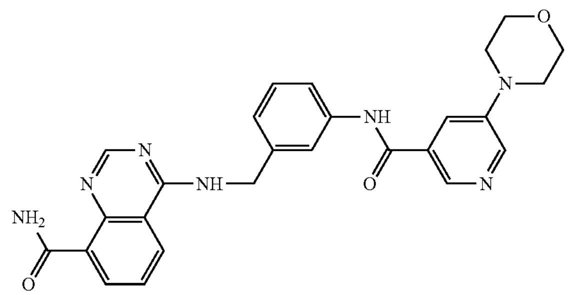 [SMILES: NC(=O)c1cccc2c(NCc3cccc(NC(=O)c4cncc(N5CCOCC5)c4)c3)ncnc12] |
| 349 | 273 | | | | 0.0190 | 4-((R)-1-Methyl-pentyl-amino)-quinazoline-8-carboxylic acid amide | 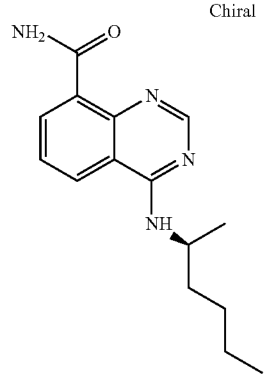 [SMILES: CCCC[C@H](C)Nc1ncnc2c(C(N)=O)cccc12] |
| 350 | 456 | | | | 0.0190 | 4-{(R)-1-[3-(4-Methoxy-3-methyl-benzoyl-amino)-phenyl]-ethylamino}-quinazoline-8-carboxylic acid amide | 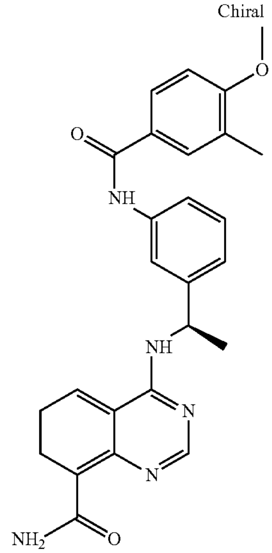 [SMILES: COc1ccc(C(=O)Nc2cccc([C@@H](C)Nc3ncnc4c3=CCCC=4C(N)=O)c2)cc1C] |
| 351 | 367 | 0.79000 | | | 0.0190 | 4-[(S)-2-(2-Methoxy-ethylamino)-1-phenyl-ethylamino]-quinazoline-8-carboxylic acid amide | 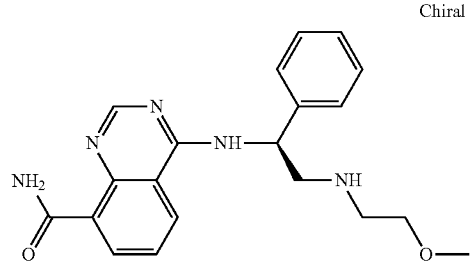 [SMILES: COCCNC[C@@H](Nc1ncnc2c(C(N)=O)cccc12)c1ccccc1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 352 | 410 | 8.0000e−05 | | | 0.0200 | 4-{(R)-1-[3-(4-Cyano-pyridin-2-ylamino)-phenyl]-ethylamino}-quinazoline-8-carboxylic acid amide | 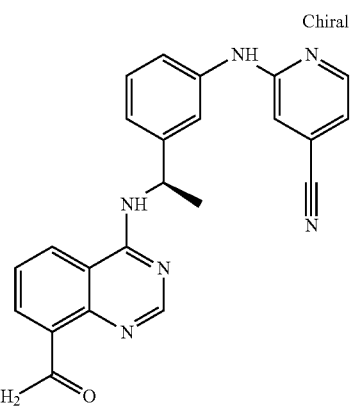 Chiral |
| 353 | 492 | 0.00020 | 0.0031 | | 0.0200 | 4-{1-[3-(3,4-Difluoro-benzoyl-amino)-phenyl]-3-methoxy-propyl-amino}-quinazoline-8-carboxylic acid amide | 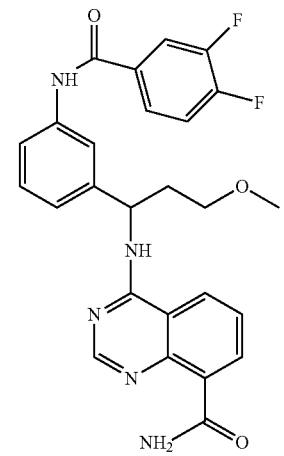 [SMILES: COCCC(Nc1ncnc2c(C(N)=O)cccc12)c1cccc(NC(=O)c2ccc(F)c(F)c2)c1] |
| 355 | 495 | | | | 0.0200 | 4-((R)-1-{3-[(2-Methyl-6-trifluoro-methyl-pyridine-3-carbonyl)-amino]-phenyl}-ethylamino)-quinazoline-8-carboxylic acid amide | 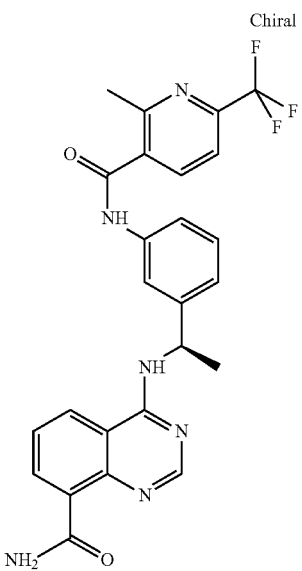 [SMILES: Cc1nc(C(F)(F)F)ccc1C(=O)Nc1cccc([C@@H](C)Nc2ncnc3c(C(N)=O)cccc23)c1] Chiral |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 356 | 496 | 0.00049 | | | 0.0210 | 4-[3-(Allyl-methyl-amino)-1-(3-benzoyl-amino-phenyl)-propyl-amino]-quinazoline-8-carboxylic acid amide | 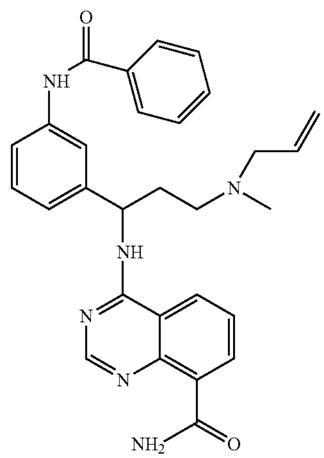 [SMILES: C=CCN(C)CCC(Nc1ncnc2c(C(N)=O)cccc12)c1cccc(NC(=O)c2ccccc2)c1] |
| 357 | 472 | 0.00069 | 0.0110 | | 0.0210 | 4-[3-({6-[(2-Hydroxy-ethyl)-methyl-amino]-pyridine-3-carbonyl}-amino)-benzyl-amino]-quinazoline-8-carboxylic acid amide | 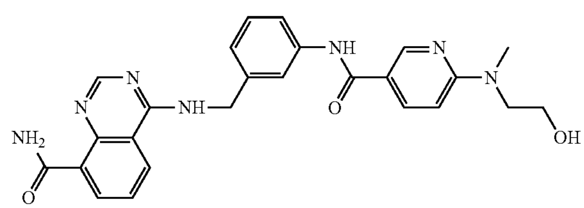 [SMILES: CN(CCO)c1ccc(C(=O)Nc2cccc(CNc3ncnc4c(C(N)=O)cccc34)c2)cn1] |
| 358 | 412 | 0.00091 | 0.0024 | | 0.0210 | 4-[1-(3-Benzoyl-amino-phenyl)-ethylamino]-quinazoline-8-carboxylic acid amide | 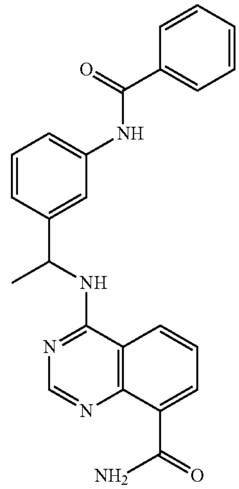 [SMILES: CC(Nc1ncnc2c(C(N)=O)cccc12)c1cccc(NC(=O)c2ccccc2)c1] |

TABLE 2-continued

| No. | MS (M+1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 359 | 416 | 0.00094 | | 0.0210 | | 4-(1-{3-[(2-Methyl-furan-3-carbonyl)-amino]-phenyl}-ethylamino)-quinazoline-8-carboxylic acid amide | 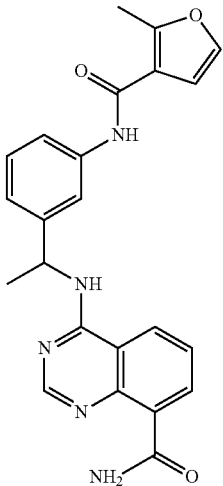 [SMILES: Cc1occc1C(=O)Nc1cccc(C(C)Nc2ncnc3c(C(N)=O)cccc23)c1] |
| 360 | 573 | 0.00100 | 0.0014 | 0.0210 | | 4-{1-[3-(4-Bromo-benzoyl-amino)-phenyl]-3-pyrrolidin-1-yl-propyl-amino}-quinazoline-8-carboxylic acid amide | 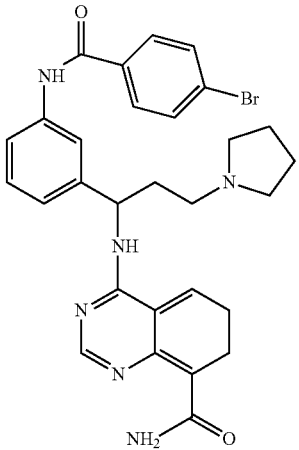 [SMILES: NC(=O)C1=c2ncnc(NC(CCN3CCCC3)c3cccc(NC(=O)c4ccc(Br)cc4)c3)c2=CCC1] |
| 361 | 517 | 0.00140 | 0.0023 | 0.0210 | | 4-{3-Dimethyl-amino-1-[3-(2-fluoro-4-methoxy-benzoyl-amino)-phenyl]-propyl-amino}-quinazoline-8-carboxylic acid amide | 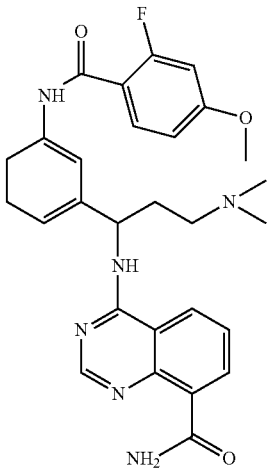 [SMILES: COc1ccc(C(=O)NC2=CC(C(CCN(C)C)Nc3ncnc4c(C(N)=O)cccc34)=CCC2)c(F)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 362 | 468 | 0.00180 | 0.0021 | 0.0210 | | 4-{3-[(2-Pyrrolidin-1-yl-pyridine-4-carbonyl)-amino]-benzyl-amino}-quinazoline-8-carboxylic acid amide | 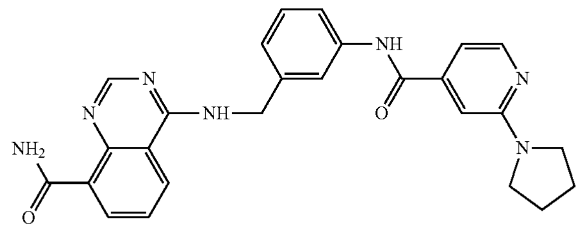 [SMILES: NC(=O)c1cccc2c(NCc3cccc(NC(=O)c4ccnc(N5CCCC5)c4)c3)ncnc12] |
| 363 | 487 | 0.01900 | 0.0078 | 0.0210 | | 4-{3-Dimethyl-amino-1-[3-(2-fluoro-benzoyl-amino)-phenyl]-propyl-amino}-quinazoline-8-carboxylic acid amide | 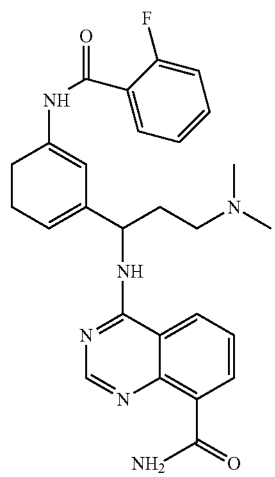 [SMILES: CN(C)CCC(Nc1ncnc2c(C(N)=O)cccc12)C1=CCCC(NC(=O)c2ccccc2F)=C1] |
| 364 | 510 | 0.00032 | | 0.0220 | 77 | 4-{1-[3-(4-Trifluoro-methoxy-benzoyl-amino)-phenyl]-propyl-amino}-quinazoline-8-carboxylic acid amide | 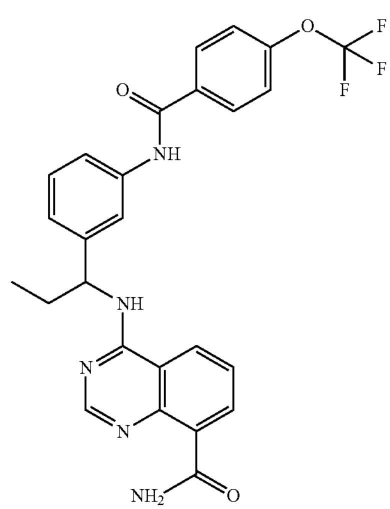 [SMILES: CCC(Nc1ncnc2c(C(N)=O)cccc12)c1cccc(NC(=O)c2ccc(OC(F)(F)F)cc2)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 365 | 553 | 0.00042 | 0.0022 | | 0.0220 | 4-{3-Dimethyl-amino-1-[3-(4-trifluoro-methoxy-benzoyl-amino)-phenyl]-propyl-amino}-quinazoline-8-carboxylic acid amide | 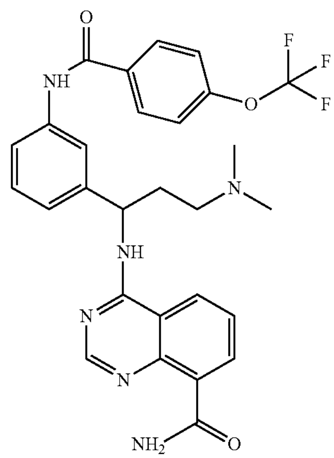 |
| 366 | 442 | | 0.00180 | | 0.0220 | 4-[1-(3-Benzoyl-amino-phenyl)-3-hydroxy-propyl-amino]-quinazoline-8-carboxylic acid amide | 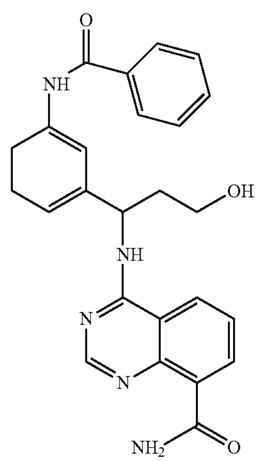 [SMILES: NC(=O)c1cccc2c(NC(CCO)C3=CCCC(NC(=O)c4ccccc4)=C3)ncnc12] |
| 367 | 350 | 0.50000 | | | 0.0220 | 4-[2-(Ethyl-methyl-amino)-1-phenyl-ethylamino]-quinazoline-8-carboxylic acid amide | 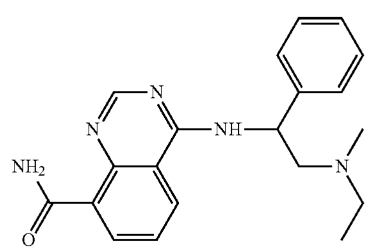 [SMILES: CCN(C)CC(Nc1ncnc2c(C(N)=O)cccc12)c1ccccc1] |
| 368 | 404 | | | | 0.0220 | 4-(2-Methyl-amino-1-phenyl-ethylamino)-6-thiophen-3-yl-quinazoline-8-carboxylic acid amide | 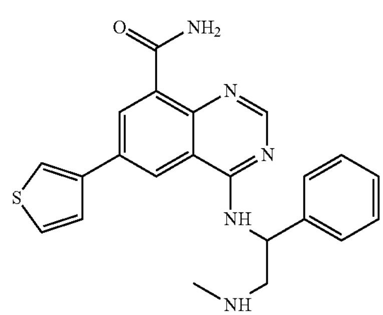 [SMILES: CNCC(Nc1ncnc2c(C(N)=O)cc(-c3ccsc3)cc12)c1ccccc1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 370 | 456 | 0.00038 | | | 0.0230 | 4-[1-(3-Benzoyl-amino-phenyl)-3-methoxy-propyl-amino]-quinazoline-8-carboxylic acid amide | 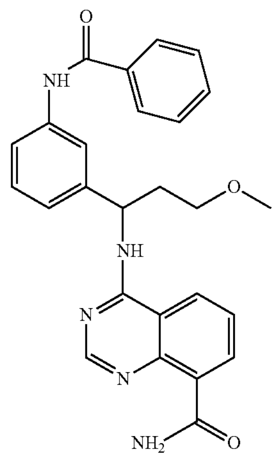 [SMILES: COCCC(Nc1ncnc2c(C(N)=O)cccc12)c1cccc(NC(=O)c2ccccc2)c1] |
| 371 | 428 | 0.00360 | | | 0.0230 | 4-(1-{3-[(5-Methyl-pyrazine-2-carbonyl)-amino]-phenyl}-ethylamino)-quinazoline-8-carboxylic acid amide | 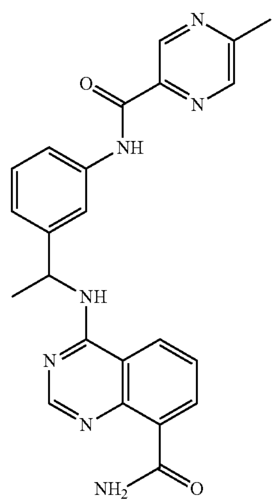 [SMILES: Cc1cnc(C(=O)Nc2cccc(C(C)Nc3ncnc4c(C(N)=O)cccc34)c2)cn1] |
| 372 | 427 | 1 | | | 0.0230 | 6-(2-Dimethyl-amino-ethoxy)-4-[1-(3-fluoro-phenyl)-2-methyl-amino-ethylamino]-quinazoline-8-carboxylic acid amide | 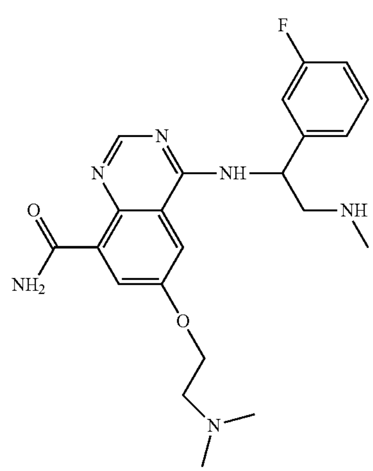 [SMILES: CNCC(Nc1ncnc2c(C(N)=O)cc(OCCN(C)C)cc12)c1cccc(F)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 373 | 477 | | | | 0.0230 | 4-((R)-1-{3-[(2-Chloro-6-methoxy-pyridine-3-carbonyl)-amino]-phenyl}-ethylamino)-quinazoline-8-carboxylic acid amide | 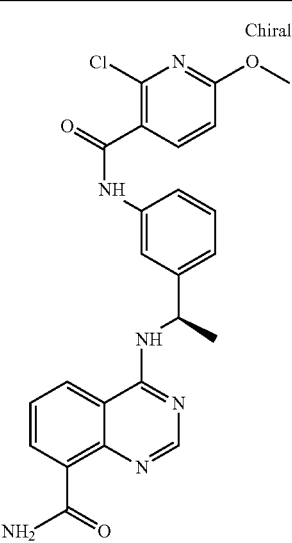 |
| 374 | 478 | 0.00012 | | | 0.0240 | 4-{(R)-1-[4-Fluoro-3-(3-fluoro-4-methoxy-benzoyl-amino)-phenyl]-ethylamino}-quinazoline-8-carboxylic acid amide | 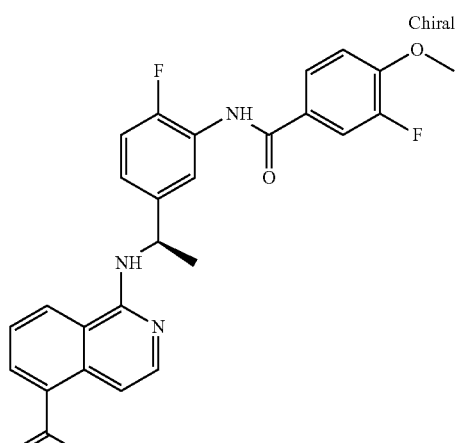 |
| 375 | 467 | 0.00029 | 0.0003 | | 0.0240 | 4-[3-(3,4-Dichloro-benzoyl-amino)-benzyl-amino]-quinazoline-8-carboxylic acid amide | 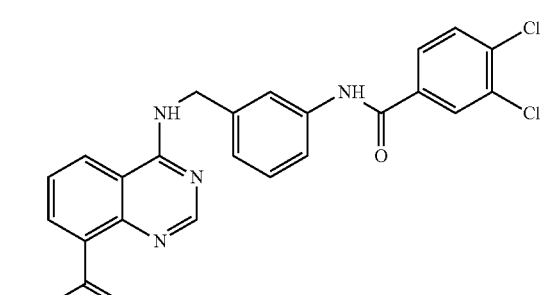 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 376 | 482 | 0.00110 | | | 0.0240 | 4-{3-[(2-Morpholin-4-yl-pyridine-4-carbonyl)-amino]-benzyl-amino}-quinazoline-8-carboxylic acid amide | 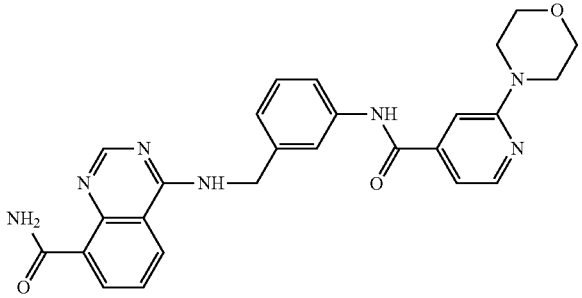 [SMILES: NC(=O)c1cccc2c(NCc3cccc(NC(=O)c4ccnc(N5CCOCC5)c4)c3)ncnc12] |
| 377 | 313 | 0.14000 | | | 0.0240 | 4-(3-Chloro-benzyl-amino)-quinazoline-8-carboxylic acid amide | 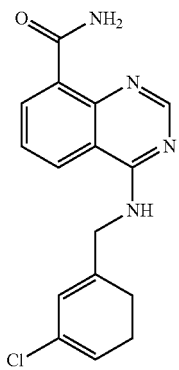 [SMILES: NC(=O)c1cccc2c(NCC3=CC(Cl)=CCC3)ncnc12] |
| 379 | 474 | 0.00099 | | | 0.0250 | 4-{1-[3-(2-Fluoro-benzoyl-amino)-phenyl]-3-methoxy-propyl-amino}-quinazoline-8-carboxylic acid amide | 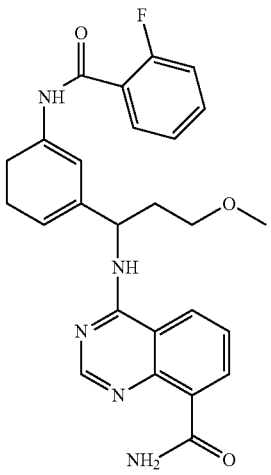 [SMILES: COCCC(Nc1ncnc2c(C(N)=O)cccc12)C1=CCCC(NC(=O)c2ccccc2F)=C1] |
| 380 | 395 | 1.6000 | | | 0.0250 | 4-[3-Dimethyl-amino-1-(3-nitro-phenyl)-propyl-amino]-quinazoline-8-carboxylic acid amide | 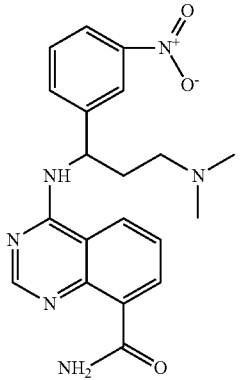 [SMILES: CN(C)CCC(Nc1ncnc2c(C(N)=O)cccc12)c1cccc([N+](=O)[O-])c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 381 | 481 | | | | 0.0250 | 4-((R)-1-{3-[(5-Trifluoro-methyl-pyridine-3-carbonyl)-amino]-phenyl}-ethylamino)-quinazoline-8-carboxylic acid amide | 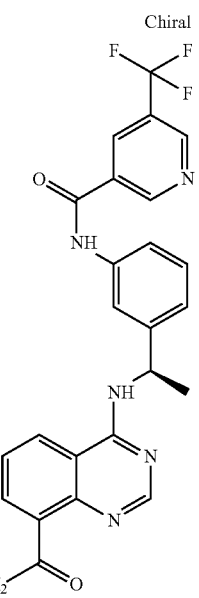 |
| 382 | 348 | | | | 0.0256 | 4-(5-Phenyl-piperidin-3-ylamino)-quinazoline-8-carboxylic acid amide | 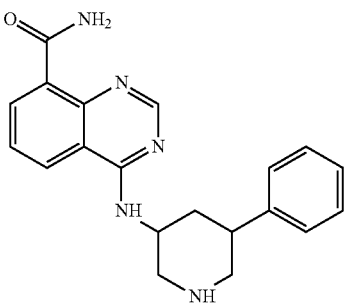 [SMILES: NC(=O)c1cccc2c(NC3CNCC(c4ccccc4)C3)ncnc12] |
| 383 | 472 | 0.00270 | 0.0130 | | 0.0260 | 4-{3-[3-(3-Hydroxy-propoxy)-benzoyl-amino]-benzyl-amino}-quinazoline-8-carboxylic acid amide | 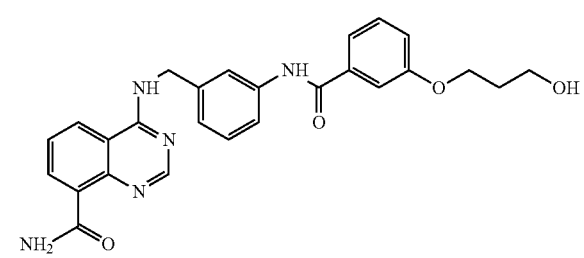 [SMILES: NC(=O)c1cccc2c(NCc3cccc(NC(=O)c4cccc(OCCCO)c4)c3)ncnc12] |
| 384 | 486 | 0.00500 | 0.0035 | | 0.0260 | 4-[3-({2-[(2-Methoxy-ethyl)-methyl-amino]-pyridine-4-carbonyl}-amino)-benzyl-amino]-quinazoline-8-carboxylic acid amide | 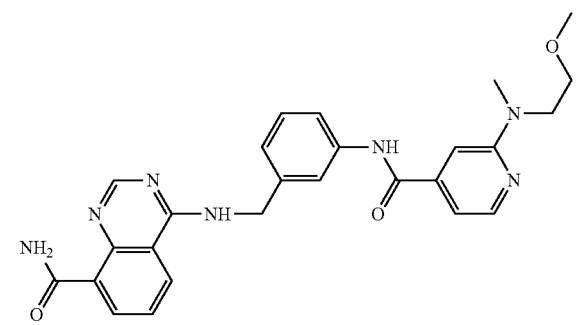 [SMILES: COCCN(C)c1cc(C(=O)Nc2cccc(CNc3ncnc4c(C(N)=O)cccc34)c2)ccn1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 385 | 455 | 0.02200 | | | 0.0260 | 4-[3-(3-Dimethyl-amino-methyl-benzoyl-amino)-benzyl-amino]-quinazoline-8-carboxylic acid amide | 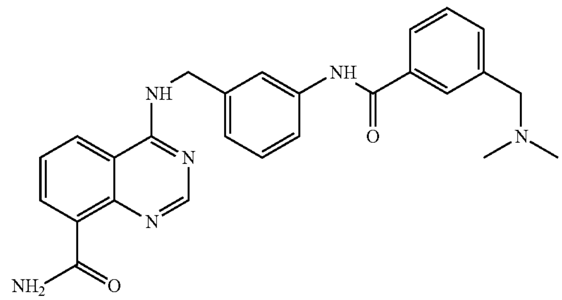 [SMILES: CN(C)Cc1cccc(C(=O)Nc2cccc(CNc3ncnc4c(C(N)=O)cccc34)c2)c1] |
| 386 | 485 | 0.04000 | | | 0.0260 | 4-{3-[3-(2-Dimethyl-amino-ethoxy)-benzoyl-amino]-benzyl-amino}-quinazoline-8-carboxylic acid amide | 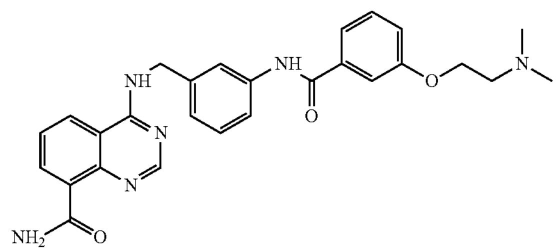 [SMILES: CN(C)CCOc1cccc(C(=O)Nc2cccc(CNc3ncnc4c(C(N)=O)cccc34)c2)c1] |
| 387 | 350 | 0.80000 | | | 0.0260 | 4-((S)-2-Isopropyl-amino-1-phenyl-ethylamino)-quinazoline-8-carboxylic acid amide | Chiral |
| 388 | 311 | | | | 0.0260 | 4-(3-Fluoro-5-methyl-benzyl-amino)-quinazoline-8-carboxylic acid amide | 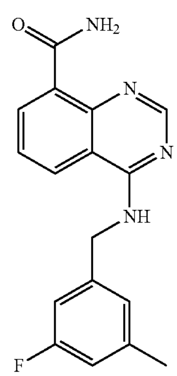 [SMILES: Cc1cc(F)cc(CNc2ncnc3c(C(N)=O)cccc23)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name |
|---|---|---|---|---|---|---|
| 389 | 444 | 0.00025 | | | 0.0260 | 4-((R)-1-{3-[(2-Methoxy-pyrimidine-5-carbonyl)-amino]-phenyl}-ethylamino)-quinazoline-8-carboxylic acid amide |
| 390 | 440 | 0.00023 | 0.00046 | | 0.0270 | 4-{3-[(2,3-Dihydro-benzofuran-5-carbonyl)-amino]-benzyl-amino}-quinazoline-8-carboxylic acid amide |
| 391 | 505 | 0.00110 | 0.0059 | | 0.0270 | 4-{1-[3-(2,6-Difluoro-benzoyl-amino)-phenyl]-3-dimethyl-amino-propyl-amino}-quinazoline-8-carboxylic acid amide |

TABLE 2-continued
| MS (M + No. 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|
| 392 545 | 0.00310 | | 0.0270 | | 4-{1-[3-(2,6-Difluoro-benzoyl-amino]-phenyl]-3-piperidin-1-yl-propyl-amino}-quinazoline-8-carboxylic acid amide | 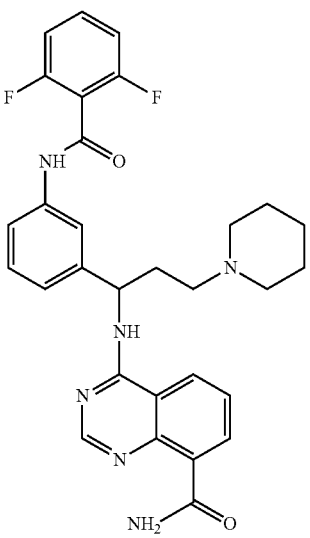 [SMILES: NC(=O)c1cccc2c(NC(CCN3CCCCC3)c3cccc(NC(=O)c4c(F)cccc4F)c3)ncnc12] |
| 394 444 | 6.0000e−05 | 0.00027 | 0.0280 | | 4-(1-{3-[(5-Isopropyl-1H-pyrazole-3-carbonyl)-amino)-phenyl}-ethylamino)-quinazoline-8-carboxylic acid amide | 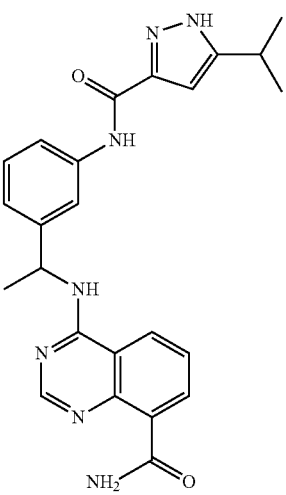 [SMILES: CC(C)c1cc(C(=O)Nc2cccc(C(C)Nc3ncnc4c(C(N)=O)cccc34)c2)n[nH]1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 395 | 498 | 0.00290 | 0.00058 | | 0.0280 | 4-(1-{3-[(2-Ethyl-5-trifluoro-methyl-2H-pyrazole-3-carbonyl)-amino]-phenyl}-ethylamino)-quinazoline-8-carboxylic acid amide | 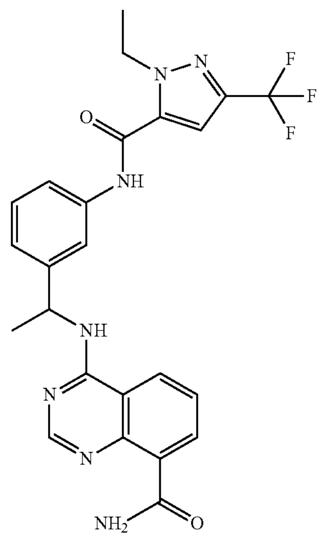 [SMILES: CCn1nc(C(F)(F)F)cc1C(=O)Nc1cccc(C(C)Nc2ncnc3c(C(N)=O)cccc23)c1] |
| 396 | 428 | 0.40000 | | | 0.0280 | 6-Benzyloxy-4-(2-methyl-amino-1-phenyl-ethylamino)-quinazoline-8-carboxylic acid amide | 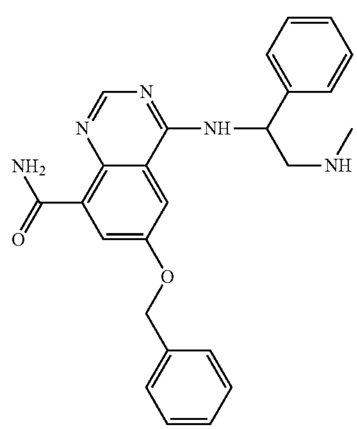 [SMILES: CNCC(Nc1ncnc2c(C(N)=O)cc(OCc3ccccc3)cc12)c1ccccc1] |
| 397 | 348 | 0.46000 | | | 0.0280 | 4-((S)-2-Cyclopropyl amino-1-phenyl-ethylamino)-quinazoline-8-carboxylic acid amide | 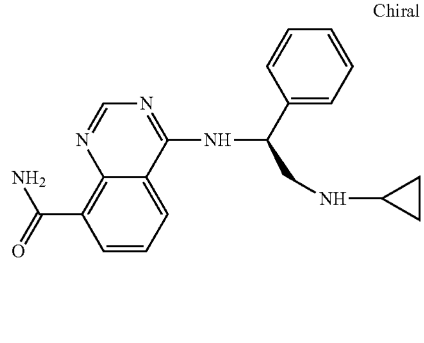 [SMILES: NC(=O)c1cccc2c(N[C@H](CNC3CC3)c3ccccc3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 398 | 458 | 0.00500 | | 0.0290 | | 4-{3-[3-(2-Hydroxy-ethoxy)-benzoyl-amino]-benzyl-amino}-quinazoline-8-carboxylic acid amide | 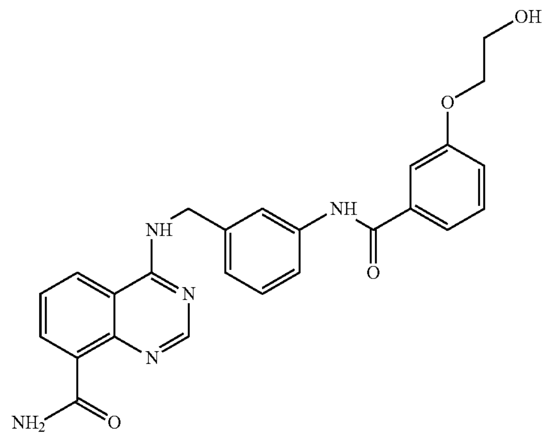 [SMILES: NC(=O)c1cccc2c(NCc3cccc(NC(=O)c4cccc(OCCO)c4)c3)ncnc12] |
| 399 | 545 | 0.00800 | | 0.0290 | | 4-{1-[3-(2,4-Difluoro-benzoyl-amino)-phenyl]-3-piperidin-1-yl-propyl-amino}-quinazoline-8-carboxylic acid amide | 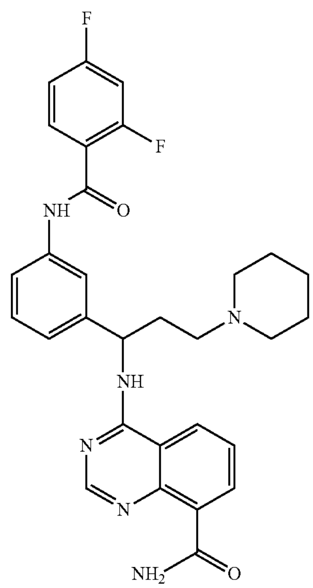 [SMILES: NC(=O)c1cccc2c(NC(CCN3CCCCC3)c3cccc(NC(=O)c4ccc(F)cc4F)c3)ncnc12] |
| 400 | 307 | | | 0.0290 | | 4-{3,5-Dimethyl-benzyl-amino)-quinazoline-8-carboxylic acid amide | 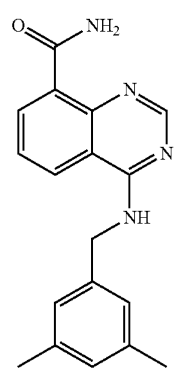 [SMILES: Cc1cc(C)cc(CNc2ncnc3c(C(N)=O)cccc23)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 401 | 514 | | | | 0.0290 | 4-{(R)-1-[3-(2-Chloro-5-trifluoro-methyl-benzoyl-amino)-phenyl]-ethylamino}-quinazoline-8-carboxylic acid amide | 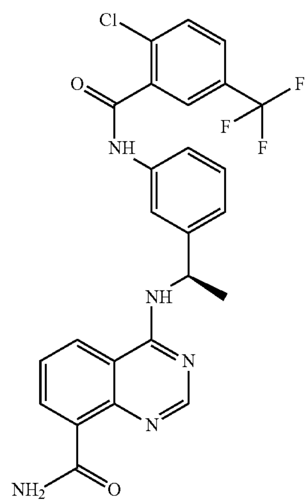 |
| 403 | 492 | 0.00018 | | | 0.0300 | 4-{1-[3-(2-Fluoro-4-methoxy-benzoyl-amino)-phenyl]-3-methoxy-propyl-amino}-quinazoline-8-carboxylic acid amide | 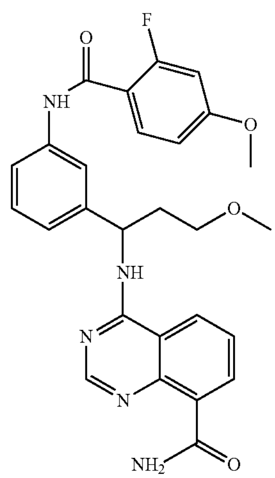 [SMILES: COCCC(Nc1ncnc2c(C(N)=O)cccc12)c1cccc(NC(=O)c2ccc(OC)cc2F)c1] |
| 404 | 442 | 0.00020 | 0.0030 | | 0.0300 | 4-[3-(4-Methoxy-3-methyl-benzoyl-amino)-benzyl-amino]-quinazoline-8-carboxylic acid amide | 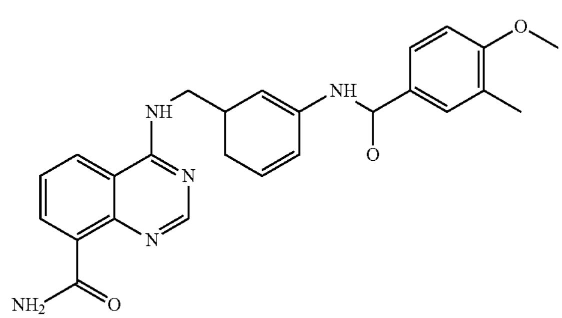 [SMILES: COc1ccc(C(O)NC2=CC(CNc3ncnc4c(C(N)=O)cccc34)CC=C2)cc1C] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 405 | 486 | 0.00030 | | | 0.0300 | 4-(1-{3-[(5-Cyclopropyl-2H-pyrazole-3-carbonyl)-amino]-phenyl}-3-methoxy-propyl-amino)-quinazoline-8-carboxylic acid amide | 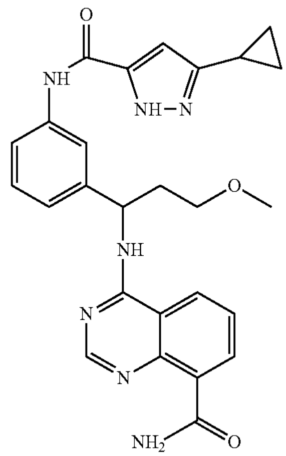 [SMILES: COCCC(Nc1ncnc2c(C(N)=O)cccc12)c1cccc(NC(=O)c2cc(C3CC3)n[nH]2)c1] |
| 406 | 364 | 0.39000 | | | 0.0300 | 4-[2-(Methyl-propyl-amino)-1-phenyl-ethylamino]-quinazoline-8-carboxylic acid amide | 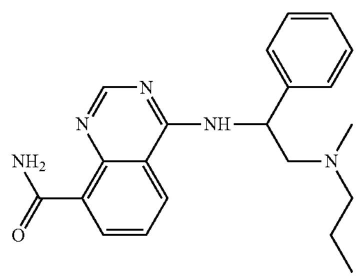 [SMILES: CCCN(C)CC(Nc1ncnc2c(C(N)=O)cccc12)c1ccccc1] |
| 408 | 595 | 0.00610 | | | 0.0310 | 4-{1-[3-(2-Fluoro-4-trifluoro-methyl-benzoyl-amino)-phenyl]-3-piperidin-1-yl-propyl-amino}-quinazoline-8-carboxylic acid amide | 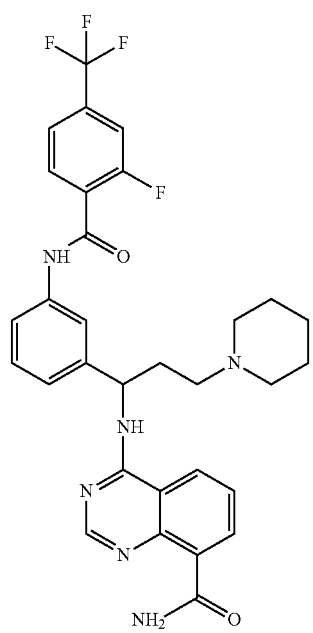 [SMILES: NC(=O)c1cccc2c(NC(CCN3CCCCC3)c3cccc(NC(=O)c4ccc(C(F)(F)F)cc4F)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 409 | 519 | 0.00820 | | | 0.0310 | 4-{1-[3-(4-Bromo-benzyl-amino)-phenyl]-2-dimethyl-amino-ethylamino}-quinazoline-8-carboxylic acid amide | 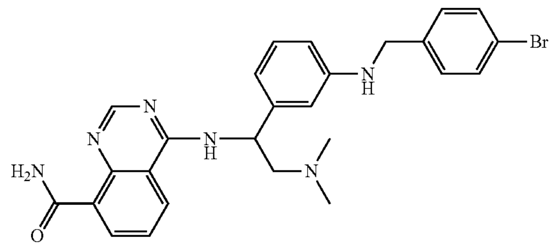 [SMILES: CN(C)CC(Nc1ncnc2c(C(N)=O)cccc12)c1cccc(NCc2ccc(Br)cc2)c1] |
| 411 | 315 | 0.43000 | | | 0.0310 | 4-(3,4-Difluoro-benzyl-amino)-quinazoline-8-carboxylic acid amide | 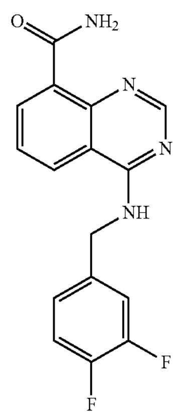 [SMILES: NC(=O)c1cccc2c(NCc3ccc(F)c(F)c3)ncnc12] |
| 412 | 368 | 0.55000 | | | 0.0310 | 4-[2-Methoxy-1-(3-nitro-phenyl)-ethylamino]-quinazoline-8-carboxylic acid amide | 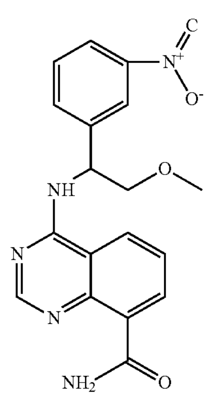 [SMILES: C=[N+]([O-])c1cccc(C(COC)Nc2ncnc3c(C(N)=O)cccc23)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 414 | 443 | 0.00053 | 0.0023 | 0.0320 | | 4-(1-{3-[(2-Methoxy-pyridine-4-carbonyl)-amino]-phenyl}-ethylamino)-quinazoline-8-carboxylic acid amide | 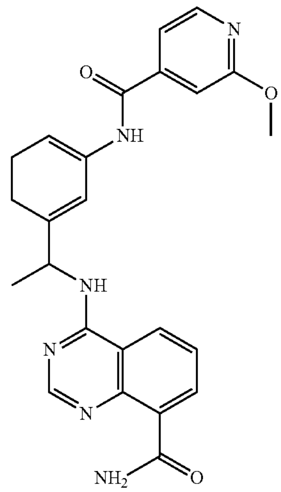 [SMILES: COc1cc(C(=O)NC2=CCCC(C(C)Nc3ncnc4c(C(N)=O)cccc34)=C2)ccn1] |
| 415 | 429 | 0.00093 | | 0.0320 | | 4-{3-[(2-Methoxy-pyridine-4-carbonyl)-amino]-benzyl-amino}-quinazoline-8-carboxylic acid amide | 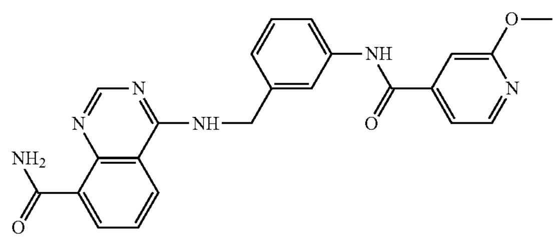 [SMILES: COc1cc(C(=O)Nc2cccc(CNc3ncnc4c(C(N)=O)cccc34)c2)ccn1] |
| 416 | 428 | 0.00310 | | 0.0320 | | 4-((R)-1-{3-[(5-Methyl-pyrazine-2-carbonyl)-amino]-phenyl}-ethylamino)-quinazoline-8-carboxylic acid amide | Chiral |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 418 | 531 | 0.00360 | | | 0.0330 | 4-{1-[3-(2,6-Difluoro-benzoyl-amino)-phenyl]-3-pyrrolidin-1-yl-propyl-amino}-quinazoline-8-carboxylic acid amide | 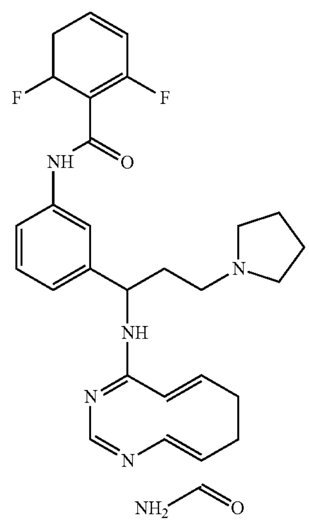 |
| 419 | 511 | 0.04000 | 0.3700 | | 0.0330 | 4-(3-{3-[4-(4-Methyl-piperazin-1-yl)-phenyl]-ureido}-benzyl-amino)-quinazoline-8-carboxylic acid amide | 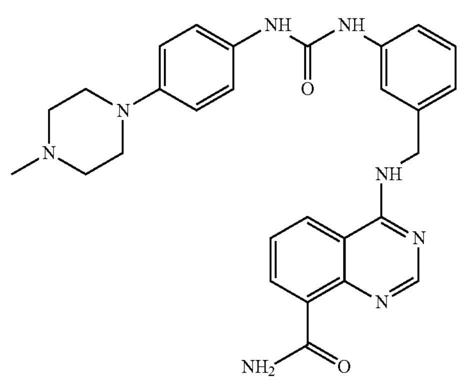 [SMILES: CN1CCN(c2ccc(NC(=O)Nc3cccc(CNc4ncnc5c(C(N)=O)cccc45)c3)cc2)CC1] |
| 420 | 350 | 0.69000 | | | 0.0330 | 4-(7-Nitro-3,4-dihydro-1H-isoquinolin-2-yl)-quinazoline-8-carboxylic acid amide | 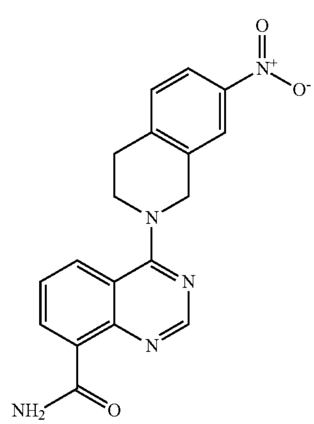 [SMILES: NC(=O)c1cccc2c(N3CCc4ccc([N+](=O)[O-])cc4C3)ncnc12] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 421 | 415 | 0.00036 | | | 0.0340 | 4-(1-{3-[(1-Methyl-1H-pyrrole-2-carbonyl)-amino]-phenyl}-ethylamino)-quinazoline-8-carboxylic acid amide | 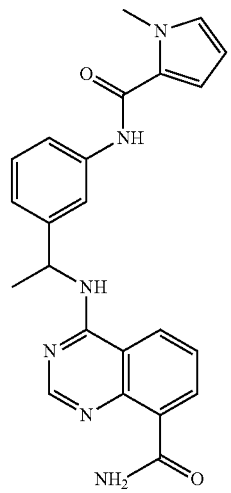 [SMILES: CC(Nc1ncnc2c(C(N)=O)cccc12)c1cccc(NC(=O)c2cccn2C)c1] |
| 422 | 531 | 0.00061 | | | 0.0340 | 4-{1-[3-(3,4-Difluoro-benzoyl-amino)-phenyl]-3-pyrrolidin-1-yl-propyl-amino}-quinazoline-8-carboxylic acid amide | 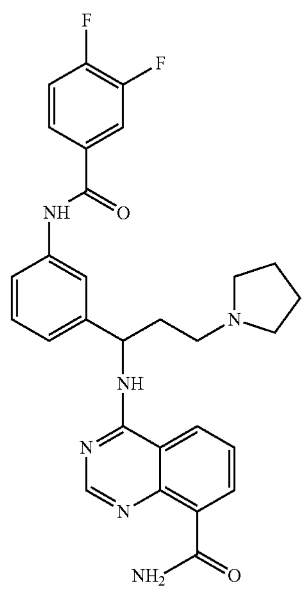 [SMILES: NC(=O)c1cccc2c(NC(CCN3CCCC3)c3cccc(NC(=O)c4ccc(F)c(F)c4)c3)ncnc12] |
| 423 | 429 | 0.00066 | 4.2000e−05 | | 0.0340 | 4-{3-[(6-Methoxy-pyridine-3-carbonyl)-amino]-benzyl-amino}-quinazoline-8-carboxylic acid amide | 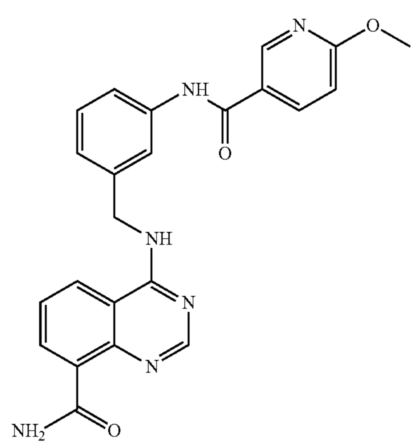 [SMILES: COc1ccc(C(=O)Nc2cccc(CNc3ncnc4c(C(N)=O)cccc34)c2)cn1] |

TABLE 2-continued
| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 424 | 368 | 0.52000 | | | 0.0340 | 4-{[3-hydroxy-1-(3-nitrophenyl)propyl]-amino}-quinazoline-8-carboxamide | 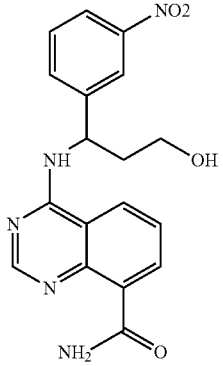 [SMILES: NC(=O)c1cccc2c(NC(CCO)c3cccc([N+](=O)[O-])c3)ncnc12] |
| 425 | 460 | 0.00025 | 0.00057000 | | 0.0350 | 4-{1-[3-(3-Fluoro-4-methoxy-benzoyl-amino)-phenyl]-ethylamino}-quinazoline-8-carboxylic acid amide | 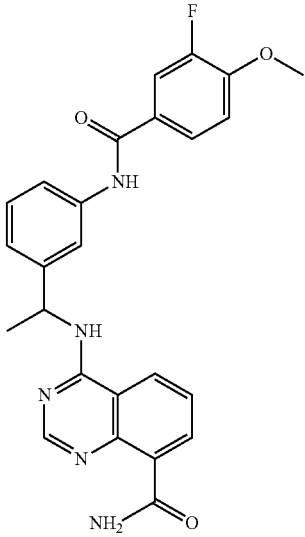 |
| 426 | 483 | 0.00037 | 4.6000e−05 | | 0.0350 | 4-{1-[3-(4-Diethyl-amino-benzoyl-amino)-phenyl]-ethylamino}-quinazoline-8-carboxylic acid amide | 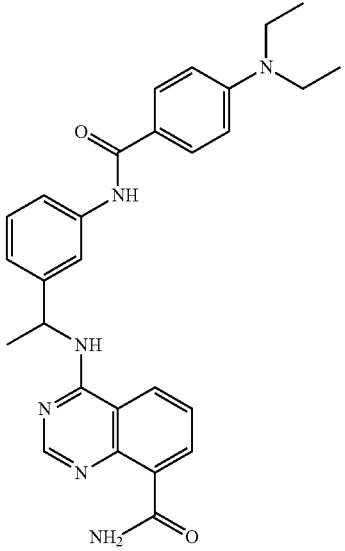 [SMILES: CCN(CC)c1ccc(C(=O)Nc2cccc(C(C)Nc3ncnc4c(C(N)=O)cccc34)c2)cc1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 427 | 327 | 0.60000 | | | 0.0350 | 4-(3-Fluoro-benzyl-amino)-5-methoxy-quinazoline-8-carboxylic acid amide |
| 428 | 473 | | | | 0.0350 | 4-((R)-1-{3-[(2,6-Dimethoxy-pyridine-3-carbonyl)-amino]-phenyl}-ethylamino)-quinazoline-8-carboxylic acid amide |
| 429 | 486 | 0.00450 | 0.0720 | | 0.0360 | 4-{3-[3-(3-Methoxy-propoxy)-benzoyl-amino)-benzyl-amino}-quinazoline-8-carboxylic acid amide |
| 430 | 471 | 0.02000 | 0.0130 | | 0.0360 | 4-{3-[3-(2-Methyl-amino-ethoxy)-benzoyl-amino]-benzyl-amino}-quinazoline-8-carboxylic acid amide |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 431 | 321 | | | | 0.0360 | 4-((R)-1-Phenyl-butylamino)-quinazoline-8-carboxylic acid amide | 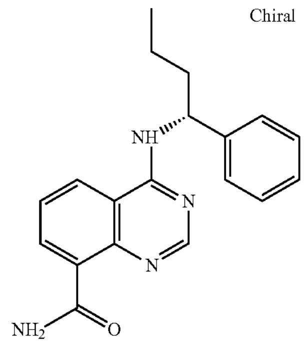 [SMILES: CCC[C@@H](Nc1ncnc2c(C(N)=O)cccc12)c1ccccc1] |
| 432 | 506 | | | | 0.0360 | 4-{(R)-1-[3-(2-Chloro-4,5-dimethoxy-benzoyl-amino)-phenyl]-ethylamino}-quinazoline-8-carboxylic acid amide | 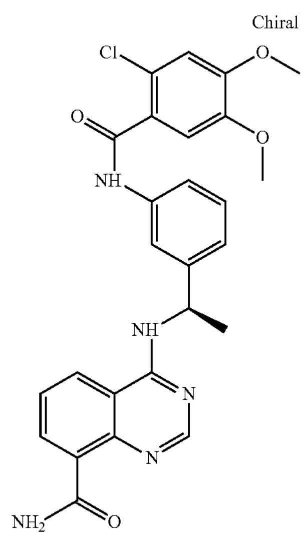 [SMILES: COc1cc(Cl)c(C(=O)Nc2cccc([C@@H](C)Nc3ncnc4c(C(N)=O)cccc34)c2)cc1OC] |
| 433 | 605 | 0.00040 | | | 0.0370 | 4-[1-[3-(4-Bromo-benzoyl-amino)-phenyl]-2-(2-dimethyl-amino-ethyl-carbamoyl)-ethylamino]-quinazoline-8-carboxylic acid amide | 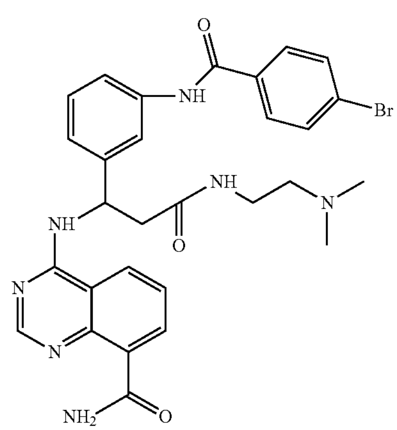 [SMILES: CN(C)CCNC(=O)CC(Nc1ncnc2c(C(N)=O)cccc12)c1cccc(NC(=O)c2ccc(Br)cc2)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 434 | 456 | 0.00022 | 0.00051 | | 0.0380 | 4-{3-[(5-Trifluoro-methyl-1H-pyrazole-3-carbonyl)-amino]-benzyl-amino}-quinazoline-8-carboxylic acid amide | 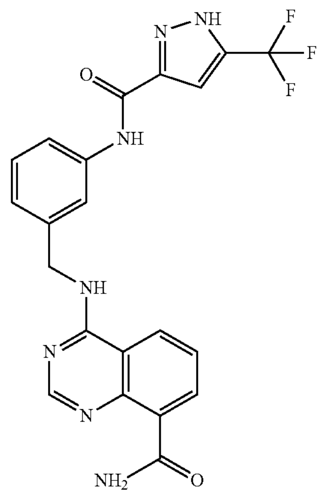 [SMILES: NC(=O)c1cccc2c(NCc3cccc(NC(=O)c4cc(C(F)(F)F)[nH]n4)c3)ncnc12] |
| 435 | 585 | 0.00100 | | | 0.0380 | {3-(8-Carbamoyl-quinazolin-4-ylamino)-3-[3-(4-methoxy-benzoyl-amino)-phenyl]-propyl}-methyl-carbamic acid tert-butyl ester | 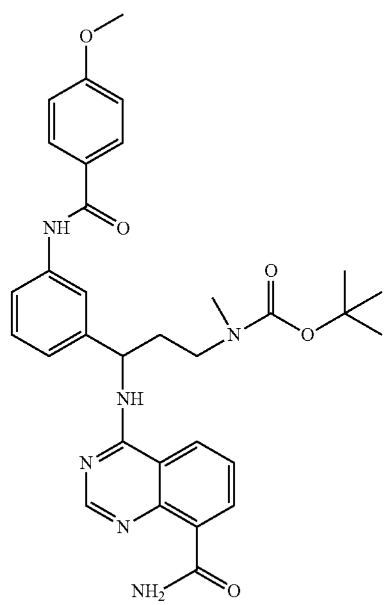 [SMILES: COc1ccc(C(=O)Nc2cccc(C(CCN(C)C(=O)OC(C)(C)C)Nc3ncnc4c(C(N)=O)cccc34)c2)cc1] |
| 436 | 425 | 0.00510 | 0.0430 | | 0.0380 | 4-[3-(1-Methyl-1H-imidazo[4,5-c]pyridin-4-ylamino)-benzyl-amino]-quinazoline-8-carboxylic acid amide | 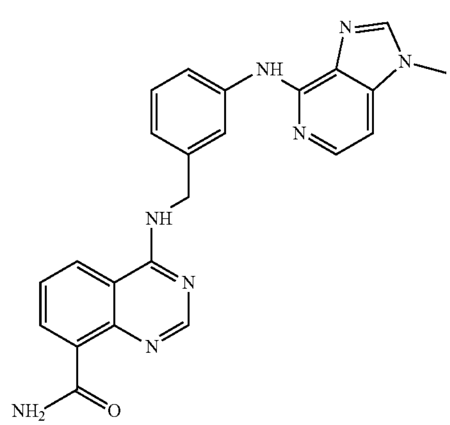 [SMILES: Cn1cnc2c(Nc3cccc(CNc4ncnc5c(C(N)=O)cccc45)c3)nccc21] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
| --- | --- | --- | --- | --- | --- | --- | --- |
| 437 | 505 | 0.00550 | 0.0092 | | 0.0380 | 4-{1-[3-(2,5-Difluoro-benzoyl-amino)-phenyl]-3-dimethyl-amino-propyl-amino}-quinazoline-8-carboxylic acid amide | 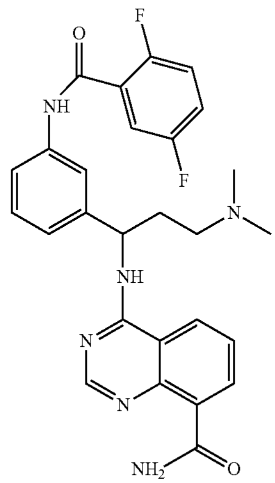 [SMILES: CN(C)CCC(Nc1ncnc2c(C(N)=O)cccc12)c1cccc(NC(=O)c2cc(F)ccc2F)c1] |
| 438 | 412 | 0.16000 | | | 0.0380 | 4-[2-Dimethyl-amino-1-(3-fluoro-phenyl)-ethylamino]-6-isopropoxy-quinazoline-8-carboxylic acid amide | 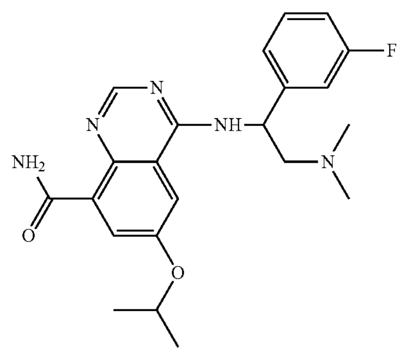 [SMILES: CC(C)Oc1cc(C(N)=O)c2ncnc(NC(CN(C)C)c3cccc(F)c3)c2c1] |
| 440 | 460 | 0.00013 | 0.00041 | | 0.0390 | 4-{(R)-1-[3-(3-Fluoro-4-methoxy-benzoyl-amino)-phenyl]-ethylamino}-quinazoline-8-carboxylic acid amide | 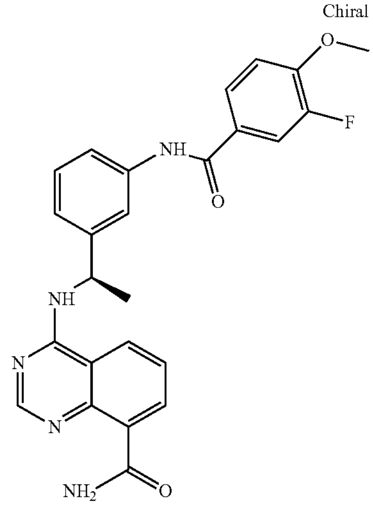 [SMILES: COc1ccc(C(=O)Nc2cccc([C@@H](C)Nc3ncnc4c(C(N)=O)cccc34)c2)cc1F] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 441 | 315 | 1.9000 | | 0.0390 | 87 | 4-(2,3-Difluoro-benzyl-amino)-quinazoline-8-carboxylic acid amide | 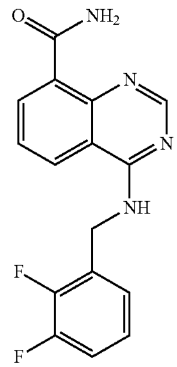 [SMILES: NC(=O)c1cccc2c(NCc3cccc(F)c3F)ncnc12] |
| 442 | 402 | 0.00056 | | 0.0400 | | 4-(1-{3-[(Furan-3-carbonyl)-amino]-phenyl}-ethylamino)-quinazoline-8-carboxylic acid amide | 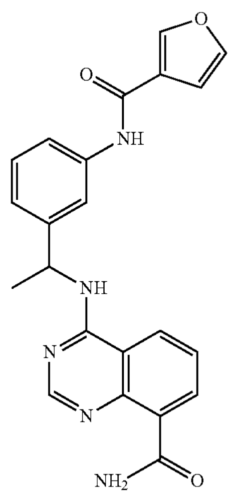 [SMILES: CC(Nc1ncnc2c(C(N)=O)cccc12)c1cccc(NC(=O)c2ccoc2)c1] |
| 443 | 307 | | | 0.0400 | | 4-((R)-1-Phenyl-propyl-amino)-quinazoline-8-carboxylic acid amide | Chiral |
| 444 | 482 | 0.00089 | 0.0023 | 0.0410 | 83 | 4-{3-[(3,4,5,6-Tetrahydro-2H-[1,2']bi-pyridinyl-4'-carbonyl)-amino]-benzyl-amino}-quinazoline-8-carboxylic acid amide | 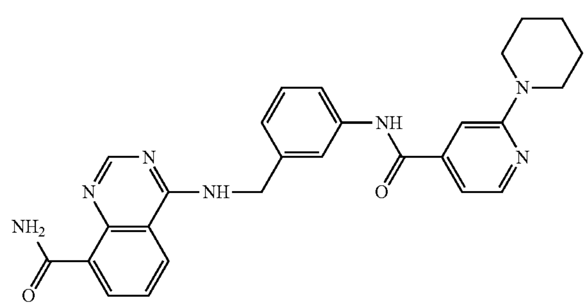 [SMILES: NC(=O)c1cccc2c(NCc3cccc(NC(=O)c4ccnc(N5CCCCC5)c4)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 445 | 329 | | | 0.0410 | 61 | 4-[1-(3,5-Difluoro-phenyl)-ethylamino]-quinazoline-8-carboxylic acid amide | 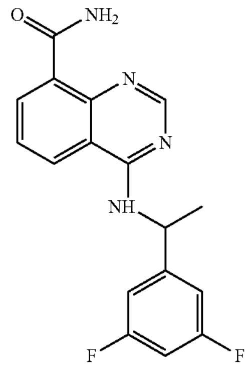 [SMILES: CC(Nc1ncnc2c(C(N)=O)cccc12)c1cc(F)cc(F)c1] |
| 446 | 497 | 0.00038 | | 0.0420 | | 4-{1-[3-(4-Morpholin-4-yl-benzoyl-amino)-phenyl]-ethylamino}-quinazoline-8-carboxyiic acid amide | 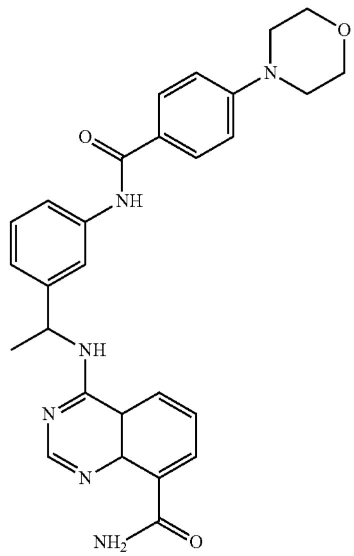 [SMILES: CC(NC1=NC=NC2C(C(N)=O)=CC=CC12)c1cccc(NC(=O)c2ccc(N3CCOCC3)cc2)c1] |
| 447 | 466 | 0.00049 | 0.00058 | 0.0420 | | 4-{3-[(6-Pyrrolidin-1-yl-pyridine-3-carbonyl)-amino]-benzyl-amino}-quinazoline-8-carboxylic acid amide | 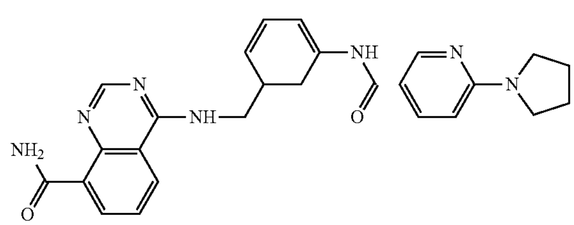 |
| 448 | 484 | 0.00230 | | 0.0420 | | 6-Hydroxy-4-{3-[(2-pyrrolidin-1-yl-pyridine-4-carbonyl)-amino]-benzyl-amino}-quinazoline-8-carboxylic acid amide | 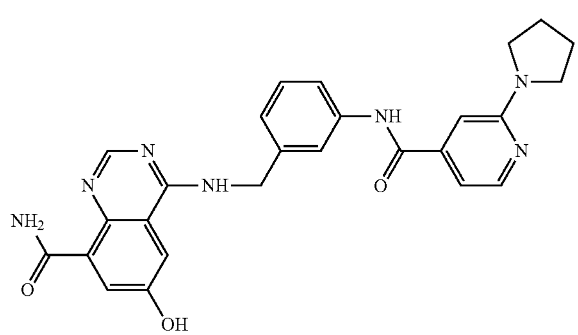 [SMILES: NC(=O)c1cc(O)cc2c(NCc3cccc(NC(=O)c4ccnc(N5CCCC5)c4)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 449 | 331 | 0.75000 | | | 0.0420 | 4-(3-Chloro-5-fluoro-benzyl-amino)-quinazoline-8-carboxylic acid amide | 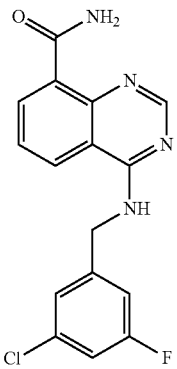 [SMILES: NC(=O)c1cccc2c(NCc3cc(F)cc(Cl)c3)ncnc12] |
| 450 | 499 | 0.00044 | 0.0011 | | 0.0430 | 4-(1-{3-[(5-Cyclopropyl-2H-pyrazole-3-carbonyl)-amino]-phenyl}-3-dimethyl-amino-propyl-amino)-quinazoline-8-carboxylic acid amide | 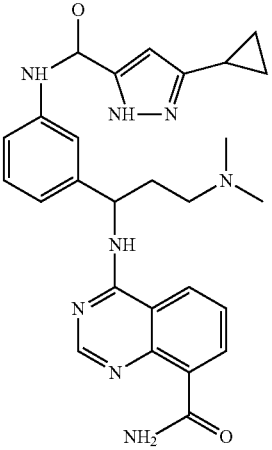 [SMILES: CN(C)CCC(Nc1ncnc2c(C(N)=O)cccc12)c1cccc(NC(O)c2cc(C3CC3)n[nH]2)c1] |
| 452 | 429 | 0.01700 | | | 0.0440 | 4-(1-{3-[(1-Oxy-pyridine-4-carbonyl)-amino]-phenyl}-ethylamino)-quinazoline-8-carboxylic acid amide | 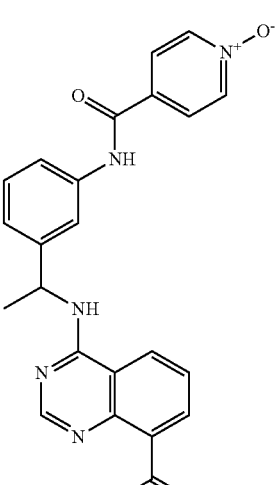 |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 453 | 428 | | | | 0.0442 | 6-(4-Methoxy-phenyl)-4-(2-methyl-amino-1-phenyl-ethylamino)-quinazoline-8-carboxylic acid amide | 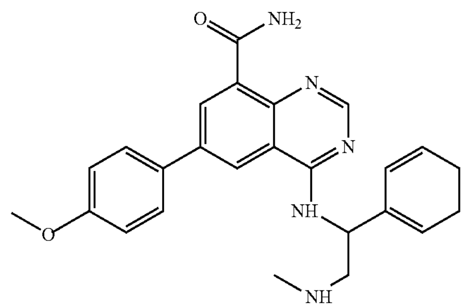 |
| 454 | 498 | | | | 0.0450 | 4-{(R)-1-[3-(3-Fluoro-5-trifluoro-methyl-benzoyl-amino)-phenyl]-ethylamino}-quinazoline-8-carboxylic acid amide | Chiral |
| 456 | 484 | 0.00160 | 0.00094 | | 0.0460 | 4-(1-{3-[(5-Methyl-2-trifluoro-methyl-furan-3-carbonyl)-amino]-phenyl}-ethylamino)-quinazoline-8-carboxylic acid amide | 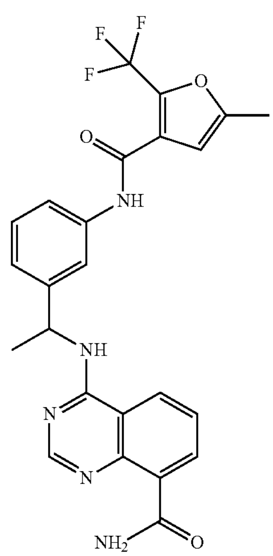 [SMILES: Cc1cc(C(=O)Nc2cccc(C(C)Nc3ncnc4c(C(N)=O)cccc34)c2)c(C(F)(F)F)o1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 457 | 481 | | | | 0.0470 | 4-((R)-1-{3-[(5-Trifluoro-methyl-pyridine-2-carbonyl)-amino]-phenyl}-ethylamino)-quinazoline-8-carboxylic acid amide | Chiral 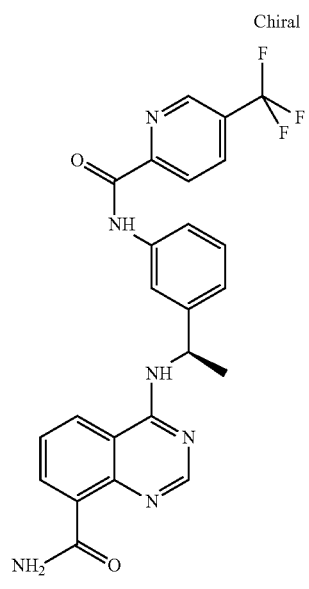 [SMILES: C[C@@H](Nc1ncnc2c(C(N)=O)cccc12)c1cccc(NC(=O)c2ccc(C(F)(F)F)cn2)c1] |
| 458 | 499 | 0.00081 | 0.0010 | | 0.0480 | 4-{3-Dimethyl-amino-1-[3-(4-methoxy-benzoyl-amino)-phenyl]-propyl-amino}-quinazoline-8-carboxylic acid amide | 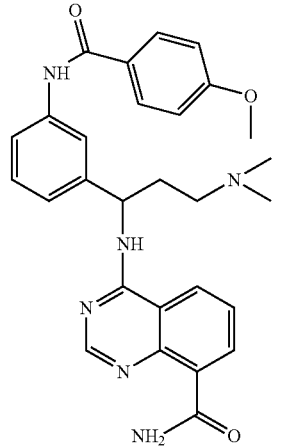 [SMILES: COc1ccc(C(=O)Nc2cccc(C(CCN(C)C)Nc3ncnc4c(C(N)=O)cccc34)c2)cc1] |
| 459 | 486 | 9.0000e−05 | | | 0.0490 | 4-[3-({6-[(2-Methoxy-ethyl)-methyl-amino]-pyridine-3-carbonyl}-amino)-benzyl-amino]-quinazoline-8-carboxylic acid amide | 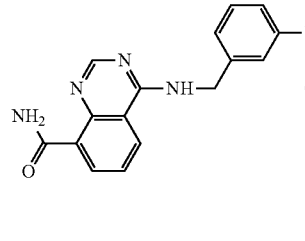 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 461 | 429 | 0.04400 | | | 0.0510 | 4-(1-{3-[(1-Oxy-pyridine-3-carbonyl)-amino]-phenyl}-ethylamino)-quinazoline-8-carboxylic acid amide |
| 462 | 540 | 5.0000e−05 | 0.0053 | | 0.0520 | 4-{3-Methoxy-1-[3-(4-trifluoro-methoxy-benzoyl-amino)-phenyl]-propyl-amino}-quinazoline-8-carboxylic acid amide |
| 463 | 457 | 0.00047 | 0.0021 | | 0.0520 | 4-(1-{3-[(2-Ethoxy-pyridine-4-carbonyl)-amino]-phenyl}-ethylamino)-quinazoline-8-carboxylic acid amide |

TABLE 2-continued

| No. | MS (M+1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 464 | 476 | 0.00140 | 0.0015 | 0.0530 | 97 | 4-[3-(4-Methane-sulfonyl-benzoyl-amino)-benzyl-amino]-quinazoline-8-carboxylic acid amide | 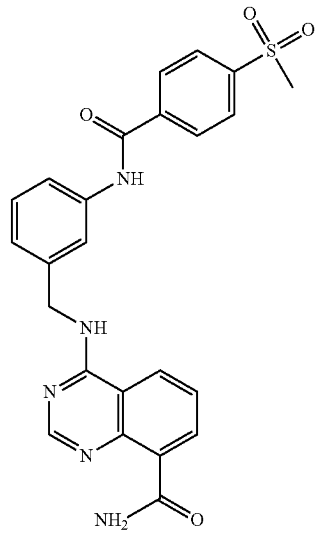 [SMILES: CS(=O)(=O)c1ccc(C(=O)Nc2cccc(CNc3ncnc4c(C(N)=O)cccc34)c2)cc1] |
| 465 | 378 | 0.05600 | | 0.0540 | 95 | 4-[(S)-2-(Ethyl-isopropyl-amino)-1-phenyl-ethylamino]-quinazoline-8-carboxylic acid amide | 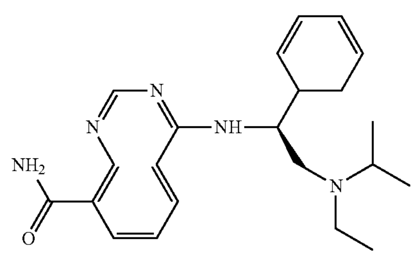 |
| 466 | 500 | 0.05100 | 0.1800 | 0.0550 | | 4-(3-{3-[4-(2-Dimethyl-amino-ethoxy)-phenyl]-ureido}-benzyl-amino)-quinazoline-8-carboxylic acid amide | 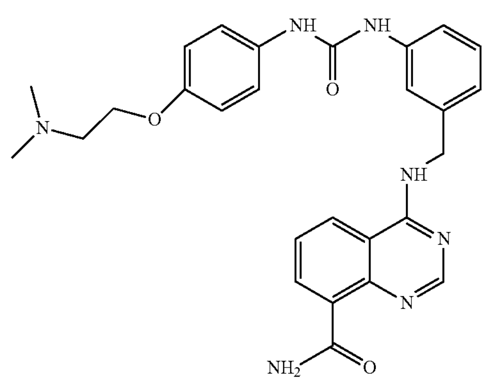 [SMILES: CN(C)CCOc1ccc(NC(=O)Nc2cccc(CNc3ncnc4c(C(N)=O)cccc34)c2)cc1] |
| 467 | 359 | 0.30000 | | 0.0550 | 89 | 4-(2-Imidazol-1-yl-1-phenyl-ethylamino)-quinazoline-8-carboxylic acid amide | 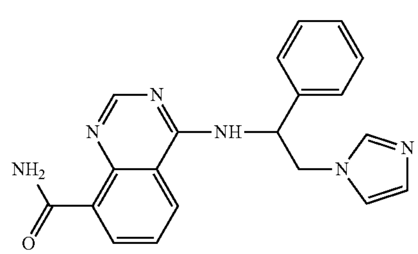 [SMILES: NC(=O)c1cccc2c(NC(Cn3ccnc3)c3ccccc3)ncnc12] |

TABLE 2-continued
| No. | MS (M+1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 469 | 498 | 0.00041 | | 0.0560 | | 4-{(R)-1-[3-(3-Fluoro-4-trifluoro-methyl-benzoyl-amino)-phenyl]-ethylamino}-quinazoline-8-carboxylic acid amide | 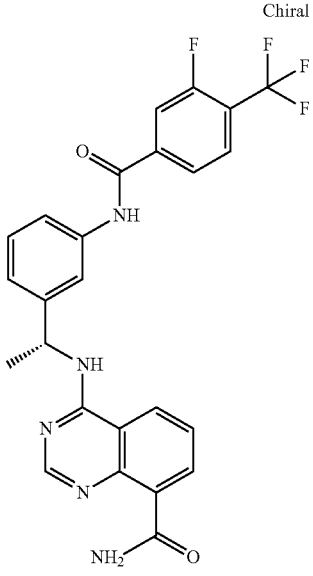 [SMILES: C[C@@H](Nc1ncnc2c(C(N)=O)cccc12)c1cccc(NC(=O)c2ccc(C(F)(F)F)c(F)c2)c1] |
| 470 | 444 | 0.00130 | | 0.0560 | | 4-((R)-1-{3-[(1-Ethyl-5-methyl-1H-pyrazole-3-carbonyl)-amino]-phenyl}-ethylamino)-quinazoline-8-carboxylic acid amide | 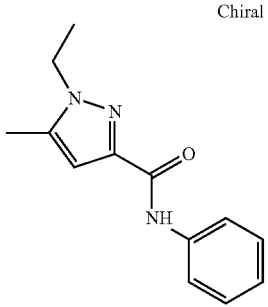 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 471 | 510 | 0.00880 | | 0.0570 | | 4-(1-{3-[4-(4-Methyl-piperazin-1-yl)-benzoyl-amino]-phenyl}-ethylamino)-quinazoline-8-carboxylic acid amide | 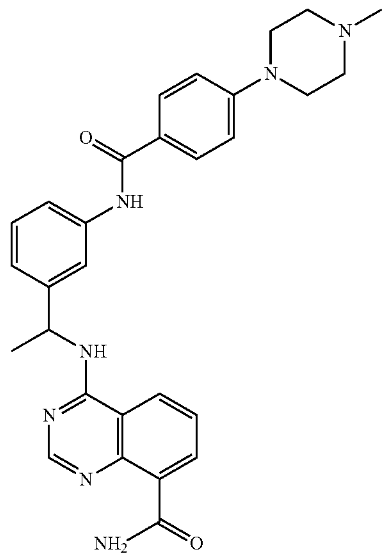 [SMILES: CC(Nc1ncnc2c(C(N)=O)cccc12)c1cccc(NC(=O)c2ccc(N3CCN(C)CC3)cc2)c1] |
| 472 | 404 | 0.00012 | | 0.0580 | | 4-{(R)-1-[3-(Cyclo-pentane-carbonyl-amino)-phenyl]-ethylamino}-quinazoline-8-carboxylic acid amide | Chiral |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 473 | 485 | 0.00023 | | 0.0580 | | 5-{3-[(S)-1-(8-Carbamoyl-quinazolin-4-ylamino)-ethyl]-phenylcarbamoyl}-pyridine-2-carboxylic acid ethyl ester | Chiral |
| 474 | 414 | 0.00120 | | 0.0590 | | 4-((R)-1-{3-[(Pyrimidine-5-carbonyl)-amino]-phenyl}-ethylamino)-quinazoline-8-carboxylic acid amide | Chiral |
| 475 | 496 | 0.00053 | | 0.0600 | 86 | 4-{1-[3-(4-Trifluoro-methoxy-benzoyl-amino)-phenyl]-ethylamino}-quinazoline-8-carboxylic acid amide | 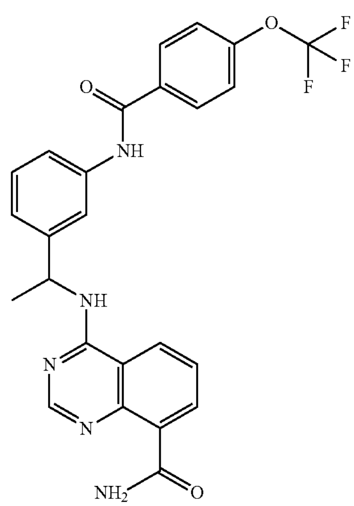 [SMILES: CC(Nc1ncnc2c(C(N)=O)cccc12)c1cccc(NC(=O)c2ccc(OC(F)(F)F)cc2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 476 | 564 | 0.00340 | 0.0058 | 0.0610 | 82 | 4-{3-[4-(4-Methyl-piperazin-1-yl)-3-trifluoro-methyl-benzoyl-amino]-benzyl-amino}-quinazoline-8-carboxylic acid amide | 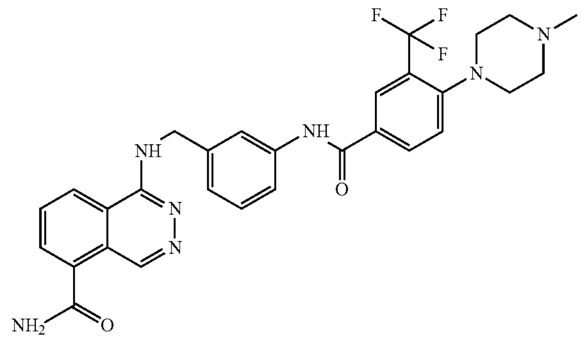 [SMILES: CN1CCN(c2ccc(C(=O)Nc3cccc(CNc4nncc5c(C(N)=O)cccc45)c3)cc2C(F)(F)F)CC1] |
| 477 | 419 | | | 0.0610 | | 2-{3-[1-(8-Carbamoyl-quinazolin-4-ylamino)-ethyl]-phenyl-amino}-oxazole-5-carboxylic acid | 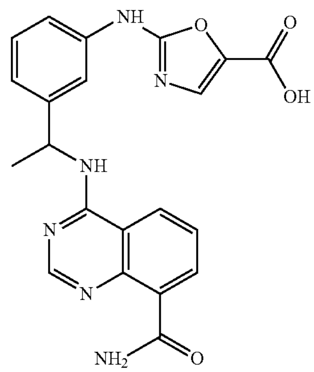 [SMILES: CC(Nc1ncnc2c(C(N)=O)cccc12)c1cccc(Nc2ncc(C(=O)O)o2)c1] |
| 478 | 432 | | | 0.0610 | | 4-((R)-1-{3-[(4-Methyl-cyclohexane-carbonyl)-amino]-phenyl}-ethylamino)-quinazoline-8-carboxylic acid amide | 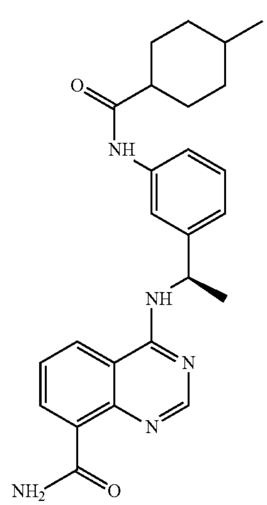 |
| 482 | 470 | 0.00022 | | 0.0640 | | 4-{3-[(2-Isobutyl-amino-pyridine-4-carbonyl)-amino]-benzyl-amino}-quinazoline-8-carboxylic acid amide | 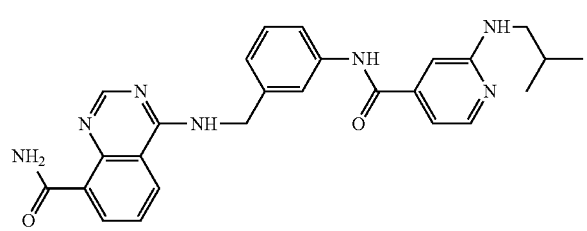 [SMILES: CC(C)CNc1cc(C(=O)Nc2cccc(CNc3ncnc4c(C(N)=O)cccc34)c2)ccn1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 483 | 299 | | | 0.0640 | | 4-((R)-1-Cyclohexyl-ethylamino)-quinazoline-8-carboxylic acid amide | 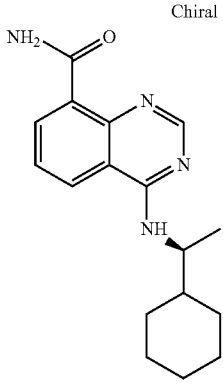 [SMILES: C[C@H](Nc1ncnc2c(C(N)=O)cccc12)C1CCCCC1] |
| 484 | 458 | 0.00440 | 0.0180 | 0.0650 | 96 | 4-(3-{[2-(2-Hydroxy-ethylamino)-pyridine-4-carbonyl]-amino}-benzyl-amino)-quinazoline-8-carboxylic acid amide | 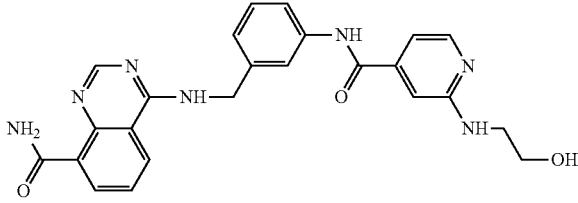 [SMILES: NC(=O)c1cccc2c(NCc3cccc(NC(=O)c4ccnc(NCCO)c4)c3)ncnc12] |
| 485 | 495 | 0.00440 | | 0.0650 | | 4-{(R)-1-[3-(4-Pyrrolidin-1-ylmethyl-benzoyl-amino)-phenyl]-ethylamino}-quinazoline-8-carboxylic acid amide | 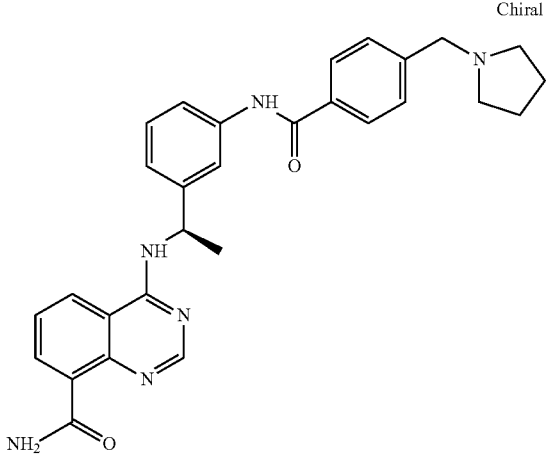 [SMILES: C[C@@H](Nc1ncnc2c(C(N)=O)cccc12)c1cccc(NC(=O)c2ccc(CN3CCCC3)cc2)c1] |
| 486 | 366 | 0.82000 | | 0.0650 | | 4-[2-Dimethyl-amino-1-(2-methoxy-phenyl)-ethylamino]-quinazoline-8-carboxylic acid amide | 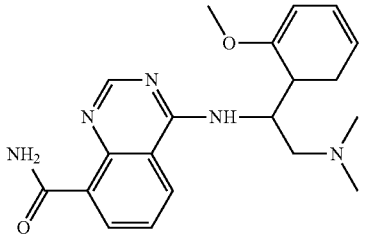 [SMILES: COC1=CC=CCC1C(CN(C)C)Nc1ncnc2c(C(N)=O)cccc12] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 487 | 486 | 0.00042 | 0.00094 | 0.0660 | 96 | 4-{3-Methoxy-1-[3-(4-methoxy-benzoyl-amino)-phenyl]-propyl-amino}-quinazoline-8-carboxylic acid amide | 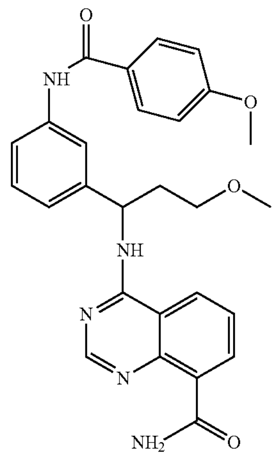 [SMILES: COCCC(Nc1ncnc2c(C(N)=O)cccc12)c1cccc(NC(=O)c2ccc(OC)cc2)c1] |
| 488 | 428 | 0.00069 | 0.00026 | 0.0660 | | 4-{3-[(6-Methyl-amino-pyridine-3-carbonyl)-amino]-benzyl-amino}-quinazoline-8-carboxylic acid amide | 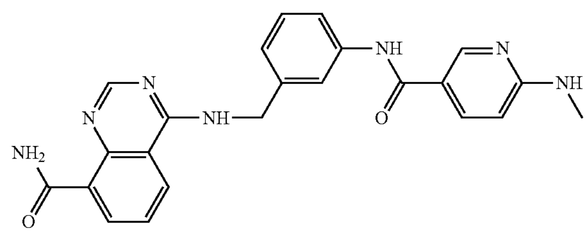 [SMILES: CNc1ccc(C(=O)Nc2cccc(CNc3ncnc4c(C(N)=O)cccc34)c2)cn1] |
| 489 | 362 | 0.15000 | | 0.0660 | 74 | 4-[(S)-2-(Cyclo-propyl-methyl-amino)-1-phenyl-ethylamino]-quinazoline-8-carboxylic acid amide | 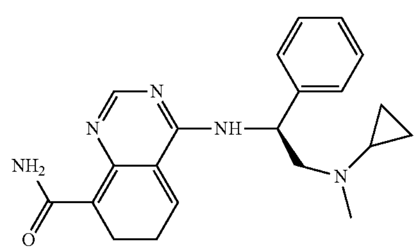 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 490 | 589 | 0.00830 | | 0.0670 | | {2-(8-Carbamoyl-quinazolin-4-ylamino)-2-[3-(3-fluoro-4-methoxy-benzoylamino)-phenyl]-ethyl}-methyl-carbamic acid tert-butyl ester | 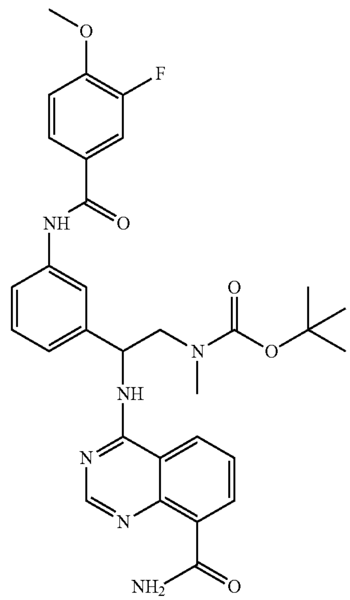 [SMILES: COc1ccc(C(=O)Nc2cccc(C(CN(C)C(=O)OC(C)(C)C)Nc3ncnc4c(C(N)=O)cccc34)c2)cc1F] |
| 491 | 510 | | | 0.0670 | | 4-{(R)-1-[3-(4-Methoxy-3-trifluoromethyl-benzoylamino)-phenyl]-ethylamino}-quinazoline-8-carboxylic acid amide | Chiral |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 492 | 461 | 0.00078 | | | 0.0680 | 4-((R)-1-{3-[(4-Isopropyl-thiazole-2-carbonyl)-amino]-phenyl}-ethylamino)-quinazoline-8-carboxylic acid amide | Chiral |
| 493 | 517 | 0.00500 | | | 0.0700 | 4-{3-Dimethyl-amino-1-[3-(3-fluoro-4-methoxy-benzoyl-amino)-phenyl]-propyl-amino}-quinazoline-8-carboxylic acid amide | 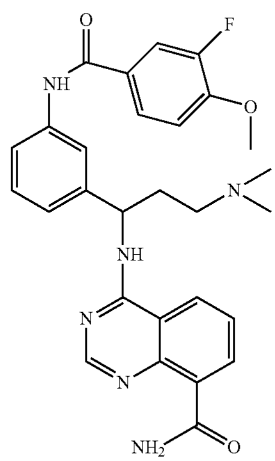 [SMILES: COc1ccc(C(=O)Nc2cccc(C(CCN(C)C)Nc3ncnc4c(C(N)=O)cccc34)c2)cc1F] |
| 494 | 421 | 1.50000 | | | 0.0700 | 4-[3-(Allyl-methyl-amino)-1-(3-nitro-phenyl)-propyl-amino]-quinazoline-8-carboxylic acid amide | 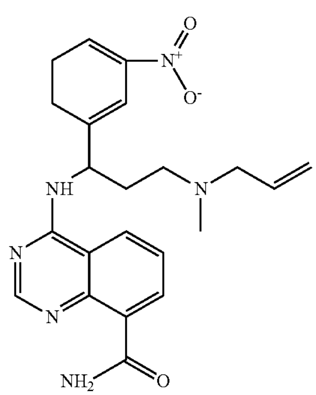 [SMILES: C=CCN(C)CCC(Nc1ncnc2c(C(N)=O)cccc12)C1=CC([N+](=O)[O-])=CCC1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 495 | 588 | 0.00042 | 0.00082 | | 0.0720 | 4-{1-[3-(4-Bromo-benzoyl-amino)-phenyl]-3-piperidin-1-yl-propyl-amino}-quinazoline-8-carboxylic acid amide | 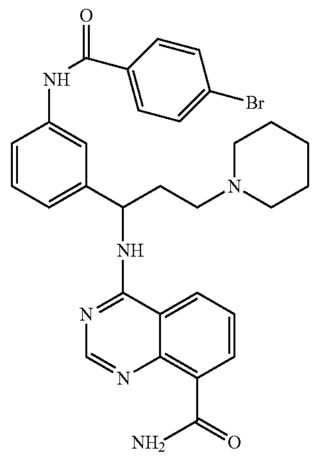 [SMILES: NC(=O)c1cccc2c(NC(CCN3CCCCC3)c3cccc(NC(=O)c4ccc(Br)cc4)c3)ncnc12] |
| 496 | 477 | 0.00057 | 4.5000e-05 | | 0.0720 | 4-{4-[(5-Trifluoro-methyl-1H-pyrazole-3-carbonyl)-amino]-benzyl-amino}-quinazoline-8-carboxylic acid amide | 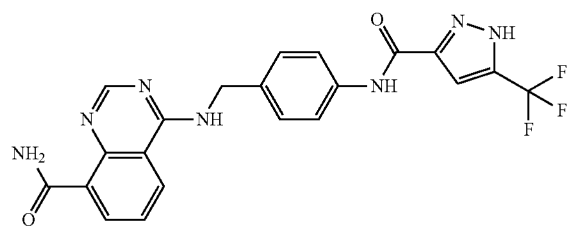 [SMILES: NC(=O)c1cccc2c(NCc3ccc(NC(=O)c4cc(C(F)(F)F)[nH]n4)cc3)ncnc12] |
| 497 | 458 | 0.00077 | 0.0036 | | 0.0720 | 4-[3-(2,4-Dimethoxy-benzoyl-amino)-benzyl-amino]-quinazoline-8-carboxylic acid amide | 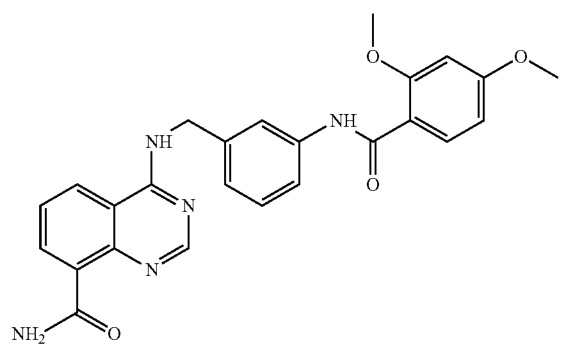 [SMILES: COc1ccc(C(=O)Nc2cccc(CNc3ncnc4c(C(N)=O)cccc34)c2)c(OC)c1] |
| 498 | 336 | 1 | | | 0.0730 | 4-((S)-1-Methyl-amino-methyl-2-phenyl-ethylamino)-quinazoline-8-carboxylic acid amide | Chiral |

TABLE 2-continued
| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 499 | 309 | 0.30000 | | 0.0740 | | 4-Benzyl-amino-5-methoxy-quinazoline-8-carboxylic acid amide | 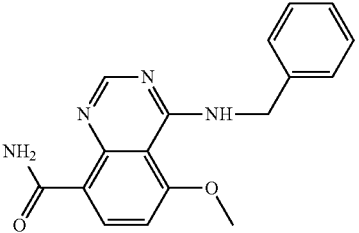 [SMILES: COc1ccc(C(N)=O)c2ncnc(NCc3ccccc3)c12] |
| 500 | 545 | 0.00140 | | 0.0750 | | 4-{1-[3-(3,4-Difluoro-benzoyl-amino)-phenyl]-3-piperidin-1-yl-propyl-amino}-quinazoline-8-carboxylic acid amide | 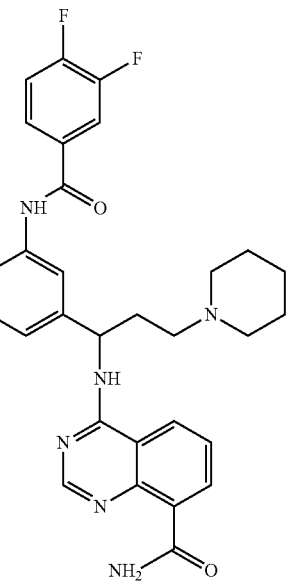 |
| 501 | 420 | 0.01200 | | 0.0760 | | 4-{3-[(2-Amino-thiazole-4-carbonyl)-amino]-benzyl-amino}-quinazoline-8-carboxylic acid amide | 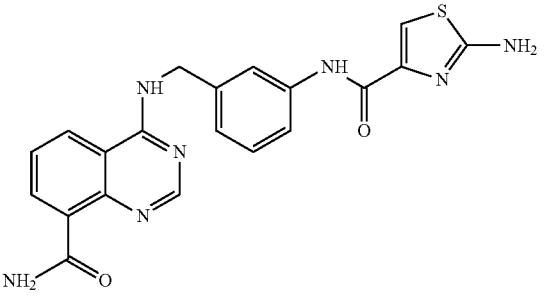 [SMILES: NC(=O)c1cccc2c(NCc3cccc(NC(=O)c4csc(N)n4)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 502 | 478 | 0.30000 | | | 0.0760 | 4-[2-Dimethyl-amino-1-(3-fluoro-phenyl)-ethylamino]-6-(4-fluoro-benzyloxy)-quinazoline-8-carboxylic acid amide | 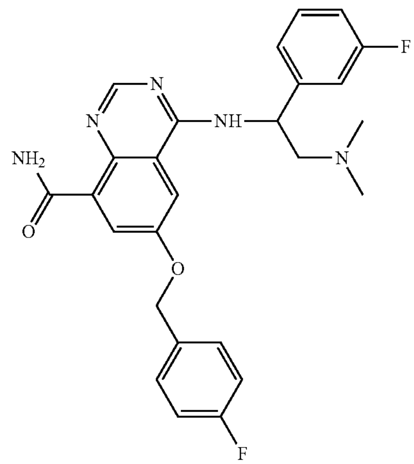 [SMILES: CN(C)CC(Nc1ncnc2c(C(N)=O)cc(OCc3ccc(F)cc3)cc12)c1cccc(F)c1] |
| 503 | 423 | 1 | | | 0.0770 | 6-(3-Dimethyl-amino-propoxy)-4-(2-methyl-amino-1-phenyl-ethylamino)-quinazoline-8-carboxylic acid amide | 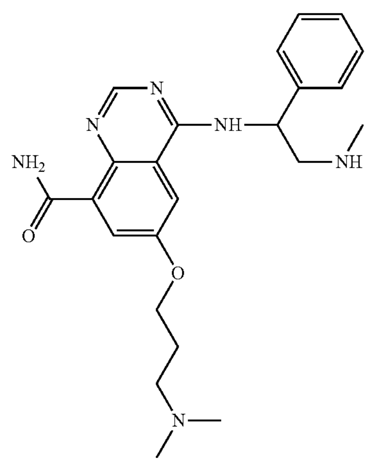 [SMILES: CNCC(Nc1ncnc2c(C(N)=O)cc(OCCCN(C)C)cc12)c1ccccc1] |
| 505 | 423 | | | | 0.0780 | 6-(4-Cyano-phenyl)-4-(2-methyl-amino-1-phenyl-ethylamino)-quinazoline-8-carboxylic acid amide | 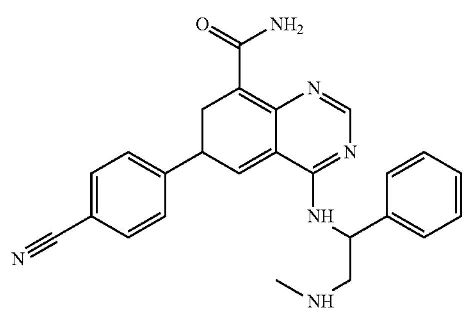 [SMILES: CNCC(Nc1ncnc2c1=CC(c1ccc(C#N)cc1)CC=2C(N)=O)c1ccccc1] |
| 506 | 437 | 0.00340 | | | 0.0790 | 4-{3-[(1H-Indole-3-carbonyl)-amino]-benzyl-amino}-quinazoline-8-carboxylic acid amide | 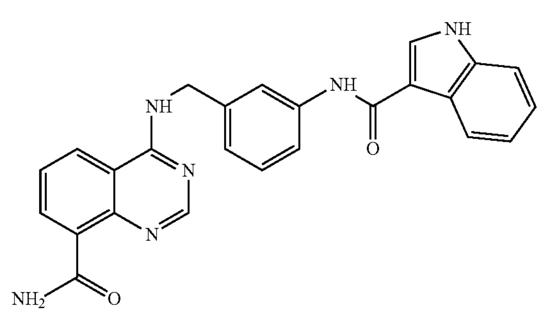 [SMILES: NC(=O)c1cccc2c(NCc3cccc(NC(=O)c4c[nH]c5ccccc45)c3)ncnc12] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 507 | 481 | 0.00740 | 0.0110 | 0.0790 | | 4-[3-(4-Pyrrolidin-1-ylmethyl-benzoyl-amino)-benzyl-amino]-quinazoline-8-carboxylic acid amide | 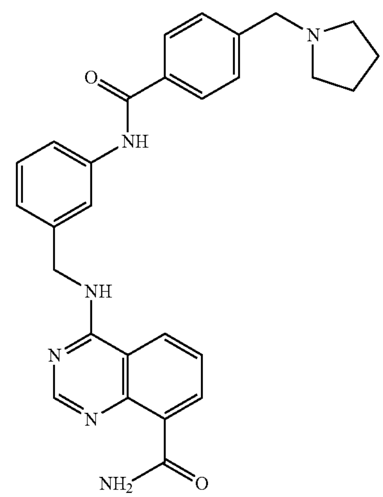 [SMILES: NC(=O)c1cccc2c(NCc3cccc(NC(=O)c4ccc(CN5CCCC5)cc4)c3)ncnc12] |
| 508 | 499 | 0.00061 | | 0.0790 | | 6-Fluoro-4-(1-{3-[(6-trifluoro-methyl-pyridine-3-carbonyl)-amino]-phenyl}-ethylamino)-quinazoline-8-carboxylic acid amide | 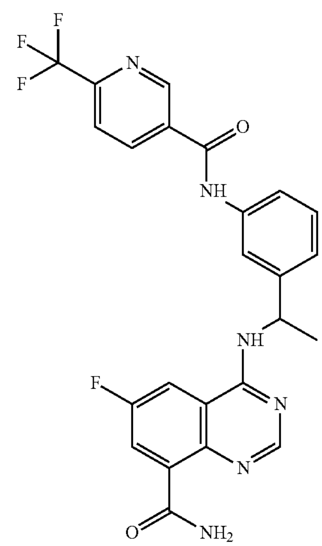 [SMILES: CC(Nc1ncnc2c(C(N)=O)cc(F)cc12)c1cccc(NC(=O)c2ccc(C(F)(F)F)nc2)c1] |
| 510 | 504 | 0.00037 | | 0.0830 | | 4-{1-[3-(3-Fluoro-4-methoxy-benzoyl-amino)-phenyl]-3-methoxy-propyl-amino}-quinazoline-8-carboxylic acid amide | 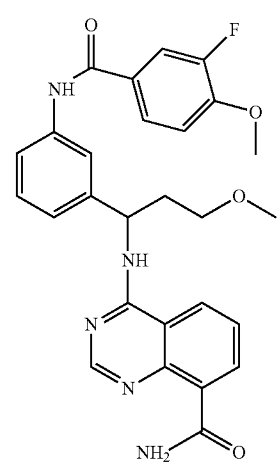 [SMILES: COCCC(Nc1ncnc2c(C(N)=O)cccc12)c1cccc(NC(=O)c2ccc(OC)c(F)c2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 511 | 362 | 0.69000 | 0.0160 | | 0.0840 | 4-((S)-1-Phenyl-2-pyrrolidin-1-yl-ethyl-amino)-quinazoline-8-carboxylic acid amide | 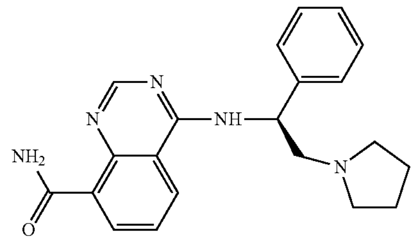 |
| 512 | 446 | 0.00073 | 0.0005 | | 0.0850 | 4-[3-(3-Fluoro-4-methoxy-benzoyl-amino)-benzyl-amino]-quinazoline-8-carboxylic acid amide | 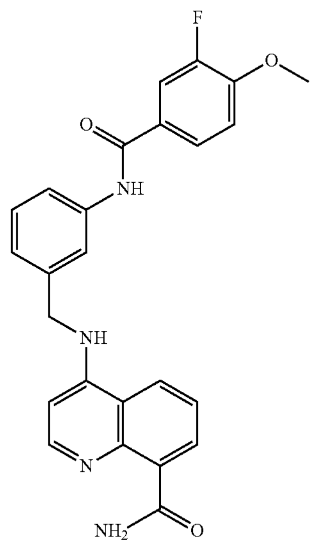 [SMILES: COc1ccc(C(=O)Nc2cccc(CNc3ccnc4c(C(N)=O)cccc34)c2)cc1F] |
| 514 | 472 | 0.00710 | 0.0200 | | 0.0860 | 4-(3-{[2-(2-Methoxy-ethylamino)-pyridine-4-carbonyl]-amino}-benzyl-amino)-quinazoline-8-carboxylic acid amide | 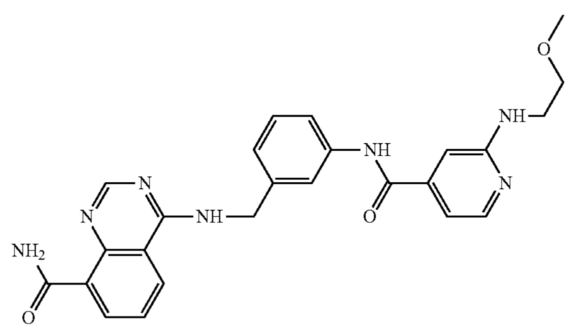 [SMILES: COCCNc1cc(C(=O)Nc2cccc(CNc3ncnc4c(C(N)=O)cccc34)c2)ccn1] |
| 515 | 396 | 0.47000 | | | 0.0860 | 4-[2-Dimethyl-amino-1-(2-methoxy-phenyl)-ethylamino]-6-methoxy-quinazoline-8-carboxylic acid amide | 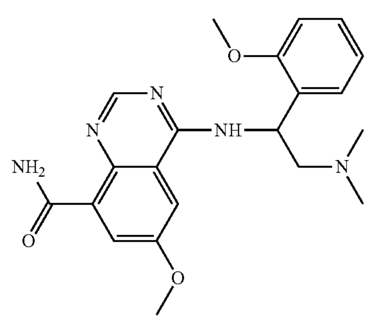 [SMILES: COc1cc(C(N)=O)c2ncnc(NC(CN(C)C)c3ccccc3OC)c2c1] |

TABLE 2-continued

| MS No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 516 | 542 | 0.00770 | | 0.0880 | | 4-(3-{3-[3-(2-Morpholin-4-yl-ethoxy)-phenyl]-ureido}-benzyl-amino)-quinazoline-8-carboxylic acid amide | 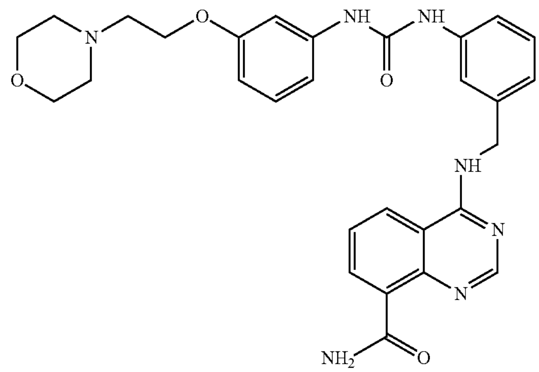 [SMILES: NC(=O)c1cccc2c(NCc3cccc(NC(=O)Nc4cccc(OCCN5CCOCC5)c4)c3)ncnc12] |
| 517 | 555 | 0.03200 | | 0.0890 | | 4-[3-(3-{3-[2-(4-Methyl-piperazin-1-yl)-ethoxy]-phenyl}-ureido)-benzyl-amino]-quinazoline-8-carboxylic acid amide | 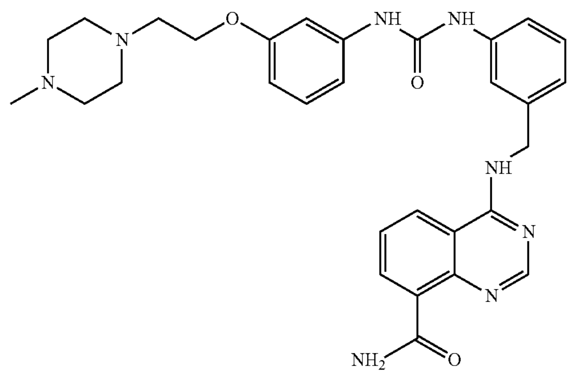 [SMILES: CN1CCN(CCOc2cccc(NC(=O)Nc3cccc(CNc4ncnc5c(C(N)=O)cccc45)c3)c2)CC1] |
| 518 | 441 | 0.00072 | | 0.0890 | | 4-((R)-1-{3-[(3,3-Difluoro-pyrrolidine-1-carbonyl)-amino]-phenyl}-ethylamino)-quinazoline-8-carboxylic acid amide | 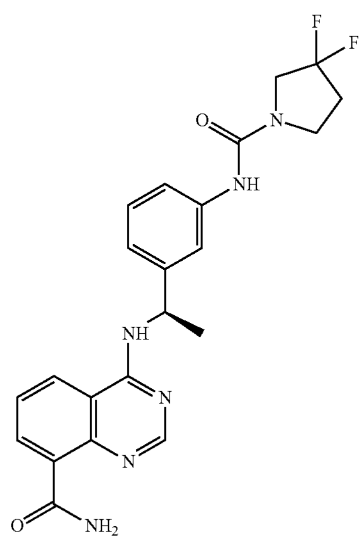 [SMILES: C[C@@H](Nc1ncnc2c(C(N)=O)cccc12)c1cccc(NC(=O)N2CCC(F)(F)C2)c1] |
| 519 | 472 | 0.00066 | | 0.0900 | | 4-(3-{[6-(2-Methoxy-ethylamino)-pyridine-3-carbonyl]-amino}-benzyl-amino)-quinazoline 8-carboxylic acid amide | 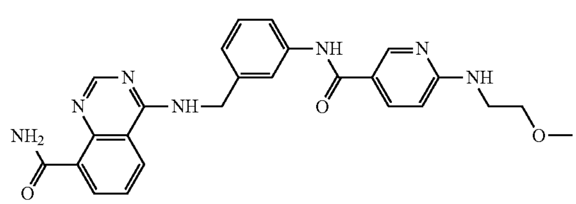 [SMILES: COCCNc1ccc(C(=O)Nc2cccc(CNc3ncnc4c(C(N)=O)cccc34)c2)cn1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 520 | 484 | 0.00048 | | 0.0910 | | 4-{3-[(6-Morpholin-4-yl-pyridine-3-carbonyl)-amino]-benzyl-amino}-quinazoline-8-carboxylic acid amide | 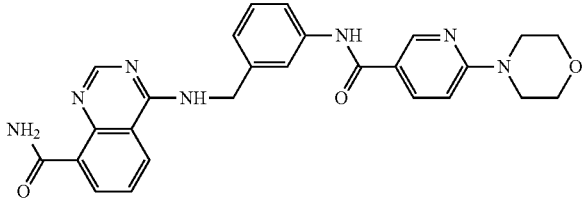 [SMILES: NC(=O)c1cccc2c(NCc3cccc(NC(=O)c4ccc(N5CCOCC5)nc4)c3)ncnc12] |
| 521 | 468 | 0.00048 | | 0.0920 | | 4-{3-[(6-Isobutyl-amino-pyridine-3-carbonyl)-amino]-benzyl-amino}-quinazoline-8-carboxylic acid amide | 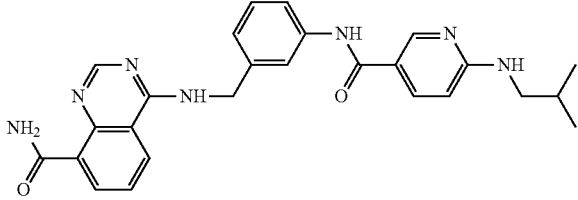 [SMILES: CC(C)CNc1ccc(C(=O)Nc2cccc(CNc3ncnc4c(C(N)=O)cccc34)c2)cn1] |
| 524 | 495 | 0.01200 | 0.0025 | 0.0930 | | 4-[1-(3-Benzoyl-amino-phenyl)-3-pyrrolidin-1-yl-propyl-amino]-quinazoline-8-carboxylic acid amide | 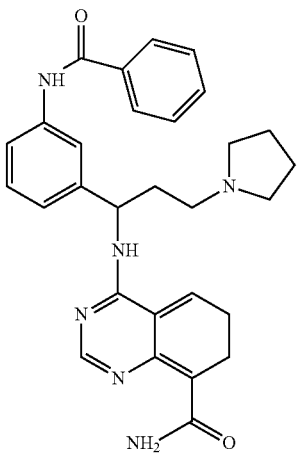 [SMILES: NC(=O)C1=c2ncnc(NC(CCN3CCCC3)c3cccc(NC(=O)c4ccccc4)c3)c2=CCC1] |
| 525 | 496 | 0.00012 | 0.0018 | 0.1000 | 87 | 4-[3-(4-Methoxy-3-trifluoro-methyl-benzoyl-amino)-benzyl-amino]-quinazoline-8-carboxylic acid amide | 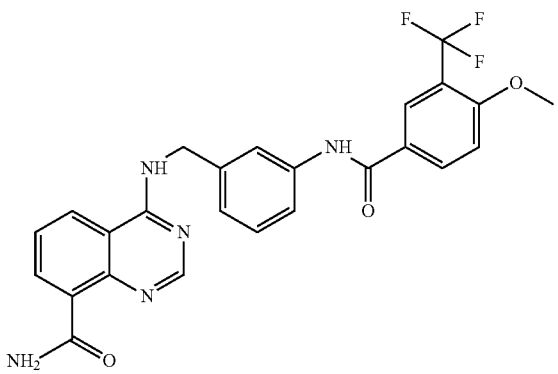 [SMILES: COc1ccc(C(=O)Nc2cccc(CNc3ncnc4c(C(N)=O)cccc34)c2)cc1C(F)(F)F] |

TABLE 2-continued

| No. | MS (M+1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 526 | 453 | 0.00031 | | | 0.1000 | 4-{1-[3-(4-Trifluoro-methyl-pyridin-2-ylamino)-phenyl]-ethylamino}-quinazoline-8-carboxylic acid amide | 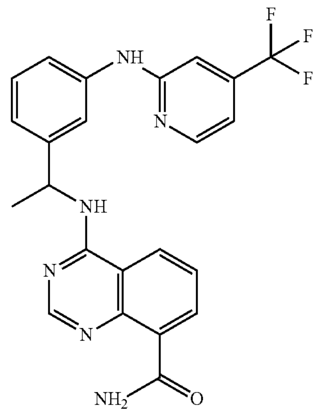 [SMILES: CC(Nc1ncnc2c(C(N)=O)cccc12)c1cccc(Nc2cc(C(F)(F)F)ccn2)c1] |
| 527 | 620 | 0.00589 | | | 0.1000 | [2-[3-(4-Bromo-benzoyl-amino)-phenyl]-2-(8-carbamoyl-quinazolin-4-ylamino)-ethyl]-methyl-carbamic acid tert-butyl ester | 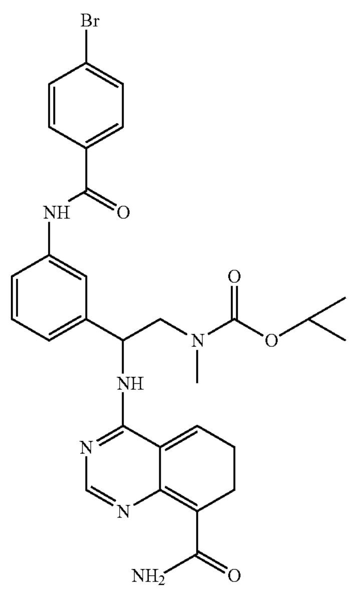 [SMILES: CC(C)OC(=O)N(C)CC(Nc1ncnc2c1=CCCC=2C(N)=O)c1cccc(NC(=O)c2ccc(Br)cc2)c1] |
| 528 | 464 | 0.01000 | | | 0.1000 | | 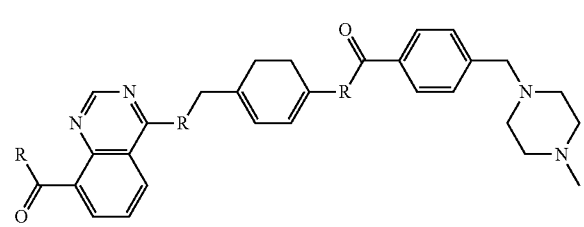 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 529 | 506 | 0.06100 | | 0.1000 | | 4-{1-[3-(4-Bromo-benzoyl-amino)-phenyl]-2-hydroxy-ethylamino}-quinazoline-8-carboxylic acid amide | 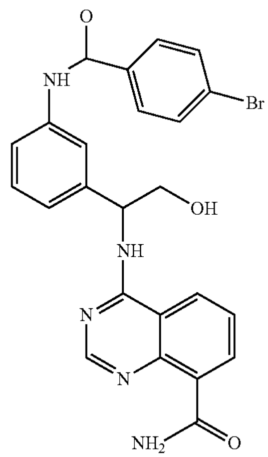 [SMILES: NC(=O)c1cccc2c(NC(CO)c3cccc(NC(O)c4ccc(Br)cc4)c3)ncnc12] |
| 530 | 356 | 1 | | 0.1000 | | 5-(2-Amino-ethoxy)-4-(3-fluoro-benzyl-amino)-quinazoline-8-carboxylic acid amide | 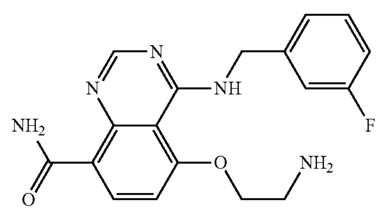 [SMILES: NCCOc1ccc(C(N)=O)c2ncnc(NCc3cccc(F)c3)c12] |
| 531 | 333 | 1.6000 | | 0.1000 | 102 | 4-(3,4,5-Trifluoro-benzyl-amino)-quinazoline-8-carboxylic acid amide | 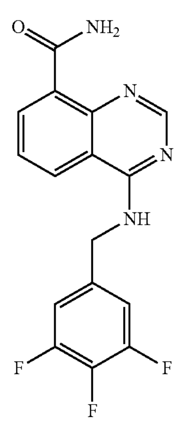 [SMILES: NC(=O)c1cccc2c(NCc3cc(F)c(F)c(F)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 532 | 497 | | | | 0.1000 | 4-((R)-1-{3-[(2-Hydroxy-6-trifluoro-methyl-pyridine-3-carbonyl)-amino]-phenyl}-ethylamino)-quinazoline-8-carboxylic acid amide | 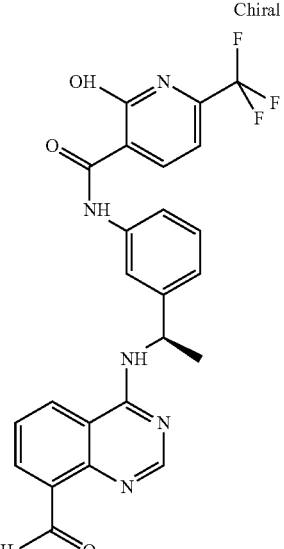 |
| 535 | 460 | 0.01400 | 0.0430 | 1 | | 4-{(S)-1-[3-(3-Fluoro-4-methoxy-benzoyl-amino)-phenyl]-ethylamino}-quinazoline-8-carboxylic acid amide | 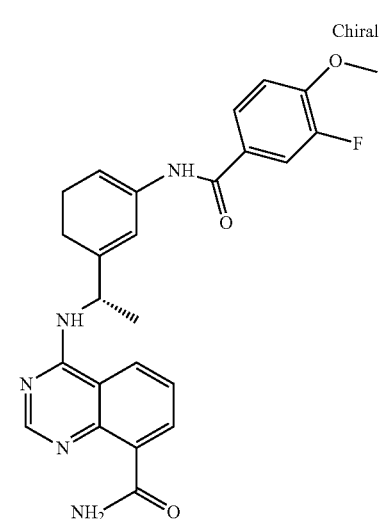 |
| 537 | 412 | 4.0000e−05 | | | | 4-((R)-1-{3-[(2,2-Difluoro-cyclo-propane-carbonyl)-amino]-phenyl}-ethylamino)-quinazoline-8-carboxylic acid amide | 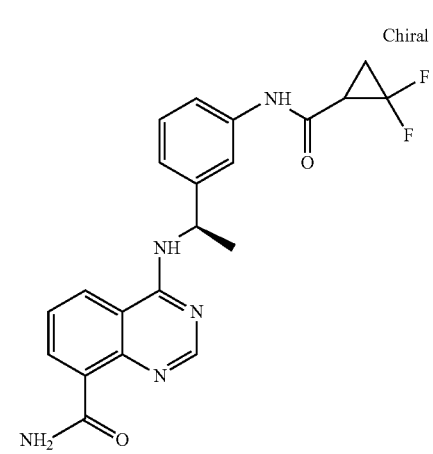 [SMILES: C[C@@H](Nc1ncnc2c(C(N)=O)cccc12)c1cccc(NC(=O)C2CC2(F)F)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 538 | 472 | 0.00010 | | | | 4-(1-{3-[(5-Cyclopropyl-2H-pyrazole-3-carbonyl)-amino]-phenyl}-3-hydroxy-propylamino)-quinazoline-8-carboxylic acid amide | 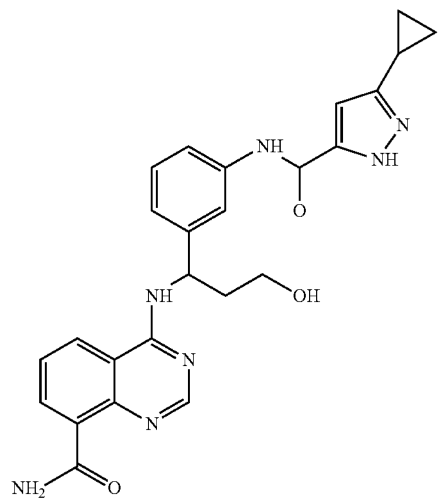 [SMILES: NC(=O)c1cccc2c(NC(CCO)c3cccc(NC(O)c4cc(C5CC5)n[nH]4)c3)ncnc12] |
| 539 | 371 | 0.00015 | | 0.00094 | | 4-[3-(Pyridin-2-ylamino)-benzylamino]-quinazoline-8-carboxylic acid amide | 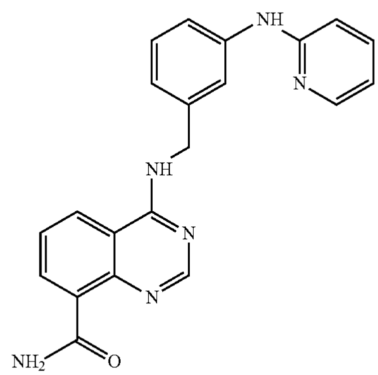 [SMILES: NC(=O)c1cccc2c(NCc3cccc(Nc4ccccn4)c3)ncnc12] |
| 540 | 439 | 0.00015 | | | | 4-[3-(4-Trifluoro-methyl-pyridin-2-ylamino)-benzyl-amino]-quinazoline-8-carboxylic acid amide | 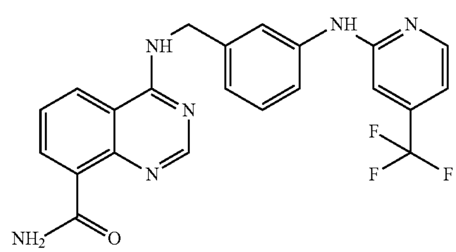 [SMILES: NC(=O)c1cccc2c(NCc3cccc(Nc4cc(C(F)(F)F)ccn4)c3)ncnc12] |
| 541 | 449 | 0.00016 | | 0.0020 | | 2-{3-[(8-Carbamoyl-quinazolin-4-ylamino)-methyl]-phenyl-amino}-thiazole-5-carboxylic acid ethyl ester | 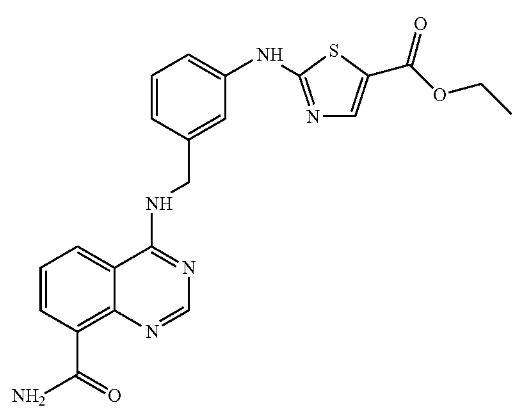 [SMILES: CCOC(=O)c1cnc(Nc2cccc(CNc3ncnc4c(C(N)=O)cccc34)c2)s1] |

TABLE 2-continued

| No. | MS (M+1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 542 | 486 | 0.00016 | | | | 4-{4-Hydroxy-1-[3-(4-methoxy-benzoyl-amino)-phenyl]-butylamino}-quinazoline-8-carboxylic acid amide | 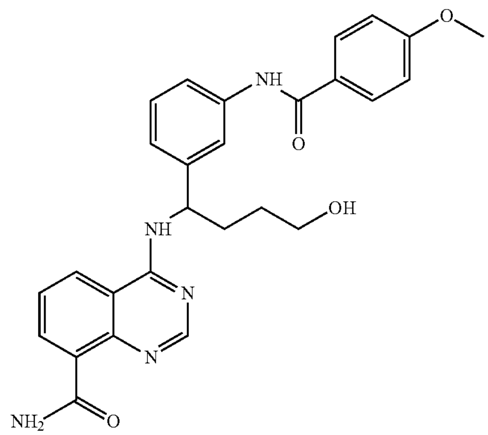 [SMILES: COc1ccc(C(=O)Nc2cccc(C(CCCO)Nc3ncnc4c(C(N)=O)cccc34)c2)cc1] |
| 543 | 437 | 0.00017 | | | | 4-{3-[(1H-Indole-6-carbonyl)-amino]-benzyl-amino}-quinazoline-8-carboxylic acid amide | 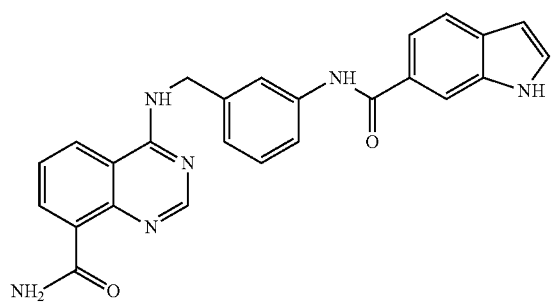 [SMILES: NC(=O)c1cccc2c(NCc3cccc(NC(=O)c4ccc5cc[nH]c5c4)c3)ncnc12] |
| 544 | 412 | 0.00018 | | | 0.1900 | 4-(1-{3-[(2,2-Difluoro-cyclo-propane-carbonyl)-amino]-phenyl}-ethylamino)-quinazoline-8-carboxylic acid amide | 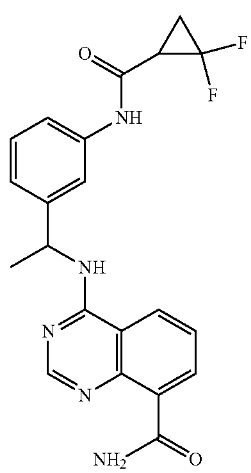 [SMILES: CC(Nc1ncnc2c(C(N)=O)cccc12)c1cccc(NC(=O)C2CC2(F)F)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 545 | 377 | 0.00019 | 0.0010 | | | 4-[3-(Thiazol-2-ylamino)-benzyl-amino]-quinazoline-8-carboxylic acid amide | 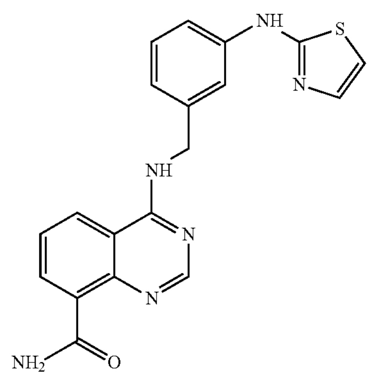 [SMILES: NC(=O)c1cccc2c(NCc3cccc(Nc4nccs4)c3)ncnc12] |
| 546 | 403 | 0.00019 | 0.0012 | | | 4-{3-[(3-Amino-1H-pyrazole-4-carbonyl)-amino]-benzyl-amino}-quinazoline-8-carboxylic acid amide | 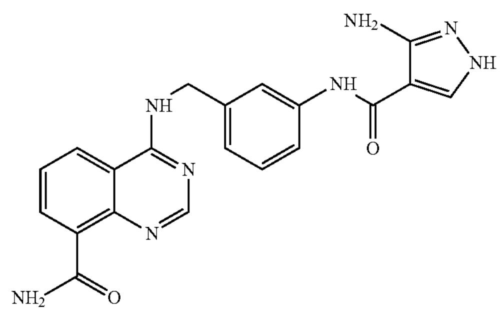 [SMILES: NC(=O)c1cccc2c(NCc3cccc(NC(=O)c4c[nH]nc4N)c3)ncnc12] |
| 547 | 486 | 0.00021 | 0.00038 | 1 | | 4-{(R)-3-Methoxy-1-[3-(4-methoxy-benzoyl-amino)-phenyl]-propyl-amino}-quinazoline-8-carboxylic acid amide | Chiral |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 548 | 377 | 0.00022 | 0.00074 | 1 | | 4-[3-(5-Amino-methyl-thiazol-2-ylamino)-benzyl-amino]-quinazoline-8-carboxylic acid amide | 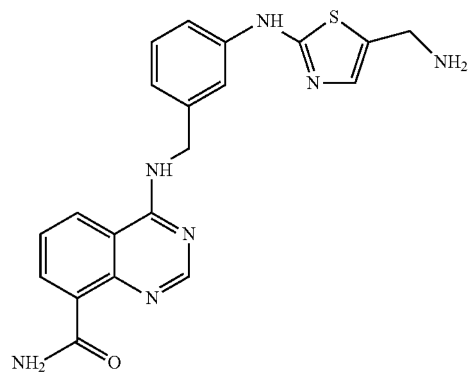 [SMILES: NCc1cnc(Nc2cccc(CNc3ncnc4c(C(N)=O)cccc34)c2)s1] |
| 549 | 396 | 0.00022 | 6.0000e−05 | | | 4-[3-(4-Cyano-pyridin-2-ylamino)-benzyl-amino]-quinazoline-8-carboxylic acid amide | 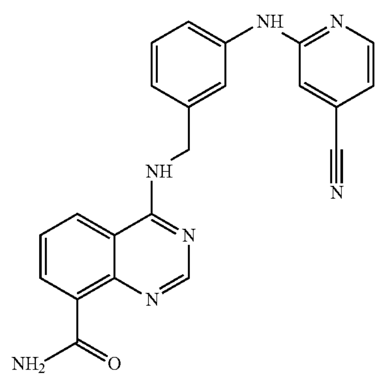 [SMILES: N#Cc1ccnc(Nc2cccc(CNc3ncnc4c(C(N)=O)cccc34)c2)c1] |
| 550 | 446 | 0.00022 | | | | 4-[2-Fluoro-3-(4-methoxy-benzoyl-amino)-benzyl-amino]-quinazoline-8-carboxylic acid amide | 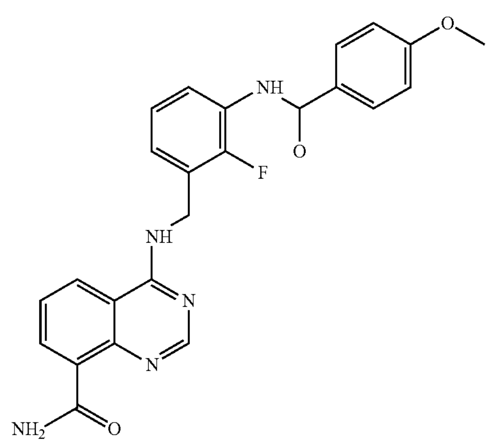 [SMILES: COc1ccc(C(O)Nc2cccc(CNc3ncnc4c(C(N)=O)cccc34)c2F)cc1] |
| 551 | 442 | 0.00024 | 0.0003 | | | 4-{3-[(4,5,6,7-Tetrahydro-1H-indazole-3-carbonyl}-amino]-benzyl-amino}-quinazoline-8-carboxylic acid amide | 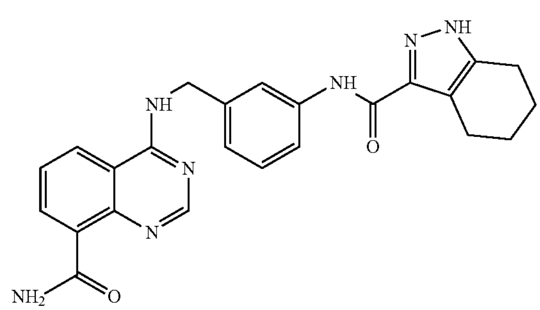 [SMILES: NC(=O)c1cccc2c(NCc3cccc(NC(=O)c4n[nH]c5c4CCCC5)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 552 | 437 | 0.00026 | | | | 4-{3-[(1H-Indole-7-carbonyl)-amino]-benzyl-amino}-quinazoline-8-carboxylic acid amide |
| 553 | 464 | 0.00029 | 0.0010 | | | 4-{3-[4-(1H-Imidazol-2-yl)-benzoyl-amino]-benzyl-amino}-quinazoline-8-carboxylic acid amide |
| 554 | 497 | 0.00030 | 0.0022 | 0.2100 | | 4-[3-(3-Methyl-4-morpholin-4-yl-benzoyl-amino)-benzyl-amino]-quinazoline-8-carboxylic acid amide |
| 555 | 485 | 0.00031 | | | | 4-(1-{3-[(5-Cyclopropyl-2H-pyrazole-3-carbonyl)-amino]-phenyl}-3-methyl-amino-propyl-amino)-quinazoline-8-carboxylic acid amide |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 556 | 525 | 0.00033 | | | | 4-(1-{3-[(5-Cyclopropyl-2H-pyrazole-3-carbonyl)-amino]-phenyl}-3-pyrrolidin-1-yl-propyl-amino)-quinazoline-8-carboxylic acid amide | 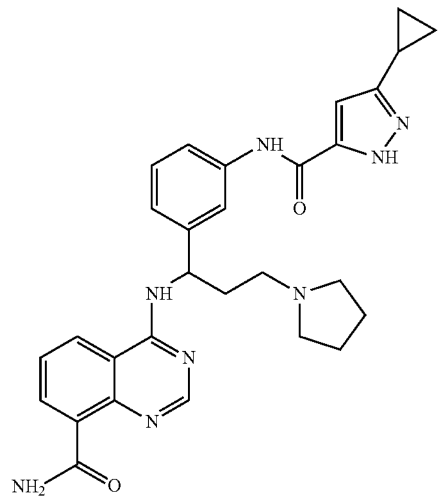 [SMILES: NC(=O)c1cccc2c(NC(CCN3CCCC3)c3cccc(NC(=O)c4cc(C5CC5)n[nH]4)c3)ncnc12] |
| 557 | 471 | 0.00037 | | | | 4-{3-[(5-Chloro-1H-indole-2-carbonyl)-amino]-benzyl-amino}-quinazoline-8-carboxylic acid amide | 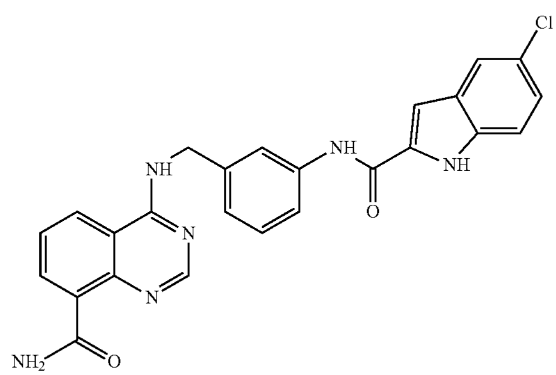 [SMILES: NC(=O)c1cccc2c(NCc3cccc(NC(=O)c4cc5cc(Cl)ccc5[nH]4)c3)ncnc12] |
| 558 | 437 | 0.00046 | | | | 4-{3-[(1H-Indole-5-carbonyl)-amino]-benzyl-amino}-quinazoline-8-carboxylic acid amide | 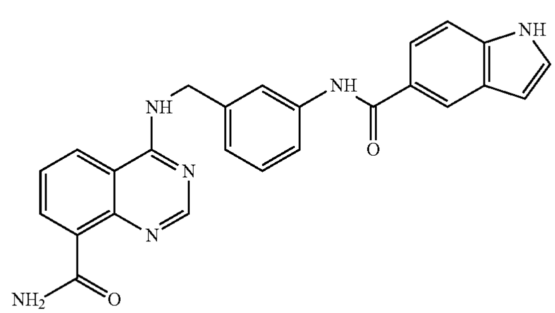 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 559 | 442 | 0.00049 | | | | 4-(1-{3-[(2,2-Difluoro-cyclo-propane-carbonyl)-amino]-phenyl}-3-hydroxy-propyl-amino)-quinazoline-8-carboxylic acid amide | 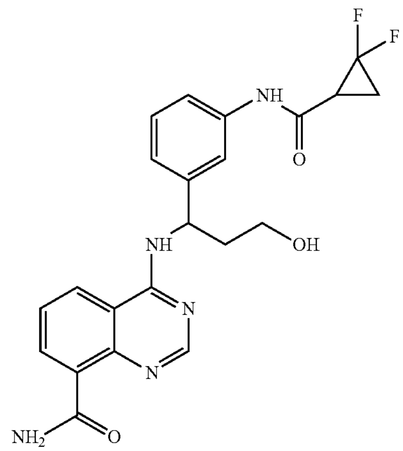 [SMILES: NC(=O)c1cccc2c(NC(CCO)c3cccc(NC(=O)C4CC4(F)F)c3)ncnc12] |
| 560 | 444 | 0.00051 | | | | 4-((R)-1-{3-[(5-Methoxy-pyrazine-2-carbonyl)-amino]-phenyl}-ethylamino)-quinazoline-8-carboxylic acid amide | 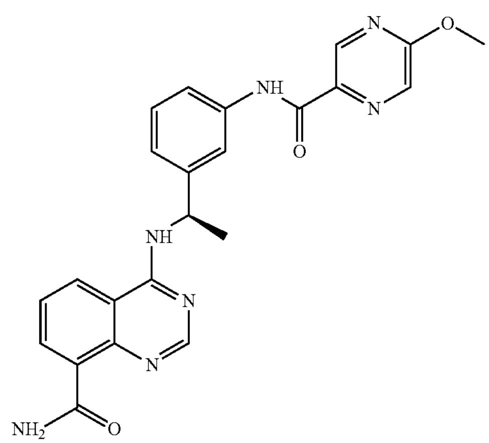 |
| 561 | 456 | 0.00053 | | | | 4-{3-[(2,3-Dihydro-benzo[1,4]-dioxine-6-carbonyl)-amino]-benzyl-amino}-quinazoline-8-carboxylic acid amide | 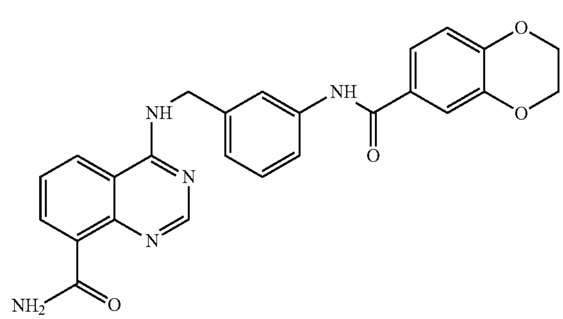 [SMILES: NC(=O)c1cccc2c(NCc3cccc(NC(=O)c4ccc5c(c4)OCCO5)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 562 | 539 | 0.00054 | | | | 4-(1-{3-[(5-Cyclopropyl-2H-pyrazole-3-carbonyl)-amino]-phenyl}-3-piperidin-1-yl-propyl-amino)-quinazoline-8-carboxylic acid amide | 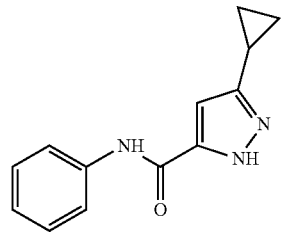 |
| 563 | 451 | 0.00056 | | | | 4-{3-[(1-Methyl-1H-indole-5-carbonyl)-amino]-benzyl-amino}-quinazoline-8-carboxylic acid amide | 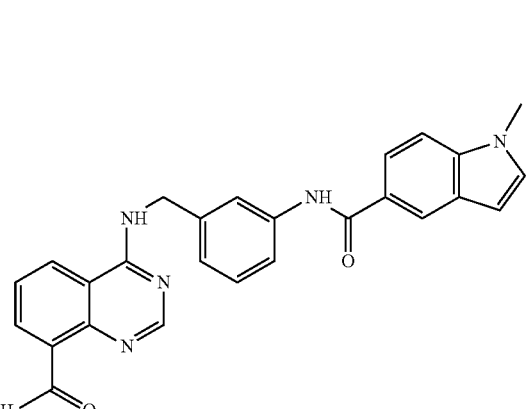 |
| 564 | 458 | 0.00058 | 0.00096 | 3.1000 | | 6-Hydroxy-methyl-4-[3-(4-methoxy-benzoyl-amino)-benzyl-amino]-quinazoline-8-carboxylic acid amide | 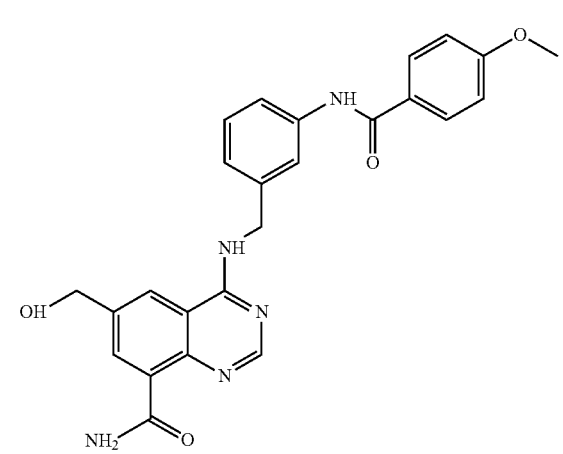 [SMILES: COc1ccc(C(=O)Nc2cccc(CNc3ncnc4c(C(N)=O)cc(CO)cc34)c2)cc1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 565 | 380 | 0.00060 | | 0.23000 | | {3-[(R)-1-(8-Carbamoyl-quinazolin-4-ylamino)-ethyl]-phenyl}-carbamic acid ethyl ester | 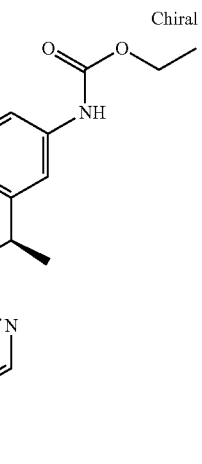 |
| 566 | 437 | 0.00072 | | | | 4-{3-[(1H-Indole-4-carbonyl)-amino]-benzyl-amino}-quinazoline-8-carboxylic acid amide | 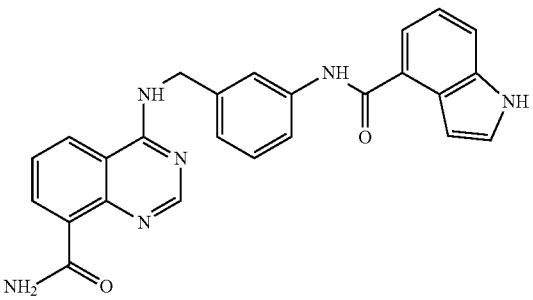 [SMILES: NC(=O)c1cccc2c(NCc3cccc(NC(=O)c4cccc5[nH]ccc45)c3)ncnc12] |
| 567 | 404 | 0.00075 | | 0.1600 | | 4-((R)-1-{3-[(2,2-Dimethyl-cyclopropane-carbonyl)-amino]-phenyl}-ethylamino)-quinazoline-8-carboxylic acid amide | 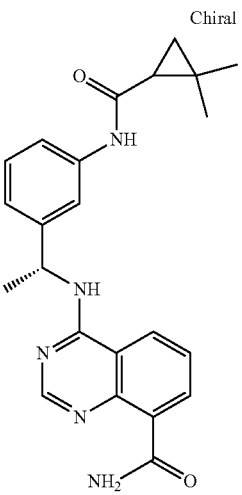 [SMILES: C[C@@H](Nc1ncnc2c(C(N)=O)cccc12)c1cccc(NC(=O)C2CC2(C)C)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 568 | 428 | 0.00083 | 0.00073 | | | 4-[3-(4-Hydroxy-methyl-benzoyl-amino)-benzyl-amino]-quinazoline-8-carboxylic acid amide | 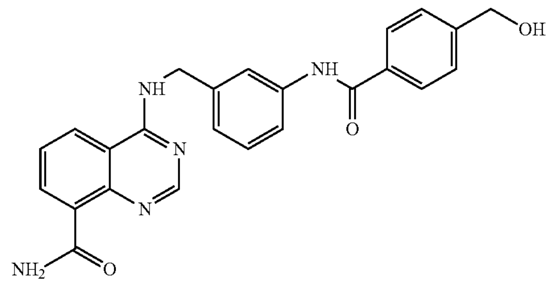 [SMILES: NC(=O)c1cccc2c(NCc3cccc(NC(=O)c4ccc(CO)cc4)c3)ncnc12] |
| 569 | 385 | 0.00085 | 0.00039 | 0.3900 | | 4-[3-(4-Methyl-pyridin-2-ylamino)-benzyl-amino]-quinazoline-8-carboxylic acid amide | 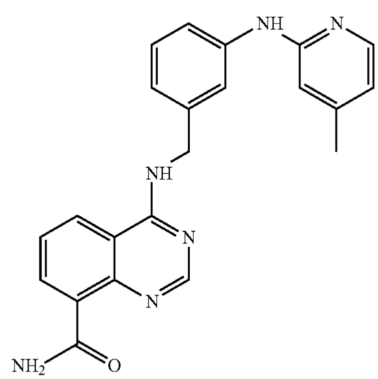 [SMILES: Cc1ccnc(Nc2cccc(CNc3ncnc4c(C(N)=O)cccc34)c2)c1] |
| 570 | 461 | 0.00086 | | 0.1500 | | 6-Chloro-4-(1-{3-[(6-methyl-pyridine-3-carbonyl)-amino]-phenyl}-ethylamino)-quinazoline-8-carboxylic acid amide | 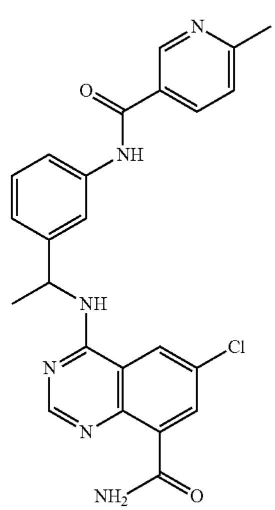 [SMILES: Cc1ccc(C(=O)Nc2cccc(C(C)Nc3ncnc4c(C(N)=O)cc(Cl)cc34)c2)cn1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 571 | 426 | 0.00086 | 0.0065 | 0.2700 | | 4-(1-{3-[(3,3-Difluorocyclobutanecarbonyl)-amino]-phenyl}-ethylamino)-quinazoline-8-carboxylic acid amide | 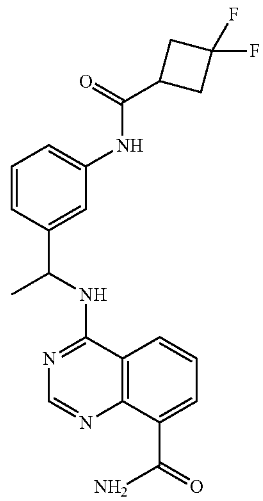 [SMILES: CC(Nc1ncnc2c(C(N)=O)cccc12)c1cccc(NC(=O)C2CC(F)(F)C2)c1] |
| 572 | 444 | 0.00086 | | 0.2900 | | 4-(1-{3-[(1-Trifluoromethyl-cyclopropane-carbonyl)-amino]-phenyl}-ethylamino)-quinazoline-8-carboxylic acid amide | 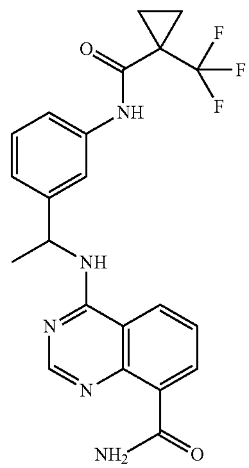 [SMILES: CC(Nc1ncnc2c(C(N)=O)cccc12)c1cccc(NC(=O)C2(C(F)(F)F)CC2)c1] |
| 573 | 482 | 0.00088 | | | | 4-((R)-1-{3-[(5-Trifluoromethyl-pyrazine-2-carbonyl)-amino]-phenyl}-ethylamino)-quinazoline-8-carboxylic acid amide | 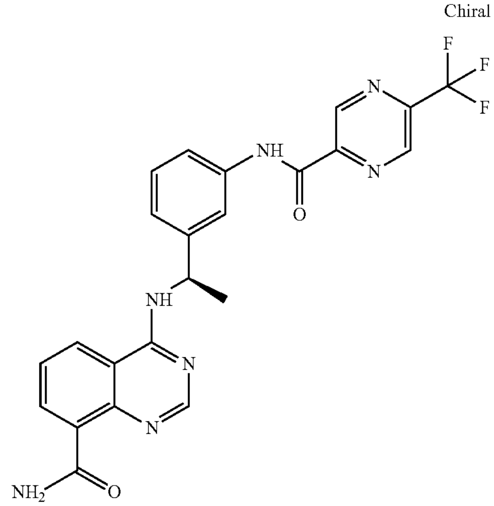 [SMILES: C[C@@H](Nc1ncnc2c(C(N)=O)cccc12)c1cccc(NC(=O)c2cnc(C(F)(F)F)cn2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 574 | 410 | 0.00100 | 0.00076 | 0.2800 | | 4-[3-(5-Cyano-methyl-pyridin-2-ylamino)-benzyl-amino)-quinazoline-8-carboxylic acid amide | 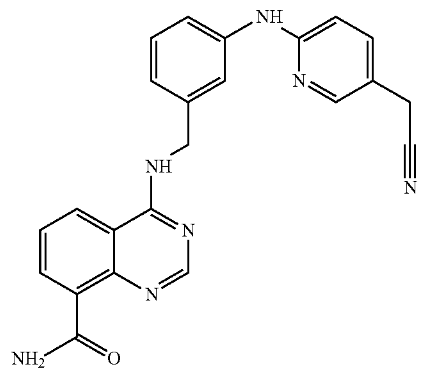 [SMILES: N#CCc1ccc(Nc2cccc(CNc3ncnc4c(C(N)=O)cccc34)c2)nc1] |
| 575 | 438 | 0.00100 | 0.0047 | | | 4-{3-[(1H-Benzo-imidazole-5-carbonyl)-amino]-benzyl-amino}-quinazoline-8-carboxylic acid amide | 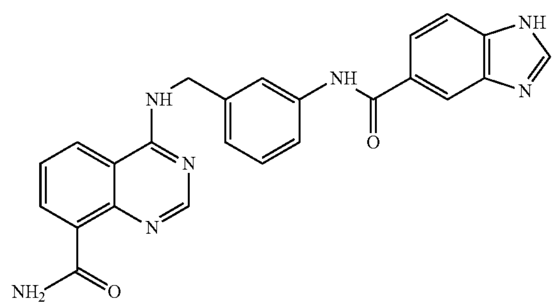 [SMILES: NC(=O)c1cccc2c(NCc3cccc(NC(=O)c4ccc5[nH]cnc5c4)c3)ncnc12] |
| 576 | 392 | 0.00110 | | 0.3300 | | 4-{(R)-1-[3-(2-Methyl-butyryl-amino)-phenyl]-ethylamino}-quinazoline-8-carboxylic acid amide | Chiral |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 577 | 488 | 0.00120 | 0.0094 | 10 | | 6-(1,2-Dihydroxy-ethyl)-4-[3-(4-methoxy-benzoyl-amino)-benzyl-amino]-quinazoline-8-carboxylic acid amide | 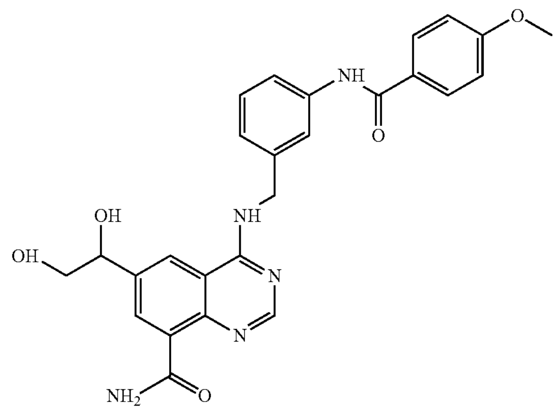 [SMILES: COc1ccc(C(=O)Nc2cccc(CNc3ncnc4c(C(N)=O)cc(C(O)CO)cc34)c2)cc1] |
| 578 | 540 | 0.00120 | | | | 4-(1-{3-[(5-Cyclopropyl-2H-pyrazole-3-carbonyl)-amino]-phenyl}-3-piperazin-1-yl-propyl-amino)-quinazoline-8-carboxylic acid amide | 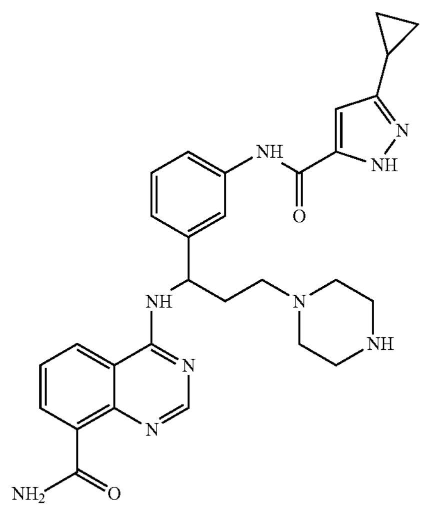 [SMILES: NC(=O)c1cccc2c(NC(CCN3CCNCC3)c3cccc(NC(=O)c4cc(C5CC5)n[nH]4)c3)ncnc12] |
| 579 | 554 | 0.00130 | | | | 4-[1-{3-[(5-Cyclopropyl-2H-pyrazole-3-carbonyl)-amino]-phenyl}-3-(4-methyl-piperazin-1-yl)-propyl-amino]-quinazoline-8-carboxylic acid amide | 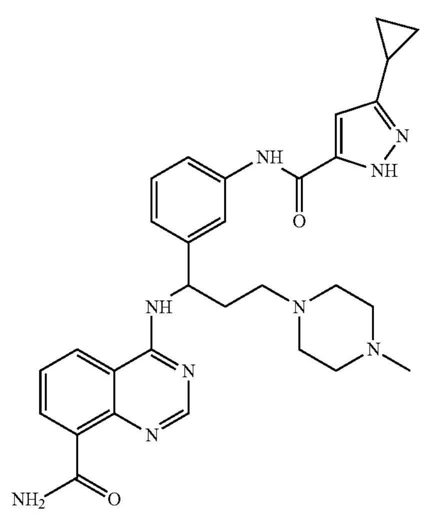 [SMILES: CN1CCN(CCC(Nc2ncnc3c(C(N)=O)cccc23)c2cccc(NC(=O)c3cc(C4CC4)n[nH]3)c2)CC1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 580 | 551 | 0.00140 | 0.0023 | 0.2100 | | 4-[3-(4-Morpholin-4-yl-3-trifluoro-methyl-benzoyl-amino)-benzyl-amino]-quinazoline-8-carboxylic acid amide | 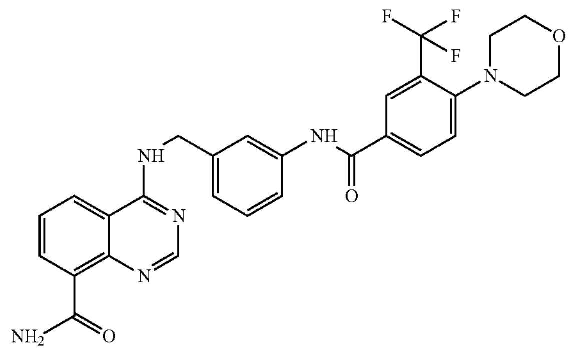 [SMILES: NC(=O)c1cccc2c(NCc3cccc(NC(=O)c4ccc(N5CCOCC5)c(C(F)(F)F)c4)c3)ncnc12] |
| 581 | 433 | 0.00140 | | 0.9100 | | 2-{3-[(8-Carbamoyl-quinazolin-4-ylamino)-methyl]-phenyl-amino}-oxazole-4-carboxylic acid ethyl ester | 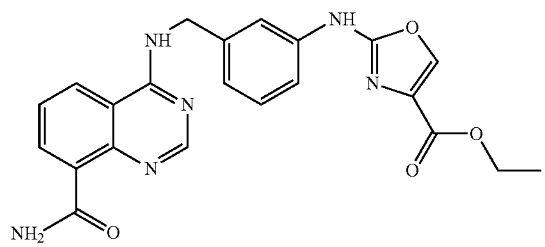 [SMILES: CCOC(=O)c1coc(Nc2cccc(CNc3ncnc4c(C(N)=O)cccc34)c2)n1] |
| 582 | 494 | 0.00150 | 0.0170 | | | 4-{3-[4-(2-Oxo-piperidin-1-yl)-benzoyl-amino]-benzyl-amino}-quinazoline-8-carboxylic acid amide | 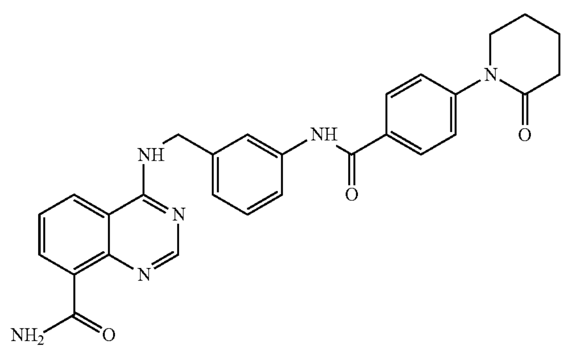 [SMILES: NC(=O)c1cccc2c(NCc3cccc(NC(=O)c4ccc(N5CCCCC5=O)cc4)c3)ncnc12] |
| 583 | 454 | 0.00150 | | | | 4-[3-(1',2',3',4',5',6'-Hexahydro-[3,4']bi-pyridinyl-6-ylamino)-benzyl-amino]-quinazoline-8-carboxylic acid amide | 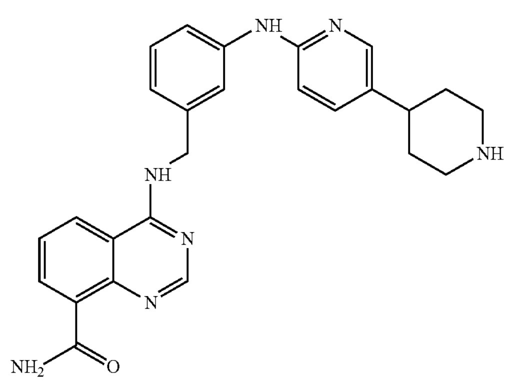 [SMILES: NC(=O)c1cccc2c(NCc3cccc(Nc4ccc(C5CCNCC5)cn4)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 584 | 458 | 0.00160 | 0.0094 | 0.4000 | | 4-(1-{3-[(1-Trifluoro-methyl-cyclobutane carbonyl)-amino]-phenyl}-ethylamino)-quinazoline-8-carboxylic acid amide | 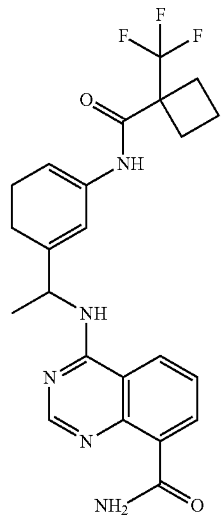 [SMILES: CC(Nc1ncnc2c(C(N)=O)cccc12)C1=CC(NC(=O)C2(C(F)(F)F)CCC2)=CCC1] |
| 585 | 480 | 0.00170 | 0.0005 | | | 4-{3-[3-(5-Methyl-[1,2,4]oxa-diazol-3-yl)-benzoyl-amino]-benzyl-amino}-quinazoline-8-carboxylic acid amide | 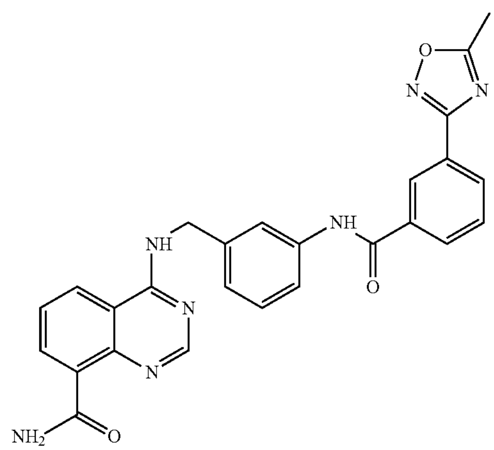 [SMILES: Cc1nc(-c2cccc(C(=O)Nc3cccc(CNc4ncnc5c(C(N)=O)cccc45)c3)c2)no1] |
| 586 | 440 | 0.00180 | 0.0005 | 0.1800 | | 4-(1-{3-[(3,3-Difluoro-cyclobutane carbonyl)-amino]-phenyl}-propyl-amino)-quinazoline-8-carboxylic acid amide | 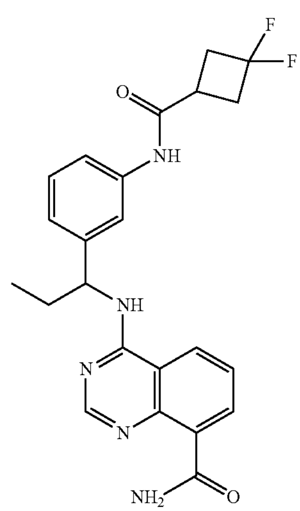 [SMILES: CCC(Nc1ncnc2c(C(N)=O)cccc12)c1cccc(NC(=O)C2CC(F)(F)C2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 587 | 454 | 0.00180 | 0.0150 | 0.8900 | | 4-{1-[3-(2,2,3,3,3-Penta-fluoro-propionyl-amino)-phenyl]-ethylamino}-quinazoline-8-carboxylic acid amide | 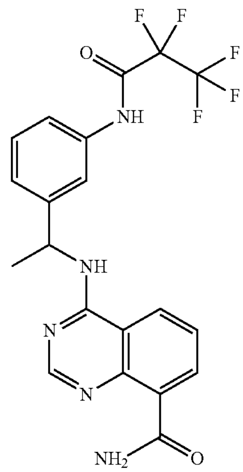 [SMILES: CC(Nc1ncnc2c(C(N)=O)cccc12)c1cccc(NC(=O)C(F)(F)C(F)(F)F)c1] |
| 588 | 483 | 0.00180 | 0.0055 | | | 4-[3-(3-Morpholin-4-yl-benzoyl-amino)-benzyl-amino]-quinazoline-8-carboxylic acid amide | 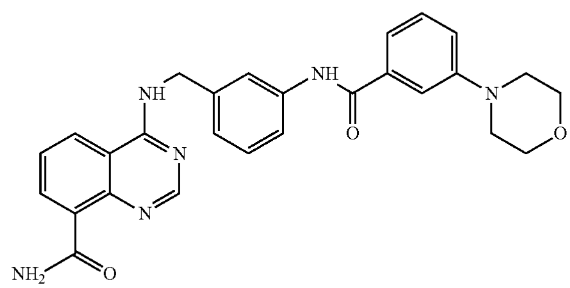 [SMILES: NC(=O)c1cccc2c(NCc3cccc(NC(=O)c4cccc(N5CCOCC5)c4)c3)ncnc12] |
| 589 | 453 | 0.00200 | | 0.3500 | | 4-{(R)-1-[3-(5-Trifluoro-methyl-pyridin-2-ylamino)-phenyl]-ethylamino}-quinazoline-8-carboxylic acid amide | Chiral |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 590 | 471 | 0.00200 | | 2.3000 | | 4-[3-(4-Methoxy-benzoyl-amino)-benzyl-amino]-6-methyl-amino-methyl-quinazoline-8-carboxylic acid amide | 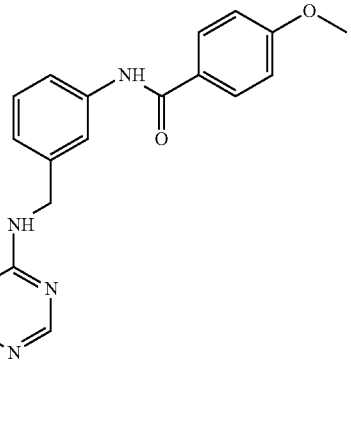 |
| 591 | 428 | 0.00210 | | 0.2800 | | {3-[(R)-1-(8-Carbamoyl-quinazolin-4-ylamino)-ethyl]-phenyl}-carbamic acid phenyl ester | 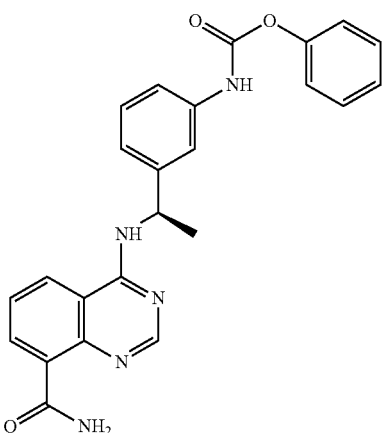 [SMILES: C[C@@H](Nc1ncnc2c(C(N)=O)cccc12)c1cccc(NC(=O)Oc2ccccc2)c1] |
| 592 | 451 | 0.00210 | | | | 4-{3-[(1-Methyl-1H-indole-3-carbonyl)-amino]-benzyl-amino}-quinazoline-8-carboxylic acid amide | 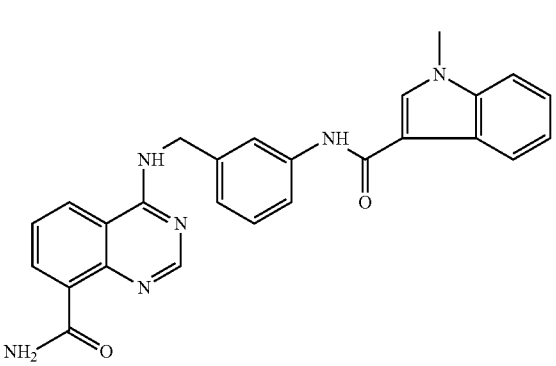 [SMILES: Cn1cc(C(=O)Nc2cccc(CNc3ncnc4c(C(N)=O)cccc34)c2)c2ccccc21] |

TABLE 2-continued

| MS No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 593 | 488 | 0.00230 | | | 0.4800 | 4-{(R)-1-[3-(3-Chloro-5-trifluoro-methyl-pyridin-2-ylamino)-phenyl]-ethylamino}-quinazoline-8-carboxylic acid amide | 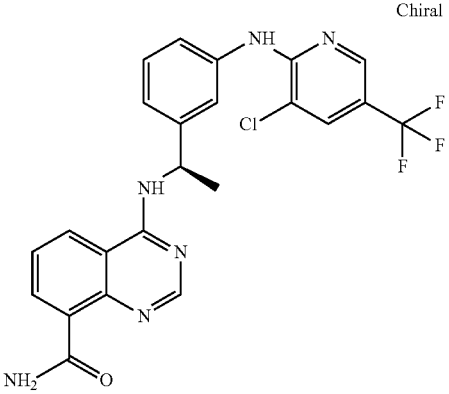 [SMILES: C[C@@H](Nc1ncnc2c(C(N)=O)cccc12)c1cccc(Nc2ncc(C(F)(F)F)cc2Cl)c1] |
| 594 | 410 | 0.00230 | 0.00018 | | 0.6600 | 4-[3-(4-Cyano-methyl-pyridin-2-ylamino)-benzylamino]-quinazoline-8-carboxylic acid amide | 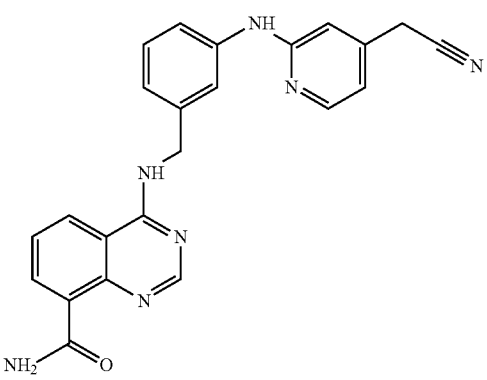 [SMILES: N#CCc1ccnc(Nc2cccc(CNc3ncnc4c(C(N)=O)cccc34)c2)c1] |
| 595 | 457 | 0.00230 | 0.0160 | | | 4-[3-(6-Methoxy-benzo-thiazol-2-ylamino)-benzyl-amino)-quinazoline-8-carboxylic acid amide | 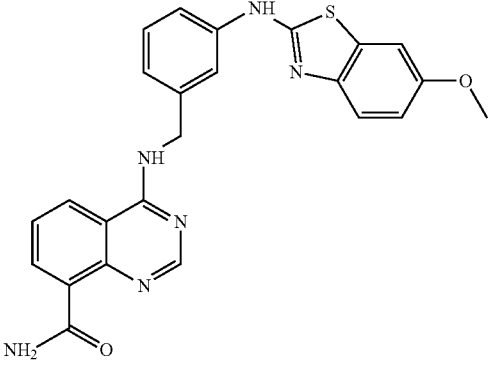 [SMILES: COc1ccc2nc(Nc3cccc(CNc4ncnc5c(C(N)=O)cccc45)c3)sc2c1] |
| 596 | 427 | 0.00230 | 0.0025 | | | 4-[3-(Benzo-thiazol-2-ylamino)-benzyl-amino]-quinazoline-8-carboxylic acid amide | 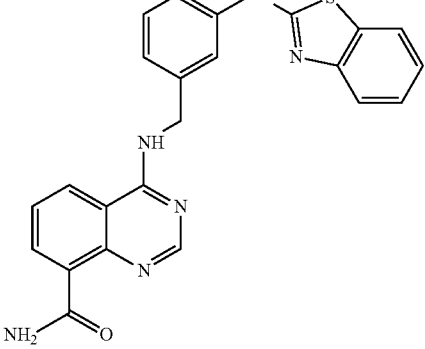 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 597 | 495 | 0.00240 | | | | 4-(1-{3-[(2,2-Difluoro-cyclo-propane-carbonyl)-amino]-phenyl}-3-pyrrolidin-1-yl-propyl-amino)-quinazoline-8-carboxylic acid amide | 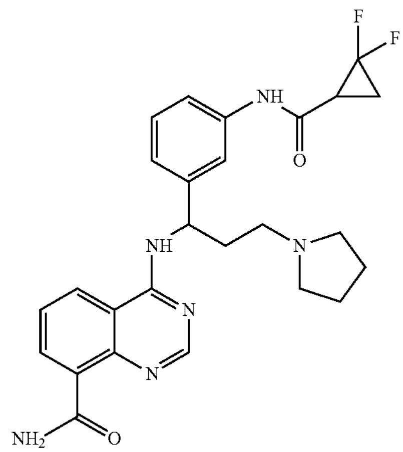 [SMILES: NC(=O)c1cccc2c(NC(CCN3CCCC3)c3cccc(NC(=O)C4CC4(F)F)c3)ncnc12] |
| 598 | 426 | 0.00250 | 0.00054 | 0.1300 | | 4-(1-{3-[(2,2-Difluoro-cyclo-propane-carbonyl)-amino]-phenyl}-propyl-amino)-quinazoline-8-carboxylic acid amide | 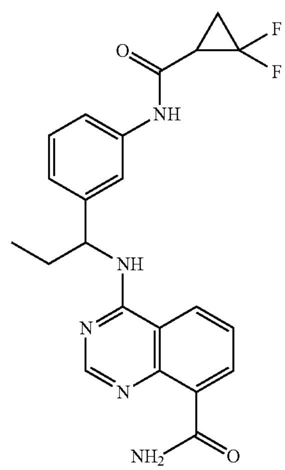 [SMILES: CCC(Nc1ncnc2c(C(N)=O)cccc12)c1cccc(NC(=O)C2CC2(F)F)c1] |
| 599 | 446 | 0.00250 | | 0.4100 | | 4-{(R)-1-[3-(4,4,4-Trifluoro-2-methyl-butyryl-amino)-phenyl]-ethylamino}-quinazoline-8-carboxylic acid amide | Chiral |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 600 | 429 | 0.00270 | 0.0068 | | | 4-(1-{3-[(6-Oxo-1,6-dihydro-pyridine-3-carbonyl)-amino]-phenyl}-ethylamino)-quinazoline-8-carboxylic acid amide | 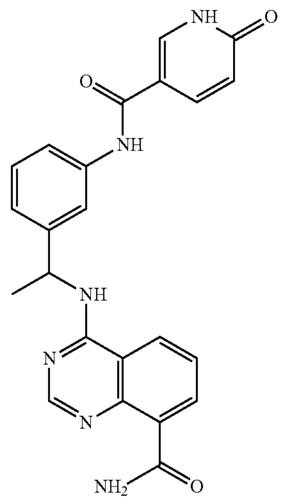 [SMILES: CC(Nc1ncnc2c(C(N)=O)cccc12)c1cccc(NC(=O)c2ccc(=O)[nH]c2)c1] |
| 601 | 418 | 0.00310 | 0.0042 | 0.3000 | | 4-{1-[3-(3,3,3-Trifluoro-propionyl-amino)-phenyl]-ethylamino}-quinazoline-8-carboxylic acid amide | 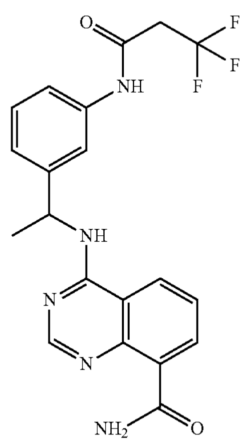 [SMILES: CC(Nc1ncnc2c(C(N)=O)cccc12)c1cccc(NC(=O)CC(F)(F)F)c1] |
| 602 | 435 | 0.00350 | | | | 4-[3-(7-Methyl-isoquinolin-1-ylamino)-benzyl-amino]-quinazoline-8-carboxylic acid amide | 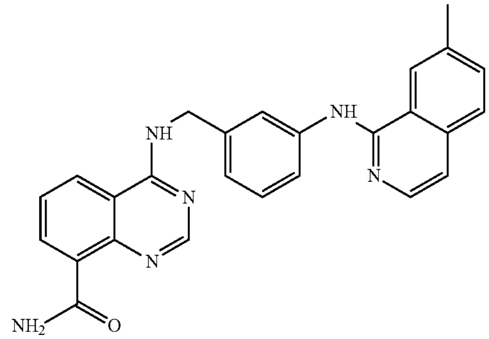 [SMILES: Cc1ccc2ccnc(Nc3cccc(CNc4ncnc5c(C(N)=O)cccc45)c3)c2c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 603 | 439 | 0.00360 | 0.0150 | | | 4-[3-(5-Trifluoro-methyl-pyridin-2-ylamino)-benzyl-amino]-quinazoline-8-carboxylic acid amide | 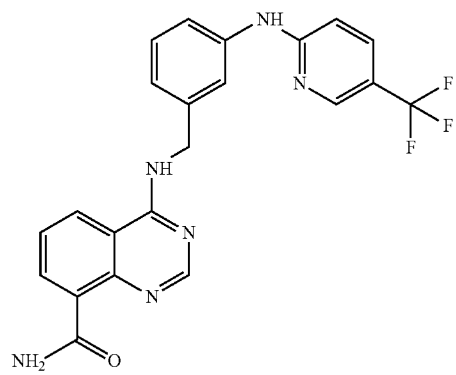 [SMILES: NC(=O)c1cccc2c(NCc3cccc(Nc4ccc(C(F)(F)F)cn4)c3)ncnc12] |
| 604 | 466 | 0.00420 | 0.0047 | 0.1600 | | 4-{3-[(4-Trifluoro-methyl-benzoyl-amino)-methyl]-pheny-amino}-quinazoline-8-carboxylic acid amide | 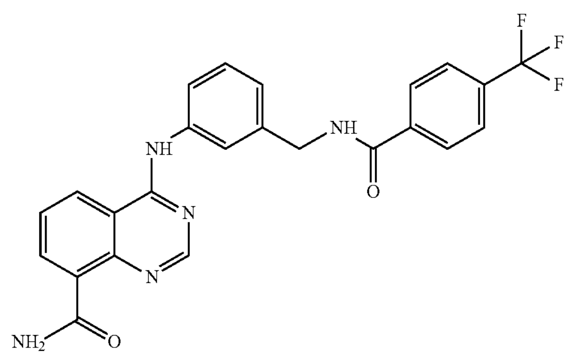 [SMILES: NC(=O)c1cccc2c(Nc3cccc(CNC(=O)c4ccc(C(F)(F)F)cc4)c3)ncnc12] |
| 605 | 438 | 0.00420 | 0.0130 | | | 4-{3-[(1H-Pyrrolo[2,3-b]pyridine-3-carbonyl)-amino]-benzyl-amino}-quinazoline-8-carboxylic acid amide | 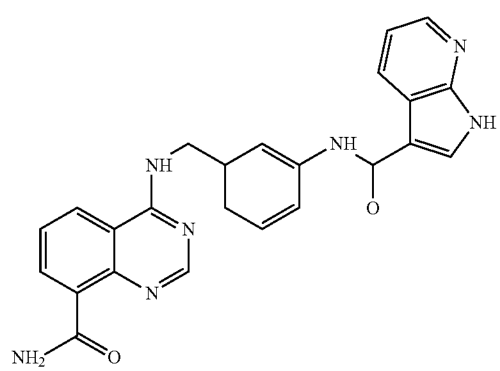 [SMILES: NC(=O)c1cccc2c(NCC3C=C(NC(O)c4c[nH]c5ncccc45)C=CC3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 606 | 433 | 0.00420 | | | | 4-((R)-1-{3-[(1-Ethyl-pyrrolidine-3-carbonyl)-amino]-phenyl}-ethylamino)-quinazoline-8-carboxylic acid amide | Chiral |
| 607 | 399 | 0.00550 | | 0.0089 | | 4-{3-[(Pyridine-4-carbonyl)-amino]-benzyl-amino}-quinazoline-8-carboxylic acid amide | 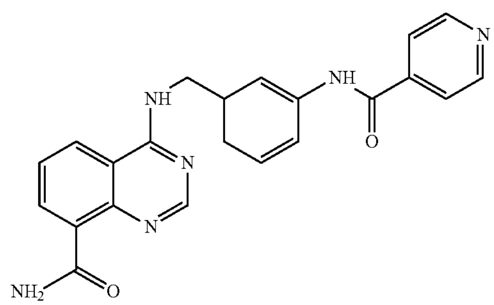 [SMILES: NC(=O)c1cccc2c(NCC3C=C(NC(=O)c4ccncc4)C=CC3)ncnc12] |
| 608 | 484 | 0.00620 | | | 0.7600 | 4-{(R)-1-[3-(5-Morpholin-4-ylmethyl-pyridin-2-ylamino)-phenyl]-ethylamino}-quinazoline-8-carboxylic acid amide | Chiral |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 609 | 472 | 0.00100 | 0.0180 | | | 4-{3-[3-(2-Methoxy-ethoxy)-benzoyl-amino]-benzyl-amino}-quinazoline-8-carboxylic acid amide | 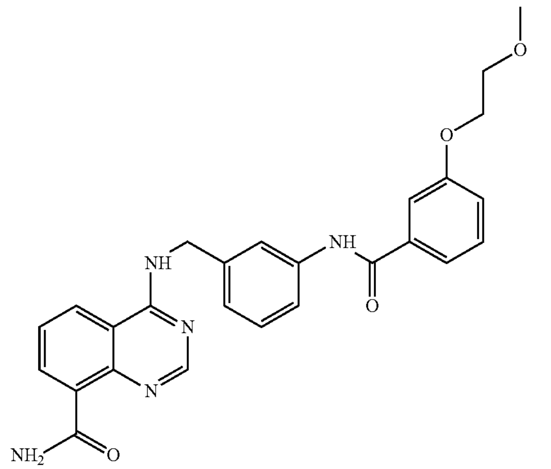 [SMILES: COCCOc1cccc(C(=O)Nc2cccc(CNc3ncnc4c(C(N)=O)cccc34)c2)c1] |
| 610 | 499 | 0.00660 | 0.0270 | | | 4-{3-[4-(3-Dimethyl-amino-propoxy)-benzoyl-amino]-benzyl-amino}-quinazoline-8-carboxylic acid amide | 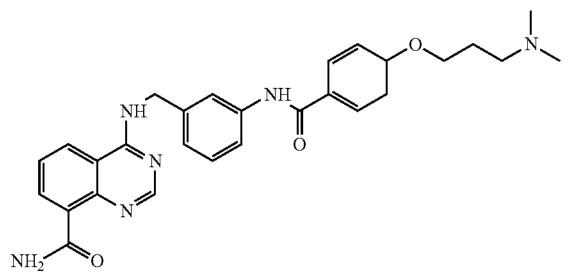 [SMILES: CN(C)CCCOC1C=CC(C(=O)Nc2cccc(CNc3ncnc4c(C(N)=O)cccc34)c2)=CC1] |
| 611 | 412 | 0.00700 | | 0.2400 | | 4-[3-(9H-Purin-6-ylamino)-benzyl-amino]-quinazoline-8-carboxylic acid amide | 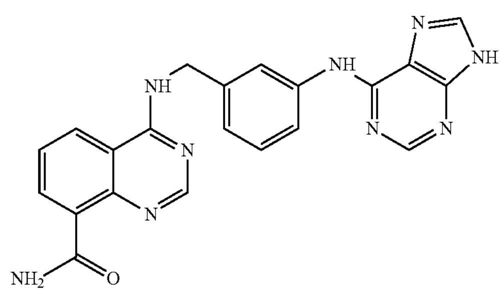 [SMILES: NC(=O)c1cccc2c(NCc3cccc(Nc4ncnc5[nH]cnc45)c3)ncnc12] |
| 612 | 556 | 0.00700 | | 5 | | 6-[(2-Diethyl-amino-ethylamino)-methyl]-4-[3-(4-methoxy-benzoyl-amino)-benzyl-amino]-quinazoline-8-carboxylic acid amide | 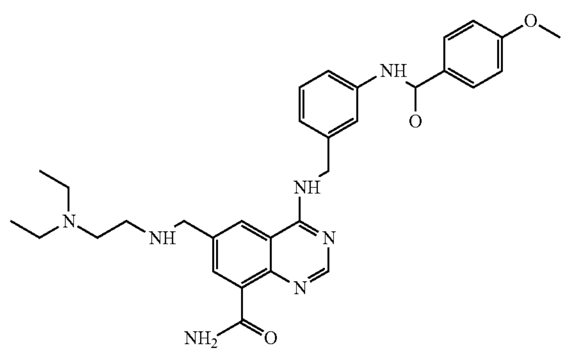 [SMILES: CCN(CC)CCNCc1cc(C(N)=O)c2ncnc(NCc3cccc(NC(O)c4ccc(OC)cc4)c3)c2c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 613 | 487 | 0.00700 | | | | 4-(3-{[(S)-1-(2,2,2-Trifluoro-acetyl)-pyrrolidine-2-carbonyl]-amino}-benzyl-amino)-quinazoline-8-carboxylic acid amide | Chiral |
| 614 | 472 | 0.00730 | | 0.0700 | | 4-{3-[2-(2-Methoxy-ethoxy)-benzoyl-amino]-benzyl-amino}-quinazoline-8-carboxylic acid amide | 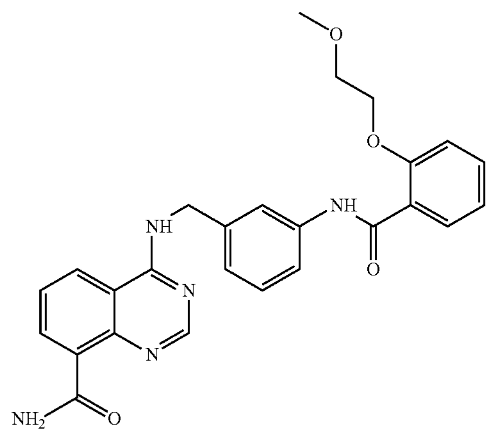 [SMILES: COCCOc1ccccc1C(=O)Nc1cccc(CNc2ncnc3c(C(N)=O)cccc23)c1] |
| 615 | 386 | 0.00760 | | | | 4-[3-(5-Amino-pyridin-2-ylamino)-benzyl-amino]-quinazoline-8-carboxylic acid amide | 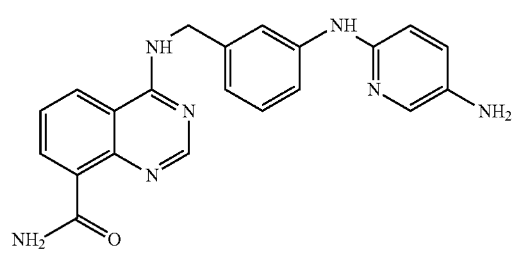 [SMILES: NC(=O)c1cccc2c(NCc3cccc(Nc4ccc(N)cn4)c3)ncnc12] |
| 616 | 425 | 0.00860 | | | 0.1300 | 4-[3-(2-Methyl-3H-imidazo[4,5-c]pyridin-4-ylamino)-benzyl-amino]-quinazoline-8-carboxylic acid amide | 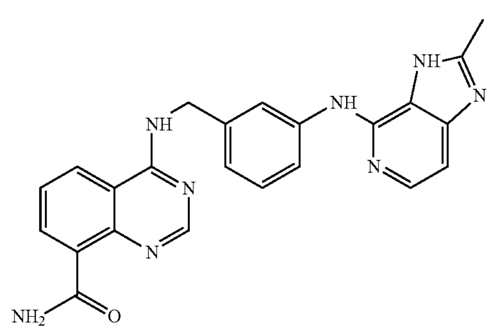 [SMILES: Cc1nc2ccnc(Nc3cccc(CNc4ncnc5c(C(N)=O)cccc45)c3)c2[nH]1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 617 | 443 | 0.00900 | 0.0016 | 0.1730 | | 4-{3-[(4,5,6,7-Tetrahydro-pyrazolo[1,5-a]pyrazine-3-carbonyl)-amino]-benzyl-amino}-quinazoline-8-carboxylic acid amide | 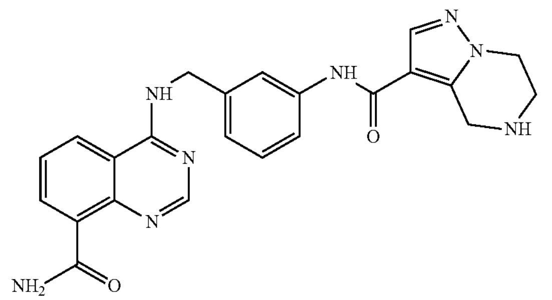 [SMILES: NC(=O)c1cccc2c(NCc3cccc(NC(=O)c4cnn5c4CNCC5)c3)ncnc12] |
| 618 | 442 | 0.00910 | 0.0320 | | | 4-[5-(4-Methoxy-benzoyl-amino)-2-methyl-benzyl-amino]-quinazoline-8-carboxylic acid amide | 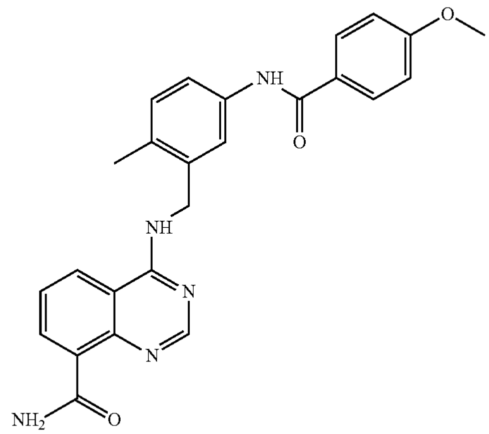 |
| 619 | 372 | 0.01100 | 0.0033 | 0.5000 | | 4-[3-(Pyrimidin-2-ylamino)-benzyl-amino]-quinazoline-8-carboxylic acid amide | 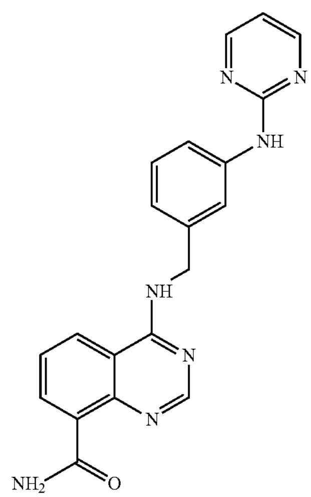 [SMILES: NC(=O)c1cccc2c(NCc3cccc(Nc4ncccn4)c3)ncnc12] |
| 620 | 399 | 0.01100 | 0.1700 | 1.6000 | | 4-(3-{[(Pyridine-3-carbonyl)-amino]-methyl}-phenyl-amino)-quinazoline-8-carboxylic acid amide | 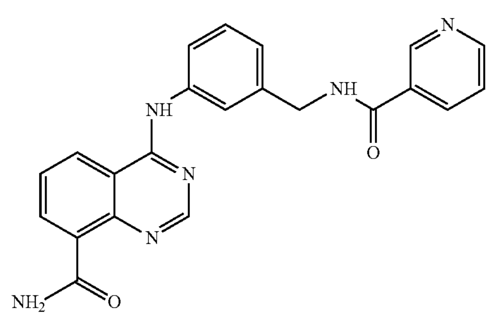 [SMILES: NC(=O)c1cccc2c(Nc3cccc(CNC(=O)c4cccnc4)c3)ncnc12] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 621 | 482 | 0.01500 | 0.0015 | 0.7500 | | 4-{3-Piperidin-1-yl-1-[3-(pyridin-2-ylamino)-phenyl]-propyl-amino}-quinazoline-8-carboxylic acid amide | 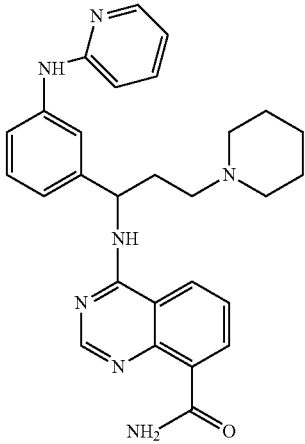 [SMILES: NC(=O)c1cccc2c(NC(CCN3CCCCC3)c3cccc(Nc4ccccn4)c3)ncnc12] |
| 622 | 484 | 0.01900 | 0.0044 | 0.5000 | | 4-{3-[2-(5-Methyl-3-trifluoro-methyl-pyrazol-1-yl)-acetyl-amino]-benzyl-amino}-quinazoline-8-carboxylic acid amide | 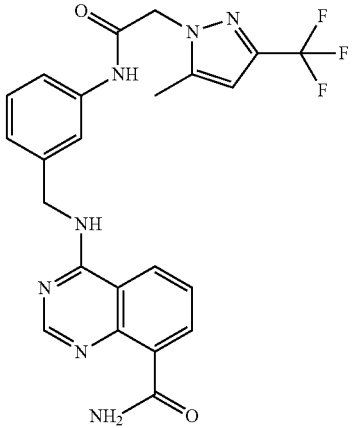 [SMILES: Cc1cc(C(F)(F)F)nn1CC(=O)Nc1cccc(CNc2ncnc3c(C(N)=O)cccc23)c1] |
| 623 | 454 | 0.01900 | 0.0200 | 1.4000 | | 4-[7-(4-Methoxy-benzoyl-amino)-3,4-dihydro-1H-isoquinolin-2-yl]-quinazoline-8-carboxylic acid amide | 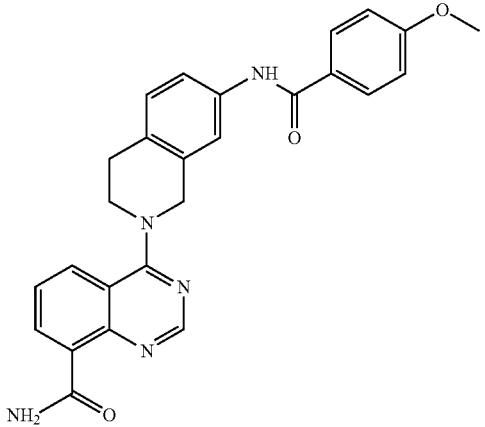 [SMILES: COc1ccc(C(=O)Nc2ccc3c(c2)CN(c2ncnc4c(C(N)=O)cccc24)CC3)cc1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 624 | 472/ 474 | 0.02000 | 0.0050 | | | 4-{3-[(5-Chloro-1H-indazole-3-carbonyl)-amino]-benzyl-amino}-quinazoline-8-carboxylic acid amide | 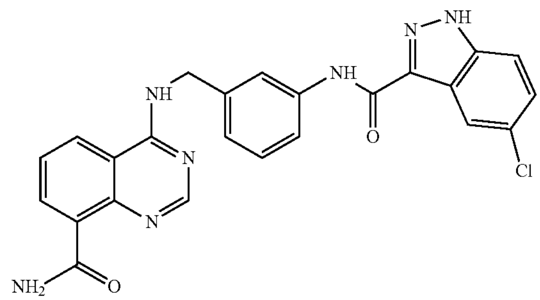 [SMILES: NC(=O)c1cccc2c(NCc3cccc(NC(=O)c4n[nH]c5ccc(Cl)cc45)c3)ncnc12] |
| 625 | 501 | 0.02500 | 0.0160 | 0.8700 | | 4-(1-{3-[(2-Morpholin-4-ylmethyl-furan-3-carbonyl)-amino]-phenyl}-ethylamino)-quinazoline-8-carboxylic acid amide | 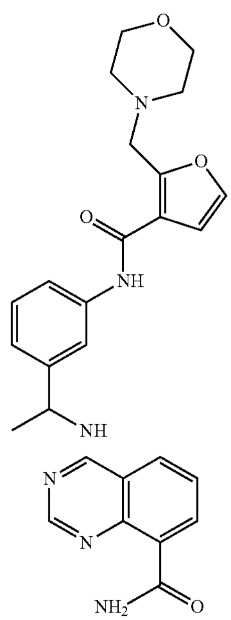 |
| 626 | 527 | 0.02700 | 0.1400 | 9.9000 | | 4-[3-(4-Methoxy-benzoyl-amino)-benzyl-amino]-6-morpholin-4-ylmethyl-quinazoline-8-carboxylic acid amide | 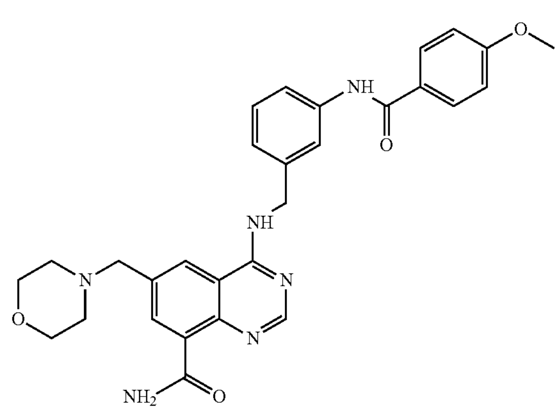 [SMILES: COc1ccc(C(=O)Nc2cccc(CNc3ncnc4c(C(N)=O)cc(CN5CCOCC5)cc34)c2)cc1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 627 | 439 | 0.02900 | | | 0.1400 | 4-[3-(2,4-Dioxo-1,4-dihydro-2H-quinazolin-3-yl)-benzyl-amino]-quinazoline-8-carboxylic acid amide | 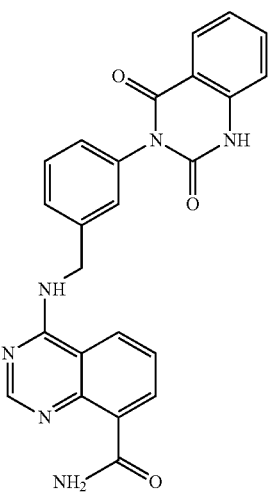 [SMILES: NC(=O)c1cccc2c(NCc3cccc(-n4c(=O)[nH]c5ccccc5c4=O)c3)ncnc12] |
| 628 | 468 | 0.02900 | 0.0050 | 0.6800 | | 4-{1-[3-(Pyridin-2-ylamino)-phenyl]-3-pyrrolidin-1-yl-propyl-amino}-quinazoline-8-carboxylic acid amide | 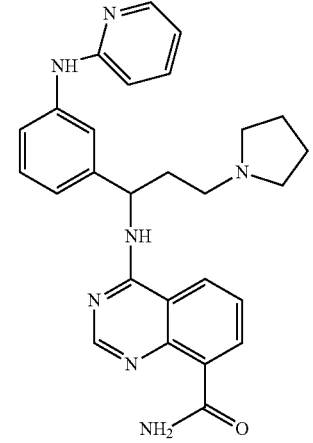 [SMILES: NC(=O)c1cccc2c(NC(CCN3CCCC3)c3cccc(Nc4ccccn4)c3)ncnc12] |
| 629 | 447 | 0.03200 | 0.0019 | 0.3200 | | 4-{3-[(1-Isopropyl-piperidine-4-carbonyl)-amino]-benzyl-amino}-quinazoline-8-carboxylic acid amide | 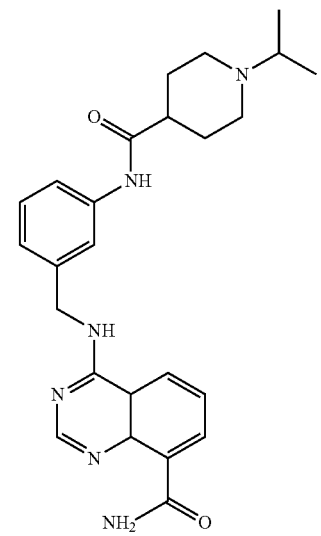 [SMILES: CC(C)N1CCC(C(=O)Nc2cccc(CNC3=NC=NC4C(C(N)=O)=CC=CC34)c2)CC1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 630 | 421 | 0.03400 | | | 1 | 4-[3-(Quinolin-2-ylamino)-benzyl-amino]-quinazoline-8-carboxylic acid amide | 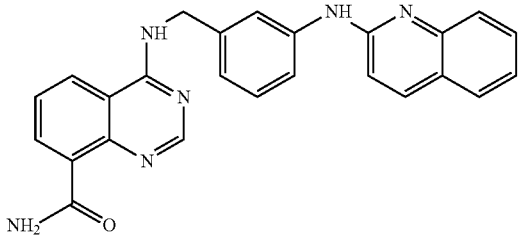 [SMILES: NC(=O)c1cccc2c(NCc3cccc(Nc4ccc5ccccc5n4)c3)ncnc12] |
| 631 | 419 | 0.03500 | 0.0380 | | 0.6900 | 4-(1-{3-[(5-Oxo-pyrrolidine-3-carbonyl)-amino]-phenyl}-ethylamino)-quinazoline-8-carboxylic acid amide | 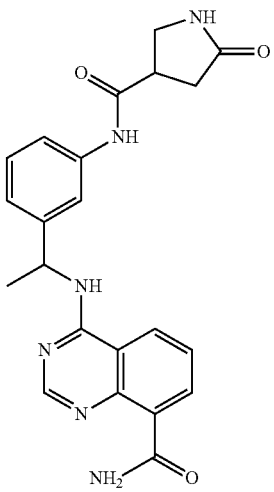 [SMILES: CC(Nc1ncnc2c(C(N)=O)cccc12)c1cccc(NC(=O)C2CNC(=O)C2)c1] |
| 632 | 470 | 0.03600 | 0.0130 | | 2.8000 | 4-[3-(4-Methoxy-benzoyl-amino)-benzyl-amino]-quinoline-3,8-dicarboxylic acid diamide | 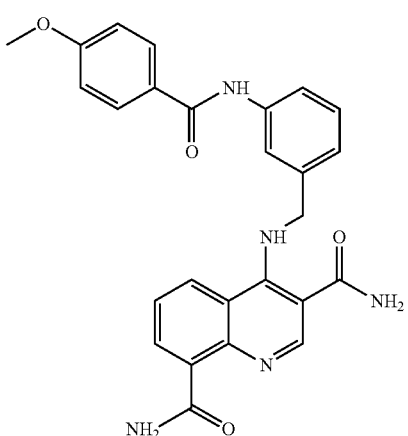 [SMILES: COc1ccc(C(=O)Nc2cccc(CNc3c(C(N)=O)cnc4c(C(N)=O)cccc34)c2)cc1] |
| 633 | 405 | 0.04000 | 0.0390 | | 1.6000 | 4-(3-{[(Piperidine-3-carbonyl)-amino]-methyl}-phenyl-amino)-quinazoline-8-carboxylic acid amide | 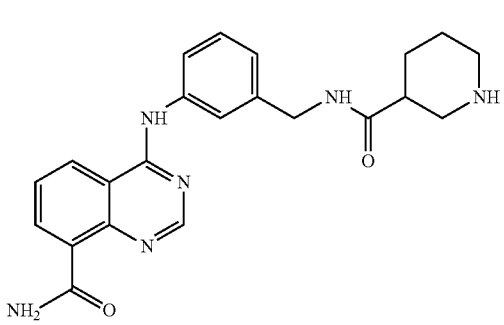 [SMILES: NC(=O)c1cccc2c(Nc3cccc(CNC(=O)C4CCCNC4)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 634 | 513 | 0.04700 | | | | 4-{3-[2-(2-Diethyl-amino-ethoxy)-benzoyl-amino]-benzyl-amino}-quinazoline-8-carboxylic acid amide | 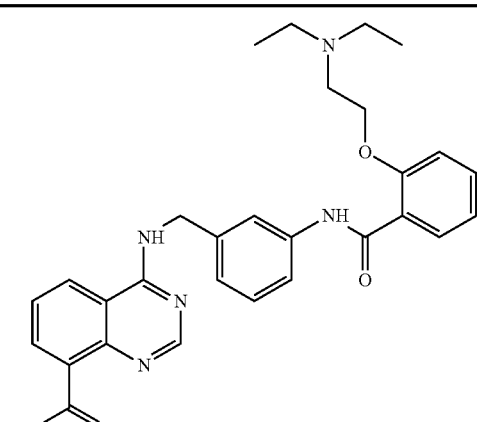 |
| 635 | 499 | 0.00960 | | | | 4-{3-[3-(3-Dimethyl-amino-propoxy)-benzoyl-amino]-benzyl-amino}-quinazoline-8-carboxylic acid amide | 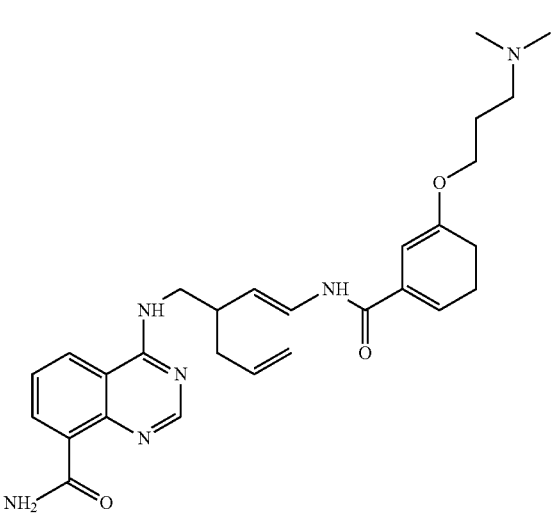 [SMILES: C=CCC(/C=C/NC(=O)C1=CCCC(OCCCN(C)C)=C1)CNc1ncnc2c(C(N)=O)cccc12] |
| 636 | 513 | 0.00980 | 0.0590 | | | 4-{3-[4-(2-Diethyl-amino-ethoxy)-benzoyl-amino]-benzyl-amino}-quinazoline-8-carboxylic acid amide | 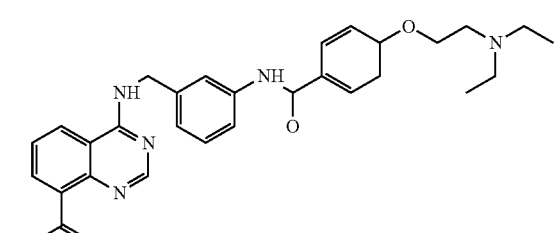 |
| 637 | 516/518 | 0.05100 | 0.0064 | | | 4-{3-[(5-Bromo-1H-indazole-3-carbonyl)-amino]-benzyl-amino}-quinazoline-8-carboxylic acid amide | 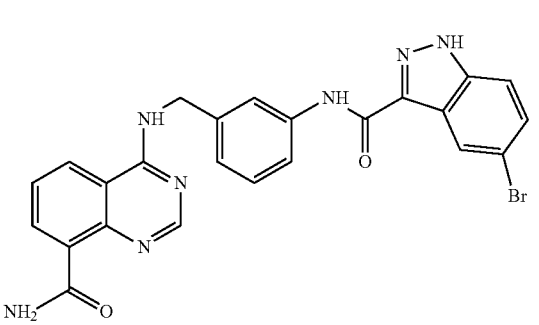 [SMILES: NC(=O)c1cccc2c(NCc3cccc(NC(=O)c4n[nH]c5ccc(Br)cc45)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 638 | 540 | 0.06900 | 0.0220 | 2.8000 | | 4-[3-(4-Methoxy-benzoyl-amino)-benzyl-amino]-6-(4-methyl-piperazin-1-ylmethyl)-quinazoline-8-carboxylic acid amide | 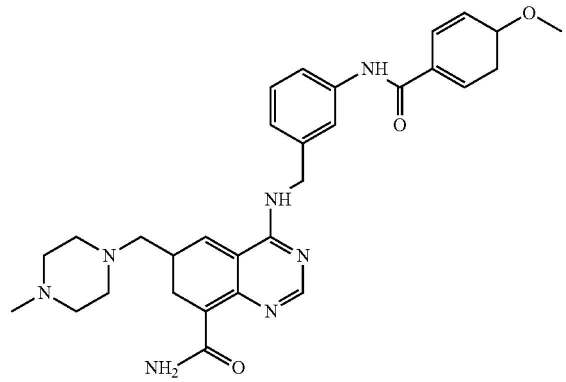 |
| 639 | 444 | 0.11000 | 0.0087 | | | 6-Hydroxy-4-{3-[(4-methoxy-benzoyl-amino)-methyl]-phenyl-amino}-quinazoline-8-carboxylic acid amide | 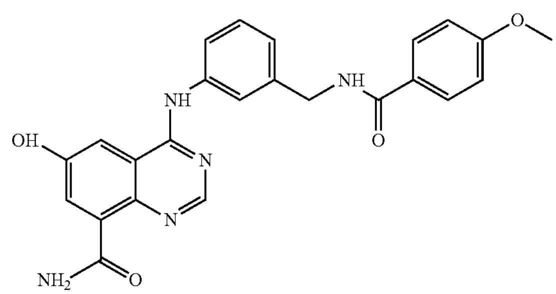 [SMILES: COc1ccc(C(=O)NCc2cccc(Nc3ncnc4c(C(N)=O)cc(O)cc34)c2)cc1] |
| 640 | 477 | 0.00025 672 | | | | 4-{(R)-1-[3-(4-Pyrrol-1-yl-benzoyl-amino)-phenyl]-ethylamino}-quinazoline-8-carboxylic acid amide | 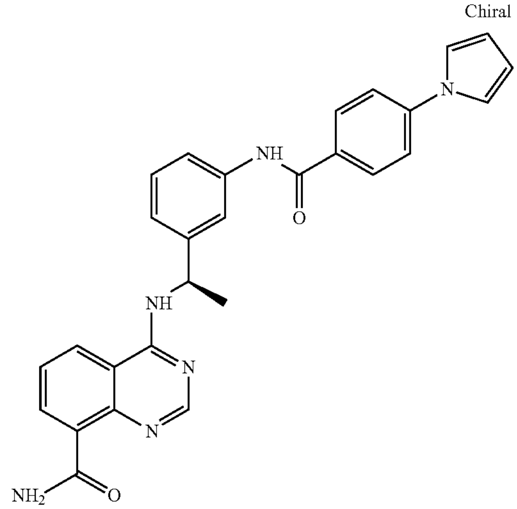 [SMILES: C[C@@H](Nc1ncnc2c(C(N)=O)cccc12)c1cccc(NC(=O)c2ccc(-n3cccc3)cc2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 642 | 399 | 0.00039 272 | | | | 4-{1-[3-(4-Methyl-pyridin-2-ylamino)-phenyl]-ethylamino}-quinazoline-8-carboxylic acid amide | 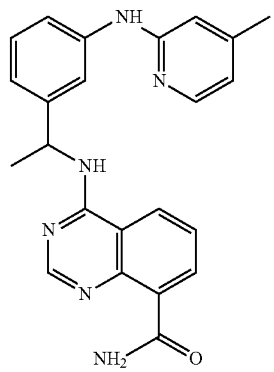 [SMILES: Cc1ccnc(Nc2cccc(C(C)Nc3ncnc4c(C(N)=O)cccc34)c2)c1] |
| 643 | 514 | 0.00044 602 | | | | 4-{(R)-1-[4-Fluoro-3-(4-trifluoro-methoxy-benzoyl-amino)-phenyl]-ethylamino}-quinazoline-8-carboxylic acid amide | 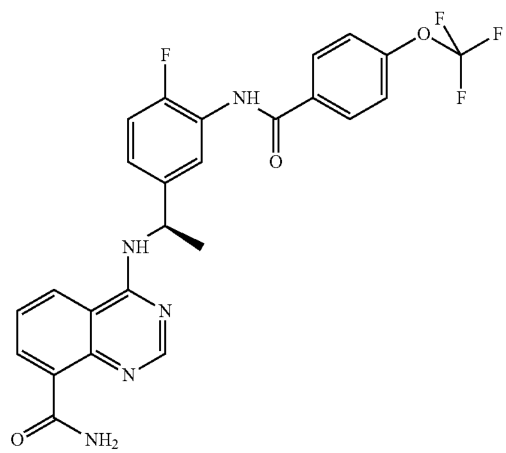 |
| 644 | 475 | 0.00131 89 | | | | 4-((R)-1-{3-[(4-tert-Butyl-thiazole-2-carbonyl)-amino]-phenyl}-ethylamino)-quinazoline-8-carboxylic acid amide | 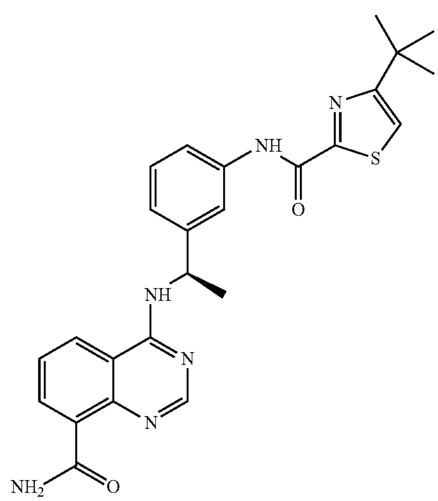 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 645 | 430 | 0.00012 | 0.00033 | | | 4-{3-[(5-Isopropyl-2H-pyrazole-3-carbonyl)-amino]-benzyl-amino}-quinazoline-8-carboxylic acid amide | 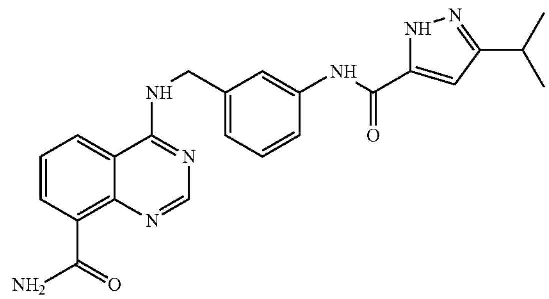 [SMILES: CC(C)c1cc(C(=O)Nc2cccc(CNc3ncnc4c(C(N)=O)cccc34)c2)[nH]n1] |
| 646 | 427 | 0.01000 | 0.0150 | | | 4-[3-(3-Methyl-amino-benzoyl-amino)-benzyl-amino]-quinazoline-8-carboxylic acid amide | 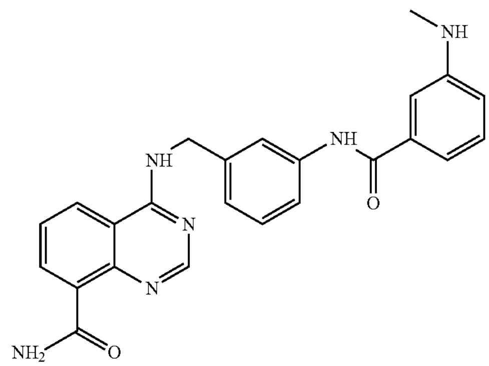 [SMILES: CNc1cccc(C(=O)Nc2cccc(CNc3ncnc4c(C(N)=O)cccc34)c2)c1] |
| 647 | 543 | 0.00480 | 0.0065 | 1 | | 6-(2-Diethyl-amino-ethoxy)-4-[3-(4-methoxy-benzoyl-amino)-benzyl-amino]-quinazoline-8-carboxylic acid amide | 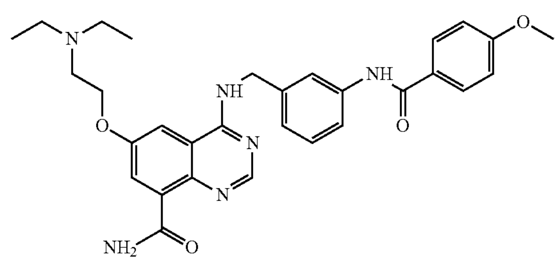 [SMILES: CCN(CC)CCOc1cc(C(N)=O)c2ncnc(NCc3cccc(NC(=O)c4ccc(OC)cc4)c3)c2c1] |
| 648 | 402 | 0.00047 | 0.0023 | | | 4-{3-[(5-Methyl-1H-pyrazole-3-carbonyl)-amino]-benzyl-amino}-quinazoline-8-carboxylic acid amide | 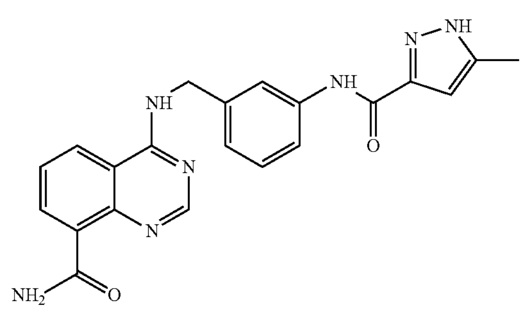 [SMILES: Cc1cc(C(=O)Nc2cccc(CNc3ncnc4c(C(N)=O)cccc34)c2)n[nH]1] |
| 649 | 412 | 0.00010 | 0.0012 | | | 4-[3-(2-Methyl-benzoyl-amino)-benzyl-amino]-quinazoline-8-carboxylic acid amide | 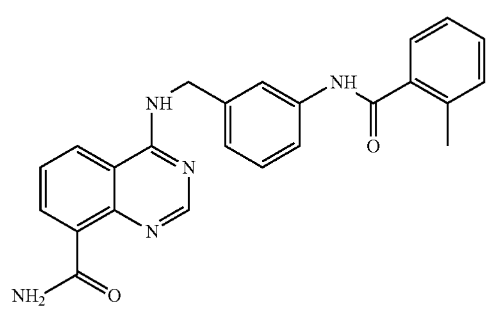 [SMILES: Cc1ccccc1C(=O)Nc1cccc(CNc2ncnc3c(C(N)=O)cccc23)c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 650 | 441 | 0.00022 | 0.0017 | | | 4-[3-(3-Dimethyl-amino-benzoyl-amino)-benzyl-amino]-quinazoline-8-carboxylic acid amide | 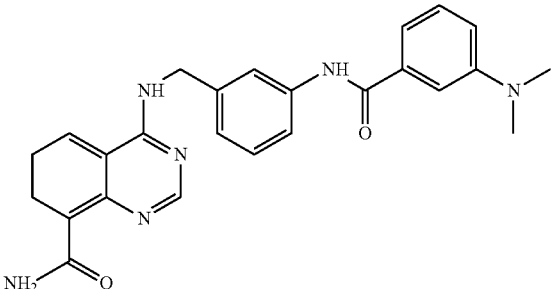 |
| 651 | 412 | 0.00017 | 6.1000e−06 | | | 4-[3-(3-Methyl-benzoyl-amino)-benzyl-amino]-quinazoline-8-carboxylic acid amide | 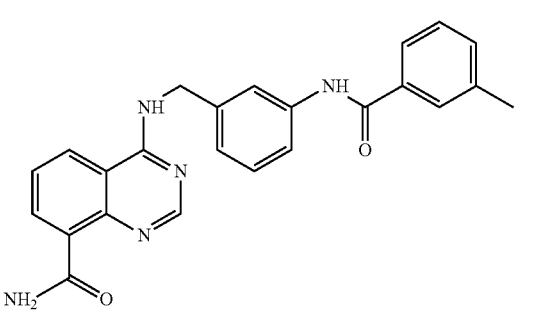 [SMILES: Cc1cccc(C(=O)Nc2cccc(CNc3ncnc4c(C(N)=O)cccc34)c2)c1] |
| 652 | 502 | 6.0000e−05 | 0.0027 | 1 | | 4-[3-(4-Methoxy-benzoyl-amino)-benzyl-amino]-6-(2-methoxy-ethoxy)-quinazoline-8-carboxylic acid amide | 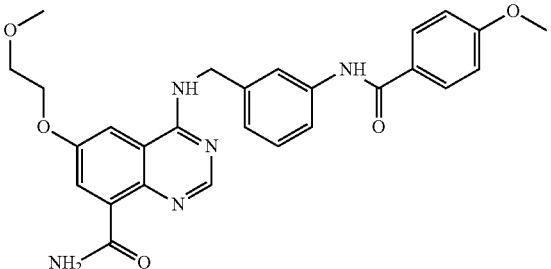 |
| 653 | 484 | 0.00012 | 0.00021 | | | 4-[3-(2-Fluoro-4-trifluoro-methyl-benzoyl-amino)-benzyl-amino]-quinazoline-8-carboxylic acid amide | 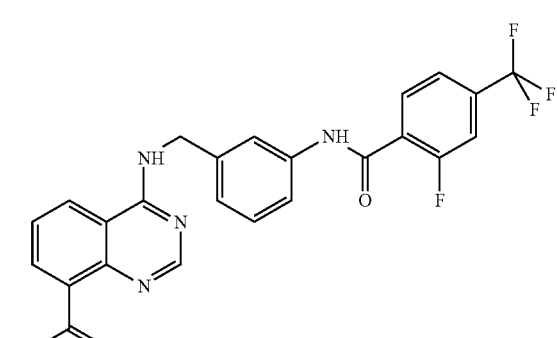 |
| 654 | 502 | 0.00020 | 0.0120 | 0.3100 | | 6-(3-Hydroxy-propoxy)-4-[3-(4-methoxy-benzoyl-amino)-benzyl-amino]-quinazoline-8-carboxylic acid amide | 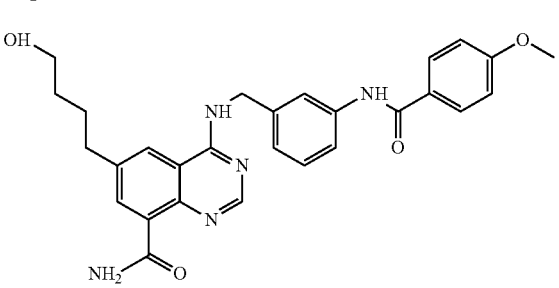 |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 655 | 442 | 0.00013 | 0.0018 | | | 4-[3-(4-Ethoxy-benzoyl-amino)-benzyl-amino]-quinazoline-8-carboxylic acid amide | 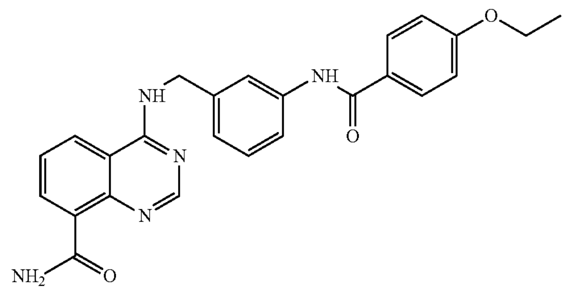 [SMILES: CCOc1ccc(C(=O)Nc2cccc(CNc3ncnc4c(C(N)=O)cccc34)c2)cc1] |
| 656 | 404 | 0.00016 | 0.0011 | | | 4-[3-(Cyclo-hexane-carbonyl-amino)-benzyl-amino]-quinazoline-8-carboxylic acid amide | 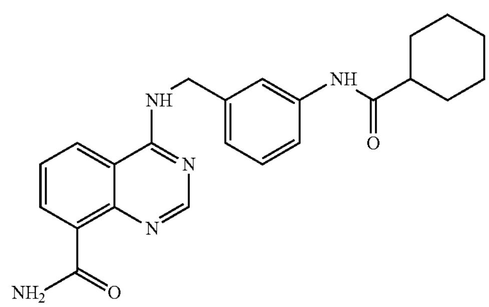 [SMILES: NC(=O)c1cccc2c(NCc3cccc(NC(=O)C4CCCCC4)c3)ncnc12] |
| 657 | 455 | 0.00065 | 0.0005 | | | 4-[3-(4-Acetyl-amino-benzoyl-amino)-benzyl-amino]-quinazoline-8-carboxylic acid amide | 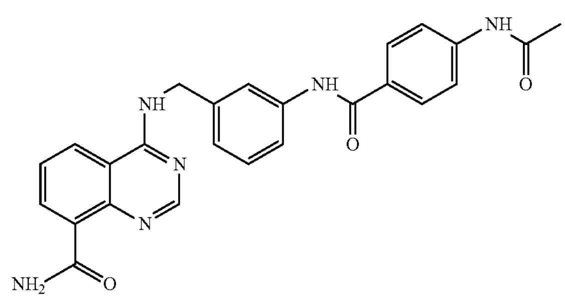 [SMILES: CC(=O)Nc1ccc(C(=O)Nc2cccc(CNc3ncnc4c(C(N)=O)cccc34)c2)cc1] |
| 658 | 478 | 6.0000e−05 | 0.0002 | | | 4-{3-[(2,2-Difluoro-benzo[1,3]-dioxole-5-carbonyl)-amino]-benzyl-amino}-quinazoline-8-carboxylic acid amide | 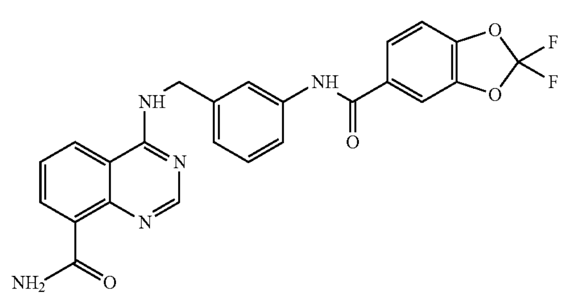 [SMILES: NC(=O)c1cccc2c(NCc3cccc(NC(=O)c4ccc5c(c4)OC(F)(F)O5)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 659 | 467 | 0.00011 | 0.00038 | | | 4-{3-[(6-Trifluoro-methyl-pyridine-3-carbonyl)-amino]-benzyl-amino}-quinazoline-8-carboxylic acid amide |
| 660 | 476/478 | 0.00054 | 0.00079 | | | 4-[3-(3-Bromo-benzoyl-amino)-benzyl-amino]-quinazoline-8-carboxylic acid amide |
| 661 | 432/434 | 0.00017 | 0.00038 | | | 4-[3-(3-Chloro-benzoyl-amino)-benzyl-amino]-quinazoline-8-carboxylic acid amide |
| 662 | 442 | 0.00330 | 0.0130 | | | 4-{[3-(4-Methoxy-benzoyl-amino)-benzyl]-methyl-amino}-quinazoline-8-carboxylic acid amide |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 663 | 405 | 0.00300 | 0.0016 | | | 4-{3-[(Piperidine-3-carbonyl)-amino]-benzyl-amino}-quinazoline-8-carboxylic acid amide | 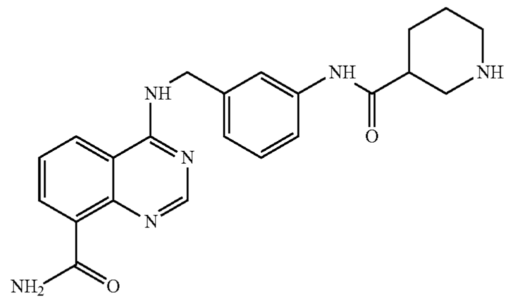 [SMILES: NC(=O)c1cccc2c(NCc3cccc(NC(=O)C4CCCNC4)c3)ncnc12] |
| 664 | 469 | 0.00018 | 0.0019 | 0.2700 | | 4-[1-(3-Benzoyl-amino-phenyl)-3-dimethyl-amino-propyl-amino]-quinazoline-8-carboxylic acid amide | 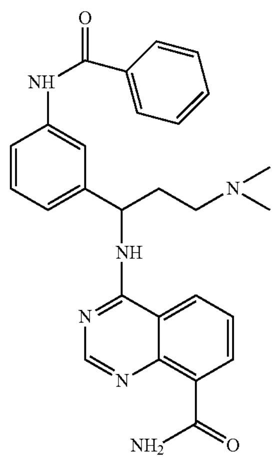 [SMILES: CN(C)CCC(Nc1ncnc2c(C(N)=O)cccc12)c1cccc(NC(=O)c2ccccc2)c1] |
| 665 | 483 | 8.0000e−05 | 0.0069 | | | 4-[3-(4-Morpholin-4-yl-benzoyl-amino)-benzyl-amino]-quinazoline-8-carboxylic acid amide | 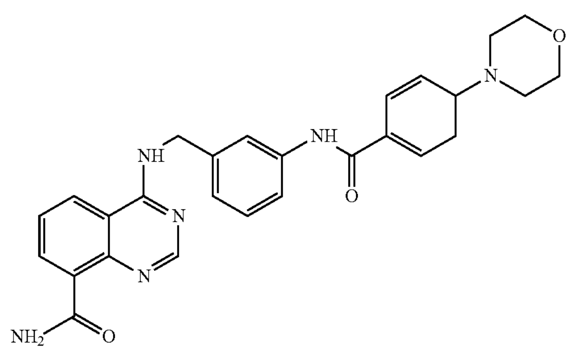 [SMILES: NC(=O)c1cccc2c(NCc3cccc(NC(=O)C4=CCC(N5CCOCC5)C=C4)c3)ncnc12] |
| 666 | 458 | 0.00031 | 0.00031 | | | 4-[3-(3,4-Dimethoxy-benzoyl-amino)-benzyl-amino]-quinazoline-8-carboxylic acid amide | 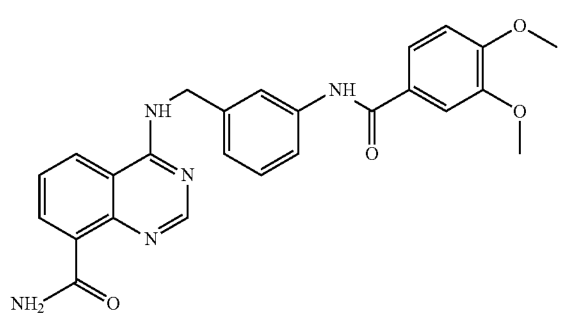 [SMILES: COc1ccc(C(=O)Nc2cccc(CNc3ncnc4c(C(N)=O)cccc34)c2)cc1OC] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 667 | 482 | 0.00072 | 0.0020 | | | 4-[3-(3-Trifluoro-methoxy-benzoyl-amino)-benzyl-amino]-quinazoline-8-carboxylic acid amide | 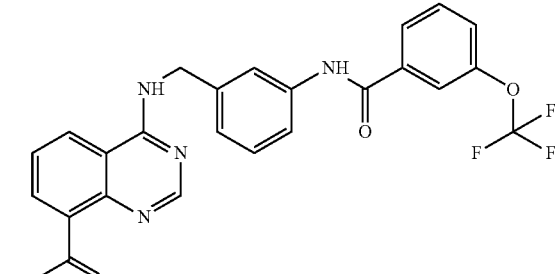 |
| 668 | 428 | 0.00037 | 0.0046 | | | 4-[3-(2-Methoxy-benzoyl-amino)-benzyl-amino]-quinazoline-8-carboxylic acid amide | 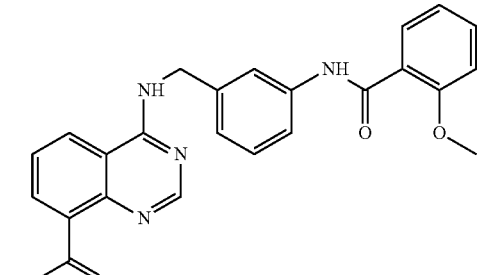 |
| 669 | 597 | 0.00900 | | | 5.5000 | 6-Benzyloxy-4-{1-[3-(4-bromo-benzoyl-amino)-phenyl]-ethylamino}-quinazoline-8-carboxylic acid amide | 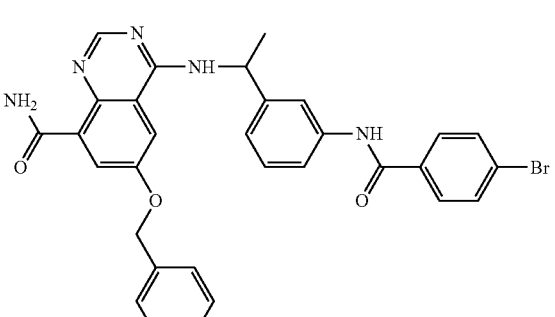 |
| 670 | 423 | 0.00063 | 0.0024 | | | 4-[3-(4-Cyano-benzoyl-amino)-benzyl-amino]-quinazoline-8-carboxylic acid amide | 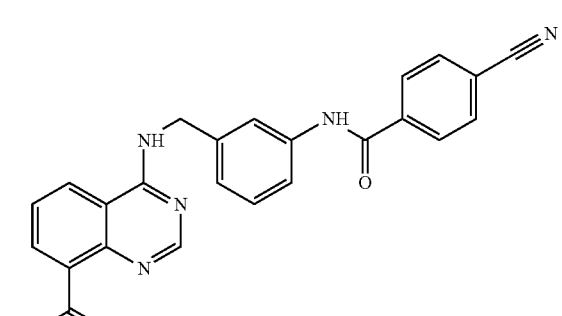 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 671 | 432 | 8.0000e−05 | 0.00018 | | | 4-[3-(4-Chloro-benzoyl-amino)-benzyl-amino]-quinazoline-8-carboxylic acid amide | 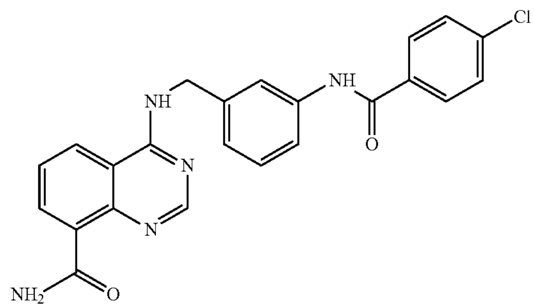 [SMILES: NC(=O)c1cccc2c(NCc3cccc(NC(=O)c4ccc(Cl)cc4)c3)ncnc12] |
| 672 | 446 | 0.01000 | 0.0140 | 0.4600 | | 4-{1-[3-(3-Fluoro-4-hydroxy-benzoyl-amino)-phenyl]-ethylamino}-quinazoline-8-carboxylic acid amide | 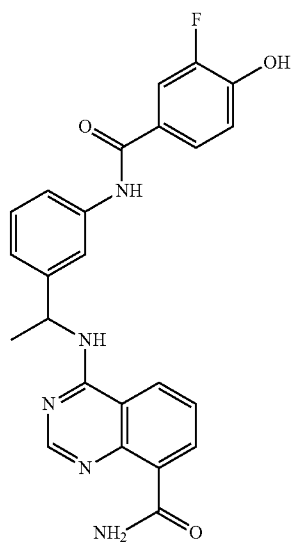 [SMILES: CC(Nc1ncnc2c(C(N)=O)cccc12)c1cccc(NC(=O)c2ccc(O)c(F)c2)c1] |
| 673 | 458 | 0.00091 | 0.0160 | | | 4-{3-[2-(2-Hydroxy-ethoxy)-benzoyl-amino]-benzyl-amino}-quinazoline-8-carboxylic acid amide | 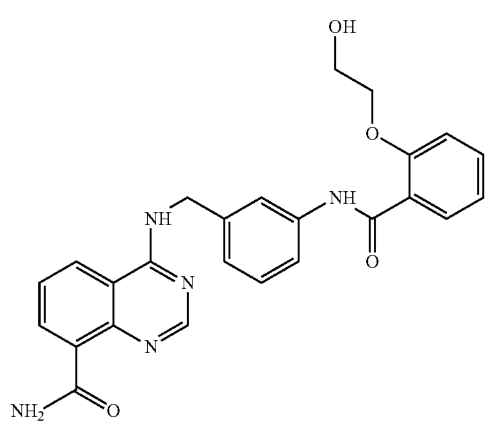 [SMILES: NC(=O)c1cccc2c(NCc3cccc(NC(=O)c4ccccc4OCCO)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 674 | 446 | 0.00290 | 0.0027 | | | 4-[2-Fluoro-5-(4-methoxy-benzoyl-amino)-benzyl-amino]-quinazoline-8-carboxylic acid amide | 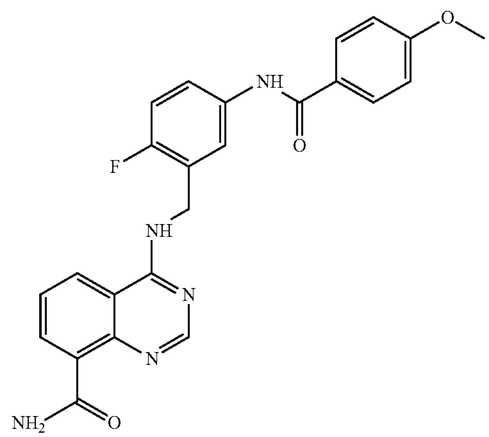 [SMILES: COc1ccc(C(=O)Nc2ccc(F)c(CNc3ncnc4c(C(N)=O)cccc34)c2)cc1] |
| 675 | 434 | 0.00031 | 0.00088 | | | 4-[3-(2,6-Difluoro-benzoyl-amino)-benzyl-amino]-quinazoline-8-carboxylic acid amide | 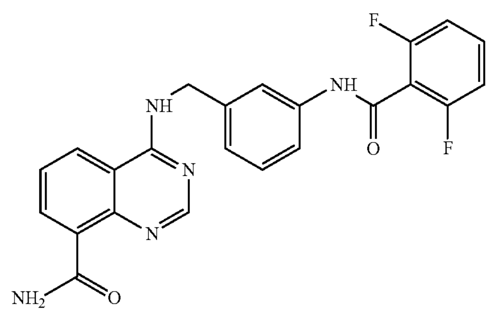 [SMILES: NC(=O)c1cccc2c(NCc3cccc(NC(=O)c4c(F)cccc4F)c3)ncnc12] |
| 676 | 442 | 0.00033 | 0.0008 | | | 4-[3-(4-Methoxy-benzoyl-amino)-4-methyl-benzyl-amino]-quinazoline-8-carboxylic acid amide | 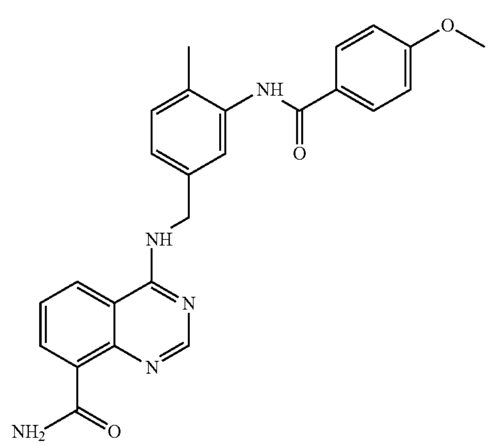 [SMILES: COc1ccc(C(=O)Nc2cc(CNc3ncnc4c(C(N)=O)cccc34)ccc2C)cc1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 677 | 469 | 0.00310 | 0.00062 | 0.5500 | | 4-{1-[3-(4-Dimethyl-amino-methyl-benzoyl-amino)-phenyl]-ethylamino}-quinazoline-8-carboxylic acid amide | 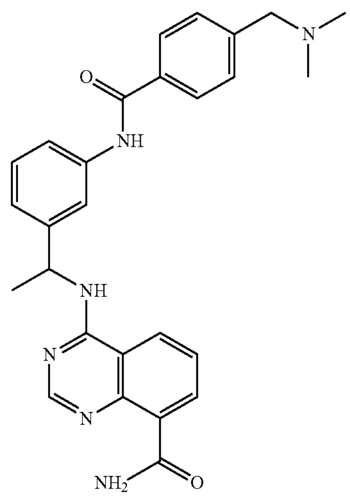 [SMILES: CC(Nc1ncnc2c(C(N)=O)cccc12)c1cccc(NC(=O)c2ccc(CN(C)C)cc2)c1] |
| 678 | 423 | 0.00780 | 0.1300 | | | 4-[3-(2-Cyano-benzoyl-amino)-benzyl-amino]-quinazoline-8-carboxylic acid amide | 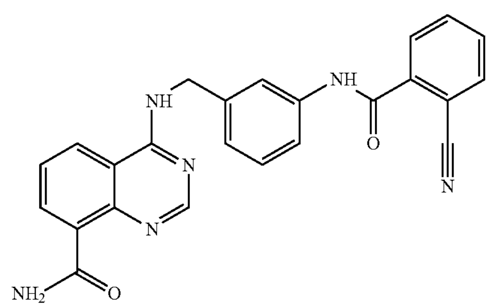 [SMILES: N#Cc1ccccc1C(=O)Nc1cccc(CNc2ncnc3c(C(N)=O)cccc23)c1] |
| 679 | 510 | 0.00730 | 0.0330 | 0.1200 | | 4-{3-[4-(4-Methyl-piperazin-1-ylmethyl)-benzoyl-amino]-benzyl-amino}-quinazoline-8-carboxylic acid amide | 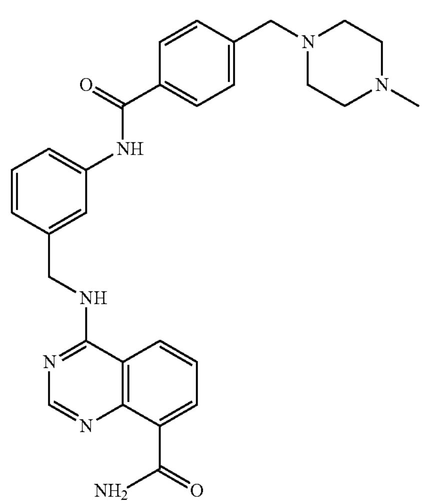 [SMILES: CN1CCN(Cc2ccc(C(=O)Nc3cccc(CNc4ncnc5c(C(N)=O)cccc45)c3)cc2)CC1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 680 | 446 | 0.00025 | | | | 6-Fluoro-4-[3-(4-methoxy-benzoyl-amino)-benzyl-amino]-quinazoline-8-carboxylic acid amide | 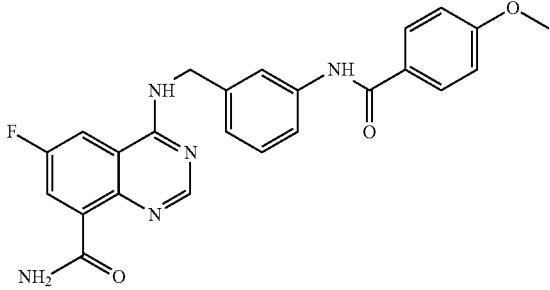 [SMILES: COc1ccc(C(=O)Nc2cccc(CNc3ncnc4c(C(N)=O)cc(F)cc34)c2)cc1] |
| 681 | 500 | 8.0000e−05 | 0.00052 | | | 4-[3-(4-Chloro-3-trifluoro-methyl-benzoyl-amino)-benzyl-amino]-quinazoline-8-carboxylic acid amide | 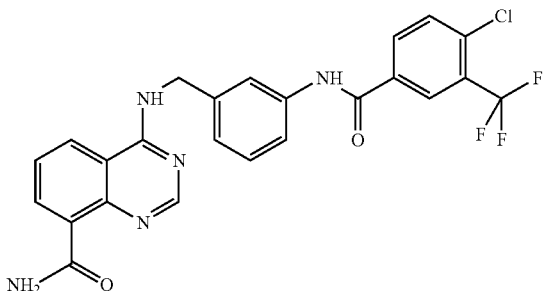 |
| 682 | 497 | 0.01200 | 0.0340 | | | 4-{3-[4-(4-Methyl-piperazin-1-yl)-benzoyl-amino]-benzyl-amino}-quinazoline-8-carboxylic acid amide | 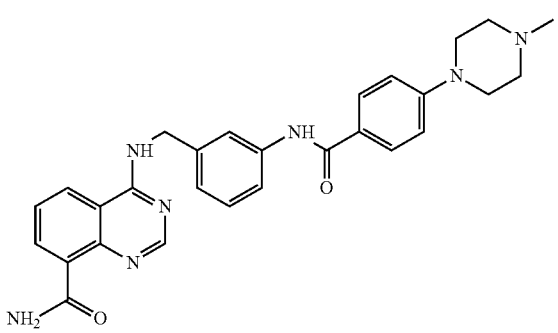 [SMILES: CN1CCN(c2ccc(C(=O)Nc3cccc(CNc4ncnc5c(C(N)=O)cccc45)c3)cc2)CC1] |
| 683 | 486 | 0.34000 | 0.0076 | 0.7800 | | 4-{(S)-3-Methoxy-1-[3-(4-methoxy-benzoyl-amino)-phenyl]-propyl-amino}-quinazoline-8-carboxylic acid amide | Chiral 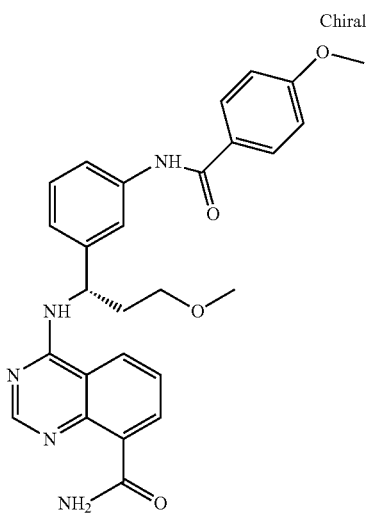 [SMILES: COCC[C@H](Nc1ncnc2c(C(N)=O)cccc12)c1cccc(NC(=O)c2ccc(OC)cc2)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 684 | 478 | 0.01100 | 0.0050 | | | 4-[3-(5-Trifluoromethyl-1H-benzoimidazol-2-ylamino)-benzylamino]-quinazoline-8-carboxylic acid amide | 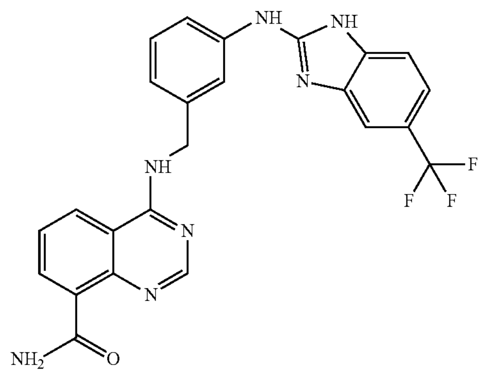 [SMILES: NC(=O)c1cccc2c(NCc3cccc(Nc4nc5cc(C(F)(F)F)ccc5[nH]4)c3)ncnc12] |
| 685 | 388 | 0.00280 | 0.0050 | | | 4-{3-[(1H-Pyrazole-3-carbonyl)-amino]-benzylamino}-quinazoline-8-carboxylic acid amide | 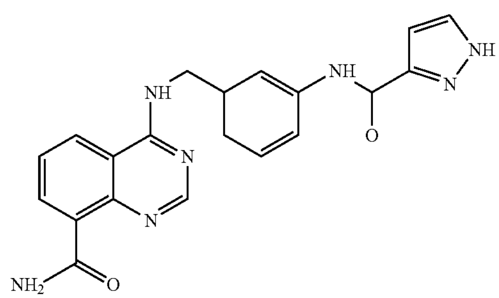 [SMILES: NC(=O)c1cccc2c(NCC3C=C(NC(O)c4cc[nH]n4)C=CC3)ncnc12] |
| 686 | 428 | 0.00023 | 8.9000e−05 | | | 4-{3-[(5-Cyclopropyl-2H-pyrazole-3-carbonyl)-amino]-benzylamino}-quinazoline-8-carboxylic acid amide | 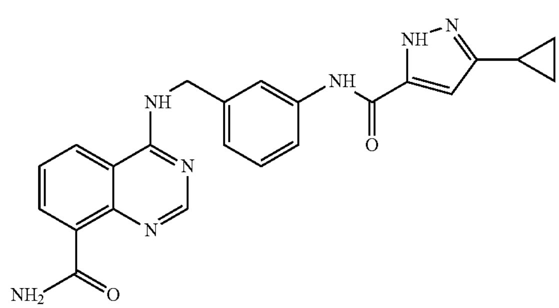 [SMILES: NC(=O)c1cccc2c(NCc3cccc(NC(=O)c4cc(C5CC5)n[nH]4)c3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 687 | 581 | 0.00120 | | | | 4-{1-[3-(2-Fluoro-4-trifluoromethyl-benzoyl-amino)-phenyl]-3-pyrrolidin-1-yl-propyl-amino}-quinazoline-8-carboxylic acid amide | 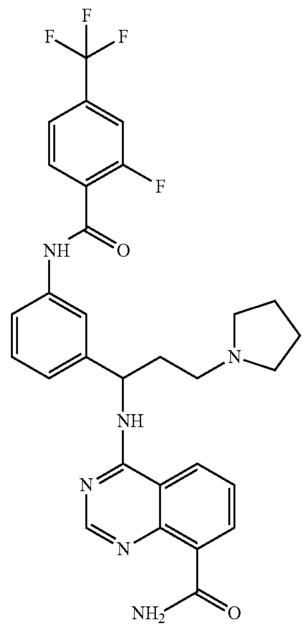 [SMILES: NC(=O)c1cccc2c(NC(CCN3CCCC3)c3cccc(NC(=O)c4ccc(C(F)(F)F)cc4F)c3)ncnc12] |
| 688 | 458 | 0.00540 | 0.0098 | | | 4-[3-(2,6-Dimethoxy-benzoyl-amino)-benzyl-amino]-quinazoline-8-carboxylic acid amide | 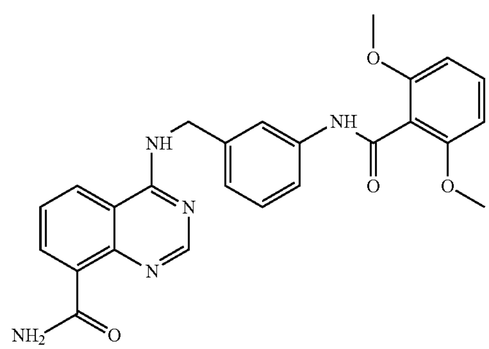 [SMILES: COc1cccc(OC)c1C(=O)Nc1cccc(CNc2ncnc3c(C(N)=O)cccc23)c1] |
| 689 | 416 | 0.00160 | 0.0020 | | | 4-[3-(2-Fluoro-benzoyl-amino)-benzyl-amino]-quinazoline-8-carboxylic acid amide | 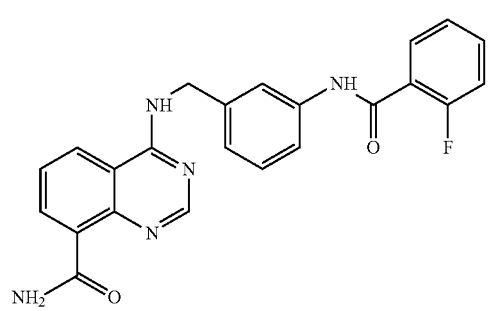 |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 690 | 474 | 0.00046 | | | | 4-{1-[3-(3-Fluoro-4-methoxy-benzoyl-amino)-phenyl]-propyl-amino}-quinazoline-8-carboxylic acid amide | 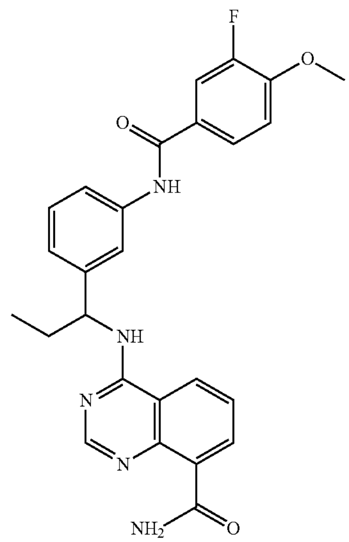 [SMILES: CCC(Nc1ncnc2c(C(N)=O)cccc12)c1cccc(NC(=O)c2ccc(OC)c(F)c2)c1] |
| 691 | 595 | 0.00039 | | | | 4-{1-[3-(2-Fluoro-5-trifluoro-methyl-benzoyl-amino)-phenyl]-3-piperidin-1-yl-propyl-amino}-quinazoline-8-carboxylic acid amide | 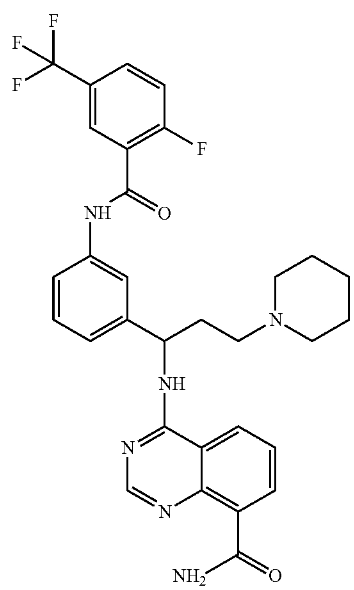 [SMILES: NC(=O)c1cccc2c(NC(CCN3CCCCC3)c3cccc(NC(=O)c4cc(C(F)(F)F)ccc4F)c3)ncnc12] |
| 692 | 308 | 0.02000 | | | 0.1200 | 4-[(R)-1-(3-Amino-phenyl)-ethylamino]-quinazoline-8-carboxylic acid amide | 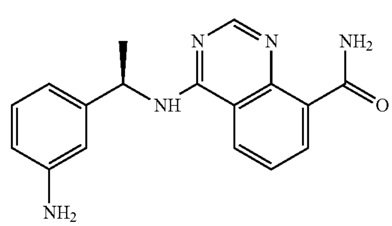 [SMILES: C[C@@H](Nc1ncnc2c(C(N)=O)cccc12)c1cccc(N)c1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 693 | 514 | 0.00018 | | 0.1500 | | 4-{(R)-1-[3-(3-Fluoro-4-trifluoro-methoxy-benzoyl-amino)-phenyl]-ethylamino}-quinazoline-8-carboxylic acid amide | Chiral 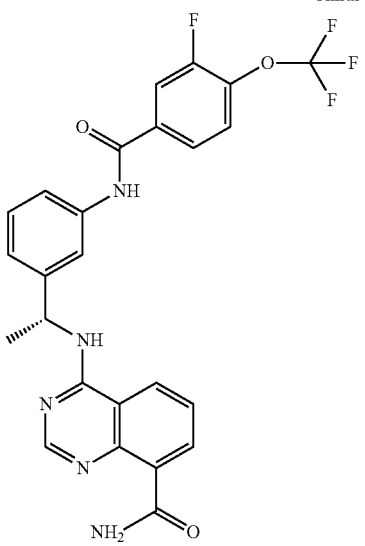 |
| 694 | 495 | 0.00400 | 0.0033 | 0.1500 | | 4-{1-[3-(4-Pyrrolidin-1-ylmethyl-benzoyl-amino)-phenyl]-ethylamino}-quinazoline-8-carboxylic acid amide | 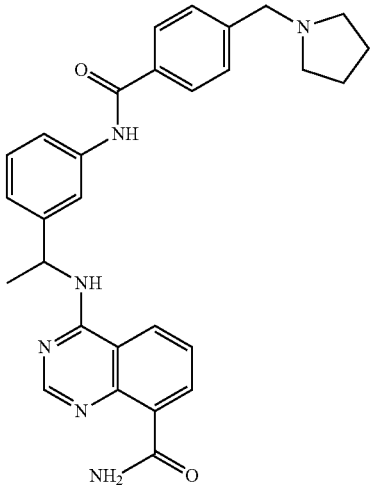 [SMILES: CC(Nc1ncnc2c(C(N)=O)cccc12)c1cccc(NC(=O)c2ccc(CN3CCCC3)cc2)c1] |
| 695 | 509 | 0.00750 | 0.0015 | 0.1900 | | 4-[1-(3-Benzoyl-amino-phenyl)-3-piperidin-1-yl-propyl-amino]-quinazoline-8-carboxylic acid amide | 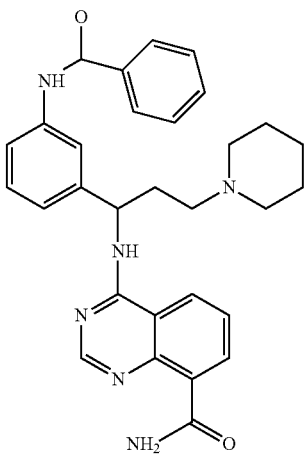 [SMILES: NC(=O)c1cccc2c(NC(CCN3CCCCC3)c3cccc(NC(O)c4ccccc4)c3)ncnc12] |

TABLE 2-continued

| No. | MS (M+1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 696 | 500 | 0.00022 | 0.0018 | 0.2000 | | 4-[4-Fluoro-3-(4-trifluoro-methoxy-benzoyl-amino)-benzyl-amino]-quinazoline-8-carboxylic acid amide | 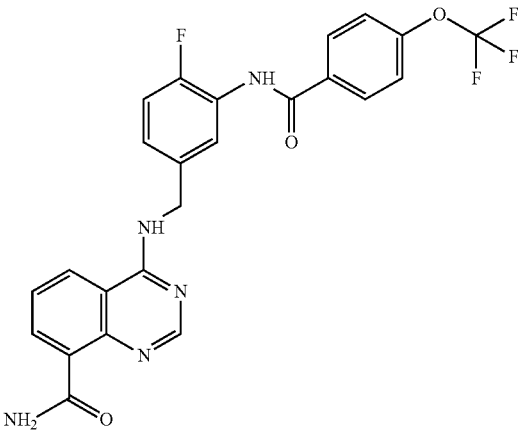 [SMILES: NC(=O)c1cccc2c(NCc3ccc(F)c(NC(=O)c4ccc(OC(F)(F)F)cc4)c3)ncnc12] |
| 697 | 525 | 0.00077 | 0.0028 | 0.2100 | | 4-{1-[3-(4-Methoxy-benzoyl-amino)-phenyl]-3-pyrrolidin-1-yl-propyl-amino}-quinazoline-8-carboxylic acid amide | 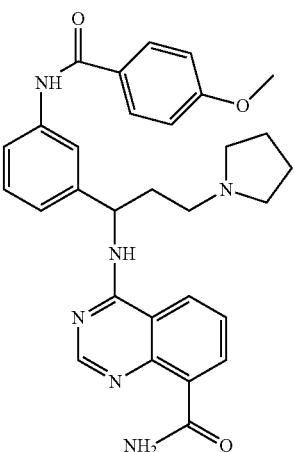 |
| 698 | 511 | 0.00590 | 0.006 | 0.2100 | | 4-{3-Azetidin-1-yl-1-[3-(4-methoxy-benzoyl-amino)-phenyl]-propyl-amino}-quinazoline-8-carboxylic acid amide | 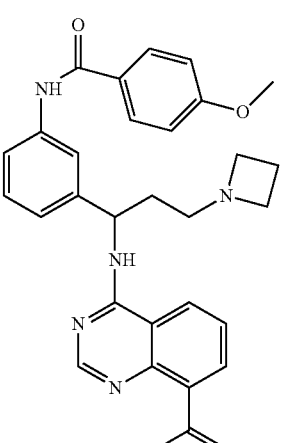 |

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 699 | 478 | 0.00083 | | 0.2300 | | 6-Fluoro-4-{1-[3-(3-fluoro-4-methoxy-benzoyl-amino)-phenyl]-ethylamino}-quinazoline-8-carboxylic acid amide | 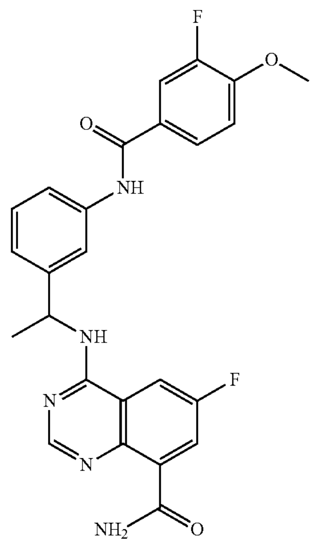 [SMILES: COc1ccc(C(=O)Nc2cccc(C(C)Nc3ncnc4c(C(N)=O)cc(F)cc34)c2)cc1F] |
| 700 | 525 | 0.00078 | | 0.2600 | | 4-{(R)-1-[3-(4-Methoxy-benzoyl-amino)-phenyl]-3-pyrrolidin-1-yl-propyl-amino}-quinazoline-8-carboxylic acid amide | Chiral |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 701 | 495 | 0.00030 | | 0.3000 | | 6-Chloro-4-{1-[3-(3-fluoro-4-methoxy-benzoyl-amino)-phenyl]-ethylamino}-quinazoline-8-carboxylic acid amide | 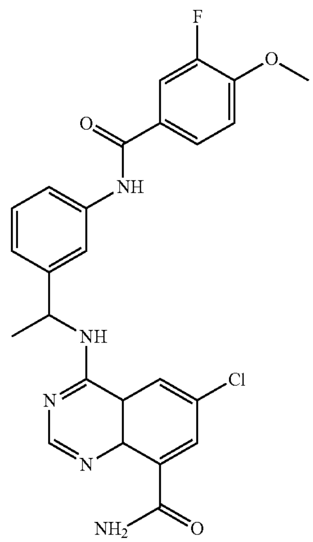 [SMILES: COc1ccc(C(=O)Nc2cccc(C(C)NC3=NC=NC4C(C(N)=O)=CC(Cl)=CC34)c2)cc1F] |
| 702 | 482 | 0.00040 | 0.00081 | 0.3300 | | 4-{3-[(3,4,5,6-Tetrahydro-2H-[1,2']bi-pyridinyl-5'-carbonyl)-amino]-benzyl-amino}-quinazoline-8-carboxylic acid amide | 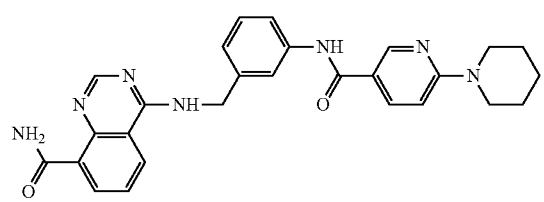 [SMILES: NC(=O)c1cccc2c(NCc3cccc(NC(=O)c4ccc(N5CCCCC5)nc4)c3)ncnc12] |
| 703 | 539 | 0.00180 | 0.0015 | 0.3400 | | 4-{1-[3-(4-Methoxy-benzoyl-amino)-phenyl]-3-piperidin-1-yl-propyl-amino}-quinazoline-8-carboxylic acid amide | 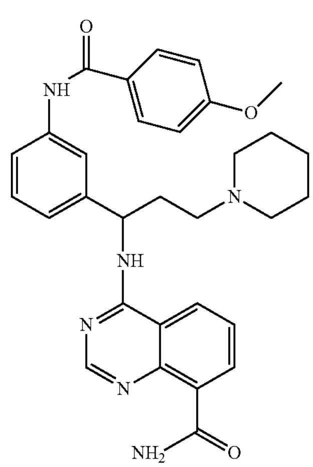 [SMILES: COc1ccc(C(=O)Nc2cccc(C(CCN3CCCCC3)Nc3ncnc4c(C(N)=O)cccc34)c2)cc1] |

TABLE 2-continued

| No. | MS (M+ 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 704 | 539 | 0.00033 | | | 0.3600 | 4-{(R)-1-[3-(4-Methoxy-benzoyl-amino)-phenyl]-3-piperidin-1-yl-propyl-amino}-quinazoline-8-carboxylic acid amide | Chiral 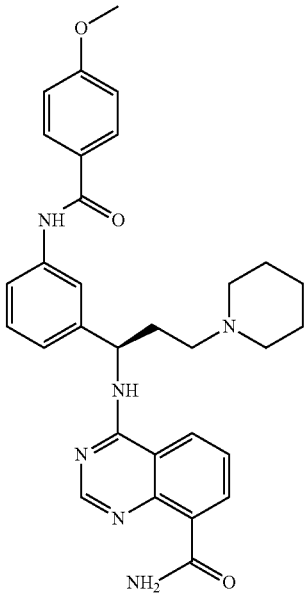 |
| 705 | 555 | 0.00780 | | | 0.9100 | 6-(2-Dimethyl-amino-ethoxy)-4-{3-[(2-pyrrolidin-1-yl-pyridine-4-carbonyl)-amino]-benzyl-amino}-quinazoline-8-carboxylic acid amide | 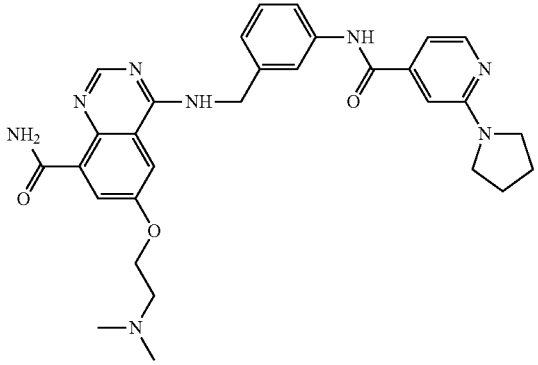 [SMILES: CN(C)CCOc1cc(C(N)=O)c2ncnc(NCc3cccc(NC(=O)c4ccnc(N5CCCC5)c4)c3)c2c1] |
| 706 | 529 | 0.00110 | | 0.0053 | 1 | 6-(3-Dimethyl-amino-propoxy)-4-[3-(4-methoxy-benzoyl-amino)-benzyl-amino]-quinazoline-8-carboxylic acid amide | 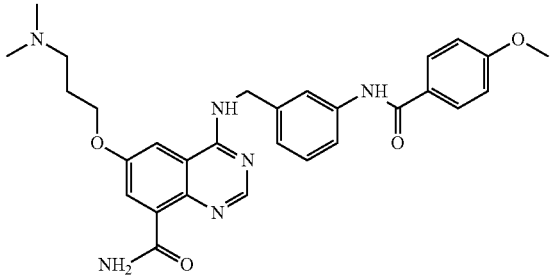 |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 707 | 597 | 0.01200 | | | 1 | 6-(2-Morpholin-4-yl-ethoxy)-4-{3-[(2-pyrrolidin-1-yl-pyridine-4-carbonyl)-amino]-benzyl-amino}-quinazoline-8-carboxylic acid amide | 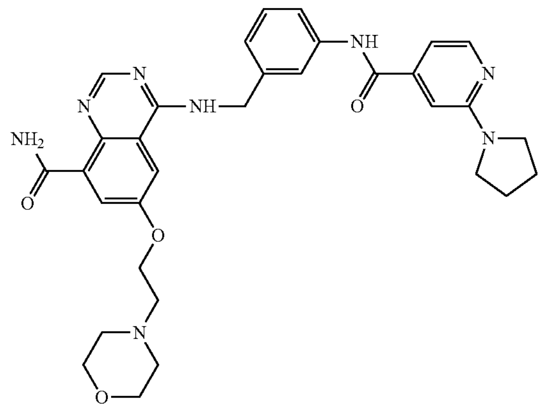 [SMILES: NC(=O)c1cc(OCCN2CCOCC2)cc2c(NCc3cccc(NC(=O)c4ccnc(N5CCCC5)c4)c3)ncnc12] |
| 708 | 474 | 0.01200 | | | 1 | 4-{(R)-1-[3-(3-Fluoro-4-methoxy-benzoyl-amino)-phenyl]-propyl-amino}-quinazoline-8-carboxylic acid amide | Chiral |
| 709 | 474 | 0.00240 | | | 1 | 4-{1-[3-(3-Fluoro-4-methoxy-benzoyl-amino)-phenyl]-ethylamino}-6-methyl-quinazoline-8-carboxylic acid amide | 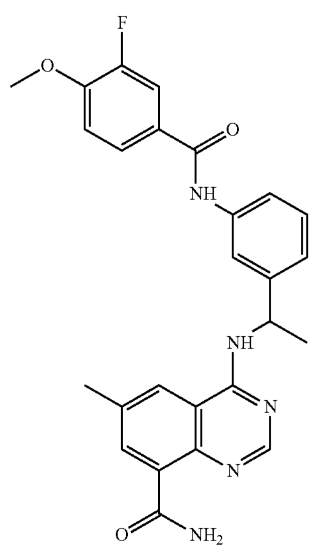 [SMILES: COc1ccc(C(=O)Nc2cccc(C(C)Nc3ncnc4c(C(N)=O)cc(C)cc34)c2)cc1F] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 710 | 514 | 0.00380 | | | 10 | {3-[1-(6-Benzyloxy-8-carbamoyl-quinazolin-4-ylamino)-ethyl]-phenyl}-carbamic acid tert-butyl ester |
| 711 | 574 | 0.02400 | 0.4000 | | 10 | 6-Benzyloxy-4-{3-[(2-pyrrolidin-1-yl-pyridine-4-carbonyl)-amino]-benzyl-amino}-quinazoline-8-carboxylic acid amide |
| 712 | 521 | 0.00055 | | | mM | 4-{1-[3-(4-Bromo-benzoyl-amino)-phenyl]-2-methoxy-ethylamino}-quinazoline-8-carboxylic acid amide |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 713 | 446 | 1.0000e−05 | | | | 4-{(R)-1-[3-(4-Fluoro-3-hydroxy-benzoyl-amino)-phenyl]-ethylamino}-quinazoline-8-carboxylic acid amide | 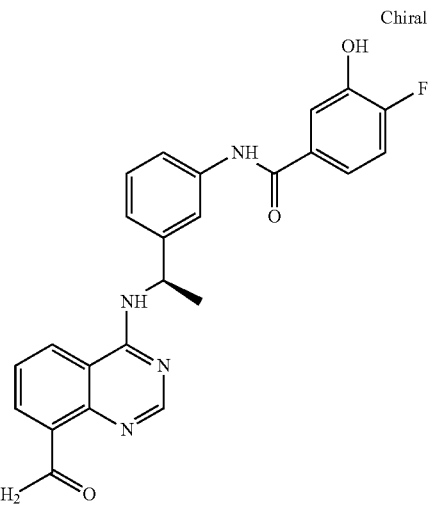 Chiral |
| 714 | 468 | 8.0000e−05 | | | | 4-[3-(4-Chloro-2,6-difluoro-benzoyl-amino)-benzyl-amino]-quinazoline-8-carboxylic acid amide | 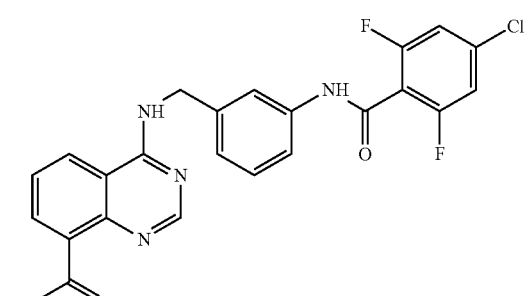 |
| 715 | 464 | 0.00011 | 0.00022 | | | 4-[3-(2,6-Difluoro-4-methoxy-benzoyl-amino)-benzyl-amino]-quinazoline-8-carboxylic acid amide | 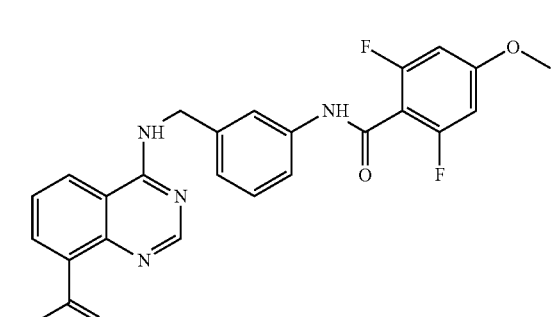 |
| 716 | 444 | 0.00012 | 0.0006 | | | 6-Hydroxy-4-[3-(4-methoxy-benzoyl-amino)-benzyl-amino]-quinazoline-8-carboxylic acid amide | 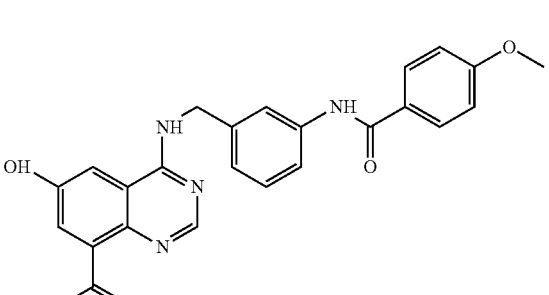 |

TABLE 2-continued

| MS No. | MS (M + 1) | Aurora A binding, IC50 [μM] | Aurora B binding, IC50 [μM] | p70S6K binding, IC50 [μM] | PDK1 binding, IC50 [μM] | Chemical Name |
|---|---|---|---|---|---|---|
| 717 | 466 | 0.00018 | 0.00068 | | | 4-[3-(4-Trifluoro-methyl-benzoyl-amino)-benzyl-amino]-quinazoline-8-carboxylic acid amide |
| 718 | 466 | 0.00022 | 0.00380 | | | 4-[3-(2-Trifluoro-methyl-benzoyl-amino)-benzyl-amino]-quinazoline-8-carboxylic acid amide |
| 719 | 485 | 0.00026 | | | | 6-Cyano-4-{1-[3-(3-fluoro-4-methoxy-benzoyl-amino)-phenyl]-ethylamino}-quinazoline-8-carboxylic acid amide |
| 720 | 354 | | | 0.5900 | 0.04400 | 4-((S)-Piperidin-3-ylamino)-6-thiophen-3-yl-quinazoline-8-carboxylic acid amide |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 721 | 354 | | | 0.7000 | 0.06000 | 4-((S)-Piperidin-3-ylamino)-6-thiophen-2-yl-quinazoline-8-carboxylic acid amide | 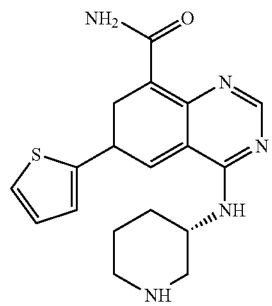 |
| 722 | 378 | | | 0.9100 | 0.06200 | 6-(4-Methoxy-phenyl)-4-((S)-piperidin-3-ylamino)-quinazoline-8-carboxylic acid amide | 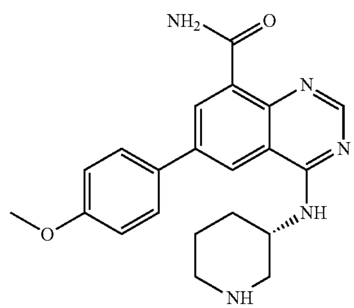 |
| 723 | 352 | | | 0.3700 | 0.09400 | 6-(1-Methyl-1H-pyrazol-4-yl)-4-((S)-piperidin-3-ylamino)-quinazoline-8-carboxylic acid amide | 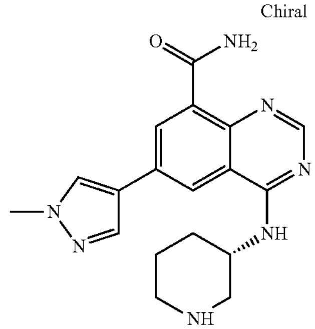 [SMILES: Cn1cc(-c2cc(C(N)=O)c3ncnc(N[C@H]4CCCNC4)c3c2)cn1] |
| 724 | 428 | | | 0.1700 | 0.09800 | 6-(6-Methoxy-naphthalen-2-yl)-4-((S)-piperidin-3-ylamino)-quinazoline-8-carboxylic acid amide | 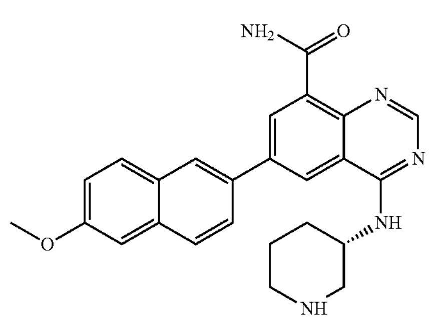 [SMILES: COc1ccc2cc(-c3cc(C(N)=O)c4ncnc(N[C@H]5CCCNC5)c4c3)ccc2c1] |

TABLE 2-continued

| No. | MS (M + 1) | Aurora A binding, IC50 [µM] | Aurora B binding, IC50 [µM] | p70S6K binding, IC50 [µM] | PDK1 binding, IC50 [µM] | Chemical Name | Structure |
|---|---|---|---|---|---|---|---|
| 725 | 432 | | | 0.5300 | 0.10000 | 4-((S)-Piperidin-3-ylamino)-6-(4-trifluoromethoxyphenyl)-quinazoline-8-carboxylic acid amide | 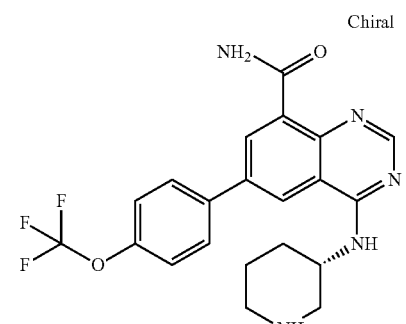 Chiral |
| 726 | 416 | | | 1 | 0.11000 | 4-((S)-Piperidin-3-ylamino)-6-(4-trifluoromethylphenyl)-quinazoline-8-carboxylic acid amide | 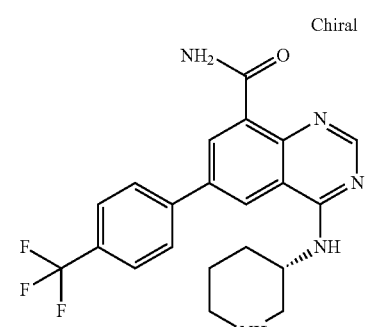 Chiral |
| 727 | 380 | 0.12000 | 0.0180 | 0.3500 | 0.16000 | 6-(1-Isopropyl-1H-pyrazol-4-yl)-4-((S)-piperidin-3-ylamino)-quinazoline-8-carboxylic acid amide | 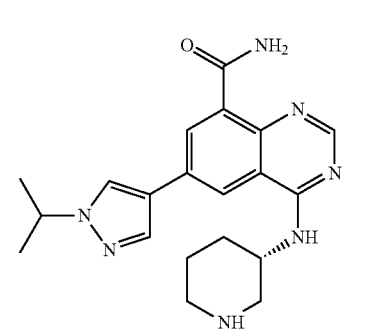 [SMILES: CC(C)n1cc(-c2cc(C(N)=O)c3ncnc(N[C@H]4CCCNC4)c3c2)cn1] |
| 728 | 391 | 0.64000 | 0.1600 | 0.8800 | 0.20000 | 6-(4-Carbamoylphenyl)-4-((S)-piperidin-3-ylamino)-quinazoline-8-carboxylic acid amide | 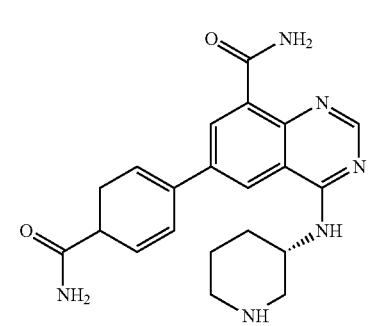 [SMILES: NC(=O)c1cc(C2=CCC(C(N)=O)C=C2)cc2c(N[C@H]3CCCNC3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 729 | 373 | | | 1 | 0.34000 | 6-(4-cyano-phenyl)-4-[(3S)-piperidin-3-ylamino]-quinazoline-8-carboxamide | 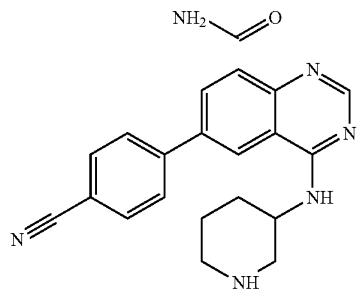 |
| 730 | 391 | 0.74000 | 0.1100 | 10 | 0.39000 | 6-(3-Carbamoyl-phenyl)-4-((S)-piperidin-3-ylamino)-quinazoline-8-carboxylic acid amide | 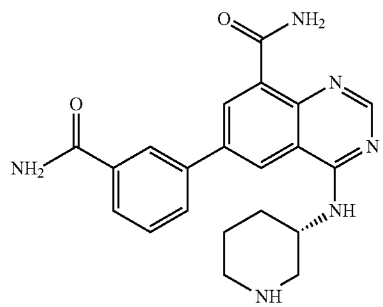 [SMILES: NC(=O)c1cccc(-c2cc(C(N)=O)c3ncnc(N[C@H]4CCCNC4)c3c2)c1] |
| 731 | 348 | | | 0.9000 | 0.51000 | 6-Phenyl-4-((S)-piperidin-3-ylamino)-quinazoline-8-carboxylic acid amide | 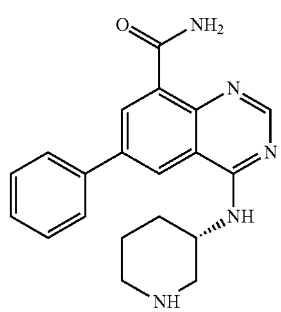 |
| 732 | 415 | | | 0.9750 | 0.52000 | 6-(3,4-dichloro-phenyl)-4-[(3S)-piperidin-3-ylamino]-quinazoline-8-carboxamide | 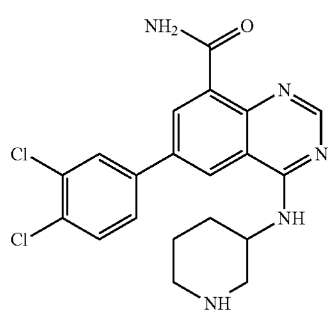 [SMILES: NC(=O)c1cc(-c2ccc(Cl)c(Cl)c2)cc2c(NC3CCCNC3)ncnc12] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 733 | 339 | | | 1 | 0.61000 | 6-isoxazol-4-yl-4-[(3S)-piperidin-3-ylamino]-quinazoline-8-carboxamide | 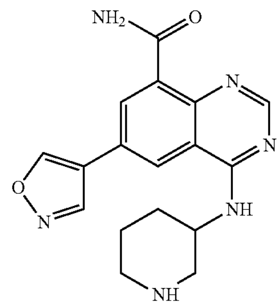 [SMILES: NC(=O)c1cc(-c2cnoc2)cc2c(NC3CCCNC3)ncnc12] |
| 734 | 391 | | | 0.8900 | 0.75000 | 4-[1-(3-Fluoro-phenyl)-ethylamino]-6-(1-methyl-1H-pyrazol-4-yl)-quinazoline-8-carboxylic acid amide | 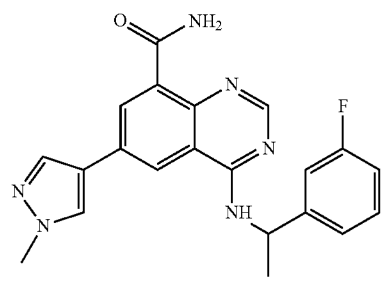 [SMILES: CC(Nc1ncnc2c(C(N)=O)cc(-c3cnn(C)c3)cc12)c1cccc(F)c1] |
| 735 | 373 | | | 0.3900 | 0.79000 | 4-((S)-Piperidin-3-ylamino)-6-((E)-styryl)-quinazoline-8-carboxylic acid amide | 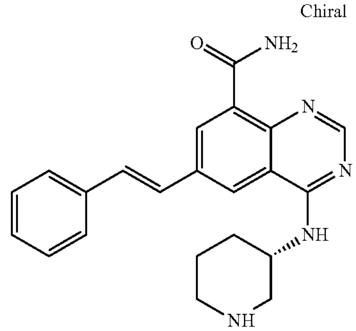 [SMILES: NC(=O)c1cc(/C=C/c2ccccc2)cc2c(N[C@H]3CCCNC3)ncnc12] |
| 736 | 377 | | | 0.5100 | 0.80000 | 4-(3-Fluoro-benzyl-amino)-6-(1-methyl-1H-pyrazol-4-yl)-quinazoline-8-carboxylic acid amide | 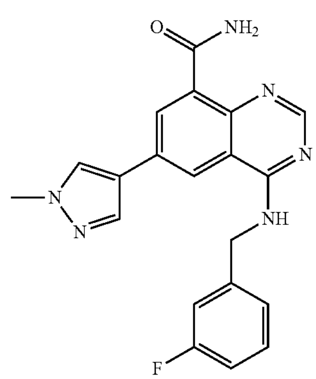 [SMILES: Cn1cc(-c2cc(C(N)=O)c3ncnc(NCc4cccc(F)c4)c3c2)cn1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 737 | 405 | | | 0.3800 | 1.1000 | 4-[1-(3-Fluoro-phenyl)-propyl-amino]-6-(1-methyl-1H-pyrazol-4-yl)-quinazoline-8-carboxylic acid amide | 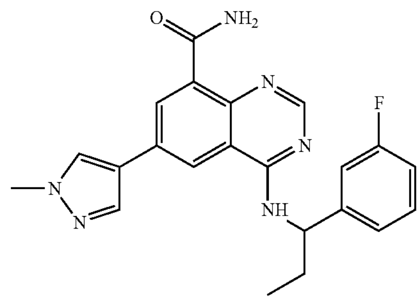 [SMILES: CCC(Nc1ncnc2c(C(N)=O)cc(-c3cnn(C)c3)cc12)c1cccc(F)c1] |
| 738 | 386 | | | | 0.0002 | 4-[(S)-1-(3-Chloro-phenyl)-2-methyl amino-ethylamino]-6-methoxy-quinazoline-8-carboxylic acid amide | 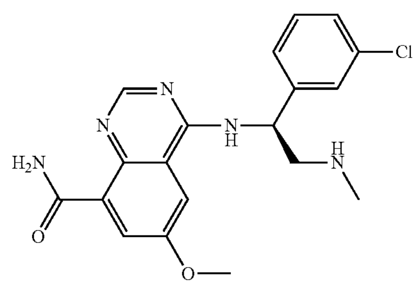 [SMILES: CNC[C@@H](Nc1ncnc2c(C(N)=O)cc(OC)cc12)c1cccc(Cl)c1] |
| 739 | 340 | | | | 0.0006 | 4-[(S)-1-(3-Fluoro-phenyl)-2-methyl amino-ethylamino]-quinazoline-8-carboxylic acid amide | 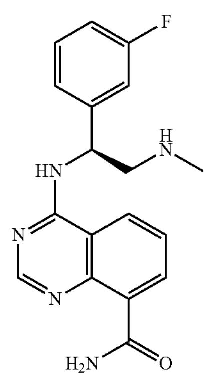 [SMILES: CNC[C@@H](Nc1ncnc2c(C(N)=O)cccc12)c1cccc(F)c1] |
| 742 | 307 | | | | 0.0140 | 4-((S)-2-Amino-1-phenyl-ethylamino)-quinoline-8-carboxylic acid amide | 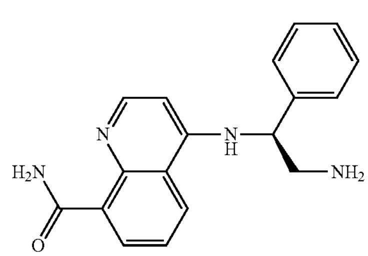 [SMILES: NC[C@@H](Nc1ccnc2c(C(N)=O)cccc12)c1ccccc1] |

TABLE 2-continued

| No. | MS (M + 1) | Aurora A binding, IC50 [μM] | Aurora B binding, IC50 [μM] | p70S6K binding, IC50 [μM] | PDK1 binding, IC50 [μM] | Chemical Name | Structure |
|---|---|---|---|---|---|---|---|
| 743 | 442 | 0.649 | | | | 4-{3-[(4-Methoxy-benzoyl)-methyl-amino]-benzyl-amino}-quinazoline-8-carboxylic acid amide | 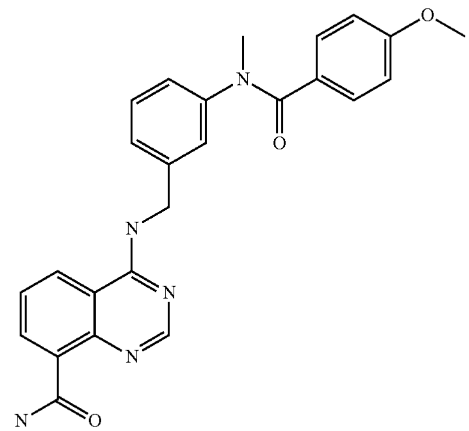 [SMILES: COc1ccc(C(=O)N(C)c2cccc(CNc3ncnc4c(C(N)=O)cccc34)c2)cc1] |
| 744 | 541 | 0.011 | | | | 4-(1-{3-[(5-Cyclo-propyl-2H-pyrazole-3-carbonyl)-amino]-phenyl}-3-morpholin-4-yl-propyl-amino)-quinazoline-8-carboxylic acid amid | 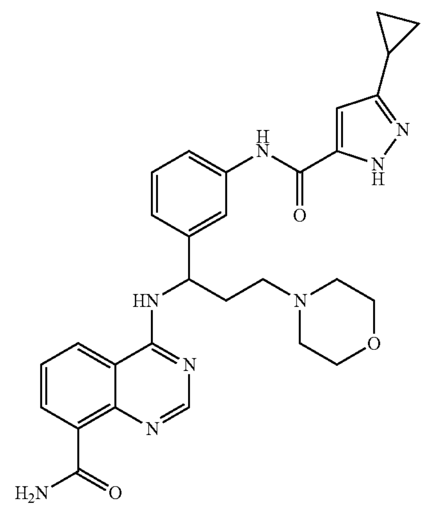 [SMILES: NC(=O)c1cccc2c(NC(CCN3CCOCC3)c3cccc(NC(=O)c4cc(C5CC5)n[nH]4)c3)ncnc12] |

The compound numbers 191, 192, 198, 200, 203, 218, 220, 226, 227, 232, 260, 289, 290, 311, 318, 327, 328, 346, 354, 378, 393, 402, 407, 410, 413, 417, 439, 451, 455, 460, 468, 479, 480, 481, 504, 509, 513, 522, 523, 533, 534, 536, 740 and 741 were omitted intentionally from Table 2.

TABLE 3

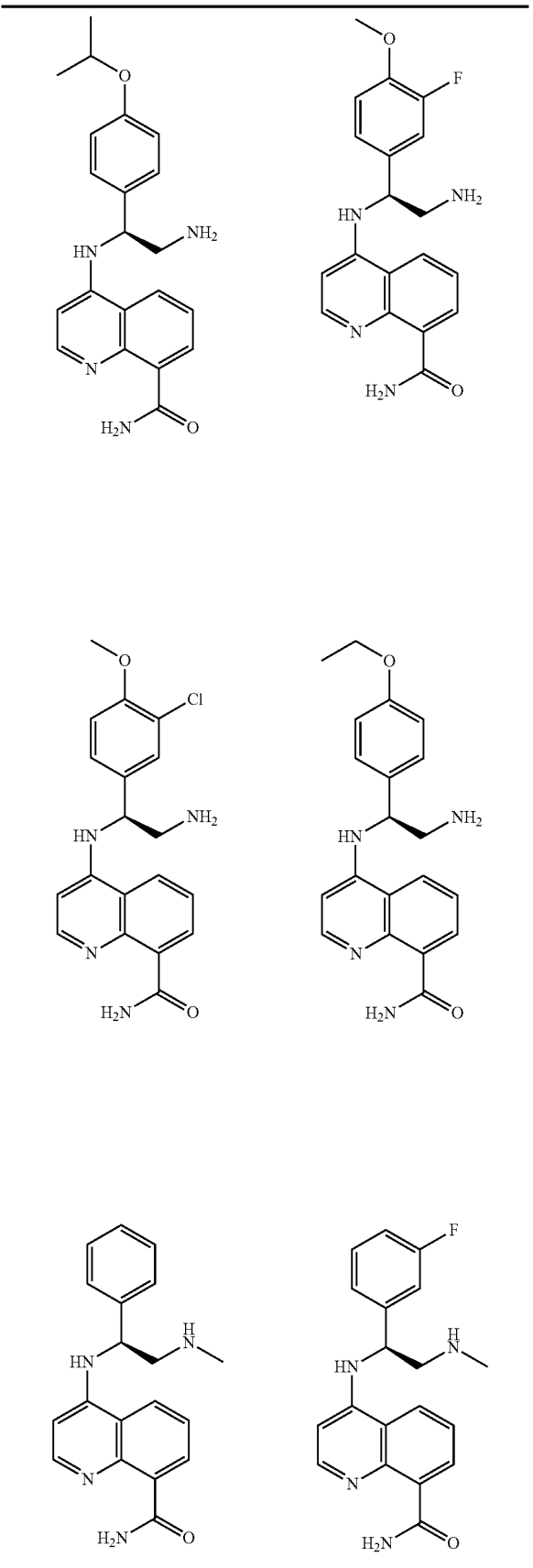

TABLE 3-continued
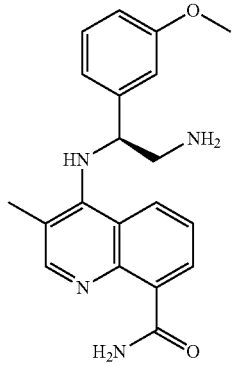
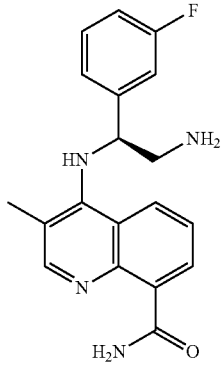 [SMILES: Cc1cnc2c(C(N)=O)cccc2c1N[C@H](CN)c1cccc(F)c1]
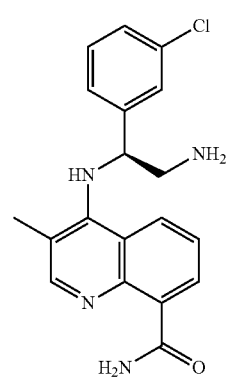 [SMILES: Cc1cnc2c(C(N)=O)cccc2c1N[C@H](CN)c1cccc(Cl)c1]
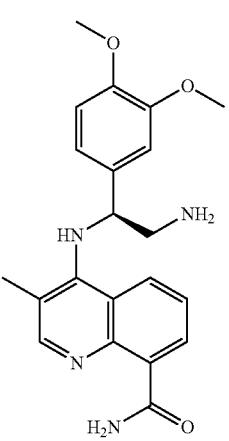
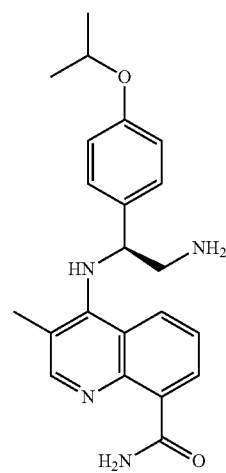 [SMILES: Cc1cnc2c(C(N)=O)cccc2c1N[C@H](CN)c1ccc(OC(C)C)cc1]
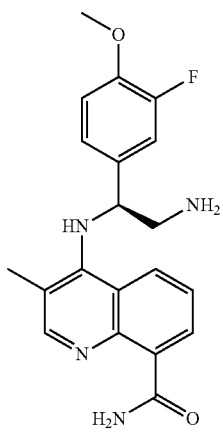 [SMILES: COc1ccc([C@@H](CN)Nc2c(C)cnc3c(C(N)=O)cccc23)cc1F]
TABLE 3-continued
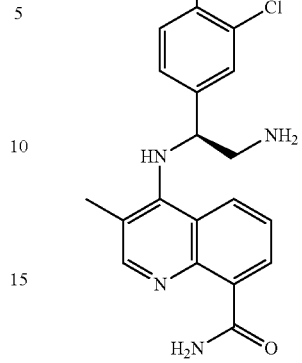
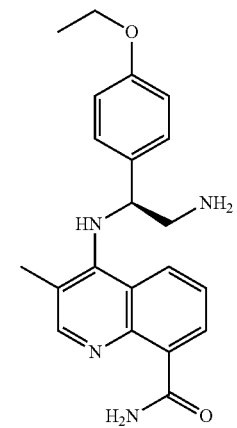 [SMILES: CCOc1ccc([C@@H](CN)Nc2c(C)cnc3c(C(N)=O)cccc23)cc1]
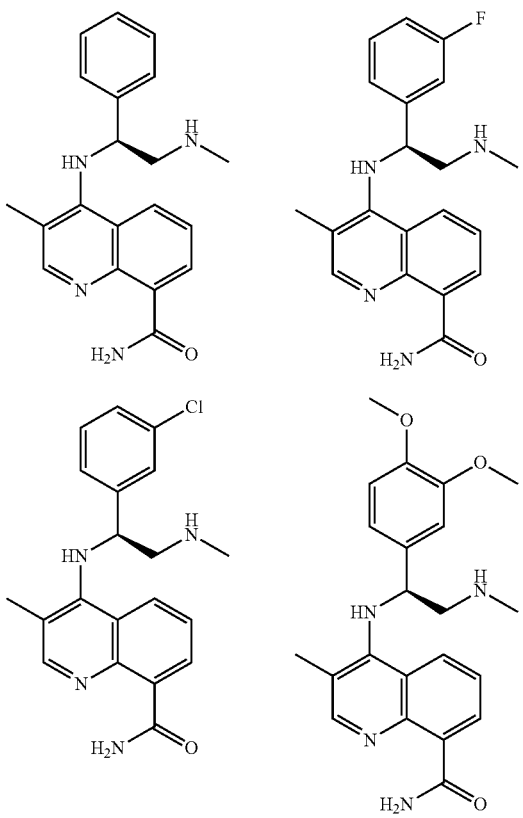
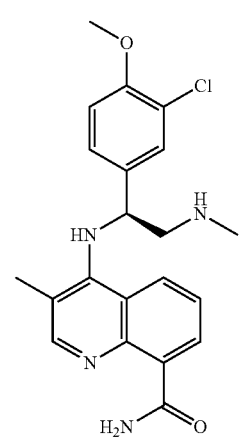

TABLE 3-continued
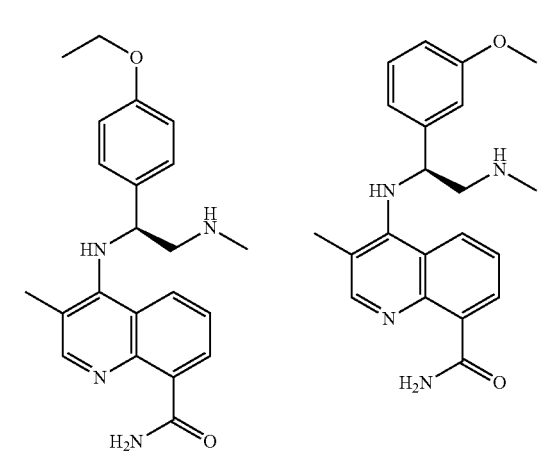
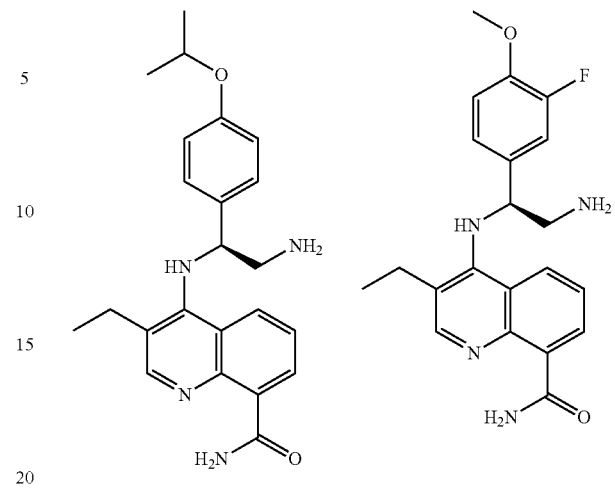
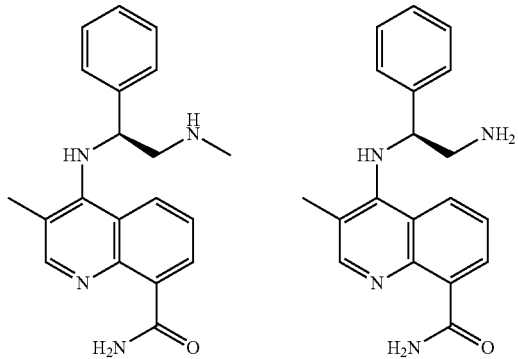
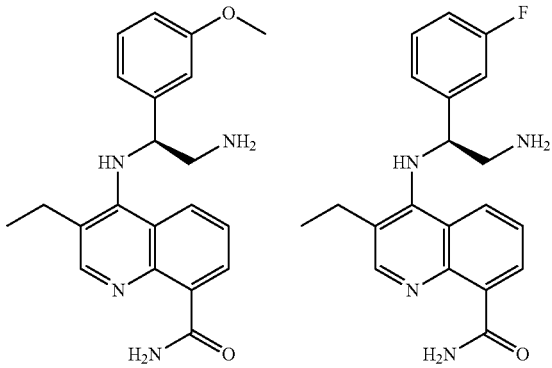
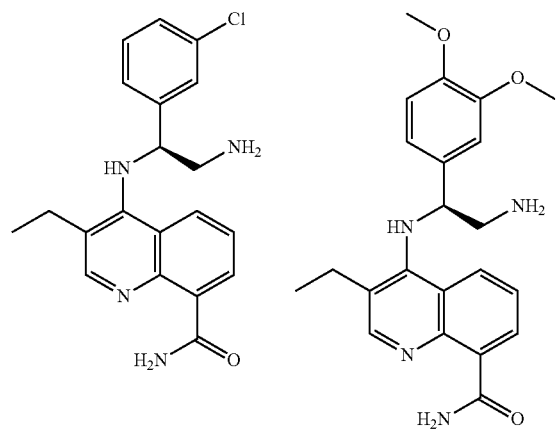
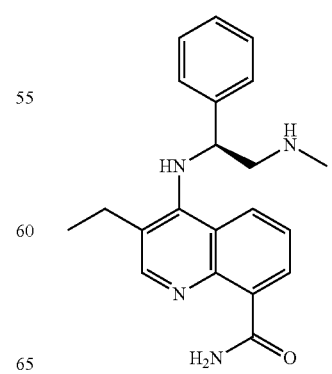

TABLE 3-continued
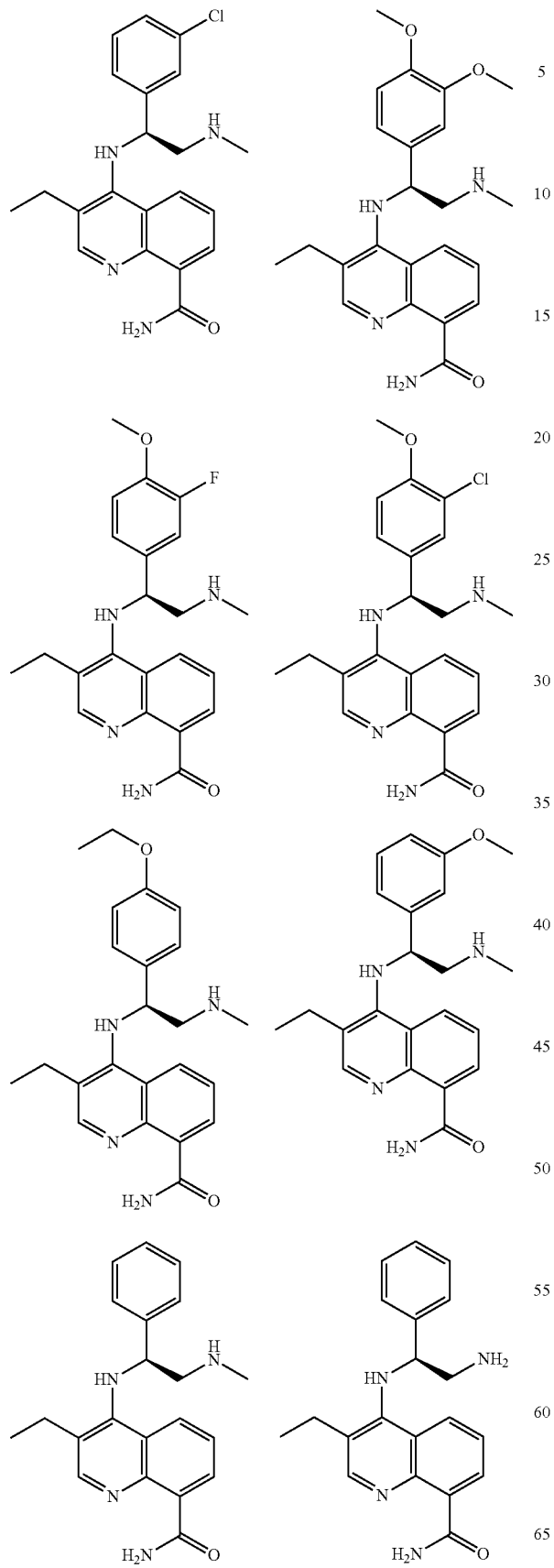
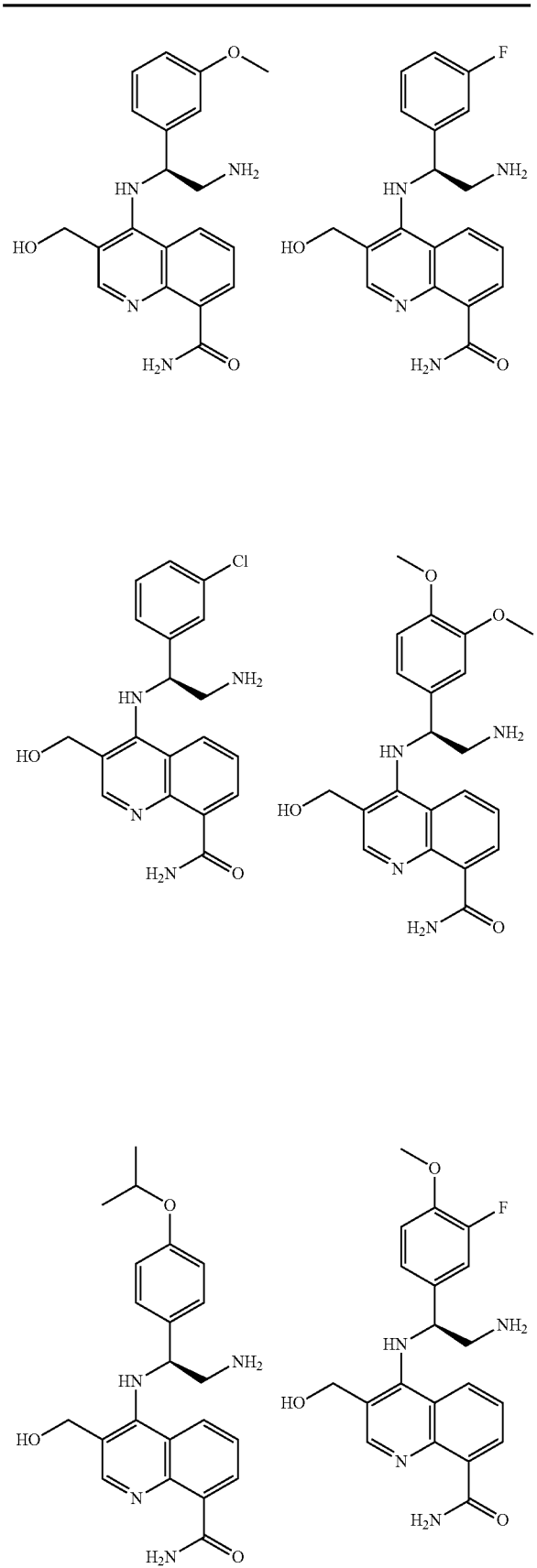

477
TABLE 3-continued
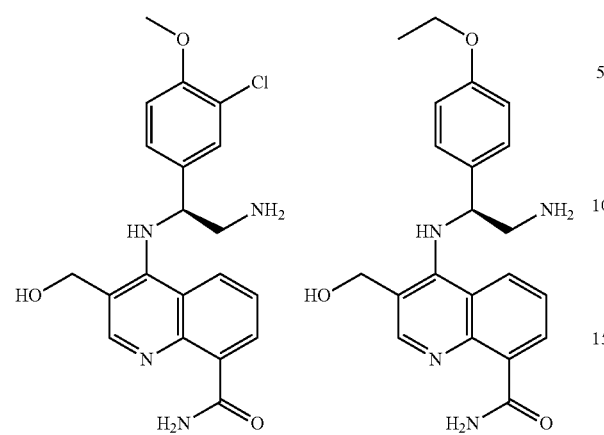
478
TABLE 3-continued
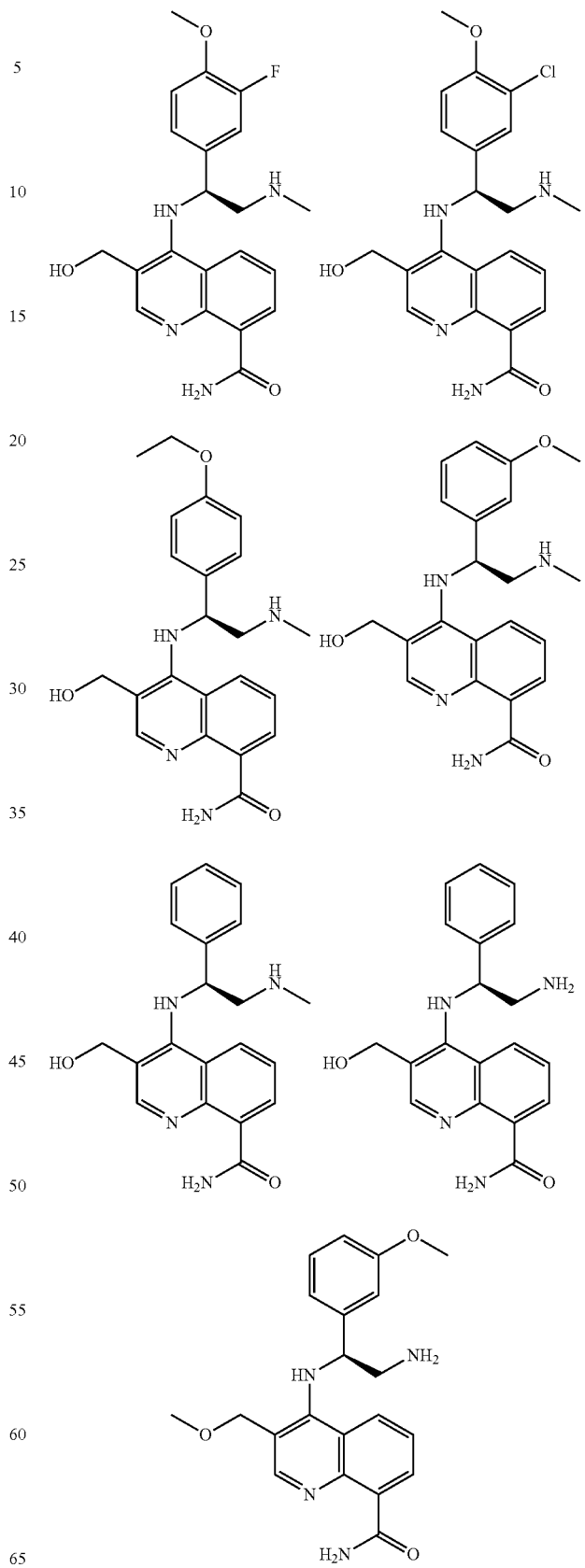

TABLE 3-continued
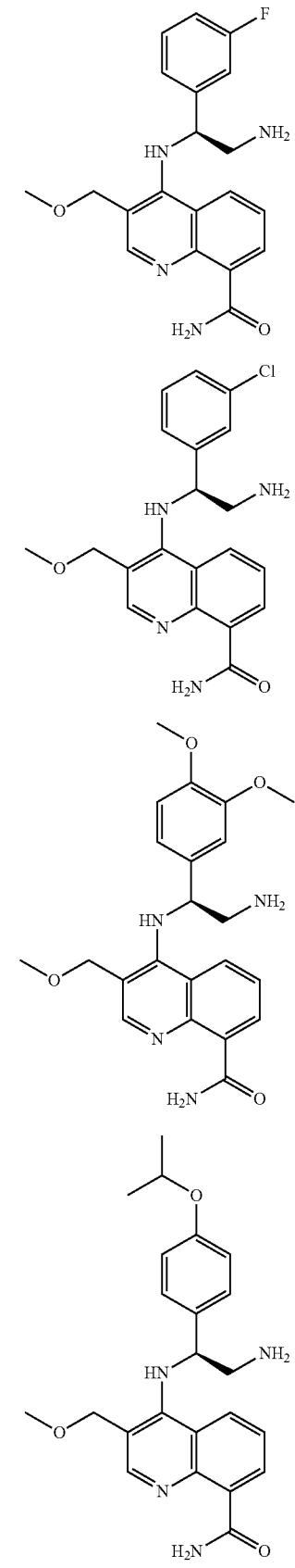
TABLE 3-continued
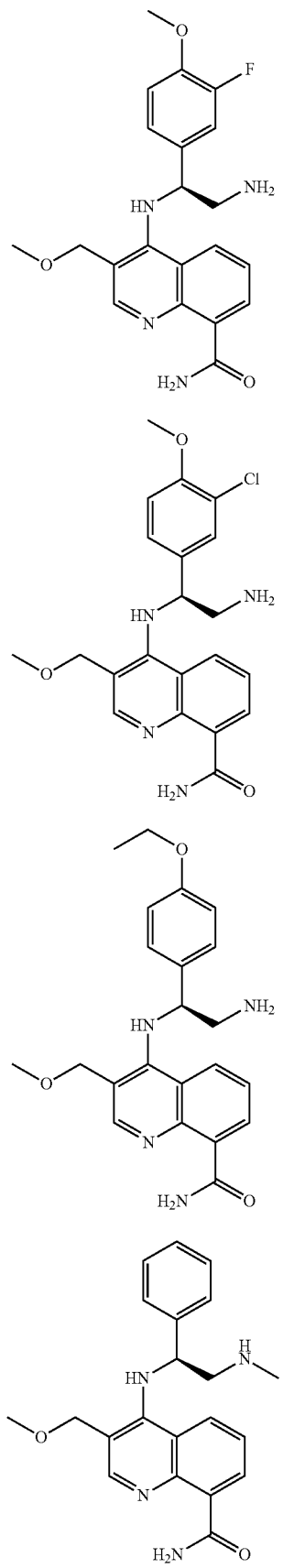

TABLE 3-continued
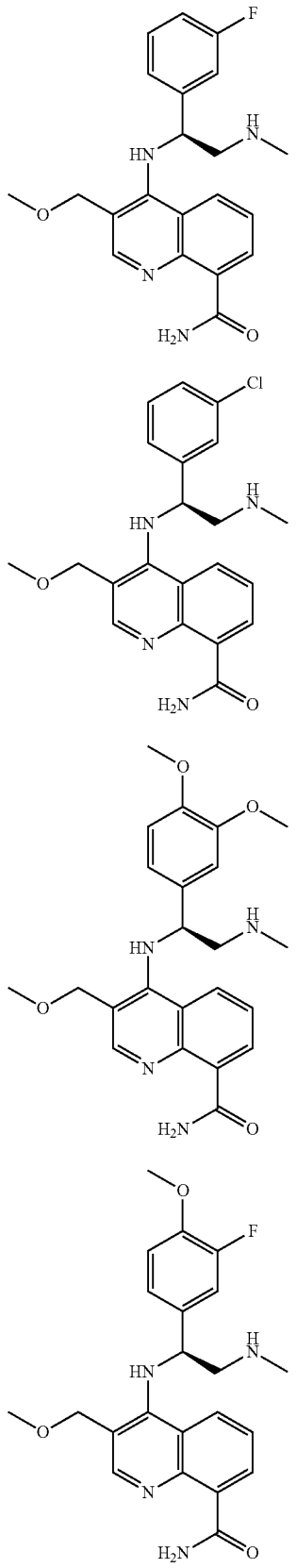
TABLE 3-continued
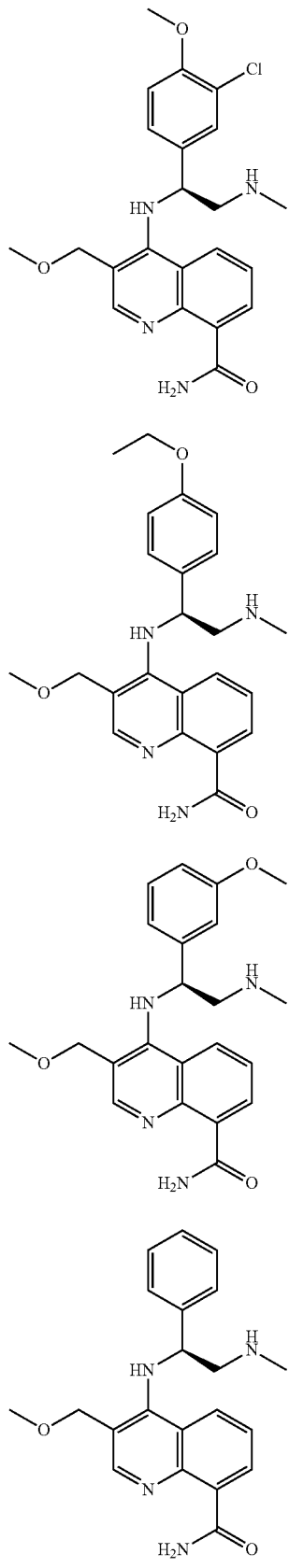

TABLE 3-continued
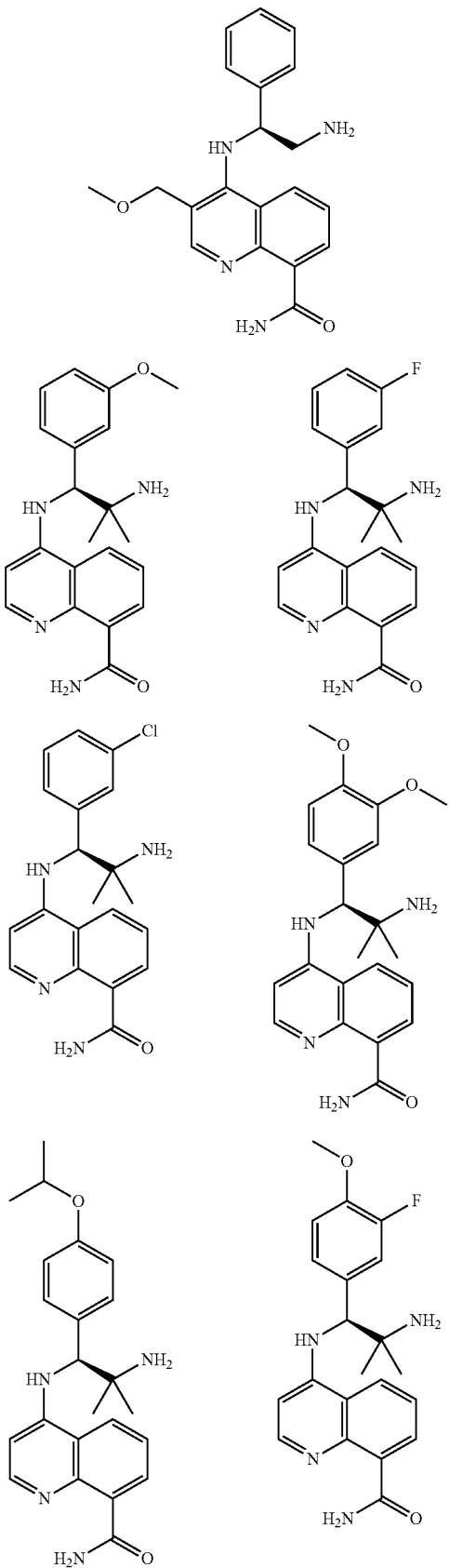
TABLE 3-continued
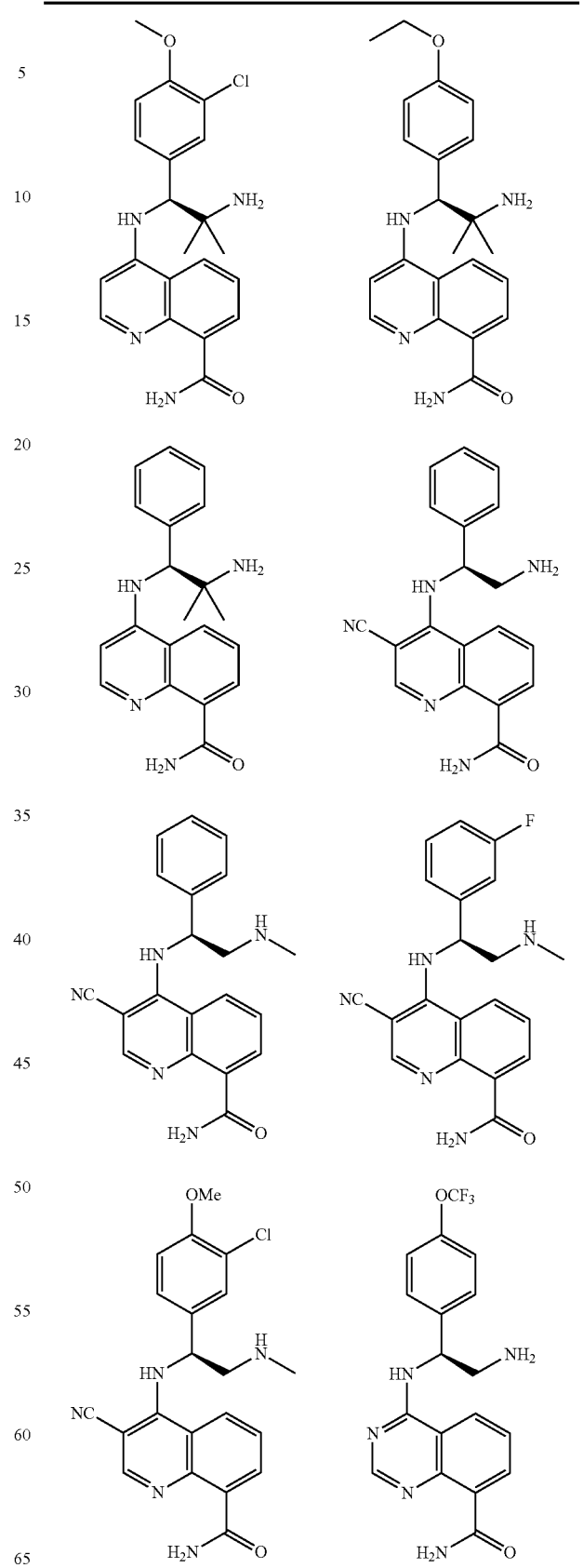

TABLE 3-continued
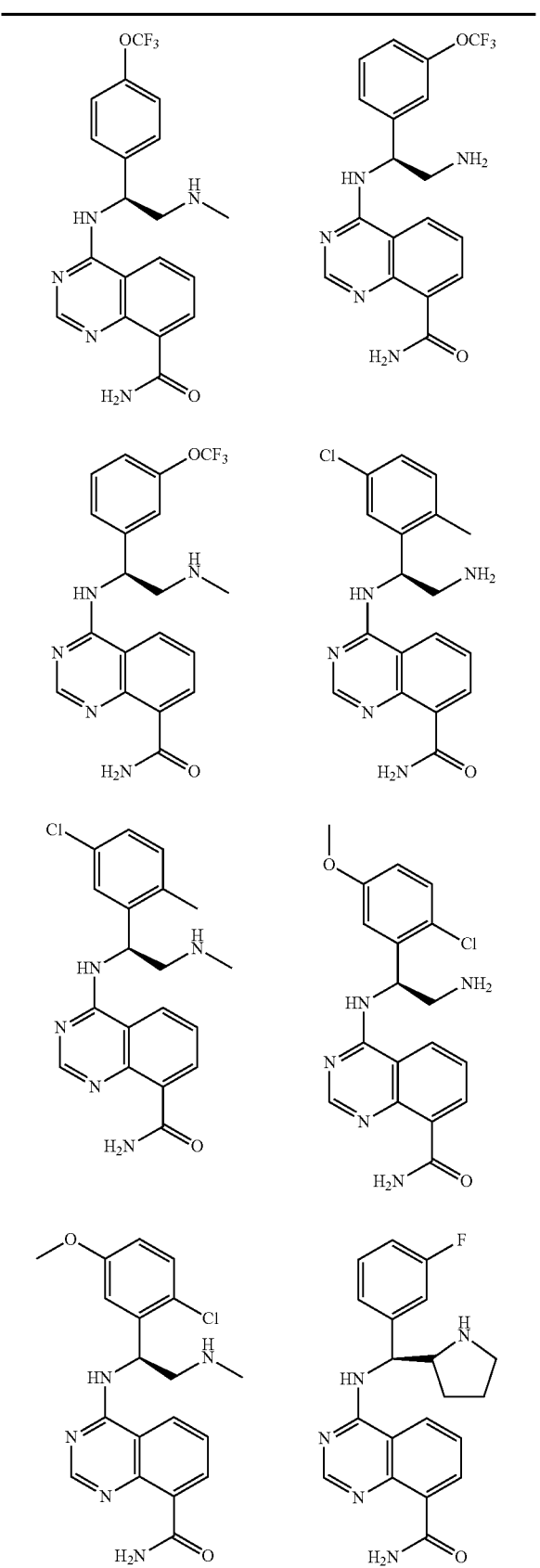
TABLE 3-continued
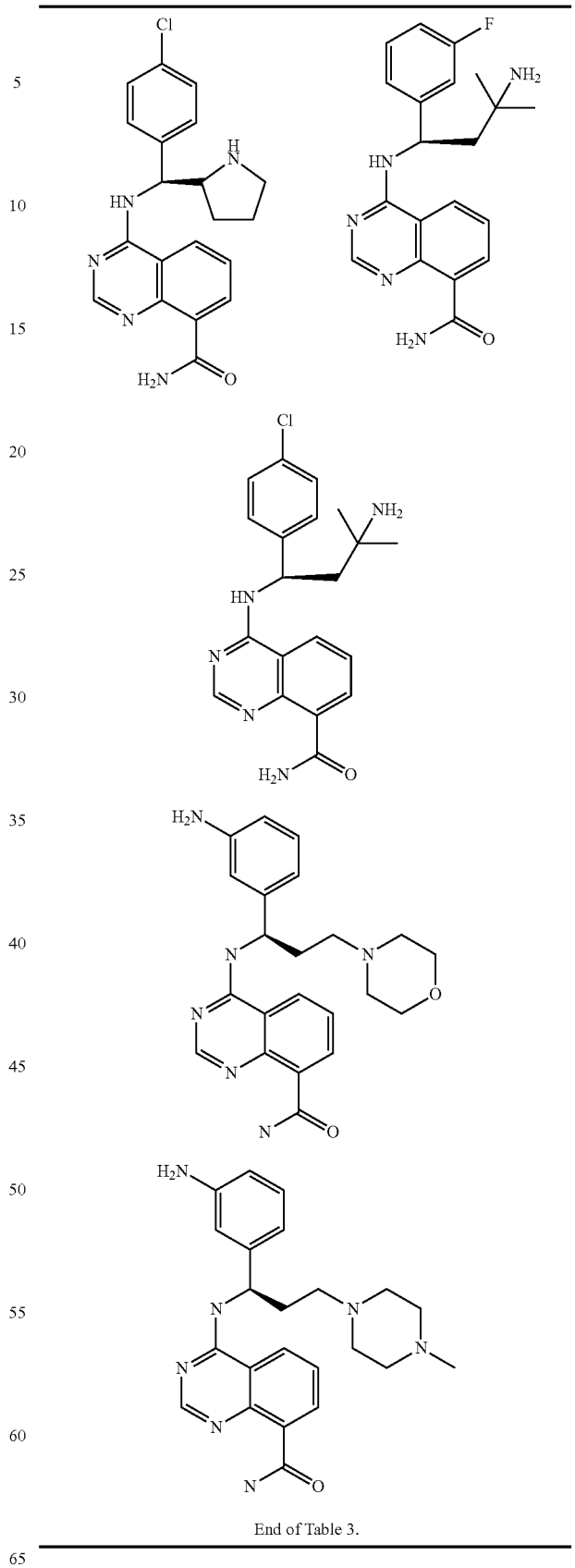
End of Table 3.
The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like.

If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt or a solvate, or a solvate of a salt. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and sclerodema, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab.

In yet another embodiment the anti-cancer therapeutic is an inhibitor of another protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective in sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of
a) an effective amount of a compound according to the invention or a physiologically acceptable salt, solvate or prodrug thereof, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

EXPERIMENTAL SECTION

Some abbreviations that may appear in this application are as follows:
Abbreviations

| Designation | |
|---|---|
| ACN | acetonitrile |
| ATP | Adenosine triphosphate |
| b | Broad peak |
| BSA | Bovine serum albumin |
| CDI | N,N-Carbonyldiimidazole |
| d | Doublet |
| DBU | 1,8-diazabicyclo[5.4.0]undec-7-ene |
| DCE | 1,2-dichloroethane |
| DCM | Dichloromethane |
| dd | Doublet of doublets |
| DIPEA | N,N-Diisopropylethylamine |
| DMEM | Dulbecco's Modified Eagle's Medium |
| DMF | N,N-Dimethylformamide |
| DMSO | dimethylsulfoxide |
| DTT | dithiothreitol |
| EDCI | 1-(3-Dimethylaminopropyl)-3-ethylcarbodiimide hydrochloride |
| EDTA | Ethylenediaminetetraacetic acid |
| equiv. | equivalents |
| Et | ethyl |
| h | hour |
| HEPES | 4-(2-hydroxyethyl)-1-piperazineethanesulfonic acid |
| HOBt | 1-hydroxybenzotriazole |
| HPLC | High pressure liquid chromatography |
| IPA | Isopropyl alcohol |
| LC/MS | Liquid chromatography coupled to mass spectrometry |
| LiHMDS | Lithium hexamethyldisilazide |
| m | multiplet |
| M | Molecular ion |
| m/z | Mass-to-charge ratio |
| Me | methyl |
| min | minute |
| MS | Mass spectrometry |
| N | Normal (unit of concentration) |
| NMO | 4-methylmorpholine N-oxide |
| NMR | Nuclear Magnetic Resonance |
| PG | Protecting group |
| psi | Pounds per square inch |
| q | Quartette (or quartet) |
| Rf | Retention factor |
| RPMI | Roswell Park Memorial Institute series of media |
| RT | Room temperature |
| Rt. | Retention time |
| s | Singlet |
| Tert | Tertiary |
| TFA | Trifluoroacetic acid |
| THAB | Tetrahexylammonium bromide |
| THF | Tetrahydrofuran |
| TLC | Thin Layer Chromatography |
| TRIS | tris(hydroxymethyl)aminomethane |
| TsOH | p-toluenesulfonic acid |
| UV | ultraviolet |
| VIS | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above. Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formulae (I), (II), (III) and Subformulae 1-39 as well as those disclosed in Tables 1, 2 and 3, according to the hereinafter described schemes and working examples.

In particular, the present invention relates to a process for the manufacture of compounds of Formula (I), wherein X is N and Y is NH, and all other substituents have the meaning as defined for Formula (I) in claim 1, wherein a carboxylic acid compound of Formula (I-III)

is reacted with LA-OH to the corresponding carboxylic LA ester of Formula (I-II)

which is then reacted with $H_2N-R^1$ to a compound of Formula (I-I)

which is finally converted to the carboxylic amide of Formula I

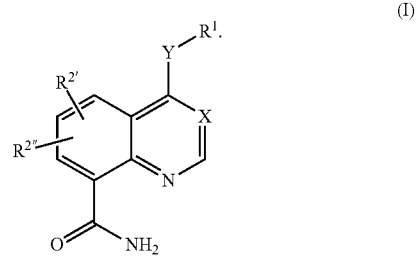

General Synthetic Procedures

Scheme 1

Scheme 1 illustrates the general route used for the synthesis of Examples 1-49 according to the Subformula (Ia) of Formula (I):

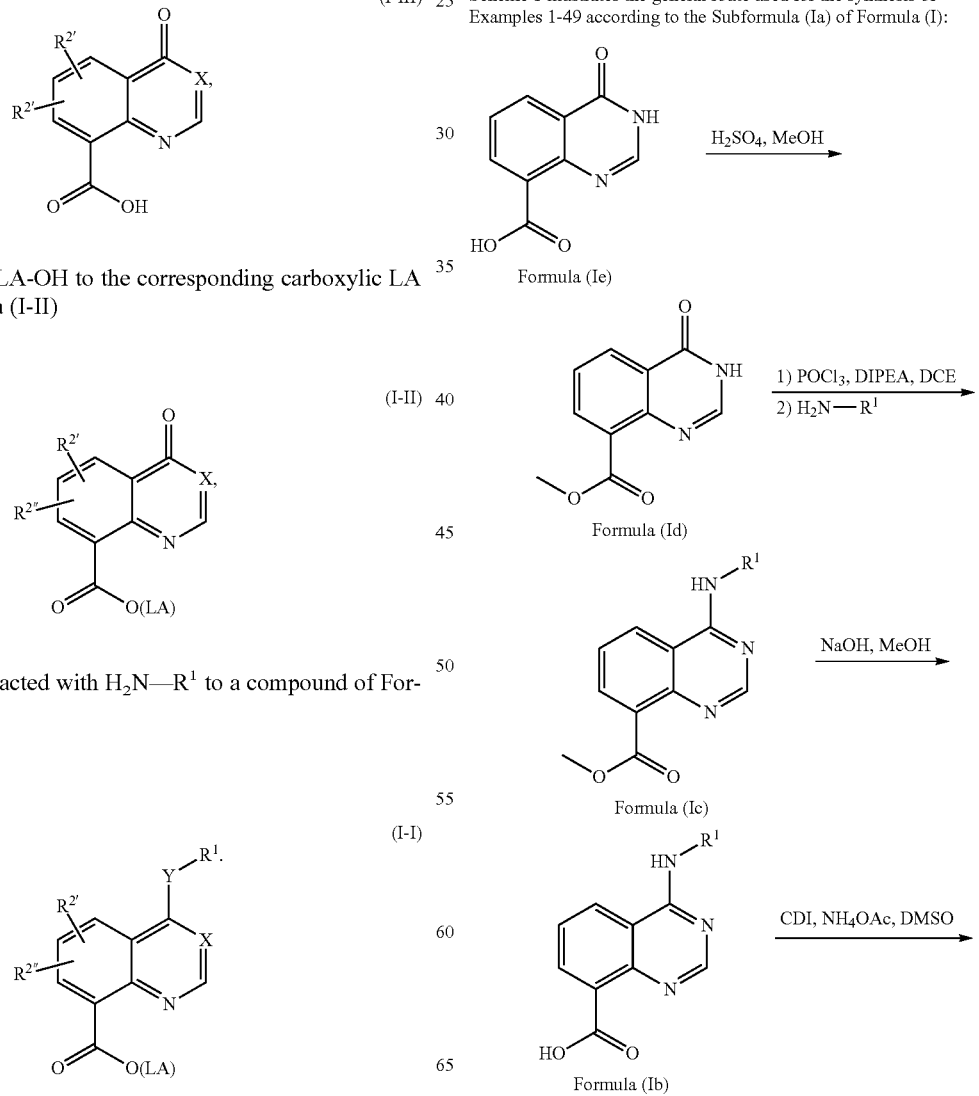

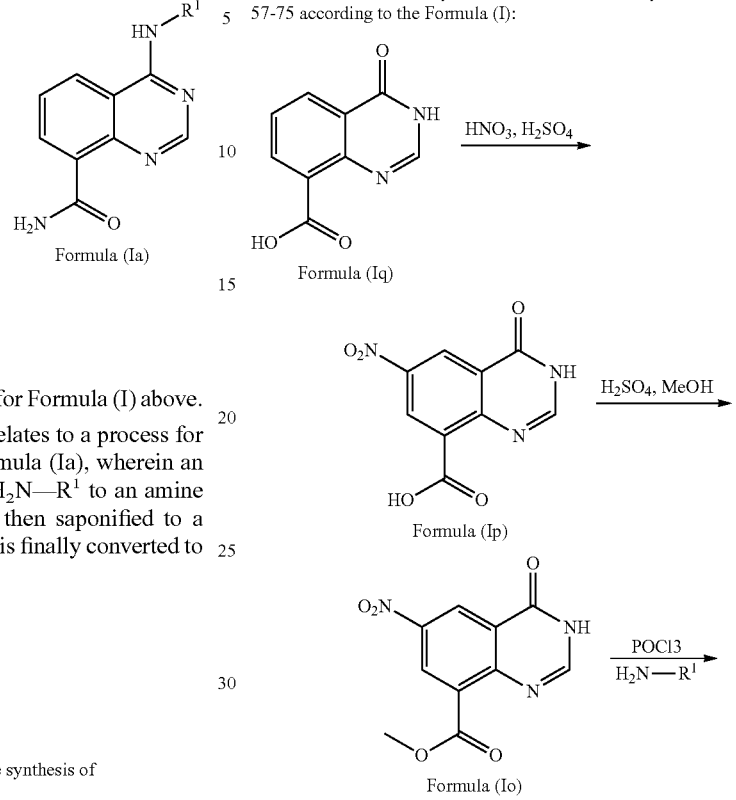

Formula (Ia)

wherein R¹ has the meaning as defined for Formula (I) above.

Accordingly, the present invention relates to a process for the manufacture of compounds of Formula (Ia), wherein an ester of Formula (Id) is reacted with $H_2N-R^1$ to an amine compound of Formula (Ic), which is then saponified to a carboxylic acid of Formula (Ib), which is finally converted to a carboxamide of Formula (Ia).

Scheme 2

Scheme 2 illustrates the general route used for the synthesis of Examples 53-56 according to the Formula (I):

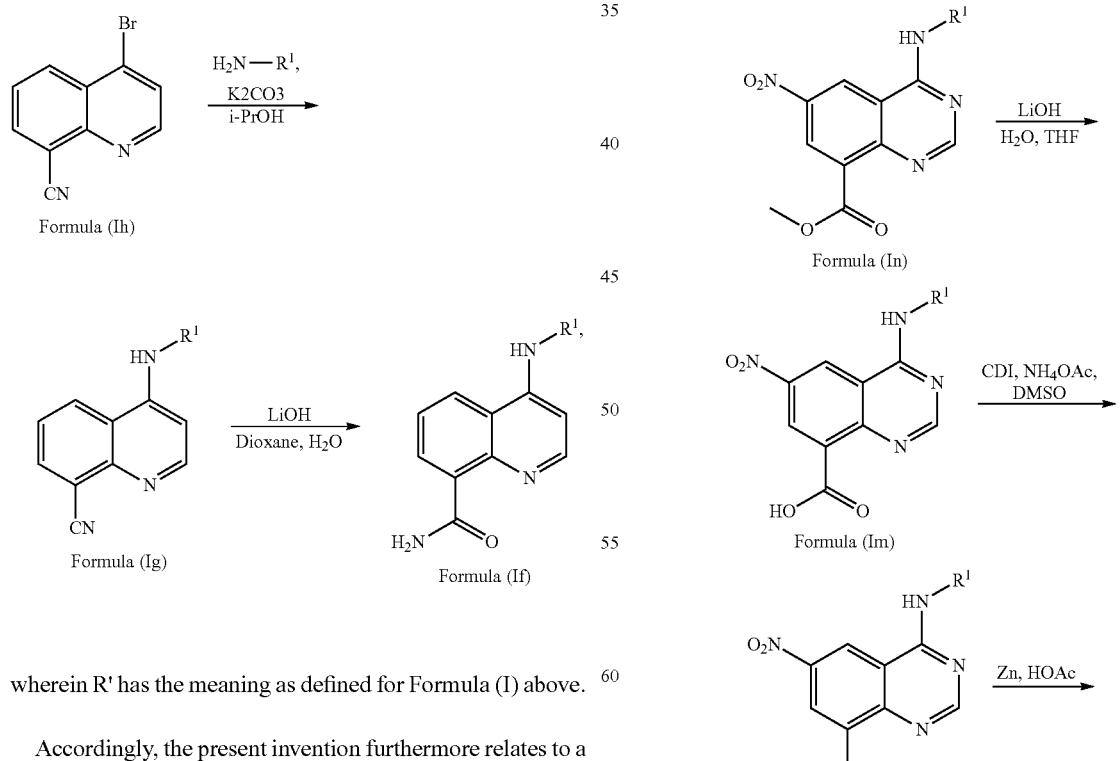

wherein R' has the meaning as defined for Formula (I) above.

Accordingly, the present invention furthermore relates to a process for the manufacture of compounds of Formula (If), wherein a compound of Formula (Ih) is reacted with $H_2N-R^1$ to an amine compound of Formula (Ig), which is then converted to a carboxamide of Formula (If).

Scheme 3

Scheme 3 illustrates the synthesis route used for the synthesis of Examples 57-75 according to the Formula (I):

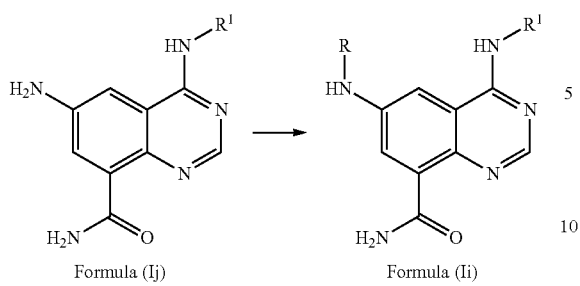

wherein R is H, A, $L^1$-Ar, COA, CO-$L^1$-Ar, $SO_2A$, $SO_2$-$L^1$-Ar, CONHA or CONH-$L^1$-Ar, and A, $L^1$, Ar and $R^1$ have the meaning as defined for Formula (I) above.

Accordingly, the present invention furthermore relates to a process for the manufacture of compounds of Formula (II), wherein an ester of Formula (Io) is reacted with $H_2N$—$R^1$ to an amine compound of Formula (In), which is then saponified to a carboxylic acid of Formula (Im), which is further converted to a carboxamide of Formula (Ik), which is then reduced to an compound of Formula (Ij), which is finally converted to a compound of Formula (Ii).

Scheme 4

Scheme 4 illustrates the general route used for the synthesis of examples 255, 275, 281, 286, 300, 319, 322, 333, 338, 353, 366, 370, 379, 403, 405, 462, 486, 510, 529 and 712 according to the Formula (I):

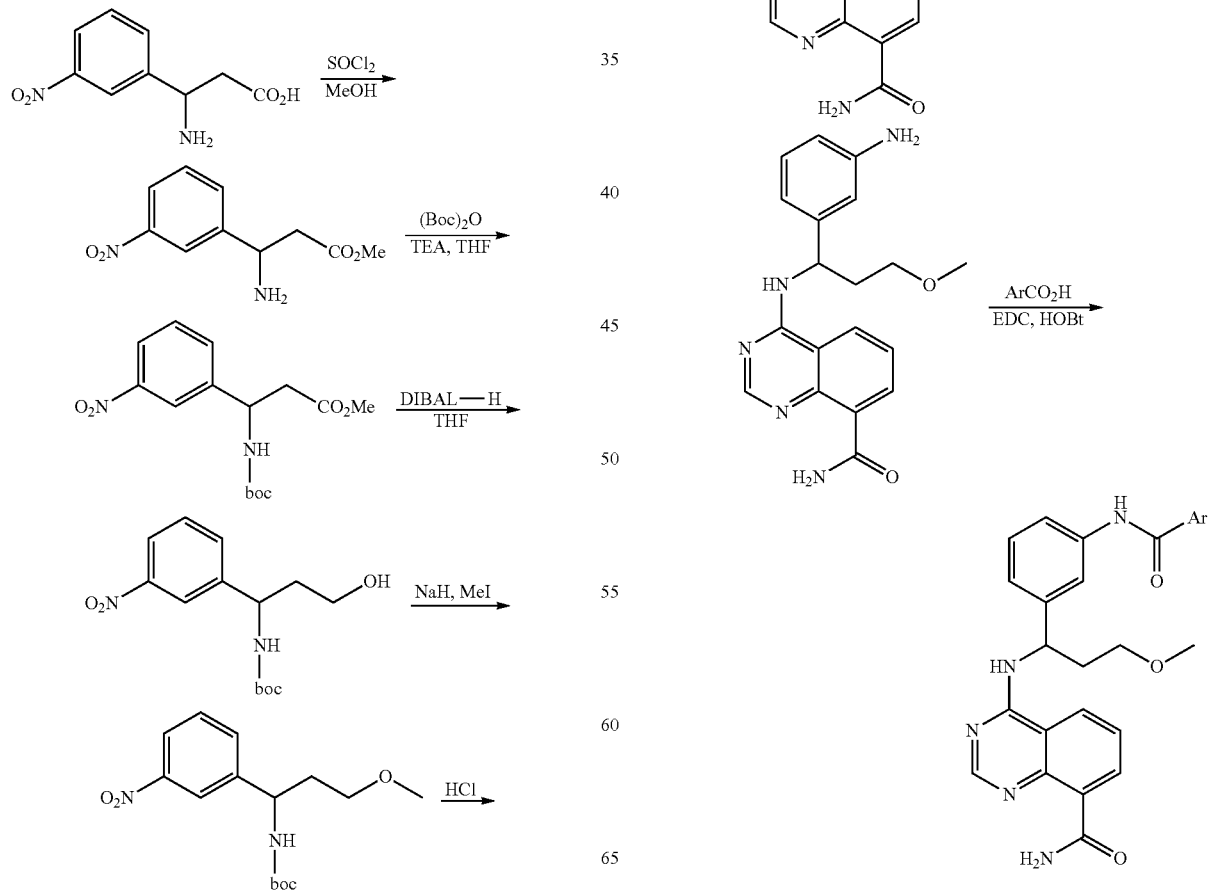

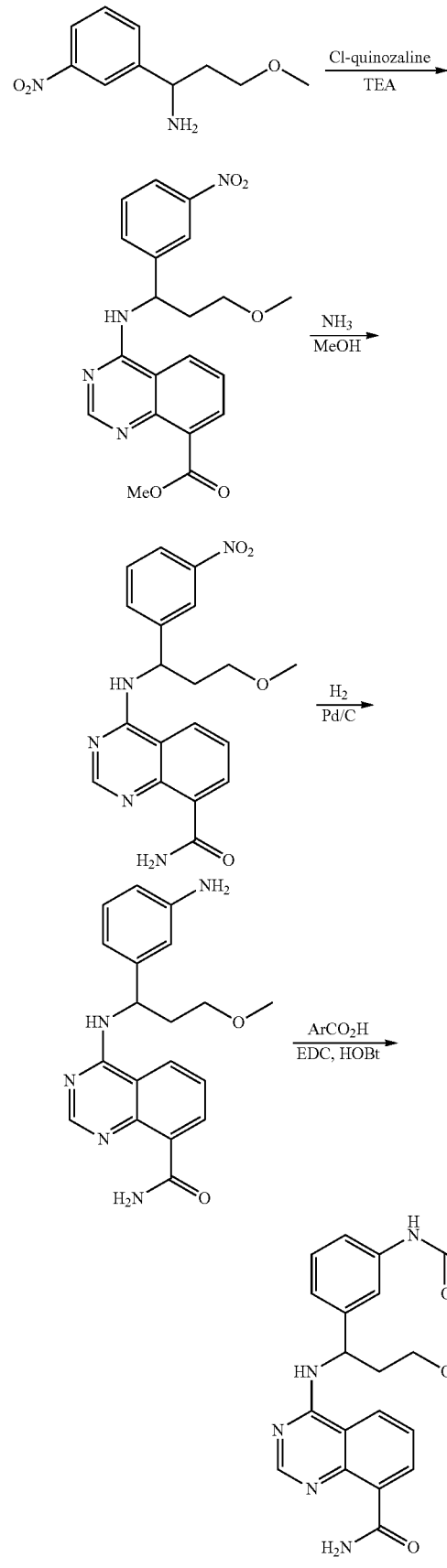

a) 3-amino-3-(3-nitrophenyl)propanoic acid methyl ester

To a solution of 3-amino-3-(3-nitrophenyl)propanoic acid (20.00 g; 95.15 mmol; 1.00 eq.) in MeOH (300 mL) was added thionyl chloride (50.00 ml; 761.22 mmol; 8.00 eq.) at 0° C. slowly. Then the mixture was warmed to room temperature and stirred overnight. The reaction mixture was evaporated and the crude product was purified by flash chromatography on silica gel (MeOH:DCM=15:85) to obtain 20 g of the title compound. LCMS [225 (M+1)].

b) 3-tert-Butoxycarbonylamino-3-(3-nitrophenyl) propanoic acid methyl ester

To a mixture of methyl 3-amino-3-(3-nitrophenyl)propanoate (1.00 g; 4.46 mmol; 1.00 eq.) and N,N-diethylethanamine (1.88 ml; 13.38 mmol; 3.00 eq.) in THF (30 mL) was added di-tert-butyl dicarbonate (1.17 g; 5.35 mmol; 1.20 eq.) in small portions. The reaction mixture was stirred overnight. The precipitated TEA salt was removed by filtration. The filtrate was concentrated and purified by flash chromatography on silica gel with 30% EtOAc/Hexanes as the eluent to provide 1.4 g of the title compound. LCMS [325 (M+1)].

c) 3-hydroxy-1-(3-nitrophenyl)propyl]-carbamic acid tert-buyl ester

To solution of methyl 3-[(tert-butoxycarbonyl)amino]-3-(3-nitrophenyl)propanoate (26.00 g; 80.16 mmol; 1.00 eq.) in anhydrous THF (200 mL) was added hydrido(diisopropyl) aluminum (280.58 ml; 1.00 M; 280.58 mmol; 3.50 eq.) at −78° C. The mixture was stirred at −78° C. for 5 h. Then it was allowed to warm to room temperature and stirred for another 15 h. The reaction was quenched with water and extracted with ether. The ethereal layer was washed with water, brine and dried over MgSO4. The solvent was removed and the crude product was purified by lash chromatography on silica gel (EtOAc:Hex=20:80 to 50:50) to get 22 g of waxy product. LCMS [196 (M−Boc].

d) 3-Methoxy-1-(3-nitrophenyl)-propylamine

To a solution of tert-butyl [3-hydroxy-1-(3-nitrophenyl) propyl]carbamate (2 g; 6.75 mmol; 1.00 eq.) in anhydrous THF (10 mL) was added NaH (567 mg; 14.17 mmol; 2.10 eq.) at 0° C. The mixture was stirred for 20 minutes and iodomethane (1.53 g; 7.42 mmol; 1.10 eq.) was added. The mixture was stirred for 2 hours at 0° C. After work up, the crude product was purified by flash chromatography on silica gel (EtOAc:Hex=1:4) to provide 1.5 g of tert-butyl [3-methoxy-1-(3-nitrophenyl)propyl]carbamate.

To a solution of tert-butyl [3-methoxy-1-(3-nitrophenyl) propyl]carbamate (1.5 g; 4.83 mmol; 1.00 eq.) in MeOH (2 mL) was added hydrogen chloride (12.08 ml; 4.00 M; 48.33 mmol; 10.00 eq.). The mixture was stirred for 2 h. After removal of the solvent, the residue was diluted with EtOAc, washed with K2CO3 solution, dried and concentrated. The crude product (1.0 g) was used as such for the next reaction without purification. LCMS [211 (M+1)].

e) 4-[1-(3-Amino-phenyl)-3-methoxy-propylamino]-quinazoline-8-carboxamide

A mixture of methyl 4-chloroquinazoline-8-carboxylate (1.0 g; 4.49 mmol, 1.0 eq.), 3-methoxy-1-(3-nitrophenyl) propan-1-amine (1.038 g; 4.94 mmol; 1.10 eq.) and triethylamine (3.16 ml; 22.46 mmol; 5.00 eq.) in acetonitrile (20 mL) was stirred overnight at 60° C. The solvent was removed and the crude methyl 4-{[3-methoxy-1-(3-nitrophenyl)propyl]amino}quinazoline-8-carboxylate (1.744 g) was used for the next reaction.

To a solution of methyl 4-{[3-methoxy-1-(3-nitrophenyl) propyl]amino}quinazoline-8-carboxylate (1.74 g; 4.40 mmol) in methanol was added methanolic ammonia (7N) (30.00 ml; 7.00 M; 210.00 mmol) and stirred for 3 days. Insoluble material was removed by filtration and concentrated. The crude 4-{[3-methoxy-1-(3-nitrophenyl)propyl] amino}quinazoline-8-carboxamide (1.5 g) of was used for the next reaction without further purification. To a solution of 4-{[3-methoxy-1-(3-nitrophenyl)propyl] amino}quinazoline-8-carboxamide (1.5 g) in MeOH (30 mL) was added palladium on active carbon (400 mg) and the mixture was hydrogenated at 40 psi for 4 h. Filtered through a pad of Celite and the solvent was removed. The crude product (1.2 g) was used as such for amide formation. LCMS [352 (M+1)].

Scheme 5

Scheme 5 illustrates the general route used for the synthesis of Examples 189, 196, 208, 209, 212, 215, 219, 223, 228, 233, 249, 252, 254, 265, 273, 287, 296, 313, 314, 332, 335, 360, 361, 363, 365, 391, 392, 399, 418, 422, 437, 450, 458, 490, 493, 495, 500, 524, 527, 664, 695, 697, 698, 700, 703, 704 according to the Formula (I):

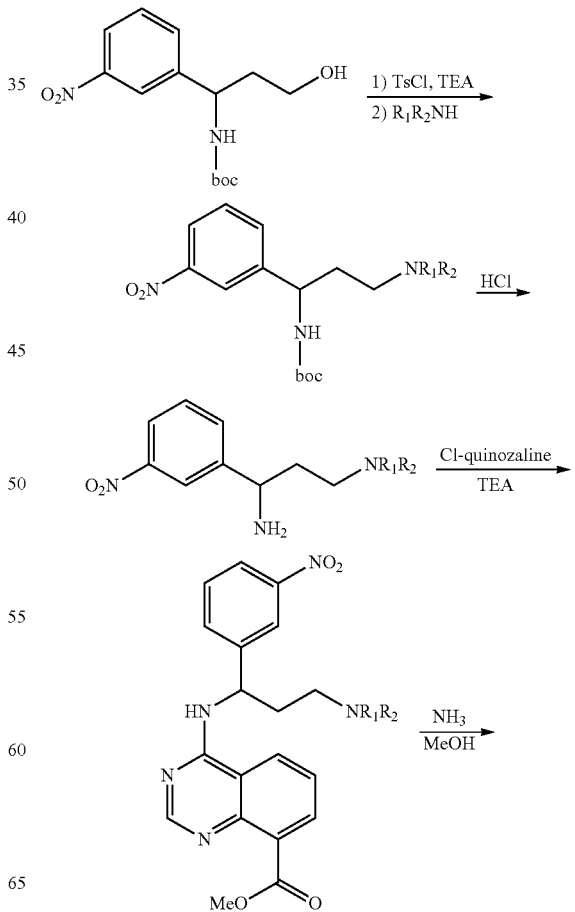

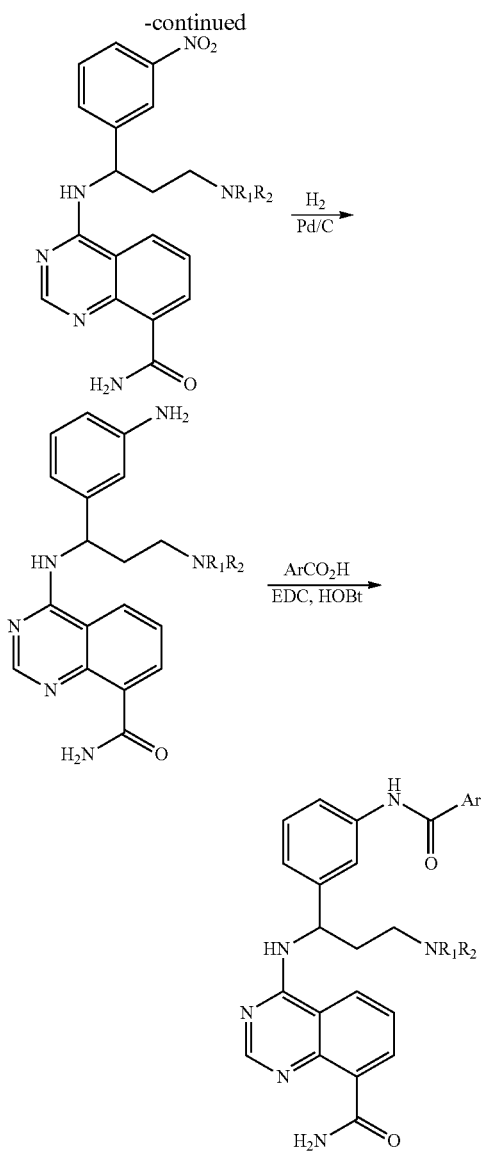

4-[1-(3-Amino-phenyl)-3-pyrrolidin-1-yl-propylamino]-quinazoline-8-carboxylic acid amide

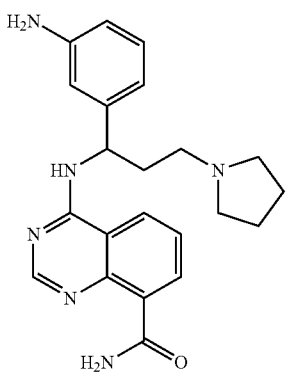 [SMILES: NC(=O)c1cccc2c(NC(CCN3CCCC3)c3cccc(N)c3)ncnc12]

To a solution of tert-butyl [3-hydroxy-1-(3-nitrophenyl)propyl]carbamate (4.00 g; 13.50 mmol; 1.00 eq.) in anhydrous DCM (15 mL) and N,N-diethylethanamine (2.82 ml; 20.25 mmol; 1.50 eq.) at 0° C. was added dropwise 4-methylbenzenesulfonyl chloride (3.09 g; 16.20 mmol; 1.20 eq.). The mixture was stirred at room temperature for 15 h. After workup, the crude product was purified by flash chromatography on silica gel (EtOAc:Hex from 10:90 to 20:80) to provide 5.5 g of the 3-[(tert-butoxycarbonyl)amino]-3-(3-nitrophenyl)propyl 4-methylbenzenesulfonate.

To a solution of 3-[(tert-butoxycarbonyl)amino]-3-(3-nitrophenyl)propyl 4-methylbenzenesulfonate (2.00 g; 4.44 mmol; 1.00 eq.) in THF (10 mL) was added pyrrolidine (3.73 ml; 44.39 mmol; 10.00 eq.) and the mixture was stirred overnight. After concentration, the oily product was used for the next reaction without any purification.

To a solution of tert-butyl [1-(3-nitrophenyl)-3-pyrrolidin-1-ylpropyl]carbamate (1.4 g. 72 mg; 4.00 mmol) in MeOH (2 mL) was added hydrogen chloride (15.00 ml; 4.00 M; 60.00 mmol) in dioxane. The mixture was stirred for 2 h. After removal of the solvent, the residue was suspended in EtOAc and washed with sat. $K_2CO_3$. Dried, concentrated. The crude 1-(3-nitrophenyl)-3-pyrrolidin-1-ylpropan-1-amine (900 mg) was used as such for the next step. LCMS [250 (M+H].

A mixture of methyl 4-chloroquinazoline-8-carboxylate (891 mg; 4.00 mmol; 1.00 eq in acetonitrile (20 mL), 1-(3-nitrophenyl)-3-pyrrolidin-1-ylpropan-1-amine (997 mg; 4.00 mmol; 1.00 eq.) and triethylamine (2.81 ml; 20.00 mmol; 5.00 eq.) was stirred overnight. The precipitated solid was filtered and dried. The crude methyl 4-{[1-(3-nitrophenyl)-3-pyrrolidin-1-ylpropyl]amino}quinazoline-8-carboxylate (1.654 g) was used for the next reaction.

A suspension of methyl 4-{[1-(3-nitrophenyl)-3-pyrrolidin-1-ylpropyl]-amino}quinazoline-8-carboxylate (1 654.83 mg; 3.80 mmol; 1.00 eq.) and ammonia (16.29 ml; 7.00 M; 114.00 mmol; 30.00 eq.) in MeOH was stirred for 2 days. After concentration, the (1.3 g) of 4-{[1-(3-nitrophenyl)-3-pyrrolidin-1-ylpropyl]-amino}quinazoline-8-carboxamide was obtained.

To a solution of 4-{[1-(3-nitrophenyl)-3-pyrrolidin-1-ylpropyl]amino}quinazoline-8-carboxamide (1.22 g; 2.90 mmol) in DMF (50 mL) was added palladium on activated carbon (200 mg) and the mixture was hydrogenated under $H_2$ overnight at 40 psi.

Filtered through a pad of Celite and the solvent was removed. The product was triturated with EtOAc, the solid was filtered and dried to get 0.95 g of the pure title compound.

The intermediate 4-[1-(3-Amino-phenyl)-3-pyrrolidin-1-yl-propylamino]-quinazoline-8-carboxylic acid amide was used for the preparation of examples 360, 418, 422, 524, 697.

Scheme 6
Scheme 6 illustrates the general route used for the synthesis of examples 240, 244, 246, 247, 250, 261, 266, 272, 280, 291, 292, 294, 299, 301, 308, 309, 321, 323, 331, 334, 339, 358, 359, 371, 383, 385, 386, 390, 394, 395, 402, 404, 414, 421, 425, 426, 429, 430, 434, 440, 442, 446, 452, 456, 461, 463, 464, 471, 472, 475, 476, 496, 497, 498, 501, 506, 507, 512, 525, 543, 544, 546, 551, 552, 553, 554, 557, 558, 561, 563, 566, 567, 568, 570, 572, 575, 580, 582, 585, 587, 588, 592, 600, 601, 605, 606, 610, 617, 622, 624, 625, 629, 631, 636, 637, 645, 646, 649, 650, 651, 653, 655, 656, 657, 658, 659, 660, 661, 663, 665, 666, 667, 668, 670, 671, 672, 677, 678, 679, 681, 682, 685, 686, 689, 693, 694, 701, 714, 715, 717 and 718 according to Formula (I):
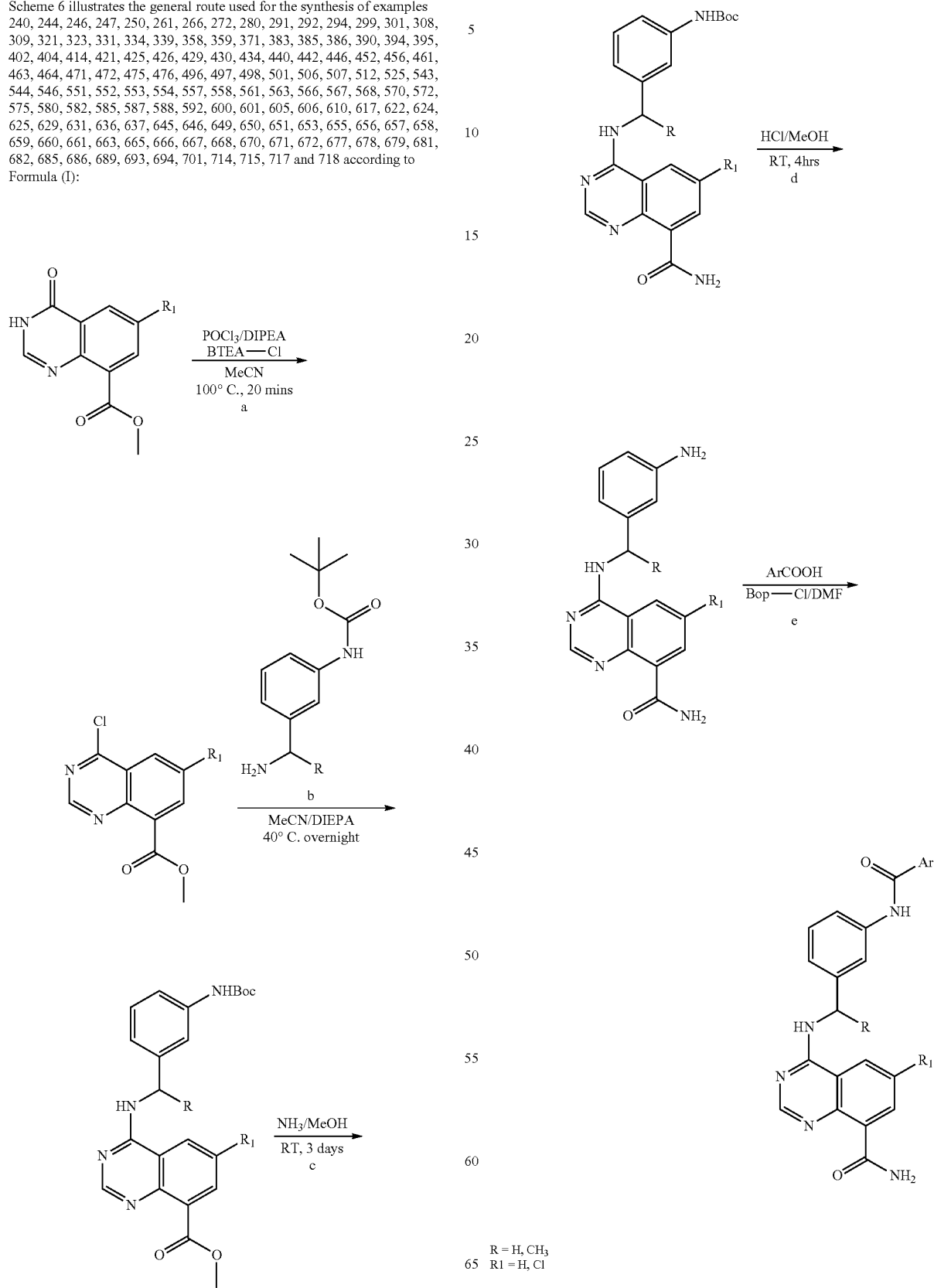
R = H, CH$_3$
R$_1$ = H, Cl

4-[1-(3-Amino-phenyl)-ethylamino]-quinazoline-8-carboxylic acid amide

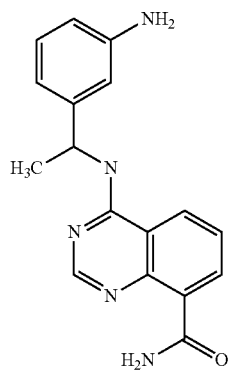 [SMILES: CC(Nc1ncnc2c(C(N)=O)cccc12)c1cccc(N)c1]

To a solution of methyl 4-oxo-3,4-dihydroquinazoline-8-carboxylate (11.80 g; 57.79 mmol; 1.00 eq.) in MeCN (50.00 ml) were added N-ethyl-N-isopropylpropan-2-amine (10.37 ml; 57.79 mmol; 1.00 eq.) followed by N-benzyl-N,N-diethylethanaminium chloride (26.33 g; 115.58 mmol; 2.00 eq.). Then added phosphorus oxychloride (26.53 ml; 288.95 mmol; 5.00 eq.) slowly. The reaction mixture was stirred for 20 min at 90° C. and poured into 400 ml of 2N NaOH containing crushed ice. The precipitated methyl 4-chloro-quinazoline-8-carboxylate was filtered, washed with water and dried to get 10.2 g. Yield 79.28%. MS (M+1) 222/224

To a mixture of methyl 4-chloroquinazoline-8-carboxylate (2.0 g; 8.98 mmol; 1.00 eq.) and N-ethyl-N-isopropylpropan-2-amine (3.23 ml; 17.97 mmol; 2.00 eq.) in acetonitrile (20.00 ml) was added tert-butyl [3-(1-aminoethyl)phenyl]carbamate (2.3 g; 9.43 mmol; 1.05 eq.), the reaction mixture was stirred at RT overnight. After concentration, methanolic ammonia (12.83 ml; 7.00 M; 89.83 mmol; 10.00 eq.) was added stirred at RT for 48 h. {3-[1-(8-Carbamoyl-quinazolin-4-ylamino)-ethyl]-phenyl}-carbamic acid tert-butyl ester was obtained as an yellow solid which was used as such for next reaction. MS (M+1) 408

To a solution of crude {3-[1-(8-Carbamoyl-quinazolin-4-ylamino)-ethyl]-phenyl}-carbamic acid tert-butyl ester in methanol (20 ml) was added methanolic hydrogen chloride (22.46 ml; 4.00 M; 89.83 mmol; 10.00 eq.). Stirred overnight and the resulting solid was filtered to obtain 2.0 g of the title product in 64% overall yield MS (M+1) 307

Scheme 7

Scheme 7 illustrates the general route used for the synthesis of examples 564, 577, 590, 612, 626, 638 according to Formula (I):

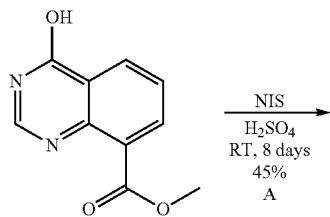

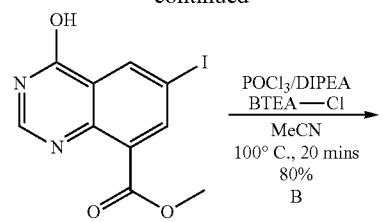

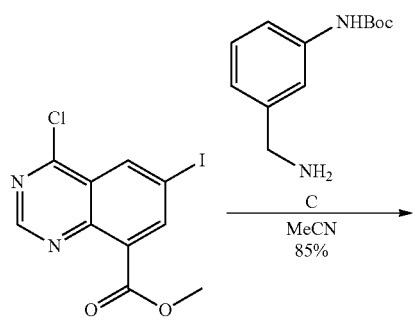

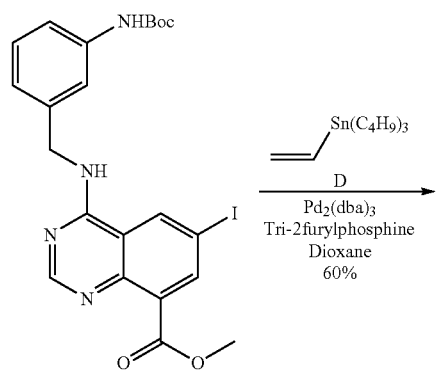

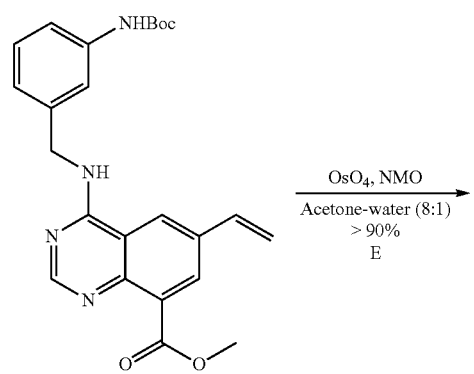

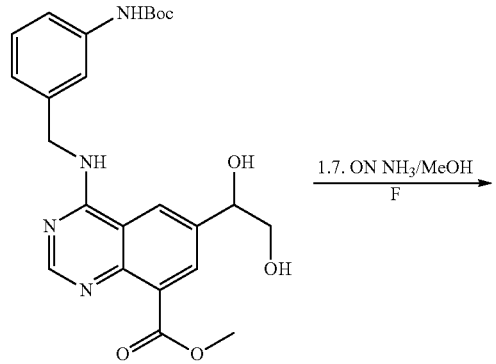

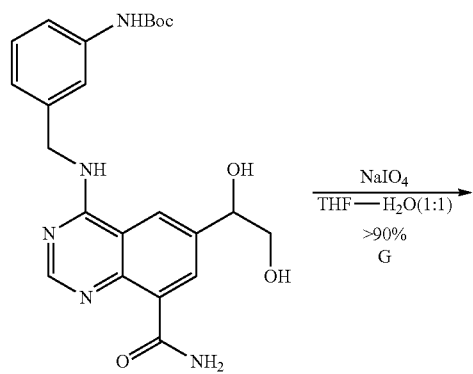

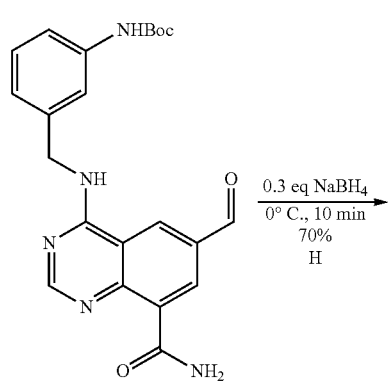

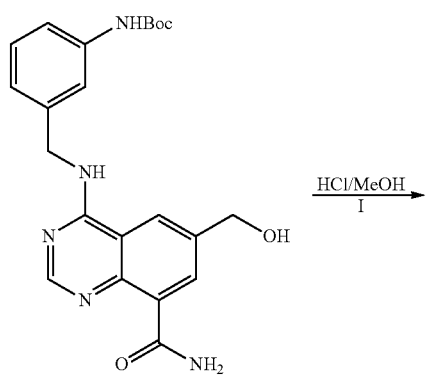

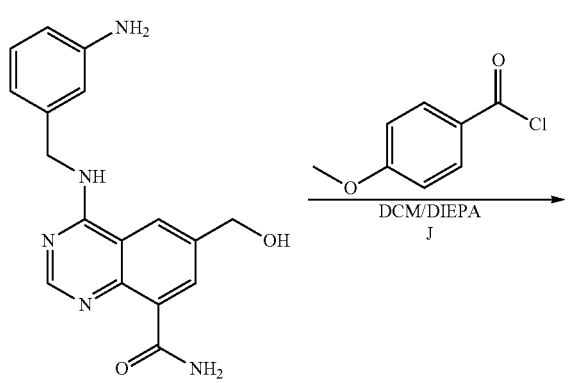

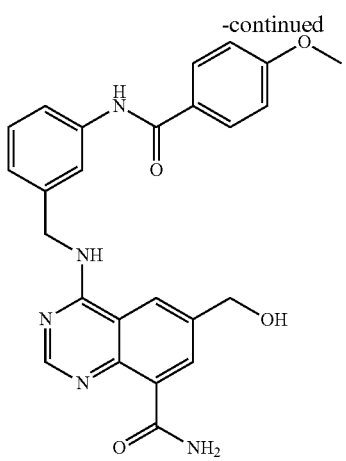

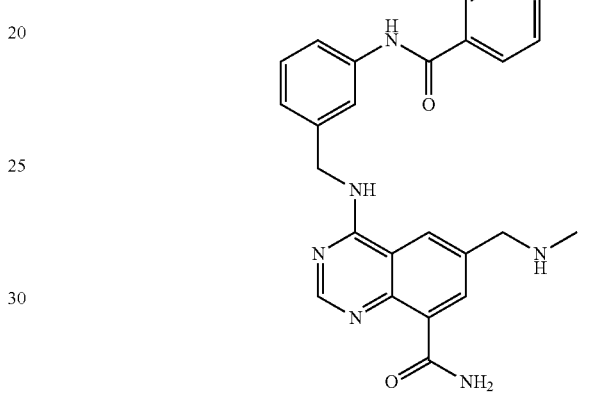

4-(3-Amino-benzylamino)-6-(1,2-dihydroxy-ethyl)-quinazoline-8-carboxylic acid amide

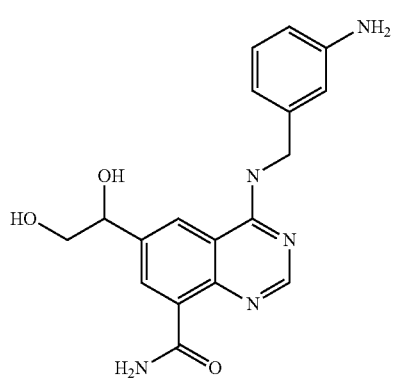 [SMILES: NC(=O)c1cc(C(O)CO)cc2c(NCc3cccc(N)c3)ncnc12]

Methyl 4-oxo-3,4-dihydroquinazoline-8-carboxylate (5.00 g; 24.49 mmol; 1.00 eq.) was dissolved in sulfuric acid (50.00 ml; 938.01 mmol; 38.31 eq.) while cooling with water bath. N-iodosuccinamide (44.07 g; 195.90 mmol; 8.00 eq.) was then added. The mixture was stirred at RT for 21 hours, then heated to 40° C. and stirred at same temperature for 8 days. Poured the reaction mixture into a cooled solution of 2N NaOH. 50 ml 5% —NaS₂SO₃ solution was added and stirred for 1 h at RT. Filtered the product methyl 6-iodo-4-oxo-3,4-dihydroquinazoline-8-carboxylate to get a white solid (3.5 g, 43.5%).

To a mixture of methyl 6-iodo-4-oxo-3,4-dihydroquinazoline-8-carboxylate (1.00 g; 3.03 mmol; 1.00 eq.) and N-ethyl-N-isopropylpropan-2-amine (0.54 ml; 3.03 mmol; 1.00 eq.) in MeCN (5.00 ml) was added N-benzyl-N,N-diethylethanaminium chloride (1.38 g; 6.06 mmol; 2.00 eq.), then phosphorus oxychloride (1.39 ml; 15.15 mmol; 5.00 eq.) was added slowly. The reaction mixture was stirred for 20 min at 90° C., poured into 2N NaOH solution (22 ml) containing crushed ice. Filtered, washed with water and collected 850 mg of the 4-Chloro-6-iodo-quinazoline-8-carboxylic acid methyl ester in 80% yield.

To a solution of methyl 4-chloro-6-iodoquinazoline-8-carboxylate (884 mg; 2.54 mmol; 1.00 eq.) in acetonitrile (10.00 ml), added N-ethyl-N-isopropylpropan-2-amine (1.14 ml; 6.34 mmol; 2.50 eq.) and tert-butyl [3-(aminomethyl)phenyl]carbamate (592 mg; 2.66 mmol; 1.05 eq.). The reaction mixture was stirred at RT overnight. The product methyl 4-({3-[(tert-butoxycarbonyl)amino]benzyl}amino)-6-iodoquinazoline-carboxylate was filtered and washed with acetonitrile and ether to 1.08 g in 79% yield.

A mixture of methyl 4-({3-[(tert-butoxycarbonyl)amino]benzyl}amino)-6-iodoquinazoline-8-carboxylate (110 mg; 0.21 mmol; 1.00 eq.), dicyclohexyl(2',6'-dimethoxybiphenyl-2-yl)phosphine (8.45 mg; 0.02 mmol; 0.10 eq.), palladium (II) acetate (2.31 mg; 0.01 mmol; 0.05 eq.) and tributyl(vinyl)stannane (0.07 ml; 0.25 mmol; 1.20 eq.) in dioxane was heated in a sealed tube for 5 min in a microwave at 100° C. The reaction mixture was diluted with EtOAc, washed with 20% KF solution, filtered, and the filtrate was washed with aq. NH4Cl and brine. After concentration, the methyl 4-({3-[(tert-butoxycarbonyl)amino]benzyl}amino)-6-vinylquinazoline-8-carboxylate was purified by flash chromatography to get 60 mg in 67% yield.

To a solution of methyl 4-({3-[(tert-butoxycarbonyl)amino]benzyl}amino)-6-vinylquinazoline-8-carboxylate (60.00 mg; 0.14 mmol; 1.00 eq.) in acetone (8.00 ml) and water (1.00 ml) added 4-methylmorpholine 4-oxide (48.53 mg; 0.41 mmol; 3.00 eq.) and 20 ul of Osmium tetroxide (2.5 wt % solution in 2-methyl 2-propanol). The reaction mixture was stirred at RT overnight, concentrated and purified the product by HPLC, to get tert-butyl [3-({[8-(aminocarbonyl)-6-(1,2-dihydroxyethyl)quinazolin-4-yl]amino}methyl)phenyl]carbamate. 62 mg, yield 95%. MS (M+1) 467

To a solution of tert-butyl [3-({[8-(aminocarbonyl)-6-(1,2-dihydroxyethyl)quinazolin-4-yl]amino}methyl)phenyl]carbamate (25.00 mg; 0.06 mmol; 1.00 eq.) in methanol was added 4.0M hydrogen chloride in dioxane (0.14 ml; 4.00 M; 0.55 mmol; 10.00 eq.). The reaction mixture was stirred at RT for 1 h and evaporated off the solvent to obtain the title compound MS (M+1) 354

This intermediate was used for the preparation of example 577.

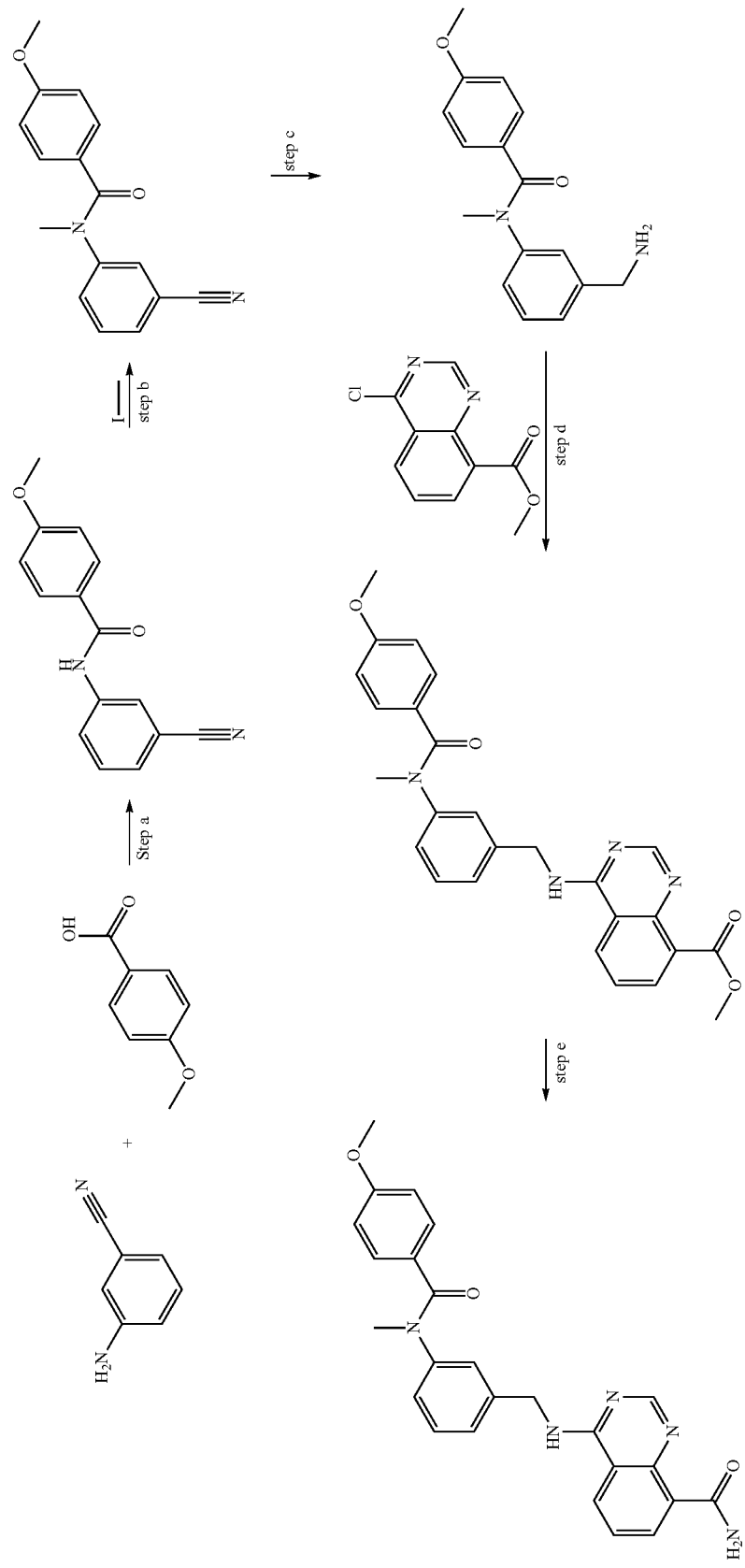
Scheme 8
Scheme 8 illustrates the general route used for the synthesis of examples 550, 618, 674, 743 according to Formula (I):

Steps (a) to (e) are carried out as described in Example 743.
Scheme 9
Scheme 9 illustrates the general route used for the synthesis of example 539.
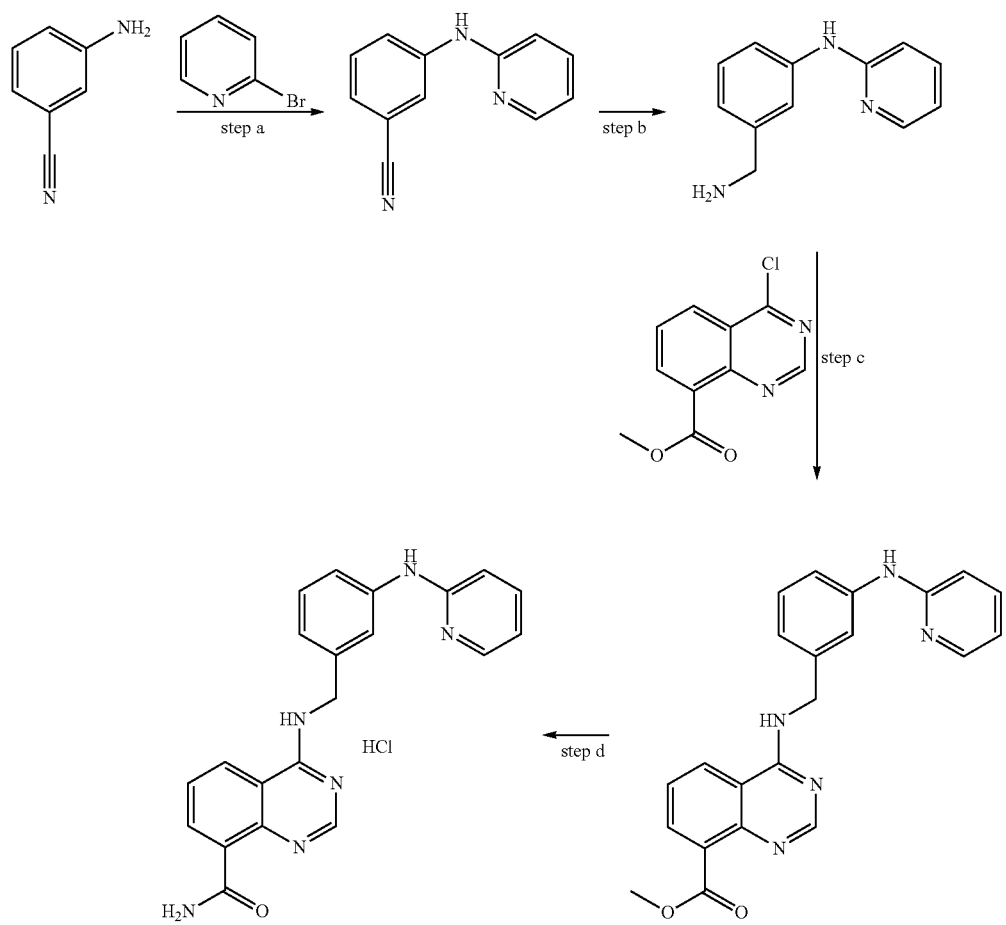
The individual steps are carried out as described in Example 539.
Scheme 10
Scheme 10 illustrates the general route used for synthesis of examples 477, 526, 549, 569, 574, 594, 603, 611, 616, 62 628 and 642.
-continued
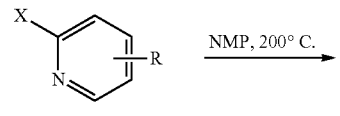
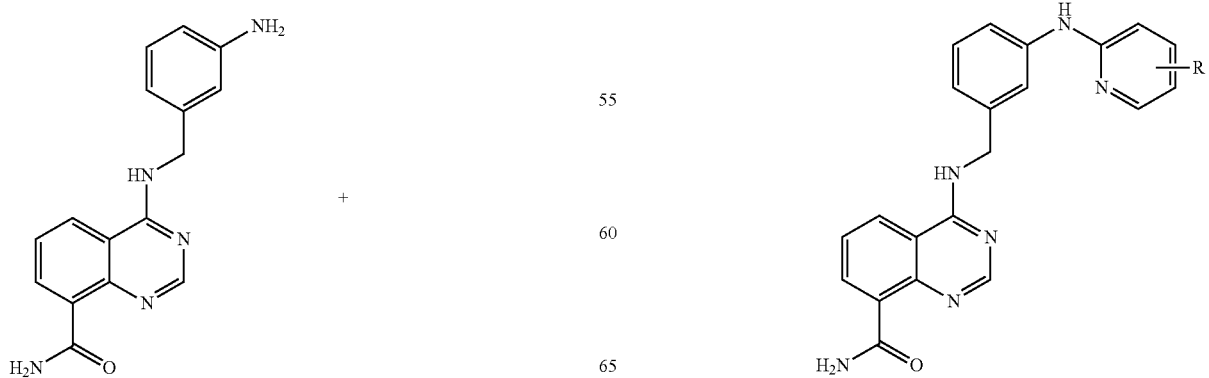

Scheme 11
Scheme 11 illustrates the general route used for the synthesis of examples 427, 540, 581, 595, 602, 615, 619, 630 and 684
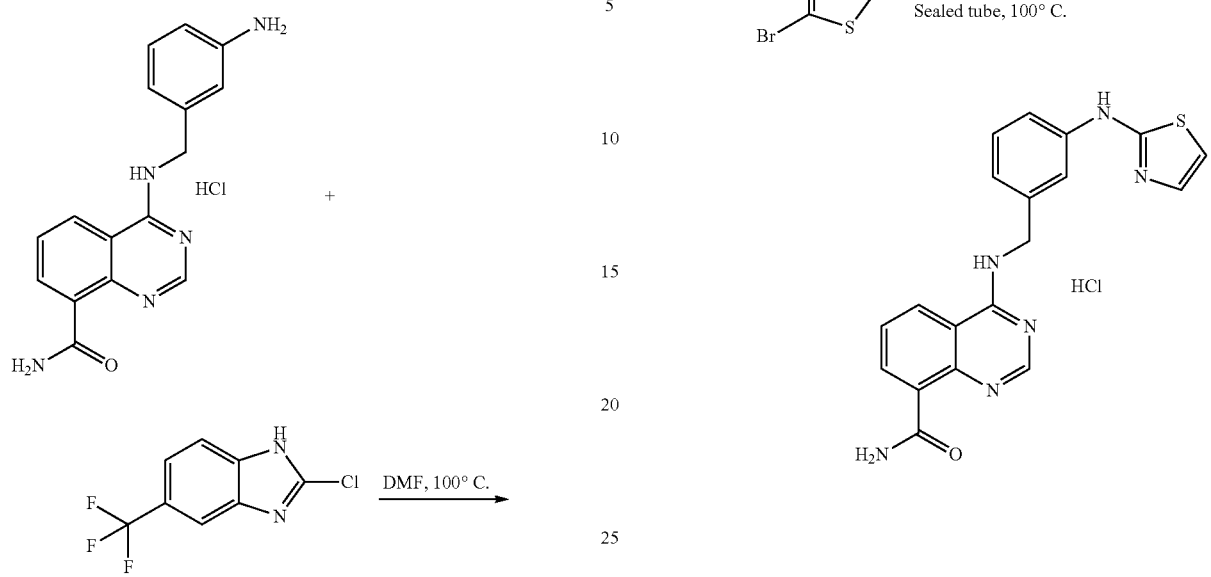
Scheme 12
Scheme 12 illustrates the general route used for synthesis of examples 541, 545 and 548.
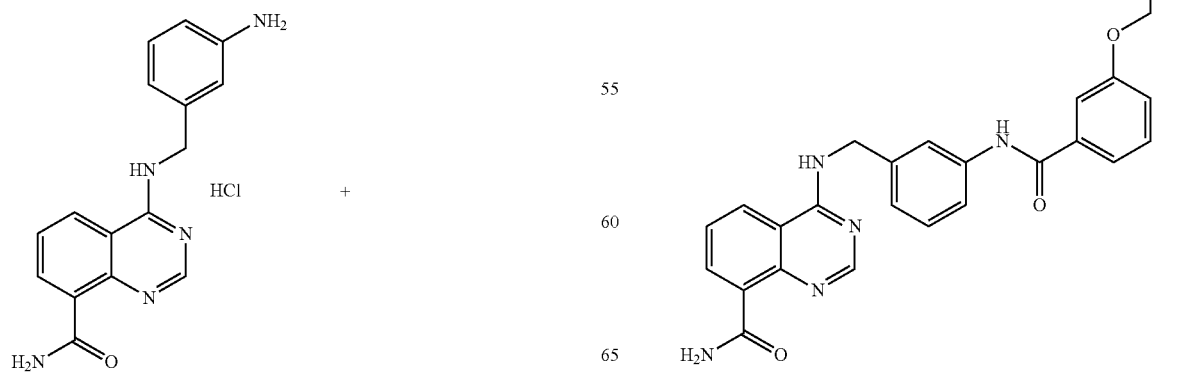
Scheme 13
Scheme 13 illustrates the general route used for the synthesis of examples 398, 609, 614, 634, 635 and 673
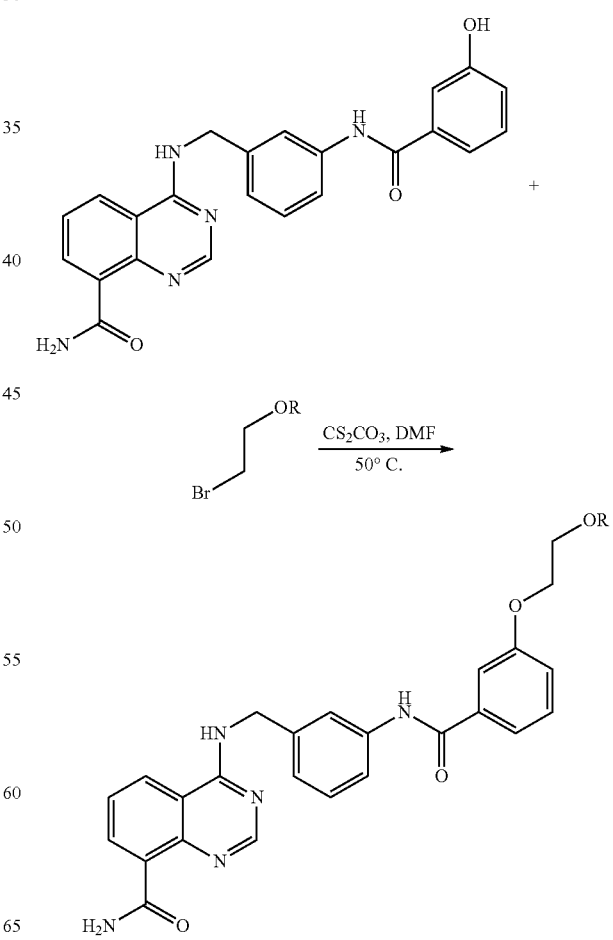

Scheme 14
Scheme 14 illustrates the general route used for the synthesis of examples 538 and 559
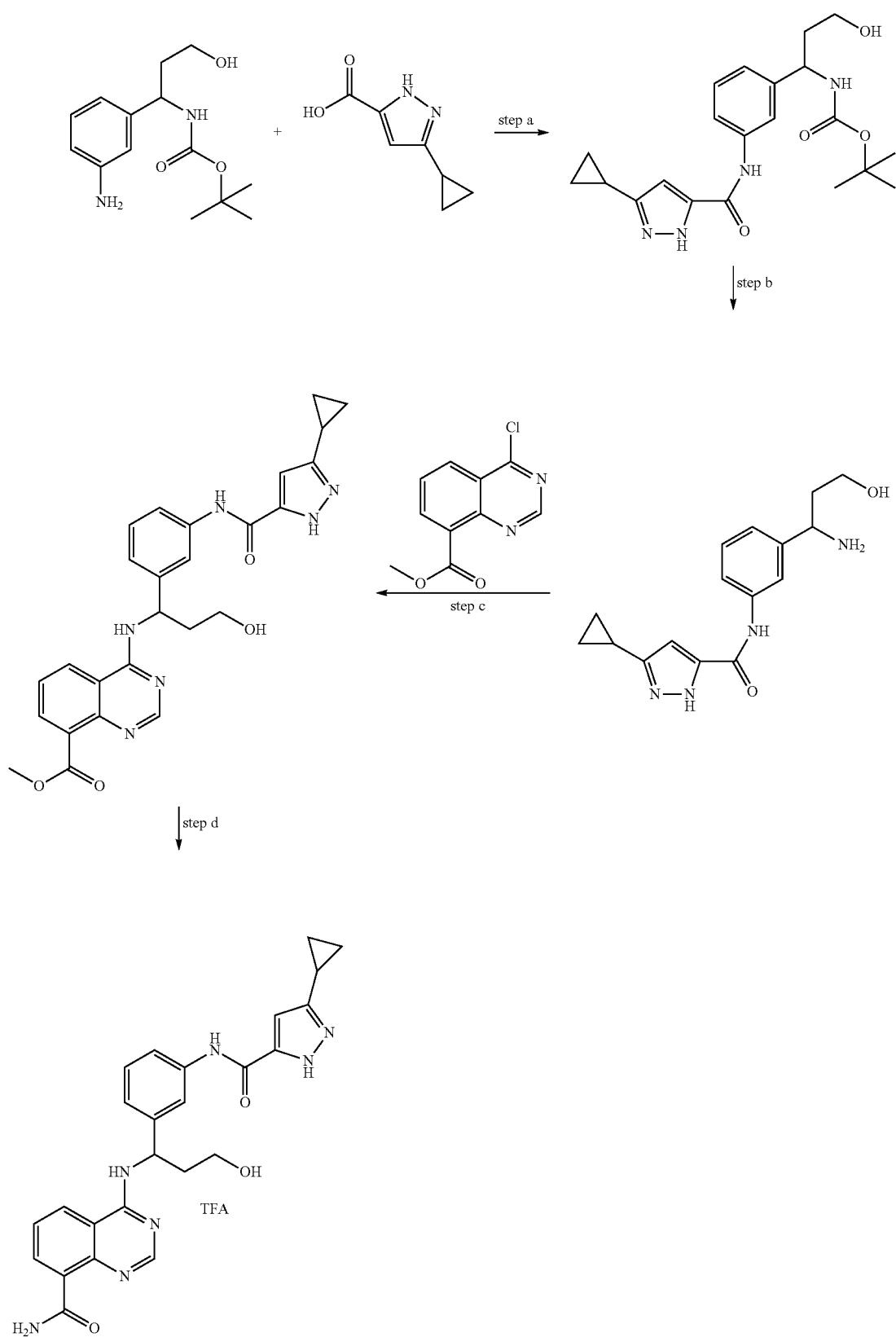

The individual steps are carried out as described in Example 538.
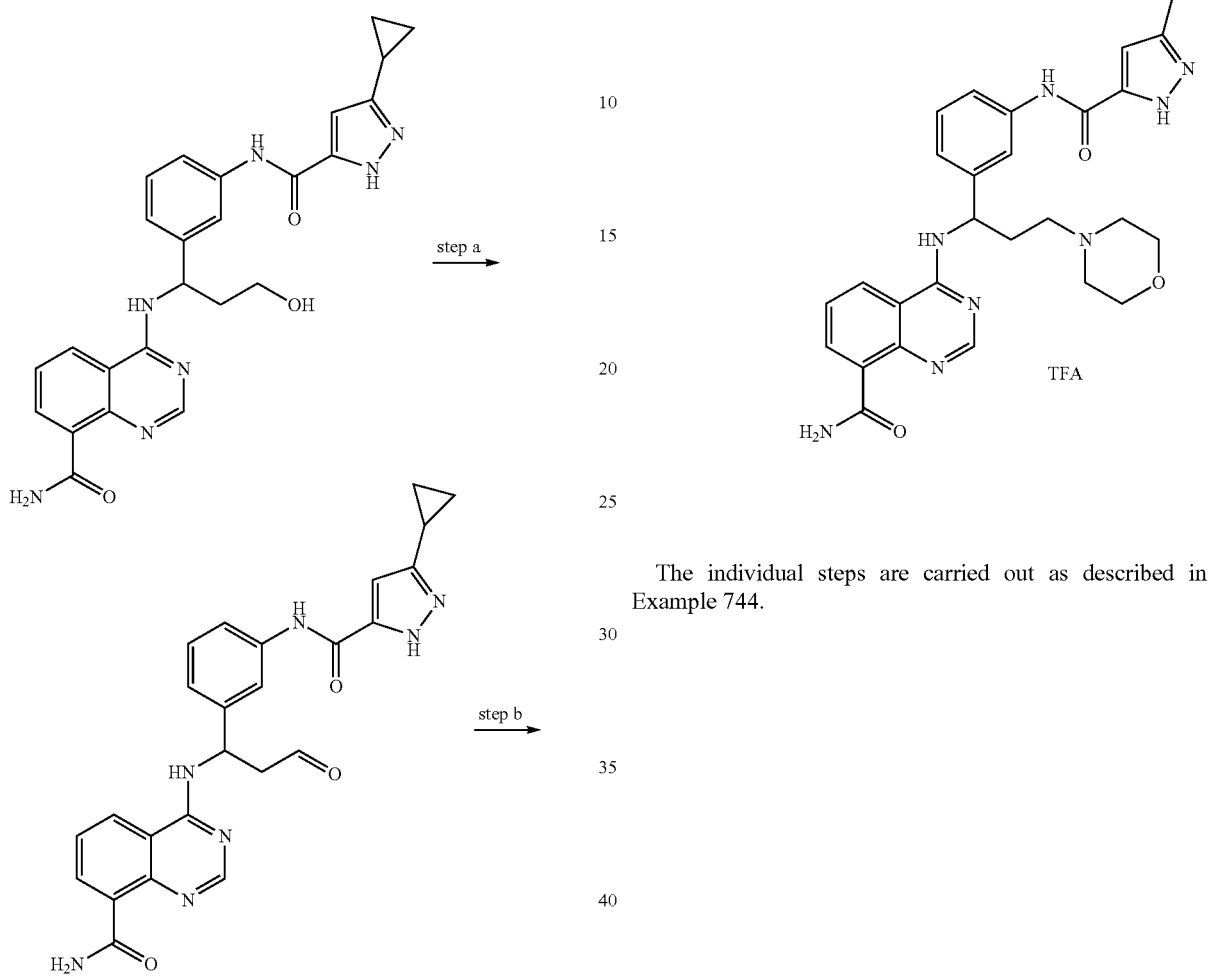
Scheme 15
Scheme 15 illustrates the general route used for the synthesis of examples 555, 556, 562, 578, 579, 597, and 744.
The individual steps are carried out as described in Example 744.
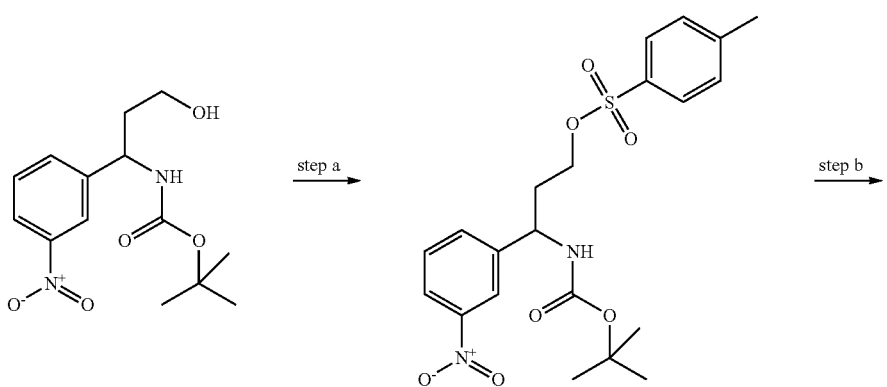
Scheme 16
Scheme 16 illustrates the general route used for the synthesis of example 542

521 522
-continued
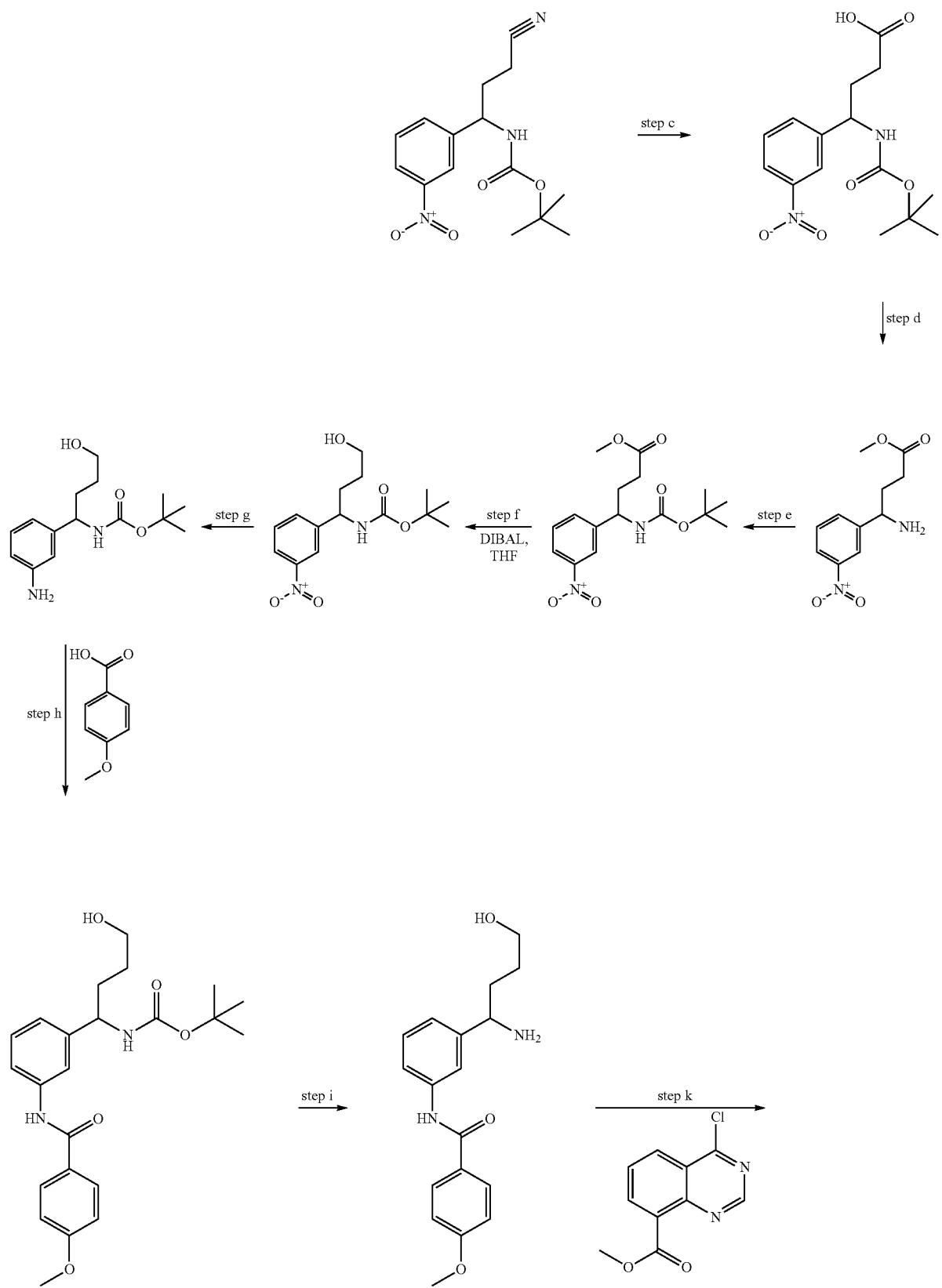

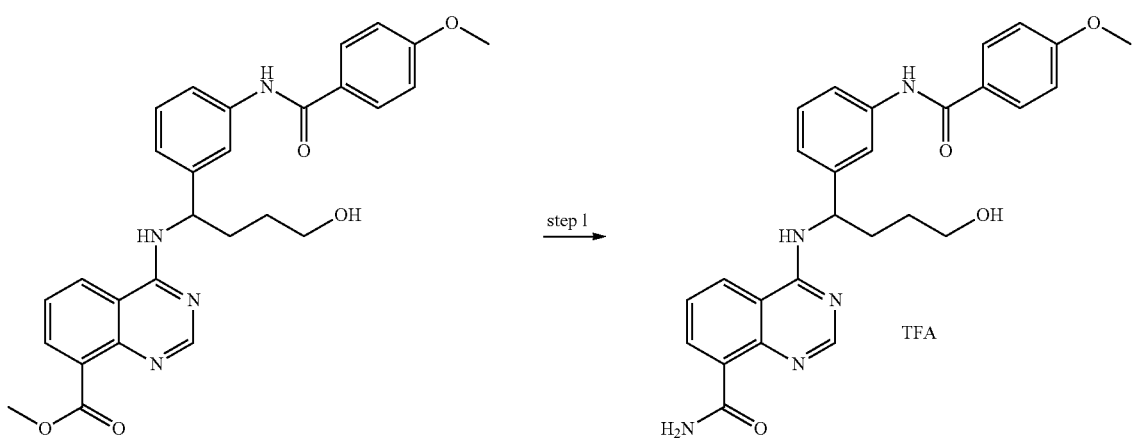

The individual steps are carried out as described in Example 542.

Analytical Methodology

Analytical LC/MS was Performed Using the Following Three Methods:

Method A: A Discovery $C^{18}$, 5 μm, 3×30 mm column was used at a flow rate of 400 μL/min, sample loop 5 μL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B: A Waters Symmetry $C^{18}$, 3.5 μm, 4.6×75 mm column at a flow rate of 1 mL/min, sample loop 10 μL, mobile phase (A) is water with 0.05% TFA, mobile phase (B) is ACN with 0.05% TFA; retention times are given in minutes. Methods details: (I) runs on a Binary Pump G1312A (Agilent) with UV/V is diode array detector G1315B (Agilent) and Agilent G1956B (SL) MS detector in ESI+mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Method C: Gradient: 4.2 min/Flow: 2 ml/min 99:01-0:100 Water+0.1% (Vol.) TFA; Acetonitril+0.1% (Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Analytical Chiral HPLC

Analytical chiral HPLC was performed using a ChiralPak AD-H column (250×4.6 mm) from Daicel Chemical Industries, Ltd. on an Agilent 1100 Series system. The method used a 5.0 μL injection volume, with a flow rate of 1 mL/min of 100% methanol for 15 min at 25° C., and UV-detection at 254 and 280 nm.

Preparative HPLC

Preparative HPLC was performed using either a Waters Atlantis $dC_{18}$ OBD™ 10 μM (30×250 mm) column or a Waters Sunfire Prep $C_{18}$ OBD 10 μM (30×250 mm) column.

The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

Examples

The working examples presented below are intended to illustrate particular embodiments of the invention, and are not intended to limit the scope of the specification or the claims in any way.

Chemical Synthesis

In this section experimental details are provided for a selection of the Example compounds listed in Tables 1 and 2 above, and synthesis intermediates thereof.

Table 1

1. Methyl 4-oxo-3,4-dihydroquinazoline-8-carboxylate

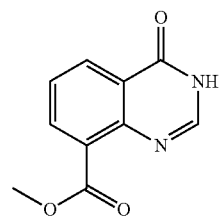

4-oxo-3,4-dihydroquinazoline-8-carboxylic acid (5.0 g, 26.3 mmol) was treated with a solution of sulfuric acid ((1.2 equivalents) in anhydrous MeOH (100 mL) under refluxing for 2 days. After cooling to rt, 2N NaOH solution was added to the reaction mixture to adjust pH~8. After removal of MeOH, methyl ester was collected by filtration, and washing with water and ethyl acetate as pale yellow solid in 94% yield.
$^1$HNMR (in DMSO): 3.84 (s, 3H), 7.42 (t, J=7.6 Hz, 1H), 7.85 (d, J=6.9 Hz, 1H), 8.16 (s, 1H), 8.20 (d, J=7.8 Hz, 1H). Mass: M+H$^+$: 205.

2. Methyl 4-{[3-(trifluoromethyl)benzyl]amino}quinazoline-8-carboxylate

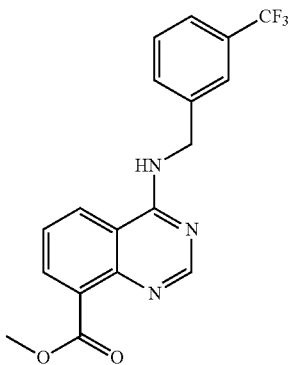 [SMILES: COC(=O)c1cccc2c(NCc3cccc(C(F)(F)F)c3)ncnc12]

To a suspension of methyl 4-oxo-3,4-dihydroquinazoline-8-carboxylate (150 mg, 0.73 mmol) in 4 mL of anhydrous DCE, POCl$_3$ (80 µL, 0.87 mmol, 1.2 equiv.) was added followed by DIPEA (630 µL, 3.6 mmol, 5.0 equiv.). The resulting mixture was stirred at 90° C. for 1-2 h. After cooling down to rt, 3-(trifluoromethyl)benzylamine (97 µL, 0.81 mmol, 1.1 equiv.) was added. The reaction mixture was stirred at 80° C. for 2-4-h. After work-up, the crude was purified by chromatography to yield the title compound in 66% yield. $^1$HNMR (in CDCl$_3$): 3.19 (s, 3H), 4.90 (s, 2H), 7.41-7.45 (m, 2H), 7.53 (t, J=8.9 Hz, 2H), 7.58 (s, 1H), 7.97 (dd, J=1.5 and 8.4 Hz, 1H), 8.04 (dd, J=1.5 and 7.3 Hz, 1H). Mass: M+H$^+$: 362.

3. 4-{[3-(trifluoromethyl)benzyl]amino}quinazoline-8-carboxylic acid

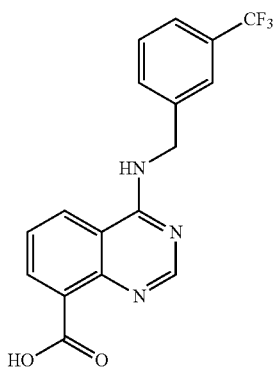 [SMILES: O=C(O)c1cccc2c(NCc3cccc(C(F)(F)F)c3)ncnc12]

A solution of methyl 4-{[3-(trifluoromethyl)benzyl]amino}quinazoline-8-carboxylate (95 mg, 0.26 mmol) in 5 mL of MeOH was treated with 2N NaOH (650 µL, 1.3 mmol, 5 equiv.) under refluxing for 5 h. After removal of MeOH, water was added to the residue and pH was adjusted to ~4 with 2N HCl. The precipitate was collected as the desired acid by filtration, and washing with water in 89% yield. $^1$HNMR (in DMSO): 4.96 (d, J=5.8 Hz, 2H), 7.56-7.61 (m, 1H), 7.64 (d, J=7.7 Hz, 1H), 7.70 (d, J=7.7 Hz, 1H), 7.74-7.78 (m, 2H), 8.54 (dd, J=1.2 and 7.4 Hz, 1H), 8.63 (dd, J=1.2 and 7.3 Hz, 1H), 8.69 (s, 1H), 9.68 (d, J=5.8 Hz, 1H). Mass: M+H$^+$: 348.

4. 4-{[3-(trifluoromethyl)benzyl]amino}quinazoline-8-carboxamide (Compound No. 134)

To a solution of 4-{[3-(trifluoromethyl)benzyl]amino}quinazoline-8-carboxylic acid (68 mg, 0.19 mmol) in 2 mL of anhydrous DMSO, CDI (47 mg, 0.29 mmol, 1.5 equiv.) was added. The resulting mixture was stirred at 50° C. for 3 h. After cooling down to rt, NH$_4$Cl (22 mg, 0.29 mmol, 1.5 equiv.) was added. The reaction mixture was stirred at rt overnight. The reaction mixture was poured into water. The white precipitate was collected as the desired product by filtration, followed by washed with water in 92% yield. $^1$HNMR (In DMSO): 4.90 (d, J=5.9 Hz, 2H), 7.56-7.69 (m, 4H), 7.74 (s, 1H), 7.86 (d, J=3.7 Hz, 1H), 8.51 (dd, J=1.5 and 8.0 Hz, 1H), 8.58 (dd, J=1.5 and 7.7 Hz, 1H), 8.59 (s, 1H), 9.24 (t, J=5.9 Hz, 1H), 10.33 (d, J=3.7 Hz, 1H). Mass: M+H$^+$: 347.

5. 4-(benzylamino)quinazoline-8-carboxamide (Compound No. 123)

The title compound was synthesized according to the procedure of Example 4 as a solid in 78% yield. $^1$HNMR (in DMSO): 4.95 (d, J=5.5 Hz, 2H), 7.33-7.43 (m, 5H), 7.85 (t, J=7.7 Hz, 1H), 8.15 (s, 1H), 8.54 (dd, J=0.7 and 7.7 Hz, 1H), 8.66 (d, J=8.0 Hz, 1H), 8.79 (s, 1H). Mass: M+H$^+$: 279.

6. 4-[(4-methoxybenzyl)amino]quinazoline-8-carboxamide (Compound No. 130)

The title compound was synthesized according to the procedure of Example 4 as a white solid in 79% yield. $^1$HNMR (in DMSO): 3.73 (s, 3H), 4.86 (d, J=5.1 Hz, 2H), 6.91 (d, J=8.8 Hz, 1H), 7.34 (d, J=8.8 Hz, 1H), 7.81 (t, J=6.8 Hz, 1H), 8.12 (s, 1H), 8.53 (d, J=7.3 Hz, 1H), 8.62 (d, J=8.0 Hz, 1H), 8.77 (s, 1H). Mass: M+H$^+$: 309.

7. 4-[(3-fluorobenzyl)amino]quinazoline-8-carboxamide (Compound No. 127)

The title compound was synthesized according to the procedure of Example 4 as an off-white solid in 81% yield. $^1$HNMR (in DMSO): 4.83 (d, J=5.9 Hz, 2H), 7.05-7.11 (m, 1H), 7.15-7.22 (m, 2H), 7.31-7.40 (m, 1H), 6.67 (t, J=5.0 Hz, 1H), 7.86 (d, J=3.7 Hz, 1H), 8.51 (dd, J=1.4 and 8.4 Hz, 1H), 8.58 (dd, J=1.4 and 7.3 Hz, 1H), 8.59 (s, 1H), 9.21 (t, J=5.9 Hz, 1H), 10.34 (d, J=3.7 Hz, 1H). Mass: M+H$^+$: 297.

8. 4-[(3,4-dichlorobenzyl)amino]quinazoline-8-carboxamide (Compound No. 129)

The title compound was synthesized according to the procedure of Example 4 as an off-white solid in 83% yield. $^1$HNMR (in DMSO): 4.80 (d, J=5.8 Hz, 2H), 7.36 (dd, J=2.0 and 8.8 Hz, 1H), 7.59 (d, J=8.4 Hz, 1H), 7.64-7.89 (m, 2H), 7.86 (d, J=3.7 Hz, 1H), 8.49 (dd, J=1.5 and 7.3 Hz, 1H), 8.58 (dd, J=1.5 and 7.4 Hz, 1H), 8.59 (s, 1H), 9.21 (t, J=5.8 Hz, 1H), 10.32 (d, J=3.7 Hz, 1H). Mass: M+H$^+$: 348.

9. 4-{[2-(4-methoxyphenyl)ethyl]amino}quinazoline-8-carboxamide (Compound No. 128)

The title compound was synthesized according to the procedure of Example 4 as a white solid in 85% yield. $^1$HNMR (in DMSO): 2.91 (t, J=7.5 Hz, 2H), 3.72 (s, 3H), 3.70-3.78 (m, 2H), 6.84-6.88 (m, 2H), 7.18 (d, J=8.4 Hz, 2H), 7.62 (t, J=7.7 Hz, 1H), 7.84 (d, J=4.0 Hz, 1H), 8.41 (dd, J=1.4 and 8.4 Hz, 1H), 8.55 (dd, J=1.4 and 7.4 Hz, 1H), 8.61 (s, 1H), 8.71 (t, J=5.5 Hz, 1H), 10.41 (d, J=3.7 Hz, 1H). Mass: M+H$^+$: 323.

10. 4-[(1-naphthylmethyl)amino]quinazoline-8-carboxamide (Compound No. 131)

The title compound was synthesized according to the procedure of Example 4 as a white solid in 54% yield. $^1$HNMR (in DMSO): 5.29 (d, J=5.1 Hz, 2H), 7.44-7.51 (m, 2H), 7.52-7.60 (m, 2H), 7.65 (t, J=8.0 Hz, 1H), 7.85-7.87 (m, 2H), 7.98 (dd, J=1.5 and 7.3 Hz, 1H), 8.20 (dd, J=1.4 and 7.4 Hz, 1H), 8.50-8.61 (m, 3H), 9.19 (t, J=5.5 Hz, 1H), 10.37 (d, J=3.7 Hz, 1H). Mass: M+H$^+$: 329.

11. 4-[(4-fluorobenzyl)amino]quinazoline-8-carboxamide (Compound No. 133)

The title compound was synthesized according to the procedure of Example 4 as an off-white solid in 78% yield. $^1$HNMR (in DMSO): 4.79 (d, J=5.9 Hz, 2H), 7.13-7.19 (m, 2H), 7.38-7.44 (m, 2H), 7.65 (t, J=7.9 Hz, 1H), 7.85 (d, J=3.6 Hz, 1H), 8.51 (dd, J=1.5 and 8.0 Hz, 1H), 8.58 (dd, J=1.5 and 8.0 Hz, 1H), 8.59 (s, 1H), 9.18 (t, J=5.9 Hz, 1H), 10.36 (d, J=3.6 Hz, 1H). Mass: M+H$^+$: 297.

12. 4-[(2-methoxybenzyl)amino]quinazoline-8-carboxamide (Compound No. 137)

The title compound was synthesized according to the procedure of Example 4 as an off-white solid in 86% yield. $^1$HNMR (in DMSO): 3.85 (s, 3H), 4.77 (d, J=5.8 Hz, 2H), 6.87 (dt, J=0.7 and 7.3 Hz, 1H), 7.02 (dd, J=0.7 and 7.7 Hz, 1H), 7.16 (dd, J=1.6 and 7.3 Hz, 1H), 7.24 (dt, J=1.7 and 7.7 Hz, 1H), 7.65 (t, J=8.0 Hz, 1H), 7.85 (d, J=3.9 Hz, 1H), 8.55-8.59 (m, 3H), 9.02 (t, J=5.7 Hz, 1H), 10.38 (d, J=3.7 Hz, 1H). Mass: M+H$^+$: 309.

13. 4-[(2-methylbenzyl)amino]quinazoline-8-carboxamide (Compound No. 135)

The title compound was synthesized according to the procedure of Example 4 as an off-white solid in 90% yield. $^1$HNMR (in DMSO): 2.37 (s, 3H), 4.78 (d, J=5.6 Hz, 2H), 7.09-7.25 (m, 4H), 7.65 (t, J=7.7 Hz, 1H), 7.85 (d, J=3.6 Hz, 1H), 8.55-8.60 (m, 3H), 9.05 (t, J=5.8 Hz, 1H), 10.37 (d, J=3.6 Hz, 1H). Mass: M+H$^+$: 293.

14. 4-morpholin-4-ylquinazoline-8-carboxamide (Compound No. 136)

The title compound was synthesized according to the procedure of Example 4 and purified by preparative HPLC as white solid in 47% yield. $^1$HNMR (in DMSO): 3.86 (t, J=4.7 Hz, 2H), 4.30 (t, J=4.6 Hz, 2H), 7.78 (t, J=8.0 Hz, 1H), 8.37 (d, J=8.1 Hz, 1H), 8.48 (d, J=7.8 Hz, 1H), 8.67 (s, 1H). Mass: M+H$^+$: 259.

15. 4-(2,3-dihydro-1H-inden-1-ylamino)quinazoline-8-carboxamide (Compound No. 138)

The title compound was synthesized according to the procedure of Example 4 as an off-white solid in 90% yield. $^1$HNMR (in DMSO): 2.07-2.16 (m, 1H), 2.51-2.62 (m, 1H), 2.88-2.96 (m, 1H), 3.01-3.11 (m, 1H), 6.08 (quart, J=8.0 Hz, 1H), 7.17 (t, J=7.1 Hz, 1H), 7.7.22-7.28 (m, 2H), 7.32 (d, J=7.67 Hz, 1H), 7.60 (t, J=7.7 Hz, 1H), 7.86 (d, J=3.7 Hz, 1H), 8.52-8.59 (m, 2H), 8.65 (s, 1H), 8.82 (d, J=8.0 Hz, 1H), 10.42 (d, J=3.7 Hz, 1H). Mass: M+H$^+$:305.

16. 4-[(tetrahydrofuran-2-ylmethyl)amino]quinazoline-8-carboxamide (Compound No. 139)

The title compound was synthesized according to the procedure of Example 4 and purified by pre-HPLC as white solid in 87% yield. $^1$HNMR (in DMSO): 1.60-1.69 (m, 1H), 1.78-1.91 (m, 2H), 1.95-2.02 (m, 1H), 3.63-3.69 (m, 1H), 3.71-3.76 (m, 2H), 3.77-3.84 (m, 1H), 4.11-4.19 (m, 1H), 7.81 (t, J=7.5 Hz, 1H), 8.11 (br, 1H), 8.53 (dd, J=1.5 and 7.7 Hz, 1H), 8.64 (d, J=8.4 Hz, 1H), 8.75 (s, 1H). Mass: M+H$^+$: 273.

17. 4-[(pyridin-2-ylmethyl)amino]quinazoline-8-carboxamide (Compound No. 142)

The title compound was synthesized according to the procedure of Example 4 and purified by pre-HPLC as white solid in 88% yield. $^1$HNMR (in DMSO): 5.06 (d, J=5.9 Hz, 2H), 7.39 (dd, J=5.1 and 7.0 Hz, 1H), 7.51 (d, J=7.7 Hz, 1H), 7.84-7.91 (m, 2H), 8.17 (s, 1H), 8.50-8.58 (m, 2H), 8.69 (d, J=7.7 Hz, 1H), 8.76 (s, 1H). Mass: M+H$^+$: 280.

18. 4-[(2,4-difluorobenzyl)amino]quinazoline-8-carboxamide (Compound No. 140)

The title compound was synthesized according to the procedure of Example 4 as a white solid in 93% yield. $^1$HNMR (in DMSO): 4.80 (d, J=5.5 Hz, 2H), 7.03 (dt, J=2.2 and 8.8 Hz, 1H), 7.26(dt, J=2.6 and 10.5 Hz, 1H), 7.45 (dt, J=6.6 and 8.8 Hz, 1H), 7.66 (t, J=8.1 Hz, 1H), 7.85 (t, J=3.7 Hz, 1H), 8.52 (dd, J=1.5 and 8.1 Hz, 1H), 8.59 (dd, J=1.5 and 7.7 Hz, 1H), 8.60 (s, 1H), 9.12 (t, J=5.5 Hz, 1H), 10.33 (d, J=3.7 Hz, 1H). Mass: M+H$^+$: 315.

19. 4-[(2-chlorobenzyl)amino]quinazoline-8-carboxamide (Compound No. 141)

The title compound was synthesized according to the procedure of Example 4 as a white solid in 90% yield. $^1$HNMR (in DMSO): 4.80 (d, J=5.5 Hz, 2H), 7.25-7.36 (m, 3H), 7.49 (dd, J=2.2 and 8.1 Hz, 1H), 7.68 (t, J=7.9 Hz, 1H), 7.85 (d, J=3.5 Hz, 1H), 8.55-8.61 (m, 3H), 9.17 (t, J=5.4 Hz, 1H), 10.33 (d, J=3.3 Hz, 1H). Mass: M+H$^+$: 313.

20. 4-{[2-(trifluoromethyl)benzyl]amino}quinazoline-8-carboxamide (Compound No. 143)

The title compound was synthesized according to the procedure of Example 4 as a white solid in 93% yield. $^1$HNMR (in DMSO): 4.80 (d, J=5.1 Hz, 2H), 7.46-7.51 (m, 2H), 7.60 (t, J=7.5 Hz, 1H), 7.70 (t, J=7.9 Hz, 1H), 7.77 (d, J=7.3 Hz, 1H), 7.86 (d, J=3.1 Hz, 1H), 8.54-8.62(m, 3H), 9.21 (t, J=5.3 Hz, 1H), 10.32 (d, J=3.6 Hz, 1H). Mass: M+H$^+$: 347.

21. 4-[(1,3-benzodioxol-5-ylmethyl)amino]quinazoline-8-carboxamide (Compound No. 144)

The title compound was synthesized according to the procedure of Example 4 as an off-white solid in 92% yield. $^1$HNMR (in DMSO): 4.71 (d, J=5.9 Hz, 2H), 5.97 (s, 2H), 6.85 (d, J=1.0 Hz, 2H), 6.96 (s, 1H), 7.64 (t, J=7.9 Hz, 1H), 7.85 (d, J=3.8 Hz, 1H), 8.49 (dd, J=1.5 and 8.0 Hz, 1H), 8.58 (dd, J=1.5 and 7.7 Hz, 1H), 8.59 (s, 1H), 9.11 (t, J=5.9 Hz, 1H), 10.37 (d, J=4.0 Hz, 1H). Mass: M+H$^+$: 323.

22. 4-[(3-methoxybenzyl)amino]quinazoline-8-carboxamide (Compound No. 145)

The title compound was synthesized according to the procedure of Example 4 as beige solid in 81% yield. $^1$HNMR (in DMSO): 3.72 (s, 3H), 4.77 (d, J=5.9 Hz, 2H), 6.79-6.84 (m, 1H), 6.92-6.94 (m, 2H), 7.24 (t, J=8.3 Hz, 1H), 7.64 (t, J=7.9 Hz, 1H), 7.86 (d, J=3.7 Hz, 1H), 8.51 (dd, J=1.4 and 8.4 Hz, 1H), 8.57 (dd, J=1.4 and 7.7 Hz, 1H), 8.58 (s, 1H), 9.17 (t, J=5.9 Hz, 1H), 10.38 (d, J=3.7 Hz, 1H). Mass: M+H$^+$: 309.

23. 4-{[4-(trifluoromethyl)benzyl]amino}quinazoline-8-carboxamide (Compound No. 146)

The title compound was synthesized according to the procedure of Example 4 as an off-white solid in 88% yield. $^1$HNMR (in DMSO): 4.89 (d, J=5.5 Hz, 2H), 7.58 (d, J=8.0 Hz, 2H), 7.65-7.70 (m, 3H), 7.87 (d, J=3.7 Hz, 1H), 8.52 (dd, J=1.5 and 8.1 Hz, 1H), 8.57 (s, 1H), 8.59 (dd, J=1.5 and 7.3 Hz, 1H), 9.29 (t, J=5.7 Hz, 1H), 10.33 (d, J=3.97 Hz, 1H). Mass: M+H$^+$: 347.

24. 4-[(2-fluorobenzyl)amino]quinazoline-8-carboxamide (Compound No. 148)

The title compound was synthesized according to the procedure of Example 4 as an off-white solid in 92% yield. $^1$HNMR (in DMSO): 4.85 (d, J=5.5 Hz, 2H), 7.14 (dt, J=1.1 and 7.3 Hz, 1H), 7.18-7.23 (m, 1H), 7.29-7.35 (m, 1H), 7.39 (dt, J=1.4 and 8.1 Hz, 1H), 7.66 (t, J=7.9 Hz, 1H), 7.85 (d, J=3.6 Hz, 1H), 8.53 (dd, J=1.5 and 8.1 Hz, 1H), 8.58 (s, 1H), 8.59 (dd, J=1.5 and 7.7 Hz, 1H), 9.14 (t, J=5.6 Hz, 1H), 10.34 (d, J=3.5 Hz, 1H). Mass: M+H$^+$: 297.

25. 4-[(3-methylbenzyl)amino]quinazoline-8-carboxamide (Compound No. 147)

The title compound was synthesized according to the procedure of Example 4 as an off-white solid in 92% yield. $^1$HNMR (in DMSO): 2.28 (s, 3H), 4.77 (d, J=5.9 Hz, 2H), 7.05 (d, J=7.0 Hz, 1H), 7.12-7.21 (m, 3H), 7.64 (t, J=7.9 Hz, 1H), 7.85 (d, J=3.6 Hz, 1H), 8.52 (dd, J=1.4 and 8.4 Hz, 1H), 8.57 (dd, J=1.4 and 7.3 Hz, 1H), 8.58 (s, 1H), 9.15 (t, J=5.8 Hz, 1H), 10.38 (d, J=3.7 Hz, 1H). Mass: M+H$^+$: 293.

26. tert-butyl [4-({[8-(aminocarbonyl)quinazolin-4-yl]amino}methyl)phenyl]carbamate (Compound No. 149)

The title compound was synthesized according to the procedure of Example 4 as an off-white solid in 95% yield. $^1$HNMR (in DMSO): 1.46 (s, 9H), 4.74 (d, J=5.5 Hz, 2H), 7.25 (d, J=8.7 Hz, 2H), 7.39 (d, J=8.5 Hz, 2H), 7.63 (t, J=7.9 Hz, 1H), 7.83 (d, J=4.0 Hz, 1H), 8.49 (dd, J=1.4 and 8.4 Hz, 1H), 8.55-8.58 (m, 2H), 9.11 (t, J=5.5 Hz, 1H), 9.31 (s, 1H), 10.38 (d, J=4.0 Hz, 1H). Mass: M+H$^+$: 394.

27. 4-[(4-hydroxybenzyl)amino]quinazoline-8-carboxamide (Compound No. 150)

The title compound was synthesized according to the procedure of Example 4 as an off-white solid in 93% yield. $^1$HNMR (in DMSO): 4.71 (d, J=5.9 Hz, 2H), 6.71 (d, J=8.4 Hz, 2H), 7.18 (d, J=8.4 Hz, 2H), 7.62 (t, J=7.7 Hz, 1H), 7.84 (d, J=4.0 Hz, 1H), 8.49 (dd, J=1.8 and 8.4 Hz, 1H), 8.56 (dd, J=1.8 and 7.7 Hz, 2H), 8.58 9s, 1H), 9.07 (t, J=5.8 Hz, 1H), 9.31 (s, 1H), 10.39 (d, J=4.0 Hz, 1H). Mass: M+H$^+$: 295.

28. 4-{[4-chloro-3-(trifluoromethyl)benzyl]amino}quinazoline-8-carboxamide (Compound No. 156

The title compound was synthesized according to the procedure of Example 4 as off-white solid in 96% yield. $^1$HNMR (in DMSO): 4.86 (d, J=5.5 Hz, 2H), 7.67-7.69 (m, 3H), 7.86 (d, J=3.7 Hz, 1H), 7.89 (s, 1H), 8.49 (dd, J=1.5 and 8.3 Hz, 1H), 8.58 (s, 1H), 8.59 (dd, J=1.5 and 7.3 Hz, 1H), 9.23 (t, J=5.8 Hz, 1H), 10.32 (d, J=3.6 Hz, 1H). Mass: M+H$^+$: 381.

29. 4-{[3,5-bis(trifluoromethyl)benzyl]amino}quinazoline-8-carboxamide (Compound No. 157)

The title compound was synthesized according to the procedure of Example 4 as off-white solid in 83% yield. $^1$HNMR (in DMSO): 4.98 (d, J=5.5 Hz, 2H), 7.87 (t, J=7.9 Hz, 1H), 7.86 (d, J=3.4 Hz, 1H), 8.01 (s, 1H), 8.09 (s, 2H), 8.49 (dd, J=1.5 nad 8.4 Hz, 1H), 8.59 (dd, J=1.5 and 7.3 Hz, 1H), 8.60 (s, 1H), 9.26 (t, J=5.8 Hz, 1H), 10.30 (d, J=3.6 Hz, 1H). Mass: M+H$^+$: 415.

30. 4-{[(1S)-1-phenylethyl]amino}quinazoline-8-carboxamide (Compound No. 132)

The title compound was synthesized according to the procedure of Example 4 as an off-white solid in 80% yield. $^1$HNMR (in DMSO): 1.61 (d, J=7.3 Hz, 3H), 5.64 (q, J=7.3 Hz, 1H), 7.23 (t, J=7.3 Hz, 1H), 7.32 (t, J=7.4 Hz, 2H), 7.44 (d, J=7.3 Hz, 2H), 7.66 (t, J=7.8 Hz, 1H), 7.83 (d, J=3.3 Hz, 1H), 8.53 (s, 1H), 8.58 (d, J=6.2 Hz, 1H), 8.68 (d, J=8.4 Hz, 1H), 8.80 (d, J=7.7 Hz, 1H), 10.35 (d, J=3.3 Hz, 1H). Mass: M+H$^+$: 293.

31. 4-{[(1R)-1-phenylethyl]amino}quinazoline-8-carboxamide (Compound No. 171)

The title compound was synthesized according to the procedure of Example 4 and purified by pre-HPLC to give a white solid as TFA salt. $^1$HNMR (in MeOD): 1.74 (d, J=7.0 Hz, 3H), 5.90 (q, J=7.0 Hz, 1H), 7.24-7.29 (m, 1H), 7.32-7.37 (m, 2H), 7.48 (d, J=7.4 Hz, 2H), 7.83 (t, J=8.1 Hz, 1H), 8.51 (dd, J=1.1 and 7.7 Hz, 1H), 8.69 (dd, J=1.1 and 8.4 Hz, 1H), 8.71 (s, 1H). Mass: M+H$^+$: 293.

32. 4-[(4-aminobenzyl)amino]quinazoline-8-carboxamide (Compound No. 151)

The title compound was prepared as light yellow solid in 95% yield by treating tert-butyl [4-({[8-(aminocarbonyl)quinazolin-4-yl]amino}methyl)phenyl]carbamate with 2N HCl/ether in DCM overnight. The precipitate was filtered, washed with ether and dried. Mass: M+H$^+$: 294.

33. tert-butyl [3-({[8-(aminocarbonyl)quinazolin-4-yl]-amino}methyl)phenyl]carbamate (Compound No. 155)

The title compound was synthesized according to the procedure of Example 4 as an off-white solid in 98% yield. Mass: M+H$^+$: 394.

34. 4-[(3-hydroxybenzyl)amino]quinazoline-8-carboxamide (Compound No. 154)

The title compound was synthesized according to the procedure of Example 4 as an off-white solid in 78% yield. Mass: M+H$^+$: 295.

35. 4-({4-[(4-fluorobenzoyl)amino]benzyl}amino)quinazoline-8-carboxamide (Compound No. 152)

4-fluorobenzoyl chloride (220 µL, 0.5 M in anhydrous DCM, 0.10 mmol, 1.1 equiv.) was added to a solution of 4-[(4-aminobenzyl)amino]quinazoline-8-carboxamide (30 mg, 0.09 mmol, 1.0 equiv.) and triethylamine (38 µL, 0.27 mmol, 3.0 equiv.) in anhydrous DCM (2 mL). The resulting mixture was stirred at rt overnight. Ether (2 mL) was added. The precipitate was filtered, washed with ether and DCM to yield the title compound in 72% yield. Mass: M+H$^+$: 416.

36. 4-[(3-aminobenzyl)amino]quinazoline-8-carboxamide (Compound No. 153)

The title compound was prepared as light yellow solid in 97% yield by treating tert-butyl [3-({[8-(aminocarbonyl)quinazolin-4-yl]amino}methyl)phenyl]carbamate with 2N HCl/ether in DCM overnight. The precipitate was filtered, washed with ether and dried. Mass: M+H$^+$: 294.

37. 4-({3-[(4-fluorobenzoyl)amino]benzyl}amino)quinazoline-8-carboxamide (Compound No. 159)

4-fluorobenzoyl chloride (240 µL, 0.5 M in anhydrous DCM, 0.11 mmol, 1.1 equiv.) was added to a solution of 4-[(3-aminobenzyl)amino]quinazoline-8-carboxamide (32 mg, 0.1 mmol, 1.0 equiv.) and triethylamine (40 µL, 0.3 mmol, 3.0 equiv.) in anhydrous DCM (2 mL). The resulting mixture was stirred at it overnight. Ether (2 mL) was added. The precipitate was filtered, washed with ether and DCM to yield the title compound in 77% yield. Mass: M+H$^+$: 416.

38. 4-({3-[(phenylsulfonyl)amino]benzyl}amino)quinazoline-8-carboxamide (Compound No. 161)

Benzenesulfonyl chloride (240 µL, 0.5 M in anhydrous DCM, 0.11 mmol, 1.1 equiv.) was added to a solution of 4-[(3-aminobenzyl)amino]quinazoline-8-carboxamide (32 mg, 0.1 mmol, 1.0 equiv.) and triethylamine (40 µL, 0.3 mmol, 3.0 equiv.) in anhydrous DCM (2 mL). The resulting mixture was stirred at rt overnight. The title compound was obtained by pre-HPLC in 36% yield. Mass: M+H$^+$: 434.

39. 4-({4-[(phenylsulfonyl)amino]benzyl}amino)quinazoline-8-carboxamide (Compound No. 160)

Benzenesulfonyl chloride (240 µL, 0.5 M in anhydrous DCM, 0.11 mmol, 1.1 equiv.) was added to a solution of 4-[(4-aminobenzyl)amino]quinazoline-8-carboxamide (32 mg, 0.1 mmol, 1.0 equiv.) and triethylamine (40 µL, 0.3 mmol, 3.0 equiv.) in anhydrous DCM (2 mL). The resulting mixture was stirred at rt overnight. The title compound was obtained by pre-HPLC in 34% yield. Mass: M+H$^+$: 434.

40. 4-({4-[(anilinocarbonyl)amino]benzyl}amino)quinazoline-8-carboxamide (Compound No. 163)

Phenyl isocyanate (240 µL, 0.5 M in anhydrous DCM, 0.11 mmol, 1.1 equiv.) was added to a solution of 4-[(4-aminobenzyl)amino]quinazoline-8-carboxamide (32 mg, 0.1 mmol, 1.0 equiv.) and triethylamine (40 µL, 0.3 mmol, 3.0 equiv.) in anhydrous DCM (2 mL). The resulting mixture was stirred at it overnight. The title compound was obtained by pre-HPLC in 27% yield. Mass: M+H$^+$: 413.

41. 4-({3-[(anilinocarbonyl)amino]benzyl}amino)quinazoline-8-carboxamide (Compound No. 162)

Phenyl isocyanate (240 µL, 0.5 M in anhydrous DCM, 0.11 mmol, 1.1 equiv.) was added to a solution of 4-[(3-aminobenzyl)amino]quinazoline-8-carboxamide (32 mg, 0.1 mmol, 1.0 equiv.) and triethylamine (40 µL, 0.3 mmol, 3.0 equiv.) in anhydrous DCM (2 mL). The resulting mixture was stirred at it overnight. The title compound was obtained by pre-HPLC in 34% yield. Mass: M+H$^+$: 413.

42. 4-{[4-(aminocarbonyl)benzyl]amino}quinazoline-8-carboxamide (Compound No. 167)

The title compound was synthesized according to the procedure of Example 4 as an off-white solid in 89% yield. Mass: M+H$^+$: 322.

43. 4-[(1-benzofuran-5-ylmethyl)amino]quinazoline-8-carboxamide (Compound No. 169)

The title compound was synthesized according to the procedure of Example 4 and purified by pre-HPLC as an off-white solid in 54% yield. Mass: M+H$^+$: 319.

44. 4-[(2,3-dihydro-1-benzofuran-5-ylmethyl)amino]quinazoline-8-carboxamide (Compound No. 168)

The title compound was synthesized according to the procedure of Example 4 and purified by pre-HPLC as a white solid in 63% yield. Mass: M+H$^+$: 321.

45. 4-{[3-chloro-4-(pyridin-2-ylmethoxy)phenyl]amino}quinazoline-8-carboxamide (Compound No. 183)

The title compound was synthesized according to the procedure of Example 4 in 79% yield. Mass: M+H$^+$: 406.

46. 4-[(3-chloro-4-fluorophenyl)amino]quinazoline-8-carboxamide (Compound No. 126)

The title compound was synthesized according to the procedure of Example 4 in 59% yield. Mass: M+H$^+$: 317.

47. 4-[(3-bromophenyl)amino]quinazoline-8-carboxamide (Compound No. 16)

The title compound was synthesized according to the procedure of Example 4 in 94% yield. Mass: M+H$^+$: 344.

48. 4-[(3-ethynylphenyl)amino]quinazoline-8-carboxamide (Compound No. 124)

The title compound was synthesized according to the procedure of Example 4 in 84% yield. Mass: M+H$^+$: 289.

49. 4-{[4-(benzoylamino)phenyl]amino}quinazoline-8-carboxamide (Compound No. 122)

The title compound was synthesized according to the procedure of Example 4 with pre-HPLC purification in 44% yield. Mass: M+H$^+$: 384.

50. 4-((S)-2-Azido-1-phenyl-ethylamino)-quinazoline-8-carboxylic acid methyl ester

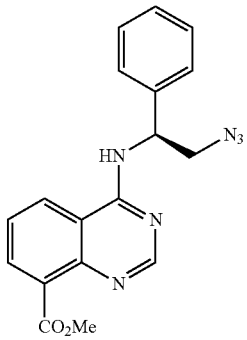 [SMILES: COC(=O)c1cccc2c(N[C@H](CN=[N+]=[N-])c3ccccc3)ncnc12]

4-Chloroquinazoline 8-methylcarboxylate (0.58 g, 2.60 mmol) and (S)-2-Azido-1-phenyl-ethylamine (0.57 g, 2.86 mmol) was combined in dry THF (15 mL) under $N_2$. Diisopropylethylamine (1.01 g, 1.4 mL, 7.80 mmol) was added and the solution stirred at 50° C. for 3 hours. The reaction was cooled, diluted with water and extracted three times with ethyl acetate. The combined extracts were washed with saturated brine, dried over $MgSO_4$ and the solvent removed under reduced pressure. Purified by chromatography on silica (0-5% methanol in $CH_2Cl_2$) to give the product as a frothy solid (0.77 g, 85%). 1H NMR (400 MHz, DMSO-$d_6$) δ ppm 3.74 (dd, J=12.57, 4.91 Hz, 1 H) 3.86 (s, 3 H) 3.87-3.91 (m, 1 H) 5.70-5.82 (m, 1 H) 7.29 (d, J=7.37 Hz, 1 H) 7.31-7.40 (m, 3 H) 7.52 (d, J=7.22 Hz, 2 H) 7.64 (dd, J=8.18, 7.39 Hz, 1 H) 7.97 (dd, J=7.22, 1.22 Hz, 1 H) 8.48 (s, 1 H) 8.60 (dd, J=8.40, 1.17 Hz, 1 H) 8.82 (d, J=8.30 Hz, 1 H).

51. 4-((S)-2-Azido-1-phenyl-ethylamino)-quinazoline-8-carboxylic acid amide (Compound No. 59)

To a solution of 4-((S)-2-Azido-1-phenyl-ethylamino)-quinazoline-8-carboxylic acid methyl ester (0.5 g, 1.48 mmol) in isopropanol (0.5 mL) and THF (0.5 mL) was added ammonium hydroxide (28-30% solution, 7.5 mL). The reaction was stirred for 24 hours then diluted with water. Solid formed collected by filtration and dried under vacuum (0.28 g, 57%). 1H NMR (400 MHz, DMSO-$d_6$) δ ppm 3.72-3.81 (m, 1 H) 3.91 (dd, J=12.57, 9.98 Hz, 1 H) 5.73-5.85 (m, 1 H) 7.25-7.32 (m, 1 H) 7.36 (t, J=7.47 Hz, 2 H) 7.52 (d, J=7.27 Hz, 2 H) 7.71 (t, J=7.86 Hz, 1 H) 7.77-7.88 (m, 1 H) 8.60 (dd, J=7.47, 1.32 Hz, 1 H) 8.58 (s, 1 H) 8.66 (dd, J=8.32, 1.39 Hz, 1 H) 8.95 (d, J=8.30 Hz, 1 H) 10.26 (br. s., 1 H).

52. 4-((S)-2-Amino-1-phenyl-ethylamino)-quinazoline-8-carboxylic acid amide (Compound No. 65)

4-((S)-2-Azido-1-phenyl-ethylamino)-quinazoline-8-carboxylic acid amide ((0.28 g, 0.84 mmol) and palladium on carbon (5%, wet type, 56 mg) were combined in ethanol (5 mL) and chloroform (1 mL) and stirred under an atmosphere of hydrogen for 48 hours. The solution was filtered, rinsed with methanol and the solvent removed under reduced pressure. The sample was redissolved in THF/methanol and hydrogen chloride (4M solution in dioxane, 1 mL) was added. The solid formed was collected by filtration and purified by recrystallization from methanol/ethyl acetate (131 mg, 51%).

1H NMR (400 MHz, DMSO-$d_6$) δ ppm 3.27-3.40 (m, 1 H) 3.84-3.98 (m, 1 H) 5.99 (br. s., 1 H) 7.29-7.36 (m, 1 H) 7.39 (t, J=7.39 Hz, 2 H) 7.60 (d, J=7.32 Hz, 2 H) 7.88 (s, 1 H) 8.16 (br. s., 1 H) 8.43 (br. s., 3 H) 8.59 (d, J=0.83 Hz, 1 H) 8.80 (s, 1 H) 9.29 (br. s., 1 H).

53. 4-{[3-(trifluoromethyl)benzyl]amino}quinoline-8-carbonitrile

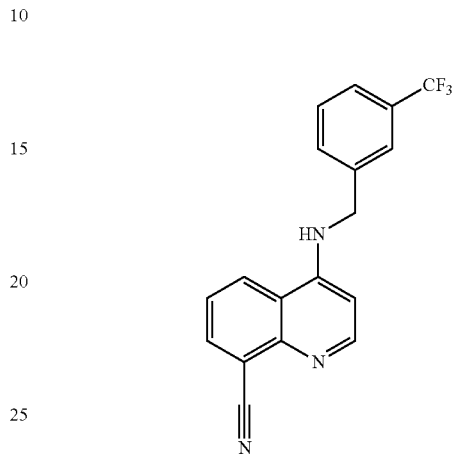

To a suspension of 4-bromoquinoline-8-carbonitrile (100 mg, 0.43 mmol) in 4 mL of iso-propanol, 3-(trifluoromethyl)benzylamine (150 mg, 0.85 mmol, 2.0 equiv.) and $K_2CO_3$ (119 mg, 0.85 mmol, 2.0 equiv.) were added. The resulting mixture was stirred at 110° C. 2 days. After work-up, the crude was purified by preparative HPLC to yield the title compound as TFA salt in 20% yield. $^1$HNMR (in MeOD): 4.96 (s, 2H), 6.96 (d, J=7.0 Hz, 1H), 7.58-7.71 (m, 3H), 7.76 (s, 1H), 7.86 (dd, J=7.7 and 8.8 Hz, 1H), 8.39 (d, J=7.3 Hz, 1H), 8.44 (dd, J=1.1 and 7.3 Hz, 1H), 8.75 (dd, J=1.1 and 8.8 Hz, 1H). Mass: M+H$^+$: 328.

54. 4-{[3-(trifluoromethyl)benzyl]amino}quinoline-8-carboxamide (Compound No. 170)

To a solution of 4-{[3-(trifluoromethyl)benzyl]amino}quinoline-8-carbonitrile (20 mg, 0.05 mmol) in 2 mL of dioxane, 2N LiOH solution (250 μL, 0.5 mmol, 10 equiv.) was added. The resulting mixture was heated at 90° C. by microwave for 20 min. After work-up, the crude was purified by preparative HPLC to yield the title compound as a white solid in 34% yield. $^1$HNMR (in DMSO): 4.92 (d, J=5.8 Hz, 2H), 6.93 (d, J=7.4 Hz, 1H), 7.62 (t, J=7.7 Hz, 1H), 7.69 (d, J=8.1 Hz, 1H), 7.74 (d, J=7.3 Hz, 1H), 7.85 9s, 1H), 7.87 (d, J=8.1 Hz, 1H), 8.22 (s, 1H), 8.48-8.54 (m, 2H), 8.75 (s, 1H), 8.80 (d, J=8.4 Hz, 1H), 10.06 (s, 1H). Mass: M+H$^+$: 346.

55. 4-[(1,3-benzodioxol-5-ylmethyl)amino]quinoline-8-carboxamide (Compound No. 158)

The title compound was synthesized according to the procedure of Example 54 as a white solid in 57% yield. $^1$HNMR (in DMSO): 4.50 (d, J=5.8 Hz, 2H), 5.97 (s, 2H), 6.50 (d, J=5.5 Hz, 1H), 6.84-6.89 (m, 2H), 6.97 (s, 1H), 7.57 (t, J=7.9 Hz, 1H), 7.75 (s, 1H), 8.13 (s, 1H), 8.41 (d, J=5.5 Hz, 1H), 8.50 (d, J=7.7 Hz, 2H). Mass: M+H$^+$: 322.

56. 4-[(3-fluorobenzyl)amino]quinoline-8-carboxamide

The title compound was synthesized according to the procedure of Example 54 as a white solid in 29% yield. ¹HNMR (in MeOD): 4.84 (s, 2H), 6.85 (d, J=7.0 Hz, 1H), 7.05 (dt, J=2.1 and 8.4 Hz, 1H), 7.15-7.19 (m, 1H), 7.24 (d, J=8.4 Hz, 1H), 7.40 (dt, J=5.9 and 8.1 Hz, 1H), 7.82 (dd, J=7.7 and 8.4 Hz, 1H), 8.41 (d, J=7.0 Hz, 1H), 8.47 (dd, J=1.1 and 7.7 Hz, 1H), 8.64 (dd, J=1.1 and 8.4 Hz, 1H). Mass: M+H⁺: 296.

57. 6-nitro-4-oxo-3,4-dihydroquinazoline-8-carboxylic acid

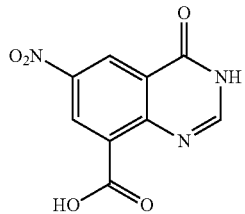 [SMILES: O=C(O)c1cc([N+](=O)[O-])cc2c(=O)[nH]cnc12]

To a suspension of 4-oxo-3,4-dihydroquinazoline-8-carboxylic acid (500 mg, 2.63 mmol) in 3 mL of sulfuric acid at 0° C., fuming nitric acid was added portionly. The resulting mixture was then stirred at 60° C. overnight. After cooling to rt, the reaction mixture was poured into ice-water slowly. The yellow precipitate was collected by filtration, and washing with water as the desired product in 84% yield. ¹HNMR (in DMSO): 8.60 (s, 1H), 8.89 (d, J=2.6 Hz, 1H), 8.91 (d, J=2.6 Hz, 1H). Mass: M+H⁺: 236.

58. Methyl 6-nitro-4-oxo-3,4-dihydroquinazoline-8-carboxylate

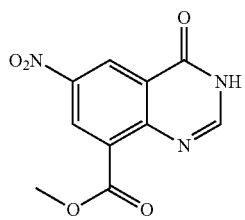 [SMILES: COC(=O)c1cc([N+](=O)[O-])cc2c(=O)[nH]cnc12]

6-nitro-4-oxo-3,4-dihydroquinazoline-8-carboxylic acid (500 mg, 2.13 mmol) was treated with a solution of sulfuric acid ((1.2 equiv.) in anhydrous MeOH (10 mL) under refluxing overnight. After cooling to rt, 2N NaOH solution was added to the reaction mixture to adjust pH~8. After removal of MeOH, methyl ester was collected by filtration, and washing with water and as yellow solid in 84% yield. ¹HNMR (in DMSO): 3.91 (s, 3H), 8.38 (s, 1H), 8.74 (d, J=2.6 Hz, 1H), 8.88 (d, J=2.6 Hz, 1H). Mass: M+H⁺: 250.

59. Methyl 4-{[4-chloro-3-(trifluoromethyl)benzyl]amino}-6-nitroquinazoline-8-carboxylate

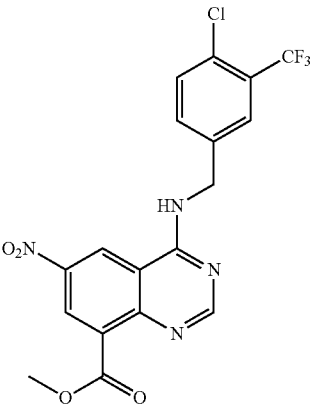 [SMILES: COC(=O)c1cc([N+](=O)[O-])cc2c(NCc3ccc(Cl)c(C(F)(F)F)c3)ncnc12]

To a solution of methyl 6-nitro-4-oxo-3,4-dihydroquinazoline-8-carboxylate (250 mg, 1.0 mmol) in 5 mL of anhydrous DCE, POCl₃ (110 μL, 1.2 mmol, 1.2 equiv.) was added followed by DIPEA (870 μL, 5.0 mmol, 5.0 equiv.). The resulting mixture was stirred at 90° C. for 1 h. After cooling down to rt, 4-chloro-3-(trifluoromethyl)benzylamine (230 mg, 1.1 mmol, 1.1 equiv.) was added. The reaction mixture was stirred at 80° C. for 3 h. After work-up, the crude was purified by flash chromatography to yield the title compound in 46% yield. ¹HNMR (in DMSO): 3.91 (s, 3H), 4.88 (d, J=5.9 Hz, 2H), 7.65-7.71 (m, 2H), 7.91 (s, 1H), 8.64 (s 1H), 8.68 (d, J=2.2 Hz, 1H), 9.49 (d, J=2.4 Hz, 1H), 9.70 (t, J=5.7 Hz, 1H). Mass: M+H⁺: 441.

60. 4-{[4-chloro-3-(trifluoromethyl)benzyl]amino}-6-nitroquinazoline-8-carboxylic acid

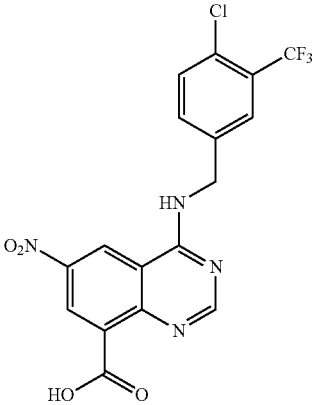 [SMILES: O=C(O)c1cc([N+](=O)[O-])cc2c(NCc3ccc(Cl)c(C(F)(F)F)c3)ncnc12]

Methyl 4-{[4-chloro-3-(trifluoromethyl)benzyl]amino}-6-nitroquinazoline-8-carboxylate (190 mg, 0.43 mmol) was treated with a mixture of 650 μL of THF and 650 μL of 2N LiOH (1.3 mmol, 3 equiv.)) at rt for 2 h. Water was added and pH was adjusted to ~4 with 2N HCl. The precipitate was collected as the desired acid by filtration, and washing with water in 97% yield. ¹HNMR (in DMSO): 4.95 (s, 2H), 7.69-7.74 (m, 2H), 7.94 (d, J=1.4 Hz, 1H), 8.81 (s, 1H), 9.02 (d, J=2.2 Hz, 1H), 9.62 (d, J=2.5 Hz, 1H). Mass: M+H⁺: 427.

61. 4-{[4-chloro-3-(trifluoromethyl)benzyl]amino}-6-nitroquinazoline-8-carboxamide (Compound No. 166)

To a solution of 4-{[4-chloro-3-(trifluoromethyl)benzyl]amino}-6-nitroquinazoline-8-carboxylic acid (40 mg, 0.09 mmol) in 1 mL of anhydrous DMSO, CDI (22 mg, 0.14 mmol, 1.5 equiv.) was added. The resulting mixture was stirred at 50° C. for 3 h. After cooling down to rt, $NH_4Cl$ (11 mg, 0.14 mmol, 1.5 equiv.) was added. The reaction mixture was stirred at it overnight. The reaction mixture was poured into water. The yellow precipitate was collected as the desired product by filtration, followed by washed with water in 96% yield. $^1$HNMR (in DMSO): 4.90 (d, J=5.5 Hz, 2H), 7.66-7.72 (m, 2H), 7.93 (s, 1H), 8.19 (d, J=3.3 Hz, 1H), 8.72 (s, 1H), 9.17 (d, J=2.6 Hz, 1H), 9.53 (d, J=2.6 Hz, 1H), 9.87 (t, J=5.8 Hz, 1H), 10.22 (d, J=3.3 Hz, 1H). Mass: M+H$^+$: 426.

62. 6-amino-4-{[4-chloro-3-(trifluoromethyl)benzyl]amino}quinazoline-8-carboxamide (Compound No. 172)

Zinc powder (115 mg, 1.76 mmol, 5.0 equiv.) was added to a suspension of 4-{[4-chloro-3-(trifluoromethyl)benzyl]amino}-6-nitroquinazoline-8-carboxamide (150 mg, 0.35 mmol, 1.0 equiv.) in acetic acid (12 mL). The resulting mixture was stirred at 80° C. for 10 min. The reaction mixture was filtered. The filtrate was concentrated and purified by pre-HPLC to yield the title compound as yellow solid in 68% yield. Mass: M+H$^+$: 396.

63. 6-(acetylamino)-4-{[4-chloro-3-(trifluoromethyl)benzyl]amino}quinazoline-8-carboxamide (Compound No. 173)

The title compound was isolated as by-product of the reaction according to example 59 as white solid in 4% yield. Mass: M+H$^+$: 438.

64. 6-nitro-4-{[3-(trifluoromethyl)benzyl]amino}quinazoline-8-carboxamide (Compound No. 164)

The title compound was synthesized according to the procedure of example 61 and purified by pre-HPLC as TFA salt in 61% yield. Mass: M+H$^+$: 392.

65. 6-amino-4-{[3-(trifluoromethyl)benzyl]amino}quinazoline-8-carboxamide (Compound No. 165)

The title compound was synthesized according to the procedure of example 62 and purified by pre-HPLC as TFA salt in 53% yield. Mass: M+H$^+$: 362.

66. 6-(benzoylamino)-4-{[4-chloro-3-(trifluoromethyl)benzyl]amino}quinazoline-8-carboxamide Benzoyl chloride (66 µL, 0.5 M in anhydrous DCM, 0.03 mmol, 1.1 equiv.) was added to a solution of TFA salt of 6-amino-4-{[4-chloro-3-(trifluoromethyl)benzyl]amino}quinazoline-8-carboxamide (15 mg, 0.03 mmol, 1.0 equiv.) and triethylamine (16 µL, 0.09 mmol, 3.0 equiv.) in anhydrous DCM (1 mL). The resulting mixture was stirred at rt for 3 h. Purification by pre-HPLC gave the title compound in 83% yield. Mass: M+H$^+$: 500.

67. 4-{[4-chloro-3-(trifluoromethyl)benzyl]amino}-6-[(3-phenylpropanoyl)amino]quinazoline-8-carboxamide (Compound No. 177)

The title compound was synthesized according to the method of example 66 in 74% yield. Mass: M+H$^+$: 528.

68. 4-{[4-chloro-3-(trifluoromethyl)benzyl]amino}-6-(isonicotinoylamino)quinazoline-8-carboxamide (Compound No. 176)

The title compound was synthesized according to the method of example 66 in 77% yield. Mass: M+H$^+$: 501.

69. 4-{[4-chloro-3-(trifluoromethyl)benzyl]amino}-6-[(isoxazol-5-ylcarbonyl)amino]quinazoline-8-carboxamide (Compound No. 179)

The title compound was synthesized according to the method of example 67 in 84% yield. Mass: M+H$^+$: 491.

70. 4-{[4-chloro-3-(trifluoromethyl)benzyl]amino}-6-[(quinoxalin-2-ylcarbonyl)amino]quinazoline-8-carboxamide (Compound No. 181)

The title compound was synthesized according to the method of example 66 in 57% yield. Mass: M+H$^+$: 552.

71. 4-{[(8-(aminocarbonyl)-4-{[4-chloro-3-(trifluoromethyl)benzyl]amino}quinazolin-6-yl)amino]carbonyl}benzenesulfonyl fluoride (Compound No. 180)

The title compound was synthesized according to the method of example 66 in 77% yield. Mass: M+H$^+$: 582.

72. 4-{[4-chloro-3-(trifluoromethyl)benzyl]amino}-6-[(2-thienylacetyl)amino]quinazoline-8-carboxamide (Compound No. 182)

The title compound was synthesized according to the method of example 66 in 60% yield. Mass: M+H$^+$: 520.

73. 4-{[4-chloro-3-(trifluoromethyl)benzyl]amino}-6-[(phenylsulfonyl)amino]quinazoline-8-carboxamide (Compound No. 174)

Benzenesullfonyl chloride (70 µL, 0.5 M in anhydrous DCM, 0.03 mmol, 1.1 equiv.) was added to a solution of TFA salt of 6-amino-4-{[4-chloro-3-(trifluoromethyl)benzyl]amino}quinazoline-8-carboxamide (16 mg, 0.03 mmol, 1.0 equiv.) and triethylamine (16 µL, 0.09 mmol, 3.0 equiv.) in anhydrous DCM (1 mL). The resulting mixture was stirred at 40° C. overnight. The title compound was obtained by pre-HPLC in 28% yield. Mass: M+H$^+$: 536.

74. 6-[(anilinocarbonyl)amino]-4-{[4-chloro-3-(trifluoromethyl)benzyl]amino}quinazoline-8-carboxamide (Compound No. 175)

Phenyl isocyanate (70 µL, 0.5 M in anhydrous DCM, 0.03 mmol, 1.1 equiv.) was added to a solution of TFA salt of 6-amino-4-{[4-chloro-3-(trifluoromethyl)benzyl]amino}quinazoline-8-carboxamide (16 mg, 0.03 mmol, 1.0 equiv.) and triethylamine (16 µL, 0.09 mmol, 3.0 equiv.) in anhydrous DCM (1 mL). The resulting mixture was stirred at 40° C. for 3 hrs. The title compound was obtained by pre-HPLC in 79% yield. Mass: M+H$^+$: 515.

75. 6-(benzylamino)-4-{[4-chloro-3-(trifluoromethyl)benzyl]amino}quinazoline-8-carboxamide (Compound No. 178)

Benzylbromide (140 µL, 0.5 M in anhydrous DCM, 0.07 mmol, 1.1 equiv.) was added to a solution of 6-amino-4-{[4-chloro-3-(trifluoromethyl)benzyl]amino}quinazoline-8-carboxamide (25 mg, 0.06 mmol, 1.0 equiv.) and cesium carbonate (62 mg, 0.19 mmol, 3.0 equiv.) in anhydrous DCM (2 mL). The resulting mixture was stirred at 50° C. overnight. The title compound was obtained by pre-HPLC in 17% yield. Mass: M+H$^+$: 486.

76. 4-Benzylamino-quinazoline-8-carboxylic acid amide (Compound No. 123)

In addition to the method described in Example 5 above, compound No. 123 was also made according to the following procedure:

Step 1. A 1 L round bottom flask was charged with 2-aminoisophthalic acid (25.0 g, 138.1 mmol) and formaldehyde (125 mL) and heated to 130° C. for 4 hours. The crude mixture was cooled to room temperature, poured on to ice water and the filtrate collected, rinsed with water and heptanes and dried (A). The aqueous solution was then concentrated and poured in to acetone and more precipitate was collected, washed with acetone and heptanes and dried (B). Both isomers were carried on in a similar fashion through the methylation step.

Step 2. A 1 L round bottom flask was charged with 4-hydroxyquinazoline-8-carboxylic acid (A), MeOH (300 mL), and H$_2$SO$_4$ (10 mL). The reaction was heated to 50° C. for 2 days. Upon cooling to room temperature, the reaction mixture was neutralized with NaHCO$_3$ and diluted with water. The methanol was removed in vacuo, and the precipitate was collected, washed with water and heptanes, then dried to give methyl 4-hydroxyquinazoline-8-carboxylate (18.3 g, 65%, over 2 steps combining both isomers from A and B).

Step 3. A 500 mL round bottom flask equipped with a stir bar, Virgreux column and nitrogen inlet was charged with 4-oxo-3,4-dihydro-quinazoline-8-carboxylic acid methyl ester, (4.1 g, 20 mmol) benzyltriethylammonium chloride, (9.1 g, 40 mmol) and N,N-dimethylaniline, (2.8 mL, 22 mmol) and acetonitrile, (80 mL). The flask was placed under nitrogen and phosphorus oxychloride was added dropwise. The reaction was heated at 50° C. for 2 hour. The reaction was cooled and solvent was evaporated under reduced pressure. The residue was re-dissolved in CH$_2$Cl$_2$ and this solution was slowly added to a well-stirred flask of water at room temperature. Addition was controlled such that the temperature in the solution did not exceed 30° C. Upon completion of addition, the solution was stirred vigorously for 10 min and the layers separated. The aqueous layer was extracted twice with CH$_2$Cl$_2$ and the combined organic fractions were washed with saturated sodium bicarbonate solution, dried over MgSO$_4$ and the solvent removed under reduced pressure to give the desired product. Amount obtained: 4.0 g, 18 mmol, 90% yield. LCMS (ESI) 223 (M+H).

Step 4 To a solution of the above chloroester in THF was added diisopropylethylamine at 25° C. After 5 minutes the desired amine was added and heated to 50° C. After the reaction was complete the reaction was concentrated in vacuo to dryness. The residue was re-dissolved in methylene chloride and washed with aqueous brine solution. The organic layer was separated and dried with sodium sulfate, concentrated and purified by ISCO Companion system.

Step 5. Formation of the carboxamide was accomplished by one of the following methods:
A. NaOMe, DMF, Formamide
B. a. LiOH, THF, MeOH, H$_2$O b. HATU, NH$_3$
C. a. LiOH, THF, MeOH, H$_2$O b. CDI, NH$_4$OAc
D. IPA, NH$_4$OH A. A vial was charged with the above ester, formamide, and DMF. The solution was heated to 50° C. and sodium methoxide solution was added and stirred overnight. The reaction was cooled to room temperature and water was added resulting in a precipitation. The precipitate was collected by filtration. If needed the material was further purified by ISCO companion or prep-HPLC.

B. (a) To a solution of above ester in THF:MeOH was added a solution of LiOH in water. Upon completion the solution was adjusted to a pH of 3-5 with 1N HCl. The precipitate was collected and carried on without further purification. If no precipitate, the solution was concentrated in vacuo to dryness and carried on crude. (b) The previous crude material was dissolved in DMF and diisopropylethylamine. HATU was added to the solution then ammonia gas was bubbled through the solution. Upon completion material was purified by prep-HPLC or ISCO companion.

C. (a) To a solution of above ester in THF:MeOH was added a solution of LiOH in water. Upon completion the solution was adjusted to a pH of 3-5 with 1N HCl. The precipitate was collected and carried on without further purification. If no precipitate, the solution was concentrated in vacuo to dryness and carried on crude. (b) The previous crude material was dissolved in DMSO and carbonyldiimidazole (CDI) was added and stirred at 25° C. overnight. Solid ammonium acetate was added and the solution was heated to 50° C. Upon completion, material was purified by prep-HPLC or ISCO companion.

D. A solution of the above ester in IPA and NH$_4$OH was stirred at 25° C. overnight. The solution was concentrated in vacuo to dryness and purified by prep-HPLC or ISCO Companion.

LCMS (ESI) 279

Example A

4-Chloro-6-methoxy-quinazoline-8-carboxylic acid methyl ester

Step 1. A 1000 mL round bottom flask equipped with a stir bar and nitrogen inlet was charged with anisidine, (25 g, 200 mmol) and THF, (400 mL). To this solution at RT was added 4.0M HCl in dioxane, (100 mL, 400 mmol). A ppt formed almost immediately. The suspension was allowed 30 min and then was filtered. The ppt was washed with Et$_2$O and dried under vacuum. A 1000 mL round bottom flask equipped with a stir bar and nitrogen inlet was charged with anisidine hydrochloride, (32 g, 200 mmol) and AcOH, (400 mL). Then bromine, (21 mL, 400 mmol) was added dropwise at ambient temperature and the mixture was stirred overnight. After 18 h the solvent was partially evaporated under reduced pressure, the precipitate was filtered and washed with EtOAc, (1000 mL). The free base was obtained by suspending the HCl salt in THF (500 mL) and aqueous sat. NaHCO$_3$, (250 mL) was added and solid Na$_2$CO$_3$/water was added until bubbling ceased. The phases were separated, the aqueous phase was extracted with EtOAc, (500 mL) (×2), dried (Na$_2$SO$_4$) and the solvent was evaporated under reduced pressure. Amount obtained: 42 g, 150 mmol, 75% yield.

Step 2. A 250 mL round bottom flask equipped with a stir bar, Vigreux column and nitrogen inlet was charged with 2,6-dibromo-4-methoxy-phenylamine, (14 g, 50 mmol) and NMP, (80 mL). Copper cyanide, (18 g, 200 mmol) was then added at ambient temperature and the reaction was heated at 140° C. oil bath temperature. The reaction was allowed left to stir for 24 h. The reaction was cooled, diluted with EtOAc, (1000 mL) and poured into 1000 mL of 10% ethylene diamine solution. The mixture was stirred vigorously for 2 h. The mixture was filtered through a pad of celite and washed with copious EtOAc (poor solubility) and the phases were split. The aqueous phase was extracted with EtOAc, (500 mL) (×3), the combined EtOAc extracts were washed with water (500 mL), dried ($Na_2SO_4$), and the solvent was evaporated under reduced pressure. The material was passed through a pad of silica gel eluting with DCM-EtOAc (10% EtOAc). Amount obtained: 5.0 g, 29 mmol, 58% yield.

Step 3. A 100 mL round bottom flask equipped with stir bar, Vigreux column and nitrogen inlet was charged with 2-amino-5-methoxy-isophthalonitrile, (3.5 g, 20 mmol) and cellosolve, (4 mL). To this stirred mixture was added KOH, (6.7 g, 120 mmol) and water, (40 mL) and the reaction mixture was heated at 110° C. oil bath temperature and left overnight. The material did not fully go into solution but after 18 h. The insoluble material was filtered through a filter paper. The filtrate was diluted with water (50 mL) and was washed with EtOAc (50 mL)×2. The EtOAc washings were discarded. The pH of the aqueous phase was carefully lowered to ~pH 5 with 6 M HCl. A yellow precipitate formed. This was filtered and washed with $Et_2O$. Amount obtained: 3.8 g, 18 mmol, 90% yield. The material was used without further purification.

Step 4. A 100 mL round bottom flask equipped with a stir bar, Vigreux column and nitrogen inlet was charged with 2-amino-5-methoxy-isophthalic acid, (3.8 g, 18 mmol) and formamide, (36 mL). The mixture was stirred and heated at 140° C. overnight. The reaction was poured into rapidly stirred ice water (100 mL) causing a precipitate to form and the pH was adjusted to approx. pH 4 using 1M HCl. The material was collected by suction filtration and was washed with $Et_2O$. Amount obtained: 2.2 g, 10 mmol, 56% yield. The material was used as is in the next step.

Step 5. A 250 mL round bottom flask equipped with a Vigreux column, nitrogen inlet and stir bar was charged with of 6-methoxy-4-oxo-3,4-dihydro-quinazoline-8-carboxylic acid, (1.1 g, 5.0 mmol) and MeOH (75 mL). To this stirred solution at RT, conc. $H_2SO_4$ (7.5 mL) in MeOH (15 mL) was added dropwise. The reaction was heated at 70° C. bath temperature and left overnight. The reaction was partially concentrated under reduced pressure and EtOAc, (250 mL) was added. Water (100 mL) and 2M NaOH was added until pH ~4, and then basified with saturated $NaHCO_3$ and phases were separated. The aqueous phase was extracted with EtOAc (250 mL) (×3), the combined EtOAc phases were washed with brine, dried, ($Na_2SO_4$) and the solvent was evaporated under reduced pressure. Amount obtained: 1.0 g, 4.3 mmol, 85% yield. The material was used as is in the next step.

Step 6. The title compound was synthesized according to Step C in the procedure of Example 76.

Example B

6-Benzyloxy-4-chloro-quinazoline-8-carboxylic acid methyl ester

The title compound was synthesized according to the procedure of Example A.

Example C (S)-2,2-Dioxo-4-phenyl-2lambda*6*-[1,2,3]oxathia-zolidine-3-carboxylic acid tert-butyl ester To a solution of thionyl chloride (3.70 mL, 50.8 mmol) in acetonitrile (50 mL) at −40° C. was added dropwise a solution of (1S)-2-2hydroxy-1-phenethylcarbamate (ref. Org. Syn. 2008, 85, 219) (4.79 g, 20.2 mmol) in acetonitrile (120 mL) via addition funnel. Pyridine (8.20 mL, 101.4 mmol) was then added dropwise and the reaction was warmed to room temperature for 2 hours. The reaction was then concentrated to ¼ volume in vacuo and 350-400 mL of ethyl acetate was added. The resulting suspension was then filtered through Celite and the solids were washed with additional ethyl acetate. The filtrate was then concentrated to a sticky solid and dried under high vacuum briefly. The resulting residue was dissolved in acetonitrile (25 mL) and $RuCl_3$—$H_2O$ (420 mg, 1.7 mmol) was added followed by sodium periodate (5.18 g, 24.2 mmol) and water (25 mL). The dark solution was stirred for 4 hours at which time it was diluted with ethyl acetate (200 mL) and water (200 mL) and the mixture was extracted with ethyl acetate three times. The combined organics were dried over sodium sulfate and concentrated to a residue that was purified by column chromatography (5% ethyl acetate/heptane to 75% ethyl acetate/heptane) to provide the product as a white solid (4.13 g, 68%).

Example D (S)-2-Azido-1-phenyl-ethylamine

To a solution of (2S)-2-[(tert-Butoxycabonyl)amino]-2-phenylethyl methanesulfonate (ref. Org. Syn. 2008, 85, 219) (5.0 g, 15.9 mmol) in DMF (40 mL) was added solid sodium azide (2.2 g, 33 mmol). The reaction was heated to 65° C. for 48 h. The reaction was cooled to room temperature and water was added to provide a white precipitate. The precipitate was filtered and dried under vacuum to afford the desired compound (3.5 g, 85%). To a solution of azide (0.75 g, 2.86 mmol) in THF (14 mL) was added HCl (as a 4M solution in dioxane, 7 mL, 28 mmol). The reaction was stirred at RT for 16 hours, then solvents were removed under reduced pressure to give the amine hydrochloride, which was used in the next step without further purification.

Example E (S)-4-(3-Fluoro-phenyl)-2,2-dioxo-2 lambda*6*-[1,2,3]oxathiazolidine-3-carboxylic acid tert-butyl ester Step 1. To a solution of 3-fluoromandelic acid (4.0 g, 23.5 mmol) in 30.0 mL of N,N-dimethylformamide (DMF) was added $Cs_2CO_3$ (11.49 g, 35.3 mmol) and the suspension was stirred at room temperature until gas evolution ceased. To the stirring suspension was added at room temperature ethyl iodide (2.28 mL, 28.2 mmol) dropwise. The reaction was stirred at room temperature for 16 hours and then saturated aqueous sodium chloride (~50 mL), water (~50 mL) and ethyl acetate (~50 mL) were added. The phases were separated and the aqueous phase was extracted two additional times with ethyl acetate. The combined organic phases were then washed with water and dried over sodium sulfate. Concentration in vacuo afforded a pale yellow oil that was dried under a low vacuum for 2 hours and then used immediately in the next step.

Step 2. A 2M solution of oxalyl chloride in dichloromethane (17.63 mL, 35.2 mmol) was diluted further with 20 mL of additional dichloromethane and cooled to −78° C. DMSO (5.0 mL, 70.5 mmol) was then added and the mixture was stirred for 15 minutes at −78° C. at which time a solution of the ester from Step 1 in 50 mL of dichloromethane was added via addition funnel. The reaction was maintained at −78° C. for 1 hour at which time N,N-diisopropylethylamine (24.6 mL, 141 mmol) was added and the dry ice/acetone bath was removed. The reaction was warmed to room temperature over 1 hour and then dichloromethane (100 mL) and water (100 mL) were added. The mixture was extracted three times with dichloromethane and the combined organics were dried over sodium sulfate and concentrated to a residue that was purified by column chromatography (heptane to 30% ethyl acetate/heptane) to provide 4.6 g of a pale yellow oil.

Step 3. The glyoxylate from Step 2 was dissolved in 75 mL of THF and (R)-2-methyl-2-propanesulfinamide (3.09 g, 24.8 mmol) was added followed by Ti(OEt)$_4$ (21.1 mL, 99.2 mmol). The reaction was heated to 75° C. for 2 hours and then at 65° C. for 12 hours at which time the reaction was cooled and added carefully to a rapidly stirring solution of saturated aqueous sodium chloride (100 mL). Ethyl acetate (75 mL) was added and the suspension was stirred for 10-15 minutes and then filtered through a pad of Celite. The solids were then washed with additional ethyl acetate and the filtrate was phase separated. The aqueous phase was extracted two more times with ethyl acetate and the combined organics were dried over sodium sulfate and concentrated to yellow oil that was purified by column chromatography (heptane to 50% ethyl acetate/heptane). The sulfinimine product was obtained as a yellow oil that was contaminated with a small amount (<10% by HPLC) of a species that exhibited an identical molecular ion in the LC/MS. The title compound is a thick yellow oil; 5.72 g, 81.3% (3 steps); LCMS (ESI) 300 (M+H).

Step 4. A 500 mL round-bottom flask containing a solution of the sulfinimine (5.72 g, 19.1 mmol) in tetrahydrofuran (80 mL) was equipped with an addition funnel. The funnel was charged with 1M borane-tetrahydrofuran complex in THF (76.4 mL, 76.4 mmol) via cannula and the solution was added to the reaction dropwise at −20° C. over a period of 20-30 minutes. The reaction was stirred for an additional 15 minutes at −20° C. and then the bath was replaced with a wet ice/water bath. The ice was allowed to melt over a period of 16 hours at which time the reaction was re-cooled to 0° C. and quenched carefully by a slow addition of saturated aqueous ammonium chloride (10-15 mL). The reaction was then diluted with water (100 mL) and ethyl acetate (50 mL) and the mixture was extracted with ethyl acetate three times. The combined organics were dried over sodium sulfate and concentrated to a thick oil that was purified by column chromatography (5% ethyl acetate/heptane to ethyl acetate) to afford a thick oil that slowly solidified to an amorphous solid under vacuum (3.62 g, 62.9%). LCMS (ESI) 260 (M+H)

Step 5. To a solution of the sulfinamide reactant (3.62 g, 12.0 mmol) in ethanol (80 mL) was added at room temperature 4N HCl in dioxane (15.0 mL, 60 mmol). The reaction was stirred for 4 hours and then concentrated in vacuo to an off-white solid (2.3 g, 100%). LCMS (ESI) 156 (M+H)

Step 6. The HCl amine salt (2.3 g, 12.0 mmol) was suspended in dioxane (40 mL) and 1N NaOH (80 mL) was added at room temperature. To the vigorously stirring yellow solution was then added di-tert-butyl dicarbonate (3.27 g, 15 mmol) and the reaction was stirred at room temperature for 16 hours. At this time water (150 mL) and ethyl acetate (100 mL) were added and the mixture was extracted with ethyl acetate three times. The combined organics were dried over sodium sulfate and concentrated to a residue that was purified by column chromatography (5% ethyl acetate/heptane to 75% ethyl acetate/heptane) to provide the product as a white solid (2.30 g, 75% over 2 steps). Rf=0.60, 50% ethyl acetate/heptane; LCMS (ESI) 256 (M+H)

Step 7. To a solution of thionyl chloride (1.64 mL, 22.5 mmol) in acetonitrile (40 mL) at −40° C. was added dropwise a solution of the [(S)-1-(3-Fluoro-phenyl)-2-hydroxy-ethyl]-carbamic acid tert-butyl ester (2.30 g, 9.0 mmol) in acetonitrile (100 mL) via addition funnel. Pyridine (3.64 mL, 45.0 mmol) was then added dropwise and the reaction was warmed to room temperature for 2 hours. The reaction was then concentrated to ¼ volume in vacuo and 350-400 mL of ethyl acetate was added. The resulting suspension was then filtered through Celite and the solids were washed with additional ethyl acetate. The filtrate was then concentrated to a sticky solid and dried under high vacuum briefly. The resulting residue was dissolved in acetonitrile (25 mL) and RuCl$_3$—H$_2$O (219 mg, 0.9 mmol) was added followed by sodium periodate (2.31 g, 10.8 mmol) and water (25 mL). The dark solution was stirred for 4 hours at which time it was diluted with ethyl acetate (100 mL) and water (100 mL) and the mixture was extracted with ethyl acetate three times. The combined organics were dried over sodium sulfate and concentrated to a residue that was purified by column chromatography (5% ethyl acetate/heptane to 75% ethyl acetate/heptane) to provide the product as a white solid (2.47 g, 86.4%).

Example F

N-Ethyl-4-nitro-benzenesulfonamide (Ref.: Ragactives, S. L. Patent: EP1813618 (2007)). To a 40-mL vial with magnetic stir bar at 25° C. was added the Ethylamine solution (0.91 g, 20 mmol, 1.3 mL, 70% w/v in water, 4.5 eq.) and methanol (5 mL). The reaction vial was cooled to 0° C. The Nosyl chloride (1.0 g, 4.5 mmol, 1 eq.) was added portionwise keeping the temperature between 0-5° C. and stirring continued ×15 min. after addition was complete. Water (10 mL) was then added. A precipitate began to form immediately. Stirring was continued at 0° C.×30 minutes. The material was collected by filtration, rinsed with water, and dried thoroughly in vacuo to afford 827 mg (79% yield). LCMS (ESI) 231 (M+H); 229 (M−H).

Example G

N-((S)-2-Amino-2-phenyl-ethyl)-N-ethyl-4-nitro-benzenesulfonamide

Step 1. To a 100-mL round bottom flask with magnetic stir bar at 25° C. was added the powdered KOH (0.37 g, 6.55 mmol, 2 eq.) and acetonitrile (10 mL). Example F (0.83 g, 3.6 mmol, 1.1 eq.) was then added and stirring continued ×10 minutes. Example C (0.98 g, 3.3 mmol, 1 eq.) was dissolved in acetonitrile (16 mL) and added to the reaction flask. Stirring was continued ×4 hours at 25° C. The reaction was quenched by addition of an approximately equal volume of 0.5N aq. HCl solution (~25 mL). The resulting mixture was extracted with EtOAc (20 mL)×3. The combined organics were washed with brine (20 mL), dried (e.g., Na$_2$SO$_4$), filtered and concentrated. The resulting residue was purified by column chromatography (ISCO CombiFlash) using a 0-30% gradient (EtOAc/Heptane) to afford 1.1 g (72% yield). LCMS (ESI) 448.2 (M−H).

Step 2. To a 100-mL round bottom flask with magnetic stir bar at 25° C. was added {(S)-2-Ethyl-(4-nitro-benzenesulfonyl)-amino]-1-phenyl-ethyl}-carbamic acid tert-butyl ester (1.06 g, 2.4 mmol, 1 eq.) and THF (20 mL). The reaction flask was cooled to 0° C. and the HCl in Dioxane (30 mL, 4M, excess) added with stirring. The reaction was stirred vigorously ×16 hours (0° C.-25° C.). The solvent was then evaporated in vacuo. The resulting residue was re-dissolved in THF (30 mL) and aq. $Na_2CO_3$ solution (30 mL, 1M) was added. Stirring was continued at 25° C.×1 hour. The mixture was then diluted with water (50 mL) and extracted with EtOAc (30 mL)×3. The combined organics were washed with brine (20 mL), dried (e.g., $Na_2SO_4$), filtered and concentrated to afford 1.05 g. Material was carried on to the next step without further purification.

Examples A-G were also used for the synthesis of other scaffolds and building blocks that were commonly used for the compounds according to Formula (I).

Table 2

Synthesis Intermediates Used in More than One of the Following Examples:

Intermediate 4-{[2-Methoxy-1-(3-aminophenyl)-ethylamine]}-quinazoline-8-carboxylic acid amide was used for the preparation of examples 281, 333 and 712. It was synthesized according to the procedure described for the preparation of 4-[1-(3-Amino-phenyl)-3-methoxy-propylamino]-quinazoline-8-carboxamide by using methyl 4-chloro-quinazoline-8-carboxylate and 2-Methoxy-1-(3-nitro-phenyl)-ethylamine, (Scheme 4) LCMS [338 (M+1)].

Intermediate 4-[(3-Piperidin-1-yl-3-aminophenyl-propylamino)]-quinazoline-8-carboxylic acid amide was used for the preparation of examples 392, 399, 495, 500, 695, 703. It was synthesized according to the procedure described for the preparation of 4-[1-(3-Amino-phenyl)-3-pyrrolidin-1-yl-propylamino]-quinazoline-8-carboxylic acid amide (Scheme 5). LCMS [405 (M+1)].

Intermediate 4-[(3-dimethylamino-1-yl-3-aminophenyl-propylamino)]-quinazoline-8-carboxylic acid amide was used for the preparation of examples 249, 254, 265, 313, 361, 363, 365, 391, 437, 450, 458 493, 664

It was synthesized according to the procedure described for the preparation of 4-[1-(3-Amino-phenyl)-3-pyrrolidin-1-yl-propylamino]-quinazoline-8-carboxylic acid amide (Scheme 5). LCMS [365 (M+1)].

Intermediate 4-[(2-dimethylamino-1-yl-(3-aminophenyl)-ethylamino)]-quinazoline-8-carboxylic acid amide was used for the preparation of the examples 219 and 233.

It was synthesized according to the procedures described for the preparation of 4-[1-(3-Amino-phenyl)-3-pyrrolidin-1-yl-propylamino]-quinazoline-8-carboxylic acid amide, (Scheme 5). LCMS [341 (M+1)].

Intermediate 4-[((R)-3-Pyrrolidin-1-yl-3-aminophenyl-prooylamino)]-quinazoline-8-carboxylic acid amide was used for the preparation of example 700.

It was synthesized according to the procedures described for the preparation of 4-[1-(3-Amino-phenyl)-3-pyrrolidin-1-yl-propylamino]-quinazoline-8-carboxylic acid amide (Scheme 5). LCMS [365 (M+1)].

Intermediate 4-[((R)-3-Piperidin-1-yl-3-aminophenyl-propylamino)]-quinazoline-8-carboxylic acid amide was used for the preparation of example 704.

It was synthesized according to the procedures described for the preparation of 4-[1-(3-Amino-phenyl)-3-pyrrolidin-1-yl-propylamino]-quinazoline-8-carboxylic acid amide (Scheme 5) LCMS [405 (M+1)].

Intermediate [2-(3-Amino-phenyl)-2-(8-carbamoyl-quinazolin-4-ylamino)-ethyl]-methyl-carbamic acid tert-butyl ester was used for the preparation of examples 527, 273, 335, 296, 490, 287, 252, 223 and 215.

It was synthesized as described in the procedure for the preparation of 4-[1-(3-Amino-phenyl)-3-pyrrolidin-1-yl-propylamino]-quinazoline-8-carboxylic acid amide, (Scheme 5) using [2-Amino-2-(3-nitro-phenyl)ethyl]-methyl-carbamic acid tert-butyl ester and methyl 4-chloro-quinazoline-8-carboxylate.

Intermediate 4-{[(1R)-1-(3-aminophenyl)ethyl]amino}quinazoline-8-carboxamide was used for the preparation of examples 261, 266, 331, 440, 472, 498, 567, 606, and 693.

Methyl 4-{[(1R)-1-(3-nitrophenyl)ethyl]amino}quinazoline-8-carboxylate

A suspension of methyl 4-chloroquinazoline-8-carboxylate (7.18 g, 32.25 mmol) in acetonitrile (70 mL), was treated with N,N-diisopropylethylamine (21.69 g, 167.81 mmol, 5 eq), followed by (1R)-1-(3-nitrophenyl)ethanamine hydrochloride (6.80 g, 33.56 mmol). The suspension was warmed to 45° C. and stirred for 4 h. The reaction mixture was slowly added to water (1000 mL) to precipitate an off-white solid. The solid was filtered to get 8.52 g (24.18 mmol, 75%). LCMS: (M+1) 353.

4-{[((1R)-1-(3-nitrophenynethyl]amino}quinazoline-8-carboxamide

A suspension of Methyl 4-{[(1R)-1-(3-nitrophenyl)ethyl]amino}quinazoline-8-carboxylate (7.26 g, 20.60 mmol) in 7 N ammonia/methanol (100 mL) was stirred at 60° C. for 24 h in a sealed pressure vessel. The clear, yellow solution was concentrated to effect precipitation of a solid, which was treated with diethyl ether (100 mL) to enrich the precipitation. The material was stored at 3° C. for 2 h and filtered to give an off-white solid. The solid was dried under vacuum at 35° C. for 4 h to get the title compound (5.70 g, 82%).

4-{[(1R)-1-(3-aminophenyl)ethyl]amino}quinazoline-8-carboxamide

A suspension of 4-{[(1R)-1-(3-nitrophenyl)ethyl]amino}quinazoline-8-carboxamide (1.50 g, 4.45 mmol) in methanol (125 mL) was shaken for 3 h in a Parr vessel under 35 psi hydrogen pressure in the presence of 30 wt % palladium on carbon (600 mg). The material was filtered through Celite, concentrated to get the title compound in 93% yield.

Intermediate 4-[1-(3-Amino-phenyl)-ethylamino]-6-chloro-quinazoline-8-carboxylic acid amide was used for the preparation of examples 570, 701.

To a solution of methyl 4,6-dichloroquinazoline-8-carboxylate (574 mg; 2.23 mmol; 1.00 eq.) in acetonenitrile (5 ml) containing N-ethyl-N-isopropylpropan-2-amine (0.80 ml; 4.47 mmol; 2.00 eq.) was added tert-butyl [3-(1-amino-ethyl)phenyl]carbamate (543 mg; 2.30 mmol; 1.03 eq.), the reaction mixture was stirred at RT overnight. Concentrated to get 4-[1-(3-tert-butoxycarbonylamino-phenyl)-ethylamino]-6-chloro-quinazoline-8-carboxylic acid methyl ester. To this crude was added methanolic ammonia (3.19 ml; 7.00 M; 22.33 mmol; 10.00 eq.) and stirred at RT for 48 h. The solvent was removed and the residue, {3-[1-(8-Carbamoyl-6-chloro-quinazolin-4-ylamino)-ethyl]-phenyl}-carbamic acid tert-butyl ester was treated with 4.0M hydrogen chloride in dioxane (5.58 ml; 4.00 M; 22.33 mmol; 10.00 eq.) and methaonl (6.45 ml). Stirred overnight, concentrated and purified by HPLC to collect the title product (130 mg) in 14% over all yield. MS (M+1) 342.

Intermediate 4-(3-Amino-benzylamino)-6-hydroxymethyl-quinazoline-8-carboxylic acid amide was used for the preparation of examples 564, 590, 626 and 638.

To a solution of tert-butyl [3-{[8-(aminocarbonyl)-6-(1,2-dihydroxyethyl)quinazolin-4-yl]amino}methyl)phenyl]carbamate (240 mg; 0.53 mmol; 1.00 eq.) in tetrahydrofuran (2.00 ml) and water (2.00 ml) added $NaIO_4$ (170 mg; 0.79 mmol; 1.50 eq.). The reaction mixture was stirred at RT for 30 min, filtered, got the tert-butyl [3-({[8-(aminocarbonyl)-6-formylquinazolin-4-yl]amino}methyl)phenyl]carbamate as a solid, which was used directly for the next reaction.

To a solution of tert-butyl [3-({[8-(aminocarbonyl)-6-formylquinazolin-4-yl]amino}methyl)phenyl]carbamate (90.00 mg; 0.21 mmol; 1.00 eq.) in tetrahydrofuran (2.00 ml) added sodium added sodium borohydride (4.04 mg; 0.11 mmol; 0.50 eq.). The reaction mixture was stirred at 0° C. for 1 h. After workup, the product was purified by HPLC to get tert-butyl [3-({[8-(aminocarbonyl)-6-(hydroxymethyl)quinazolin-4-yl]amino}methyl)phenyl]carbamate (60 mg, 66%) MS (M+1) 424.

To a solution of tert-butyl [3-({[8-(aminocarbonyl)-6-(hydroxymethyl)quinazolin-4-yl]amino}methyl)phenyl]carbamate (20 mg; 0.05 mmol; 1.00 eq.) in methanol (1 ml) added 4.0M hydrogen chloride in dioxane (1 ml; 4.00 M; 4.00 mmol; 84.69 eq.). The reaction mixture was stirred at RT for 3 h. Concentrated to obtain title product. MS (M+1) 324.

Example Compounds

Example 94

4-{3-[(2-Chloro-pyridine-4-carbonyl)-amino]-benzylamino}-quinazoline-8-carboxylic acid amide Step 1. To a 40-mL vial with magnetic stir bar at 25° C. under a nitrogen atmosphere was added 4-Chloro-quinazoline-8-carboxylic acid methyl ester (0.46 g, 2.08 mmol, 1 eq.) and anhydrous THF (15 mL). The Diisopropylethylamine (0.81 g, 1.09 mL, 6.25 mmol, 3 eq.) was then added followed by the amine (0.6 g, 2.3 mmol, 1.1 eq.). The resulting mixture was heated in a capped vial at 50° C. overnight with stirring. The solvent was evaporated in vacuo and the resulting residue re-dissolved in EtOAc (50 mL). The mixture was washed with saturated aqueous $NaHCO_3$ solution (30 mL), brine (30 mL), and dried (e.g., $Na_2SO_4$), filtered and concentrated. The resulting residue was purified by column chromatography (ISCO CombiFlash) using a 0-100% gradient (EtOAc/DCM) afforded 595 mg (64% yield) of the desired compound. LCMS (ESI) 448 (M+H).

Step 2. To a 40-mL vial with magnetic stirbar at r.t. was added the 4-{3-[(2-Chloro-pyridine-4-carbonyl)-amino]-benzylamino}-quinazoline-8-carboxylic acid methyl ester (0.6 g, 1.34 mmol, 1 eq.) and THF (6 mL) and 2-propanol (6 mL). An approx. equal volume (i.e.; 6 mL) of concentrated aqueous ammonium hydroxide solution (28-30% soln.) was then added and stirring continued overnight. Water (15 mL) was added to the reaction mixture and a white precipitate immediately began to form. The precipitate was collected and dried thoroughly in vacuo and afforded 314 mg (55% yield). Material was carried on to the next synthetic step without further purification. LCMS (ESI) 433 (M+H)

Example 97

6-Benzyloxy-4-(4-trifluoromethyl-benzylamino)-quinazoline-8-carboxylic acid amide Step 1. To a solution of the aniline (2.41 g, 9.7 mmol) in N,N-dimethylformamide (20 mL) was added 20 mL N,N-dimethylformamide dimethyl acetal. The reaction was heated to 90° C. for 3 h and then the DMF-DMA was removed under reduced pressure. The solution was diluted with ethyl acetate and water and extracted with ethyl acetate (3×). The combined ethyl acetate layers were washed with water, dried over sodium sulfate and concentrated under reduced pressure to afford the formamidine product as a light brown solid (2.94 g, 100%). LCMS (ESI) 305 (M+H)

Step 2. To a solution of the formamidine (1.5 g, 4.9 mmol) in acetic acid (35 mL) was added 4-trifluoromethyl benzyl amine (0.15 mL, 7.4 mmol) and the reaction was heated to 120° C. for 3 h and then concentrated to a solid. The solid was partitioned between ethyl acetate and 1M aqueous sodium carbonate and this mixture was extracted with ethyl acetate (3×). The combined ethyl acetate layers were dried over sodium sulfate and concentrated to a solid that was triturated with dichloromethane and diethyl ether to afford an off-white solid that was pure product. The supernatant from the trituration was then columned to provide additional product. The combined solids (1.58 g total) amounted to a 74% yield. LCMS (ESI) 435 (M+H)

Step 3. To a solution of the 6-Benzyloxy-4-(4-trifluoromethyl-benzylamino)-quinazoline-8-carbonitrile (380 mg, 1 eq) in DMSO (20 mL) was added 10 wt % aqueous $K_2CO_3$ (6.68 mL, 5 eq) followed by 33% $H_2O_2$ (790 □L, 8 eq) at room temperature. The resulting light suspension was stirred for 12 h at room temperature and then diluted with water (~20-40 mL). A white precipitate formed that was collected by filtration (crop A). The filtrate was then extracted with ethyl acetate (3×25 mL) and the combined organic layers were dried over sodium sulfate, concentrated to an oil and columned (50 to 90% ethyl acetate/heptane) to afford an off-white solid (crop B). The two crops of carboxamide product (A+B, each ~90% pure by HPLC) were then combined in a 20 mL vial and triturated with minimal dichloromethane followed by ether. Trituration afforded a white solid (342.6 mg, 86%) LCMS (ESI) 453 (M+H)

Example 101

6-Hydroxy-4-(4-trifluoromethyl-benzylamino)-quinazoline-8-carboxylic acid amide

To a solution of the benzyl ether (973 mg, 2.2 mmol) in ethanol (170 mL) was added 5% Pd/C (10 mol %) and the reaction mixture was placed under a hydrogen atmosphere by capping the flask with a hydrogen balloon. After stirring for 2 h at room temperature, the reaction was complete as judged by TLC. The suspension was then filtered through a pad of Celite and the solids were washed with methanol (~750 mL). The filtrate was concentrated under reduced pressure to afford the phenol as a pale yellow solid (701 mg, 90%) that was judged as pure by $^1H$ NMR and HPLC analysis. LCMS (ESI) 363 (M+H)

Example 103

6-(2-Morpholin-4-yl-ethoxy)-4-(4-trifluoromethyl-benzylamino)-quinazoline-8-carboxylic acid amide To a solution of 6-Hydroxy-4-(4-trifluoromethyl-benzylamino)-quinazoline-8-carboxylic acid amide (85 mg, 0.2 mmol) in N,N-dimethylformamide (3.0 mL) was added cesium carbonate (229 mg, 0.6 mmol). The mixture was stirred vigorously for 10-15 minutes and 4-(2-Chloro-ethyl)-morpholine hydrochloride (48 mg, 0.26 mmol) was added followed by tetrabutylammonium iodide (10 mol %). The reaction was heated to 55° C. for 16 hours and then cooled to room temperature and diluted with water (15 mL) and ethyl acetate (10 mL). The phases were separated and the aqueous phase was extracted further with ethyl acetate (3×10 mL). The combined organic phases were then washed with water, dried over sodium sulfate and concentrated to a residue that was purified by column chromatography (dichloromethane to 90% dichloromethane/9% methanol/1% ammonium hydroxide) to afford the title compound as an off-white solid (83.5 mg, 75%). LCMS (ESI) 476 (M+H)

Example 184

6-methoxy-4-(2-methylamino-1-phenyl-ethylamino)-quinazoline-8-carboxylic acid amide A scintillation vial equipped with a stir bar was charged with [2-(8-carbamoyl-6-methoxy-quinazolin-4-ylamino)-2-phenyl-ethyl]-methyl-carbamic acid tert-butyl ester (150 mg, 0.33 mmol) and THF, (5 mL). Then, 4 M HCl in dioxane, (5 mL) was added at RT and the mixture was stirred overnight. After 18 h, a white precipitate had formed and LCMS indicated consumption of SM. The mixture was diluted with $Et_2O$ (30 mL) and the precipitate was filtered through a filter paper and washed with $Et_2O$, (30 mL). The solid was dried under vacuum. Amount obtained: 114 mg, 0.32 mmol, 100% yield. LCMS (ESI) 352 (M+H).

Example 189

4-{1-[3-(3,4-Difluoro-benzoylamino)-phenyl]-2-methylamino-ethylamino}-quinazoline-8-carboxylic acid amide The title compound was synthesized according to the procedure described for the preparation of Example 462. LCMS [477 (M+1)].

Example 196

4-{1-[3-(4-Bromo-benzoylamino)-Phenyl]-2-methylamino-ethylamino}-quinazoline-8-carboxylic acid amide The title compound was synthesized according to the procedure described for the preparation of Example 462. LCMS [520.8 (M+2)].

Example 201

4-(2-Dimethylamino-1-{3-[(2-pyrrolidin-1-yl-pyridine-4-carbonyl)-amino]-phenyl}-ethylamino)-quinazoline-8-carboxylic acid amide To a 10-mL microwave-rated vial with magnetic stir bar at r.t. was added 4-(1-{3-[(2-Chloro-pyridine-4-carbonyl)-amino]-phenyl}-2-dimethylamino-ethylamino)-quinazoline-8-carboxylic acid amide (0.045 g, 0.092 mmol, 1 eq.), t-BuOH (2 mL), DMSO (1 mL), and Pyrrolidine (0.076 mL, 0.92 mmol, 10 eq.). The vial was capped and heated under microwave conditions (50 W, 20 min. ramp, 110° C., STND, 1 hr. hold time) followed by addition of another aliquot of Pyrrolidine (0.1 mL) then microwaved (70 W, 20 min. ramp, 140° C., STND, 1 hr. hold time). Reaction was diluted with water (20 mL) and extracted with EtOAc (3×30 mL). The combined organics were washed with brine, dried (e.g., $Na_2SO_4$), filtered and concentrated. The resulting residue was purified via preparative HPLC afforded the desired compound as a white solid (17.3 mg, 36% yield) LCMS (ESI) 525 (M+H).

Example 207

4-(1-{3-[(2-Chloro-pyridine-4-carbonyl)-amino]-phenyl}-2-dimethylamino-ethylamino)-quinazoline-8-carboxylic acid amide Step 1. To a 40-mL vial with magnetic stir bar at 25° C. was added 2-Chloro-N-{3-[2-dimethylamino-1-(1,3-dioxo-1,3-dihydro-isoindol-2-yl)-ethyl]-phenyl}-isonicotinamide (0.6 g, 1.3 mmol, 1 eq.) and anhydrous THF (5 mL) and anhydrous MeOH (5 mL). The Hydrazine hydrate (0.67 g, 0.65 mL, 13 mmol, 10 eq.) was then added and stirring continued ×16 hours. The resulting solid was removed by filtration and rinsed with methanol (50 mL). The filtrate was concentrated in vacuo affording the desired product: 0.49 g. LCMS (ESI) 319 (M+H); 317 (M−H).

Step 2. To a 40-mL vial with magnetic stir bar at 25° C. under a nitrogen atmosphere was added 4-Chloro-quinazoline-8-carboxylic acid methyl ester (0.25 g, 1.14 mmol) and anhydrous THF (15 mL). DIEA (0.6 mL, 3.4 mmol) was then added followed with N-[3-(1-Amino-2-dimethylamino-ethyl)-phenyl]-2-chloro-isonicotinamide (0.4 g, 1.25 mmol). The resulting mixture was heated in a capped vial at 50-55° C.×16 hours with stirring. The solvent was evaporated in vacuo and the resulting residue re-dissolved in EtOAc (50 mL). The mixture was washed with saturated aqueous $NaHCO_3$ solution (30 mL), water (30 mL), brine (30 mL), and dried (e.g., $Na_2SO_4$), filtered and concentrated. The resulting residue was purified by column chromatography (ISCO CombiFlash) using a 0-100% gradient (EtOAc/DCM) to afford 0.2482 g (39% yield).

Step 3. To a 40-mL vial with magnetic stirbar at 25° C. was added 4-(1-{3-[(2-Chloro-pyridine-4-carbonyl)-amino]-phenyl}-2-dimethylamino-ethylamino)-quinazoline-8-carboxylic acid methyl ester (0.25 g, 0.495 mmol, 1 eq.) and THF (5 mL) and iPrOH (5 mL). An approx. equal volume of concentrated aq. $NH_4OH$ solution (28-30% soln.) was then added and stirring continued overnight. The reaction mixture was heated at 50° C.×4 hours in order to drive the reaction to completion. $H_2O$ (25 mL) was added to the reaction mixture and a precipitate immediately began to form. The precipitate was collected and discarded, and the aqueous layer was evaporated under nitrogen affording the desired product, 0.23 g (96% yield).

Example 208

4-{1-[3-(benzoylamino)-phenyl]-2-methylamino-ethylamino}-quinazoline-8-carboxylic acid amide The title compound was synthesized according to the procedure described for the preparation of Example 462. LCMS [441 (M+1)].

Example 209

4-{1-[3-(2,6-Difluoro-benzoylamino)-phenyl]-2-methylamino-ethylamino}-quinazoline-8-carboxylic acid amide The title compound was synthesized according to the procedure described for the preparation of Example 462. LCMS [477 (M+1)].

Example 212

4-{1-[3-(3-fluoro-4-methoxy-benzoylamino)-phenyl]-2-methylamino-ethylamino}-quinazoline-8-carboxylic acid amide The title compound was synthesized according to the procedure described for the preparation of Example 462. LCMS [489 (M+1)].

Example 215

4-{1-[3-(4-Methoxy-benzoylamino)-phenyl]-2-methylamino-ethylamino}-quinazoline-8-carboxylic acid amide The title compound was synthesized according to the procedure described for the preparation of Example 462. LCMS [471 (M+1)].

Example 219

4-{2-Dimethylamino-1-[3-(4-methoxy-benzoylamino)-phenyl]-ethylamino}-quinazoline-8-carboxylic acid amide The title compound was synthesized according to the procedure described for the preparation of Example 462. LCMS [485 (M+1)].

Example 223

4-{1-[3-(4-Trifluoromethoxy-benzoylamino)-phenyl]-2-methylamino-ethylamino}-quinazoline-8-carboxylic acid amide The title compound was synthesized according to the procedure described for the preparation of Example 462. LCMS [525 (M+1)].

Example 228

4-{1-[3-(2-fluoro-4-methoxy-benzoylamino)-phenyl]-2-methylamino-ethylamino}-quinazoline-8-carboxylic acid amide The title compound was synthesized according to the procedure described for the preparation of Example 462. LCMS [489 (M+1)].

Example 233

4-{2-Dimethylamino-1-[3-(3-fluoro-4-methoxy-benzoylamino)-phenyl]-ethylamino}-quinazoline-8-carboxylic acid amide The title compound was synthesized according to the procedure described for the preparation of Example 462. LCMS [503 (M+1)]. $^1$H NMR (400 MHz, DMSO-D$_6$): 2.9311 (s, 6H), 3.8506 (m, 2H), 3.9330 (s, 3H), 6.1292 (m, 1H), 7.3116 (m, 2H), 7.3336 (m, 2H), 7.6345 (m, 1H), 7.8116 (m, 3H), 8.0250 (m, 2H), 8.6414 (m, 2H), 8.7018 (s, 1H), 9.5691 (s, 1H), 10.2359 (s, 1H).

Example 238

4-{3-Allyl-methylamino-1-[3-(4-bromo-benzoylamino)-phenyl]-propylamino}-quinazoline-8-carboxylic acid amide The title compound was synthesized according to the procedure described for the preparation of Example 462. LCMS [574 (M+1)].

Example 240

4-(1-{3-[(Benzo[-1,3]-dioxole-5-carbonyl)-amino]-phenyl}-ethylamino)-quinazoline-8-carboxylic acid amide The title compound was synthesized according to the procedure described for the preparation of Example 425. MS (M+1) 456

Example 244

4-[3-(2,4-Difluoro-benzoylamino)-benzylamino]-quinazoline-8-carboxylic acid amide The title compound was prepared according to Example 667.

42 mg, off-white solid. Product is the trifluoroacetic acid salt.

Rt.=2.26 min (method C), LCMS: 434 (M+H).

Example 246

4-{1-[3-(3-Fluoro-4-methyl-benzoylamino)-phenyl]-ethylamino}-quinazoline-8-carboxylic acid amide The title compound was synthesized according to the procedure described for the preparation of Example 425. MS (M+1) 444

Example 247

4-{1-[3-(4-Fluoro-3-hydroxy-benzoylamino)-Phenyl]-ethylamino}-quinazoline-8-carboxylic acid amide The title compound was synthesized according to the procedure described for the preparation of Example 425. MS (M+1) 446

Example 249

4-{3-Dimethylamino-1-[3-(2,4-difluoro-benzoylamino)-phenyl]-propylamino}-quinazoline-8-carboxylic acid amide The title compound was synthesized according to the procedure described for the preparation of Example 462. LCMS [505 (M+1)].

Example 250

4-[3-(2,4-Dichloro-benzoylamino)-benzylamino]-quinazoline-8-carboxylic acid amide The title compound was prepared according to Example 667.
53 mg, off-white solid. Product is the trifluoroacetic acid salt.
Rt.=2.45 min (method C), LCMS: 467 (M+H).

Example 252

4-{1-[3-(4-Trifluoromethyl-benzoylamino)-phenyl]-2-methylamino-ethylamino}-quinazoline-8-carboxylic acid amide The title compound was synthesized according to the procedure described for the preparation of Example 462. LCMS [509 (M+1)].

Example 254

4-{3-Dimethylamino-1-[3-(4-trifluoromethyl-benzoylamino)-phenyl]-proqylamino}-quinazoline-8-carboxylic acid amide The title compound was synthesized according to the procedure described for the preparation of Example 462. LCMS [537 (M+1)].

Example 255

4-{3-Methoxy-1-[3-(2,4-difluoro-benzoylamino)-phenyl]-propylamino}-quinazoline-8-carboxylic acid amide The title compound was synthesized according to the procedure described for the preparation of Example 462. LCMS [491.9 (M+1)].

Example 261

4-{(R)-1-[3-(3,4-Dimethyl-benzoylamino)-phenyl]-ethylamino}-quinazoline-8-carboxylic acid amide The title compound was synthesized according to the procedure described for the preparation of Example 425. MS (M+1) 440.

Example 262

6-benzyloxy-4-[1-(3-chloro-phenyl)-2-methylamino-ethylamino]-quinazoline-8-carboxylic acid amide A scintillation vial equipped with a stir bar was charged with [2-(6-benzyloxy-8-carbamoyl-quinazolin-4-ylamino)-2-(3-chloro-phenyl)-ethyl]-methyl-carbamic acid tert-butyl ester (20 mg, 0.035 mmol) and THF, (3 mL). Then, 4 M HCl in dioxane, (3 mL) was added at RT and the mixture was stirred overnight. After 18 h, a white precipitate had formed and LCMS indicated consumption of SM. The mixture was diluted with Et$_2$O (30 mL) and the precipitate was filtered through a filter paper and washed with Et$_2$O, (30 mL). The solid was dried under vacuum. Amount obtained: 15 mg, 0.034 mmol, 97% yield. LCMS (ESI) 462 (M+H).

Example 265

4-{3-Dimethylamino-1-[3-(4-bromo-benzoylamino)-phenyl]-propylamino}-quinazoline-8-carboxylic acid amide The title compound was synthesized according to the procedure described for the preparation of Example 462. LCMS [548 (M+1)].

Example 266

4-((R)-1-{3-[(6-Cyano-pyridine-3-carbonyl)-amino]-phenyl}-ethylamino)-quinazoline-8-carboxylic acid amide The title compound was synthesized according to the procedure described for the preparation of Example 425. MS (M+1) 438.

Example 272

4-{1-[3-(4-Bromo-benzoylamino)-phenyl]-ethylamino}-quinazoline-8-carboxylic acid amide The title compound was synthesized according to the procedure described for the preparation of Example 425. MS (M+1) 491

Example 273

{2-[8-Carbamoyl-quinazolin-4-ylamino)-2,3-(benzoylamino)-phenyl]-ethyl}-methyl-carbamic acid tert-butyl The title compound was synthesized according to the procedure described for the preparation of Example 462. LCMS [541 (M+1)].

Example 274

4-[2-Dimethylamino-1-(3-methoxy-phenyl)-ethylamino]-quinazoline-8-carboxylic acid amide To a solution of 2-Bromo-1-(3-methoxy-phenyl)-ethanone (2.0 g, 8.77 mmol) in CHCl$_3$ (10.0 mL) and cooled to 0° C. DIPEA (3.05 mL, 17.54 mmol) was added to this and dimethylamine (6.57 mL of 2M solution in THF, 13.15 mmol) was added slowly. The reaction mixture was stirred at 0-25° C. for 1 h. Reaction was diluted with DCM (20.0 mL) and washed with water (5.0 mL) and brine (5.0 mL) and dried over anhydrous MgSO$_4$. The solution was filtered and concentrated to give the intermediate (1.0 g, 59%).

Step 2. To a solution of 2-Dimethylamino-1-(3-methoxy-phenyl)-ethanone (1.0 g, 5.64 mmol) in pyridine (10.0 mL) was added NH$_2$OH.HCl (1.9 g, 28.2 mmol) and the reaction mixture was stirred at 25° C. for 16 h. The mixture was diluted with water (100 mL) and was extracted with DCM (×3), dried (Na$_2$SO$_4$) and the solvent was evaporated under reduced pressure to give crude product, (0.75 g, 64%). The material was used as is in the next step.

Step 3. To a solution of 2-Dimethylamino-1-(3-methoxy-phenyl)-ethanone oxime (0.75 g, 3.6 mmol) in THF (8.0 mL) was added LAH (4.5 mL of 2.0M THF solution, 9.01 mmol) at 0° C. After the addition is over, the reaction was refluxed for 3 h. The reaction was carefully quenched with water (5.0 mL) followed by 2N NaOH (10.0 ml). Additional 20 mL of THF was added and the organic layer was separated from the white solid and concentrated. The crude was dissolved in EtOAc (50.0 mL) and extracted with 1N HCl (2×20 mL) and the aqueous layer was made basic using 2N NaOH and extracted with DCM/MeOH (10%) and dried over anhydrous MgSO4 and concentrated to give product amine (0.44 g, 63% yield).

Step 4. The title compound was synthesized according to the procedure of Example 76.

LCMS (ESI) 366 (M+H);

Example 275

4-{3-Methoxy-1-[3-(2,6-difluoro-benzoylamino)-phenyl]-propylamino}-quinazoline-8-carboxylic acid amide The title compound was synthesized according to the procedure described for the preparation of Example 462. LCMS [492 (M+1)].

Example 277

4-[2-dimethylamino-1-(3-fluoro-phenyl)-ethylamino]-6-ethoxy-quinazoline-8-carboxylic acid amide A Wheaton vial equipped with a stir bar was charged with 4-[2-dimethylamino-1-(3-fluoro-phenyl)-ethylamino]-6-hydroxy-quinazoline-8-carboxylic acid amide, (37 mg, 0.1 mmol) $Cs_2CO_3$, (100 mg, 0.3 mmol) and dry DMF, (1 mL). The mixture was heated at 60° C. for 1 h. It was then cooled to RT and ethylbromide (11 mg, 0.1 mmol) was added a solution in DMF (0.5 mL). The mixture was left to stir overnight. After 18 h, LCMS indicated consumption of SM. The mixture was diluted with EtOAc, (30 mL) and added to water, (30 mL). The phases were separated and the aqueous was extracted with EtOAc, (30 mL) (×2). The EtOAc phase was washed with sat. LiCl, (30 mL) dried ($Na_2SO_4$) and the solvent was evaporated under reduced pressure. The material was purified by chromatography using a 4 g silica cartridge eluting with DCM-[DCM-MeOH—$NH_4OH$ (9:1:0.1)], gradient 0 to 100% cocktail. Amount obtained: 6 mg, 0.015 mmol, 15% yield.

LCMS (ESI) 398 (M+H).

Example 279

4-((S)-2-Ethylamino-1-phenyl-ethylamino)-quinazoline-8-carboxylic acid amide

Step 1. To a 250-mL round bottom flask with magnetic stir bar at 25° C. under a nitrogen atmosphere and fitted with a Vigreux column was added 4-Chloro-quinazoline-8-carboxylic acid methyl ester (0.5 g, 2.25 mmol, 1 eq.) and anhydrous THF (40 mL). DIEA (0.87 g, 1.17 mL, 6.7 mmol, 3 eq.) was then added followed by Example G (0.86 g, 2.5 mmol, 1.1 eq.). The resulting mixture was heated at 70-75° C.×16 hours with stirring. The solvent was evaporated in vacuo and the resulting residue re-dissolved in EtOAc (50 mL). The mixture was washed with saturated aqueous $NaHCO_3$ solution (30 mL), water (30 mL), brine (30 mL), and dried (e.g., $Na_2SO_4$), filtered and concentrated. The resulting residue was purified by column chromatography (ISCO CombiFlash) using a 0-45% gradient (EtOAc/DCM) to afford 0.6872 g (51% yield). LCMS (ESI) 536 (M+H).

Step 2. To a 40-mL vial with magnetic stirbar at 25° C. was added the 4-{(S)-2-[Ethyl-(4-nitro-benzenesulfonyl)-amino]-1-phenyl-ethylamino}-quinazoline-8-carboxylic acid methyl ester (0.69 g, 1.29 mmol, 1 eq.) and THF (10 mL) and 2-propanol (10 mL). An approx. equal volume (i.e.; 10 mL) of concentrated aqueous ammonium hydroxide solution (28-30% soln.) was then added and stirring continued over the weekend (×96 hours). The reaction mixture was poured into a beaker containing water (30 mL) and a precipitate immediately began to form. The precipitate was collected and dried thoroughly in vacuo. The material required further purification via preparative HPLC to afford the product as a white solid (0.4573 g 68% yield). LCMS (ESI) 521 (M+H).

Step 3. To a 40-mL vial with magnetic stirbar at 25° C. under a nitrogen atmosphere was added 4-{(S)-2-[Ethyl-(4-nitro-benzenesulfonyl)-amino]-1-phenyl-ethylamino}-quinazoline-8-carboxylic acid amide (0.45 g, 0.86 mmol, 1 eq.) and anhydrous acetonitrile (25 mL). The Cesium carbonate (0.84 g, 2.6 mmol, 3 eq.) was added followed by the thiophenol (0.14 g, 1.3 mmol, 0.13 mL, 1.5 eq.). Stirring was continued at 25° C.×16 hours. The reaction mixture was diluted with saturated aqueous $NH_4Cl$ solution (40 mL) and extracted with EtOAc (30 mL)×3. The combined organics were washed with brine (20 mL), dried (e.g., $Na_2SO_4$), filtered and concentrated. The resulting residue was purified by column chromatography (ISCO CombiFlash) using a 0-100% gradient (10% MeOH in EtOAc/EtOAc) to afford 58.3 mg (21% yield). LCMS (ESI) 336.2 (M+H).

Example 280

4-{1-[3-(4-Bromo-3-fluoro-benzoylamino)-phenyl]-ethylamino}-quinazoline-8-carboxylic acid amide The title compound was synthesized according to the procedure described for the preparation of Example 425. MS (M+1) 509

Example 281

4-{1-[3-(benzoylamino)-phenyl]-2-methoxy-ethylamino}-quinazoline-8-carboxylic acid amide The title compound was synthesized according to the procedure described for the preparation of Example 462. LCMS [442 (M+1)].

Example 284

4-(3-Amino-1-phenyl-propylamino)-quinazoline-8-carboxylic acid amide

[(R)-3-(8-Carbamoyl-quinazolin-4-ylamino)-3-phenyl-propyl]-carbamic acid benzyl ester (20 mg, 0.04 mmol) was dissolved in EtOH (5 mL) and treated with 5% Pd/C under 1 atm of $H_2$. Upon completion the reaction was filtered through a pad of celite, and the pad was washed with EtOH. The crude material was purified by silica gel (10% MeOH/$CH_2Cl_2$) to afford the desired compound (7 mg, 50%). LCMS (ESI) 322 (M+H)

Example 286

4-{3-Methoxy-1-[3-(4-trifluoromethyl-benzoylamino)-phenyl]-propylamino}-quinazoline-8-carboxylic acid amide The title compound was synthesized according to the procedure described for the preparation of Example 462. LCMS

Example 287

{2-[8-Carbamoyl-quinazolin-4-ylamino)-2-[3-(2-fluoro-4-methoxy-benzoylamino)-phenyl]-ethyl}-methyl-carbamic acid tert-butyl The title compound was synthesized according to the procedure described for the preparation of Example 462. LCMS [589 (M+1)].

Example 291

4-(1-{3-[(6-Trifluoromethyl-pyridine-3-carbonyl)-amino]-phenyl}-ethylamino)-quinazoline-8-carboxylic acidamide The title compound was synthesized according to the procedure described for the preparation of Example 425 MS (M+1) 481

Example 292

4-(1-{3-[(6-Methoxy-pyridine-3-carbonyl)-amino]-phenyl}-ethylamino)-quinazoline-8-carboxylic acid amide The title compound was synthesized according to the procedure described for the preparation of Example 425. MS (M+1) 443

Example 294

4-{1-[3-(4-Cyano-3-fluoro-benzoylamino)-phenyl]-ethylamino}-quinazoline-8-carboxylic acid amide The title compound was synthesized according to the procedure described for the preparation of Example 425. MS (M+1) 454

Example 296

{2-[8-Carbamoyl-quinazolin-4-ylamino)-2-[3-(3,4-difluoro-benzoylamino)-phenyl]-ethyl}-methyl-carbamic acid tert-butyl The title compound was synthesized according to the procedure described for the preparation of Example 462. LCMS [577 (M+1)].

Example 299

4-{1-[3-(4-Chloro-3-fluoro-benzoylamino)-phenyl]-ethylamino}-quinazoline-8-carboxylic acid amide The title compound was synthesized according to the procedure described for the preparation of Example 425. MS (M+1) 464

Example 300

4-{3-Methoxy-1-[3-(2,3-difluoro-benzoylamino)-phenyl]-propylamino}-quinazoline-8-carboxylic acid amide The title compound was synthesized according to the procedure described for the preparation of Example 462. LCMS [492 (M+1)].

Example 301

4-(1-{3-[(6-Chloro-pyridine-3-carbonyl)-amino]-phenyl}-ethylamino)-quinazoline-8-carboxylic acid amide The title compound was synthesized according to the procedure described for the preparation of Example 425. MS (M+1) 447

Example 305

6-hydroxy-4-(2-methylamino-1-phenyl-ethylamino)-quinazoline-8-carboxylic acid amide A 250 mL round bottom flask equipped with a stir bar was evacuated and flushed with nitrogen. To this flask was added Pd/C (5%), (6 mg) and EtOH, (30 mL). Then 6-benzyloxy-4-(2-methylamino-1-phenyl-ethylamino)-quinazoline-8-carboxylic acid amide, (64 mg, 0.15 mmol) was added as a solid. The solution was evacuated and flushed three times with nitrogen and then evacuated and flushed three times with hydrogen. The mixture was left to stir over the weekend. It was evacuated/flushed three times with nitrogen and the mixture was filtered through a pad of celite eluting with 10% MeOH in DCM and the solvent was evaporated under reduced pressure. Amount obtained: 20 mg, 0.06 mmol, 40% yield. LCMS (ESI) 338 (M+H).

Example 308

4-(1-{3-[(5-Trifluoromethyl-2H-pyrazole-3-carbonyl)-amino]-phenyl}-ethylamino)-quinazoline-8-carboxylic acid amide The title compound was synthesized according to the procedure described for the preparation of Example 425. MS (M+1) 470

Example 309

4-(1-{3-[(6-Methyl-pyridine-3-carbonyl)-amino]-phenyl}-ethylamino)-quinazoline-8-carboxylic acid amide The title compound was synthesized according to the procedure described for the preparation of Example 425. MS (M+1) 427

Example 313

4-{3-Dimethylamino-1-[3-(2,3-difluoro-benzoylamino)-phenyl]-propylamino}-quinazoline-8-carboxylic acid amide The title compound was synthesized according to the procedure described for the preparation of Example 462. LCMS [505 (M+1)].

Example 314

4-{1-[3-(2,4-Difluoro-benzoylamino)-phenyl]-3-pyrrolidin-1-yl-propylamino}-quinazoline-8-carboxylic acid amide The title compound was synthesized according to the procedure described for the preparation of Example 462. LCMS [531.0 (M+1)].

Example 319

4-{1-[3-(4-Bromo-benzoylamino)-phenyl]-3-methoxy-propylamino}-quinazoline-8-carboxylic acid amide The title compound was synthesized according to the procedure described for the preparation of Example 462. LCMS [535 (M+1)].

Example 321

4-[3-(4-Chloro-3-fluoro-benzoylamino)-benzylamino]-quinazoline-8-carboxylic acid amide The title compound was synthesized according to the procedure described for the preparation of Example 425. (M+1) 450.

Example 322

4-{3-Methoxy-1-[3-(2,5-difluoro-benzoylamino)-phenyl]-propylamino}-quinazoline-8-carboxylic acid amide The title compound was synthesized according to the procedure described for the preparation of Example 462. LCMS [492 (M+1)].

Example 323

4-{1-[3-(3-Fluoro-benzoylamino)-phenyl]-ethylamino}-quinazoline-8-carboxylic acid amide The title compound was synthesized according to the procedure described for the preparation of Example 425. MS (M+1) 430

Example 325

4-[1-(3-Chloro-phenyl)-2-dimethylamino-ethylamino]-6-hydroxy-quinazoline-8-carboxylic acid amide In a 20 mL scintillation vial 6-Benzyloxy-4-[1-(3-chloro-phenyl)-2-dimethylamino-ethylamino]-quinazoline-8-carboxylic acid amide was taken in 5 ml of aqueous HBr solution and stirred at room temperature for 2 h. Reaction was concentrated and dissolved in methanol and the crude was purified on preparative HPLC to give the product, (7.0 mg, 13% yield). LCMS (ESI) 386 (M+H)

Example 330

4-{3-Allyl-methylamino-1-[3-(4-methoxy-benzoylamino)-phenyl]-propylamino}-quinazoline-8-carboxylic acid amide The title compound was synthesized according to the procedure described for the preparation of Example 462. LCMS [525 (M+1)].

Example 332

4-{1-[3-(4-Bromo-benzoylamino)-phenyl]-3-azetidin-1-yl-propylamino}-quinazoline-8-carboxylic acid amide The title compound was synthesized according to the procedure described for the preparation of Example 462. LCMS [559.1 (M), 561.0 (M+2H)].

Example 333

4-{2-Methoxy-1-[3-(4-methoxy-benzoylamino)-phenyl]-ethylamino}-quinazoline-8-carboxylic acid amide The title compound was synthesized according to the procedure described for the preparation of Example 462. LCMS [450 (M+1)].

Example 334

4-(1-{3-[(2,3-Dihydro-benzo[1,4]dioxine-6-carbonyl)-amino]-phenyl}-ethylamino)-quinazoline-8-carboxylic acid amide The title compound was synthesized according to the procedure described for the preparation of Example 425. MS (M+1) 470

Example 335

{2-[8-Carbamoyl-quinazolin-4-ylamino)-2-[3-(2,6-difluoro-benzoylamino)-phenyl]-ethyl}-methyl-carbamic acid tert-butyl The title compound was synthesized according to the procedure described for the preparation of Example 462. LCMS [577 (M+1)].

Example 336

4-[2-dimethylamino-1-(3-fluoro-phenyl)-ethylamino]-6-hydroxy-quinazoline-8-carboxylic acid amide A 500 mL round bottom flask equipped with a stir bar was evacuated and flushed with nitrogen. To this flask was added Pd/C (5%), (50 mg) and dry EtOH, (200 mL). Then 6-benzyloxy-4-[2-dimethylamino-1-(3-fluoro-phenyl)-ethylamino]-quinazoline-8-carboxylic acid amide, (919 mg, mmol) was added as a solid. The solution was evacuated and flushed three times with nitrogen and then ammonium formate, (1.3 g, 20 mmol) was added. The mixture was then heated at reflux for 45 min. The flask was evacuated/flushed three times with nitrogen and the mixture was filtered through a pad of celite eluting with 10% MeOH in DCM. The solvent was evaporated under reduced pressure. The material was purified by chromatography using a 40 g silica cartridge eluting with DCM-[DCM-MeOH—NH$_4$OH (9:1:0.1)], gradient 0 to 100% cocktail. Amount obtained: 683 mg, 1.85 mmol, 93% yield. LCMS (ESI) 370 (M+H).

Example 338

4-{3-Hydroxy-1-[3-(4-methoxy-benzoylamino)-phenyl]-propylamino}-quinazoline-8-carboxylic acid amide The title compound was synthesized according to the procedure described for the preparation of Example 462. LCMS [472.1 (M+1)].

Example 339

4-[3-(2-Fluoro-5-trifluoromethyl-benzoylamino)-benzylamino]-quinazoline-8-carboxylic acid amide The title compound was prepared according to Example 667.
53 mg, off-white solid. Product is the trifluoroacetic acid salt.
Rt.=2.55 min (method C), LCMS: 484 (M+H).

Example 348

4-{3-[(5-Morpholin-4-yl-pyridine-3-carbonyl)-amino]-benzylamino}-quinazoline-8-carboxamide Step 1. To a 40-mL vial with magnetic stir bar at 25° C. under a nitrogen atmosphere was added Methyl 5-Bromonicotinate (0.5 g, 2.3 mmol, 1 eq.), morpholine (0.3 g, 0.3 mL, 3.5 mmol, 1.5 eq.), and toluene (5 mL). Cesium carbonate (2.26 g, 6.9 mmol, 3 eq.), Palladium (II) acetate (0.052 g, 0.23 mmol, 0.1 eq.), and BINAP (0.29 g, 0.46 mmol, 0.2 eq.) were then added and the reaction vial heated with stirring at 80° C.×16 hours. The reaction was diluted with EtOAc (30 mL) and filtered through a pad of Celite®. The Celite® pad was rinsed thoroughly with EtOAc and the eluent dried over anhydrous Na$_2$SO$_4$, filtered and concentrated. The resulting residue was purified by column chromatography (ISCO CombiFlash) using a 0-50% gradient (EtOAc/DCM) to afford 422 mg (81% yield).

Step 2. To a 40-mL vial with magnetic stir bar at 25° C. was added Methyl 5-Morpholin-4-yl-nicotinate (0.42 g, 1.89 mmol, 1 eq.) and methanol (10 mL). Aqueous sodium hydroxide solution (0.94 mL, 10M, 9.45 mmol, 5 eq.) was then added and the reaction vial heated with stirring at 65° C.×16 hours. The reaction mixture was concentrated in vacuo and the resulting residue dissolved in a minimal volume of H$_2$O (2-3 mL). The mixture was acidified with glacial acetic acid (AcOH) to pH 3. The resulting precipitate was collected and dried thoroughly in vacuo to afford 244 mg (62% yield).

Step 3. To a 40-mL vial with magnetic stir bar at 25° C. under a nitrogen atmosphere was added (3-Amino-benzyl)-carbamic acid tert-butyl ester (0.23 g, 1.05 mmol, 1 eq.) and anhydrous DMF (10 mL). The 5-Morpholin-4-yl-nicotinic acid (0.24 g, 1.15 mmol, 1.1 eq.) was added followed by the Diisopropylethylamine (0.68 g, 0.91 mL, 5.2 mmol, 5 eq.) and the HATU (0.48 g, 1.26 mmol, 1.2 eq.). The reaction mixture was stirred overnight at 25° C. The reaction mixture was then taken up in EtOAc (50 mL) and washed with H$_2$O (20 mL), saturated aq. LiCl solution (20 mL), brine (20 mL), dried (e.g., Na$_2$SO$_4$), filtered and concentrated. The resulting residue was purified by column chromatography (ISCO CombiFlash) using a 0-100% gradient (EtOAc/Heptane) to afford 250 mg (57% yield).

Step 4. To a 40-mL vial with magnetic stir bar at 25° C. was added {3-[(5-Morpholin-4-yl-pyridine-3-carbonyl)-amino]-benzyl}-carbamic acid tert-butyl ester (0.25 g, 0.61 mmol, 1 eq.) and anhydrous DCM (3 mL). The reaction vial was cooled to 0° C. and the HCl in 1,4-Dioxane (0.75 mL, 4M, 3 mmol, 5 eq.) was added drop-wise with vigorous stirring. Stirring was continued ×16 hours and was allowed to equilibrate to 25° C. The reaction material was transferred to a 100-mL round bottom flask and the solvent evaporated in vacuo. The resulting residue was re-dissolved in MeOH (5 mL), the solvent evaporated, and the residue dried thoroughly in vacuo to afford 214 mg. The material was carried on to the next synthetic step without purification.

Step 5. To a 40-mL vial with magnetic stir bar at 25° C. under a nitrogen atmosphere was added 4-Chloro-quinazoline-8-carboxylic acid methyl ester (0.14 g, 0.61 mmol, 1 eq.) and anhydrous THF (10 mL). The Diisopropylethylamine (0.24 g, 0.32 mL, 1.8 mmol, 3 eq.) was then added followed by the amine (0.21 g, 0.67 mmol, 1.1 eq.). The resulting mixture was heated in a capped vial at 50° C.×16 hours with stirring. The solvent was evaporated in vacuo and the resulting residue re-dissolved in EtOAc (30 mL). The mixture was washed with saturated aqueous NaHCO$_3$ solution (20 mL), H$_2$O (20 mL), brine (20 mL), and dried (e.g., Na$_2$SO$_4$), filtered and concentrated. The resulting residue was purified by column chromatography (ISCO CombiFlash) using a 0-85% gradient (EtOAc/DCM) to afford 116 mg. LCMS (ESI) 499.2 (M+H).

Step 6. To a 40-mL vial with magnetic stirbar at 25° C. was added 4-{3-[(5-Morpholin-4-yl-pyridine-3-carbonyl)-amino]-benzylamino}-quinazoline-8-carboxylic acid methyl ester (0.12 g, 0.24 mmol, 1 eq.) and THF (2 mL) and 2-propanol (2 mL). An approx. equal volume (i.e.; 2 mL) of concentrated aqueous ammonium hydroxide solution (28-30% soln.) was then added and stirring continued over the weekend (×96 hours). Water (15 mL) was added to the reaction mixture and a precipitate immediately began to form. The precipitate was collected and dried thoroughly in vacuo. The material required further purification via preparative HPLC. The isolated material was re-dissolved in THF (1 mL), iPrOH (1 mL), and DMSO (1 mL) to which concentrated aqueous ammonium hydroxide solution (28-30%) (1 mL) was added and heated at 50° C.×36 hours. H$_2$O (10 mL) was added to the reaction mixture and the resulting white precipitate collected and dried thoroughly in vacuo to afford 50.2 mg (45% yield). LCMS (ESI) 484.2 (M+H).

Example 353

4-{3-Methoxy-1-[3-(3,4-difluoro-benzoylamino)-phenyl]-propylamino}-quinazoline-8-carboxylic acid amide The title compound was synthesized according to the procedure described for the preparation of Example 462. LCMS [492 (M+1)]. 1H NMR (400 MHz, DMSO-D6): 2.1875 (m, 1H), 2.3432 (m, 1H), 3.2379 (s, 3H), 3.3835 (m, 1H), 3.4522 (m, 1H), 5.7107 (m, 1H), 7.0524 (m, 2H), 7.2017 (m, 1H), 7.3317 (m, 1H), 7.6285 (m, 1H), 7.9371 (m, 6H), 8.0791 (m, 1H), 8.5544 (m, 1H), 8.6647 (s, 1H), 8.7836 (s, 1H), 10.3385 (s, 1H).

Example 356

4-{3-Allyl-methylamino-1-[3-(benzoylamino)-phenyl]-propylamino}-quinazoline-8-carboxylic acid amide The title compound was synthesized according to the procedure described for the preparation of Example 462. LCMS [495 (M+1)].

Example 358

4-[1-(3-Benzoylamino-phenyl)-ethylamino]-quinazoline-8-carboxylic acid amide

The title compound was synthesized according to the procedure described for the preparation of Example 425. MS (M+1) 412

Example 359

4-(1-{3-[(2-Methyl-furan-3-carbonyl)-amino]-phenyl}-ethylamino)-quinazoline-8-carboxylic acid amide The title compound was synthesized according to the procedure described for the preparation of Example 425. MS (M+1) 416

Example 360

4-{1-[3-(4-Bromo-benzoylamino)-phenyl]-3-pyrrolidin-1-yl-propylamino}-quinazoline-8-carboxylic acid amide The title compound was synthesized according to the procedure described for the preparation of Example 462. LCMS [573.2 (M+1)]. $^1$H NMR (400 MHz, DMSO-D$_6$): 1.8532 (m, 2H), 2.0043 (m, 2H), 2.3111 (m, 2H), 3.0432 (m, 2H), 3.2892 (m, 4H), 5.6823 (m, 1H), 6.8784 (m, 2H), 7.2756 (d, 1H), 7.3512 (t, 1H), 7.5442 (m, 2H), 7.5745 (m, 1H), 7.6326 (m, 1H), 7.8225 (m, 1H), 7.9382 (d, 2H), 8.5804 (d, 1H), 8.6714 (s, 1H), 8.7852 (m, 1H), 9.6971 (br, 1H), 10.3722 (s, 1H).

Example 361

4-{3-Dimethylamino-1-[3-(2-fluoro-4-methoxy-benzoylamino)-phenyl]-propylamino}-quinazoline-8-carboxylic acid amide The title compound was synthesized according to the procedure described for the preparation of Example 462. LCMS [517 (M+1)].

Example 362

4-{3-[(2-Pyrrolidin-1-yl-pyridine-4-carbonyl)-amino]-benzylamino}-quinazoline-8-carboxylic acid amide To a 10-mL microwave-rated vial with magnetic stir bar at r.t. was added 4-{3-[(2-Chloro-pyridine-4-carbonyl)-amino]-benzylamino}-quinazoline-8-carboxylic acid amide (0.05 g, 0.115 mmol, 1 eq.), t-BuOH (2 mL), DMSO (1 mL), and pyrrolidine (0.1 mL, 1.15 mmol, 10 eq.). The vial was capped and heated under microwave conditions (50 W, 3 min. ramp, 110° C., STND, 1 hr. hold time) followed by addition of another aliquot of pyrrolidine (0.1 mL) then microwaved (70 W, 3 min. ramp, 140° C., STND, 1 hr. hold time). Reaction was diluted with water (20 mL) and extracted with DCM (3×30 mL). The combined organics were washed with brine, dried (e.g., Na$_2$SO$_4$), filtered and concentrated. The resulting residue was purified by column chromatography (ISCO CombiFlash) using a 0-30% gradient (10% MeOH in EtOAc/EtOAc) afforded 25 mg (49% yield). LCMS (ESI) 468 (M+H).

Example 363

4-{3-Dimethylamino-1-[3-(2-fluoro-benzoylamino)-phenyl]-propylamino}-quinazoline-8-carboxylic acid amide)

The title compound was synthesized according to the procedure described for the preparation of Example 462. LCMS [487 (M+1)].

Example 365

4-{3-Dimethylamino-1-[3-(4-trifluoromethoxy-benzoylamino)-phenyl]-propylamino}-quinazoline-8-carboxylic acid amide The title compound was synthesized according to the procedure described for the preparation of Example 462. LCMS [553 (M+1)]

Example 366

4-{3-Hydroxy-1-[3-(benzoylamino)-phenyl]-propylamino}-quinazoline-8-carboxylic acid amide The title compound was synthesized according to the procedure described for the preparation of Example 462. LCMS [442.1 (M+1)].

Example 367

4-[2-(ethyl-methyl-amino)-1-phenyl-ethylamino]-quinazoline-8-carboxylic acid amide A 20 mL scintillation vial equipped with a stir bar was charged with 4-(2-methylamino-1-phenyl-ethylamino)-quinazoline-8-carboxylic acid amide hydrochloride salt, (32 mg, 0.1 mmol), EtOH, (5 mL) and Et$_3$N, (0.03 mL, 0.2 mmol). The mixture was stirred until the amine had dissolved. Then AcOH (10 drops) was added followed by acetaldehyde, (0.1 mL, 2.0 mmol) and then NaBH(OAc)$_3$, (212 mg, 1.0 mmol). The mixture was stirred at RT. After 30 minutes, the reaction was quenched by addition of 1N NaOH, (20 mL) diluted with EtOAc (25 mL) and the phases were split. The aqueous was extracted with EtOAc, (25 mL) (×2), dried (Na$_2$SO$_4$) and the solvent was evaporated under reduced pressure. The material was purified by chromatography eluting with DCM-[DCM-MeOH—NH$_4$OH (9:1:0.1)] Amount obtained: 15 mg, 40% yield. LCMS (ESI) 350 (M+H).

Example 370

4-{1-[3-(benzoylamino)-phenyl]-3-methoxy-propylamino}-quinazoline-8-carboxylic acid amide The title compound was synthesized according to the procedure described for the preparation of Example 462. LCMS [456 (M+1)].

Example 371

4-(1-{3-[(5-Methyl-pyrazine-2-carbonyl)-amino]-phenyl}-ethylamino)-quinazoline-8-carboxylic acid amide The title compound was synthesized according to the procedure described for the preparation of Example 425. MS (M+1) 428

Example 379

4-{3-Methoxy-1-[3-(2-fluoro-benzoylamino)-phenyl]-propylamino}-quinazoline-8-carboxylic acid amide The title compound was synthesized according to the procedure described for the preparation of Example 462. LCMS [474 (M+1)].

Example 385

4-[3-(3-Dimethylaminomethyl-benzoylamino)-benzylamino]-quinazoline-8-carboxylic acid amide The title compound was prepared according to Example 667.
38 mg, off-white solid. Product is the trifluoroacetic acid salt.
Rt.=1.84 min (method C), LCMS: 455 (M+H).

Example 386

4-{3-[3-(2-Dimethylamino-ethoxy)-benzoylamino]-benzylamino}-quinazoline-8-carboxylic acid amide The title compound was prepared according to Example 667.
31 mg, off-white solid. Product is the trifluoroacetic acid salt.
Rt.=1.89 min (method C), LCMS: 485 (M+H).

Example 390

4-{3-[(2,3-Dihydro-benzofuran-5-carbonyl)-amino]-benzylamino}-quinazoline-8-carboxylic acid amide The title compound was prepared according to Example 667.
38 mg, off-white solid. Product is the trifluoroacetic acid salt.
Rt.=2.24 min (method C), LCMS: 440 (M+H).

Example 391

4-{3-Dimethylamino-1-[3-(2,6-difluoro-benzoylamino)-phenyl]-propylamino}-quinazoline-8-carboxylic acid amide The title compound was synthesized according to the procedure described for the preparation of Example 462. LCMS [505 (M+1)].

Example 392

4-{1-[3-(2,6-Difluoro-benzoylamino)-phenyl]-3-piperidin-1-yl-propylamino}-quinazoline-8-carboxylic acid amide The title compound was synthesized according to the procedure described for the preparation of Example 462. LCMS [545.0 (M+1)].

Example 394

4-(1-{3-[(5-Isopropyl-1H-pyrazole-3-carbonyl)-amino]-phenyl}-ethylamino)-quinazoline-8-carboxylic acid amide The title compound was synthesized according to the procedure described for the preparation of Example 425. MS (M+1) 444

Example 396

6-benzyloxy-4-(2-methylamino-1-phenyl-ethylamino)-quinazoline-8-carboxylic acid amide A scintillation vial equipped with a stir bar was charged with [2-(6-benzyloxy-8-carbamoyl-quinazolin-4-ylamino)-2-phenyl-ethyl]-methyl-carbamic acid tert-butyl ester (81 mg, 0.15 mmol) and THF, (3 mL). Then, 4 M HCl in dioxane, (3 mL) was added at RT and the mixture was stirred overnight. After 18 h, a white precipitate had formed and LCMS indicated consumption of SM. The mixture was diluted with Et$_2$O (30 mL) and the precipitate was filtered through a filter paper and washed with Et$_2$O, (30 mL). The solid was dried under vacuum. Amount obtained: 50 mg, 0.12 mmol, 78% yield. LCMS (ESI) 428 (M+H).

Example 399

4-{1-[3-(2,4-Difluoro-benzoylamino)-phenyl]-3-piperidin-1-yl-propylamino}-quinazoline-8-carboxylic acid amide The title compound was synthesized according to the procedure described for the preparation of Example 462. LCMS [545.0 (M+1)].

Example 402

4-{3-[(5-Methyl-1H-pyrazole-3-carbonyl)-amino]-benzylamino}-quinazoline-8-carboxylic acid amide The title compound was prepared according to Example 667.
42.7 mg, off-white solid. Product is the trifluoroacetic acid salt.
Rt.=1.98 min (method C), LCMS: 402 (M+H).

Example 403

4-{3-Methoxy-1-[3-(2-fluoro-4-methoxy-benzoylamino)-phenyl]-propylamino}-quinazoline-8-carboxylic acid amide The title compound was synthesized according to the procedure described for the preparation of Example 462. LCMS [492 (M+1)].

Example 404

4-[3-(4-Methoxy-3-methyl-benzoylamino)-benzylamino]-quinazoline-8-carboxylic acid amide The title compound was prepared according to Example 667.
37 mg, off-white solid. Product is the trifluoroacetic acid salt.
Rt.=2.41 min (method C), LCMS: 442 (M+H).

Example 405

4-(1-{3-[5(5-Cyclopropyl-1H-pyrazole-3-carbony)-amino]-phenyl}-3-methoxy-propylamino)-quinazoline-8-carboxylic acid amide The title compound was synthesized according to the procedure described for the preparation of Example 462. LCMS [486 (M+1)].

Example 414

4-(1-{3-[(2-Methoxy-pyridine-4-carbonyl)-amino]-phenyl}-ethylamino)-quinazoline-8-carboxylic acid amide The title compound was synthesized according to the procedure described for the preparation of Example 425. MS (M+1) 443

Example 418

4-{1-[3-(2,4-Difluoro-benzoylamino)-phenyl]-3-pyrrolidin-1-yl-propylamino}-quinazoline-8-carboxylic acid amide The title compound was synthesized according to the procedure described for the preparation of Example 462. LCMS [531.0 (M+1)].

Example 421

4-(1-{3-[(1-Methyl-1H-pyrrole-2-carbonyl)-amino]-phenyl}-ethylamino)-quinazoline-8-carboxylic acid amide The title compound was synthesized according to the procedure described for the preparation of Example 425. MS (M+1) 415

Example 422

4-{1-[3-(3,4-Difluoro-benzoylamino)-phenyl]-3-pyrrolidin-1-yl-propylamino}-quinazoline-8-carboxylic acid amide The title compound was synthesized according to the procedure described for the preparation of Example 462. LCMS [531.0 (M+1)].

Example 423

4-{3[(6-Methoxy-pyridine-3-carbonyl)-amino]-benzylamino}-quinazoline-8-carboxylic acid amide Step 1. To a 500-mL round bottom flask with magnetic stir bar at 25° C. under a nitrogen atmosphere was added the 3-Amino-benzylamine (5 g, 41 mmol, 1 eq.) and anhydrous DCM (150 mL). DIEA (10.6 g, 14.3 mL, 82 mmol, 2 eq.) was then added, and the reaction vessel was cooled to 0° C. The di-tert-butyl dicarbonate (9.8 g, 45 mmol, 1.1 eq.) was dissolved in anhydrous DCM (15 mL) and added rapidly dropwise to the reaction vessel. The reaction was then stirred overnight and allowed to equilibrate to room temperature. The mixture was washed with saturated aqueous NaHCO$_3$ solution (50 mL), brine (50 mL), and dried (e.g., Na$_2$SO$_4$), filtered and concentrated to afford 10.8 g Step 2. To a 40-mL vial with magnetic stir bar at 25° C. under a nitrogen atmosphere was added (3-Amino-benzyl)-carbamic acid tert-butyl ester (1.5 g, 6.75 mmol, 1 eq.) and anhydrous DMF (25 mL). The 2-Methoxy-pyridine-5-carboxylic acid (1.14 g, 7.4 mmol, 1.1 eq.) was added followed by the Diisopropylethylamine (4.36 g, 5.9 mL, 33.7 mmol, 5 eq.) and the HATU (3.08 g, 8.1 mmol, 1.2 eq.). The reaction mixture was stirred overnight at 25° C. The reaction mixture was then taken up in EtOAc (150 mL) and washed with water (30 mL), saturated aq. LiCl solution (30 mL), brine (30 mL), dried (e.g., Na$_2$SO$_4$), filtered and concentrated. The resulting residue was purified by column chromatography (ISCO CombiFlash) using a 0-50% gradient (EtOAc/Heptane) afforded 1.60 g (68% yield).

Step 3. To a 40-mL vial with magnetic stir bar at 25° C. was added {3-[(6-Methoxy-pyridine-3-carbonyl)-amino]-benzyl}-carbamic acid tert-butyl ester (1.66 g, 4.7 mmol, 1 eq.) and anhydrous DCM (20 mL). The reaction vial was cooled to 0° C. and the HCl in 1,4-Dioxane (5.9 mL, 4M, 23.8 mmol, 5 eq.) was added drop-wise with vigorous stirring. Stirring was continued overnight and was allowed to equilibrate to 25° C. The reaction material was transferred to a 250-mL round bottom flask and the solvent evaporated in vacuo. The resulting residue was re-dissolved in methanol (15 mL), the solvent evaporated, and the residue dried thoroughly in vacuo. The material was carried on to the next synthetic step without purification to afford 1.6 g. LCMS (ESI) 258 (M+H).

Step 4. To a 40-mL vial with magnetic stir bar at 25° C. under a nitrogen atmosphere was added 4-Chloro-quinazoline-8-carboxylic acid methyl ester (0.15 g, 0.67 mmol, 1 eq.) and anhydrous THF (8 mL). The Diisopropylethylamine (0.26 g, 0.35 mL, 2 mmol, 3 eq.) was then added followed by N-(3-Aminomethyl-phenyl)-6-methoxynicotinamide (0.19 g, 0.74 mmol, 1.1 eq.). The resulting mixture was heated in a capped vial at 50° C.×96 hours with stirring. The solvent was evaporated in vacuo and the resulting residue re-dissolved in EtOAc (50 mL). The mixture was washed with saturated aqueous NaHCO$_3$ solution (30 mL), water (30 mL), brine (30 mL), and dried (e.g., Na$_2$SO$_4$), filtered and concentrated. The resulting residue was purified by column chromatography (ISCO CombiFlash) using a 0-90% gradient (EtOAc/DCM) to afford 181 mg (60% yield). LCMS (ESI) 444.2 (M+H).

Step 5. To a 40-mL vial with magnetic stirbar at 25° C. was added 4-{3-[(6-Methoxy-pyridine-3-carbonyl)-amino]-benzylamino}-quinazoline-8-carboxylic acid methyl ester (0.18 g, 0.4 mmol, 1 eq.) and THF (2 mL) and 2-propanol (2 mL). An approx. equal volume (i.e.; 2 mL) of concentrated aqueous ammonium hydroxide solution (28-30% soln.) was then added and stirring continued overnight. Water (15 mL) was added to the reaction mixture and a precipitate immediately began to form. The precipitate was collected and purified further via preparative HPLC afforded the desired compound as a white solid (13.9 mg) LCMS (ESI) 429.2 (M+H).

Example 425

4-{1-[3-(3-Fluoro-4-methoxy-benzoylamino)-phenyl]-ethylamino}-quinazoline-8-carboxylic acid amide To a solution of 3-fluoro-4-methoxybenzoic acid (26.00 mg; 0.15 mmol; 1.00 eq.) in DMF were added bis(2-oxo-1,3-oxazolidin-3-yl)phosphinic chloride (35.01 mg; 0.14 mmol; 0.90 eq.), 4-{[1-(3-aminophenyl)ethyl]amino}quinazoline-8-carboxamide (41.33 mg; 0.13 mmol; 0.88 eq.), and N-ethyl-N-isopropylpropan-2-amine (0.07 ml; 0.38 mmol; 2.50 eq.). The reaction mixture was stirred overnight at RT. Purified the crude by HPLC to obtain 20 mg of the title product in 28% yield. MS (M+1) 460

Example 426

4-{1-[3-(4-Diethylamino-benzoylamino)-phenyl]-ethylamino}-quinazoline-8-carboxylic acid amide The title compound was synthesized according to the procedure described for the preparation of Example 425. MS (M+1) 483.

Example 427

4-[3-(Benzothiazol-2-ylamino)-benzylamino]-quinazoline-8-carboxylic acid amide

The title compound was prepared according to Example 684 starting 4-(3-Amino-benzylamino)-quinazoline-8-carboxylic acid amide hydrochloride and 2-Chloro-benzothiazole:

22.1 mg, Rt.=2.29 min (method C), LCMS: 427 (M+H). Product is the hydrochloride salt.
$^1$H NMR (500 MHz, DMSO) δ 11.17 (s, 1H), 10.55 (s, 1H), 8.94-8.73 (m, 3H), 8.58 (d, J=7.6, 1H), 8.20 (s, 1H), 7.92 (t, J=7.9, 1H), 7.87 (s, 1H), 7.76 (d, J=7.8, 1H), 7.68 (d, J=8.1, 1H), 7.38-7.21 (m, 3H), 7.17-7.04 (m, 2H), 5.01 (d, J=5.7, 2H).

Example 429

4-{3-[3-(3-Methoxy-propoxy)-benzoylamino]-benzylamino}-quinazoline-8-carboxylic acid amide The title compound was prepared according to Example 667.
57 mg, off-white solid. Product is the trifluoroacetic acid salt.
Rt.=2.41 min (method C), LCMS: 486 (M+H).

Example 430

4-{3-[3-(2-Methylamino-ethoxy)-benzoylamino]-benzylamino}-quinazoline-8-carboxylic acid amide a) [2-(3-{3[(8-Carbamoyl-quinazolin-4-ylamino)-methyl]-phenylcarbamoyl}-phenoxy)-ethyl]-methyl-carbamic acid tert-butyl ester The title compound was prepared according to Example 667.
12 mg, off-white solid. Product is the trifluoroacetic acid salt.
Rt.=2.68 min (method C), LCMS: 571 (M+H).

b) 12 mq (0.11 mmol [2-(3-{3-[(8-Carbamoyl-quinazolin-4-ylamino)-methyl]-phenylcarbamoyl}-phenoxy)-ethyl]-methyl-carbamic acid tert-butyl ester were dissolved in 2 ml dioxane and 88 μl 4 N HCl in dioxane were added. The mixture was stirred overnight, filtered and washed with dioxane.
8 mg, off-white solid. Product is the hydrochloride salt.
Rt.=1.88 min (method C), LCMS: 471 (M+H).

Example 434

4-{3-[(5-Trifluoromethyl-1H-pyrazole-3-carbonyl)-amino]-benzylamino}-quinazoline-8-carboxylic acid amide The title compound was synthesized according to the procedure described for the preparation of Example 425. (M+1) 456

Example 437

4-{3-Dimethylamino-1-[3-(2,5-difluoro-benzoylamino)-phenyl]-propylamino}-quinazoline-8-carboxylic acid amide The title compound was synthesized according to the procedure described for the preparation of Example 462. LCMS [505 (M+1)].

Example 440

4-[((1R)-1-{3-[(3-fluoro-4-methoxybenzoyl)amino]phenyl}ethyl)amino]quinazoline-8-carboxamide A suspension of 4-{[(1R)-1-(3-aminophenyl)ethyl]amino}quinazoline-8-carboxamide (2.0 g, 6.51 mmol) in dry pyridine (50 mL) was treated with 3-fluoro-4-methoxybenzoyl chloride (1.51 g, 8.01 mmol, 1.23 eq), and the contents were stirred at room temp for 45 min. The clear-yellow solution was slowly added to water (1000 mL), and the white precipitate was filtered, washed with water (300 mL) and dried under vacuum at 35° C. to get the title compound in 98% yield (2.93 g).

Example 442

4-(1-{3-[(Furan-3-carbonyl)-amino]-phenyl}-ethylamino)-quinazoline-8-carboxylic acid amide The title compound was synthesized according to the procedure described for the preparation of Example 425. MS (M+1) 402

Example 446

4-{1-[3-(4-Morpholin-4-yl-benzoylamino)-phenyl]-ethylamino}-quinazoline-8-carboxylic acid amide The title compound was synthesized according to the procedure described for the preparation of Example 425. MS (M+1) 497

Example 450

4-(1-{3-[(5-Cyclopropyl-1H-pyrazole-3-carbony)-amino]-phenyl}-3-dimethylamino-propylamino)-quinazoline-8-carboxylic acid amide The title compound was synthesized according to the procedure described for the preparation of Example 462. LCMS [499 (M+1)].

Example 452

4-(1-{3-[(1-Oxy-pyridine-4-carbonyl)-amino]-phenyl}-ethylamino)-quinazoline-8-carboxylic acid amide The title compound was synthesized according to the procedure described for the preparation of Example 425. MS (M+1) 429

Example 456

4-(1-{3[(5-Methyl-2-trifluoromethyl-furan-3-carbonyl)-amino]-phenyl}-ethylamino)-quinazoline-8-carboxylic acid amide The title compound was synthesized according to the procedure described for the preparation of Example 425. MS (M+1) 484

Example 458

4-{3-Dimethylamino-1-[3-(4-methoxy-benzoylamino)-phenyl]-propylamino}-quinazoline-8-carboxylic acid amide The title compound was synthesized according to the procedure described for the preparation of Example 462. LCMS [499 (M+1)].

Example 461

4-(1-{3[(1-Oxy-pyridine-3-carbonyl)-amino]-phenyl}-ethylamino)-quinazoline-8-carboxylic acid amide The title compound was synthesized according to the procedure described for the preparation of Example 425. MS (M+1) 429

Example 462

4-{3-Methoxy-1-[3-(4-trifluoromethoxy-benzoylamino)-phenyl]-propylamino}-quinazoline-8-carboxylic acid amide A mixture of 4-{[1-(3-aminophenyl)-3-methoxypropyl]amino}quinazoline-8-carboxamide (50.00 mg; 0.14 mmol; 1.00 eq.), N-[3-(dimethylamino)propyl]-N'-ethylcarbodiimide hydrochloride (30 mg; 0.16 mmol; 1.10 eq.) and 1H-1,2,3-benzotriazol-1-ol (22 mg; 0.16 mmol; 1.10 eq.) in dry DMF (1 mL) were added 4-(trifluoromethoxy)benzoic acid (33 mg; 0.16 mmol; 1.10 eq.) and N-ethyl-N-isopropylpropan-2-amine (0.08 ml; 0.43 mmol; 3.00 eq.). The mixture was stirred overnight. After concentration, the crude was purified by reverse phase HPLC to obtain 26 mg of the title product in 34% yield.

LCMS [540 (M+1)]. $^1$H NMR (400 MHz, DMSO-D$_6$): 2.1875 (m, 1H), 2.3432 (m, 1H), 3.2379 (s, 3H), 3.3835 (m, 1H), 3.4522 (m, 1H), 5.7150 (m, 1H), 7.0524 (m, 2H), 7.2017 (m, 1H), 7.3317 (m, 1H), 7.6285 (m, 1H), 7.9371 (m, 6H), 8.0791 (m, 1H), 8.5544 (m, 1H), 8.6647 (s, 1H), 8.8136 (s, 1H), 10.3786 (s, 1H).

Example 463

4-(1-{3-[(2-Ethoxy-pyridine-4-carbonyl)-amino]-phenyl}-ethylamino)-quinazoline-8-carboxylic acid amide The title compound was synthesized according to the procedure described for the preparation of Example 425.MS (M+1) 457

Example 471

4-(1-{3-[4-(4-Methyl-piperazin-1-yl)-benzoylamino]-phenyl}-ethylamino)-quinazoline-8-carboxylic acid amide The title compound was synthesized according to the procedure described for the preparation of Example 425. MS (M+1) 510

Example 475

4-{1-[3-(4-Trifluoromethoxy-benzoylamino)-phenyl]-ethylamino}-quinazoline-8-carboxylic acid amide The title compound was synthesized according to the procedure described for the preparation of Example 425. MS (M+1) 496

Example 476

4-{3-[4-(4-Methyl-piperazin-14)-3-trifluoromethyl-benzoylamino]-benzylamino}-quinazoline-8-carboxylic acid amide The title compound was prepared according to Example 667.

57 mg, off-white solid. Product is the trifluoroacetic acid salt.

Rt.=2.09 min (method C), LCMS: 564 (M+H).

Example 477

2-{3-[1-(8-Carbamoyl-quinazolin-4-ylamino)-ethyl]-phenylamino}-oxazole-5-carboxylic acid 2-{3-[1-(8-Carbamoyl-quinazolin-4-ylamino)-ethyl]-phenylamino}-oxazole-5-carboxylic acid ethyl ester was prepared according to Example 549 starting 4-{[1-(3-aminophenyl)ethyl]amino}quinazoline-8-carboxamide and ethyl 2-chloro-1,3-oxazole-5-carboxylate. LCMS (M+1) 447.

The ester was hydrolyzed with 1N NaOH at 60° C. for 2 h to get the title compound. LCMS (M+1) 419.

Example 490

{2-[8-Carbamoyl-quinazolin-4-ylamino)-2-[3-(3-fluoro-4-methoxy-benzoylamino)-phenyl]-ethyl}-methyl-carbamic acid tert-butyl The title compound was synthesized according to the procedure described for the preparation of Example 462. LCMS [589 (M+1)].

Example 493

4-{3-Dimethylamino-1-[3-(3-fluoro-4-methoxy-benzoylamino)-phenyl]-propylamino}-quinazoline-8-carboxylic acid amide The title compound was synthesized according to the procedure described for the preparation of Example 462. LCMS [517 (M+1)].

Example 496

4-{4[(5-Trifluoromethyl-1H-pyrazole-3-carbonyl)-amino]-benzylamino}-quinazoline-8-carboxylic acid amide The title compound was synthesized according to the procedure described for the preparation of Example 425. MS (M+1) 477

Example 497

4-[3-(2,4-Dimethoxy-benzoylamino)-benzylamino]-quinazoline-8-carboxylic acid amide The title compound was prepared according to Example 667.
52 mg, off-white solid. Product is the trifluoroacetic acid salt.
Rt.=2.42 min (method C), LCMS: 458 (M+H).

Example 499

4-Benzylamino-5-methoxy-quinazoline-8-carboxylic acid amide

Step 1 To a solution of 2-Amino-6-methoxy-benzoic acid (0.167 g, 0.1 mmol) in DMF (3 mL) was added NBS (0.177 g, 0.1 mmol) and the reaction was stirred at room temperature for 1 h. Reaction mixture was diluted with methanol (3 mL) and the crude containing the region isomers was purified on preparative HPLC using Water/MeOH (0.1% TFA) as eluent to give product (0.08 g, 33%). LCMS (ESI) 246 (M+H);
Steps 2-3 are according to the procedure of Example 76.
Step 4 In a 40 ml scintillation vial 4-Benzylamino-5-methoxy-quinazoline-8-carbonitrile (0.55 g, 0.187 mmol) was taken in DMSO (12.0 mL) and MeOH (8.0 mL). $K_2CO_3$ (0.258 g, 1.87 mmol) in water (2.0 mL) was added followed by $H_2O_2$ (0.212 g, 1.87 mmol) and the reaction was stirred under nitrogen at r.t., for 18 h. The reaction was extracted with ethyl acetate (3×30 mL), and concentrated. Water (2.0 mL) was added and the resulting solid product was filtered to afford the desired intermediate (0.032 g, 56%).
Step 5 The title compound was synthesized according to the procedure of Example 76.
LCMS (ESI) 309 (M+H)

Example 501

4-{3-[(2-Amino-thiazole-4-carbonyl)-amino]-benzylamino}-quinazoline-8-carboxylic acid amide a) (4-{3-[(8-Carbamoyl-quinazolin-4-ylamino)-methyl]-phenylcarbamoyl}-thiazol-2-yl)-carbamic acid tert-butyl ester The title compound was prepared according to Example 667
64 mg, off-white solid.
Rt.=2.51 min (method C), LCMS: 520 (M+H).
b) 64 mg (0.12 mmol) of (4-{3-[(8-Carbamoyl-quinazolin-4-ylamino)-methyl]-phenylcarbamoyl}-thiazol-2-yl)-carbamic acid tert-butyl ester were dissolved in 1.0 ml dioxane and 620 µl 4 N HCl in dioxane were added. The mixture was stirred overnight and evaporated to dryness.
52 mg, off-white solid. Product is the hydrochloride salt.
Rt.=1.84 min (method C), LCMS: 420 (M+H).

Example 503

6-(3-dimethylamino-propoxy)-4-(2-methylamino-1-phenyl-ethylamino)-quinazoline-8-carboxylic acid amide Step 1. A scintillation vial equipped with a stir bar was charged with [2-(8-carbamoyl-6-hydroxy-quinazolin-4-ylamino)-2-phenyl-ethyl]-methyl-carbamic acid tert-butyl ester, (110 mg, 0.25 mmol), (2-chloro-ethyl)-dimethyl-amine hydrochloride, (40 mg, 0.28 mmol) $Cs_2CO_3$, (244 mg, 0.75 mmol) and $Bu_4NI$, (10 mg). To this mixture was added dry DMF (4 mL) and the reaction was heated at 60° C. overnight. After 18 h, LCMS indicated consumption of SM. The mixture diluted with EtOAc (30 mL) and added to water (100 mL). The phases were separated and the aqueous was extracted with EtOAc (30 mL) (×2). The EtOAc phase was washed with sat. LiCl, (50 mL) dried ($Na_2SO_4$) and the solvent was evaporated under reduced pressure. The material was purified by chromatography using a 12 g silica cartridge eluting with DCM-[DCM-MeOH—$NH_4OH$ (9:1:0.1)], gradient 0 to 50% cocktail. Amount obtained: 67 mg, 0.13 mmol, 53% yield.
LCMS (ESI) 370 (M+H).
Step 2. The title compound was synthesized according to the procedure of Example 184. LCMS (ESI) 423 (M+H).

Example 506

4-{3-[(1H-Indole-3-carbonyl)-amino]-benzylamino}-quinazoline-8-carboxylic acid amide The title compound was prepared according to Example 667.
22 mg, off-white solid. Product is the trifluoroacetic acid salt.
Rt.=2.23 min (method C), LCMS: 437 (M+H).

Example 507

4-[3-(4-Pyrrolidin-1-ylmethyl-benzoylamino)-benzylamino]-quinazoline-8-carboxylic acid amide The title compound was synthesized according to the procedure described for the preparation of Example 425. (M+1) 481

Example 510

4-{3-Methoxy-1-[3-(3-fluoro-4-methoxy-benzoylamino)-phenyl]-propylamino}-quinazoline-8-carboxylic acid amide The title compound was synthesized according to the procedure described for the preparation of Example 462. LCMS [504 (M+1)].

Example 512

4-[3-(3-Fluoro-4-methoxy-benzoylamino)-benzylamino]-quinazoline-8-carboxylic acid amide The title compound was synthesized according to the procedure described for the preparation of Example 425. (M+1) 446

Example 524

4-{1-[3-benzoylamino-phenyl]-3-pyrrolidin-1-yl-propylamino}-quinazoline-8-carboxylic acid amide The title compound was synthesized according to the procedure described for the preparation of Example 462. LCMS [495.2 (M+1)].

Example 525

4-[3-(4-Methoxy-3-trifluoromethyl-benzoylamino)-benzylamino]-quinazoline-8-carboxylic acid amide The title compound was prepared according to Example 667.
33 mg, off-white solid. Product is the trifluoroacetic acid salt.
Rt.=2.58 min (method C), LCMS: 496 (M+H).

Example 526

4-{1-[3-(4-Trifluoromethyl-pyridin-2-ylamino)-phenyl]-ethylamino}-quinazoline-8-carboxylic acid amide The title compound was prepared according to Example 549. LC MS (M+1) 453.

Example 527

{2-[8-Carbamoyl-quinazolin-4-ylamino)-2-[3-(4-bromo-benzoylamino)-phenyl]-ethyl}-methyl-carbamic acid tert-butyl The title compound was synthesized according to the procedure described for the preparation of Example 462. LCMS [620 (M+1)].

Example 529

4-{2-Hydroxy-1-[3-(4-bromo-benzoylamino)-phenyl]-ethylamino}-quinazoline-8-carboxylic acid amide The title compound was synthesized according to the procedure described for the preparation of Example 462. LCMS [506.1 (M)].

The intermediate 4-[1-(3-Amino-phenyl)-2-hydroxy-ethylamino]-quinazoline-8-carboxylic acid amide was used for the preparation of example 529.

It was synthesized according to the procedure described for the preparation of 4-[1-(3-Amino-phenyl)-3-methoxy-propylamino]-quinazoline-8-carboxamide by using methyl 4-chloroquinazoline-8-carboxylate and 2-Amino-2-(3-nitrophenyl)-ethanol, (Scheme 4).

Example 538

4-(1-{3-[(5-Cyclopropyl-2H-pyrazole-3-carbonyl)-amino]-phenyl}-3-hydroxy-propylamino)-quinazoline-8-carboxylic acid amide Step a: (1-{3-[(5-Cyclopropyl-2H-pyrazole-3-carbonyl)-amino]-phenyl}-3-hydroxy-propyl)-carbamic acid tert-butyl ester 529 mg (3.4 mmol) 5-Cyclopropyl-2H-pyrazole-3-carboxylic acid were suspended in 9 ml THF and 834 mg (3.4 mmol) EEDQ were added. The mixture was stirred for 10 min at room temperature and subsequently 900 mg (3.4 mmol) [1-(3-Amino-phenyl)-3-hydroxy-propyl]-carbamic acid tert-butyl ester dissolved in 9 ml THF were added. The mixture was stirred overnight at room temperature, evaporated to dryness. The residue was dissolved in ethyl acetate and washed with 1 N NaOH, 10% citric acid and brine. The organic layer was dried over $Na_2SO_4$ and evaporated to dryness. 1.37 g, clear oil.

Rt.=2.56 min (method C), LCMS: 301 (M−boc+H).

Step b: 5-Cyclopropyl-2H-pyrazole-3-carboxylic acid [3-(1-amino-3-hydroxy-propyl)-phenyl]-amide 1.5 g (0.3.1 mmol) (1-{3-[(5-Cyclopropyl-2H-pyrazole-3-carbonyl)-amino]-phenyl}-3-hydroxy-propyl)-carbamic acid tert-butyl ester were dissolved in 40 ml dioxane and 15 ml 4 N HCl in dioxane were added. The mixture was stirred overnight, filtered and washed with dioxane. To this residue, 0.1 N NaOH and ethyl acetate was added, the aqueus phase was washed with ethyl acetate twice, the organic layer was dried over $Na_2SO_4$ and evaporated to dryness.

700 mg, clear oil.

Rt.=1.84 min (method C), LCMS: 301 (M+H).

Step c and d were performed as described in the example 743 to obtain 4-(1-{3-[(5-Cyclopropyl-2H-pyrazole-3-carbonyl)-amino]-phenyl}-3-hydroxy-propylamino)-quinazoline-8-carboxylic acid amide 700 mg, off-white solid. Product is the trifluoroacetic acid salt.

Rt.=2.07 min (method C), LCMS: 472 (M+H).

$^1$H NMR (500 MHz, DMSO) δ 13.00 (s, 1H), 9.81 (s, 1H), 8.72 (d, J=7.4, 1H), 8.63 (s, 1H), 8.49 (d, J=7.5, 1H), 7.95 (b, 1H), 7.85 (s, 1H), 7.76 (b, 1H), 7.58 (d, J=8.2, 1H), 7.22 (t, J=7.9, 1H), 7.11 (d, J=7.7, 1H), 6.37 (s, 1H), 5.66 (s, 1H), 3.48-3.43 (m, 2H), 2.18 (dd, J=14.0, 8.7, 1H), 2.04 (dd, J=13.3, 6.7, 1H), 1.92-1.84 (m, 1H), 0.92-0.86 (m, 2H), 0.71-0.59 (m, 2H).

Example 539

4-[3-(Pyridin-2-ylamino)-benzylamino]-quinazoline-8-carboxylic acid amide

Step a:
1 g (8.4 mmol) 3-Aminobenzonitrile and 844 µl 2-bromopyridine were mixed and slowly heated to 175° C. and stirred for 1 h. After cooling, the residue was dissolved in 100 ml dichloromethane and 50 ml water. The pH was adjusted to 8-9 using 1N NaOH. The organic layer was separated, dried over $Na_2SO_4$ and evaporated. The crude product was used without further purification.

1.55 g, Rt.=1.63 min (method C), LCMS: 196 (M+H).

Step b, c and d: these steps were performed as described for steps c, d, e of Example 743 to obtain the title compound.

25 mg, off-white solid. Rt.=1.69 min (method C), LCMS: 371 (M+H).

Product is the hydrochloride salt.

$^1$H NMR (500 MHz, DMSO) δ 11.08 (b, 1H), 9.90 (b, 1H), 8.88 (d, J=8.0, 1H), 8.83 (s, 1H), 8.56 (dd, J=7.6, 0.8, 1H), 8.17 (s, 1H), 8.03 (dd, J=5.6, 1.2, 1H), 7.88 (t, J=8.0, 1H), 7.77 (s, 1H), 7.62 (s, 1H), 7.48 (d, J=7.7, 1H), 7.34 (t, J=7.8, 1H), 7.15 (s, 1H), 7.02 (d, J=7.2, 1H), 6.87 (s, 1H), 4.96 (d, J=5.7, 2H).

Example 540

4-[3-(4-Trifluoromethyl-pyridin-2-ylamino)-benzylamino]-quinazoline-8-carboxylic acid amide The title compound was prepared according to Example 684 starting 4-(3-Amino-benzylamino)-quinazoline-8-carboxylic acid amide hydrochloride and 2-Chloro-4-trifluoromethyl-pyridine at 120° C.

14 mg, yellow solid.

Rt.=2.31 min (method C), LCMS: 439 (M+H).

$^1$H NMR (500 MHz, DMSO) δ 10.41 (b, 1H), 9.43 (s, 1H), 8.76 (s, 1H), 8.65 (d, J=8.3, 1 H), 8.56 (d, J=7.4, 1H), 8.28 (d, J=5.3, 1H), 8.05 (b, 1H), 7.82 (s, 1H), 7.67-7.61 (m, 2H), 7.27 (t, J=7.8, 1H), 7.05 (s, 1H), 6.98 (dd, J=17.7, 6.4, 2H), 4.93 (d, J=5.3, 2H).

Example 541

2-{3-[(8-Carbamoyl-quinazolin-4-ylamino)-methyl]-phenylamino}-thiazole-5-carboxylic acid ethyl ester The title compound was prepared according to Example 545.

21.1 mg, Rt.=2.34 min (method C), LCMS: 449 (M+H).

Product is the hydrochloride salt.

$^1$H NMR (500 MHz, DMSO) δ 10.95 (b, 1H), 10.85 (s, 1H), 8.99-8.69 (m, 3H), 8.55 (d, J=6.9, 1H), 8.18 (s, 1H), 7.93-7.83 (m, 2H), 7.68 (s, 1H), 7.56 (d, J=8.1, 1H), 7.34 (t, J=7.9, 1H), 7.11 (d, J=7.8, 1H), 4.96 (d, J=5.8, 2H), 4.24 (q, J=7.1, 2H), 1.27 (t, J=7.1, 3H).

Example 542

4-{4-Hydroxy-1-[3-(4-methoxy-benzoylamino)-phenyl]-butylamino}-quinazoline-8-carboxylic acid amide Step a: Toluene-4-sulfonic acid 3-tert-butoxycarbonylamino-3-(3-nitro-phenyl)-propyl ester 2 g (6.75 mmol) [3-Hydroxy-1-(3-nitro-phenyl)-propyl]-carbamic acid tert-butyl ester were dissolved in 10 ml dichloromethane and 1.4 ml (20.1 mmol) triethylamine. Under ice-cooling, 1.54 g (8.10 mmol) toluene sulfonic acid chloride in 5 ml dichloromethane were added and the mixture was stirred 30 min at 0° C. and 18 h at room temperature. The reaction mixture was diluted with 10 ml water and 30 ml dichloromethane, the organic layer was separated and washed with water, dried over $Na_2SO_4$ and evaporated to dryness. The crude product was used without further purification.

3.05 g, Rt.=3.35 min (method C), LCMS: 351 (M−boc+H).

Step b:
[3-Cyano-1-(3-nitro-phenyl)-propyl]-carbamic acid tert-butyl ester 1.88 g (4.16 mmol) Toluene-4-sulfonic acid 3-tert-butoxycarbonylamino-3-(3-nitro-phenyl)-propyl ester were dissolved in 5 ml DMF and 306 mg (6.24 mmol) sodium cyanide were added. The mixture was stirred for 5 h at 60° C. The reaction mixture was poured into 50 ml water, the precipitate was filtered, washed with water and dried in vacuo. The crude product was used without further purification.

1.5 g, off-white solid, Rt.=2.86 min (method C), LCMS: 206 (M−boc+H).

Step c: 4-Amino-4-(3-nitro-phenyl)-butyric acid 1.5 g (4.3 mmol) [3-Cyano-1-(3-nitro-phenyl)-propyl]-carbamic acid tert-butyl ester and 3.2 ml conc. HCl were heated for 5 h at 90° C. in a closed vessel. After cooling, water was added and the precipitate was filtered.

570 mg, off-white solid, Rt.=1.50 min (method C), LCMS: 225 (M+H).

Step d: 4-Amino-4-(3-nitro-phenyl)-butyric acid methyl ester 680 mg (2.49 mmol) 4-Amino-4-(3-nitro-phenyl)-butyric acid were suspended in 5 ml methanol and 635 µl (8.75 mmol) thionyl chloride were added. The mixture was stirred at room temperature overnight. The reaction mixture was evaporated to dryness, methanol was added and again evaporated to dryness.

650 mg, off-white solid, Rt.=1.82 min (method C), LCMS: 239 (M+H).

Step e: 4-tert-Butoxycarbonylamino-4-(3-nitro-phenyl)-butyric acid methyl ester 650 mg (2.25 mmol) 4-Amino-4-(3-nitro-phenyl)-butyric acid methyl ester was suspended in 20 ml THF and 1.25 ml (9.0 mmol) triethylamine. A solution of Di-tert-butyldicarbonate in 5 ml THF was added and the mixture was stirred overnight. The solvent was evaporated and the residue was dissolved in ethyl acetate and water. The organic layer was separated, dried over $Na_2SO_4$ and evaporated to dryness. The crude product was used without further purification.

785 mg, oil, Rt.=2.99 min (method C), LCMS: 239 (M−boc+H).

Step f: [4-Hydroxy-1-(3-nitro-phenyl)-butyl]-carbamic acid tert-butyl ester was prepared as described above using DIBAL as a reducing agent.

122 mg, yellow oil, Rt.=2.66 min (method C), LCMS: 211 (M−boc+H).

Step g: [1-(3-Amino-phenyl)-4-hydroxy-butyl]-carbamic acid tert-butyl ester was prepared as described above using Pd/C and hydrogen in methanol.

104 mg, yellow oil, Rt.=1.88 min (method C), LCMS: 164 (M−boc+H).

Step h: {4-Hydroxy-1-[3-(4-methoxy-benzoylamino)-phenyl]-butyl}-carbamic acid tert-butyl ester was prepared as described in Example 538 using 1-(3-Amino-phenyl)-4-hydroxy-butyl]-carbamic acid tert-butyl ester, 4-methoxybenzoic acid and EEDQ.

40 mg, yellow oil, Rt.=2.73 min (method C), LCMS: 315 (M−boc+H).

Step i to l were performed as described in the examples 538 (step b) and 743 (Steps c and d) yielding 4-{4-Hydroxy-1-[3-(4-methoxy-benzoylamino)-phenyl]-butylamino}-quinazoline-8-carboxylic acid amide:

21 mg, off-white solid, Rt.=2.21 min (method C), LCMS: 486 (M+H).

Product is the trifluoroacetic acid salt.

$^1$H NMR (500 MHz, DMSO) δ 10.06 (s, 1H), 8.82 (d, J=7.8, 1H), 8.70 (s, 1H), 8.55 (d, J=7.5, 1H), 8.01 (b, 1H), 7.93 (t, J=8.9, 3H), 7.81 (b, 1H), 7.62 (d, J=9.0, 1H), 7.31 (t, J=7.9, 1H), 7.21 (d, J=7.7, 1H), 7.04 (d, J=8.9, 2H), 5.59 (d, J=6.8, 1H), 3.83 (s, 3H), 3.50-3.42 (m, 2H), 2.16-1.98 (m, 2H), 1.65-1.54 (m, 1H), 1.54-1.43 (m, 1H).

Example 543

4-{3-[(4,5,6,7-Tetrahydro-pyrazolo[1,5-a]pyrazine-3-carbonyl)-amino]-benzylamino}-quinazoline-8-carboxylic acid amide a) 3-{3-[(8-Carbamoyl-quinazolin-4-ylamino)-methyl]-phenylcarbamoyl}-6,7-dihydro-4H-pyrazolo[1,5-a]pyrazine-5-carboxylic acid tert-butyl ester The title compound was prepared according to Example 667.

37 mg, off-white solid. Product is the trifluoroacetic acid salt.

Rt.=2.39 min (method C), LCMS: 543 (M+H).

b) 37 mg (0.56 mmol) 3-{3-[(8-Carbamoyl-quinazolin-4-ylamino)-methyl]-phenylcarbamoyl}-6,7-dihydro-4H-pyrazolo[1,5-a]pyrazine-5-carboxylic acid tert-butyl ester were dissolved in 1.5 ml dioxane and 280 μl 4 N HCl in dioxane were added. The mixture was stirred overnight and evaporated to dryness.

30 mg, off-white solid. Product is the hydrochloride salt. Rt.=1.69 min (method C), LCMS: 443 (M+H).

Example 543

4-{3-[(1H-Indole-6-carbonyl)-amino]-benzylamino}-quinazoline-8-carboxylic acid amide The title compound was prepared according to Example 667.

33 mg, off-white solid. Product is the trifluoroacetic acid salt.

Rt.=2.24 min (method C), LCMS: 437 (M+H).

Example 544

4-(1-{3-[(2,2-Difluoro-cyclopropanecarbonyl)-amino]-phenyl}-ethylamino)-quinazoline-8-carboxylic acid amide The title compound was synthesized according to the procedure described for the preparation of Example 425. MS (M+1) 412

Example 545

4-[3-(Thiazol-2-ylamino)-benzylamino]-quinazoline-8-carboxylic acid amide 50 mg (0.11 mmol) 4-(3-Amino-benzylamino)-quinazoline-8-carboxylic acid amide hydrochloride was suspended in 2.7 ml water and 0.3 ml ethanol. 13.3 μl conc. HCl were added and 9.6 μl (0.11 mmol) 32-bromothiazole was added. The mixture was stirred in a sealed vessel overnight at 100° C. The reaction mixture was cooled and ethyl acetate and 1N NaOH were added. The organic layer was separated, dried over Na$_2$SO$_4$ and evaporated. The crude mixture was purified using preparative HPLC. The product was treated with HCl in methanol and concentrated in the SpeedVac.

6.0 mg, off-white solid. Rt.=1.77 min (method C), LCMS: 377 (M+H).

Product is the hydrochloride salt.

$^1$H NMR (500 MHz, DMSO) δ 11.09-10.55 (m, 1H), 10.21 (s, 1H), 8.90 (b, 1H) 8.84 (s, 1H), 8.76 (d, J=8.2, 1H), 8.56 (d, J=6.7, 1H), 8.18 (s, 1H), 7.90 (t, J=7.9, 1H), 7.69 (s, 1H), 7.59-7.50 (m, 1H), 7.29 (t, J=7.9, 1H), 7.20 (d, J=3.7, 1H), 7.00 (d, J=7.7, 1H), 6.90 (d, J=3.7, 1H), 4.96 (d, J=5.7, 2H).

Example 546

4-{3-[(3-Amino-1H-pyrazole-4-carbonyl)-amino]-benzylamino}-quinazoline-8-carboxylic acid amide 15.5 mg, off-white solid. Product is the trifluoroacetic acid salt.

Rt.=1.80 min (method C), LCMS: 403 (M+H).

$^1$H NMR (500 MHz, DMSO) δ 10.94 (s, 1H), 9.55 (s, 1H), 8.89 (b, 1H), 8.85-8.72 (m, 2H), 8.59-8.50 (m, 1H), 8.14 (d, J=23.4, 2H), 7.88 (t, J=8.0, 1H), 7.76 (s, 1H), 7.62 (d, J=9.0, 1H), 7.28 (t, J=7.9, 1H), 7.09 (d, J=7.7, 1H), 4.94 (d, J=5.7, 2H).

Example 548

4-[3-(5-Aminomethyl-thiazol-2-ylamino)-benzylamino]-quinazoline-8-carboxylic acid amide a) 4-{3-[5-(1,3-Dioxo-1,3-dihydro-isoindol-2-ylmethyl)-thiazol-2-ylamino]-benzylamino}-quinazoline-8-carboxylic acid amide The title compound was prepared according to Example 545.

24 mg, Rt.=2.22 min (method C), LCMS: 536 (M+H).

Product is the trifluoroacetic acid salt.

b) 24 mg (0.04 mmol) 4-{3-[5-(1,3-Dioxo-1,3-dihydro-isoindol-2-ylmethyl)-thiazol-2-ylamino]-benzylamino}-quinazoline-8-carboxylic acid amide trifluoroacetic acid salt were dissolved in 1 ml ethanol and treated with 10 μl (0.21 mmol) hydrazine hydrate. The mixture was stirred overnight at 50° C. in a closed vessel. Additional 40 μl hydrazine hydrate were added and the mixture was stirred at 60° C. for 24 h. The reaction mixture was evaporated and the crude product was purified using preparative HPLC. The product was treated with HCl in methanol and concentrated in the SpeedVac.

6.0 mg, off-white solid. Rt.=1.77 min (method C), LCMS: 377 (M+H).

Product is the hydrochloride salt.

$^1$H NMR (500 MHz, DMSO) δ 11.17 (b, 1H), 10.41 (s, 1H), 9.07-8.74 (m, 3H), 8.57 (d, J=6.8, 1H), 8.31 (b, 3H), 8.18

(s, 1H), 7.89 (t, J=7.9, 1H), 7.70-7.53 (m, 2H), 7.27 (dd, J=15.3, 7.4, 2H), 7.02 (d, J=7.6, 1H), 4.94 (d, J=5.8, 2H), 4.11 (t, J=5.6, 2H).

Example 549

4-[3-(4-Cyano-Pyridin-2-ylamino)-benzylamino]-quinazoline-8-carboxylic acid amide 50 mg (0.15 mmol) 4-(3-Amino-benzylamino)-quinazoline-8-carboxylic acid amide hydrochloride and 21 mg (0.11 mmol) 2-Chloro-4-cyanopyridine were dissolved in 200 µl NMP and irradiated in the microwave at 200° C. for 3 h. The reaction mixture was directly purified using preparative HPLC. The product was treated with HCl in methanol and concentrated in the SpeedVac.

4.2 mg, off-white solid. Rt.=2.14 min (method C), LCMS: 396 (M+H).

Product is the hydrochloride salt.

Example 550

4-[2-Fluoro-3-(4-methoxy-benzoylamino)-benzylamino]-quinazoline-8-carboxylic acid amide The title compound was prepared according to example 4-{3-[(4-Methoxy-benzoyl)-methyl-amino]-benzylamino}-quinazoline-8-carboxylic acid amide, starting from 3-Amino-2-fluoro-benzonitrile and 4-Methoxy-benzoic acid:

109 mg, white solid, Rt.=2.24 min (method C), LCMS: 446 (M+H).

Product is the hydrochloride salt.

$^1$H NMR (500 MHz, DMSO) δ 10.32 (s, 1H), 9.91 (s, 1H), 9.14 (t, J=5.4, 1H), 8.59 (b, 2H), 8.54 (d, J=8.0, 1H), 7.97 (d, J=8.7, 2H), 7.78 (b, 1H), 7.66 (t, J=7.8, 1H), 7.50 (t, J=7.2, 1H), 7.22 (t, J=6.8, 1H), 7.12 (dd, J=17.2, 9.4, 1H), 7.06 (d, J=8.7, 2H), 4.89 (d, J=5.3, 2H), 3.84 (s, 3H).

Example 551

4-{3-[(4,5,6,7-Tetrahydro-1H-indazole-3-carbonyl)-amino]-benzylamino}-quinazoline-8-carboxylic acid amide The title compound was prepared according to Example 667.

40.6 mg, off-white solid. Product is the trifluoroacetic acid salt.

Rt.=2.29 min (method C), LCMS: 442 (M+H).

Example 552

4-{3-[(1H-Indole-7-carbonyl)-amino]-benzylamino}-quinazoline-8-carboxylic acid amide The title compound was prepared according to Example 667.

39 mg, off-white solid. Product is the trifluoroacetic acid salt.

Rt.=2.24 min (method C), LCMS: 437 (M+H).

Example 553

4-{3-[4-(1H-Imidazol-2-yl)-benzoylamino]-benzylamino}-quinazoline-8-carboxylic acid amide The title compound was prepared according to Example 667.

14.4 mg, off-white solid. Product is the trifluoroacetic acid salt.

Rt.=1.82 min (method C), LCMS: 464 (M+H).

Example 554

4-[3-(3-Methyl-4-morpholin-4-yl-benzoylamino)-benzylamino]-quinazoline-8-carboxylic acid amide The title compound was prepared according to Example 667.

37 mg, off-white solid. Product is the trifluoroacetic acid salt.

Rt.=2.35 min (method C), LCMS: 497 (M+H).

Example 555

4-(1-{3[(5-Cyclopropyl-2H-pyrazole-3-carbonyl)-amino]-phenyl}-3-methylamino-propylamino)-quinazoline-8-carboxylic acid amide The title compound was prepared according to Example 744 using methylamine in methanol.

6 mg, off-white solid. Product is the trifluoroacetic acid salt.

Rt.=1.93 min (method C), LCMS: 485 (M+H).

Example 556

4-(1-{3-[(5-Cyclopropyl-2H-pyrazole-3-carbonyl)-amino]-phenyl}-3-pyrrolidin-1-yl-propylamino)-quinazoline-8-carboxylic acid amide The title compound was prepared according to Example 4-(1-{3-[(5-Cyclopropyl-2H-pyrazole-3-carbonyl)-amino]-phenyl}-3-morpholin-4-yl-propylamino)-quinazoline-8-carboxylic acid amide.

9 mg, off-white solid. Product is the trifluoroacetic acid salt.

Rt.=1.98 min (method C), LCMS: 525 (M+H).

Example 557

4-{3-[(5-Chloro-1H-indole-2-carbonyl)-amino]-benzylamino}-quinazoline-8-carboxylic acid amide The title compound was prepared according to Example 667.

57 mg, off-white solid.

Rt.=2.59 min (method C), LCMS: 471 (M+H).

$^1$H NMR (500 MHz, DMSO) δ 11.87 (s, 1H), 10.36 (d, J=3.9, 1H), 10.24 (s, 1H), 9.21 (t, J=5.9, 1H), 8.61-8.56 (m, 2H), 8.54 (dd, J=8.3, 1.4, 1H), 7.84-7.76 (m, 2H), 7.76-7.70 (m, 2H), 7.68-7.64 (m, 1H), 7.44 (d, J=8.7, 1H), 7.39-7.27 (m, 2H), 7.20 (dd, J=8.7, 2.1, 1H), 7.13 (d, J=7.8, 1H), 4.86 (d, J=5.8, 2H).

Example 558

4-{3-[(1H-Indole-5-carbonyl)-amino]-benzylamino}-quinazoline-8-carboxylic acid amide The title compound was prepared according to Example 667.

23 mg, off-white solid. Product is the trifluoroacetic acid salt.

Rt.=2.18 min (method C), LCMS: 437 (M+H).

Example 559

4-(1-{3-[(2,2-Difluoro-cyclopropanecarbonyl)-amino]-phenyl}-3-hydroxy-propylamino)-quinazoline-8-carboxylic acid amide The title compound was prepared according to Example 538.

40 mg, off-white solid. Product is the trifluoroacetic acid salt.

Rt.=1.97 min (method C), LCMS: 442 (M+H).

$^1$H NMR (500 MHz, DMSO) δ 10.38 (s, 1H), 9.54 (b, 1H), 8.77 (d, J=2.8, 1H), 8.68 (s, 1H), 8.55 (d, J=7.5, 1H), 7.99 (s, 1H), 7.81 (s, 1H), 7.71 (s, 1H), 7.43 (d, J=7.9, 1H), 7.28 (t, J=7.9, 1H), 7.18 (d, J=7.5, 1H), 5.70 (s, 1H), 3.53-3.45 (m, 2H), 2.77 (ddd, J=13.6, 11.0, 8.2, 1H), 2.28-2.18 (m, 1H), 2.10-2.03 (m, 1H), 2.02-1.88 (m, 2H).

Example 561

4-{3-[(2,3-Dihydro-benzo[1,4]dioxine-6-carbonyl)-amino]-benzylamino}-quinazoline-8-carboxylic acid amide The title compound was prepared according to Example 667.

24 mg, off-white solid. Product is the trifluoroacetic acid salt.

Rt.=2.23 min (method C), LCMS: 456 (M+H).

$^1$H NMR (500 MHz, DMSO) δ 10.02 (s, 1H), 8.74 (b, 1H), 8.63 (d, J=8.0, 1H), 8.55 (d, J=6.7, 1H), 8.03 (b, 1H), 7.81 (s, 2H), 7.67 (d, J=9.1, 1H), 7.53-7.43 (m, 2H), 7.31 (t, J=7.9, 1H), 7.12 (d, J=7.6, 1H), 6.96 (d, J=8.4, 1H), 4.92 (d, J=4.9, 2H), 4.29 (ddd, J=10.7, 3.6, 1.8, 4H).

Example 562

4-(1-{3-[(5-Cyclopropyl-2H-pyrazole-3-carbonyl)-amino]-phenyl}-3-piperidin-1-yl-propylamino)-quinazoline-8-carboxylic acid amide The title compound was prepared according to Example 744.

9 mg, off-white solid. Product is the trifluoroacetic acid salt.

Rt.=2.03 min (method C), LCMS: 539 (M+H).

Example 563

4-{3-[(1-Methyl-1H-indole-5-carbonyl)-amino]-benzylamino}-quinazoline-8-carboxylic acid amide The title compound was prepared according to Example 667.

22 mg, off-white solid. Product is the trifluoroacetic acid salt.

Rt.=2.33 min (method C), LCMS: 451 (M+H).

Example 564

6-Hydroxymethyl-4-[3-(4-methoxy-benzoylamino)-benzylamino]-quinazoline-8-carboxylic acid amide The reaction mixture of 4-[(3-aminobenzyl)amino]-6-(hydroxymethyl)quinazoline-8-carboxamide hydrochloride (20 mg; 0.06 mmol; 1.00 eq.) and N-ethyl-N-isopropylpropan-2-amine (0.03 ml; 0.17 mmol; 3.00 eq.) in DCM was added 4-methoxybenzoyl chloride (11 mg; 0.06 mmol; 1.10 eq.). The reaction mixture was stirred at RT for 1 hr. Purified by HPLC, to get the title compound (18 mg, yield 71%) MS (M+1) 458.

Example 566

4-{3-[(1H-Indole-4-carbonyl)-amino]-benzylamino}-quinazoline-8-carboxylic acid amide The title compound was prepared according to Example 667.

23 mg, off-white solid. Product is the trifluoroacetic acid salt.

Rt.=2.17 min (method C), LCMS: 437 (M+H).

Example 567

4-((R)-1-{3-[(2,2-Dimethyl-cyclopropanecarbonyl)-amino]-phenyl}-ethylamino)-quinazoline-8-carboxylic acid amide The title compound was synthesized according to the procedure described for the preparation of Example 425. MS (M+1) 404.

Example 568

4-[3-(4-Hydroxymethyl-benzoylamino)-benzylamino]-quinazoline-8-carboxylic acid amide The title compound was prepared according to Example 667.

16.7 mg, off-white solid. Product is the hydrochloride salt.

Rt.=1.98 min (method C), LCMS: 428 (M+H).

Example 569

4-[3-(4-Methyl-pyridin-2-ylamino)-benzylamino]-quinazoline-8-carboxylic acid amide The title compound was prepared according to Example 549 starting 4-(3-Amino-benzylamino)-quinazoline-8-carboxylic acid amide hydrochloride and 2-Bromo-4-methyl-pyridine:

8.4 mg, Rt.=1.80 min (method C), LCMS: 385 (M+H).

Product is the hydrochloride salt.

$^1$H NMR (500 MHz, DMSO) δ 8.80 (s, 2H), 8.55 (d, J=6.8, 1H), 8.15 (b, 1H), 7.91 (d, J=5.9, 2H), 7.86 (t, J=7.9, 1H), 7.54 (s, 1H), 7.39 (d, J=28.6, 2H), 7.18 (b, 1H), 6.81 (d, J=34.6, 2H), 4.95 (d, J=5.4, 2H), 2.29 (s, 3H).

Example 570

6-Chloro-4-(1-{3-[(6-methyl-pyridine-3-carbonyl)-amino]-phenyl}-ethylamino)-quinazoline-8-carboxylic acid amide The title compound was synthesized according to the procedure described for the preparation of Example 425. MS (M+1) 461.

Example 572

4-(1-{3-[(1-Trifluoromethyl-cyclopropanecarbonyl)-amino]-phenyl}-ethyl amino)-quinazoline-8-carboxylic acid amide The title compound was synthesized according to the procedure described for the preparation of Example 425. MS (M+1) 444

Example 574

4-[3-(5-Cyanomethyl-pyridin-2-ylamino)-benzylamino]-quinazoline-8-carboxylic acid amide The title compound was prepared according to Example 616 starting 4-(3-Amino-benzylamino)-quinazoline-8-carboxylic acid amide hydrochloride and (6-Bromo-pyridin-3-yl)-acetonitrile.

13 mg, Rt.=1.73 min (method C), LCMS: 410 (M+H). Product is the hydrochloride salt.

$^1$H NMR (500 MHz, DMSO) δ 11.07 (b, 1H), 9.42 (b, 1H), 9.05-8.72 (m, 3H), 8.56 (d, J=7.0, 1H), 8.18 (s, 1H), 8.01 (d, J=2.1, 1H), 7.89 (t, J=8.0, 1H), 7.66 (s, 1H), 7.59 (dd, J=11.5, 8.6, 2H), 7.27 (t, J=7.9, 1H), 7.02 (d, J=7.5, 1H), 6.92 (d, J=8.7, 1H), 4.95 (d, J=5.8, 2H), 3.90 (s, 2H).

Example 575

4-{3-[(1H-Benzoimidazole-5-carbonyl)-amino]-benzylamino}-quinazoline-8-carboxylic acid amide The title compound was prepared according to Example 667.

32 mg, off-white solid. Product is the trifluoroacetic acid salt.

Rt.=1.79 min (method C), LCMS: 438 (M+H).

Example 577

6-(1,2-Dihydroxy-ethyl)-4-[3-(4-methoxy-benzoylamino)-benzylamino]-quinazoline-8-carboxylic acid amide MS: (M+1): 488

The title compound was synthesized according to the procedure described for the preparation of Example 564.

Intermediate 443-Amino-benzylamino)-6-(1,2-dihydroxy-ethyl)-quinazoline-8-carboxylic acid amide was used for the preparation of example 577.

Methyl 4-oxo-3,4-dihydroquinazoline-8-carboxylate (5.00 g; 24.49 mmol; 1.00 eq.) was dissolved in sulfuric acid (50.00 ml; 938.01 mmol; 38.31 eq.) while cooling with water bath. N-iodosuccinamide (44.07 g; 195.90 mmol; 8.00 eq.) was then added. The mixture was stirred at RT for 21 hours, then heated to 40° C. and stirred at same temperature for 8 days. Poured the reaction mixture into a cooled solution of 2N NaOH. 50 ml 5% —NaS$_2$SO$_3$ solution was added and stirred for 1 h at RT. Filtered the product methyl 6-iodo-4-oxo-3,4-dihydroquinazoline-8-carboxylate to get a white solid (3.5 g, 43.5%).

To a mixture of methyl 6-iodo-4-oxo-3,4-dihydroquinazoline-8-carboxylate (1.00 g; 3.03 mmol; 1.00 eq.) and N-ethyl-N-isopropylpropan-2-amine (0.54 ml; 3.03 mmol; 1.00 eq.) in MeCN (5.00 ml) was added N-benzyl-N,N-diethylethanaminium chloride (1.38 g; 6.06 mmol; 2.00 eq.), then phosphorus oxychloride (1.39 ml; 15.15 mmol; 5.00 eq.) was added slowly. The reaction mixture was stirred for 20 min at 90° C., poured into 2N NaOH solution (22 ml) containing crushed ice. Filtered, washed with water and collected 850 mg of the 4-Chloro-6-iodo-quinazoline-8-carboxylic acid methyl ester in 80% yield.

To a solution of methyl 4-chloro-6-iodoquinazoline-8-carboxylate (884 mg; 2.54 mmol; 1.00 eq.) in acetonitrile (10.00 ml), added N-ethyl-N-isopropylpropan-2-amine (1.14 ml; 6.34 mmol; 2.50 eq.) and tert-butyl [3-(aminomethyl)phenyl] carbamate (592 mg; 2.66 mmol; 1.05 eq.). The reaction mixture was stirred at RT overnight. The product methyl 4-({3-[(tert-butoxycarbonyl)amino]benzyl}amino)-6-iodoquinazoline-carboxylate was filtered and washed with acetonitrile and ether to 1.08 g in 79% yield.

A mixture of methyl 4-({3-[(tert-butoxycarbonyl)amino] benzyl}amino)-6-iodoquinazoline-8-carboxylate (110 mg; 0.21 mmol; 1.00 eq.), dicyclohexyl(2',6'-dimethoxybiphenyl-2-yl)phosphine (8.45 mg; 0.02 mmol; 0.10 eq.), palladium (II) acetate (2.31 mg; 0.01 mmol; 0.05 eq.) and tributyl(vinyl)stannane (0.07 ml; 0.25 mmol; 1.20 eq.) in dioxane was heated in a sealed tube for 5 min in a microwave at 100° C. The reaction mixture was diluted with EtOAc, washed with 20% KF solution, filtered, and the filtrate was washed with aq. NH$_4$Cl and brine. After concentration, the methyl 4-({3-[(tert-butoxycarbonyl)amino]benzyl}amino)-6-vinylquinazoline-8-carboxylate was purified by flash chromatography to get 60 mg in 67% yield.

To a solution of methyl 4-({3-[(tert-butoxycarbonyl) amino]benzyl}amino)-6-vinylquinazoline-8-carboxylate (60.00 mg; 0.14 mmol; 1.00 eq.) in acetone (8.00 ml) and water (1.00 ml) added 4-methylmorpholine 4-oxide (48.53 mg; 0.41 mmol; 3.00 eq.) and 20 ul of Osmium tetroxide (2.5 wt % solution in 2-methyl 2-propanol). The reaction mixture was stirred at RT overnight, concentrated and purified the product by HPLC, to get tert-butyl [3-({[8-(aminocarbonyl)-6-(1,2-dihydroxyethyl)quinazolin-4-yl]amino}methyl)phenyl]carbamate. 62 mg, yield 95%. MS (M+1) 467

To a solution of tert-butyl [3-({[8-(aminocarbonyl)-6-(1,2-dihydroxyethyl)quinazolin-4-yl]amino}methyl)phenyl]carbamate (25.00 mg; 0.06 mmol; 1.00 eq.) in methanol was added 4.0M hydrogen chloride in dioxane (0.14 ml; 4.00 M; 0.55 mmol; 10.00 eq.). The reaction mixture was stirred at RT for 1 h and evaporated off the solvent to obtain the title compound MS (M+1) 354.

Example 578

4-(1-{3-[5-Cyclopropyl-2H-pyrazole-3-carbonyl)-amino]-phenyl}-3-piperazin-1-yl-propylamino)-quinazoline-8-carboxylic acid amide a) 4-(3-(8-Carbamoyl-quinazolin-4-ylamino)-3-{3-[(5-cyclopropyl-2H-pyrazole-3-carbonyl)-amino]-phenyl}-propyl)-piperazine-1-carboxylic acid tert-butyl ester The title compound was prepared according to Example 744.

55 mg, yellow oil.

Rt.=2.27 min (method C), LCMS: 640 (M+H).

b) 55 mg (0.56 mmol 4-(3-(8-Carbamoyl-quinazolin-4-ylamino)-3-{3-[(5-cyclopropyl-2H-pyrazole-3-carbonyl)-amino]-phenyl}-propyl)-piperazine-1-carboxylic acid tert-butyl ester were dissolved in 1.0 ml dioxane and 350 μl 4 N HCl in dioxane were added. The mixture was stirred overnight, the solid was filtered and washed with dioxane.

27 mg, yellow solid. Product is the hydrochloride salt.

Rt.=1.89 min (method C), LCMS: 540 (M+H).

¹H NMR (500 MHz, DMSO) δ 11.91 (b, 1H), 9.90 (s, 1H), 9.07 (s, 1H), 8.73 (s, 1H), 8.58 (d, J=7.1, 1H), 8.03 (s, 1H), 7.96 (s, 1H), 7.82 (s, 1H), 7.68 (d, J=7.7, 1H), 7.36-7.23 (m, 2H), 6.43 (s, 1H), 5.68 (s, 1H), 3.3-3.4 (overlaid, 8H), 2.45-2.55 (overlaid, 2H), 1.99-1.91 (m, 1H), 1.01-0.91 (m, 2H), 0.79-0.68 (m, 2H).

Example 579

4-[1-{3-[(5-Cyclopropyl-2H-pyrazole-3-carbonyl)-amino]-phenyl}-3-(4-methyl-piperazin-1-yl)-propylamino]-quinazoline-8-carboxylic acid amide The title compound was prepared according to Example 744.
7 mg, off-white solid. Product is the trifluoroacetic acid salt.
Rt.=1.96 min (method C), LCMS: 554 (M+H).

Example 580

4-[3-(4-Morpholin-4-yl-3-trifluoromethyl-benzoylamino)-benzylamino]-quinazoline-8-carboxylic acid amide The title compound was prepared according to Example 667.
67 mg, off-white solid. Product is the trifluoroacetic acid salt.
Rt.=2.59 min (method C), LCMS: 551 (M+H).

Example 581

2-{3-[(8-Carbamoyl-quinazolin-4-ylamino)-methyl]-phenylamino}-oxazole-4-carboxylic acid ethyl ester The title compound was prepared according to Example 684 starting 4-(3-Amino-benzylamino)-quinazoline-8-carboxylic acid amide hydrochloride and 2-Chloro-oxazole-4-carboxylic acid ethyl ester at 120° C.:
10 mg, Product is the hydrochloride salt.
Rt.=2.22 min (method C), LCMS: 433 (M+H).

Example 582

4-{3-[4-(2-oxo-piperidin-1-yl)-benzoylamino]-benzylamino}-quinazoline-8-carboxylic acid amide The title compound was prepared according to example 667.
14.2 mg, off-white solid. Product is the hydrochloride salt.
Rt.=2.15 min (method C), LCMS: 495 (M+H).

Example 583

4-[3-(1',2',3',4',5',6'-Hexahydro-[3,4']bipyridinyl-6-ylamino)-benzylamino]-quinazoline-8-carboxylic acid amide Step a: 6-(3-Cyano-phenylamino)-3',4',5',6'-tetrahydro-2'H-[3,4']bipyridinyl-1'-carboxylic acid tert-butyl ester To 88 mg (0.31 mmol) 6-Fluoro-3',4',5',6'-tetrahydro-2'H-[3,4]bipyridinyl-1'-carboxylic acid tert-butyl ester and 37 mg (0.31 mmol) 3-Aminobenzonitrile 1 ml THF was added. Under nitrogen atmosphere, 241 µl (1.42 mmol) sodium bis(trimethylsilyl)-amide were added, the mixture was stirred at room temperature for 5 min and subsequently the mixture was irradiated in the microwave at 120° C. for 20 min. The reaction mixture was evaporated, dissolved in ethyl acetate and washed with water. The organic layer was dried over Na₂SO₄, evaporated and purified using flash chromatography.
23 mg, off-white solid.
Rt.=2.59 min (method C), LCMS: 379 (M+H).
Step b-d were performed as in Example 743 to obtain 6-{3-[(8-Carbamoyl-quinazolin-4-ylamino)-methyl]-phenylamino}-3',4',5',6'-tetrahydro-2'H-[3,4']bipyridinyl-1'-carboxylic acid tert-butyl ester, which was converted to the title product by deprotecting the t-butoxycarbonyl group with HCl in dioxane.
10 mg, off-white solid. Product is the hydrochloride salt.
Rt.=1.65 min (method C), LCMS: 454 (M+H).

Example 585

4-{3-[3-(5-Methyl-[1,2,4]oxadiazol-3-yl)-benzoylamino]-benzylamino}-quinazoline-8-carboxylic acid amide The title compound was prepared according to Example 667.
58 mg, off-white solid. Product is the trifluoroacetic acid salt.
Rt.=2.32 min (method C), LCMS: 480 (M+H).
¹H NMR (500 MHz, DMSO) δ 10.46 (s, 1H), 8.75 (b, 1H), 8.64 (d, J=7.8, 1H), 8.55 (dd, J=11.9, 5.3, 1H), 8.53 (t, J=1.5, 1H), 8.18 (dd, J=9.0, 1.3, 1H), 8.12 (dd, J=6.6, 1.5, 1H), 8.02 (b, 1H), 7.83 (s, 2H), 7.71 (t, J=7.8, 2H), 7.35 (t, J=7.9, 1H), 7.17 (d, J=7.6, 1H), 4.94 (d, J=4.6, 2H), 2.69 (s, 3H).

Example 587

4-{1-[3-(2,2,3,3,3-Pentafluoro-propionylamino)-phenyl]-ethylamino}-quinazoline-8-carboxylic acid amide The title compound was synthesized according to the procedure described for the preparation of Example 425. MS (M+1) 454

Example 588

4-[3-(3-Morpholin-4-yl-benzoylamino)-benzylamino]-quinazoline-8-carboxylic acid amide The title compound was prepared according to Example 667.
14.1 mg, off-white solid. Product is the hydrochloride salt.
Rt.=2.16 min (method C), Rt.=2.16 min (method C), LCMS: 483 (M+H).
¹H NMR (500 MHz, DMSO) δ 10.77 (b, 1H), 10.15 (s, 1H), 8.83 (s, 1H), 8.74 (d, J=8.1, 1H), 8.55 (d, J=7.6, 1H), 8.16 (s, 1H), 7.88 (t, J=7.9, 1H), 7.84 (s, 1H), 7.67 (d, J=8.9, 1H), 7.41 (s, 1H), 7.34 (dd, J=12.7, 6.8, 3H), 7.18-7.12 (m, 2H), 4.97 (d, J=5.7, 2H), 3.75 (dd, J=10.1, 5.2, 4H), 3.21-3.13 (m, 4H).

Example 590

4-[3-(4-Methoxy-benzoylamino)-benzylamino]-6-methylaminomethyl-quinazoline-8-carboxylic acid amide To a stirred solution of 6-(hydroxymethyl)-4-({3-[(4-methoxybenzoyl)amino]benzyl}amino)quinazoline-8-carboxamide (12.40 mg; 0.03 mmol; 1.00 eq.) in 1,2-dimethoxyethane (1.00 ml) added methanesulfonyl chloride (0.00 ml; 0.04 mmol; 1.50 eq.) (1.0M solution) at 0° C., stirred for 30 min, then added methyl amine (0.07 ml; 2.00 M; 0.14 mmol; 5.00 eq.) and the reaction mixture was stirred at RT overnight. Purified by HPLC to collect the desired product. MS (M+1) 471.

Example 592

4-{3-[(1-Methyl-1H-indole-3-carbonyl)-amino]-benzylamino}-quinazoline-8-carboxylic acid amide The title compound was prepared according to Example 667.
10 mg, off-white solid. Product is the trifluoroacetic acid salt.
Rt.=2.36 min (method C), LCMS: 451 (M+H).

Example 595

4-[3-(6-Methoxy-benzothiazol-2-ylamino)-benzylamino]-quinazoline-8-carboxylic acid amide The title compound was prepared according to Example 684 starting 4-(3-Amino-benzylamino)-quinazoline-8-carboxylic acid amide hydrochloride and 2-Chloro-6-methoxy-benzothiazole:
6.5 mg, Rt.=2.33 min (method C), LCMS: 457 (M+H). Product is the hydrochloride salt.
$^1$H NMR (500 MHz, DMSO) b 11.06 (b, 1H), 10.36 (s, 1H), 8.95-8.80 (m, 3H), 8.58 (d, J=6.9, 1H), 8.20 (s, 1H), 7.92 (t, J=8.0, 1H), 7.84 (s, 1H), 7.75-7.48 (m, 2H), 7.40 (d, J=2.6, 1H), 7.33 (t, J=7.9, 1H), 7.18 (d, J=8.8, 1H), 7.06 (d, J=7.7, 1H), 6.87 (dd, J=8.8, 2.6, 1H), 5.00 (d, J=5.8, 2H), 3.76 (s, 3H).

Example 597

4-(1-{3-[(2,2-Difluoro-cyclopropanecarbonyl)-amino]-phenyl}-3-pyrrolidin-1-yl-propylamino)-quinazoline-8-carboxylic acid amide The title compound was prepared according to Example 744.
8 mg, off-white solid. Product is the trifluoroacetic acid salt.
Rt.=1.89 min (method C), LCMS: 495 (M+H).

Example 600

4-(1-{3-[(6-oxo-1,6-dihydro-pyridine-3-carbonyl)-amino]-phenyl}-ethylamino)-quinazoline-8-carboxylic acid amide The title compound was synthesized according to the procedure described for the preparation of Example 425. MS (M+1) 429

Example 601

4-{1-[3-(3,3,3-Trifluoro-propionylamino)-phenyl]-ethylamino}-quinazoline-8-carboxylic acid amide The title compound was synthesized according to the procedure described for the preparation of Example 425. MS (M+1) 418

Example 602

4-[3-(7-Methyl-isoquinolin-1-ylamino)-benzylamino]-quinazoline-8-carboxylic acid amide The title compound was prepared according to Example 684 starting 4-(3-Amino-benzylamino)-quinazoline-8-carboxylic acid amide hydrochloride and 1-Chloro-7-methyl-isoquinoline at 120° C.:
12 mg, Product is the hydrochloride salt.
Rt.=2.01 min (method C), LCMS: 435 (M+H).

Example 605

4-{3[(1H-Pyrrolo[2,3-b]pyridine-3-carbonyl-amino]-benzylamino}-quinazoline-8-carboxylic acid amide The title compound was prepared according to Example 667.
9.4 mg, off-white solid. Product is the trifluoroacetic acid salt.
Rt.=1.95 min (method C), LCMS: 438 (M+H).

Example 606

4-((R)-1-{3-[(1-Ethyl-pyrrolidine-3-carbonyl)-amino]-phenyl}-ethylamino)-quinazoline-8-carboxylic acid amide The title compound was synthesized according to the procedure described for the preparation of Example 425. MS (M+1) 433.

Example 609

4-{3-[3-(2-Methoxy-ethoxy)-benzoylamino]-benzylamino}-quinazoline-8-carboxylic acid amide 41 mg (0.1 mmol) 4-[3-(3-Hydroxy-benzoylamino)-benzylamino]-quinazoline-8-carboxylic acid amide were dissolved in 1 ml DMF. 97 mg (0.3 mmol) Cs$_2$CO$_3$ and 15 mg (0.11 mmol) 1-Bromo-2-methoxy-ethane were added. The mixture was stirred for 5 days at 50° C. Water was added to the reaction mixture, the percipitate was filtered and dried. 15.9 mg, off-white solid.
Rt.=2.26 min (method C), LCMS: 472 (M+H).
$^1$H NMR (500 MHz, DMSO) δ 10.31 (b, 1H), 10.15 (s, 1H), 9.22 (b, 1H), 8.70-8.47 (m, 3H), 7.83 (b, 1H), 7.77 (s, 1H), 7.69 (d, J=8.9, 2H), 7.51-7.43 (m, 2H), 7.40 (t, J=7.9, 1H), 7.31 (t, J=7.9, 1H), 7.18-7.08 (m, 2H), 4.85 (d, J=5.2, 2H), 4.15 (dd, J=5.4, 3.8, 2H), 3.72-3.60 (m, 2H), 3.31 (s, 3H).

Example 610

4-{3-[4-(3-Dimethylamino-propoxy)-benzoylamino]-benzylamino}-quinazoline-8-carboxylic acid amide The title compound was prepared according to Example 667.
17.0 mg, off-white solid. Product is the hydrochloride salt.
Rt.=1.94 min (method C), LCMS: 499 (M+H).

Example 611

4-[3-(9H-Purin-6-ylamino)-benzylamino]-quinazoline-8-carboxylic acid amide

The title compound was prepared according to Example 549 starting 4-(3-Amino-benzylamino)-quinazoline-8-carboxylic acid amide hydrochloride and 6-Chloro-9H-purine. Reaction conditions: 120° C. in the microwave for 3 h:
22 mg, off-white solid. Product is the hydrochloride salt. Rt.=1.75 min (method C), LCMS: 412 (M+H).

Example 612

6-[(2-Diethylamino-ethylamino)-methyl]-4-[3-(4-methoxy-benzoylamino)-benzylamino]-quinazoline-8-carboxylic acid amide The title compound was synthesized according to the procedure described for the preparation of Example 590. MS (M+1) 556.

Example 614

4-{3-[2-(2-Methoxy-ethoxy)-benzoylamino]-benzylamino}-quinazoline-8-carboxylic acid amide The title compound was prepared according to Example 609.
13 mg, off-white solid.
Rt.=2.40 min (method C), LCMS: 472 (M+H).
$^1$H NMR (500 MHz, DMSO) δ 10.36 (s, 1H), 10.15 (s, 1H), 9.18 (t, J=5.7, 1H), 8.66-8.41 (m, 3H), 7.86-7.75 (m, 2H), 7.71 (s, 1H), 7.65 (t, J=7.9, 2H), 7.55-7.46 (m, 1H), 7.31 (t, J=7.9, 1H), 7.20 (d, J=8.3, 1H), 7.10 (dd, J=16.1, 8.2, 2H), 4.84 (d, J=5.7, 2H), 4.31-4.23 (m, 2H), 3.73-3.61 (m, 2H), 3.22 (s, 3H).

Example 616

4-[3-(1-Methyl-1H-imidazo[4,5-c]pyridin-4-ylamino)-benzylamino]-quinazoline-8-carboxylic acid amide The title compound was prepared according to Example 549 starting 4-(3-Amino-benzylamino)-quinazoline-8-carboxylic acid amide hydrochloride and 4-Chloro-1-methyl-1H-imidazo[4,5-c]pyridine. Reaction conditions: 120° C. in the microwave for 10 h:
21 mg, Rt.=1.69 min (method C), LCMS: 425 (M+H).
Product is the hydrochloride salt.
$^1$H NMR (500 MHz, DMSO) δ 13.07 (b, 1H), 11.46 (b, 1H), 11.07 (b, 1H), 9.09 (d, J=8.4, 1H), 8.95-8.78 (m, 2H), 8.56 (d, J=7.6, 1H), 8.52 (s, 1H), 8.17 (s, 1H), 7.86 (t, J=8.0, 1H), 7.73 (d, J=6.9, 1H), 7.62 (s, 1H), 7.48 (t, J=7.7, 1H), 7.45-7.34 (m, 3H), 5.01 (d, J=5.6, 2H), 3.94 (s, 3H).

Example 618

4-[5-(4-Methoxy-benzoylamino)-2-methyl-benzylamino]-quinazoline-8-carboxylic acid amide 4-[5-(4-Methoxy-benzoylamino)-2-methyl-benzylamino]-quinazoline-8-carboxylic acid amide was prepared according to example 4-{3-[(4-Methoxy-benzoyl)-methyl-amino]-benzylamino}-quinazoline-8-carboxylic acid amide, starting from 5-Amino-2-methyl-benzonitrile and 4-methoxy-benzoic acid:
41 mg, white solid, Rt.=2.27 min (method C), LCMS: 442 (M+H).
Product is the hydrochloride salt.
$^1$H NMR (500 MHz, DMSO) δ 10.61 (b, 1H), 9.96 (s, 1H), 8.96 (b, 1H), 8.86-8.74 (m, 2H), 8.56 (d, J=7.5, 1H), 8.14 (b, 1H), 7.87 (d, J=8.8, 3H), 7.65 (d, J=4.5, 2H), 7.19 (d, J=8.9, 1H), 7.01 (d, J=8.8, 2H), 4.90 (t, J=10.0, 2H), 3.83 (s, 3H), 2.36 (s, 3H).

Example 619

4-[3-(Pyrimidin-2-ylamino)-benzylamino]-quinazoline-8-carboxylic acid amide

The title compound was prepared according to Example 684 starting 4-(3-Amino-benzylamino)-quinazoline-8-carboxylic acid amide hydrochloride and 2-Chloro-pyrimidine at 120° C.:
4 mg, Rt.=1.90 min (method C), LCMS: 372 (M+H).
Product is the hydrochloride salt.

Example 622

4-{3-[2-(5-Methyl-3-trifluoromethyl-pyrazol-1-yl)-acetylamino]-benzylamino}-quinazoline-8-carboxylic acid amide The title compound was synthesized according to the procedure described for the preparation of Example 425. (M+1) 484

Example 624

4-{3-[(5-Chloro-1H-indazole-3-carbonyl)-amino]-benzylamino}-quinazoline-8-carboxylic acid amide The title compound was prepared according to Example 667.
12.5 mg, off-white solid. Product is the trifluoroacetic acid salt.
Rt.=2.51 min (method C), LCMS: 472/474 (M+H).

Example 625

4-(1-{3-[(2-Morpholin-4-ylmethyl-furan-3-carbonyl)-amino]-phenyl}-ethylamino)-quinazoline-8-carboxylic acid amide The title compound was synthesized according to the procedure described for the preparation of Example 425. MS (M+1) 501

Example 626

4-[3-(4-Methoxy-benzoylamino)-benzylamino]-6-morpholin-4-ylmethyl-quinazoline-8-carboxylic acid amide The title compound was synthesized according to the procedure described for the preparation of Example 590. MS (M+1) 527.

Example 628

4-{1-[3-(Pyridin-2-ylamino)-phenyl]-3-pyrrolidin-1-yl-propylamino}-quinazoline-8-carboxylic acid amide The title compound was prepared according to Example 549 starting with 4-[1-(3-Amino-phenyl)-3-pyrrolidin-1-yl-propylamino]-quinazoline-8-carboxylic acid amide and 2-chloro-pyridine. LCMS [468.1 (M+1)].

Example 629

4-{3-[(1-Isopropyl-piperidine-4-carbonyl)-amino]-benzylamino}-quinazoline-8-carboxylic acid amide The title compound was synthesized according to the procedure described for the preparation of Example 425. (M+1) 447

Example 630

4-[3-(Quinolin-2-ylamino)-benzylamino]-quinazoline-8-carboxylic acid amide

The title compound was prepared according to Example 684 starting 4-(3-Amino-benzylamino)-quinazoline-8-carboxylic acid amide hydrochloride and 2-Chloro-quinoline at 120° C.:
26 mg, Product is the hydrochloride salt.
Rt.=1.94 min (method C), LCMS: 421 (M+H).
$^1$H NMR (500 MHz, DMSO) δ 14.30 (b, 1H), 11.29 (s, 1H), 9.10-8.75 (m, 3H), 8.58 (d, J=7.1, 1H), 8.26 (b, 1H), 8.18 (s, 1H), 7.90 (t, J=7.9, 2H), 7.83 (s, 1H), 7.57 (s, 3H), 7.42 (d, J=7.3, 2H), 7.22 (s, 2H), 5.02 (d, J=5.8, 2H).

Example 631

4-(1-{3-[(5-oxo-pyrrolidine-3-carbonyl)-amino]-phenyl}-ethylamino)-quinazoline-8-carboxylic acid amide The title compound was synthesized according to the procedure described for the preparation of Example 425. MS (M+1) 419

Example 634

4-{3-[2-(2-Diethylamino-ethoxy)-benzoylamino]-benzylamino}-quinazoline-8-carboxylic acid amide The title compound was prepared according to Example 609.
27 mg, off-white solid.
Rt.=1.94 min (method C), LCMS: 513 (M+H).

Example 635

4-{3-[3-(3-Dimethylamino-propoxy)-benzoylamino]-benzylamino}-quinazoline-8-carboxylic acid amide The title compound was prepared according to Example 609.
3 mg, off-white solid. Product is the trifluoroacetic acid salt.
Rt.=1.94 min (method C), LCMS: 499 (M+H).

Example 636

4-{3-[4-(2-Diethylamino-ethoxy)-benzoylamino]-benzylamino}-quinazoline-8-carboxylic acid amide The title compound was prepared according to Example 667.
21.4 mg, off-white solid. Product is the trifluoroacetic acid salt.
Rt.=2.01 min (method C), LCMS: 513 (M+H).

Example 637

4-{3-[(5-Bromo-1H-indazole-3-carbonyl)-amino]-benzylamino}-quinazoline-8-carboxylic acid amide The title compound was prepared according to Example 667.
8.5 mg, off-white solid. Product is the trifluoroacetic acid salt.
Rt.=2.54 min (method C), LCMS: 516/518 (M+H).

Example 638

4-[3-(4-Methoxy-benzoylamino)-benzylamino]-6-(4-methyl-piperazin-1-ylmethyl)-Quinazoline-8-carboxylic acid amide The title compound was synthesized according to the procedure described for the preparation of Example 590. MS (M+1) 540.

Example 642

4-{1-[3-(4-Methyl-pyridin-2-ylamino)-phenyl]-ethylamino}-quinazoline-8-carboxylic acid amide The title compound was prepared according to Example 549. LC MS (M+1) 399.

Example 645

4-{3-[(5-Isopropyl-2H-pyrazole-3-carbonyl)-amino]-benzylamino}-quinazoline-8-carboxylic acid amide The title compound was prepared according to Example 667.
20.3 mg, off-white solid. Product is the trifluoroacetic acid salt.
Rt.=2.24 min (method C), LCMS: 430 (M+H).

Example 646

4-[3-(3-Methylamino-benzoylamino)-benzylamino]-quinazoline-8-carboxylic acid amide a) (3-(3-[(8-Carbamoyl-quinazolin-4-ylamino)-methyl]-phenylcarbamoyl-phenyl)-methyl-carbamic acid tert-butyl ester The title compound was prepared according to Example 667.
59 mg, off-white solid.
Rt.=2.49 min (method C), LCMS: 527 (M+H).

b) 4-[3-(3-Methylamino-benzoylamino)-benzylamino]-quinazoline-8-carboxylic acid amide 59 mg (0.11 mmol) (3-{3-[(8-Carbamoyl-quinazolin-4-ylamino)-methyl]-phenylcarbamoyl}-phenyl)-methyl-carbamic acid tert-butyl ester were dissolved in 3 ml dioxane and 560 µl 4 N HCl in dioxane were added. The mixture was stirred overnight, filtered and washed with dioxane.

50 mg, off-white solid. Product is the hydrochloride salt.
Rt.=1.80 min (method C), LCMS: 427 (M+H).
$^1$H NMR (400 MHz, DMSO) δ 10.35 (b, 1H), 8.80 (b, 2H), 8.63-8.54 (m, 1H), 8.39 (b, 3H), 8.20-8.08 (m, 2H), 7.92-7.82 (m, 1H), 7.86 (s, 2H), 7.75 (d, J=9.0, 1H), 7.67 (d, J=7.7, 1H), 7.56 (t, J=7.7, 1H), 7.34 (t, J=7.9, 1H), 7.18 (d, J=7.8, 1H), 4.96 (d, J=5.4, 2H), 4.11 (q, J=5.8, 3H).

Example 649

4-[3-(2-Methyl-benzoylamino)-benzylamino]-quinazoline-8-carboxylic acid amide The title compound was prepared according to Example 667.
15.5 mg, off-white solid. Product is the trifluoroacetic acid salt.
Rt.=2.26 min (method C), LCMS: 412 (M+H).

Example 650

4-[3-(3-Dimethylamino-benzoylamino)-benzylamino]-quinazoline-8-carboxylic acid amide The title compound was prepared according to Example 667.
5.6 mg, off-white solid. Rt.=1.90 min (method C), Product is the hydrochloride salt. Rt.=1.90 min (method C), LCMS: 441 (M+H).

Example 651

4-[3-(3-Methyl-benzoylamino)-benzylamino]-quinazoline-8-carboxylic acid amide The title compound was prepared according to Example 667.
15.7 mg, off-white solid.
Rt.=2.37 min (method C), LCMS: 412 (M+H).

Example 653

4-[3-(2-Fluoro-4-trifluoromethyl-benzoylamino)-benzylamino]-quinazoline-8-carboxylic acid amide The title compound was prepared according to Example 667.
58 mg, off-white solid. Product is the trifluoroacetic acid salt.
Rt.=2.56 min (method C), LCMS: 484 (M+H).

Example 655

4-[3-(4-Ethoxy-benzoylamino)-benzylamino]-quinazoline-8-carboxylic acid amide The title compound was prepared according to Example 667.
24.7 mg, off-white solid.
Rt.=2.41 min (method C), LCMS: 442 (M+H).

Example 656

4-[3-(Cyclohexanecarbonyl-amino)-benzylamino]-quinazoline-8-carboxylic acid amide The title compound was prepared according to Example 667.
11.2 mg, off-white solid. Product is the hydrochloride salt.
Rt.=2.30 min (method C), LCMS: 404 (M+H).
$^1$H NMR (500 MHz, DMSO) δ 10.77 (b, 1H), 9.78 (s, 1H), 9.10-8.75 (b, 1H), 8.81 (s, 1H), 8.72 (d, J=7.7, 1H), 8.55 (d, J=6.8, 1H), 8.15 (s, 1H), 7.87 (t, J=7.9, 1H), 7.67 (s, 1H), 7.51 (d, J=8.1, 1H), 7.25 (t, J=7.9, 1H), 7.07 (d, J=7.6, 1H), 4.91 (d, J=5.6, 2H), 2.33-2.21 (m, 1H), 1.80-1.60 (m, 5H), 1.43-1.13 (m, 5H).

Example 657

4-[3-(4-Acetylamino-benzoylamino)-benzylamino]-quinazoline-8-carboxylic acid amide The title compound was prepared according to Example 667.
5.2 mg, off-white solid. Product is the trifluoroacetic acid salt.
Rt.=2.05 min (method C), LCMS: 455 (M+H).

Example 659

4-{3[(6-Trifluoromethyl-pyridine-3-carbonyl)-amino]-benzylamino}-quinazoline-8-carboxylic acid amide The title compound was prepared according to Example 667.
7.8 mg, off-white solid.
Rt.=2.33 min (method C), LCMS: 467 (M+H).

Example 660

4-[3-(3-Bromo-benzoylamino)-benzylamino]-quinazoline-8-carboxylic acid amide The title compound was prepared according to Example 667.
10.2 mg, off-white solid. Product is the hydrochloride salt.
Rt.=2.43 min (method C), LCMS: 476/478 (M+H).

Example 661

4-[3-(3-Chloro-benzoylamino)-benzylamino]-quinazoline-8-carboxylic acid amide The title compound was prepared according to Example 667.
17.2 mg, off-white solid.
Rt.=2.44 min (method C), LCMS: 432/434 (M+H).
$^1$H NMR (500 MHz, DMSO) δ 10.35 (s, 1H), 10.30 (s, 1H), 9.20 (s, 1H), 8.58 (d, J=6.1, 2H), 8.53 (d, J=8.3, 1H), 7.96 (s, 1H), 7.87 (d, J=7.8, 1H), 7.79 (d, J=3.4, 1H), 7.75 (s, 1H), 7.73-7.60 (m, 3H), 7.54 (t, J=7.9, 1H), 7.32 (t, J=7.9, 1H), 7.14 (d, J=7.6, 1H), 4.84 (d, J=5.7, 2H).

Example 663

4-{3-[(Piperidine-3-carbonyl)-amino]-benzylamino}-quinazoline-8-carboxylic acid amide The title compound was prepared according to Example 667. The Boc protecting group was removed by treatment with HCl in methanol. After Boc-deprotection the crude product was purified using preparative HPLC.

5.6 mg, off-white solid. Product is the trifluoroacetic acid salt. Rt.=1.72 min (method C), LCMS: 405 (M+H).

Example 664

4-{3-Dimethylamino-1-[3-(benzoylamino)-phenyl]-propylamino}-quinazoline-8-carboxylic acid amide The title compound was synthesized according to the procedure described for the preparation of Example 462. LCMS [469 (M+1)].

Example 665

4-[3-(4-Morpholin-4-yl-benzoylamino)-benzylamino]-quinazoline-8-carboxylic acid amide The title compound was prepared according to Example 667
13.5 mg, off-white solid. Product is the hydrochloride salt. Rt.=2.20 min (method C), LCMS: 483 (M+H).

Example 666

4-[3-(3,4-Dimethoxy-benzoylamino)-benzylamino]-quinazoline-8-carboxylic acid amide The title compound was prepared according to Example 667.
33 mg, off-white solid. Product is the trifluoroacetic acid salt.
Rt.=2.18 min (method C), LCMS: 458 (M+H).

Example 667

4-[3-(3-Trifluoromethoxy-benzoylamino)-benzylamino]-quinazoline-8-carboxylic acid amide 22.3 mg (0.1 mmol) 4-trifluoromethoxy-benzoic acid were dissolved in 1 ml DMF. 41.8 mg (0.2 mmol) EDCl, 15.0 mg (0.1 mmol) HOBt and 48.5 µl (0.4 mmol) 4-methylmorpholine were added and the mixture was stirred for 15 min. Subsequently, 50 mg (0.1 mmol) 4-(2-Amino-benzylamino)-quinazoline-8-carboxylic acid amide were added and the mixture was stirred overnight at room temperature. The reaction mixture was purified using preparative HPLC and converted into the hydrochloride salt by treatment with excess HCl in methanol. 18.3 mg, off-white solid.
Rt.=2.61 min (method C), LCMS: 482 (M+H).

Example 668

4-[3-(2-Methoxy-benzoylamino)-benzylamino]-quinazoline-8-carboxylic acid amide

The title compound was prepared according to Example 667.

24.3 mg, off-white solid. Product is the hydrochloride salt. Rt.=2.32 min (method C), LCMS: 428 (M+H). $^1$H NMR (500 MHz, DMSO) δ 10.88 (b, 1H), 10.10 (s, 1H), 8.90 (b, 1H), 8.83 (s, 1H), 8.78 (d, J=8.4, 1H), 8.55 (dd, J=7.6, 0.9, 1H), 8.16 (s, 1H), 7.91-7.82 (m, 2H), 7.63 (d, J=8.0, 1H), 7.58 (dd, J=7.5, 1.6, 1H), 7.53-7.44 (m, 1H), 7.31 (t, J=7.9, 1H), 7.15 (t, J=7.4, 2H), 7.05 (t, J=7.4, 1H), 4.96 (d, J=5.7, 2H), 3.87 (s, 3H).

Example 670

4-[3-(4-Cyano-benzoylamino)-benzylamino]-quinazoline-8-carboxylic acid amide

The title compound was prepared according to Example 667.
6.9 mg, off-white solid. Product is the hydrochloride salt. Rt.=2.19 min (method C), LCMS: 423 (M+H).

Example 671

4-[3-(4-Chloro-benzoylamino)-benzylamino]-quinazoline-8-carboxylic acid amide

The title compound was prepared according to Example 667.
9.9 mg, off-white solid. Product is the hydrochloride salt. Rt.=2.39 min (method C), LCMS: 432 (M+H).

Example 672

4-{1-[3-(3-Fluoro-4-hydroxy-benzoylamino)-phenyl]-ethylamino}-quinazoline-8-carboxylic acid amide The title compound was synthesized according to the procedure described for the preparation of Example 425. MS (M+1) 446

Example 673

4-{3-[2-(2-Hydroxy-ethoxy)-benzoylamino]-benzylamino}-quinazoline-8-carboxylic acid amide The title compound was prepared according to Example 609. The product was purified using preparative HPLC. The product was treated with HCl in methanol and concentrated in the SpeedVac.
7.7 mg, off-white solid. Product is the hydrochloride salt. Rt.=2.19 min (method C), LCMS: 458 (M+H).
$^1$H NMR (500 MHz, DMSO) δ 10.82 (b, 1H), 10.33 (s, 1H), 8.5-9.0 (m, 3H), 8.15 (b, 1H), 7.95-7.77 (m, 3H), 7.70 (d, J=7.9, 1H), 7.56-7.46 (m, 1H), 7.33 (t, J=7.9, 1H), 7.21 (d, J=8.3, 1H), 7.16 (d, J=7.7, 1H), 7.10 (t, J=7.5, 1H), 4.97 (d, J=5.6, 2H), 4.27-4.13 (m, 2H), 3.76-3.66 (m, 2H).

Example 674

4-[2-Fluoro-5-(4-methoxy-benzoylamino)-benzylamino]-quinazoline-8-carboxylic acid amide 4-[2-Fluoro-5-(4-methoxy-benzoylamino)-benzylamino]-quinazoline-8-carboxylic acid amide was prepared according to example
4-{3-[(4-Methoxy-benzoyl)-methyl-amino]-benzylamino}-quinazoline-8-carboxylic acid amide, starting from 5-Amino-2-fluoro-benzonitrile and 4-methoxy-benzoic acid:

Example 677

4-{1-[3-(4-Dimethylaminomethyl-benzoylamino)-phenyl]-ethylamino}-quinazoline-8-carboxylic acid amide The title compound was synthesized according to the procedure described for the preparation of Example 425. MS (M+1) 469

Example 678

4-[3-(2-Cyano-benzoylamino)-benzylamino]-quinazoline-8-carboxylic acid amide

The title compound was prepared according to Example 667.

22.2 mg, off-white solid. Product is the trifluoroacetic acid salt.

Rt.=2.11 min (method C), LCMS: 423 (M+H).

$^1$H NMR (500 MHz, DMSO) δ 10.62 (s, 1H), 8.73 (b, 1H), 8.62 (d, J=7.4, 1H), 8.55 (d, J=6.6, 1H), 8.00 (b, 1H), 7.97 (d, J=7.5, 1H), 7.87 (d, J=7.4, 1H), 7.84-7.74 (m, 3H), 7.72 (t, J=7.6, 1H), 7.65 (d, J=8.3, 1H), 7.36 (t, J=7.9, 1H), 7.19 (d, J=7.7, 1H), 4.93 (d, J=4.0, 2H).

Example 679

4-{3-[4-(4-Methyl-piperazin-1-ylmethyl)-benzoylamino]-benzylamino}-quinazoline-8-carboxylic acid amide The title compound was synthesized according to the procedure described for the preparation of Example 425. (M+1) 510

Example 681

4-[3-(4-Chloro-3-trifluoromethyl-benzoylamino)-benzylamino]-quinazoline-8-carboxylic acid amide The title compound was prepared according to Example 667.

59 mg, off-white solid. Product is the trifluoroacetic acid salt.

Rt.=2.69 min (method C), LCMS: 500 (M+H).

Example 682

4-{3-[4-(4-Methyl-piperazin-1-yl)-benzoylamino]-benzylamino}-quinazoline-8-carboxylic acid amide The title compound was prepared according to Example 667.

30.8 mg, off-white solid. Product is the trifluoroacetic acid salt.

Rt.=1.90 min (method C), LCMS: 497 (M+H).

Example 684

4-[3-(5-Trifluoromethyl-1H-benzoimidazol-2-ylamino)-benzylamino]-quinazoline-8-carboxylic acid amide 33 mg (0.11 mmol) 4-(3-Amino-benzylamino)-quinazoline-8-carboxylic acid amide hydrochloride and 24 mg (0.11 mmol) 2-Chloro-5-trifluoromethyl-1H-benzoimidazole were dissolved in 500 µl DMF and stirred at 100° C. for 15 h. The reaction mixture was directly purified using preparative HPLC. The product was treated with HCl in methanol and concentrated in the SpeedVac.

11.0 mg, off-white solid. Rt.=2.15 min (method C), LCMS: 478 (M+H).

Product is the hydrochloride salt.

$^1$H NMR (500 MHz, DMSO) δ 10.99 (b, 2H), 8.89 (d, J=7.9, 1H), 8.82 (s, 1H), 8.56 (d, J=7.0, 1H), 8.16 (d, J=5.5, 1H), 7.88 (t, J=7.9, 1H), 7.72 (s, 1H), 7.57 (s, 1H), 7.55-7.39 (m, 5H), 7.31-7.19 (m, 1H), 5.01 (d, J=5.6, 2H).

Example 685

4-{3-[(1H-Pyrazole-3-carbonyl)-amino]-benzylamino}-quinazoline-8-carboxylic acid amide The title compound was prepared according to Example 667.

3.6 mg, off-white solid. Product is the hydrochloride salt. Rt.=1.99 min (method C), LCMS: 388 (M+H).

Example 686

4-{3[(5-Cyclopropyl-2H-pyrazole-3-carbonyl)-amino]-benzylamino}-quinazoline-8-carboxylic acid amide The title compound was prepared according to Example 667.

15.5 mg, off-white solid. Product is the hydrochloride salt. Rt.=2.14 min (method C), LCMS: 428 (M+H). $^1$H NMR (500 MHz, DMSO) δ 10.90 (b, 1H), 9.89 (s, 1H), 8.95-8.80 (m, 2H), 8.77 (d, J=8.2, 1H), 8.55 (d, J=6.9, 1H), 8.18 (s, 1H), 7.90 (t, J=8.0, 1H), 7.85, s, 1H), 7.72 (d, J=8.0, 1H), 7.30 (t, J=7.9, 1H), 7.13 (d, J=7.6, 1H), 6.42 (s, 1H), 4.96 (d, J=5.8, 2H), 1.99-1.89 (m, 1H), 0.99-0.92 (m, 2H), 0.77-0.69 (m, 2H).

Example 689

4-[3-(2-Fluoro-benzoylamino)-benzylamino]-quinazoline-8-carboxylic acid amide

The title compound was prepared according to Example 667.

18.3 mg, off-white solid. Product is the hydrochloride salt. Rt.=2.20 min (method C), LCMS: 416 (M+H).

Example 693

4-{(R)-1-[3-(3-Fluoro-4-trifluoromethoxy-benzoylamino)-phenyl]-ethylamino}-quinazoline-8-carboxylic acid amide The title compound was synthesized according to the procedure described for the preparation of Example 425. MS (M+1) 514.

Example 694

4-{1-[3-(4-Pyrrolidin-1-ylmethyl-benzoylamino)-phenyl]-ethylamino}-quinazoline-8-carboxylic acid amide The title compound was synthesized according to the procedure described for the preparation of Example 425. MS (M+1) 495

---

5 mg, white solid, Rt.=2.26 min (method C), LCMS: 446 (M+H).

Product is the hydrochloride salt.

Example 695

4-{1-[3-benzoylamino-phenyl]-3-piperidin-1-yl-propylamino}-quinazoline-8-carboxylic acid amide The title compound was synthesized according to the procedure described for the preparation of Example 462. LCMS [509.2 (M+1)].

Example 697

4-{1-[3-(4-Methoxy-benzoylamino)-phenyl]-3-pyrrolidin-1-yl-propylamino}-quinazoline-8-carboxylic acid amide The title compound was synthesized according to the procedure described for the preparation of Example 462. LCMS [525.2 (M+1)]. $^1$H NMR (400 MHz, DMSO-D$_6$): 1.8532 (m, 2H), 2.0043 (m, 2H), 2.3111 (m, 2H), 3.0432 (m, 2H), 3.2892 (m, 4H), 3.8656 (s, 3H), 5.6823 (m, 1H), 6.8784 (m, 2H), 7.2756 (d, 1H), 7.3512 (t, 1H), 7.5442 (m, 2H), 7.5745 (m, 1H), 7.6326 (m, 1H), 7.8225 (m, 1H), 7.9382 (d, 2H), 8.5804 (d, 1H), 8.6714 (s, 1H), 8.7852 (m, 1H), 9.7171 (br, 1H), 10.2322 (s, 1H).

Example 698

4-{1-[3-(4-Methoxy-benzoylamino)-phenyl]-3-azetidin-1-yl-propylamino}-quinazoline-8-carboxylic acid amide The title compound was synthesized according to the procedure described for the preparation of Example 462. LCMS [511 (M+1)].

Example 701

6-Chloro-4-{1-[3-(3-fluoro-4-methoxy-benzoylamino)-phenyl]-ethylamino}-quinazoline-8-carboxylic acid amide The title compound was synthesized according to the procedure described for the preparation of Example 425. MS (M+1) 495

Example 703

4-{1-[3-(4-Methoxy-benzoylamino)-phenyl]-3-piperidin-1-yl-propylamino}-quinazoline-8-carboxylic acid amide The title compound was synthesized according to the procedure described for the preparation of Example 462. LCMS [539.2 (M+1)].

Example 712

4-{1-[3-(4-Bromo-benzoylamino)-phenyl]-2-methoxy-ethylamino}-quinazoline-8-carboxylic acid amide The title compound was synthesized according to the procedure described for the preparation of Example 462. LCMS [521 (M+1)].

Example 714

4-[3-(4-Chloro-2,6-difluoro-benzoylamino)-benzylamino]-quinazoline-8-carboxylic acid amide The title compound was prepared according to Example 667.

58 mg, off-white solid. Product is the trifluoroacetic acid salt.

Rt.=2.42 min (method C), LCMS: 468 (M+H).

Example 715

4-[3-(2,6-Difluoro-4-methoxy-benzoylamino)-benzylamino]-quinazoline-8-carboxylic acid amide The title compound was prepared according to Example 667.

44 mg, off-white solid. Product is the trifluoroacetic acid salt.

Rt.=2.31 min (method C), LCMS: 464 (M+H).

Example 717

4-[3-(4-Trifluoromethyl-benzoylamino)-benzylamino]-quinazoline-8-carboxylic acid amide The title compound was prepared according to Example 667.

10.1 mg, off-white solid. Product is the hydrochloride salt.
Rt.=2.51 min (method C), LCMS: 466 (M+H).

Example 718

4-[3-(2-Trifluoromethyl-benzoylamino)-benzylamino]-quinazoline-8-carboxylic acid amide The title compound was prepared according to Example 667.

28.0 mg, off-white solid. Product is the hydrochloride salt.
Rt.=2.31 min (method C), LCMS: 466 (M+H).

Example 731

6-Phenyl-4-[(3S)-piperidin-3-ylamino]quinazoline-8-carboxamide

Step 1: Methyl 6-iodo-4-oxo-1,4-dihydroquinazoline-8-carboxylate

To a solution of Methyl 4-oxo-1,4-dihydroquinazoline-8-carboxylate (6.0 g, 0.0294 mol) in sulphuric acid (48 mL) was added N-Iodosuccinimide (53 g, 0.2382 mol; 4 equiv of NIS was added at the beginning of reaction and the remaining NIS was added at day-2, day-3 and day-4 of the reaction in equal portions). The reaction mixture was stirred at 40° C. for 8 days and cooled to room temperature. (The completion of reaction was monitored by LCMS). The reaction mixture was carefully poured on-to ice cold solution of saturated potassium carbonate and maintained a basic pH. The precipitate was filtered, washed with water and dried. This solid was further suspended in saturated sodium bicarbonate (100 mL) containing methanol (20 mL). After stirring for 30 min, the insoluble solid was collected by filtration. This material was further slurred in a mixture of chloroform and methanol (1:1) and filtered and dried under vacuum to afford (5.5 g, 56%) of the title compound as an off white solid. TLC—: Chloroform/Methanol: (9/1): R$_f$=0.25. LCMS: Mass found (M+1, 331.0).

Step 2: Methyl 4-chloro-6-iodoquinazoline-8-carboxylate

Added DMF (1.00 ml) to oxalyl chloride (50.00 ml). Then added methyl 6-iodo-4-oxo-1,4-dihydroquinazoline-8-carboxylate (2 500.00 mg; 7.57 mmol; 1.00 eq.). Stirred this heterogenous mixture in a sealed tube at 55 deg C. for 17.5 hours.

Cooled reaction to room temperature. Quenched reaction with cold saturated potassium carbonate. Filtered the resulting solids and washed with 10% potassium carbonate. Dried to give a tan solid. LCMS: M+1=330, 345 and 348 present (due to MeOH and water addition to chloride under LCMS conditions). Obtained 2.54 grams of product as a tan solid.

Step 3: Methyl 4-{[(3S)-1-(tert-butoxycarbonyl)piperidin-3-yl]amino}-6-iodoquinazoline-8-carboxylate Dissolved tert-butyl (3S)-3-aminopiperidine-1-carboxylate (632.11 mg; 3.16 mmol; 1.10 eq.) in MeCN (18.00 ml) and TEA (1.00 ml). Added this mixture to methyl 4-chloro-6-iodoquinazoline-8-carboxylate (1000.00 mg; 2.87 mmol; 1.00 eq.). Stirred reaction at room temperature for 45 hours. LCMS indicated M+1=513 present. Diluted reaction with water and 1N NaOH. Filtered the resulting precipitate. Washed with water and dried to give a yellowish solid (210 mg). Carried material on without further purification. LCMS: M+1=513

Step 4: tert-butyl (3S)-3-{[8-(aminocarbonyl)-6-iodoquinazolin-4-yl]amino}piperidine-1-carboxylate Dissolved methyl 4-{[(3S)-1-(tert-butoxycarbonyl)piperidin-3-yl]amino}-6-iodoquinazoline-8-carboxylate (380.00 mg; 0.74 mmol; 1.00 eq.) in iPrOH (2.00 ml) and DMSO (2.00 ml) and then added ammonium hydroxide (5.00 ml). Stirred mixture at room temperature for 2.5 days. LCMS: M+1=498 major peak. Partially concentrated reaction. Diluted with water and filtered the resulting solids. Washed with water and dried to give an off-white solid (110 mg). LCMS: M+1=498.

Step 5: tert-butyl (3S)-3-{[8-(aminocarbonyl)-6-phenylquinazolin-4-yl]amino}piperidine-1-carboxylate Combined phenylboronic acid (16.18 mg; 0.13 mmol; 1.20 eq.), tert-butyl (3S)-3-{[8-(aminocarbonyl)-6-iodoquinazolin-4-yl]amino}piperidine-1-carboxylate (55.00 mg; 0.11 mmol; 1.00 eq.), and bis(tri-tert-butylphosphoranyl)palladium (5.67 mg; 0.01 mmol; 0.10 eq.) in a microwave tube. Then added THF (0.70 ml) followed by cesium carbonate (0.22 ml; 2.00 M; 0.44 mmol; 4.00 eq.). Heated reaction in the microwave at 130 deg C. for 20 minutes. LCMS: M+1=448 major peak (266 present). Concentrated reaction. Purified by silica gel chromatography (Biotage; 10 g column; 15 mL/min; 1-10% MeOH/CH2Cl2). Concentrated product to give an oil. LCMS: M+1=448 major peak.

Step 6: 6-phenyl-4-[(3S)-piperidin-3-ylamino]quinazoline-8-carboxamide

Dissolved tert-butyl (3S)-3-{[8-(aminocarbonyl)-6-phenylquinazolin-4-yl]amino}piperidine-1-carboxylate (30.00 mg; 0.07 mmol; 1.00 eq.) in methanol (3.00 ml) and then added hydrogen chloride (2.00 ml) (2.0 M in diethyl ether) with stirring. Stirred reaction at room temperature for 18 hours. LCMS: M+1=348 major peak.

Partially concentrated reaction. Added water and extracted with diethyl ether. Froze the water layer and placed on the lyophilizer. Obtained the product as an off-white solid (13 mg).

Example 739

4-[(S)-1-(3-Fluoro-phenyl)-2-methylamino-ethylamino]-quinazoline-8-carboxylic acid amide The title compound was synthesized according to the procedure of Example 279. 1H NMR (400 MHz, DMSO-d6) □ ppm 2.36 (s, 3 H) 2.87-3.01 (m, 1 H) 3.06-3.22 (m, 1 H) 5.60-5.72 (m, 1 H) 7.00-7.13 (m, 1 H) 7.23-7.42 (m, 3 H) 7.69 (d, J=8.10 Hz, 1 H) 7.76-7.88 (m, 1 H) 8.54 (s, 1 H) 8.59 (dd, J=7.49, 1.44 Hz, 1 H) 8.68 (dd, J=8.27, 1.49 Hz, 1 H) 10.30 (brs, 1H). LCMS (ESI) 340 (M+H)

Example 742

4-((S)-2-Amino-1-phenyl-ethylamino)-quinoline-8-carboxylic acid amide

Step 1. A solution of 4-Chloro-quinoline-8-carbonitrile (200 mg, 1.1 mmol), (S)-Phenylglycinol (160 mg, 1.2 mmol), pyridinium hydrochloride (138 mg, 1.2 mmol) in 2-methoxyethanol (3.5 mL) was placed in a microwave 150° C., 50 Watts for 2 h. The solution was diluted with ethyl acetate and washed with brine solution. Purification by silica gel (20-80% ethyl acetate/heptane) afforded 4-((S)-2-Hydroxy-1-phenyl ethylamino)-quinoline-8-carbonitrile (320 mg, 33%) as a white solid. LCMS (ESI) 290 (M+H).

Step 2. A suspension of 4-((S)-2-Hydroxy-1-phenyl-ethylamino)-quinoline-8-carbonitrile (34 mg, 0.12 mmol), TEA (0.04 mL, 0.24 mmol) in CH$_2$Cl$_2$ (1.2 mL) was cooled to 0° C. before the addition of MsCl (0.01 mL, 0.13 mmol). The solution was stirred for 20 min. Before diluting with methylene chloride and washing with aqueous ammonium chloride. The sample was carried on crude. LCMS (ESI) 368 (M+H)

Step 3. NaN$_3$ (16 mg, 0.24 mmol) was added to a solution of the above compound in DMF (1.0 mL). The solution was heated to 60° C. for 18 h. The solution was diluted with EtOAc and washed with H$_2$O. The sample was carried on crude.

Step 4. 4-((S)-2-Azido-1-phenyl-ethylamino)-quinoline-8-carbonitrile (165 mg, 0.52 mmol) was dissolved in EtOH and aqueous NaOH (1.0 M, 0.79 mL) was added followed by H$_2$O$_2$ (0.079 mL, 2.6 mmol) and heated to 50° C. After 6 h the reaction was diluted with ethyl acetate and washed with 1% aqueous HCl. Purification by silica gel (0-10% MeOH/CH$_2$Cl$_2$) afforded —((S)-2-Azido-1-phenyl-ethylamino)-quinoline-8-carboxylic acid amide (88 mg, 50%) as a white powder. LCMS (ESI) 333 (M+H)

Step 5. —((S)-2-Azido-1-phenyl-ethylamino)-quinoline-8-carboxylic acid amide was dissolved in EtOAc (5 mL) and 5% Pd/C was added before the addition of hydrogen (1 atm). The reaction stirred overnight before filtering through a pad of celite. The desired compound was obtained by precipitation with heptane from CH$_2$Cl$_2$. LCMS (ESI) 307 (M+H) 1H NMR (400 MHz, DMSO-d6) d ppm 10.86 (1 H, d, J=3.51 Hz) 8.74 (1 H, dd, J=8.49, 1.46 Hz) 8.53 (1 H, dd, J=7.22, 1.37 Hz) 8.33 (1 H, d, J=5.47 Hz) 7.57-7.72 (2 H, m) 7.42 (1 H, d, J=7.03 Hz) 7.32 (1 H, t, J=7.52 Hz) 7.19-7.26 (1 H, m) 6.31 (1 H, d, J=5.86 Hz) 4.61 (1 H, brs) 2.89-3.10 (2 H, m)

Example 743

4-{3-[(4-Methoxy-benzoyl)-methyl-amino]-benzylamino}-quinazoline-8-carboxylic acid amide Step a: N-(3-Cyano-phenyl)-4-methoxy-benzamide 5.0 g (33 mmol) 4-methoxybenzoic acid were dissolved in 50 ml DMF. 12.8 g (66 mmol) EDCl, 9.2 g (66 mmol) HOBt and 14.8 ml (132 mmol) 4-methylmorpholine were added and the mixture was stirred for 15 min. Subsequently, 3.9 g (33 mmol) 3-aminobenzonitrile were added and the mixture was stirred for 48 h at room temperature and 6 h at 80° C. The reaction mixture was poured in 500 ml water and the precipitate was filtered, washed and dried.

6.0 g (72%) off-white solid, Rt.=2.66 min (method c), LCMS: 253 (M+H).

Step b: N-(3-Cyano-phenyl)-4-methoxy-N-methyl-benzamide 500 mg (1.9 mmol) N-(3-Cyano-phenyl)-4-methoxy-benzamide were dissolved in 25 ml THF and 150 mg sodium hydride (60% in oil, 3.7 mmol) were added. The reaction was stirred for 1 h at room temperature, 172 µl (2.8 mmol) methyl iodide were added and the mixture was stirred for 2 h at 60° C. To the reaction mixture water was added and subsequently extracted with ethyl acetate, dried over $Na_2SO_4$ and evaporated to dryness.

450 mg (83%) yellow oil, Rt.=2.54 min (method C), LCMS: 267 (M+H).

Step c: N-(3-Aminomethyl-phenyl)-4-methoxy-N-methyl-benzamide 450 mg (1.7 mmol) N-(3-Cyano-phenyl)-4-methoxy-N-methyl-benzamide were dissolved in 10 ml $NH_3$ in methanol (10%) and 10 ml THF. 500 mg Sponge nickel catalyst were added and the mixture was hydrogenated for 14 h at 5 bar pressure. The mixture was filtered and the filtrate was evaporated.

450 mg, grey oil, Rt.=1.86 min (method C), LCMS: 271 (M+H).

Step d: 4-{3-[(4-Methoxy-benzoyl)-methyl-amino]-benzylamino}-quinazoline-8-carboxylic acid methyl ester 101 mg (0.37 mmol) N-(3-Aminomethyl-phenyl)-4-methoxy-N-methyl-benzamide were dissolved in 3 ml acetonitrile and 260 µl (1.87 mmol) triethylamine. 130 mg (0.37 mmol) 4-Chloro-quinazoline-8-carboxylic acid methyl ester were added and the mixture was stirred overnight. The solvent was removed, water was added and the mixture was extracted with ethyl acetate. The organic layer was dried over $Na_2SO_4$ and evaporated to dryness. The crude product was used in the next step without further purification.

Rt.=2.26 min (method C), LCMS: 457 (M+H).

Step e: 4-{3-[(4-Methoxy-benzoyl)-methyl-amino]-benzylamino}-quinazoline-8-carboxylic acid amide 4-{3-[(4-Methoxy-benzoyl)-methyl-amino]-benzylamino}-quinazoline-8-carboxylic acid methyl ester from step d was dissolved in 1 ml 7N $NH_3$ in methanol in a sealed vessel and stirred for 24 h at room temperature. The reaction mixture was evaporated and purified using preparative HPLC. The product was treated with HCl in methanol and concentrated in the SpeedVac.

27 mg, white solid, Rt.=2.11 min (method C), LCMS: 442 (M+H).

Product is the hydrochloride salt.

$^1$H NMR (500 MHz, DMSO) δ 8.78 (s, 1H), 8.58 (t, J=7.9, 2H), 7.88 (t, J=8.0, 1H), 7.30 (t, J=7.8, 1H), 7.19 (dd, J=26.3, 7.8, 2H), 7.14-7.02 (m, 3H), 6.46 (d, J=8.8, 2H), 4.82 (s, 2H), 3.50 (s, 3H), 3.33 (s, 3H).

Example 744

4-(1-{3-[(5-Cyclopropyl-2H-pyrazole-3-carbonyl)-amino]-phenyl}-3-morpholin-4-yl-propylamino)-quinazoline-8-carboxylic acid amide Step a: 4-(1-{3-[(5-Cyclopropyl-2H-pyrazole-3-carbonyl)-amino]-phenyl}-3-oxo-propylamino)-quinazoline-8-carboxylic acid amide: 227 mg (0.46 mmol) 4-(1-{3-[(5-Cyclopropyl-2H-pyrazole-3-carbonyl)-amino]-phenyl}-3-hydroxy-propylamino)-quinazoline-8-carboxylic acid amide were dissolved in 2.5 ml DMSO and 1.98 ml (0.59 mmol) 0.3 M Dess-Martin Periodane in dichloromethane wee added to the mixture. The mixture was stirred for 2 h at room temperature, 20 ml water and 2 ml 1N NaOH were added and the precipitate was filtered, washed with water and dried in vacuo. 245 mg, off-white solid.

Rt.=2.02 min (method C), LCMS: 470 (M+H).

Step b: 4-(1-{3-[(5-Cyclopropyl-2H-pyrazole-3-carbonyl)-amino]-phenyl}-3-morpholin-4-yl-propylamino)-quinazoline-8-carboxylic acid amide 20 mg (0.043 mmol) 4-(1-{3-[(5-Cyclopropyl-2H-pyrazole-3-carbonyl)-amino]-phenyl}-3-oxo-propylamino)-quinazoline-8-carboxylic acid amide, 7.5 µl (0.086 mmol), 20 µl acetic acid and 1 ml THF were stirred for 10 min at room temperature. Subsequently, 18.2 mg (0.086 mmol) sodium triacetoxy borohydride were added and the mixture was stirred at room temperature for 3 days. The reaction mixture was purified using preparative HPLC.

5 mg, off-white solid. Product is the trifluoroacetic acid salt.

Rt.=1.96 min (method C), LCMS: 541 (M+H).

Biological Activity

P70S6K Enzyme Assay

P70S6K inhibitor compounds are diluted and plated in 96 well plates. A reaction mixture including the following components is then added to the compound plate to initiate the enzyme reaction; P70S6K (3 nM, T412E mutant, Millipore) is mixed with 24 µM ATP in an assay buffer containing 100 mM Hepes (pH 7.5), 5 mM MgCl2, 1 mM DTT, 0.015% Brij and 1 µM of the substrate peptide FITC-AHA-AKRRRLSS-LRA-OH (derived from the S6 ribosomal protein sequence, FITC=fluorescein isothiocyanate, AHA=6-aminohexanoic acid). The reaction is incubated for 90 min at 25° C., before the addition of 10 mM EDTA to stop the reaction. The proportion of substrate and product (phosphorylated) peptide is analysed on a Caliper Life Sciences Lab Chip 3000, using a pressure of −1.4 psi, and upstream and downstream voltages of −3000 and −700 respectively. Product peaks are resolved before substrate peaks on the resulting chromatograms.

Aurora Kinase Enzyme Assay

The Aurora assays described here are performed on two Caliper Life Sciences systems: the LC3000 and the Desktop Profiler. These provide data on enzyme activity via measurement of the relative amounts of phosphorylated or unphosphorylated fluorescently labelled substrate peptide at the end of an enzymatic reaction. These different states of peptide are resolved by applying a potential difference across the sample. The presence of the charged phosphate group on the product (as opposed to the substrate) causes a different peptide mobility between the two peptides. This is visualized by excitation of the fluorescent label on the substrate and product peptides and represented as peaks within the analysis software.

LC3000 Method

In order to measure inhibitor activity of Aurora A inhibitors in the Caliper Life Sciences LC3000, a TTP Mosquito liquid handling instrument is used to place 0.25 ul of the appropriate concentration of inhibitor in 100% DMSO (for a dose response curve calculation) into each well of a 384-well plate. To this reaction components are added to a final volume of 25 ul:

0.067 ng/ul GST-Aurora A (Carna Biosciences 05-101. N-terminal GST fusion with full length Aurora A (1-403 amino acids), accession number NP_940835.1).
15 uM ATP (Fluka, 02055)
1 mM DTT (Sigma, D0632)
1 mM MgCl2 (Sigma, M1028)
1 uM substrate peptide (sequence FITC-LRRASLG-(CONH2), synthesized by Tufts Peptide Synthesis service.
100 mM HEPES pH 7.5 (Calbiochem, 391338)
0.015% Brij-35 (Sigma, B4184)

The reaction is incubated for 90 min at 25 C, and then stopped by the addition of 70 ul of Stop buffer (100 mM HEPES pH 7.5, 0.015% Brij-35, 10 mM EDTA (Sigma, E7889)). The plate is read on a Caliper LC3000 in an Off-Chip mobility shift assay format, using the following parameters for a 12-sipper chip: screening pressure—1.8 psi, upstream voltage—2700, downstream voltage—1000. These conditions cause unphosphorylated substrate and phosphorylated product peptide to resolve as separate peaks allowing direct measurement of percentage of conversion of substrate to product. The percent conversion can be plotted against concentration of inhibitor to produce a sigmoidal dose response curve, from which an IC50 can be calculated using XLFit for Microsoft Excel.

Desktop Profiler Method

The Desktop Profiler utilizes the same principle as the LC3000 for calculating percentage conversion of a subtrate to product. Caliper Life Sciences provides proprietary flash frozen pre-made 384 well plates containing selected kinases. Each column in the 384 well plate contains a particular selected kinase. A second plate, the 'substrate plate' contains a mix of fluorescently labeled peptide substrate and ATP. These are arranged in columns so that transfer for substrate plate to enzyme plate provides the correct enzyme with the correct substrate/ATP concentration. Compounds are added to a thawed enzyme plate in the desired format, in single concentrations. Reactions are initiated by transfer of the substrate/ATP mix from the substrate plate. The enzyme plate is incubated for 90 mins at 25 C. The reaction is stopped by addition of 70 ul of Stop Buffer (100 mM HEPES pH 7.5, 0.015% Brij-35, 10 mM EDTA (Sigma, E7889)).

Reading of the plate in the Profiler is identical to the LC3000, and the ratio between substrate and product peaks provides the activity of the enzyme in that well. This is best represented by a plate heat map which colors each well by percent inhibition as compared to positive and negative controls (no inhibitors and no ATP respectively).

PDK1 Enzyme Assay

The kinase assay is performed as 384-well Flashplate assay (PerkinElmer LAS Germany GmbH). 3.4 nM His6-PDK1 (Delta 1-50) (PDK1 that has a His-tag consisting of six histidines and lacks the first fifty amino acids), 400 nM PDKtide (Biotin-bA-bAKTFCGTPEYLAPEVRREPRILSEE-EQEMFRDFDYIADWC as the substrate, and 4 µM ATP (spiked with 0.25 µCi 33P-ATP/well) are incubated in a total volume of 50 µl (50 mM TRIS, 10 mM Mg-acetate, 0.1% Mercaptoethanol, 0.02 Brij35, 0.1% BSA, pH 7.5) with or without test compound (5-10 concentrations) for 60 Min at 30° C. The reaction is stopped with 25 µl 200 mM EDTA. After 30 Min at room temperature the liquid is removed and each well washed thrice with 100 ml 0.9% sodium chloride solution. Nonspecific reaction is determined in presence of 100 nM of the high affinity protein kinase inhibitor Staurosporine. Radioactivity is measured in a Topcount (PerkinElmer LAS Germany GmbH). Results are calculated with the program RS1 (Brooks Automation, Inc.).

To assess the inhibitory potential of the compounds, IC50-values were determined, as shown in Tables 1, 2 and 3 above.

The invention claimed is:
1. A compound of Formula (I):

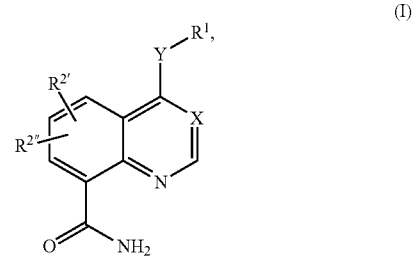

and pharmaceutically acceptable salts thereof,
wherein:
X is N,
Y is NH, O or absent,
$R^1$ is $L^1$-$R^4$-$L^2$-$R^5$-$L^3$-$R^6$, $L^1$-$R^4$-$L^2$-$R^5$ or $L^1$-$R^4$,
$R^{2'}$, $R^{2''}$ independently of one another, are H, A, Hal, OH, OA, SH, CN, $NH_2$, $NO_2$, NHA, NH-$L^1$-Ar, NHCOA, NHCO-$L^1$-Ar, $NHSO_2A$, $NHSO_2$-$L^1$-Ar, NHCONHA or NHCONH-$L^1$-Ar, $L^1$-Ar, O-$L^1$-Ar, $L^1$-$R^4$,
$L^1$, $L^3$ each, independently of one another, are a single bond, unbranched or branched alkylene having 1, 2, 3, 4 or 5 C atoms, which may be unsubstituted or mono- or disubstituted with Hal, OH, CN, $NH_2$, NH(LA), $N(LA)_2$, $NO_2$, COOH, $N_3$, ethenyl or ethynyl, and/or monosubstituted with $R^4$, and in which one or two $CH_2$ groups may be replaced by an O or S atom or by an —NH—, —N(LA)-, —CONH—, —N(LA)COO—, —$SO_2$— or —NHCO— group,
$R^4$, $R^5$, $R^6$ each, independently of one another, are Ar, or monocyclic alkyl having 3, 4, 5, 6 or 7 ring atoms, in which one or two $CH_2$ groups may be replaced by an O or S atom and/or by an —NH—, —NA-, —CHA-, —CH=N— or —CH=CH— group, and/or in which the connecting CH group may be replaced by an N atom, and which may be mono- or disubstituted by Hal or LA,
$L^2$ is —NHCO—, —NHCOO—, —NHCOOH—, —NH-CONA-, —NHCOA-, —O—, —S—, —NH—, —$NHSO_2$—, —$SO_2NH$—, —CONH—, —CONH-CONH—, —NHCONHCO—, or -A-, Ar is a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono-, di- or trisubstituted by Hal, A, OH, SH, OA, $NH_2$, NHA, $NA_2$, $NO_2$, CN, OCN, SCN, COOH, COOA, $CONH_2$, CONHA, $CONA_2$, NHCOA, NHCONHA, $NHCONH_2$, $NHSO_2A$, CHO, COA, $SO_2NH_2$, $SO_2A$ and/or $SO_2Hal$, and in which a ring N-atom may be substituted by an O-atom to form an N-oxide group, and in which in the case of a bicyclic aromatic cycle on of the two rings may be partly saturated, A is unbranched or branched linear or cyclic alkyl having 1, 2, 3, 4, 5, 6, 7 or 8 C atoms, in which one or two $CH_2$ groups may be replaced by an O or S atom and/or by an —NH—, —CO—, —NHCOO—, —NHCONH—, —N(LA)-, —CONH—, —NHCO— or —CH=CH— group, and in which 1-3 H atoms may be replaced by Hal, and in which one or two $CH_3$ groups may be replaced by OH, SH, $NH_2$, NH(LA), $N(LA)_2$, NHCOOH, $NHCONH_2$ or CN, LA is unbranched or branched, linear alkyl having 1, 2, 3 or 4 C atoms, and Hal is F, Cl, Br or I.

2. The compounds as claimed in claim 1 further comprising Formulae (II):

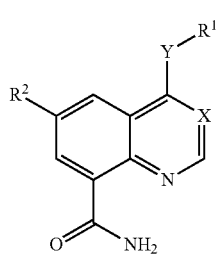

(II)

and pharmaceutically acceptable salts thereof,
wherein $R^2$ has the meaning indicated for $R^{2'}$, $R^{2''}$ of Formula (I), and $R^1$ and X have the meaning indicated for Formula (I).

3. The compounds as claimed in claim 1 further comprising Formulae (III):

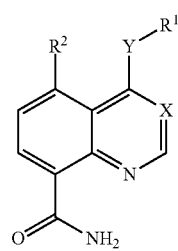

(III)

and pharmaceutically acceptable salts thereof,
wherein $R^2$ has the meaning indicated for $R^{2'}$, $R^{2''}$ of Formula (I), and $R^1$ and X have the meaning indicated for Formula (I).

4. The compound as claimed in claim 1 in which the residues not designated in greater detail have the meaning indicated for the Formula (I) according to claim 1, but in which:
in Subformula 4
X is N,
Y is NH,
in Subformula 5
X is N,
Y is O,
in Subformula 6
X is N,
Y is NH,
$R^1$ is $L^1$-$R^4$-$L^2$-$R^5$ or $L^1$-$R^4$,
$L^1$ is a bond,
in Subformula 7
X is N,
Y is NH,
$L^1$ is methylene,
in Subformula 8
X is N,
Y is NH,
$L^1$ is methylene,
$R^2$ is H, methoxy, ethoxy or amino,
in Subformula 9
X is N,
Y is NH,
$L^1$ is methylene which is unsubstituted or substituted with methyl, aminomethyl, methoxymethyl, azidomethyl or triazolylmethyl
$R^2$ is H, methoxy, ethoxy or amino,
in Subformula 10
X is N,
Y is NH,
$L^1$ is methylene which is substituted with aminomethyl,
in Subformula 11
X is N,
Y is NH,
$L^1$ is methylene which is substituted with aminomethyl,
$R^2$ is H, methoxy, ethoxy or amino,
in Subformula 12
X is N,
Y is NH,
$R^1$ is $L^1$-$R^4$,
$L^1$ is methylene which is substituted with aminomethyl,
$R^2$ is H, methoxy, ethoxy or amino,
in Subformula 13
X is N,
Y is NH,
$R^1$ is $L^1$-$R^4$-$L^2$-$R^5$ or $L^1$-$R^4$,
$L^1$ is methylene which is unsubstituted or substituted with aminomethyl,
$R^2$ is H, methoxy, ethoxy or amino,
in Subformula 14
X is N,
Y is NH,
$R^1$ is $L^1$-$R^4$-$L^2$-$R^5$ or $L^1$-$R^4$,
$L^1$ is methylene,
$R^2$ is H, methoxy, ethoxy or amino,
in Subformula 15
X is N,
Y is NH,
$R^1$ is $L^1$-$R^4$-$L^2$-$R^5$ or $L^1$-$R^4$,
$L^1$ is methylene,
$R^2$ is H, methoxy or amino,
in Subformula 16
X is N,
Y is NH,
$R^1$ is $L^1$-$R^4$,
$L^1$ is methylene,
$R^2$ is H, methoxy or amino,
in Subformula 17
X is N, Y is NH,
R¹ is L¹-R⁴,
L¹ is methylene,
R⁴ is phenyl which is unsubstituted or monosubstituted with Hal or CF₃, or disubstituted with Hal,
R² is H, methoxy or amino,
in Subformula 18
X is N,
Y is NH,
R¹ is L¹-R⁴,
L¹ is methylene,
R⁴ is phenyl which is unsubstituted or monosubstituted with Hal or CF₃, or disubstituted with Hal,
R² is H,
in Subformula 19
X is N,
Y is NH,
R¹ is L¹-R⁴-L²-R⁵,
L¹ is methylene,
R⁴ is phenylene,
L² is NHCO or NHCONH,
R² is H or methoxy,
in Subformula 20
X is N,
Y is NH,
R¹ is L¹-R⁴-L²-R⁵,
L¹ is methylene,
R⁴ is phenylene,
L² is NHCO or NHCONH,
R⁵ is phenyl which is unsubstituted or mono- or disubstituted with Hal,
R² is H or methoxy,
in Subformula 21
X is N,
Y is NH,
R¹ is L¹-R⁴-L²-R⁵,
L¹ is methylene,
R⁴ is phenylene,
L² is NHCO,
R⁵ is phenyl which is unsubstituted or mono- or disubstituted with Hal,
R² is H or methoxy,
in Subformula 22
X is N,
Y is NH,
R¹ is L¹-R⁴-L²-R⁵,
L¹ is methylene,
R⁴ is phenylene,
L² is NHCO or NHCONH,
R⁵ is phenyl which is unsubstituted, or mono- or disubstituted with Hal,
R² is H,
in Subformula 23
X is N,
R¹ is L¹-R⁴-L²-R⁵,
R⁴ is phenylene,
R⁵ benzo-1,3-dioxolyl,
in Subformula 24
X is N,
Y is NH,
L¹ is methylene which is unsubstituted or substituted with aminomethyl, (methyl-amino)methyl, (dimethyl-amino)methyl, methyl, ethyl, 2-hydroxyethyl, methoxymethyl, 2-(dimethyl-amino)ethyl, (ethyl-amino)methyl, 2-(methoxy)ethyl, 2-(allyl-methyl-amino)ethyl, ((tert. butyl-oxy-carbonyl)-methyl-amino)methyl, 2-(pyrrolidin-1-yl)ethyl, 2-(azetidin-1-yl)ethyl, 2-(piperidin-1-yl)ethyl or 2-(piperazin-1-yl)ethyl,
in Subformula 25
X is N,
Y is NH,
L¹ is methylene which is unsubstituted or substituted with (methyl-amino)methyl, (dimethyl-amino)methyl, methyl or 2-(dimethyl-amino)ethyl,
in Subformula 26
X is N,
Y is NH,
R¹ is L¹-R⁴-L²-R⁵,
R⁴ is phenylene,
L² is —NHCO—, —NH—, —NHCH₂—, NHCOOCH₂— or —NHCONH—,
in Subformula 27
X is N,
Y is NH,
R¹ is L¹-R⁴-L²-R⁵,
R⁴ is phenylene,
L² is —NHCO—, —NH—, —NHCH₂—, NHCOOCH₂— or —NHCONH—,
R⁵ is Ar which is unsubstituted or substituted as defined for Ar in claim 1,
in Subformula 28
X is N,
Y is NH,
R¹ is L¹-R⁴-L²-R⁵,
R⁴ is phenylene,
L² is —NHCO—, —NH—, —NHCH₂—, NHCOOCH₂— or —NHCONH—,
R⁵ is phenyl, pyridyl, benzo-1,3-dioxolyl, pyrazolyl or thiazolyl, all of which are unsubstituted or substituted as defined for Ar in claim 1,
in Subformula 29
X is N,
Y is NH,
L¹ is methylene which is unsubstituted or substituted with aminomethyl, (methyl-amino)methyl, (dimethyl-amino)methyl, methyl, ethyl, 2-hydroxyethyl, methoxymethyl, 2-(dimethyl-amino)ethyl, (ethyl-amino)methyl, 2-(methoxy)ethyl, 2-(allyl-methyl-amino)ethyl, ((tert. butyl-oxy-carbonyl)-methyl-amino)methyl, 2-(pyrrolidin-1-yl)ethyl, 2-(azetidin-1-yl)ethyl, 2-(piperidin-1-yl)ethyl or 2-(piperazin-1-yl)ethyl,
R² is H or methoxy,
in Subformula 30
X is N,
Y is NH,
L¹ is methylene which is unsubstituted or substituted with (methyl-amino)methyl, (dimethyl-amino)methyl, methyl or 2-(dimethyl-amino)ethyl,
R² is H or methoxy,
in Subformula 31
X is N,
Y is NH,
R¹ is L¹-R⁴-L²-R⁵,
R⁴ is phenylene,
L² is —NHCO—, —NH—, —NHCH₂—, NHCOOCH₂— or —NHCONH—,
R² is H or methoxy,
in Subformula 32
X is N,
Y is NH,
R¹ is L¹-R⁴-L²-R⁵,
R⁴ is phenylene, $L^2$ is —NHCO—, —NH—, —NHCH$_2$—, NHCOOCH$_2$— or —NHCONH—,
$R^5$ is Ar which is unsubstituted or substituted as defined for Ar in claim 1,
$R^2$ is H or methoxy,
in Subformula 33
X is N,
Y is NH,
$R^1$ is $L^1$-$R^4$-$L^2$-$R^5$,
$R^4$ is phenylene,
$L^2$ is —NHCO—, —NH—, —NHCH$_2$—, NHCOOCH$_2$— or —NHCONH—,
$R^5$ is phenyl, pyridyl, benzo-1,3-dioxolyl, pyrazolyl or thiazolyl, all of which are unsubstituted or substituted as defined for Ar in claim 1,
$R^2$ is H or methoxy,
in Subformula 34
X is N,
Y is NH,
$R^1$ is $L^1$-$R^4$-$L^2$-$R^5$,
$L^1$ is methylene which is unsubstituted or substituted with (methyl-amino)methyl, (dimethyl-amino)methyl, methyl or 2-(dimethyl-amino)ethyl,
$R^4$ is phenylene,
$L^2$ is —NHCO—, —NH—, —NHCH$_2$—, NHCOOCH$_2$— or —NHCONH—,
$R^5$ is Ar which is unsubstituted or substituted as defined for Ar in claim 1,
$R^2$ is H or methoxy,
in Subformula 35
X is N,
Y is NH,
$R^1$ is $L^1$-$R^4$,
$R^2$ is $L^1$-Ar,
in Subformula 36
X is N,
Y is NH,
$R^1$ is $L^1$-$R^4$,
$L^1$ is a bond,
in Subformula 37
X is N,
Y is NH,
$R^1$ is $L^1$-$R^4$,
$R^4$ is piperidinyl,
in Subformula 38
X is N,
Y is NH,
$R^1$ is $L^1$-$R^4$,
$R^4$ is piperidinyl,
$R^2$ is $L^1$-Ar,
$L^1$ is a bond,
and pharmaceutically acceptable salts thereof.

5. The compounds according to claim 2 or claim 3 in which the residues not designated in greater detail have the meaning indicated for the Formula (I) according to claim 1, but in which:
in Subformula 4
X is N,
Y is NH,
in Subformula 5
X is N,
Y is O,
in Subformula 6
X is N,
Y is NH,
$R^1$ is $L^1$-$R^4$-$L^2$-$R^5$ or $L^1$-$R^4$,
$L^1$ is a bond,
in Subformula 7
X is N,
Y is NH,
$L^1$ is methylene,
in Subformula 8
X is N,
Y is NH,
$L^1$ is methylene,
$R^2$ is H, methoxy, ethoxy or amino,
in Subformula 9
X is N,
Y is NH,
$L^1$ is methylene which is unsubstituted or substituted with methyl, aminomethyl, methoxymethyl, azidomethyl or triazolylmethyl
$R^2$ is H, methoxy, ethoxy or amino,
in Subformula 10
X is N,
Y is NH,
$L^1$ is methylene which is substituted with aminomethyl,
in Subformula 11
X is N,
Y is NH,
$L^1$ is methylene which is substituted with aminomethyl,
$R^2$ is H, methoxy, ethoxy or amino,
in Subformula 12
X is N,
Y is NH,
$R^1$ is $L^1$-$R^4$,
$L^1$ is methylene which is substituted with aminomethyl.
$R^2$ is H, methoxy, ethoxy or amino,
in Subformula 13
X is N,
Y is NH,
$R^1$ is $L^1$-$R^4$-$L^2$-$R^5$ or $L^1$-$R^4$,
$L^1$ is methylene which is unsubstituted or substituted with aminomethyl,
$R^2$ is H, methoxy, ethoxy or amino,
in Subformula 14
X is N,
Y is NH,
$R^1$ is $L^1$-$R^4$-$L^2$-$R^5$ or $L^1$-$R^4$,
$L^1$ is methylene,
$R^2$ is H, methoxy, ethoxy or amino,
in Subformula 15
X is N,
Y is NH,
$R^1$ is $L^1$-$R^4$-$L^2$-$R^5$ or $L^1$-$R^4$,
$L^1$ is methylene,
$R^2$ is H, methoxy or amino,
in Subformula 16
X is N,
Y is NH,
$R^1$ is $L^1$-$R^4$,
$L^1$ is methylene,
$R^2$ is H, methoxy or amino,
in Subformula 17
X is N,
Y is NH,
$R^1$ is $L^1$-$R^4$,
$L^1$ is methylene,
$R^4$ is phenyl which is unsubstituted or monosubstituted with Hal or $CF_3$, or disubstituted with Hal,
$R^2$ is 1-1, methoxy or amino,
in Subformula 18
X is N,
Y is NH, $R^1$ is $L^1$-$R^4$,
$L^1$ is methylene,
$R^4$ is phenyl which is unsubstituted or monosubstituted with Hal or $CF_3$, or disubstituted with Hal,
$R^2$ is H,
in Subformula 19
X is N,
Y is NH,
$R^1$ is $L^1$-$R^4$-$L^2$-$R^5$,
$L^1$ is methylene,
$R^4$ is phenylene,
$L^2$ is NHCO or NHCONH,
$R^2$ is H or methoxy,
in Subformula 20
X is N,
Y is NH,
$R^1$ is $L^1$-$R^4$-$L^2$-$R^5$,
$L^1$ is methylene,
$R^4$ is phenylene,
$L^2$ is NHCO or NHCONH,
$R^5$ is phenyl which is unsubstituted or mono- or disubstituted with Hal,
$R^2$ is H or methoxy,
in Subformula 21
X is N,
Y is NH,
$R^1$ is $L^1$-$R^4$-$L^2$-$R^5$,
$L^1$ is methylene,
$R^4$ is phenylene,
$L^2$ is NHCO,
$R^5$ is phenyl which is unsubstituted or mono- or disubstituted with Hal,
$R^2$ is H or methoxy,
in Subformula 22
X is N,
Y is NH,
$R^1$ is $L^1$-$R^4$-$L^2$-$R^5$,
$L^1$ is methylene,
$R^4$ is phenylene,
$L^2$ is NHCO or NHCONH,
$R^5$ is phenyl which is unsubstituted, or mono- or disubstituted with Hal,
$R^2$ is H,
in Subformula 23
X is N,
$R^1$ is $L^1$-$R^4$-$L^2$-$R^5$,
$R^4$ is phenylene,
$R^5$ benzo-1,3-dioxolyl,
in Subformula 24
X is N,
Y is NH,
$L^1$ is methylene which is unsubstituted or substituted with aminomethyl, (methyl-amino)methyl, (dimethyl-amino)methyl, methyl, ethyl, 2-hydroxyethyl, methoxymethyl, 2-(dimethyl-amino)ethyl, (ethyl-amino)methyl, 2-(methoxy)ethyl, 2-(allyl-methyl-amino)ethyl, ((tert. butyl-oxy-carbonyl)-methyl-amino)methyl, 2-(pyrrolidin-1-yl)ethyl, 2-(azetidin-1-yl)ethyl, 2-(piperidin-1-yl)ethyl or 2-(piperazin-1-yl)ethyl,
in Subformula 25
X is N,
Y is NH,
$L^1$ is methylene which is unsubstituted or substituted with (methyl-amino)methyl, (dimethyl-amino)methyl, methyl or 2-(dimethyl-amino)ethyl,
in Subformula 26
X is N,
Y is NH,
$R^1$ is $L^1$-$R^4$-$L^2$-$R^5$,
$R^4$ is phenylene,
$L^2$ is —NHCO—, —NH—, —NHCH$_2$—, NHCOOCH$_2$— or —NHCONH—,
in Subformula 27
X is N,
Y is NH,
$R^1$ is $L^1$-$R^4$-$L^2$-$R^5$,
$R^4$ is phenylene,
$L^2$ is —NHCO—, —NH—, —NHCH$_2$—, NHCOOCH$_2$— or —NHCONH—,
$R^5$ is Ar which is unsubstituted or substituted as defined for Ar in claim 1,
in Subformula 28
X is N,
Y is NH,
$R^1$ is $L^1$-$R^4$-$L^2$-$R^5$,
$R^4$ is phenylene,
$L^2$ is —NHCO—, —NH—, —NHCH$_2$—, NHCOOCH$_2$— or —NHCONH—,
$R^5$ is phenyl, pyridyl, benzo-1,3-dioxolyl, pyrazolyl or thiazolyl, all of which are unsubstituted or substituted as defined for Ar in claim 1,
in Subformula 29
X is N,
Y is NH,
$L^1$ is methylene which is unsubstituted or substituted with aminomethyl, (methyl-amino)methyl, (dimethyl-amino)methyl, methyl, ethyl, 2-hydroxyethyl, methoxymethyl, 2-(dimethyl-amino)ethyl, (ethyl-amino)methyl, 2-(methoxy)ethyl, 2-(allyl-methyl-amino)ethyl, ((tert. butyl-oxy-carbonyl)-methyl-amino)methyl, 2-(pyrrolidin-1-yl)ethyl, 2-(azetidin-1-yl)ethyl, 2-(piperidin-1-yl)ethyl or 2-(piperazin-1-yl)ethyl,
$R^2$ is H or methoxy,
in Subformula 30
X is N,
Y is NH,
$L^1$ is methylene which is unsubstituted or substituted with (methyl-amino)methyl, (dimethyl-amino)methyl, methyl or 2-(dimethyl-amino)ethyl,
$R^2$ is H or methoxy,
in Subformula 31
X is N,
Y is NH,
$R^1$ is $L^1$-$R^4$-$L^2$-$R^5$,
$R^4$ is phenylene,
$L^2$ is —NHCO—, —NH—, —NHCH$_2$—, NHCOOCH$_2$— or —NHCONH—,
$R^2$ is H or methoxy,
in Subformula 32
X is N,
Y is NH,
$R^1$ is $L^1$-$R^4$-$L^2$-$R^5$,
$R^4$ is phenylene,
$L^2$ is —NHCO—, —NH—, —NHCH$_2$—, NHCOOCH$_2$— or —NHCONH—,
$R^5$ is Ar which is unsubstituted or substituted as defined for Ar in claim 1,
$R^2$ is H or methoxy,
in Subformula 33
X is N,
Y is NH,
$R^1$ is $L^1$-$R^4$-$L^2$-$R^5$, R⁴ is phenylene,
L² is —NHCO—, —NH—, —NHCH₂—, NHCOOCH₂— or —NHCONH—,
R⁵ is phenyl, pyridyl, benzo-1,3-dioxolyl, pyrazolyl or thiazolyl, all of which are unsubstituted or substituted as defined for Ar in claim 1,
R² is H or methoxy,
in Subformula 34
X is N,
Y is NH,
R¹ is L¹-R⁴-L²-R⁵,
L¹ is methylene which is unsubstituted or substituted with (methyl-amino)methyl, (dimethyl-amino)methyl, methyl or 2-(dimethyl-amino)ethyl,
R⁴ is phenylene,
L² is —NHCO—, —NH—, —NHCH₂—, NHCOOCH₂— or —NHCONH—,
R⁵ is Ar which is unsubstituted or substituted as defined for Ar in claim 1,
R² is H or methoxy,
in Subformula 35
X is N,
Y is NH,
R¹ is L¹-R⁴,
R² is L¹-Ar,
in Subformula 36
X is N,
Y is NH,
R¹ is L¹-R⁴,
L¹ is a bond,
in Subformula 37
X is N,
Y is NH,
R¹ is L¹-R⁴,
R⁴ is piperidinyl,
in Subformula 38
X is N,
Y is NH,
R¹ is L¹-R⁴,
R⁴ is piperidinyl,
R² is L¹-Ar,
L¹ is a bond,
and pharmaceutically acceptable salts thereof.

6. The compound as claimed in claim 4 wherein the substituent designated "R⁴" in Subformulae 19, 20, 21, 22, 23, 26, 27, 28, 31, 32, 33 and 34 further comprises meta-phenylene.

7. The compound as claimed in claim 5 wherein the substituent designated "R⁴" in Subformulae 19, 20, 21, 22, 23, 26, 27, 28, 31, 32, 33 and 34 further comprises meta-phenylene.

8. The compound according to claim 1, wherein the compound is selected from the group consisting of:
4-[2-Amino-1-(3,4-dichloro-phenyl)-ethylamino] quinazoline-8-carboxylic acid amide,
4-[2-Amino-1-(3-fluoro-phenyl)-ethylamino]-quinazoline-8-carboxylic acid amide,
4-[2-Amino-1-(3,4-dimethoxy-phenyl)-ethylamino]-quinazoline-8-carboxylic acid amide,
4-(2-Amino-1-p-tolyl-ethylamino)-quinazoline-8-carboxylic acid amide,
4-((S)-2-Amino-1-phenyl-ethylamino)-quinazoline-8-carboxylic acid amide,
4-[2-Amino-1-(4-methoxy-phenyl)-ethylamino]quinazoline-8-carboxylic acid amide,
6-Methoxy-4-(2-methylamino-1-phenyl-ethylamino)-quinazoline-8-carboxylic acid amide,
4-[2-Dimethylamino-1-(4-trifluoromethyl-phenyl)-ethylamino]-quinazoline-8-carboxylic acid amide,
4-((R)-2-Methylamino-1-phenyl-ethylamino)-quinazoline-8-carboxylic acid amide,
4-[1-(3,4-Dichloro-phenyl)-2-methylamino-ethylamino]-quinazoline-8-carboxylic acid amide,
4-((S)-2-Amino-1-phenyl-ethylamino)-6-methoxy-quinazoline-8-carboxylic acid amide,
4-{1-[3-(3,4-Difluoro-benzoylamino)-phenyl]-2-methylamino-ethylamino}-quinazoline-8-carboxylic acid amide,
4-[1-(3-Fluoro-phenyl)-2-methylamino-ethylamino]-6-methoxy-quinazoline-8-carboxylic acid amide,
4-[2-Amino-1-(3-fluoro-phenyl)-ethylamino]-quinazoline-8-carboxylic acid amide,
4-[2-Amino-1-(3,4-dichloro-phenyl)-ethylamino]-quinazoline-8-carboxylic acid amide,
4-(3,4-Dimethyl-benzylamino)-quinazoline-8-carboxylic acid amide,
4-{2-Dimethylamino-1-[3-(4-trifluoromethyl-benzoylamino)-phenyl]-ethylamino}-quinazoline-8-carboxylic acid amide,
4-{2-Dimethylamino-1-[3-(2-fluoro-benzoylamino)-phenyl]-ethylamino}-quinazoline-8-carboxylic acid amide,
4-{1-[3-(4-Bromo-benzoylamino)-phenyl]-2-methylamino-ethylamino}-quinazoline-8-carboxylic acid amide,
4-{1-[3-(4-Bromo-benzoylamino)-phenyl]-2-dimethylamino-ethylamino}-quinazoline-8-carboxylic acid amide,
4-(2-Amino-1-p-tolyl-ethylamino)-quinazoline-8-carboxylic acid amide,
4-[1-(3-Chloro-phenyl)-2-methylamino-ethylamino]-quinazoline-8-carboxylic acid amide,
4-[2-Amino-1-(4-methoxy-phenyl)-ethylamino]-quinazoline-8-carboxylic acid amide,
4-(2-Dimethylamino-1-{3-[(2-pyrrolidin-1-yl-pyridine-4-carbonyl)-amino]-phenyl}-ethylamino)-quinazoline-8-carboxylic acid amide,
4-[(S)-1-(3-Fluoro-phenyl)-2-methylamino-ethylamino]-6-methoxy-quinazoline-8-carboxylic acid amide,
4-((S)-2-Amino-1-phenyl-ethylamino)-quinazoline-8-carboxylic acid amide,
4-[1-(3-Chloro-phenyl)-2-methylamino-ethylamino]-6-methoxy-quinazoline-8-carboxylic acid amide,
4-[1-(3,4-Dichloro-phenyl)-2-dimethylamino-ethylamino]-quinazoline-8-carboxylic acid amide,
4-(2-Dimethylamino-1-{3-[(3,4,5,6-tetrahydro-2H-[1,2']bipyridinyl-4'-carbonyl)-amino]-phenyl}-ethylamino)-quinazoline-8-carboxylic acid amide,
4-(1-{3-[(2-Chloro-pyridine-4-carbonyl)-amino]-phenyl}-2-dimethylamino-ethylamino)-quinazoline-8-carboxylic acid amide,
4-[1-(3-Benzoylamino-phenyl)-2-methylamino-ethylamino]-quinazoline-8-carboxylic acid amide,
4-{1-[3-(2,6-Difluoro-benzoylamino)-phenyl]-2-methylamino-ethylamino}-quinazoline-8-carboxylic acid amide,
4-[1-(3-Bromo-phenyl)-2-dimethylamino-ethylamino]-quinazoline-8-carboxylic acid amide,
4-[1-(3-Fluoro-phenyl)-2-methylamino-ethylamino]-quinazoline-8-carboxylic acid amide,
4-{1-[3-(3-Fluoro-4-methoxy-benzoylamino)-phenyl]-2-methylamino-ethylamino}-quinazoline-8-carboxylic acid amide, 4-{2-Dimethylamino-1-[3-(2-fluoro-4-trifluoromethyl-benzoylamino)-phenyl]-ethylamino}-quinazoline-8-carboxylic acid amide,
4-(2-Dimethylamino-1-{3-[(2-dimethylamino-pyridine-4-carbonyl)-amino]-phenyl}-ethylamino)-quinazoline-8-carboxylic acid amide,
4-{1-[3-(4-Methoxy-benzoylamino)-phenyl]-2-methylamino-ethylamino}-quinazoline-8-carboxylic acid amide,
4-(2-Dimethylamino-1-{3-[(5-pyrrolidin-1-yl-pyridine-3-carbonyl)-amino]-phenyl}-ethylamino)-quinazoline-8-carboxylic acid amide,
4-[1-(3-Chloro-phenyl)-2-dimethylamino-ethylamino]-quinazoline-8-carboxylic acid amide,
4-(4-Chloro-3-trifluoromethyl-benzylamino)-quinazoline-8-carboxylic acid amide,
4-{2-Dimethylamino-1-[3-(4-methoxy-benzoylamino)-phenyl]-ethylamino}-quinazoline-8-carboxylic acid amide,
4-[2-Amino-1-(3-chloro-phenyl)-ethylamino]-quinazoline-8-carboxylic acid amide,
5-Methoxy-4-(2-methylamino-1-phenyl-ethylamino)-quinazoline-8-carboxylic acid amide,
4-[1-(4-Methoxy-phenyl)-2-methylamino-ethylamino]-quinazoline-8-carboxylic acid amide,
4-{2-Methylamino-1-[3-(4-trifluoromethoxy-benzoylamino)-phenyl]-ethylamino}-quinazoline-8-carboxylic acid amide,
4-[1-(4-Chloro-phenyl)-2-dimethylamino-ethylamino]-6-methoxy-quinazoline-8-carboxylic acid amide,
4-{2-Amino-1-[3-(4-fluoro-benzoylamino)-phenyl]-ethylamino}-quinazoline-8-carboxylic acid amide,
4-(3,4-Dichloro-benzylamino)-quinazoline-8-carboxylic acid amide,
4-[2-Amino-1-(3,4-dimethoxy-phenyl)-ethylamino]-quinazoline-8-carboxylic acid amide,
4-{1-[3-(2-Fluoro-4-methoxy-benzoylamino)-phenyl]-2-methylamino-ethylamino}-quinazoline-8-carboxylic acid amide,
4-[2-Dimethylamino-1-(3-{[2-(2-methyl-pyrrolidin-1-yl)-pyridine-4-carbonyl]-amino}-phenyl)-ethylamino]-quinazoline-8-carboxylic acid amide,
6-Methoxy-4-((S)-2-methylamino-1-phenyl-ethylamino)-quinazoline-8-carboxylic acid amide,
4-[1-(3-{[2-(3-Diethylamino-pyrrolidin-1-yl)-pyridine-4-carbonyl]-amino}-phenyl)-2-dimethylamino-ethylamino]-quinazoline-8-carboxylic acid amide,
4-(4-Trifluoromethyl-benzylamino)-quinazoline-8-carboxylic acid amide,
4-{(2-Dimethylamino-1-[3-(3-fluoro-4-methoxy-benzoylamino)-phenyl]-ethylamino}-quinazoline-8-carboxylic acid amide,
4-{(R)-1-[3-(2-Fluoro-4-trifluoromethyl-benzoylamino)-phenyl]-ethylamino}-quinazoline-8-carboxylic acid amide,
4-((S)-2-Ethylamino-1-phenyl-ethylamino)-6-methoxy-quinazoline-8-carboxylic acid amide,
4-[(S)-2-Dimethylamino-1-(3-fluoro-phenyl)-ethylamino]-6-methoxy-quinazoline-8-carboxylic acid amide,
4-[(S)-2-Ethylamino-1-(3-fluoro-phenyl)-ethylamino]-quinazoline-8-carboxylic acid amide,
4-{3-(Allyl-methyl-amino)-1-[3-(4-bromo-benzoylamino)-phenyl]-propylamino}-quinazoline-8-carboxylic acid amide,
4-((R)-1-{3-[(6-Methoxy-pyridine-3-carbonyl)-amino]-phenyl}-ethylamino)-quinazoline-8-carboxylic acid amide,
4-(1-{3-[(Benzo[1,3]dioxole-5-carbonyl)-amino]-phenyl}-ethylamino)-quinazoline-8-carboxylic acid amide,
4-((R)-1-{3-[(5-Isopropyl-1H-pyrazole-3-carbonyl)-amino]-phenyl}-ethylamino)-quinazoline-8-carboxylic acid amide,
4-[2-Amino-1-(3-methoxy-phenyl)-ethylamino]-quinazoline-8-carboxylic acid amide, tert-butyl [2-{[8-(aminocarbonyl)quinazolin-4-yl]amino}-2-(3-nitrophenyl)ethyl]methylcarbamate,
4-[3-(2,4-Difluoro-benzoylamino)-benzylamino]-quinazoline-8-carboxylic acid amide,
4-((S)-2-Dimethylamino-1-phenyl-ethylamino)-quinazoline-8-carboxylic acid amide,
4-{1-[3-(3-Fluoro-4-methyl-benzoylamino)-phenyl]-ethylamino}-quinazoline-8-carboxylic acid amide,
4-{1-[3-(4-Fluoro-3-hydroxy-benzoylamino)-phenyl]-ethylamino}-quinazoline-8-carboxylic acid amide,
4-(2-Methylamino-1-phenyl-ethylamino)-quinazoline-8-carboxylic acid amide,
4-{1-[3-(2,4-Difluoro-benzoylamino)-phenyl]-3-dimethylamino-propylamino}-quinazoline-8-carboxylic acid amide,
4-[3-(2,4-Dichloro-benzoylamino)-benzylamino]-quinazoline-8-carboxylic acid amide,
4-(1-{3-[(6-Methoxy-pyridine-3-carbonyl)-amino]-phenyl}-propylamino)-quinazoline-8-carboxylic acid amide,
4-{2-Methylamino-1-[3-(4-trifluoromethyl-benzoylamino)-phenyl]-ethylamino}-quinazoline-8-carboxylic acid amide,
4-((R)-1-{3-[(6-Methyl-pyridine-3-carbonyl)-amino]-phenyl}-ethylamino)-quinazoline-8-carboxylic acid amide,
4-{3-Dimethylamino-1-[3-(4-trifluoromethyl-benzoylamino)-phenyl]-propylamino}-quinazoline-8-carboxylic acid amide,
4-{1-[3-(2,4-Difluoro-benzoylamino)-phenyl]-3-methoxy-propylamino}-quinazoline-8-carboxylic acid amide,
4-{[2-(dimethylamino)-1-(3-nitrophenyl)ethyl]amino}quinazoline-8-carboxamide,
4-[2-(1H-Indol-3-yl)-ethylamino]-quinazoline-8-carboxylic acid amide,
4-{3-[(5-Pyrrolidin-1-yl-pyridine-3-carbonyl)-amino]-benzylamino}-quinazoline-8-carboxylic acid amide,
6-Cyclopropylmethoxy-4-[2-dimethylamino-1-(3-fluoro-phenyl)-ethylamino]-quinazoline-8-carboxylic acid amide,
6-Methoxy-4-(4-trifluoromethyl-benzylamino)-quinazoline-8-carboxylic acid amide,
4-{(R)-1-[3-(3,4-Dimethyl-benzoylamino)-pheny]-ethylamino}-quinazoline-8-carboxylic acid amide,
6-Benzyloxy-4-[1-(3-chloro-phenyl)-2-methylamino-ethylamino]-quinazoline-8-carboxylic acid amide,
4-{(R)-1-[3-(2-Fluoro-5-trifluoromethyl-benzoylamino)-phenyl]-ethylamino}-quinazoline-8-carboxylic acid amide,
4-[3-({2-[(2-Hydroxy-ethyl)-methyl-amino]-pyridine-4-carbonyl}-amino)-benzylamino]-quinazoline-8-carboxylic acid amide,
4-{1-[3-(4-Bromo-benzoylamino)-phenyl]-3-dimethylamino-propylamino}-quinazoline-8-carboxylic acid amide, 4-((R)-1-{3-[(6-Cyano-pyridine-3-carbonyl)-amino]-phenyl}-ethylamino)-quinazoline-8-carboxylic acid amide,
4-((R)-1-{3-[(5-Chloro-6-methoxy-pyridine-3-carbonyl)-amino]-phenyl}-ethylamino)-quinazoline-8-carboxylic acid amide,
4-((R)-1-{3-[(5-tert-Butyl-2H-pyrazole-3-carbonyl)-amino]-phenyl}-ethylamino)-quinazoline-8-carboxylic acid amide,
4-((R)-1-{3-[(2-Methoxy-pyridine-4-carbonyl)-amino]-phenyl}-ethylamino)-quinazoline-8-carboxylic acid amide,
4-((R)-1-{3-[(Benzo[1,3]dioxole-5-carbonyl)-amino]-phenyl}-ethylamino)-quinazoline-8-carboxylic acid amide,
4-(1-{3-[(5-tert-Butyl-2H-pyrazole-3-carbonyl)-amino]-phenyl}-ethylamino)-quinazoline-8-carboxylic acid amide,
4-{1-[3-(4-Bromo-benzoylamino)-phenyl]-ethylamino}-quinazoline-8-carboxylic acid amide,
[2-(3-Benzoylamino-phenyl)-2-(8-carbamoyl-quinazolin-4-ylamino)-ethyl]-methyl-carbamic acid tert-butyl ester,
4-[2-Dimethylamino-1-(3-methoxy-phenyl)-ethylamino]-quinazoline-8-carboxylic acid amide,
4-{1-[3-(2,6-Difluoro-benzoylamino)-phenyl]-3-methoxy-propylamino}-quinazoline-8-carboxylic acid amide,
4-{(R)-1-[3-(4-Chloro-3-methyl-benzoylamino)-phenyl]-ethylamino}-quinazoline-8-carboxylic acid amide,
4-[2-Dimethylamino-1-(3-fluoro-phenyl)-ethylamino]-6-ethoxy-quinazoline-8-carboxylic acid amide,
4-((R)-1-{3-[(5,6-Dimethoxy-pyridine-3-carbonyl)-amino]-phenyl}-ethylamino)-quinazoline-8-carboxylic acid amide,
4-((S)-2-Ethylamino-1-phenyl-ethylamino)-quinazoline-8-carboxylic acid amide,
4-[(S)-1-(3-Chloro-phenyl)-2-methylamino-ethylamino]-6-methoxy-quinazoline-8-carboxylic acid amide,
4-[(S)-1-(3-Fluoro-phenyl)-2-methylamino-ethylamino]-quinazoline-8-carboxylic acid amide,
4-[(E)-(R)-1-(2-Amino-ethyl)-2-vinyl-penta-2,4-dienylamino]-quinazoline-8-carboxylic acid amide,
6-Chloro-4-[(S)-1-(3-fluoro-phenyl)-2-methyl amino-ethylamino]-quinazoline-8-carboxylic acid amide,
4-((R)-1-{3-[(2,2-Difluoro-cyclopropanecarbonyl)-amino]-phenyl}-ethylamino)-quinazoline-8-carboxylic acid amide, and pharmaceutically acceptable salts thereof.

9. A pharmaceutical composition comprising: i) a compound according to claim 1 or a pharmaceutically acceptable salt thereof, as active ingredient and ii) a pharmaceutically acceptable carrier.

10. A process for the manufacture of the compounds of Formula (I), wherein Y is NH, and all other substituents have the meaning as defined for Formula (I) in claim 1 comprising:
i) reacting a carboxylic acid compound of Formula (I-III)

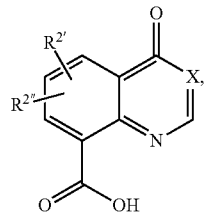

(I-III)

with LA-OH to the corresponding carboxylic LA ester of Formula (I-II),

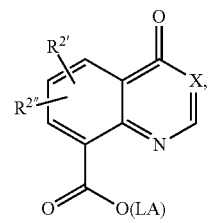

(I-II)

ii) reacting said carboxylic LA ester of Formula (I-II) with $H_2N—R^1$ to yield a compound of Formula (I-I),

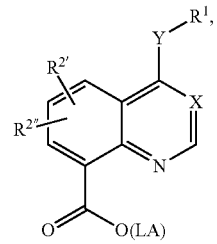

(I-I)

and iii) further reacting said compound of Formula (I-I) under conditions such that said compound of Formula (I-I) is converted into the carboxylic amide of Formula I

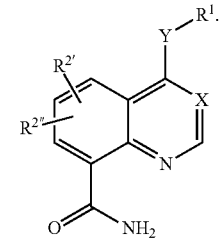

(I)

* * * * *